US010920283B2

(12) United States Patent
Gordon et al.

(10) Patent No.: US 10,920,283 B2
(45) Date of Patent: Feb. 16, 2021

(54) METHODS TO ESTABLISH AND RESTORE NORMAL GUT MICROBIOTA FUNCTION OF SUBJECT IN NEED THEREOF

(71) Applicant: Washington University, St. Louis, MO (US)

(72) Inventors: Jeffrey I. Gordon, St. Louis, MO (US); Sathish Subramanian, St. Louis, MO (US); Ansel Hsiao, St. Louis, MO (US)

(*) Notice: Subject to any disclaimer, the term of this patent is extended or adjusted under 35 U.S.C. 154(b) by 321 days.

(21) Appl. No.: 15/033,416

(22) PCT Filed: Nov. 3, 2014

(86) PCT No.: PCT/US2014/063711
§ 371 (c)(1),
(2) Date: Apr. 29, 2016

(87) PCT Pub. No.: WO2015/066625
PCT Pub. Date: May 7, 2015

(65) Prior Publication Data
US 2016/0326574 A1 Nov. 10, 2016

Related U.S. Application Data

(60) Provisional application No. 61/898,938, filed on Nov. 1, 2013.

(51) Int. Cl.
*G01N 33/48* (2006.01)
*C12Q 1/689* (2018.01)
*C12Q 1/10* (2006.01)
*G06G 7/58* (2006.01)

(52) U.S. Cl.
CPC ............ *C12Q 1/689* (2013.01); *C12Q 1/10* (2013.01); *C12Q 2600/158* (2013.01); *G01N 2800/06* (2013.01)

(58) Field of Classification Search
None
See application file for complete search history.

(56) References Cited

U.S. PATENT DOCUMENTS

| | | |
|---|---|---|
| 6,190,591 B1 | 2/2001 | van Lengerich |
| 6,566,495 B1 | 5/2003 | Fodor et al. |
| 2001/0036672 A1 | 11/2001 | Anderson et al. |
| 2001/0053519 A1 | 12/2001 | Fodor et al. |
| 2003/0220373 A1 | 11/2003 | Jaye et al. |
| 2004/0043017 A1 | 3/2004 | Masci et al. |
| 2004/0091893 A1 | 5/2004 | Gordon et al. |
| 2005/0239706 A1 | 10/2005 | Backhed et al. |
| 2006/0229905 A1 | 10/2006 | Swain |
| 2010/0008949 A1 | 1/2010 | Francis et al. |
| 2010/0172874 A1 | 7/2010 | Turnbaugh et al. |
| 2010/0184624 A1 | 7/2010 | Samuel et al. |
| 2010/0311686 A1 | 12/2010 | Kasper et al. |
| 2011/0177976 A1 | 7/2011 | Gordon et al. |
| 2012/0121753 A1 | 5/2012 | Kim et al. |
| 2013/0217592 A1 | 8/2013 | Samuel et al. |
| 2014/0045744 A1 | 2/2014 | Gordon et al. |
| 2014/0093478 A1 | 4/2014 | Turnbaugh et al. |
| 2014/0128289 A1 | 5/2014 | Gordon et al. |
| 2016/0000837 A1 | 1/2016 | Rey et al. |

FOREIGN PATENT DOCUMENTS

| | | |
|---|---|---|
| EP | 2310532 B1 | 7/2014 |
| WO | 2008076696 A1 | 6/2008 |
| WO | 2008151032 A2 | 12/2008 |
| WO | 2010002890 A2 | 1/2010 |
| WO | 2011096808 A1 | 8/2011 |
| WO | 2012122522 A2 | 9/2012 |
| WO | 2013036290 A1 | 3/2013 |
| WO | 2014127351 A2 | 8/2014 |
| WO | 2015066625 A2 | 5/2015 |

OTHER PUBLICATIONS

Ansel et al., "Pharmaceutical Dosage Forms and Drug Delivery Systems," 1995, 6th Ed., Media, PA., Williams & Wilkins.
Ausubel et al., "Current Protocols in Molecular Biology," Greene Publ. Assoc., Wiley-Interscience, New York.
Bertani et al., "EMBO Workshop on Molecular Genetics of Archaebacteria and the International Workshop on Biology and Biochemistry of Archaebacteria," 1985, p. 398.
Coutinho et al., "Recent Advances in Carbohydrate Bioengineering," 1999, pp. 3-12.
Goodman & Goldman's, "The Pharmacological Basis of Therapeutics," Appendix II, Ninth Edition, 1996, pp. 1707-1711.
Goodman & Goldman's, "The Pharmacological Basis of Therapeutics," Appendix II, Tenth Edition, 2001, pp. 475-493.
Hoover, J., "Remington's Pharmaceutical Sciences," 1975, Mack Publishing Co., Easton, PA.
Liberman et al., "Pharmaceutical Dosage Forms," 1980, Marcel Decker, New York, NY.
Manzi et al., "Current Protocols in Molecular Biology," 1995.

(Continued)

*Primary Examiner* — Eric S Dejong

(74) *Attorney, Agent, or Firm* — Polsinelli PC

(57) ABSTRACT

The present invention provides a method to define normal maturation of the gut microbiota using a limited number of bacterial taxa found in the gut microbiota. Regressing the relative abundance of age-discriminatory taxa in their gut microbiota against the chronological age of each healthy subject at the time a sample of the gut microbiota was collected produces a regression model that may be used to characterize the maturity of another subject's gut microbiota to provide a measure of gastrointestinal health without having to query the whole microbiota. The present invention also provides composition and methods for preventing and/or treating a disease in a subject in need thereof.

12 Claims, 113 Drawing Sheets

Figure 1A:
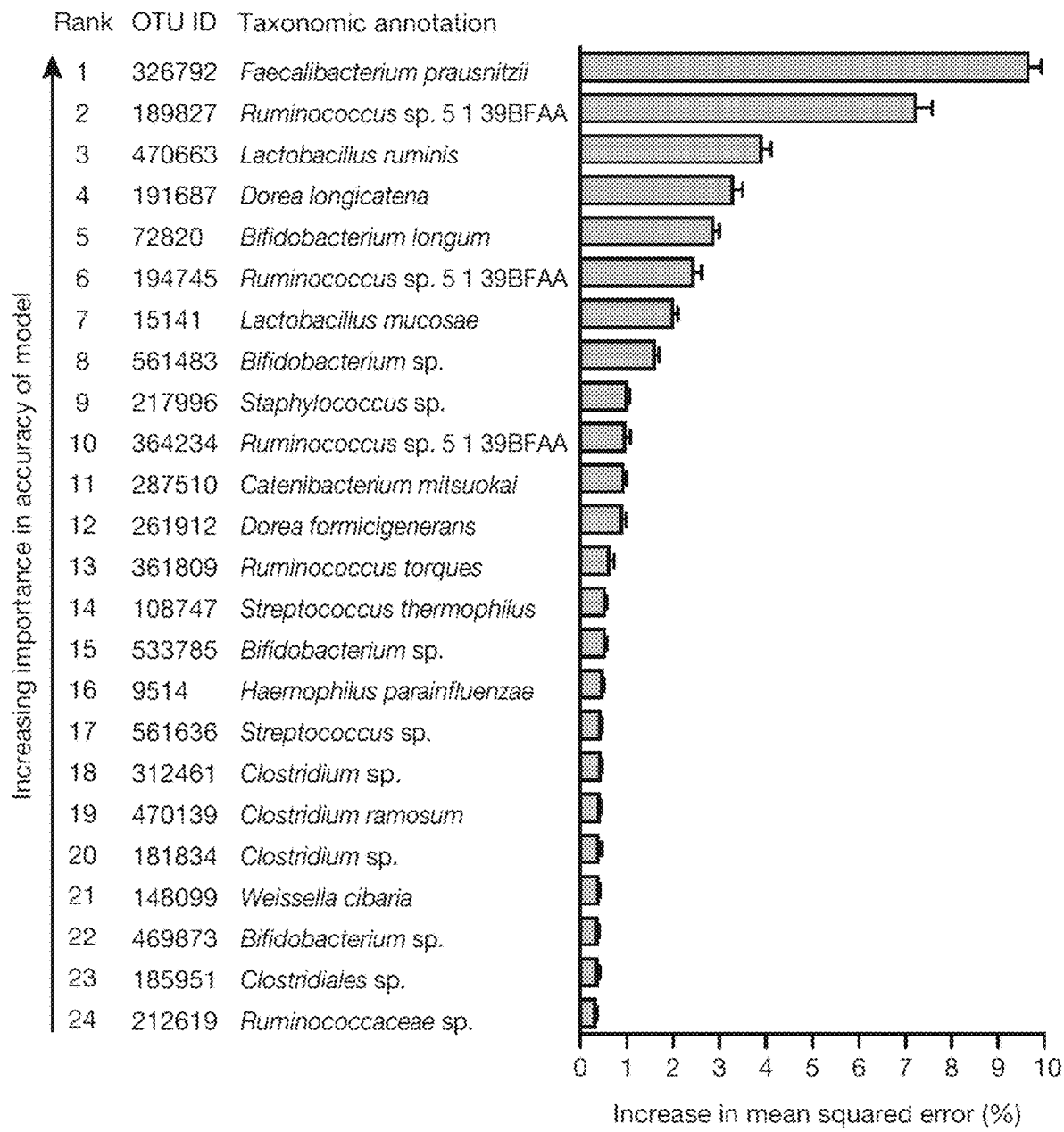

(93 of 113 Drawing Sheet(s) Filed in Color)

Specification includes a Sequence Listing.

(56) References Cited

OTHER PUBLICATIONS

Passonneau et al., "Enzymatic Analysis: A practical guide," 1993.
Sambrook et al., "Molecular Cloning, A Laboratory Manual," Cold Spring Harbor Laboratory.
Miller, V. et al., "Identification of toxS, a Regulatory Gene Whose Product Enhances ToxR-Mediated Activation of the Cholera Toxin Promoter," J. Bacteriol., Mar. 1989, pp. 1288-1293, vol. 171, No. 3.
Mondal, D. et al., "Contribution of Enteric Infection, Altered Intestinal Barrier Function, and Maternal Malnutrition to Infant Malnutrition in Bangladesh," Clin. Infect. Dis., Jan. 15, 2012, pp. 185-192, vol. 54.
Morgan, D. et al., "Non-prescription antimicrobial use worldwide: a systematic review," NIH Public Access, Author Manuscript, available in PMC Jan. 14, 2013, pp. 1-22, published in final edited form as: Lancet Infect. Dis., Sep. 2011, pp. 692-701, vol. 11, No. 9.
Muegge, B. et al., "Diet Drives Convergence in Gut Microbiome Functions Across Mammalian Phylogeny and Within Humans," Sci., May 20, 2011, pp. 970-974, vol. 332, No. 6032.
Nahar, B. et al., "Effects of a community-based approach of food and psychosocial stimulation on growth and development of severely malnourished children in Bangladesh: a randomised trial," Eur. J. Clin. Nutr., 2012, pp. 701-109, vol. 66, Nature Publishing Group.
Office Action dated Sep. 22, 2017 from related U.S. Appl. No. 14/768,394; 5 pgs.
Olivier, V. et al., "Hemolysin and the Multifunctional Autoprocessing RTX Toxin Are Virulence Factors during Intestinal Infection of Mice with Vibrio cholerae El Tor O1 Strains," Infect. Immun., Oct. 2007, pp. 5035-5042, vol. 75, No. 10.
Olivier, V. et al., "Prolonged Colonization of Mice by Vibrio cholerae El Tor O1 Depends on Accessory Toxins," Infect. Immun., Oct. 2007, pp. 5043-5051, vol. 75, No. 10.
Palmer, C. et al., "Development of the Human Infant Intestinal Microbiota," PLoS Biol., Jul. 2007, pp. 1556-1573, vol. 5, No. 7, e177.
Pathela, P. et al., "Diarrheal illness in a cohort of children 0-2 years of age in rural Bangladesh: I. Incidence and risk factors," Acta Paediatr., Apr. 2006, pp. 430-437, vol. 95, No. 4.
Pereira, C. et al., "AI-2-mediated signalling in bacteria," FEMS Microbiol. Rev., 2013, pp. 156-181, vol. 37, Blackwell Publishing Ltd.
Prentice, A. et al., "Critical windows for nutritional interventions against stunting," Am. J. Clin. Nutr., 2013, pp. 911-918, vol. 97.
Ridaura, V. et al., "Gut Microbiota from Twins Discordant for Obesity Modulate Metabolism in Mice," Sci., Sep. 6, 2013, pp. 1241214-1 to 1241214-10, vol. 341, No. 6150.
Rodrigue, S. et al., "Unlocking Short Read Sequencing for Metagenomics," PLoS ONE, Jul. 2010, pp. 1-9, vol. 5, No. 7, e11840.
Schauder, S. et al., "The LuxS family of bacterial autoinducers: biosynthesis of a novel quorum-sensing signal molecule," Mol. Microbiol., 2001, pp. 463-476, vol. 41, No. 2, Blackwell Science Ltd.
Smith, M. et al., "Gut Microbiomes of Malawian Twin Pairs Discordant for Kwashiorkor," Sci., Feb. 1, 2013, pp. 548-554, vol. 339, No. 6119.
Soergel, D. et al., "Selection of primers for optimal taxonomic classification of environmental 16S rRNA gene sequences," ISME J., 2012, pp. 1440-1444, vol. 6.
Subramanian, S. et al., "Persistent Gut Microbiota Immaturity in Malnourished Bangladeshi Children," Nature, HHS Public Access, Author Manuscript, available in PMC Dec. 19, 2014, pp. 1-182, published in final edited form as: Nature, Jun. 19, 2014, pp. 417-421, vol. 510, No. 7505.
Sun, J. et al., "Is autoinducer-2 a universal signal for interspecies communication: a comparative genomic and phylogenetic analysis of the synthesis and signal transduction pathways," BMC Evol. Biol., 2004, pp. 1-11, vol. 4, No. 36.

Surette, M. et al., "Quorum sensing in *Escherichia coli, Salmonella typhimurium*, and Vibrio harveyi: A new family of genes responsible for autoinducer production," PNAS, Feb. 1999, pp. 1639-1644, vol. 96.
Taga, M. et al., "The LuxS-dependent autoinducer Al-2 controls the expression of an ABC transporter that functions in Al-2 uptake in *Salmonella typhimurium*," Mol. Microbiol., 2001, pp. 777-793, vol. 42, No. 3.
Tang, W. et al., "Intestinal Microbial Metabolism of Phosphatidylcholine and Cardiovascular Risk," N. Engl. J. Med., Apr. 25, 2013, pp. 1575-1584, vol. 368, No. 17.
Taylor, R. et al., "Use of phoA gene fusions to identify a pilus colonization factor coordinately regulated with cholera toxin," PNAS, May 1987, pp. 2833-2837, vol. 84.
Victora, C. et al., "Worldwide Timing of Growth Faltering: Revisiting Implications for Interventions," Pediatrics, Mar. 2010, pp. e473-e480, vol. 125, No. 3.
Walters, M. et al., "AI-3 Synthesis Is Not Dependent on IuxS in *Escherichia coli*," J. Bacteriol., Aug. 2006, pp. 5668-5681, vol. 188, No. 16.
White, R. et al., "Novel Developmental Analyses Identify Longitudinal Patterns of Early Gut Microbiota that Affect Infant Growth," PLoS Comput. Biol., May 2013, pp. 1-9, vol. 9, No. 5, e1003042.
World Health Organization, "Cholera, 2013," Wkly. Epidemiol. Rec., Aug. 1, 2014, pp. 345-356, vol. 89, No. 21.
World Health Organization, "WHO Child Growth Standards: Growth velocity based on weight, length and head circumference: Methods and development," Department of Nutrition for Health and Development, 2009, pp. 1-242.
Wu, G. et al., "Linking Long-Term Dietary Patterns with Gut Microbial Enterotypes," Sci., Oct. 7, 2011, pp. 105-108, vol. 334, No. 6052.
Yang, M. et al., "Bile salt-induced intermolecular disulfide bond formation activates Vibrio cholerae virulence," PNAS, Feb. 5, 2013, pp. 2348-2353, vol. 110, No. 6.
Yatsunenko, T. et al., "Human gut microbiome viewed across age and geography," HHS Public Access Author Manuscript, available in PMC Dec. 14, 2012, pp. 1-16, published in final edited form as: Nature, pp. 222-227, vol. 486, No. 7402.
Zhu, J. et al., "Quorum-sensing regulators control virulence gene expression in Vibrio cholerae," PNAS, Mar. 5, 2002, pp. 3129-3134, vol. 99, No. 5.
Altschul et al., "Basic Local Alignment Search Tool", J. Mol. Biol., 1990, pp. 403-410, vol. 215.
Altschul et al., "Gapped BLAST and PSI-BLASt: a new generation of protein database search programs", Nucleic Acids Research, 1997, pp. 3389-3402, vol. 25, No. 17.
Apweiler et al., "The InterPro database, an integrated documentation resource for protein families, domains and functional sites", Nucleic Acids Research, 2001, pp. 37-40, vol. 29, No. 1.
Ashburner et al., "Gene Ontology: tool for the unification of biology", Nat. Genet, 2000, pp. 25-29, vol. 25, No. 1.
Badger et al., "CRITICA: Coding Region Identification Tool Invoking Comparative Analysis", Mol. Biol. Evol., 1999, pp. 512-524, vol. 16, No. 4.
Berk et al., "Function of coenzyme F420-dependent NADP reductase in methanogenic archaea containing an NADP-dependent alcohol dehydrogenase", Arch Microbiol, 1997, pp. 396-402, vol. 168.
Bernal-Mizrachi et al., "Respiratory Uncoupling Lowers Blood Pressure Through a Leptin-Dependent Mechanism in Genetically Obese Mice", Arteriosclerosis, Thrombosis, and Vascular Biology, 2002, pp. 961-968, vol. 22, No. 6.
Besemer et al., "GeneMarkS: a self-training method for prediction of gene starts in microbial genomes. Implications for finding sequence motifs in regulatory regions", Nucleic Acids Research, 2001, pp. 2607-2618, vol. 29, No. 12.
Bjerketorp et al., "Rapid lab-on-a-chip profiling of human gut bacteria", Journal of Microbiological Methods, 2008, pp. 82-90, vol. 72, No. 1.
Bouchard, "Inhibition of Food Intake by Inhibitors of Fatty Acid Synthase", The New England Journal of Medicine, 2000, pp. 1888-1889, vol. 343, No. 25.

(56) References Cited

OTHER PUBLICATIONS

Brugger et al., "Mobile elements in archaeal genomes", FEMS Microbiology Letters, 2002, pp. 131-141, vol. 206.
Bry et al., "A Model of Host-Microbial Interactions in an Open Mammalian Ecosystem", Science, 1996, pp. 1380-1383, vol. 273.
Cabello et al., "Nitrate reduction and the nitrogen cycle in archaea", Microbiology, 2004, pp. 3527-3546, vol. 150.
Carver et al., "ACT: the Artemis comparison tool", Bioinformatics, 2005, pp. 3422-3423, vol. 21, No. 16.
Caspi et al., "MetaCyc: a multiorganism database of metabolic pathways and enzymes", Nucleic Acids Research, 2006, pp. D511-D516, vol. 34.
Chenna et al., "Multiple sequence alignment with the Clustal series of programs", Nucleic Acids Research, 2003, pp. 3497-3500, vol. 31, No. 13.
Cole et al., "The Ribosomal Database Project (RDP-II): sequences and tools for high-throughput rRNA analysis", Nucleic Acids Research, 2005, pp. D294-296, vol. 33.
Coyne et al., "Human Symbionts Use a Host-Like Pathway for Surface Fucosylation", Science, 2005, pp. 1778-1781, vol. 307.
Dailey et al., "Acetohydroxy Acid Synthase I Is Required for Isoleucine and Valine Biosynthesis by *Salmonella typhimurium* LT2 during Growth on Acetate or Long-Chain Fatty Acids", J. Bacteriology, 1987, pp. 917-919, vol. 169, No. 2.
Delcher et al., "Improved microbial gene identification with GLIMMER", Nucleic Acids Research, 1999, pp. 4636-4641, vol. 27, No. 23.
DeLong et al., "Community Genomics Among Stratified Microbial Assemblages in the Ocean's Interior", Science, 2006, pp. 496-503, vol. 311.
DeSantis et al., "NAST: a multiple sequence alignment server for comparative analysis of 16S rRNA genes", Nucleic Acids Research, 2006, pp. W394-W399, vol. 34.
DiBaise et al., "Gut Microbiota and Its Possible Relationship With Obesity", Mayo Clin. Proc., 2008, pp. 460-469, vol. 83, No. 4.
Dumitru et al., "Targeting Methanopterin Biosynthesis to Inhibit Methanogenesis", Applied and Environmental Microbiology, 2003, pp. 7236-7241, vol. 69, No. 12.
Eckburg et al., "Diversity of the Human Intestinal Microbial Flora", Science, 2005, pp. 1635-1638, vol. 308.
Eckburg et al., "Archaea and Their Potential Role in Human Disease", Infection and Immunity, 2003, pp. 591-596, vol. 71, No. 2.
Egan et al., "Structural Studies on the Sialic Acid Polysaccharide Antigen of *Escherichia coli* Strain Bos-12", Biochemistry, 1977, pp. 3687-3692, vol. 16, No. 16.
European Search Report dated Dec. 21, 2011 from related European Patent Application No. 09774341.3; 10 pgs.
Extended European Search Report dated Sep. 27, 2016 from related European Patent Application No. 14751570.4; 10 pgs.
Faith J. et al., "Predicting a Human Gut Microbiota's Response to Diet in Gnotobiotic Mice," Science, Jul. 1, 2011, pp. 101-104, vol. 33, No. 6038.
Fouts, "Phage_Finder: Automated identification and classification of prophage regions in complete bacterial genome sequences", Nucleic Acids Research, 2006, pp. 5839-5851, vol. 34, No. 20.
Fricke et al., "The Genome Sequence of Methanosphaera stadtmanae Reveals Why This Human Intestinal Archaeon Is Restricted to Methanol and H2 for Methane Formation and ATP Synthesis", J. Bacteriology, 2006, pp. 642-658, vol. 188, No. 2.
Gibson et al., "Use of a Three-Stage Continuous Culture System to Study the Effect of Mucin on Dissimilatory Sulfate Reduction and Methanogenesis by Mixed Populations on Human Gut Bacteria", Applied and Environmental Microbiology, 1988, pp. 2750-2755, vol. 54, No. 11.
Gibson et al., "Growth and activities of sulphate-reducing bacteria in gut contents of healthy subjects and patients with ulcerative colitis," FEMS Microbiology Ecology, 1991, pp. 103-112, vol. 86, No. 2.

Gill et al., "Metagenomic Analysis of the Human Distal Gut Microbiome", Science, 2006, pp. 1355-1359, vol. 312.
Gordon et al., "Consed: A Graphical Tool for Sequence Finishing", Genome Research, 1998, pp. 195-202; vol. 8.
Hall et al., "Protein Microarray Technology", Mech Ageing Dev., 2007, pp. 161-167, vol. 128, No. 1.
Hooper et al., "29 Combining Gnotobiotic Mouse Models with Functional Genomics to Define the Impact of the Microflora on Host Physiology", Methods in Microbiology, 2002, pp. 559-589, vol. 31.
Hooper et al., "Medusa: a simple tool for interaction graph analysis", Bioinformatics, 2005, pp. 4432-4433, vol. 21, No. 24.
Huyghe et al., "Novel Microarray Design Strategy to Study Complex Bacterial Communities", Applied and Environmental Microbiology, 2008, pp. 1876-1885, vol. 74, No. 6.
Huang et al., "PCAP: A Whole-Genome Assembly Program", Genome Research, 2003, pp. 2164-2170, vol. 13, No. 9.
Huber et al., "Bellerophon: a program to detect chimeric sequences in multiple sequence alignments", Bioinformatics, 2004, pp. 2317-2319, vol. 20, No. 14.
Inagaki et al., "Regulation of antibacterial defense in the small intestine by the nuclear bile acid receptor", PNAS, 2006, pp. 3920-3925, vol. 103, No. 10.
International Search Report and Written Opinion dated Oct. 27, 2014 from related International Patent Application No. PCT/US2014/045141; 16 pgs.
International Search Report and Written Opinion dated Sep. 10, 2014 from related International Patent Application No. PCT/US14/16883; 12 pgs.
International Search Report and Written Opinion dated Oct. 2, 2008 from related International Patent Application No. PCT/US07/87003; 6 pgs.
International Search Report and Written Opinion dated Dec. 16, 2008 from related International Patent Application No. PCT/US08/65344; 10 pgs.
International Search Report and Written Opinion dated Dec. 30, 2009 from related International Patent Application No. PCT/US09/049253; 12 pgs.
International Search Report and Written Opinion dated Aug. 17, 2012 from related International Patent Application No. PCT/US12/28600; 11 pgs.
Kanehisa et al., "The KEGG resource for deciphering the genome", Nucleic Acids Research, 2004, pp. D277-D280, vol. 32.
Ahmed, T. et al., "Management of Severe Malnutrition and Diarrhea," Indian J. Pediatr., Jan. 2001, pp. 45-51, vol. 68, No. 1.
Ahmed, T. et al., "Mortality in severely malnourished children with diarrhoea and use of a standardised management protocol," Lancet, 1999, pp. 1919-1922, vol. 353.
Ahmed, T. et al., "Use of a standardized protocol based on local diet results in satisfactory rates of weight gain of severely malnourished children undergoing nutritional rehabilitation," J. Pediatr. Gastroenterol. Nutr., Jun. 2004, 2 pgs., vol. 39, No. p. S277, Poster Session Abstracts P0580, Lippincott Williams & Wilkins, Inc.
Anders, S. et al., "Differential expression analysis for sequence count data," Genome Biol., 2010, pp. 1-12, vol. 11, No. R106.
Ashraf, H. et al., A Follow-up Experience of 6 months after Treatment of Children with Severe Acute Malnutrition in Dhaka, Bangladesh, J. Trop. Pediatr., 2012, pp. 253-257, vol. 58, No. 4.
Bassler, B. et al., "Multiple signalling systems controlling expression of luminescence in Vibrio harveyi: sequence and function of genes encoding a second sensory pathway," Mol. Microbiol., 1994, pp. 273-286, vol. 13, No. 2.
Bokulich, N. et al., "Quality-filtering vastly improves diversity estimates from Illumina amplicon sequencing," Nature Meth., Jan. 2013, pp. 57-59, vol. 10, No. 1, with Online Methods, 1 pg., Nature Publishing Group.
Breiman, L., "Random Forests," Mach. Learn. 2001, pp. 5-32, vol. 45, Kluwer Academic Publishers, The Netherlands.
Caporaso, J. et al., "QIIME allows analysis of high-throughput community sequencing data," NIH Public Access, Author Manuscript, available in PMC Aug. 16, 2011, pp. 1-4, published in final edited form as: Nat. Methods, May 2010, pp. 335-336, vol. 7, No. 5.

(56) References Cited

OTHER PUBLICATIONS

Caporaso, J., "Moving pictures of the human microbiome," Genome Biol., 2011, pp. 1-8, vol. 12, No. R50.
Chowdhury, F. et al., "Impact of Rapid Urbanization on the Rates of Infection by Vibrio cholerae O1 and Enterotoxigenic *Escherichia coli* in Dhaka, Bangladesh," PLoS Negl. Trop. Dis., Apr. 2011, pp. 1-8, vol. 5, No. 4, e999.
Cole, J. et al., "The ribosomal database project (RDP-II): introducing myRDP space and quality controlled public data," Nucleic Acids Res., 2007, pp. D169-D172, vol. 35.
David, L. et al., "Diet rapidly and reproducibly alters the human gut microbiome," NIH Public Access, Author Manuscript, available in PMC Jul. 23, 2014, pp. 1-23, published in final edited form as: Nature, Jan. 23, 2014, pp. 559-563, vol. 505, No. 7484.
Desantis, T. et al., "Greengenes, a Chimera-Checked 16S rRNA Gene Database and Workbench Compatible with ARB," Appl. Environ. Microbiol., Jul. 2006, pp. 5069-5072, vol. 72, No. 7.
Dewey, K. et al., "Infant weight-for-length is positively associated with subsequent linear growth across four different populations," Matern. Child Nutr., Jan. 2005, pp. 11-20, vol. 1, No. 1, Blackwell Publishing Ltd.
Dirita, V., "Co-ordinate expression of virulence genes by ToxR in Vibrio cholerae," Mol. Microbiol., 1992, pp. 451-458, vol. 6, No. 4.
Duan, F. et al., Engineered bacterial communication prevents Vibrio cholerae virulence in an infant mouse model, PNAS, Jun. 22, 2010, pp. 11260-11264, vol. 107, No. 25.
Dufrene, M. et al., "Species Assemblages and Indicator Species: The Need for a Flexible Asymmetrical Approach," Ecol. Monogr., Aug. 1997, p. 345-366, vol. 67, No. 3.
Edgar, R., "Search and clustering orders of magnitude faster than BLAST," Bioinformatics, 2010, pp. 2460-2461, vol. 26, No. 19.
Faith, J. et al., "The Long-Term Stability of the Human Gut Microbiota," Sci., Jul. 5, 2013, pp. 1237439-1 to 1237439-8, vol. 341, No. 6141.
Faiz, M. et al., "Antimicrobial resistance: Bangladesh experience," Reg. Health Forum, 2011, 1-8, vol. 15, No. 1.
Gronlund, M-M. et al., "Influence of mother's intestinal microbiota on gut colonization in the infant," Gut Microbes, Jul./Aug. 2011, pp. 227-233, vol. 2, No. 4.
Guo, F. et al., "Taxonomic Precision of Different Hypervariable Regions of 16S rRNA Gene and Annotation Methods for Functional Bacterial Groups in Biological Wastewater Treatment," PLOS One, Oct. 2013, pp. 1-11, vol. 8, No. 10, e76185.
Hamady, M et al., "Microbial community profiling for human microbiome projects: Tools, techniques, and challenges," Genome Res., 2009, pp. 1141-1152, vol. 19, Cold Spring Harbor Laboratory Press.
Herrington, D. et al., "Toxin, Toxin-Coregulated Pili, and the toxR Regulon Are Essential for Vibrio Cholerae Pathogenesis in Humans," J. Exp. Med., Oct. 1988, pp. 1487-1492, vol. 168, The Rockefeller University Press.
Higgins, D. et al., "The major Vibrio cholerae autoinducer and its role in virulence factor production," Nature, Dec. 6, 2007, pp. 883-886, vol. 450.
Higgins, D. et al., "The Virulence Gene Activator ToxT from Vibrio cholerae Is a Member of the AraC Family of Transcriptional Activators," J. Bacteriol., Nov. 1992, pp. 6974-6980, vol. 174, No. 21.
Higgins, D. et al., "Transcriptional control of toxT, a regulatory gene in the ToxR regulon of Vibrio cholerae," Mol. Microbiol., 1994, pp. 17-29, vol. 14, No. 1.
Hsiao, A. et al., "Members of the human gut microbiota involved in recovery from Vibrio cholerae infection," HHS Public Access, Author Manuscript, available in PMC May 20, 2015, pp. 1-30, published in final edited form as: Nature, Nov. 20, 2014, pp. 423-426, vol. 515, No. 7527.
Hsiao, A. et al., "Vibrio cholerae virulence regulator—coordinated evasion of host immunity," PNAS, Sep. 26, 2006, pp. 14542-14547, vol. 103, No. 39.

International Search Report and Written Opinion dated Feb. 6, 2015 from related International Patent Application No. PCT/US2014/063711; 15 pgs.
Iwanaga, M. et al., "Culture Conditions for Stimulating Cholera Toxin Production by Vibrio cholerae O1 El Tor," Microbiol. Immunol., 1986, pp. 1075-1083, vol. 30, No. 11.
Kanehisa, M. et al., "KEGG: Kyoto Encyclopedia of Genes and Genomes," Nucleic Acids Res., 2000, pp. 27-30, vol. 28, No. 1, Oxford University Press.
Koenig, J. et al., "Succession of microbial consortia in the developing infant gut microbiome," PNAS, Mar. 15, 2011, pp. 4578-4585, vol. 108, Suppl. 1.
Kovacikova, G. et al., "Regulation of virulence gene expression in Vibrio cholerae by quorum sensing: HapR functions at the aphA promoter," Mol. Microbiol., 2002, pp. 1135-1147, vol. 46, No. 4, Blackwell Publishing Ltd.
Kristiansson, E. et al., "ShotgunFunctionalizeR: an R-package for functional comparison of metagenomes," Bioinformatics, 2009, pp. 2737-2738, vol. 25, No. 20, Oxford University Press.
Langmead, B. et al., "Ultrafast and memory-efficient alignment of short DNA sequences to the human genome," Genome Biol., 2009, pp. R25.1-R25.10, vol. 10, No. 3.
Larkin, M. et al., "Clustal W and Clustal X version 2.0," Bioinformatics, 2007, pp. 2947-2948, vol. 23, No. 21.
Lazzerini, M. et al., "Specially formulated foods for treating children with moderate acute malnutrition in low- and middle-income countries (Review)," The Cochrane Library, 2013, pp. 1-151, Issue 6, John Wiley & Sons, Ltd.
Lee, S. et al., "Regulation and Temporal Expression Patterns of Vibrio cholerae Virulence Genes during Infection," Cell, Dec. 10, 1999, pp. 625-634, vol. 99, Cell Press.
Liaw, A. et al., "Classification and Regression by randomForest," R News, Dec. 2002, pp. 18-22, vol. 2/3.
Lin, A. et al., "Distinct Distal Gut Microbiome Diversity and Composition in Healthy Children from Bangladesh and the United States," PLoS ONE, Jan. 2013, pp. 1-19, vol. 8, No. 1, e53838.
Liu, Z. et al., "Mucosal penetration primes Vibrio cholerae for host colonization by repressing quorum sensing," PNAS, Jul. 15, 2008, pp. 9769-9774, vol. 105, No. 28.
Liu, Z. et al. "Temporal Quorum-Sensing Induction Regulates Vibrio cholerae Biofilm Architecture," Infect. Immun., Jan. 2007, pp. 122-126, vol. 75, No. 1.
Liu, Z. et al., "The Transcriptional Regulator VqmA Increases Expression of the Quorum-Sensing Activator HapR in Vibrio cholerae," J. Bacteriol., Apr. 2006, pp. 2446-2453, vol. 188, No. 7.
Martens, E. et al., "Recognition and Degradation of Plant Cell Wall Polysaccharides by Two Human Gut Symbionts," PLoS Biol., Dec. 2011, pp. 1-16, vol. 9, No. 12, e1001221.
McDonald, D. et al., "An improved Greengenes taxonomy with explicit ranks for ecological and evolutionary analyses of bacteria and archaea," ISME J., 2012, pp. 610-618, vol. 6.
McNulty, N. et al., "Effects of Diet on Resource Utilization by a Model Human Gut Microbiota Containing Bacteroides cellulosilyticus WH2, a Symbiont with an Extensive Glycobiome," PLoS Biol., Aug. 2013, pp. 1-20, vol. 11, No. 8, e1001637.
McNulty, N. et al., "The Impact of a Consortium of Fermented Milk Strains on the Gut Microbiome of Gnotobiotic Mice and Monozygotic Twins," Sci. Translat. Med., Oct. 26, 2011, pp. 1-14, vol. 3, No. 106, 106ra106.
Miller, M. et al., "Parallel Quorum Sensing Systems Converge to Regulate Virulence in Vibrio cholerae," Cell, Aug. 9, 2002, pp. 303-314, vol. 110, Cell Press.
Karlin et al., "Methods for assessing the statistical significance of molecular sequence features by using general scoring schemes", Proc. Natl. Acad. Sci., 1990, pp. 2264-2268, vol. 87.
Kunin et al., "Measuring genome conservation across taxa: divided strains and united kingdoms", Nucleic Acids Research, 2005, pp. 616-621, vol. 33, No. 2.
Kurtz et al., "Versatile and open software for comparing large genomes", Genome Biology, 2004, pp. R12.1-R12.9, vol. 5, No. 2, Article R12.
Ley et al., "Obesity alters gut microbial ecology", PNAS, 2005, pp. 11070-11075, vol. 102, No. 31.

(56) References Cited

OTHER PUBLICATIONS

Ley et al., "Microbial Ecology: Human gut microbes associated with obesity", Nature, 2006, pp. 1022-1023, vol. 444.

Loubinoux J. et al., "Sulfate-reducing bacteria in human feces and their association with inflammatory bowel diseases," FEMS Microbiology Ecology, Jan. 1, 2002, pp. 107-112, vol. 40.

Lowe et al., "tRNAscan-SE: a program for improved detection of transfer RNA genes in genomic sequence", Nucleic Acids Research, 1997, pp. 955-964, vol. 25, No. 5.

Lozupone et al., "UniFrac—An online tool for comparing microbial community diversity in a phylogenetic context", BMC Bioinformatics, 2006, 14 pgs.; vol. 7, No. 371.

Lozupone et al., "UniFrac: a New Phylogenetic Method for Comparing Microbial Communities", Applied and Environmental Microbiology, 2005, pp. 8228-8235, vol. 71, No. 12.

Ludwig et al., "ARB: a software environment for sequence data", Nucleic Acids Research, 2004, pp. 1363-1371, vol. 32, No. 4.

Luo et al. "Pseudomurein endoisopeptidases PeiW and PeiP, two moderately related members of a novel family of proteases produced in Methanothermobacter strains", FEMS Microbiology Letters, 2002, pp. 47-51, vol. 208.

Mandard et al., "The Direct Peroxisome Proliferator-activated Receptor Target Fasting-induced Adipose Factor (FIAF/PGAR/ANGPTL4) Is Present in Blood Plasma as a Truncated Protein That Is Increased by Fenofibrate Treatment", J. Biol. Chem., 2004, pp. 34411-34420, vol. 279, No. 33.

Mazmanian et al., "An Immunomodulatory Molecule of Symbiotic Bacteria Directs Maturation of the Host Immune System", Cell, 2005, pp. 107-118, vol. 122.

Miller et al., "Isolation of Methanobrevibacter smithii from Human Feces", Applied and Environmental Microbiology, 1982, pp. 227-232, vol. 43, No. 1.

Mulder et al., "InterPro, progress and status in 2005", Nucleic Acids Research, 2005, pp. D201-D205, vol. 33.

Neuschwander-Tetri et al., "Nonalcoholic Steatohepatitis: Summary of an AASLD Single Topic Conference", Hepatology, 2003, pp. 1202-1219, vol. 37, No. 5.

Office Action dated May 8, 2013 from related European Application No. 07869090.6; 5 pgs.

Office Action dated Nov. 6, 2012 from related U.S. Appl. No. 12/519,958; 10 pgs.

Office Action dated Apr. 9, 2013 from related U.S. Appl. No. 12/519,958; 8 pgs.

Office Action dated Jul. 3, 2013 from related U.S. Appl. No. 13/002,137; 16 pgs.

Office Action dated Jan. 14, 2015 from related U.S. Appl. No. 13/764,427; 7 pgs.

Office Action dated Oct. 23, 2014 from related U.S. Appl. No. 14/022,000; 9 pgs.

Papineau et al., "Composition and Structure of Microbial Communities from Stromatolites of Hamelin Pool in Shark Bay, Western Australia", Applied and Environmental Microbiology, 2005, pp. 4822-4832, vol. 71, No. 8.

Prangishvili et al., "Evolutionary genomics of archaeal viruses: Unique viral genomes in the third domain of life", Virus Research, 2006, pp. 52-67, vol. 117.

Rockett et al., "DNA arrays: technology, options and toxicological applications", Xenobiotica, 2000, pp. 155-177, vol. 30, No. 2.

Rodriguez-Brito et al., "An application of statistics to comparative metagenomics", BMC Bioinformatics, 2006, vol. 7, No. 162; 11 pgs.

Saldanha, "Java Treeview—extensible visualization of microarray data", Bioinformatics, 2004, pp. 3246-3248, vol. 20, No. 17.

Samuel B. et al., "A humanized gnotobiotic mouse model of host-archaeal-bacterial mutualism" PNAS, Jun. 27, 2006, pp. 10011-10016, vol. 103, No. 26.

Salyers et al., "Fermentation of Mucins and Plant Polysaccharides by Anaerobic Bacteria from the Human Colon", Applied and Environmental Microbiology, 1977, pp. 529-533, vol. 34, No. 5.

Schloss et al., "Introducing DOTUR, a Computer Program for Defining Operational Taxonomic Units and Estimating Species Richness", Applied and Environmental Microbiology, 2005, pp. 1501-1506, vol. 71, No. 3.

Siguier et al., "ISfinder: the reference centre for bacterial insertion sequences", Nucleic Acids Research, 2006, pp. D32-D36, vol. 34.

Silverman et al., "Liver Pathology in Morbidly Obese Patients with and without Diabetes", Am. J. Gastroenterology, 1990, pp. 1349-1355, vol. 85, No. 10.

Sonnenburg et al., "Specificity of Polysaccharide Use in Intestinal Bacteroides Species Determines Diet-Induced Microbiota Alterations", Cell, 2010, pp. 1241-1252, vol. 141.

Sonnenburg et al., "Glycan Foraging in Vivo by an Intestine-Adapted Bacterial Symbiont", Science, 2005, pp. 1955-1959, vol. 307.

Sonnenburg et al., "A hybrid two-component system protein of a prominent human gut symbiont couples glycan sensing in vivo to carbohydrate metabolism", PNAS, 2006, pp. 8834-8839, vol. 103, No. 23.

Stamatakis, "RAxML-VI-HPC: maximum likelihood-based phylogenetic analyses with thousands of taxa and mixed models", Bioinformatics, 2006, pp. 2688-2690, vol. 22, No. 21.

Supplementary European Search Report dated Jul. 11, 2012 from related European Application No. 07869090.6; 6 pgs.

Suyama et al. "PAL2NAL: robust conversion of protein sequence alignments into the corresponding codon alignments", Nucleic Acids Research, 2006, pp. W609-W612, vol. 34.

Tatusov et al., "The COG database: new developments in phylogenetic classification of proteins from complete genomes", Nucleic Acids Research, 2001, pp. 22-28, vol. 29, No. 1.

Tringe et al., "Comparative Metagenomics of Microbial Communities", Science, 2005, pp. 554-557, vol. 308.

Turnbaugh et al., "An obesity-associated gut microbiome with increased capacity for energy harvest", Nature, 2006, pp. 1027-1031, vol. 444.

Turnbaugh et al., "The Effect of Diet on the Human Gut Microbiome: A Metagenomic Analysis in Humanized Gnotobiotic Mice", Science Translational Medicine, 2009, pp. 1-10, vol. 1, No. 6.

Vimr et al., "Diversity of Microbial Sialic Acid Metabolism", Microbiology and Molecular Biology Reviews, 2004, pp. 132-153, vol. 68, No. 1.

Von Mering et al., "STRING: a database of predicted functional associations between proteins", Nucleic Acids Research, 2003, pp. 258-261, vol. 31, No. 1.

Von Mering et al., "STRING: known and predicted protein-protein associations, integrated and transferred across organisms", Nucleic Acids Research, 2005, pp. D433-D437, vol. 33.

Wallace, "Ruminal Microbial Metabolism of Peptides and Amino Acids", J. Nutrition, 1996, pp. 1326S-1334S, vol. 126.

Wanless et al., "Fatty Liver Hepatitis (Steatohepatitis) and Obesity: An Autopsy Study with Analysis of Risk Factors", Hepatology, 1990, pp. 1106-1110, vol. 12, No. 5.

Xu et al. "A Genomic View of the Human-Bacteroides thetaiotaomicron Symbiosis", Science, 2003, pp. 2074-2076, vol. 299.

Zabarovsky et al., "Restriction site tagged (RST) microarrays: a novel technique to study the species composition of complex microbial systems", Nucleic Acids Research, 2003, e95, vol. 31, No. 16; 8 pgs.

Peet "Relative diversity indices." Ecology 56.2 (1975): 496-498.

Office Action dated Aug. 13, 2015 from related U.S. Appl. No. 14/022,000; 8 pgs.

Office Action dated Sep. 16, 2015 from related U.S. Appl. No. 14/049,911; 9 pgs.

Office Action dated Nov. 10, 2015 from related U.S. Appl. No. 14/147,163; 14 pgs.

METHODS TO ESTABLISH AND RESTORE NORMAL GUT MICROBIOTA FUNCTION OF SUBJECT IN NEED THEREOF

CROSS REFERENCE TO RELATED APPLICATIONS

This application claims the priority of PCT application No. PCT/US2014/063711, filed Nov. 3, 2014, which claims priority to U.S. provisional application No. 61/898,938, filed Nov. 1, 2013, each of which is hereby incorporated by reference in its entirety.

FIELD OF THE INVENTION

The present invention provides a method to define normal maturation of the gut microbiota using a limited number of bacterial taxa found in the gut microbiota. Regressing the relative abundance of age-discriminatory taxa in their gut microbiota against the chronological age of each healthy subject at the time a sample of the gut microbiota was collected produces a regression model that may be used to characterize the maturity of another subject's gut microbiota to provide a measure of gastrointestinal health without having to query the whole microbiota. The present invention also provides composition and methods for preventing and/or treating a disease in a subject in need thereof.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821(f).

BACKGROUND OF THE INVENTION

Systematic analyses of the gut microbiota in different healthy and unhealthy populations have been undertaken in the scientific community for many years. The gut microbiota comprises a complex community whose composition is in flux in infants and is generally stable in adults. Disease, illness, and diet, among other factors, have been shown to affect the proportional representation of the bacterial species comprising the gut microbiota. Accordingly, the gut microbiota is viewed as both a diagnostic and therapeutic target. There remains a need in the art, therefore, for methods to define microbiota maturity using bacterial taxonomic biomarkers that are highly discriminatory for age as a way to characterize the health status of the gut microbiota.

SUMMARY OF THE INVENTION

In an aspect, the present disclosure encompasses a method to determine the maturity of a subject's gut microbiota, the method comprising (a) calculating a relative abundance for each bacterial taxon in a group, from a fecal sample obtained from the subject, wherein the group comprises at least the bacterial taxa listed in rows 1 to 6 of Table A; (b) applying the relative abundances of the bacterial taxa from step (a) to a regression model to determine a microbiota age for the subject's gut microbiota, wherein the model regresses, for a group of healthy subjects, relative abundances of the same bacterial taxa, as determined from a plurality of gut microbiota samples obtained over time for each healthy subject in the group, against the chronological age of each healthy subject in the group at the time the gut microbiota sample was obtained; and (c) calculating the maturity of the subject's gut microbiota, wherein the calculation for maturity is defined as relative maturity, and relative maturity=(microbiota age of the subject)−(microbiota age of a healthy subject of a similar chronological age. In certain embodiments, the group comprises at least the bacterial taxa listed in rows 1 to 6 of Table A and at least one bacterial taxon listed in rows 7 to 24 of Table A.

In another aspect, the present disclosure encompasses a method to determine the maturity of a subject's gut microbiota, the method comprising (a) calculating a relative abundance for each bacterial taxon in a group, from a fecal sample obtained from the subject, wherein the group comprises at least 24 bacterial taxa listed in Table A; (b) applying the relative abundances of the bacterial taxa from step (a) to a regression model to determine a microbiota age for the subject's gut microbiota, wherein the model regresses, for a group of healthy subjects, relative abundances of the same bacterial taxa, as determined from a plurality of gut microbiota samples obtained over time for each healthy subject in the group, against the chronological age of each healthy subject in the group at the time the gut microbiota sample was obtained; and (c) calculating the maturity of the subject's gut microbiota, wherein the calculation for maturity is defined as relative maturity, and relative maturity=(microbiota age of the subject)−(microbiota age of a healthy subject of a similar chronological age. In certain embodiments, the group comprises the bacterial taxa listed in Table B.

In another aspect, the present disclosure encompasses a method to classify a subject, the method comprising (a) calculating a relative abundance for each bacterial taxon in a group, from a fecal sample obtained from the subject, wherein the group comprises at least the bacterial taxa listed in rows 1 to 6 of Table A; (b) applying the relative abundances of the bacterial taxa from step (a) to a regression model to determine a microbiota age for the subject's gut microbiota, wherein the model regresses, for a group of healthy subjects, relative abundances of the same bacterial taxa, as determined from a plurality of gut microbiota samples obtained over time for each healthy subject in the group, against the chronological age of each healthy subject in the group at the time the gut microbiota sample was obtained; and (c) classifying the subject as having normal gut maturation when the microbiota age of the subject is substantially similar to the microbiota age of a healthy subject with a similar chronological age. In certain embodiments, the group comprises at least the bacterial taxa listed in rows 1 to 6 of Table A and at least one bacterial taxon listed in rows 7 to 24 of Table A.

In another aspect, the present disclosure encompasses a method to classify a subject, the method comprising (a) calculating a relative abundance for each bacterial taxon in a group, from a fecal sample obtained from the subject, wherein the group comprises at least 24 bacterial taxa listed in Table A; (b) applying the relative abundances of the bacterial taxa from step (a) to a regression model to determine a microbiota age for the subject's gut microbiota, wherein the model regresses, for a group of healthy subjects, relative abundances of the same bacterial taxa, as determined from a plurality of gut microbiota samples obtained over time for each healthy subject in the group, against the chronological age of each healthy subject in the group at the time the gut microbiota sample was obtained; and (c) classifying the subject as having normal gut maturation when the microbiota age of the subject is substantially similar to the microbiota age of a healthy subject with a similar chronological age. In certain embodiments, the group comprises the bacterial taxa listed in Table B.

In another aspect, the present disclosure encompasses a method to classify a subject, the method comprising calculating a relative abundance for each bacterial taxon in a group, from a fecal sample obtained from the subject, wherein the group comprises at least the bacterial taxa listed in rows 1 to 6 of Table A; applying the relative abundances of the bacterial taxa from step (a) and chronological age of the subject to a classification model, wherein the classification model is trained on datasets comprising measurements obtained from a plurality of healthy subjects and a plurality of undernourished subjects, and the measurements including (i) relative abundances of the same bacterial taxa in step (a), as determined from a plurality of gut microbiota samples obtained over time for each healthy and undernourished subject, and (ii) chronological age of the subject at the time the gut microbiota sample was obtained; and wherein the classification model assigns the subject to a category. In certain embodiments, the group comprises at least the bacterial taxa listed in rows 1 to 6 of Table A and at least one bacterial taxon listed in rows 7 to 24 of Table A.

In another aspect, the present disclosure encompasses a method to classify a subject, the method comprising calculating a relative abundance for each bacterial taxon in a group, from a fecal sample obtained from the subject, wherein the group comprises at least 24 bacterial taxa listed in Table A; applying the relative abundances of the bacterial taxa from step (a) and chronological age of the subject to a age-classification model, wherein the classification model is trained on datasets comprising measurements obtained from a plurality of healthy subjects and a plurality of undernourished subjects, and the measurements including (i) relative abundances of the same bacterial taxa in step (a), as determined from a plurality of gut microbiota samples obtained over time for each healthy and undernourished subject, and (ii) chronological age of the subject at the time the gut microbiota sample was obtained; and wherein the classification model assigns the subject to a category. In certain embodiments, the group comprises the bacterial taxa listed in Table B.

In another aspect, the present disclosure encompasses a method for identifying an effect of a therapy, the method comprising (a) calculating a relative abundance for each bacterial taxon in a group, from a fecal sample obtained from the subject before and after administration of the therapy, wherein the group comprises at least the bacterial taxa listed in rows 1 to 6 of Table A; (b) applying the relative abundances of the bacterial taxa from step (a) to a regression model to determine a microbiota age for the subject's gut microbiota before and after therapy, wherein the model regresses, for a group of healthy subjects, relative abundances of the same bacterial taxa, as determined from a plurality of gut microbiota samples obtained over time for each healthy subject in the group, against the chronological age of each healthy subject in the group at the time the gut microbiota sample was collected; wherein the therapy has an effect when the microbiota age of the subject changes after therapy. In certain embodiments, the group comprises at least the bacterial taxa listed in rows 1 to 6 of Table A and at least one bacterial taxon listed in rows 7 to 24 of Table A.

In another aspect, the present disclosure encompasses a method for identifying an effect of a therapy, the method comprising (a) calculating a relative abundance for each bacterial taxon in a group, from a fecal sample obtained from the subject before and after administration of the therapy, wherein the group comprises at least 24 bacterial taxa listed in Table A; (b) applying the relative abundances of the bacterial taxa from step (a) to a regression model to determine a microbiota age for the subject's gut microbiota before and after therapy, wherein the model regresses, for a group of healthy subjects, relative abundances of the same bacterial taxa, as determined from a plurality of gut microbiota samples obtained over time for each healthy subject in the group, against the chronological age of each healthy subject in the group at the time the gut microbiota sample was collected; wherein the therapy has an effect when the microbiota age of the subject changes after therapy. In certain embodiments, the group comprises the bacterial taxa listed in Table B.

In another aspect, the present disclosure encompasses method for identifying an effect of a therapy, the method comprising (a) identifying a set of age-discriminatory bacterial taxa within the bacterial taxa comprising the gut microbiota a group of healthy subject's gut microbiota, the method comprising (i) providing, for each healthy subject, a relative abundance for the bacterial taxa comprising the subject's gut microbiota, wherein the relative abundance of the bacterial taxa in the healthy subject's gut microbiota was determined from a plurality of gut microbiota samples obtained at intervals of time; (ii) regressing the relative abundances of the bacterial taxa comprising each healthy subject's gut microbiota against the chronological age of the healthy subject at the time the gut microbiota sample was collected, thereby producing a prediction of a gut microbiota age that is based only on the relative abundance of age-discriminatory bacterial taxa present in the subject's gut microbiota; and (iii) selecting the minimum number of bacterial taxa from step (ii) that is needed to produce a prediction that is substantially similar to or better than the prediction of step (ii); calculating a relative abundance for each bacterial taxon in the set of age-discriminatory taxa from step (a)(iii), using a fecal sample obtained from a subject before and after administration of the therapy; and applying the relative abundances from step (b) to the prediction of gut microbiota age from step (a)(iii) to determine the microbiota age of the subject's gut microbiota before and after therapy; wherein the therapy has an effect when the microbiota age of the subject changes after therapy.

In another aspect, the present disclosure encompasses a composition comprising at least one of the bacterial taxa listed in Table A. The present disclosure also contemplates a method of preventing or treating acute malnutrition, acute diarrhea, or chronic diarrhea in a subject in need thereof, the method comprising administering to the subject a composition comprising at least one of the bacterial taxa listed in Table A.

In another aspect, the present disclosure encompasses a composition comprising a combination of bacterial taxa, the combination comprising of at least two bacterial taxa listed in Table B. The present disclosure also contemplates a method of preventing or treating acute malnutrition, acute diarrhea, or chronic diarrhea in a subject in need thereof, the method comprising administering to the subject a composition comprising a combination of bacterial taxa, wherein the combination comprises at least two bacterial taxa listed in Table B.

In another aspect, the present disclosure encompasses a composition comprising a combination of bacterial taxa listed, wherein the combination is selected from combinations listed in Table D. The present disclosure also contemplates a method of preventing or treating acute malnutrition, acute diarrhea, or chronic diarrhea in a subject in need thereof, the method comprising administering to the subject a composition comprising a combination of bacterial taxa, wherein the combination is selected from combinations listed in Table D.

Other aspects and iterations of the invention are described more thoroughly below.

REFERENCE TO COLOR FIGURES

The application file contains at least one photograph executed in color. Copies of this patent application publication with color photographs will be provided by the Office upon request and payment of the necessary fee.

Figure 1:
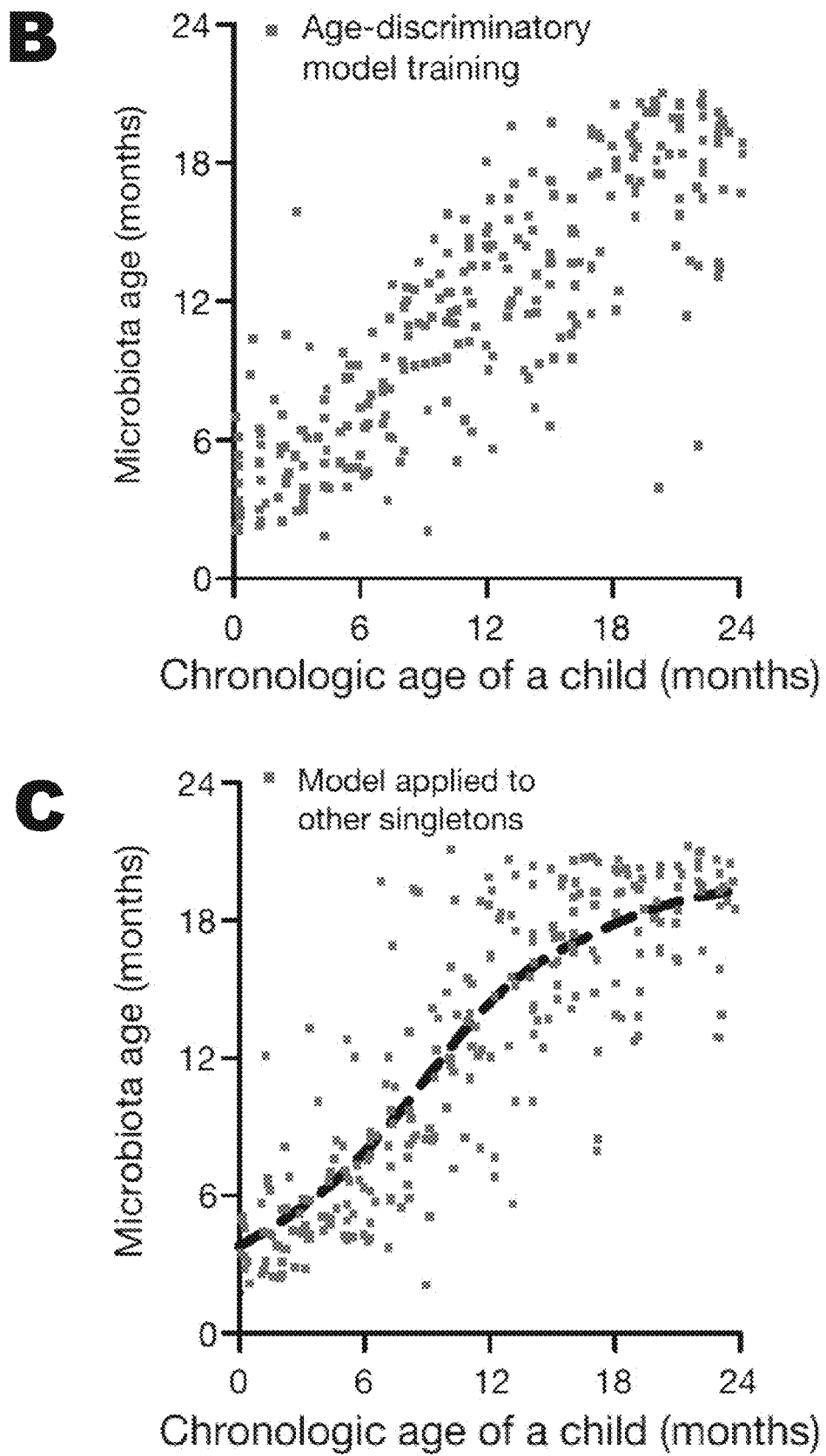

FIG. 1 depicts graphs and a heat map showing bacterial taxonomic biomarkers for defining gut-microbiota maturation in healthy Bangladeshi children during the first 2 years of life. (A) Twenty-four age-discriminatory bacterial taxa were identified by applying Random Forests regression of their relative abundances in faecal samples against chronologic age in 12 healthy children (n=272 faecal samples). Shown are 97%-identity OTUs with their deepest level of confident taxonomic annotation (also see Table 5), ranked in descending order of their importance to the accuracy of the model. Importance was determined based on the percentage increase in mean-squared error of microbiota age prediction when the relative abundance values of each taxon were randomly permuted (mean importance±s.d., n=100 replicates). (E) The insert shows tenfold cross-validation error as a function of the number of input 97%-identity OTUs used to regress against the chronologic age of children in the training set, in order of variable importance (blue line). (B-D) Microbiota age predictions in a birth cohort of healthy singletons used to train the 24 bacterial taxa model (B, brown, each circle represents an individual faecal sample). The trained model was subsequently applied to two sets of healthy children: 13 singletons set aside for model testing (C, green circles, n=276 faecal samples) and another birth cohort of 25 twins and triplets (D, blue circles, n=448 faecal samples). The curve is a smoothed spline fit between microbiota age and chronologic age in the validation sets (C,D), accounting for the observed sigmoidal relationship (see Methods for Examples 1-9). (F-H) Heatmap of mean relative abundances of the 24 age-predictive bacterial taxa plotted against the chronologic age of healthy singletons used to train the Random Forests model (F), and correspondingly in the healthy singletons (G), and twins and triplets (H) used to validate the model (hierarchical clustering performed using the Spearman rank correlation distance metric).

Figure 1D:
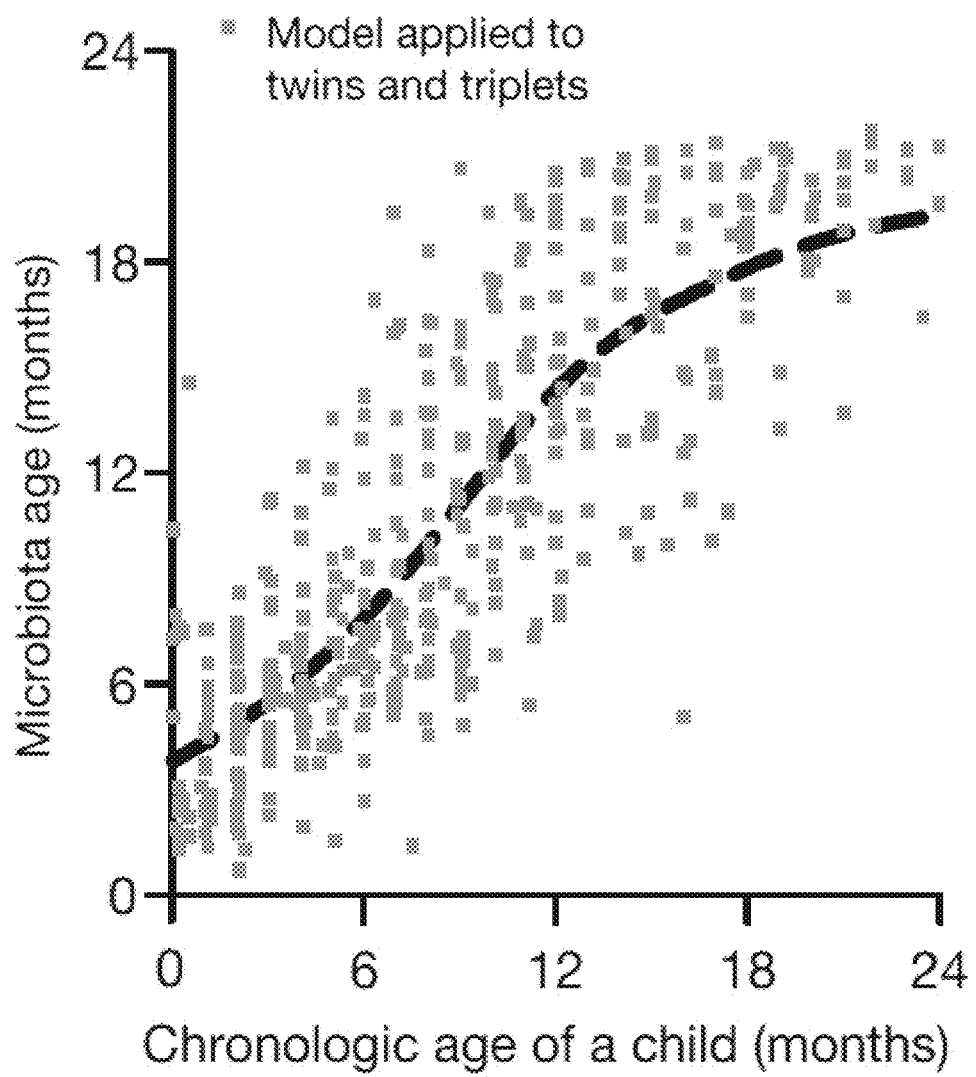
Figure 1E:
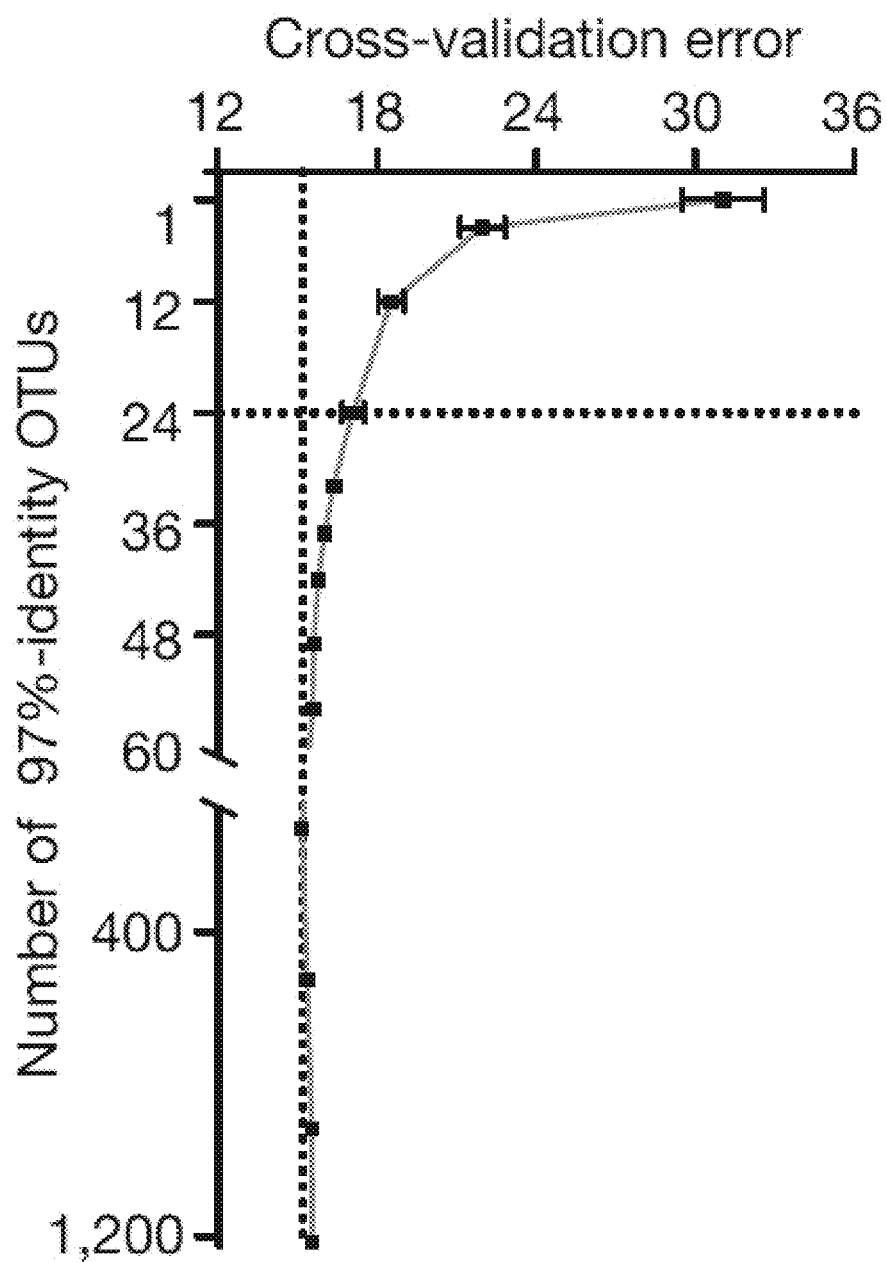
Figure 1F:
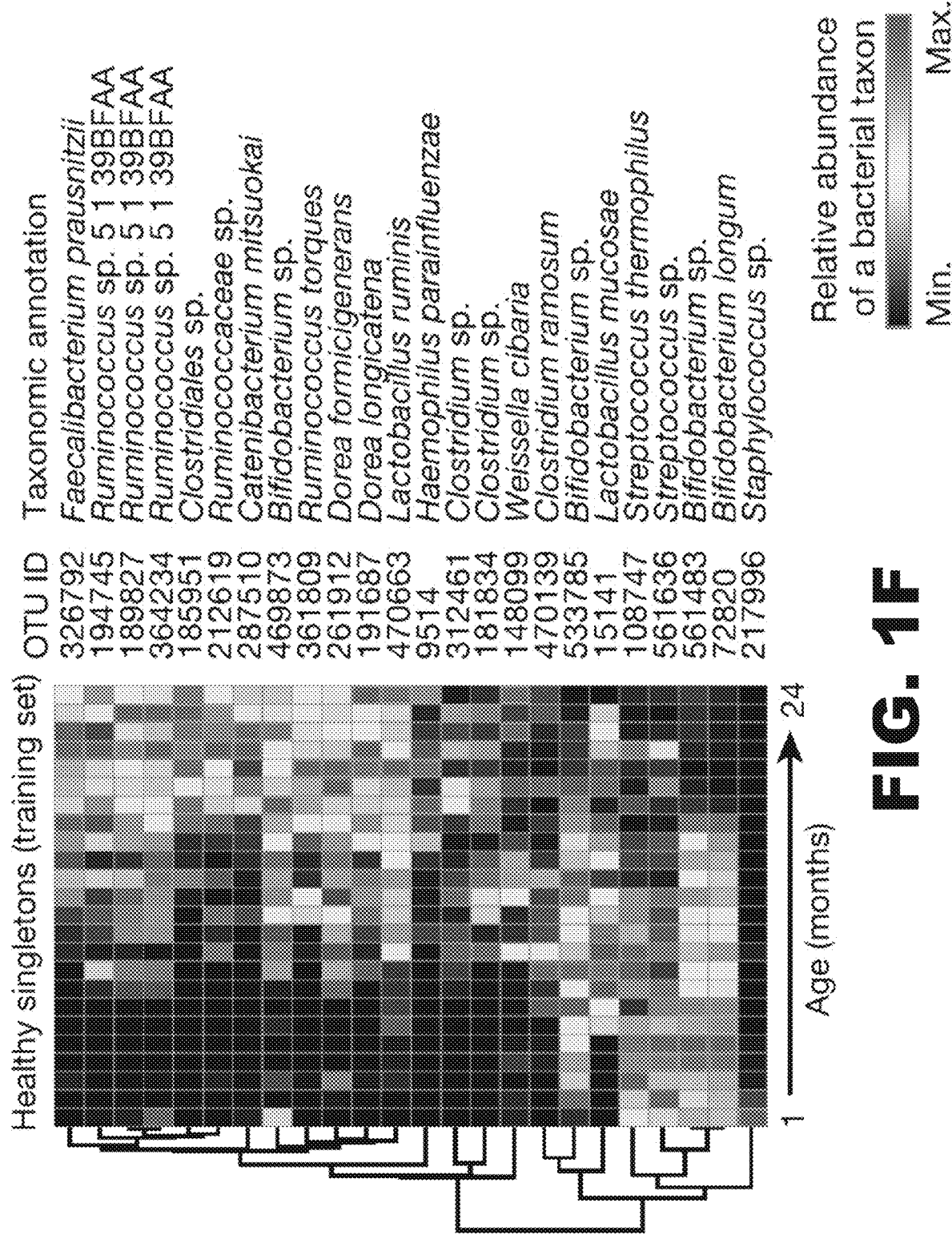
Figure 1G:
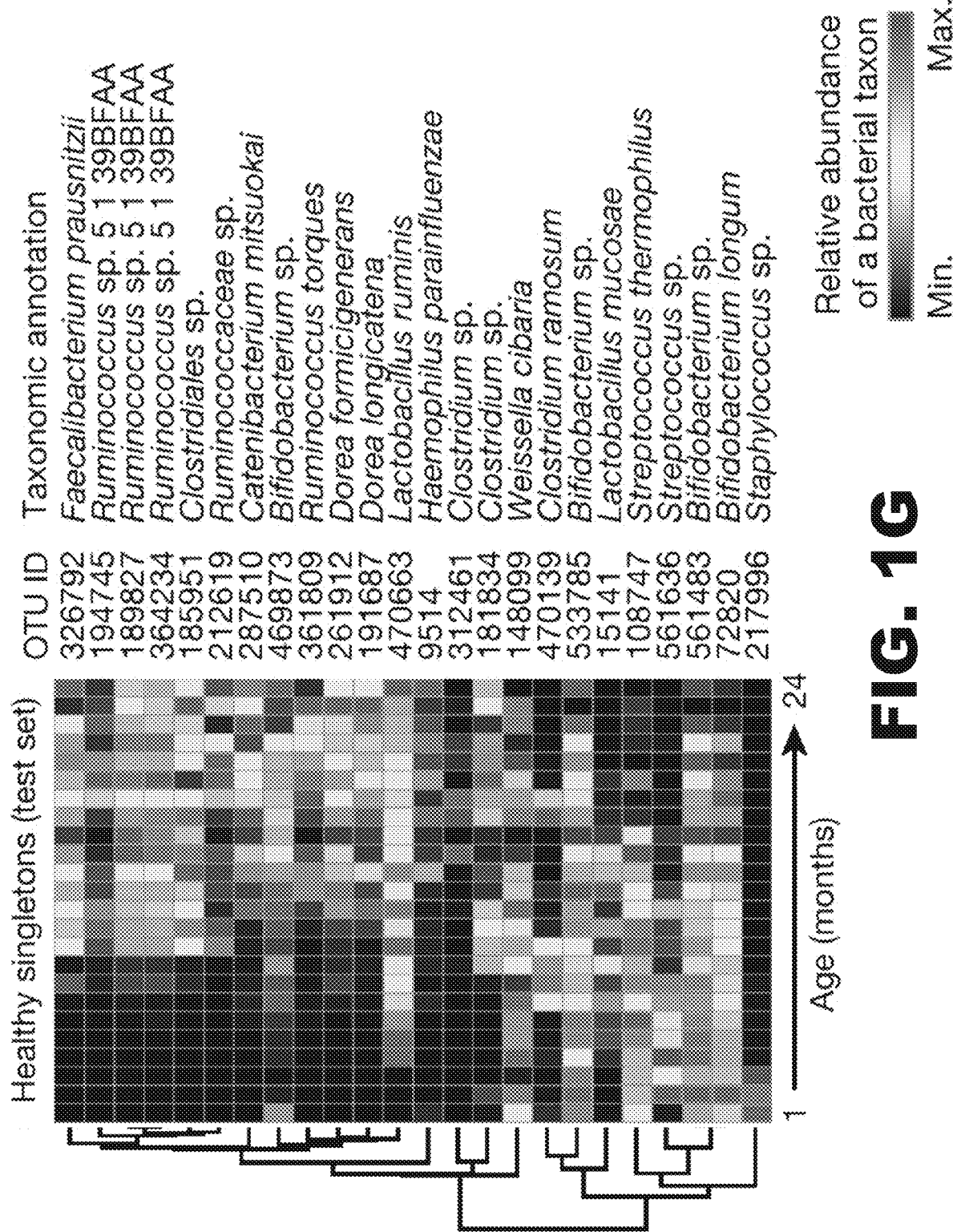
Figure 1H:
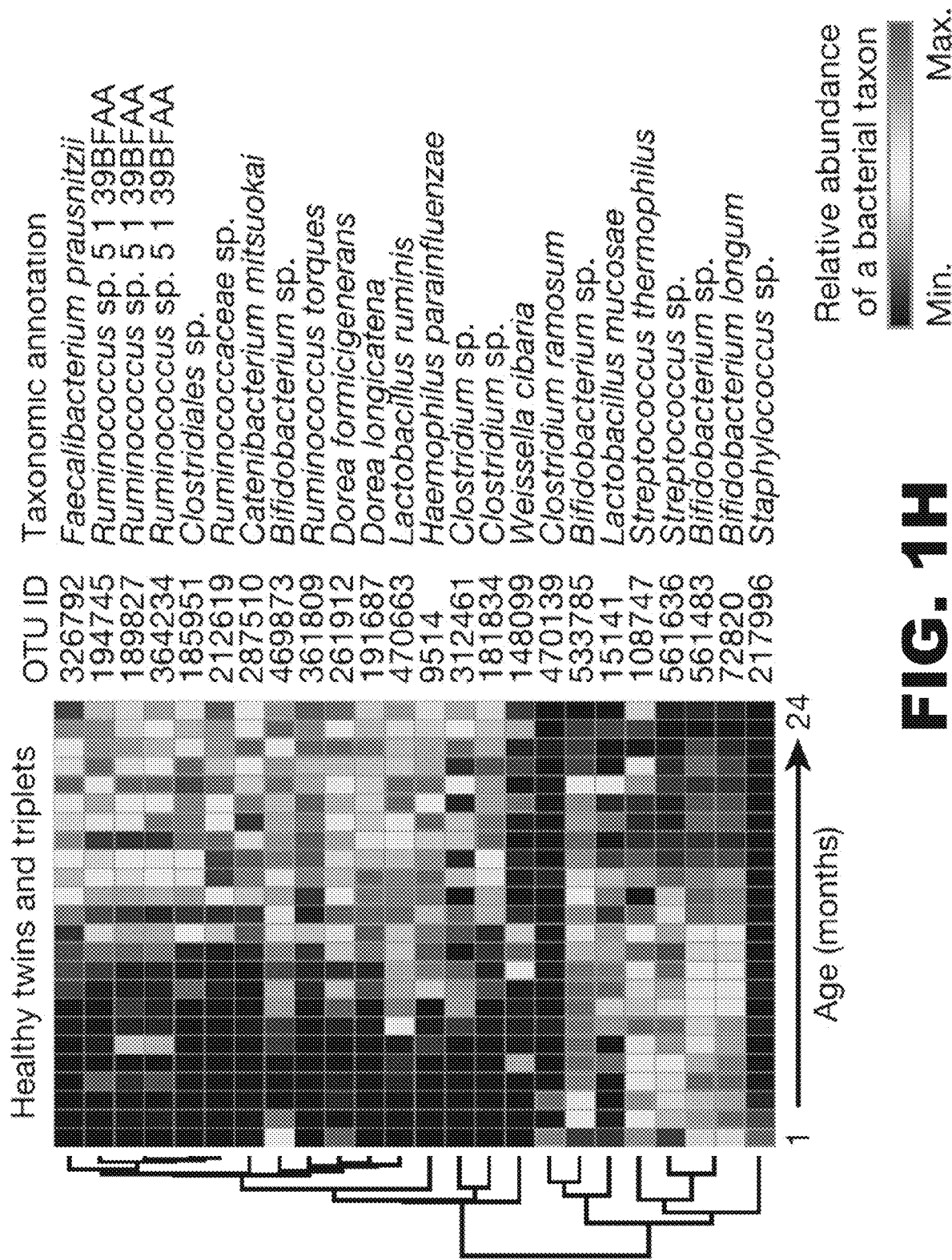
Figure 2A:
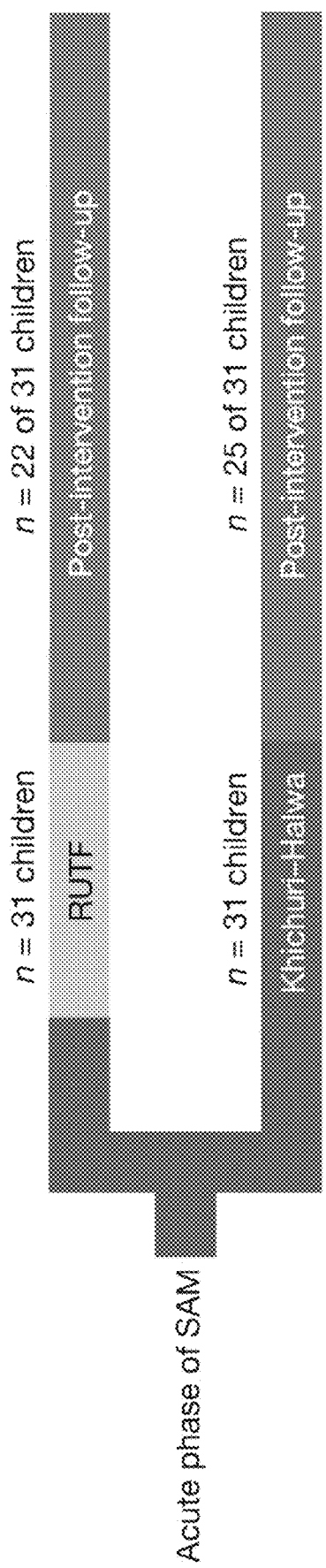
Figure 2B:
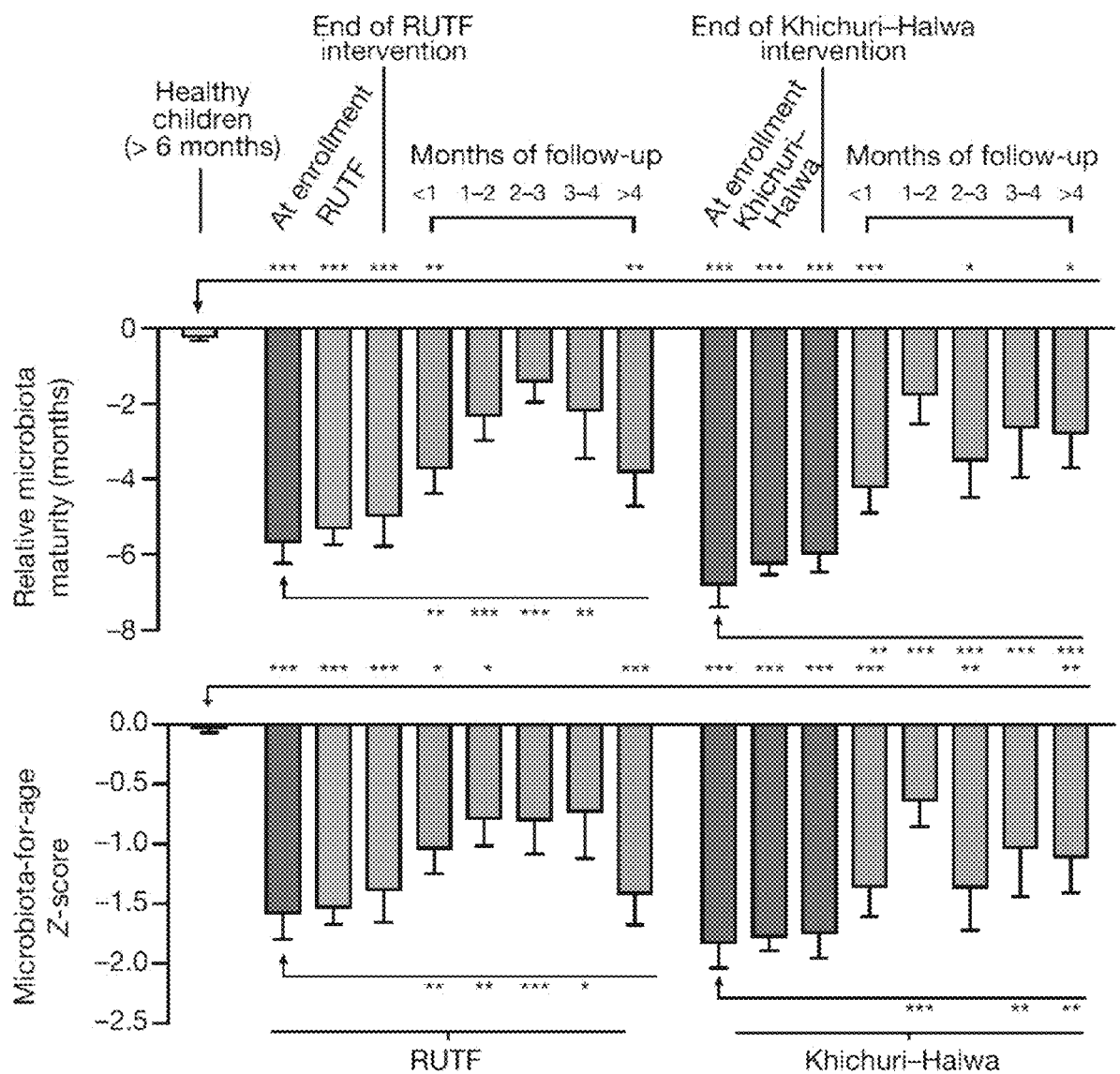
Figure 2:
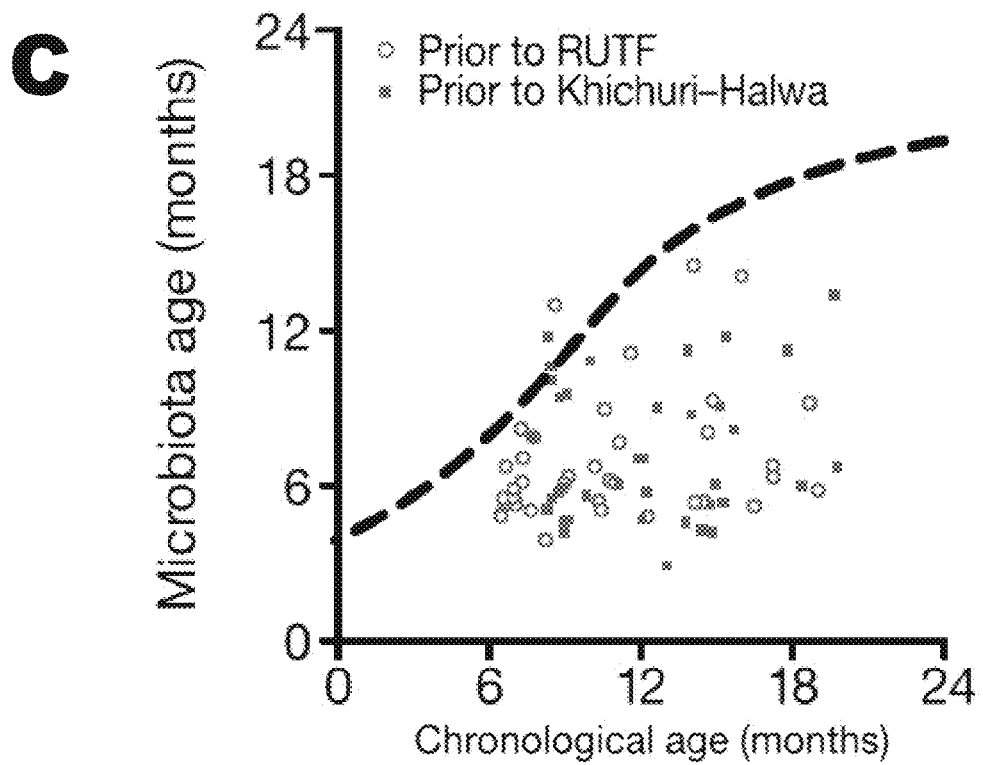
Figure 2:
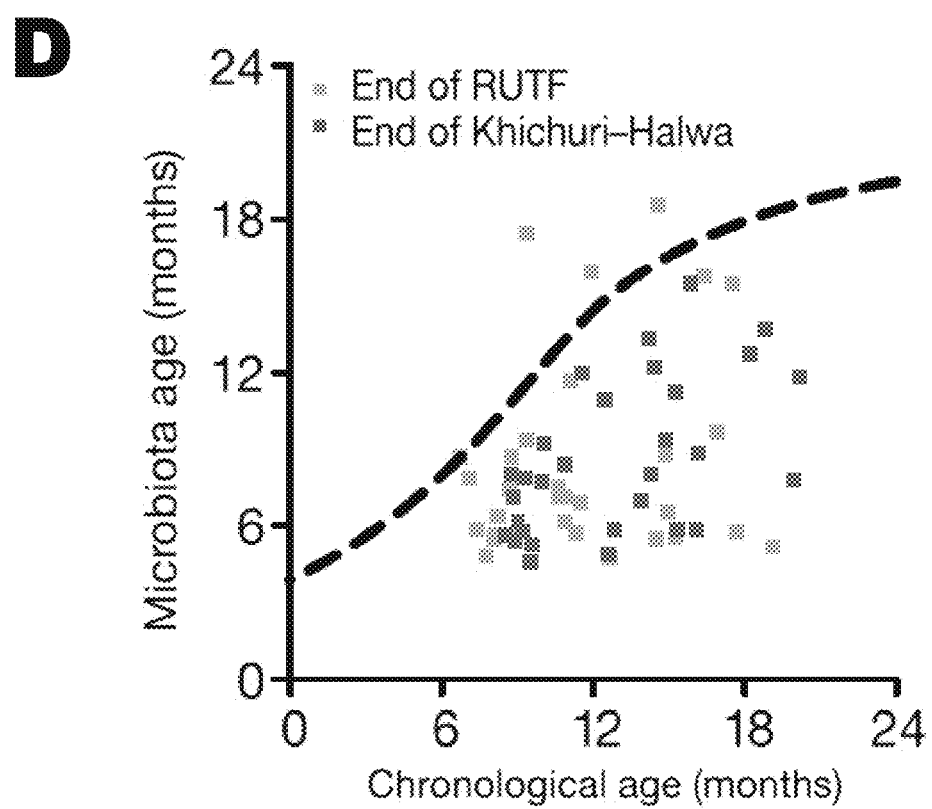
Figure 2:
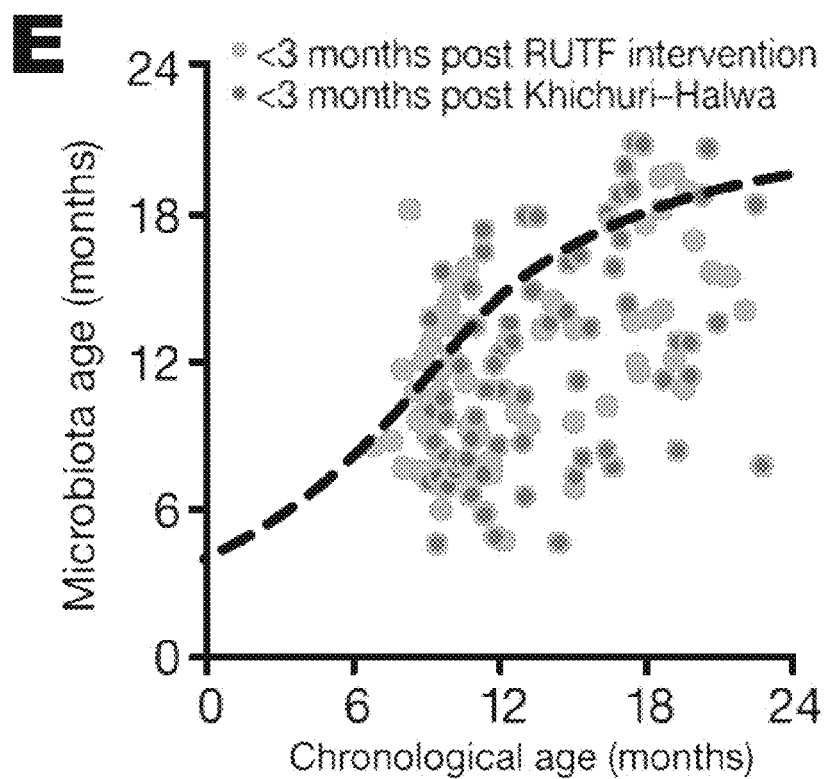
Figure 2:
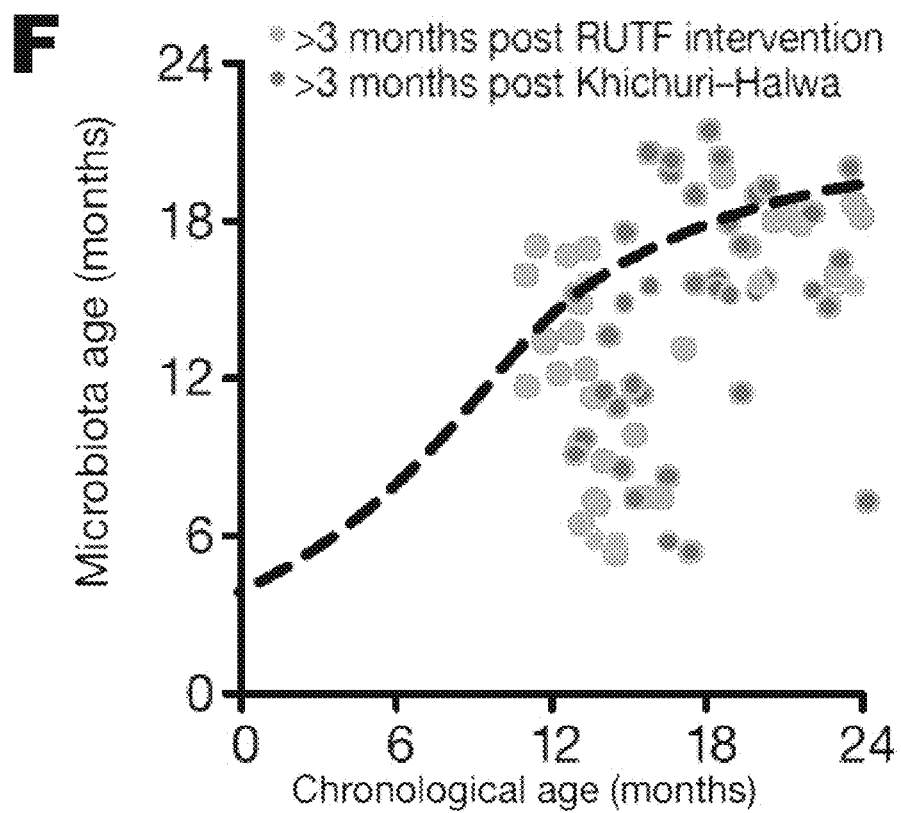

FIG. 2 depicts graphs and a schematic showing persistent immaturity of the gut microbiota in children with SAM. (A) Design of the randomized interventional trial. (B) Microbiota maturity defined during various phases of treatment and follow-up in children with SAM. Relative microbiota maturity in the upper portion of the panel is based on the difference between calculated microbiota age (Random-Forests-based sparse 24-taxon model) and values calculated in healthy children of similar chronologic age, as interpolated over the first 2 years of life using a spline curve. In the lower portion of the panel, maturity is expressed as a microbiota-for-age Z-score (MAZ). Mean values±s.e.m. are plotted. The significance of differences between microbiota indices at various stages of the clinical trial is indicated relative to healthy controls (arrows above the bars) and versus samples collected at enrollment for each intervention group (arrows below the bars) (post-hoc Dunnett's multiple comparison procedure of linear mixed models; *P<0.05, P<0.01, *P<0.001). Healthy children not used to train the Random Forests model served as healthy controls (n=38). (C-F), Plot of microbiota age for each child with SAM at enrollment (C), at the conclusion of the food intervention phase (D), and within (E) and beyond (F) 3 months of follow-up. The curve shown in each panel was fit using predictions in healthy children: this curve is the same as that replicated across each plot in FIG. 1B-D.

Figure 3A:
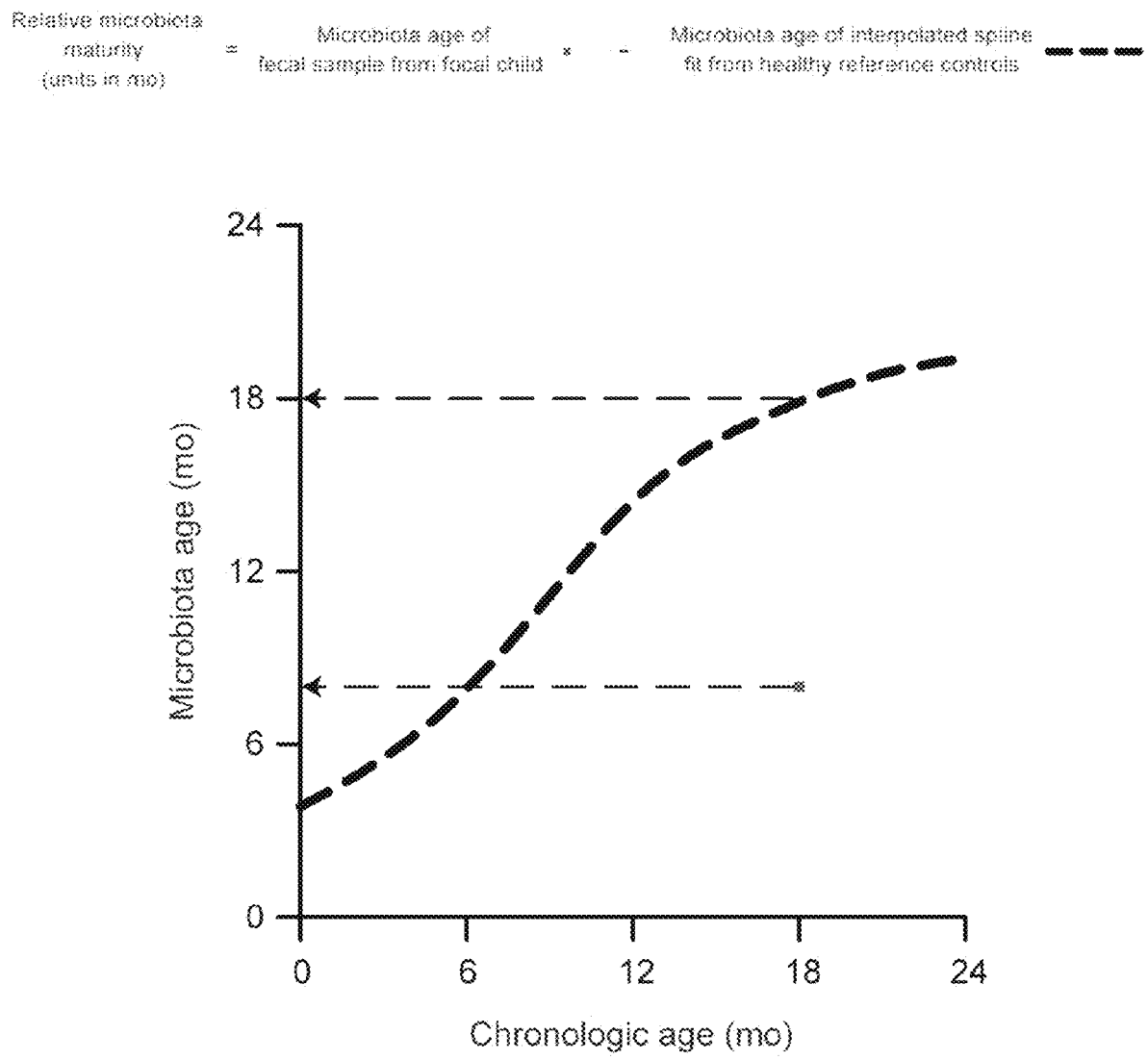
Figure 3B:
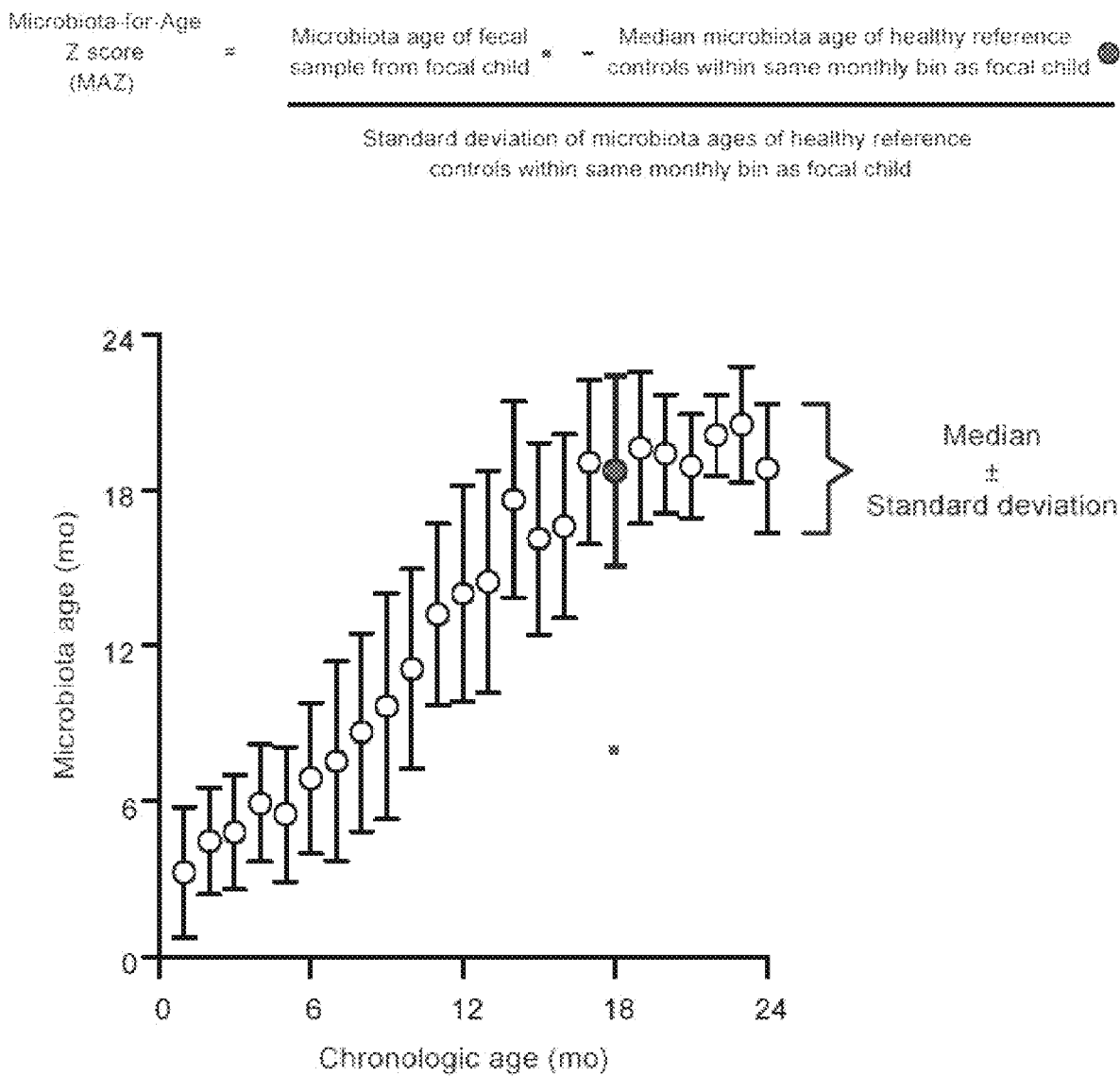

FIG. 3 depicts illustrations of the equations used to calculate 'relative microbiota maturity' and 'microbiota-for-age Z-score'. (A,B) The procedure to calculate both microbiota maturation metrics are shown for a single faecal sample from a focal child (pink circle) relative to microbiota age values calculated in healthy reference controls. These reference values are computed in samples collected from children used to validate the Random-Forests-based sparse 24-taxon model and are shown in (A), as a broken line of the interpolated spline fit and in (B), as median±s.d. values for each monthly chronologic age bin from months 1 to 24.

Figure 4:
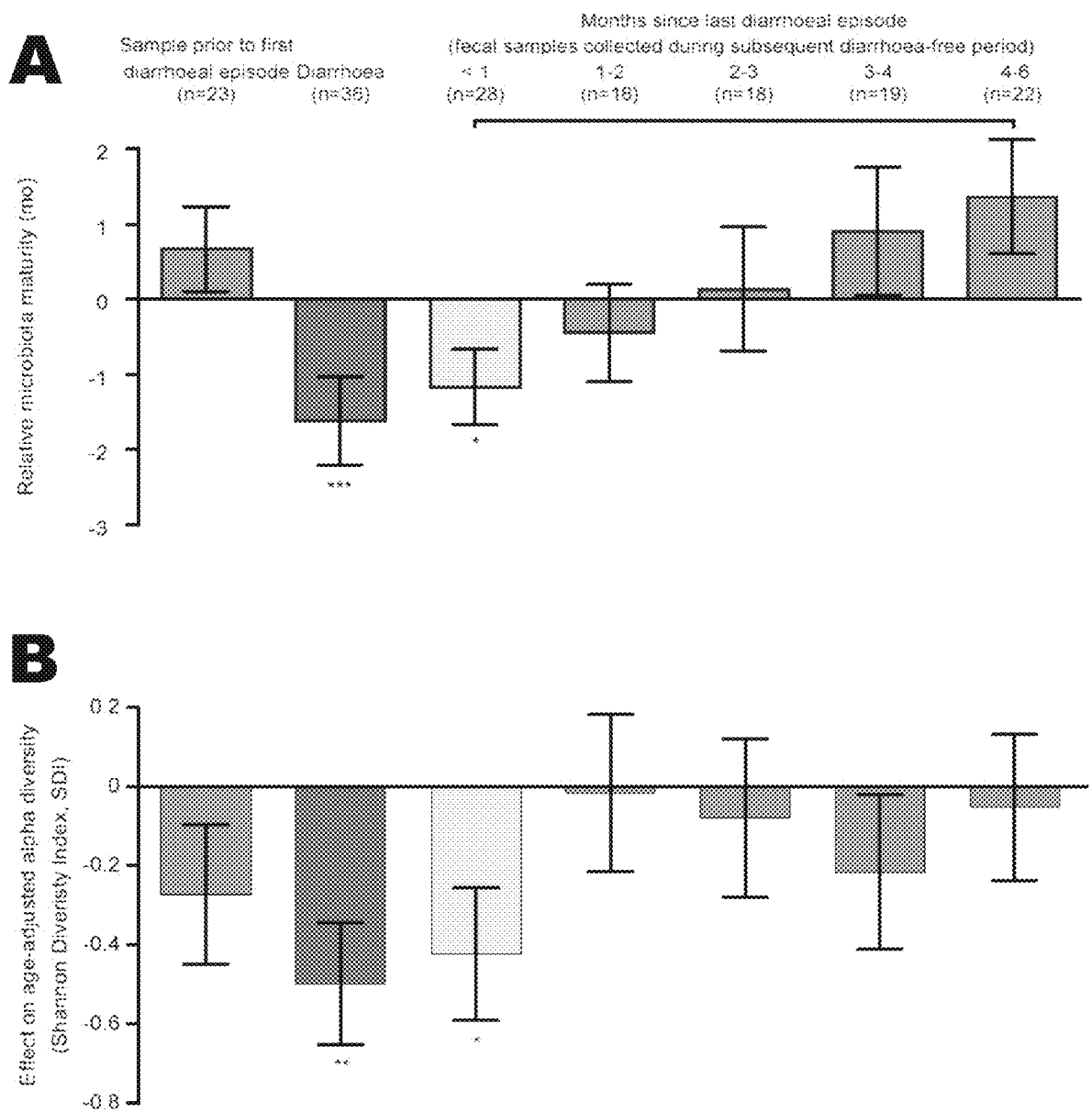

FIG. 4 depicts graphs showing transient microbiota immaturity and reduction in diversity associated with diarrhoea in healthy twins and triplets. (A) The transient effect of diarrhoea in healthy children. Seventeen children from 10 families with healthy twins or triplets had a total of 36 diarrhoeal illnesses where faecal samples were collected. Faecal samples collected in the months immediately before and following diarrhoea in these children were examined in an analysis that included multiple environmental factors in the 'healthy twins and triplets' birth cohort. Linear mixed models of these specified environmental factors indicated that 'diarrhoea', 'month following diarrhoea' and 'presence of formula in diet' have significant effects on relative microbiota maturity, while accounting for random effects arising from within-family and within-child dependence in measurements of this maturity metric. The factors 'postnatal age', 'presence or absence of solid foods', 'exclusive breast-feeding', 'enteropathogen detected by microscopy', 'antibiotics' as well as 'other periods relative to diarrhoea' had no significant effect. The numbers of faecal samples (n) are shown in parenthesis. Mean values±s.e.m. are plotted. *P<0.05, ***P<0.001. See Table 6 for the effects of dietary and environmental covariates. (B) Effect of diarrhoea and recovery on age-adjusted Shannon diversity index (SDI). Mean values of effect on SDI±s.e.m. are plotted. *P<0.05, **P<0.01.

Figure 5A:
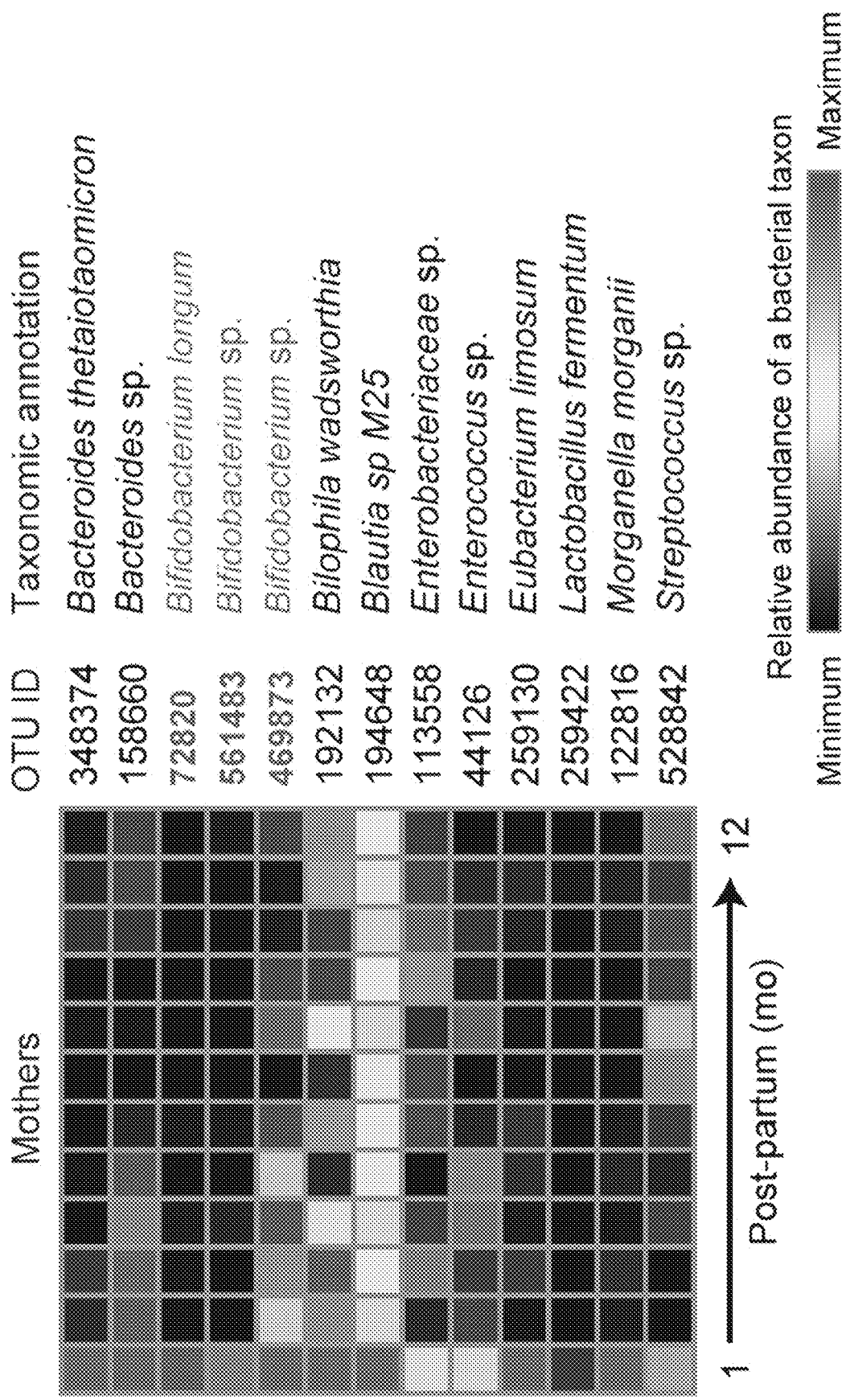
Figure 5B:
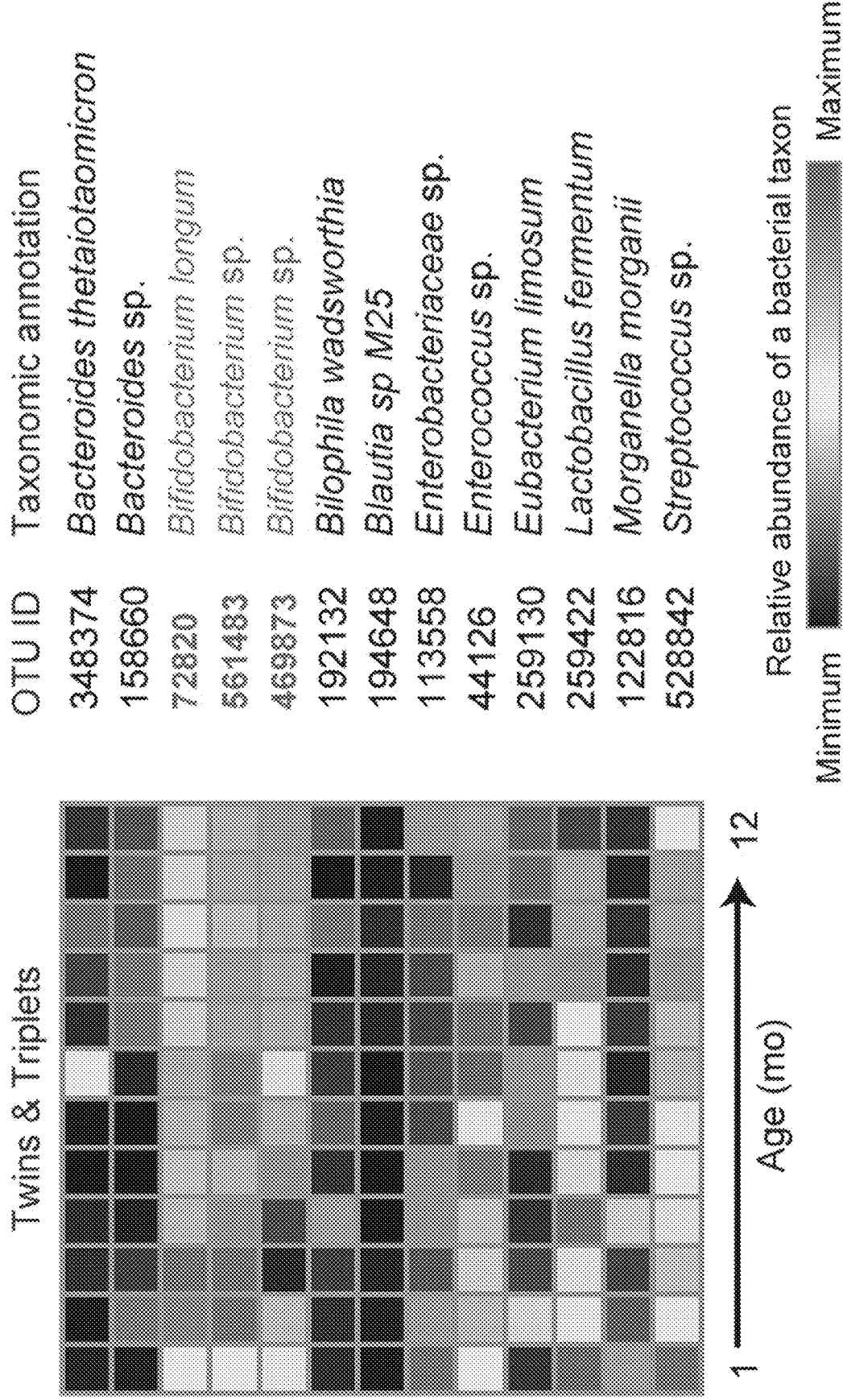
Figure 5:
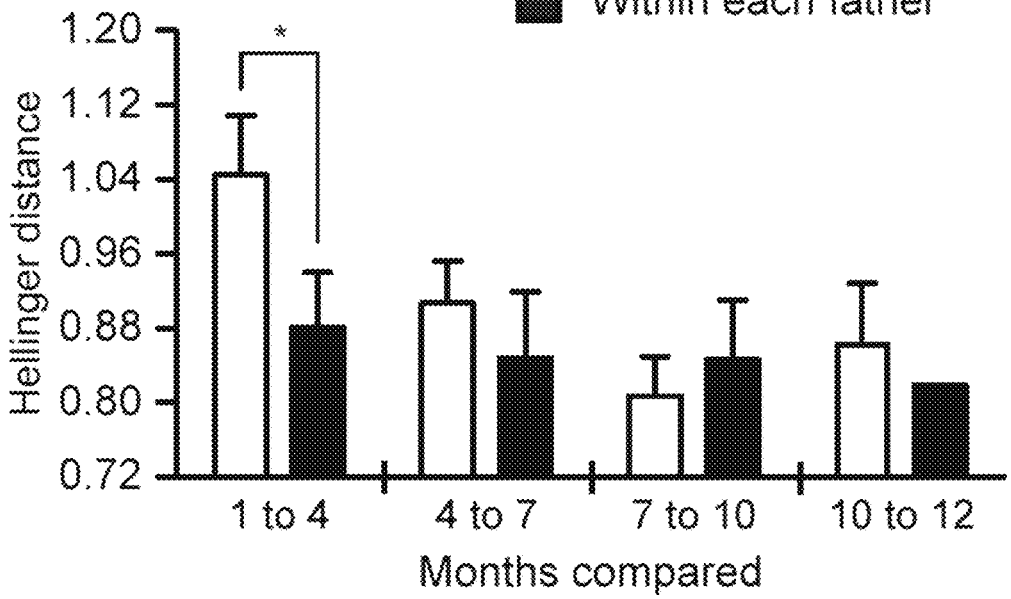
Figure 5:
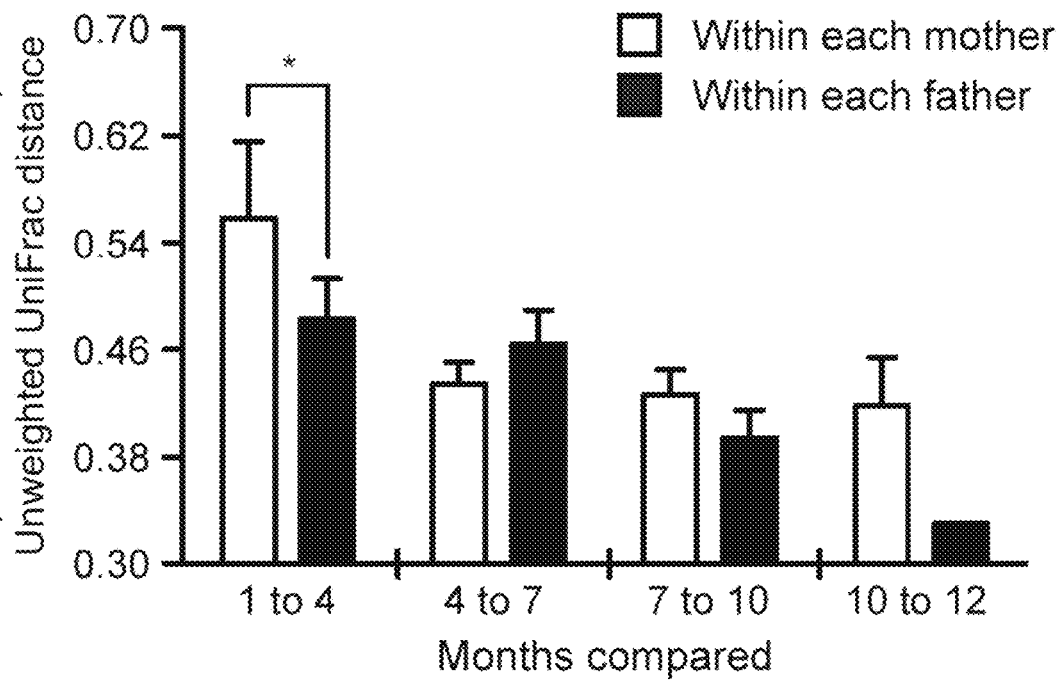
Figure 5:
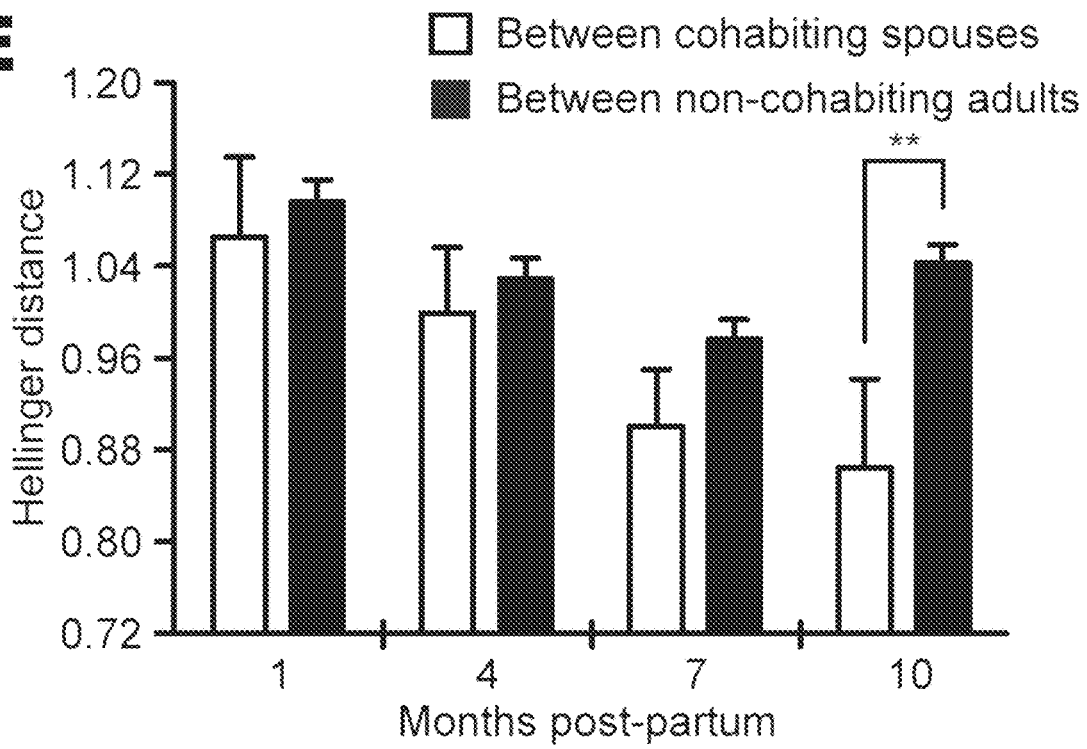
Figure 5:
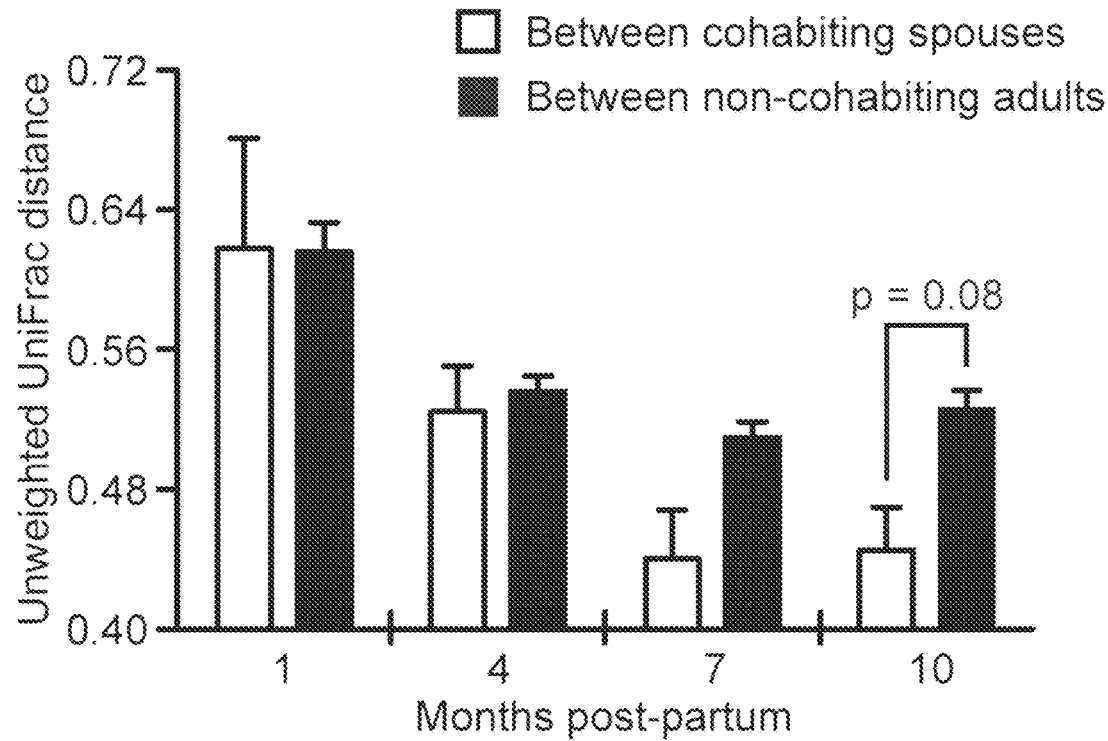
Figure 5:
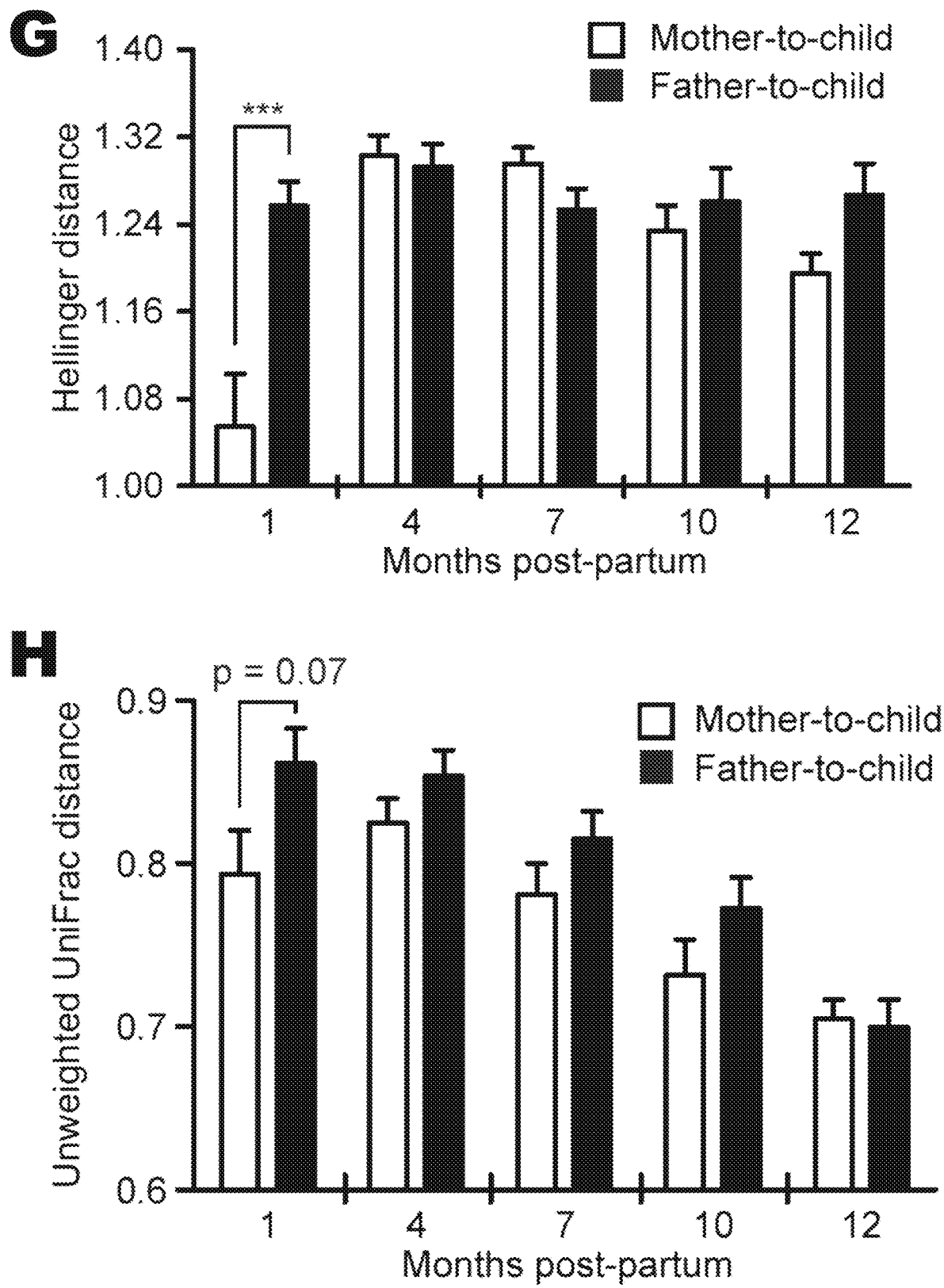

FIG. 5 depicts heatmaps and graphs showing gut microbiota variation in families with twins and triplets during the first year of life. (A) Maternal influence. Heatmap of the mean relative abundances of 13 bacterial taxa (97%-identity OTUs) found to be statistically significantly enriched in the first month post-partum in the faecal microbiota of mothers (see column labelled 1) compared to microbiota sampled between the second and twelfth months post-partum (FDR-corrected P<0.05; ANOVA of linear mixed-effects model with random by-mother intercepts). (B) An analogous heatmap of the relative abundance of these taxa in their twin or triplet offspring is shown. Three of these 97%-identity OTUs are members of the top 24 age-discriminatory taxa (blue) and belong to the genus *Bifidobacterium*. (C-J), comparisons of maternal, paternal and infant microbiota. Mean values±s.e.m. of Hellinger and unweighted UniFrac distances between the faecal microbiota of family members sampled over time were computed. Samples obtained at postnatal months 1, 4, 10 and 12 from twins and triplets, mothers and fathers were analysed (n=12 fathers; 12 mothers; 25 children). (C,D) Intrapersonal variation in the bacterial component of the maternal microbiota is greater between the first and fourth months after childbirth than variation in fathers. (E,F) Distances between the faecal microbiota of spouses (each mother-father pair) compared to distances between all unrelated adults (male-female pairs). The microbial signature of co-habitation is only evident 10 months following childbirth. (G-J) The degree of similarity between mother and infant during the first postpartum month is significantly greater than the similarity between microbiota of fathers and infants (G,H) while the faecal microbiota of co-twins are significantly more similar to one another than to age-matched unrelated children during the first year of life (IA. For all distance analyses, Hellinger and unweighted UniFrac distance matrices were permuted 1,000 times between the groups tested. P values represent the fraction of times permuted differences between tested groups were greater than real differences between groups. *P<0.05, P<0.01, *P<0.001.

Figure 6A:
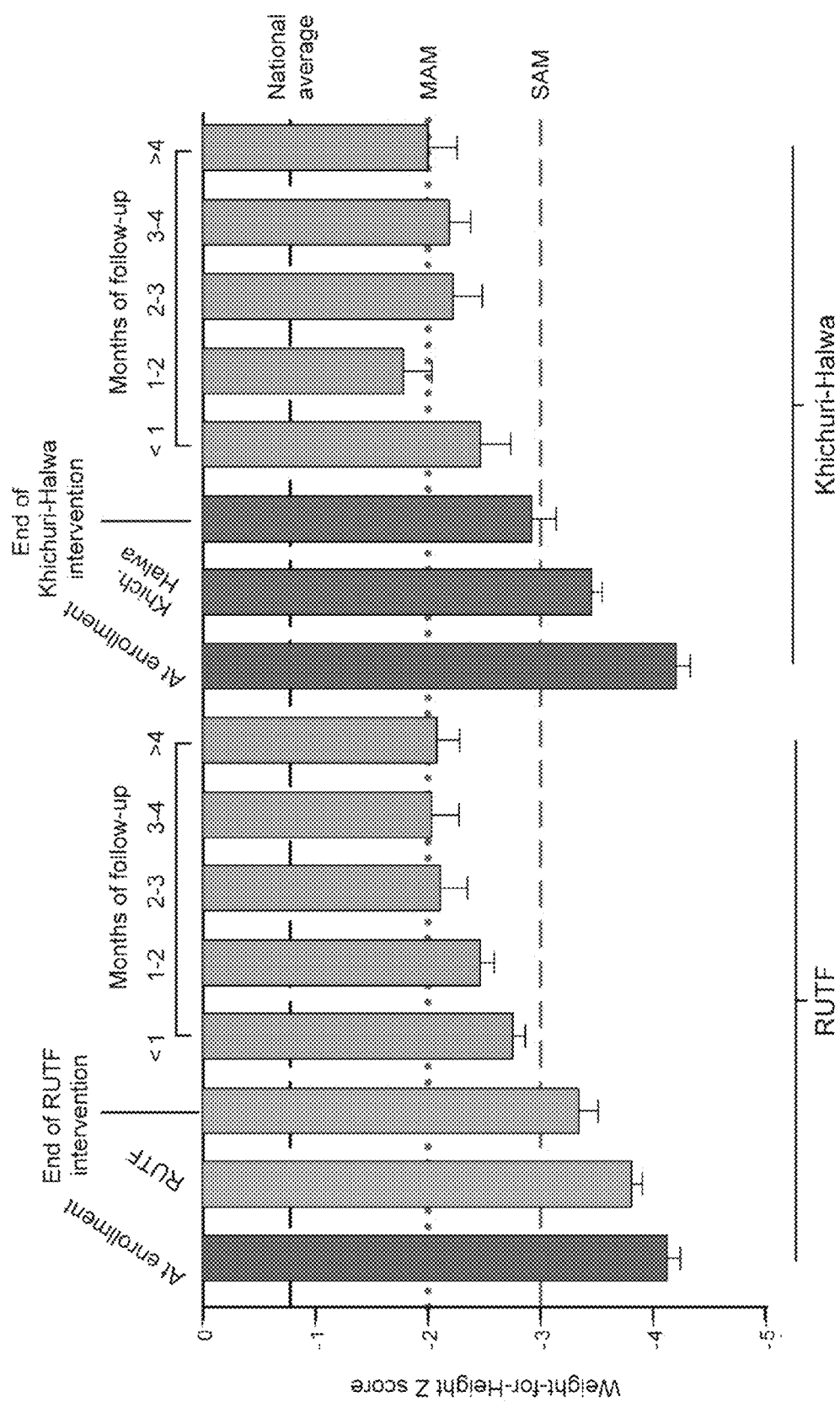
Figure 6B:
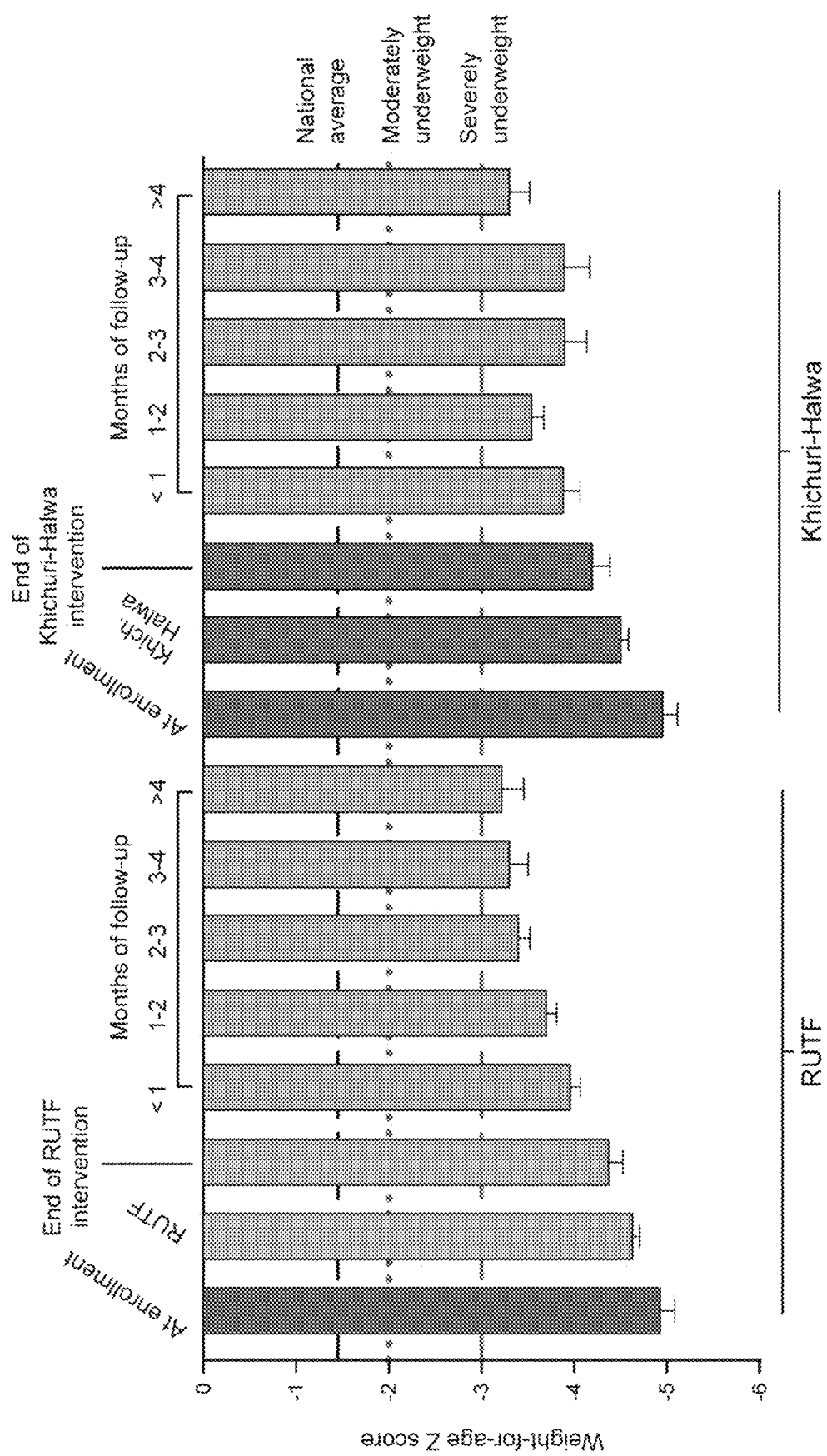
Figure 6C:
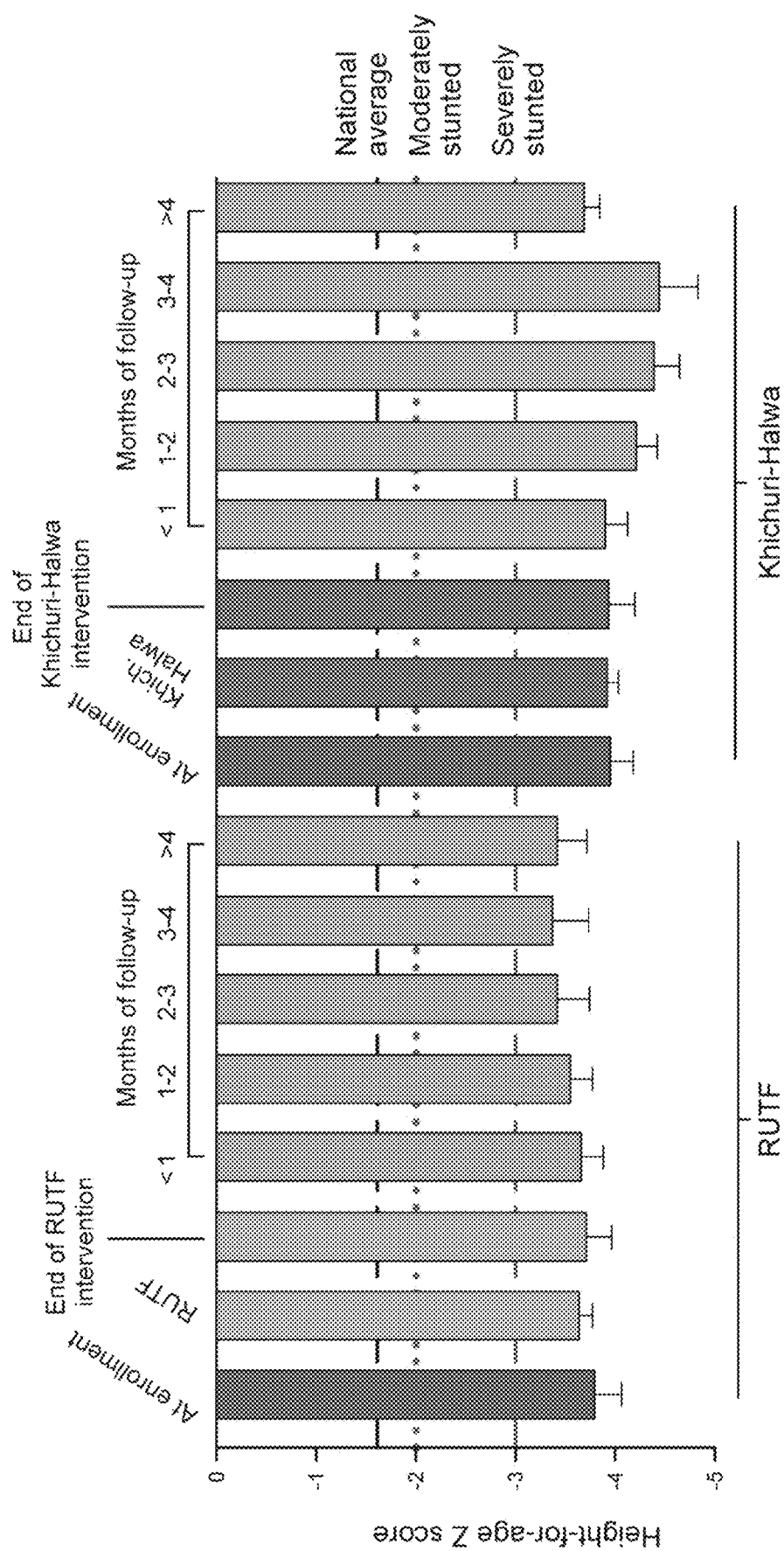

FIG. 6 graphically depicts anthropometric measures of nutritional status in children with SAM before, during and after both food interventions. (A-C) Weight-for-height Z-scores (WHZ) (A) height-for-age Z-scores (HAZ) (B) and weight-for-age Z-scores (WAZ) (C). Mean values±s.e.m. are plotted and referenced to national average anthropometric values for children surveyed between the ages of 6 and 24 months during the 2011 Bangladeshi Demographic Health Survey (BDHS)[28].

Figure 7:
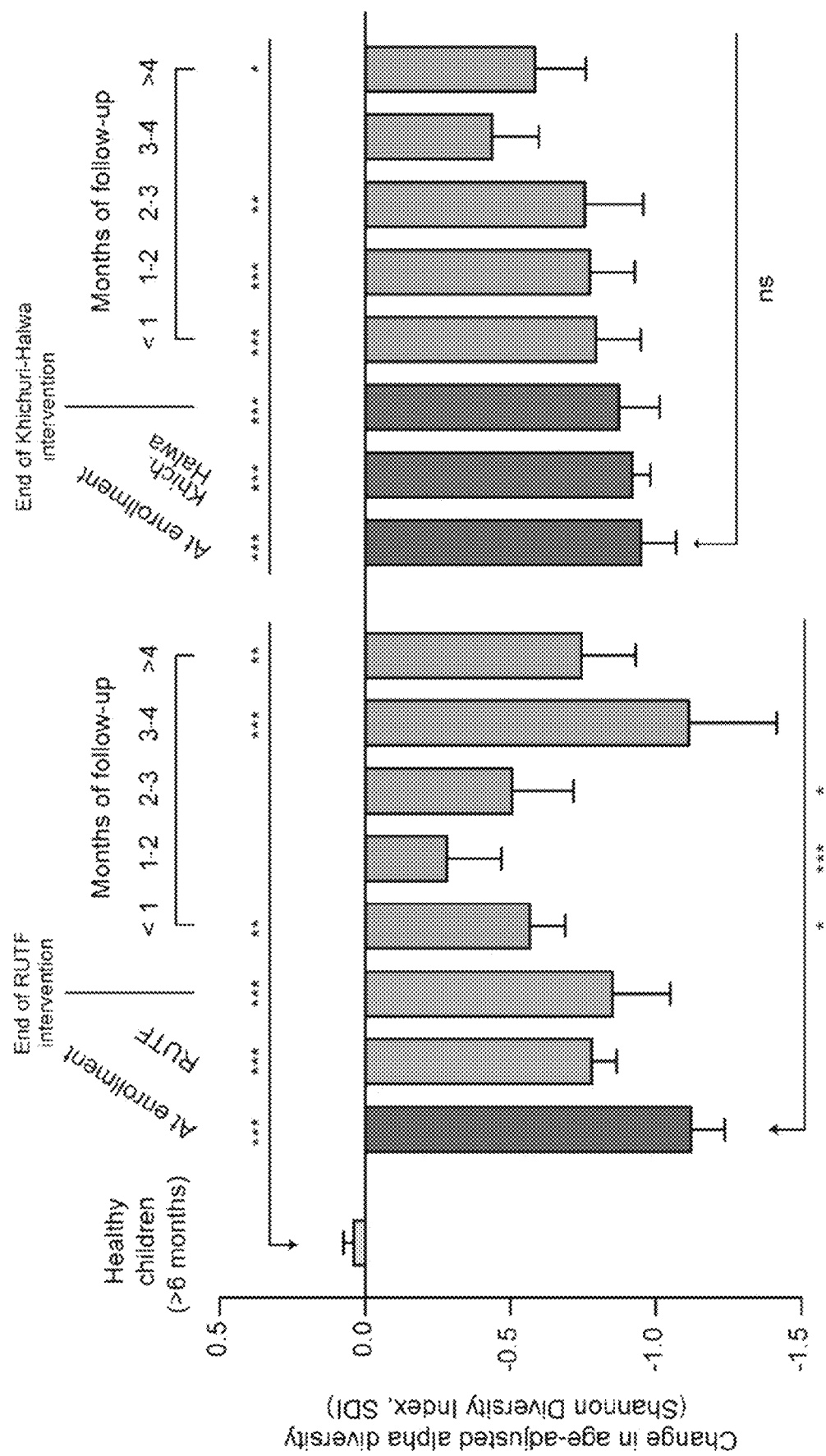

FIG. 7 graphically depicts persistent reduction of diversity in the gut microbiota of children with SAM. Age-adjusted Shannon diversity index for faecal microbiota samples collected from healthy children (n=50), and from children with SAM at various phases of the clinical trial (mean values±s.e.m. are plotted). The significance of differences between SDI at various stages of the clinical trial is indicated relative to healthy controls (above the bars) and versus the time of enrollment before treatment (below the bars). *P<0.05, P<0.01, *P<0.001 (post-hoc Dunnett's multiple comparison procedure of linear mixed models). See Table 12.

Figure 8A:
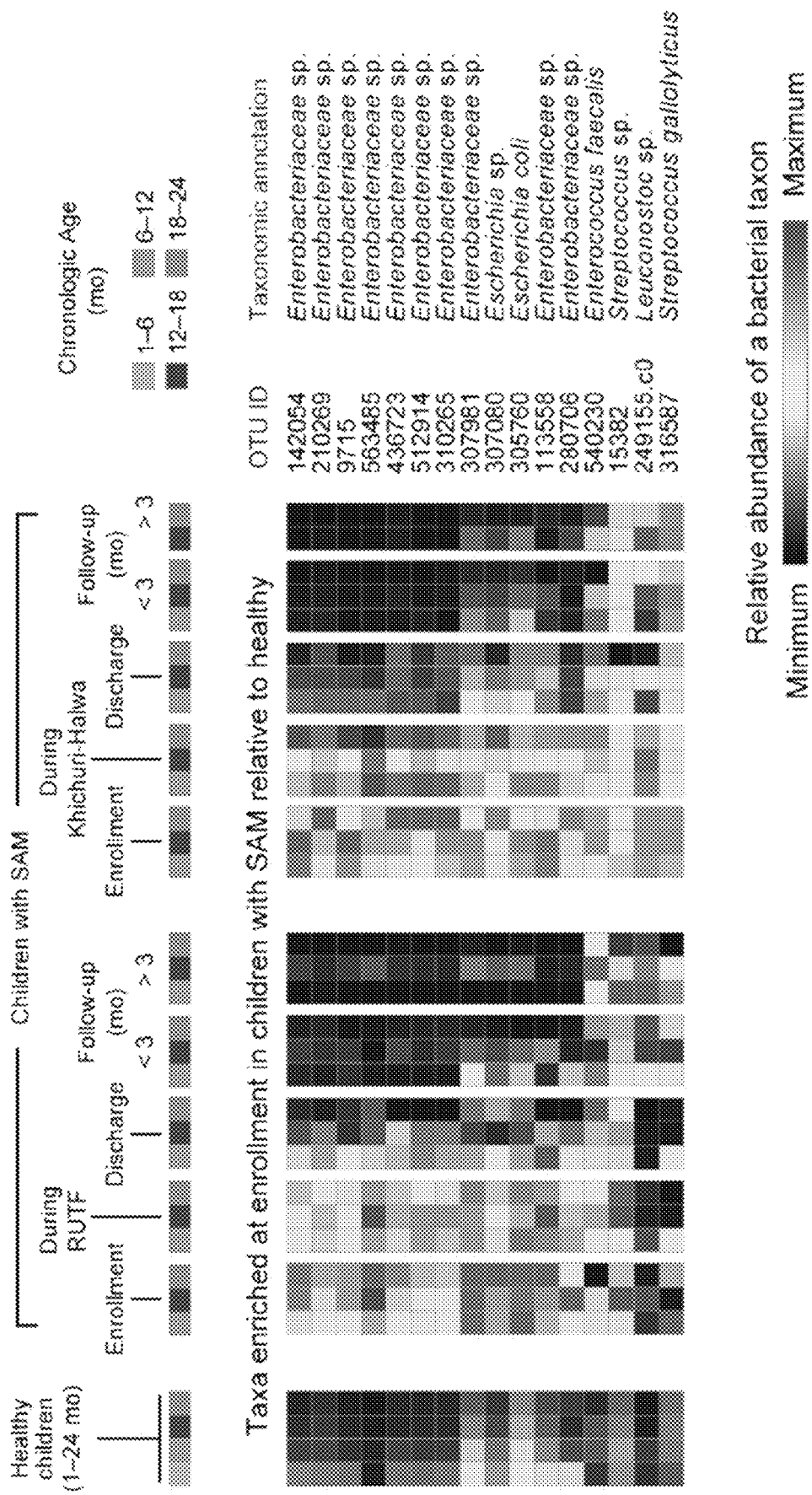
Figure 8B:
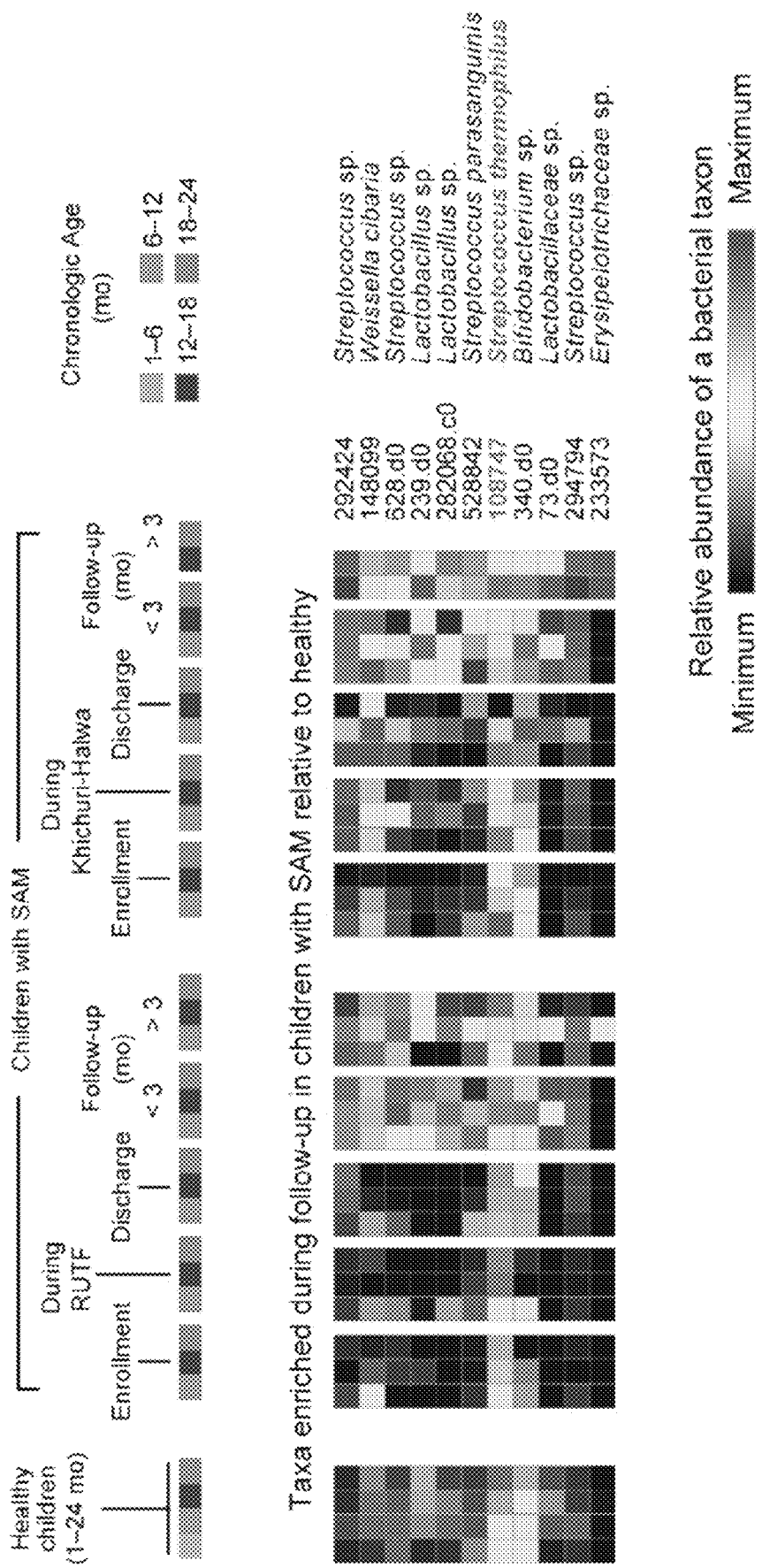
Figure 8C:
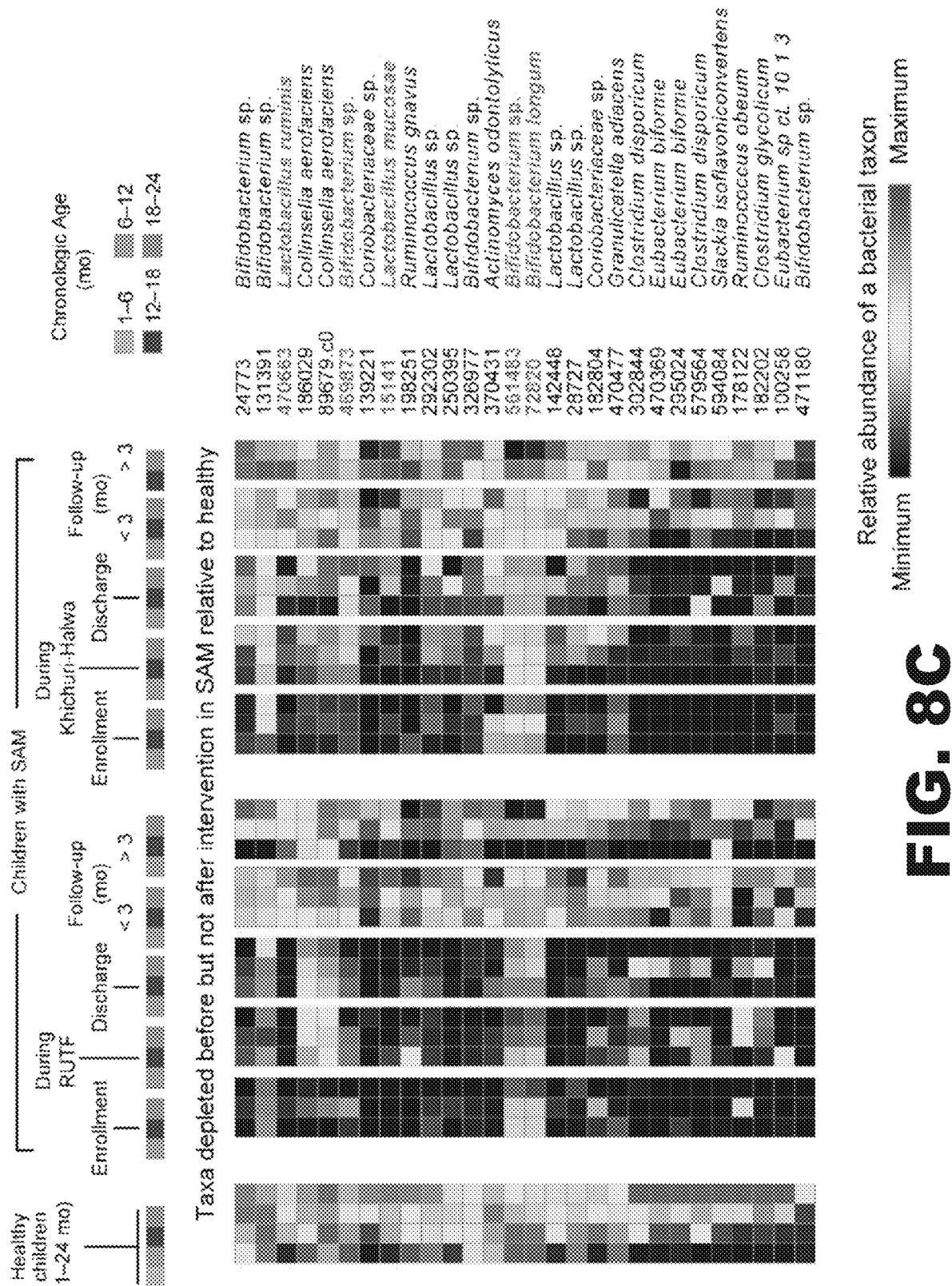
Figure 9A:
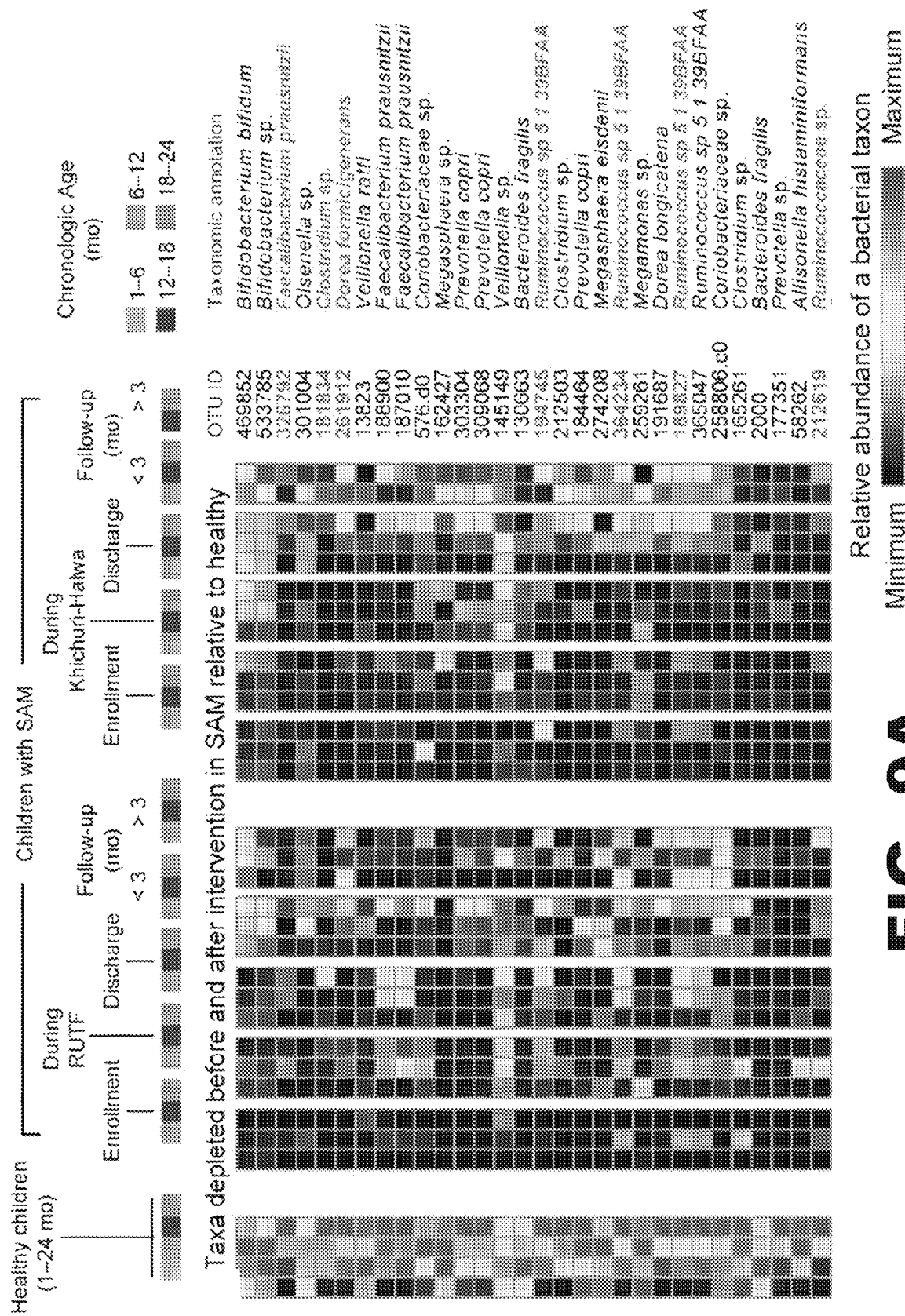
Figure 9B:
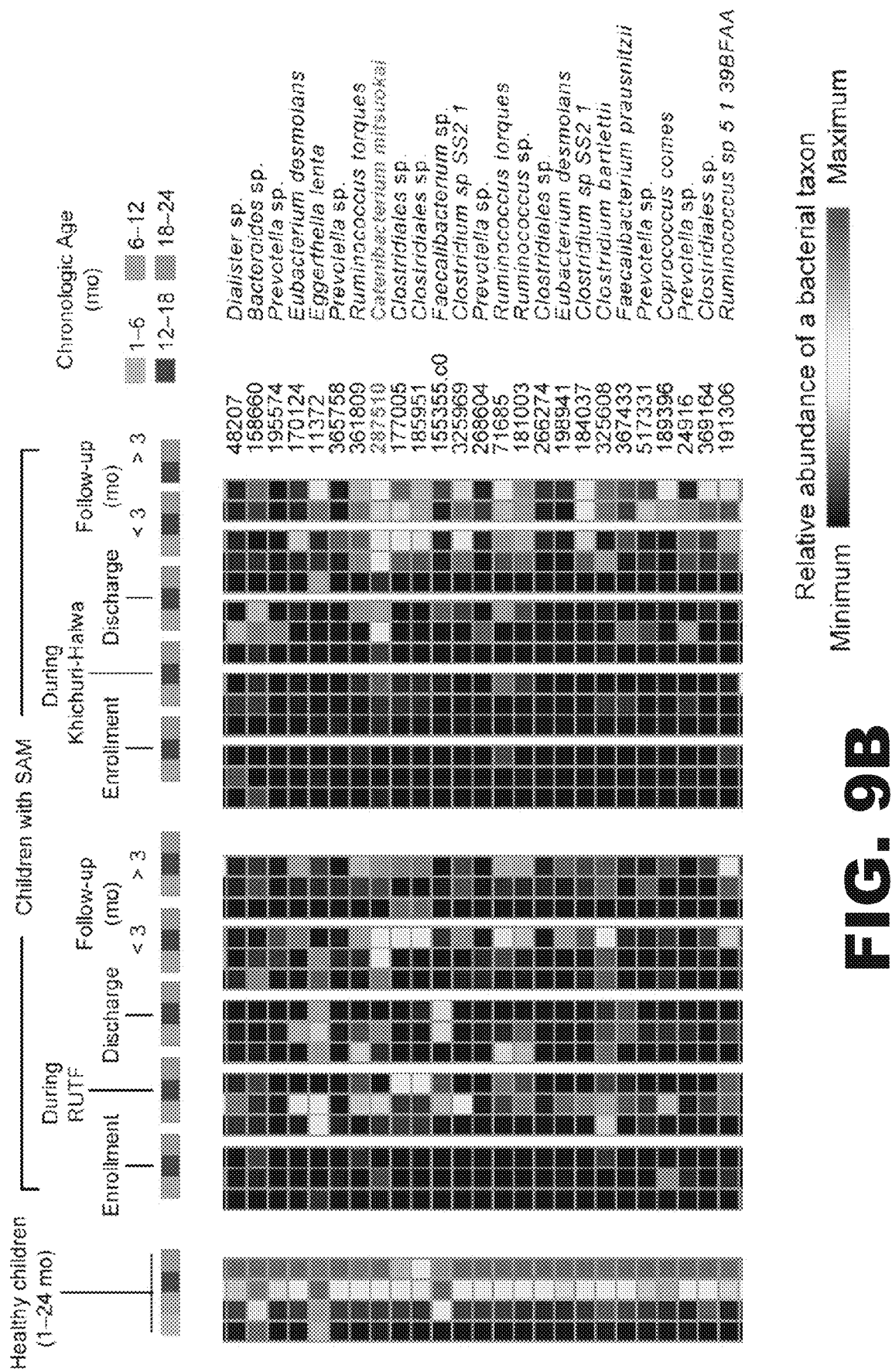
Figure 9C:
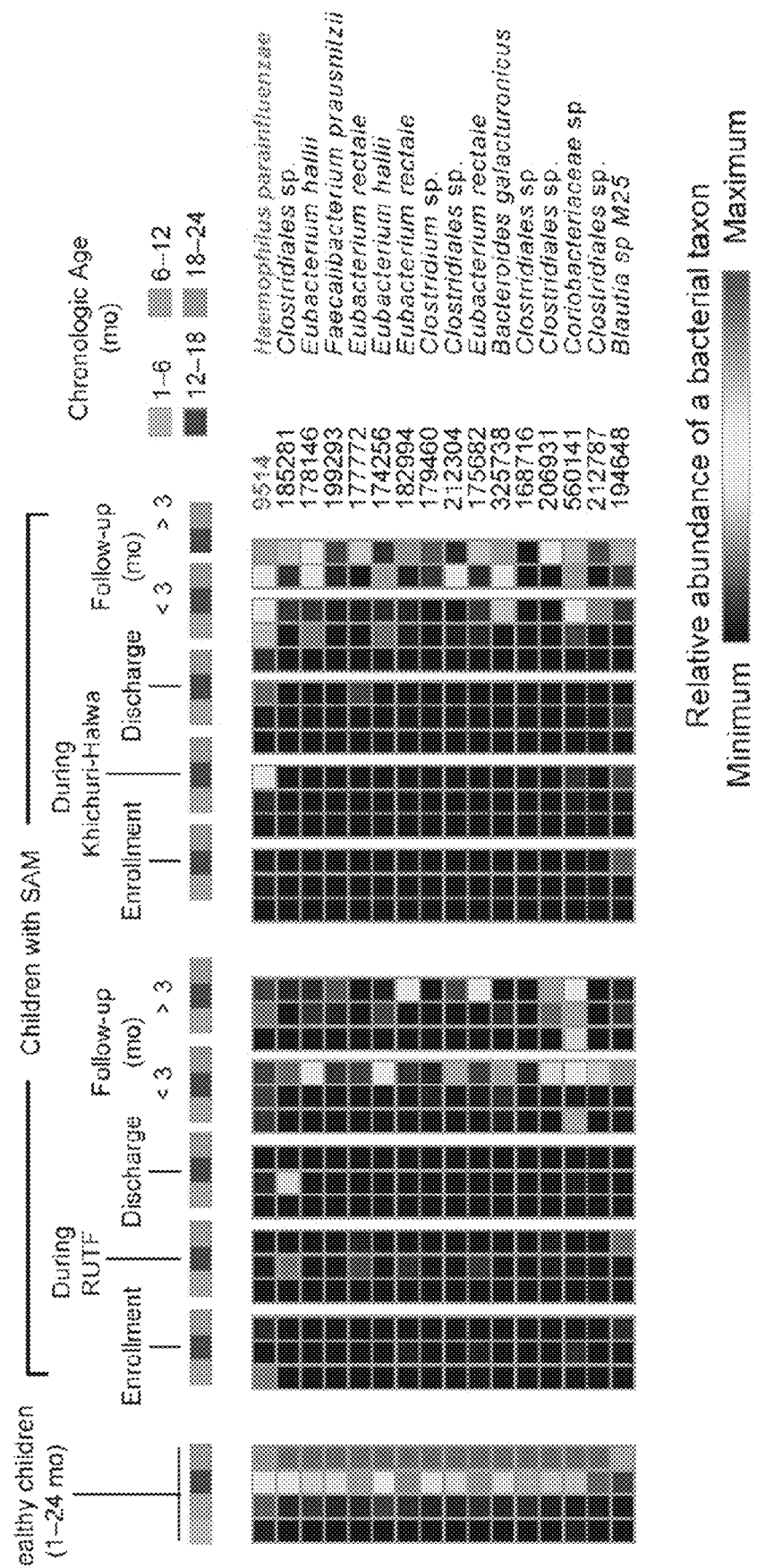
Figure 9D:
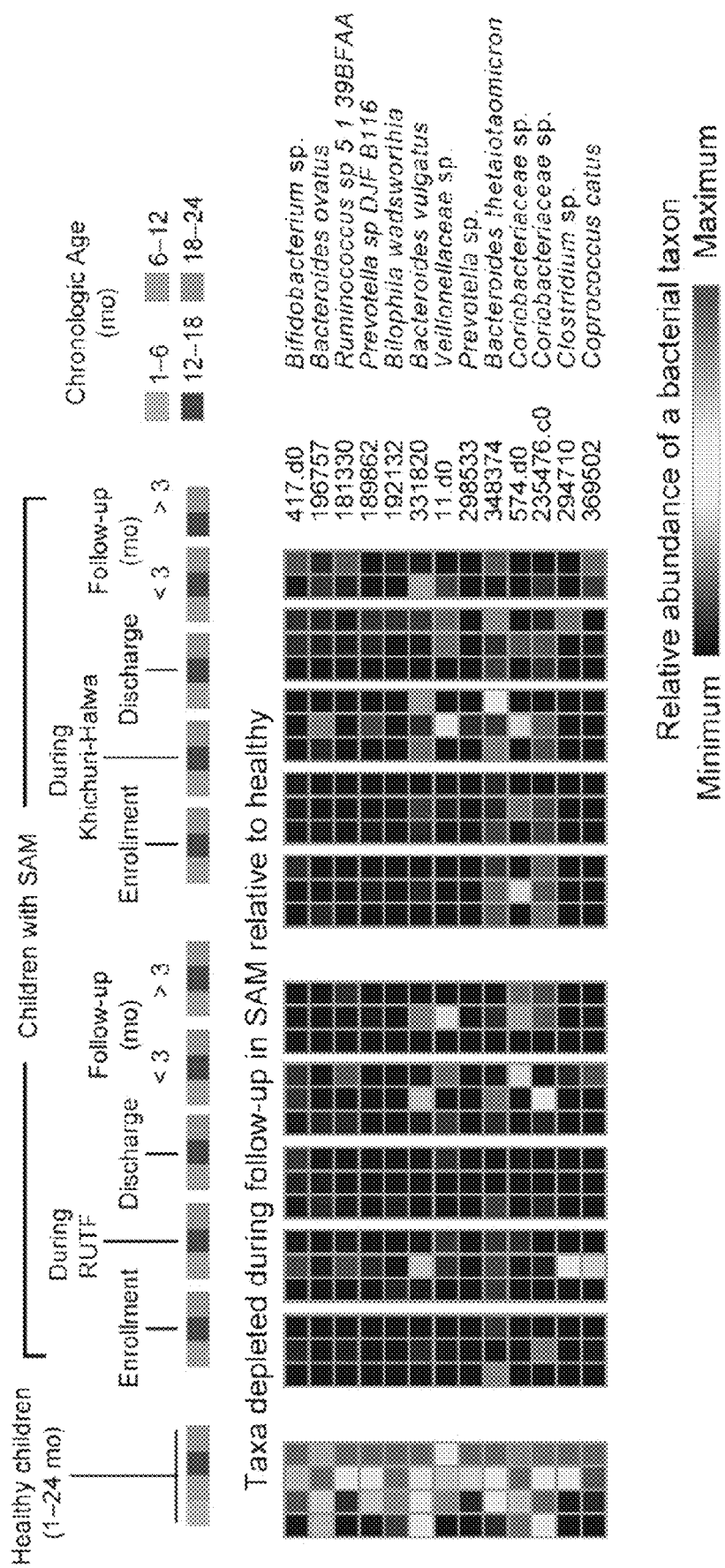
Figure 9E:
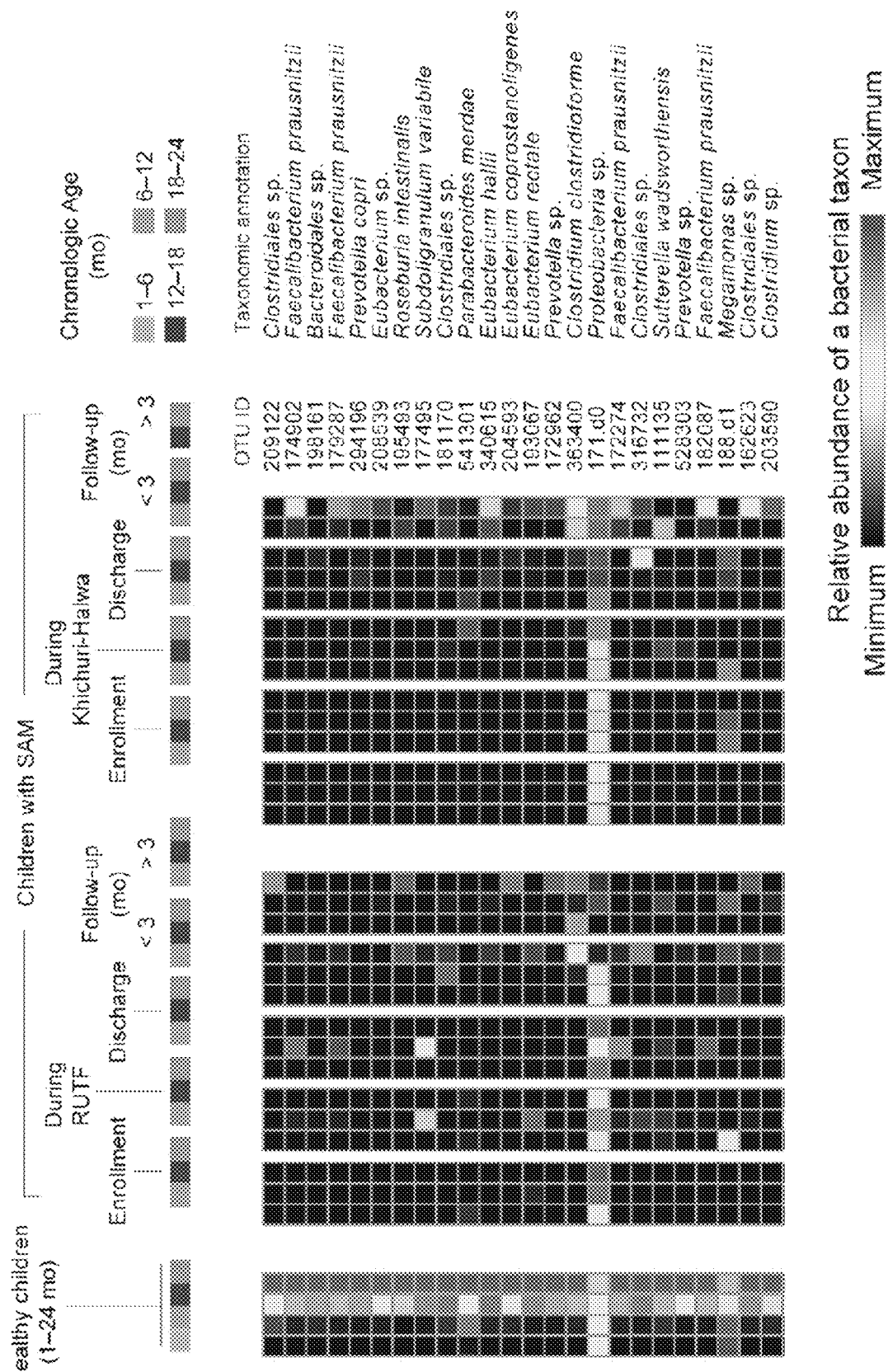
Figure 9F:
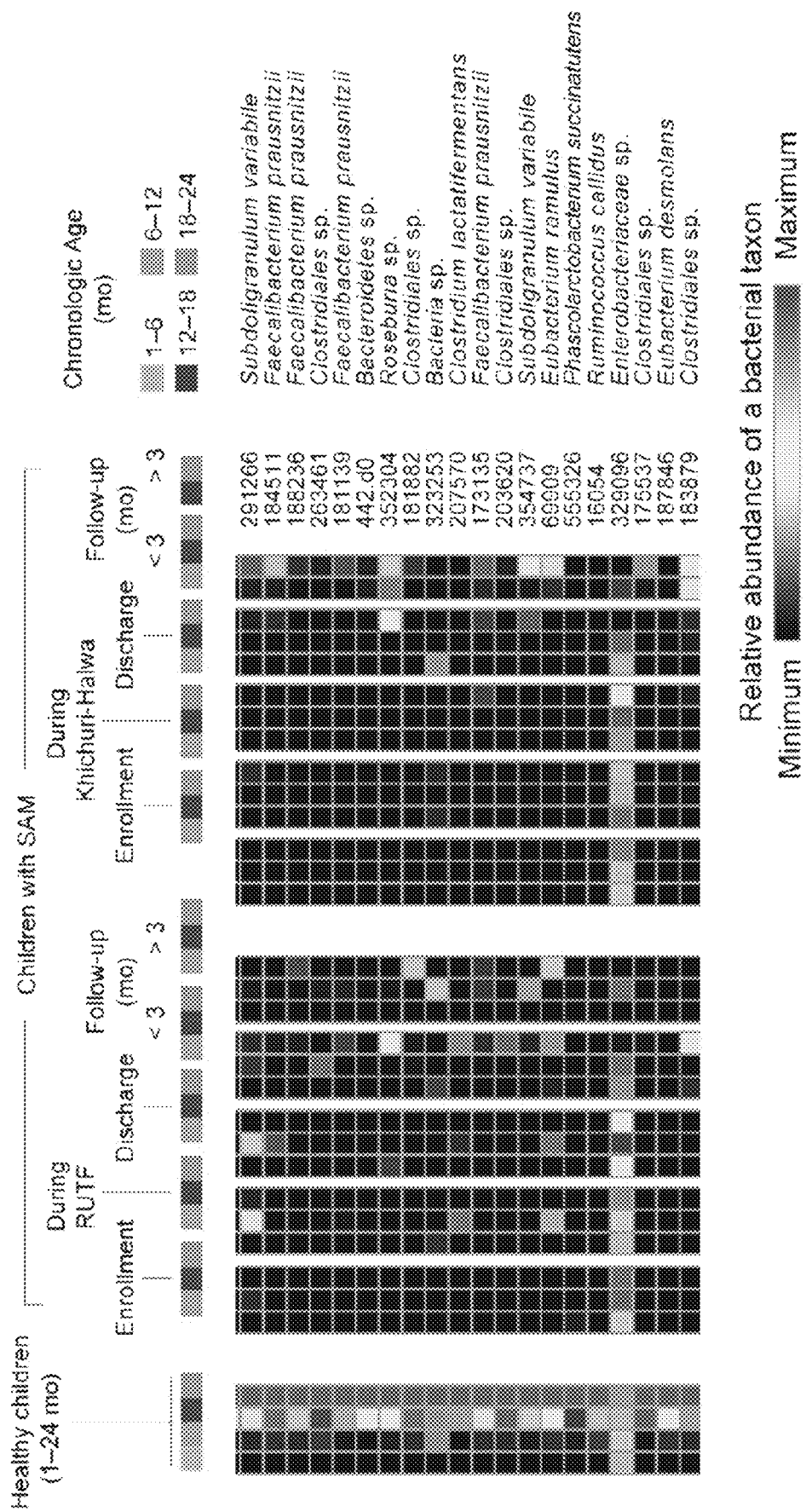
Figure 9G:
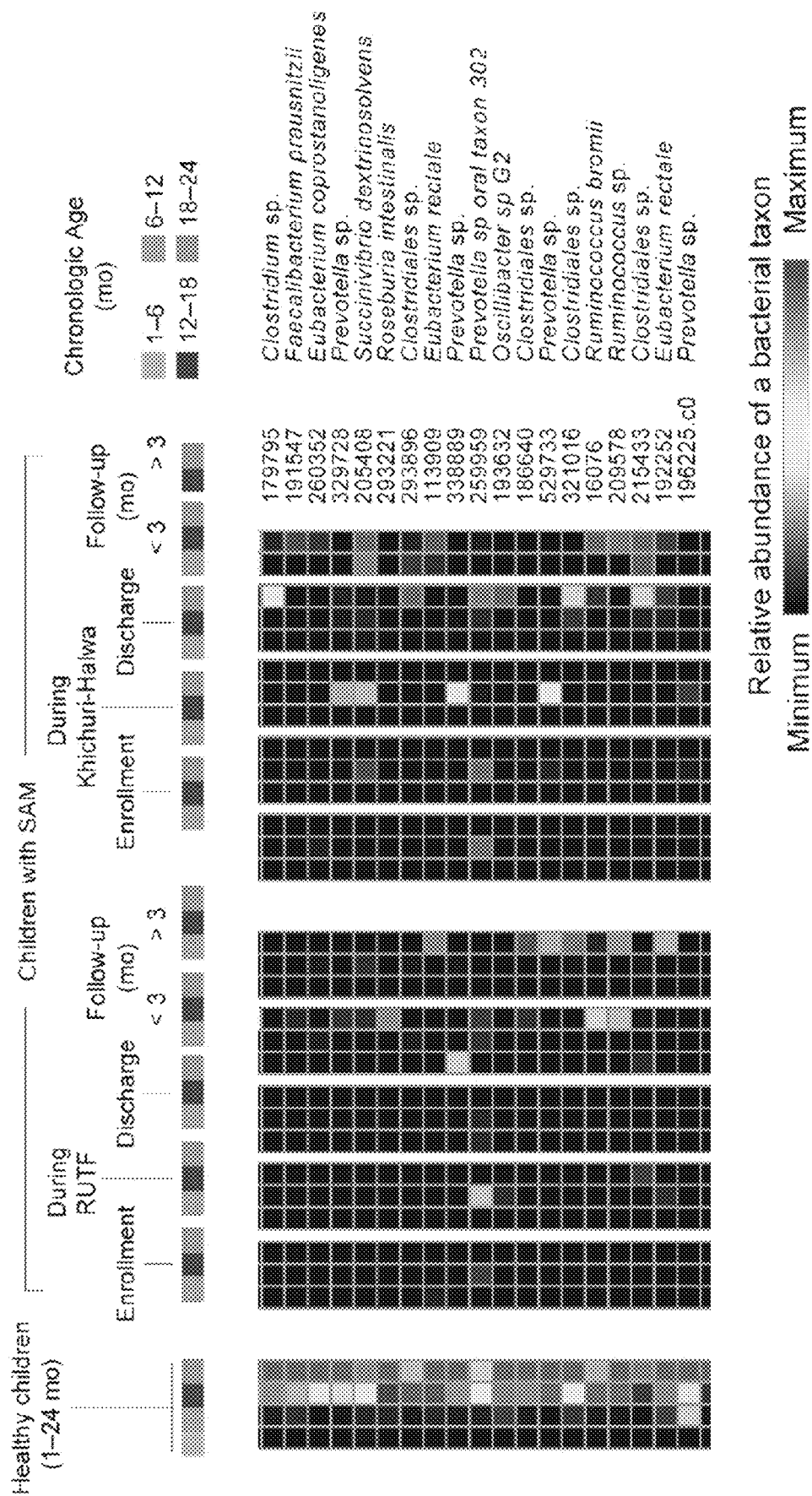
Figure 9H:
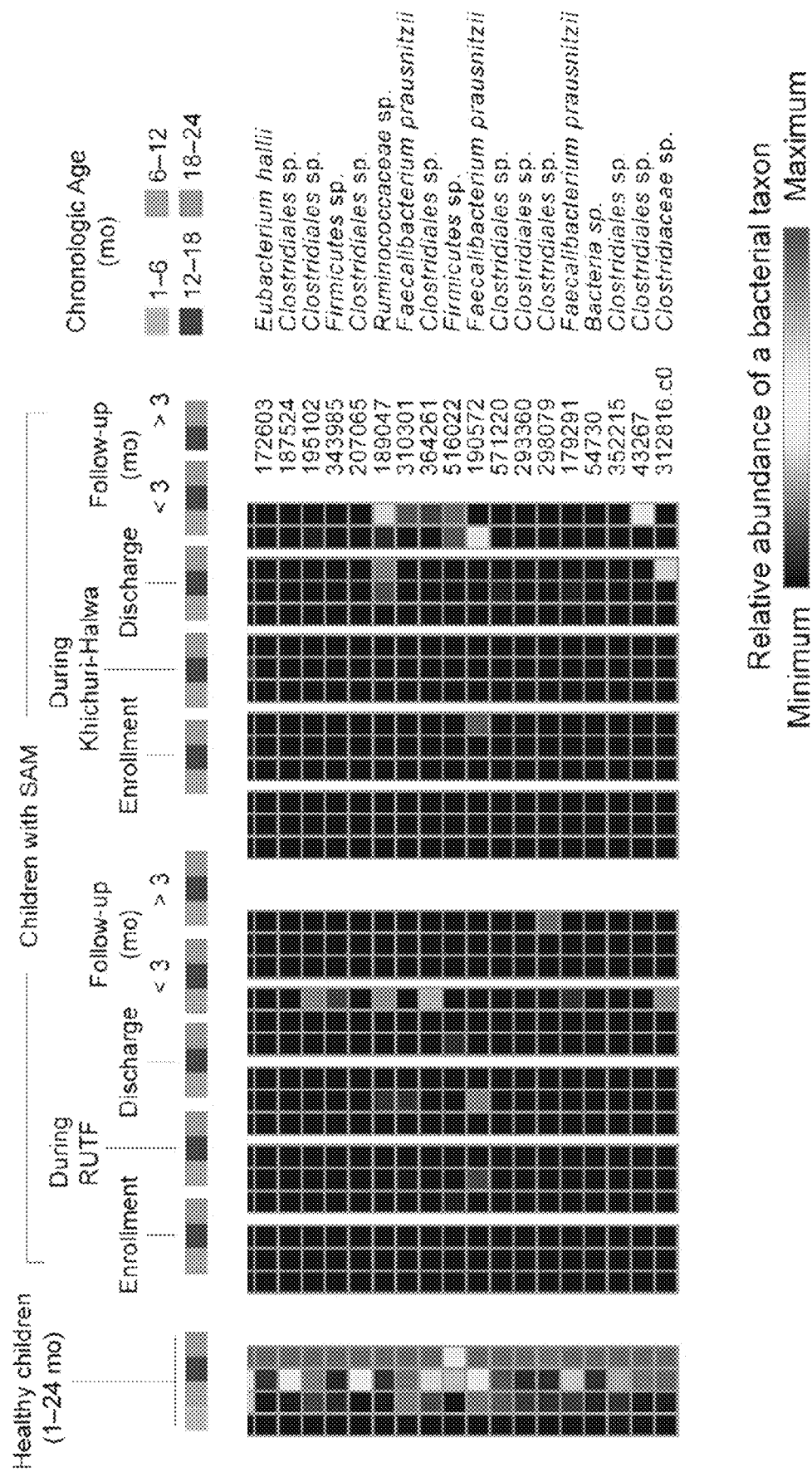

FIG. 8 depicts heatmaps of bacterial taxa significantly altered during the acute phase of treatment and nutritional rehabilitation in the microbiota of children with SAM compared to similar-age healthy children. Bacterial taxa (97%-identity OTUs) significantly altered (FDR-corrected P<0.05) in children with SAM are shown (see Table 13 for P values and effect size for individual taxa). Three groups of bacterial taxa are shown: those enriched before the food intervention (A); those enriched during the follow-up phase compared to healthy controls (B); and those that are initially depleted but return to healthy levels (C). Members of the top 24 age-discriminatory taxa are highlighted in blue. Note that there were no children represented in the Khichuri-Halwa arm under the age of 12 months during the 'follow-up after 3 months' period.

FIG. 9 depicts heatmaps of bacterial taxa altered during long term follow-up in the faecal microbiota of children with SAM compared to similar-age healthy children. (A-H) Bacterial taxa (97%-identity OTUs) significantly altered (FDR-corrected P<0.05) in children with SAM are shown (see Table 13 for P values and effect sizes for individual taxa). (A-C) Taxa depleted across all phases of SAM relative to healthy. (D-H) Those depleted during the follow-up phase. Members of the top 24 age-discriminatory taxa are highlighted in blue. Note that there were no children under the age of 12 months represented in the Khichuri-Halwa treatment arm during the 'follow-up after 3 months' period.

Figure 10:
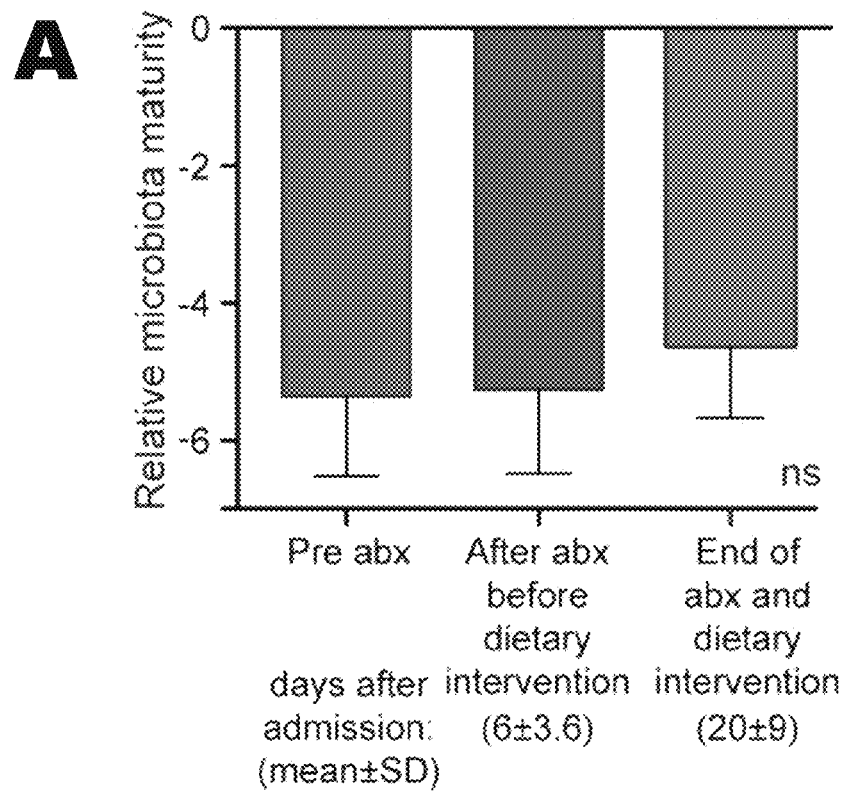
Figure 10:
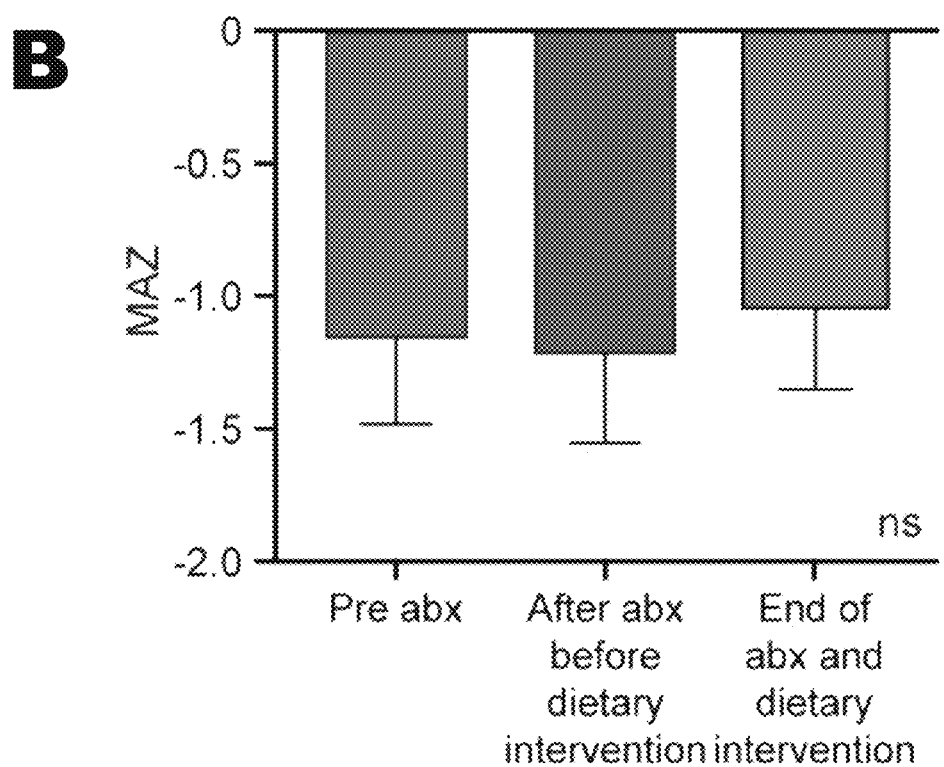
Figure 10:
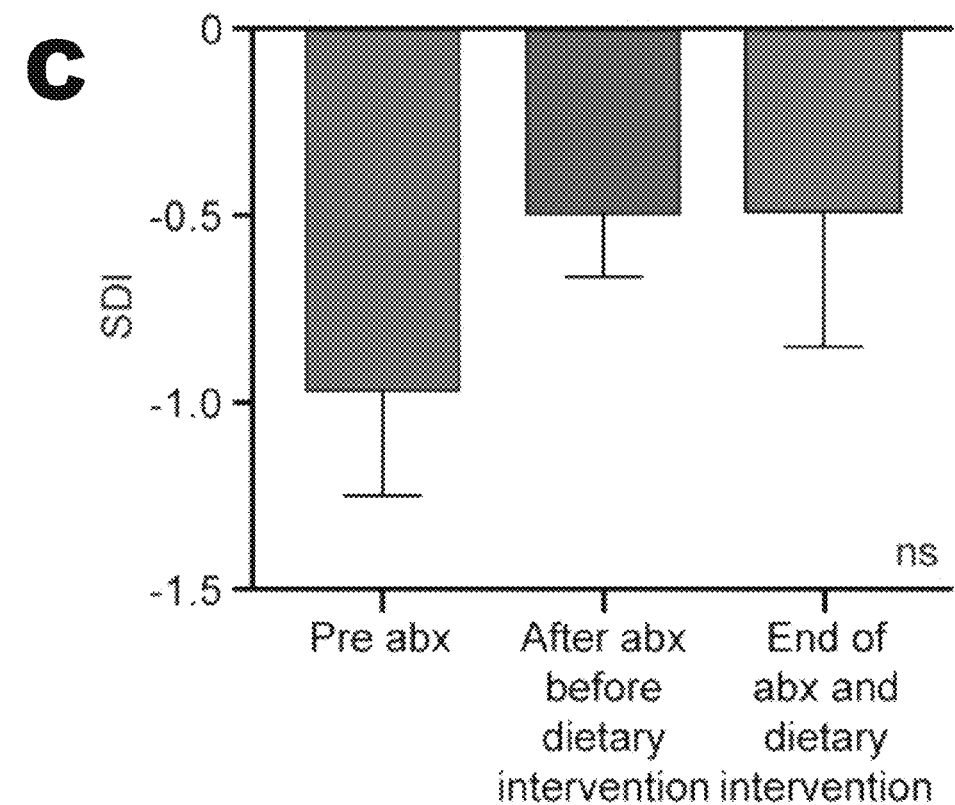
Figure 10:
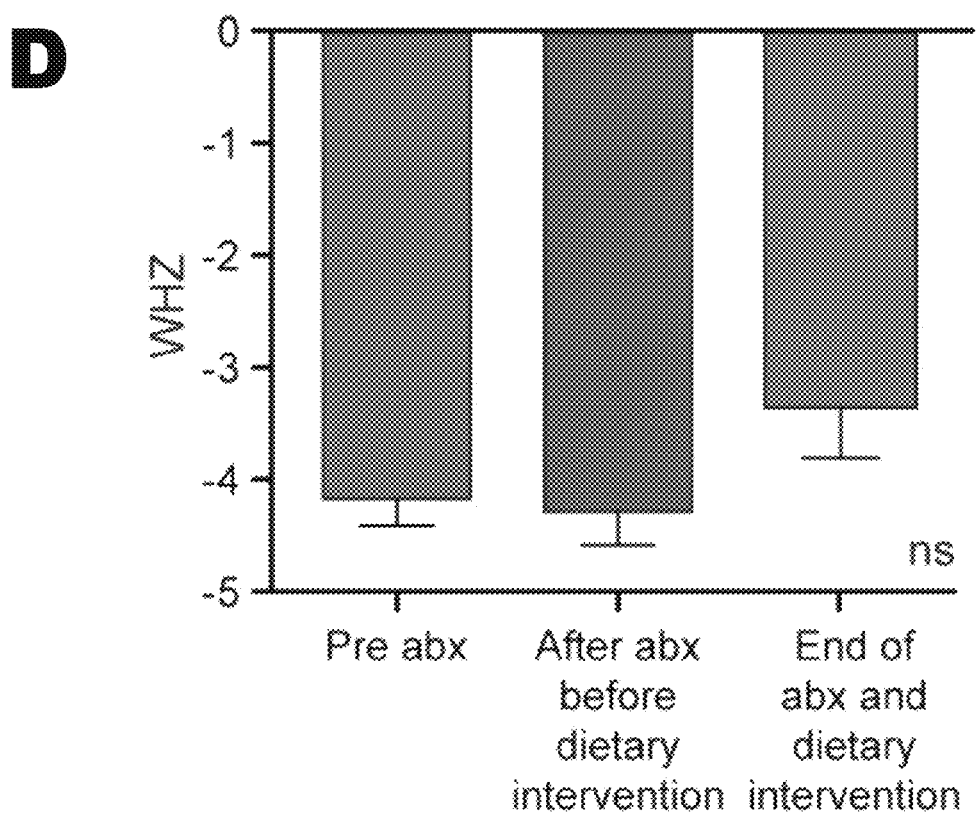

FIG. 10 graphically depicts the effects of antibiotics on the microbiota of children with SAM. Plots of microbiota and anthropometric parameters in nine children sampled before antibiotics (abx), after oral amoxicillin plus parenteral gentamicin and ampicillin, and at the end of the antibiotic and dietary interventions administered over the course of nutritional rehabilitation in the hospital. All comparisons were made relative to the pre-antibiotic sample using the non-parametric Wilcoxon matched-pairs rank test, in which each child served as his or her own control. (A-C) Microbiota parameters, plotted as mean values±s.e.m., include (A) relative microbiota maturity, (B) microbiota-for-age Z-score (MAZ), and (C) SDI. WHZ scores are provided in D. (E,F) The two predominant bacterial family-level taxa showing significant changes following antibiotic treatment. (E) family Streptococcaceae and (F) family *Enterobacteriaceae*. ns, not significant; **P<0.01.

Figure 11:
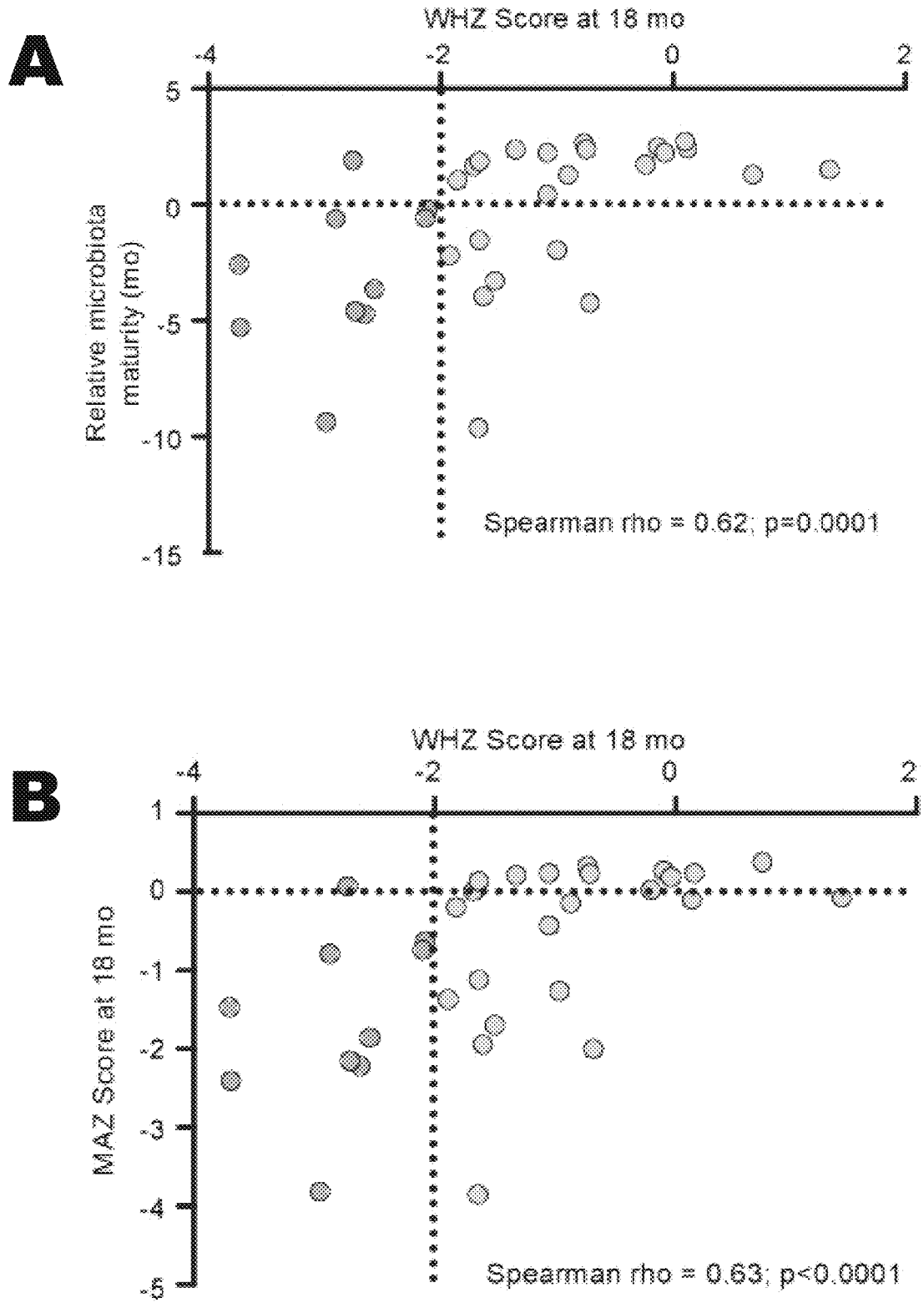
Figure 11:
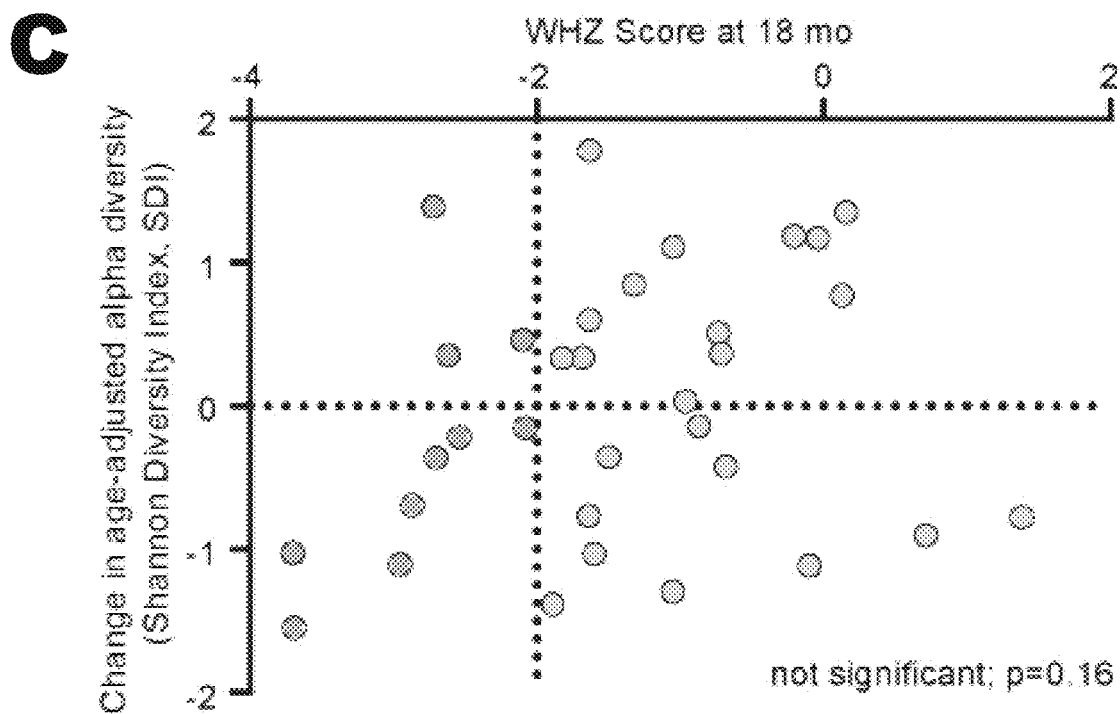
Figure 11:
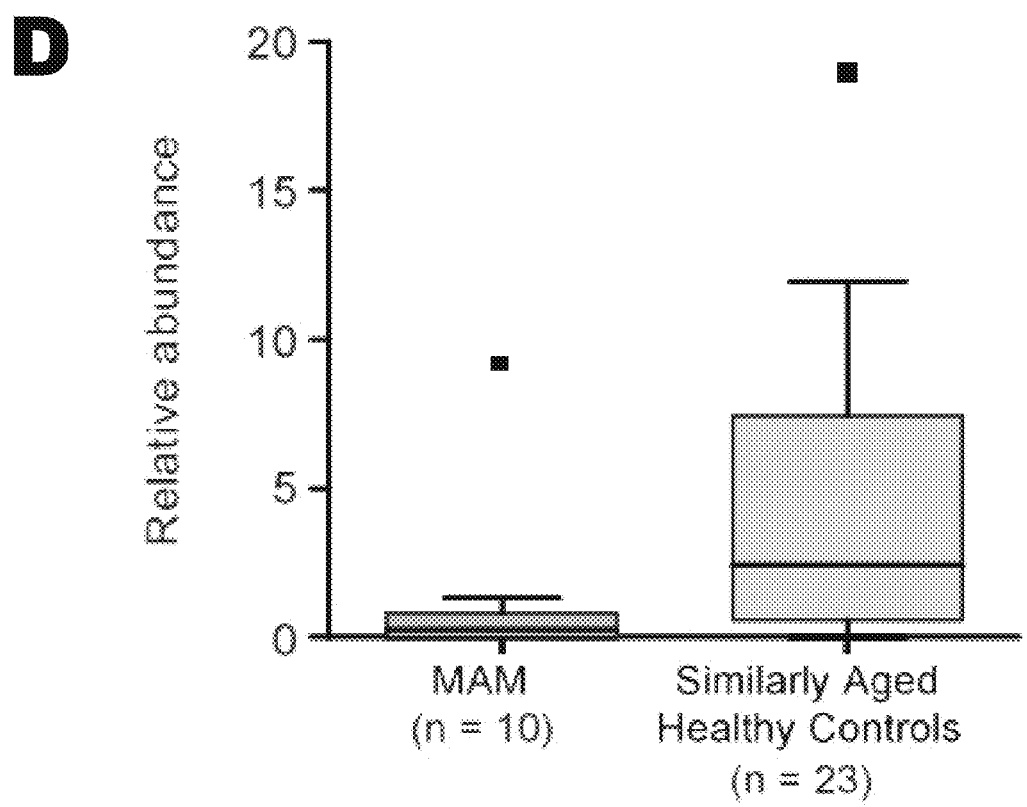
Figure 11:
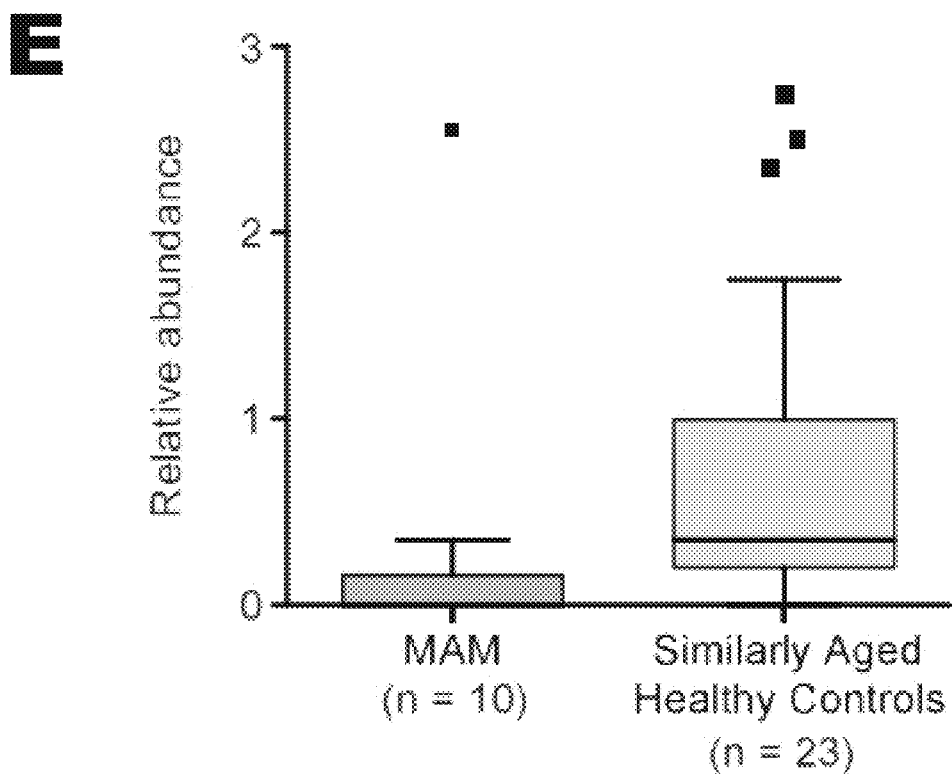
Figure 11:
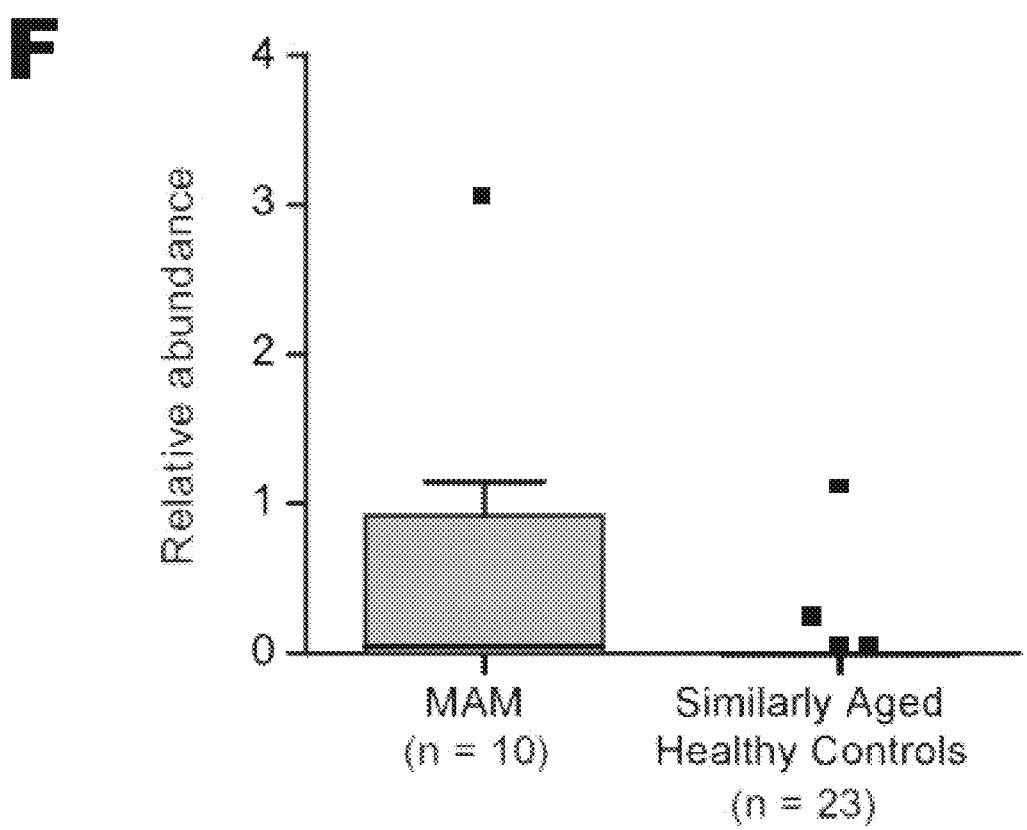
Figure 11:
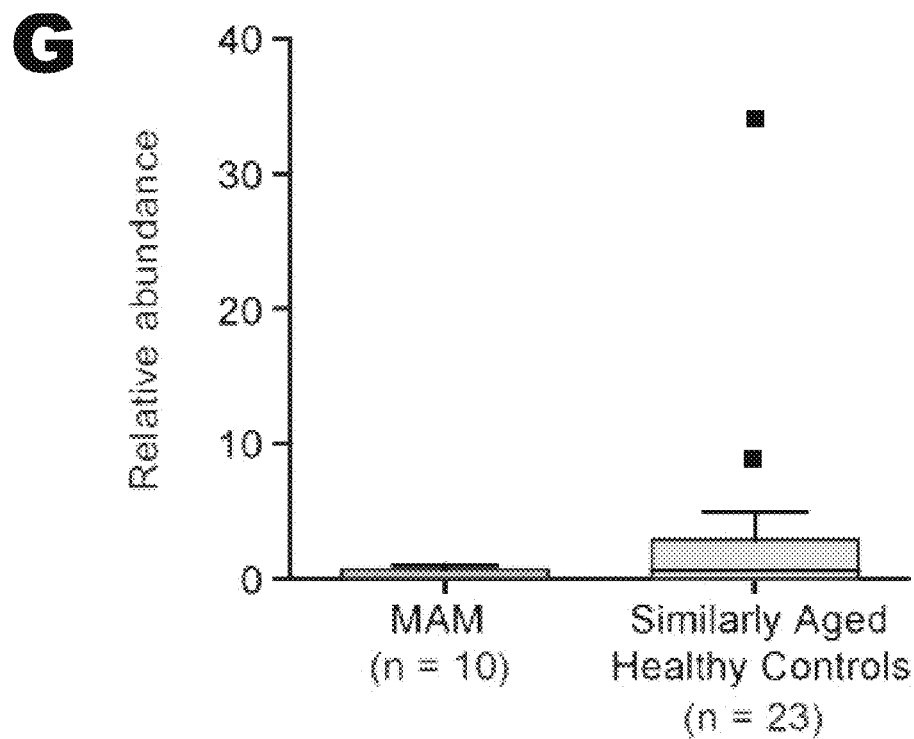
Figure 11:
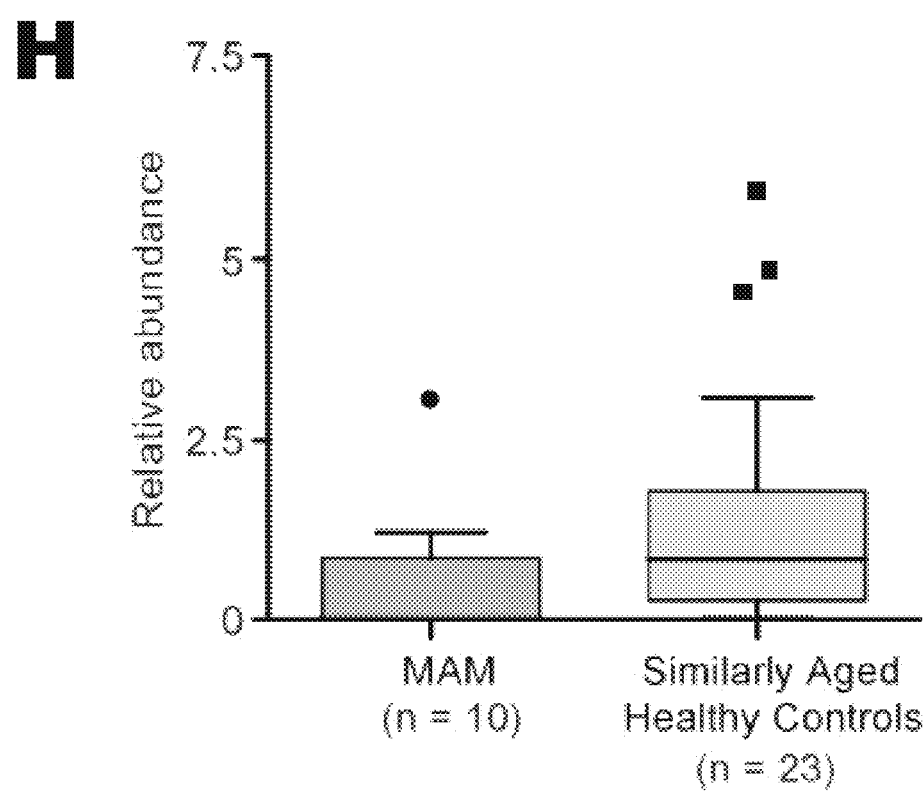
Figure 11:
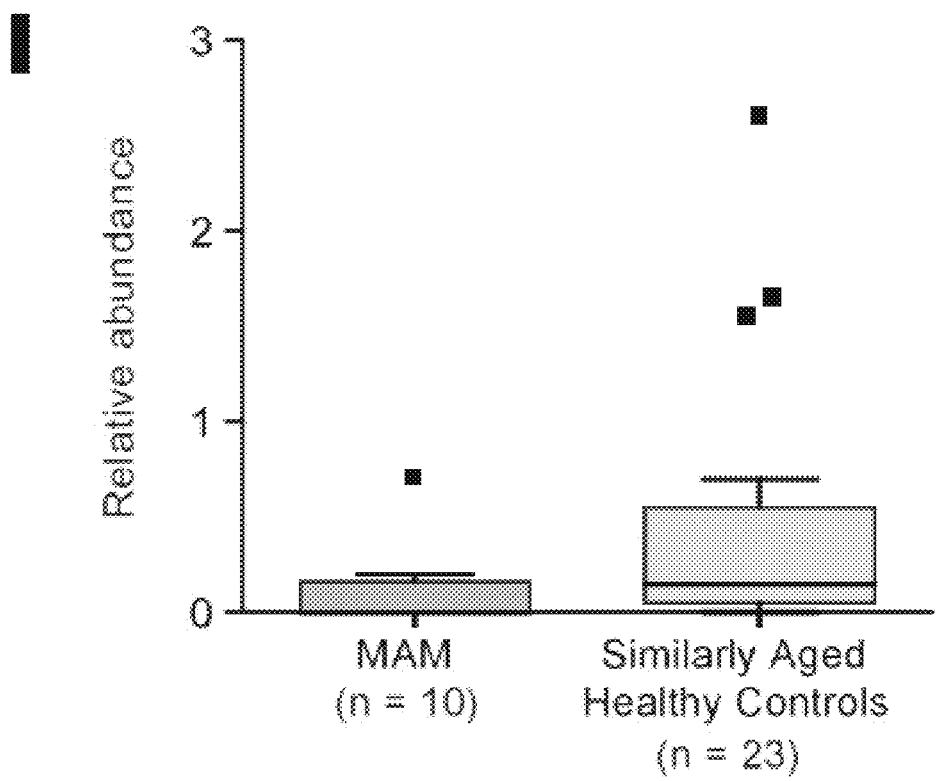
Figure 11:
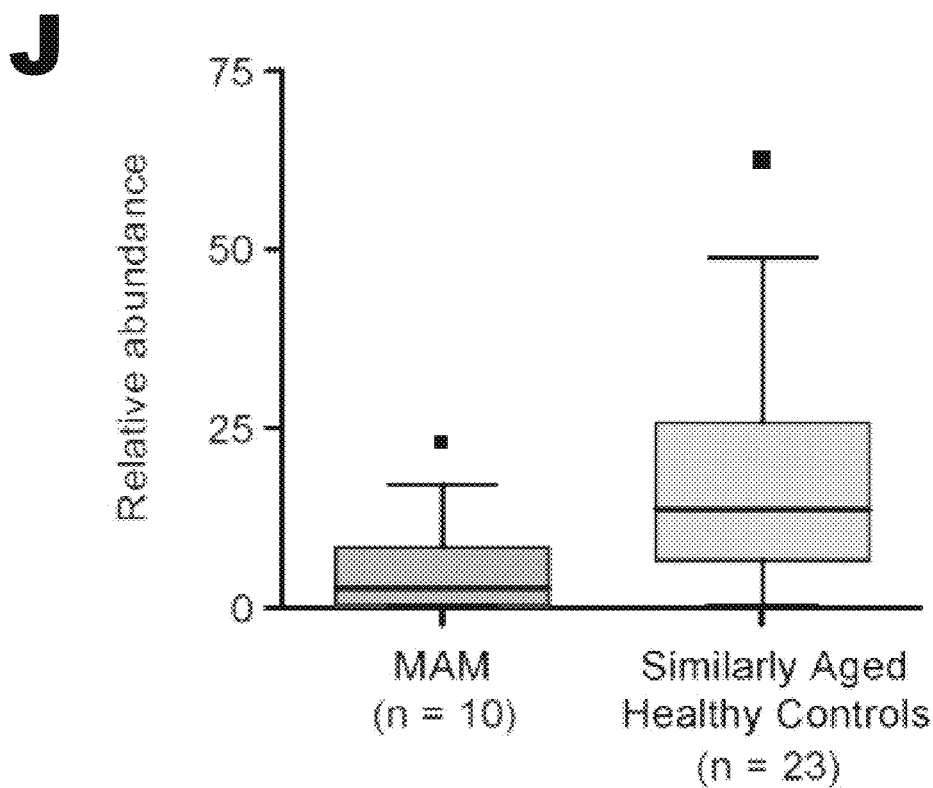
Figure 11:
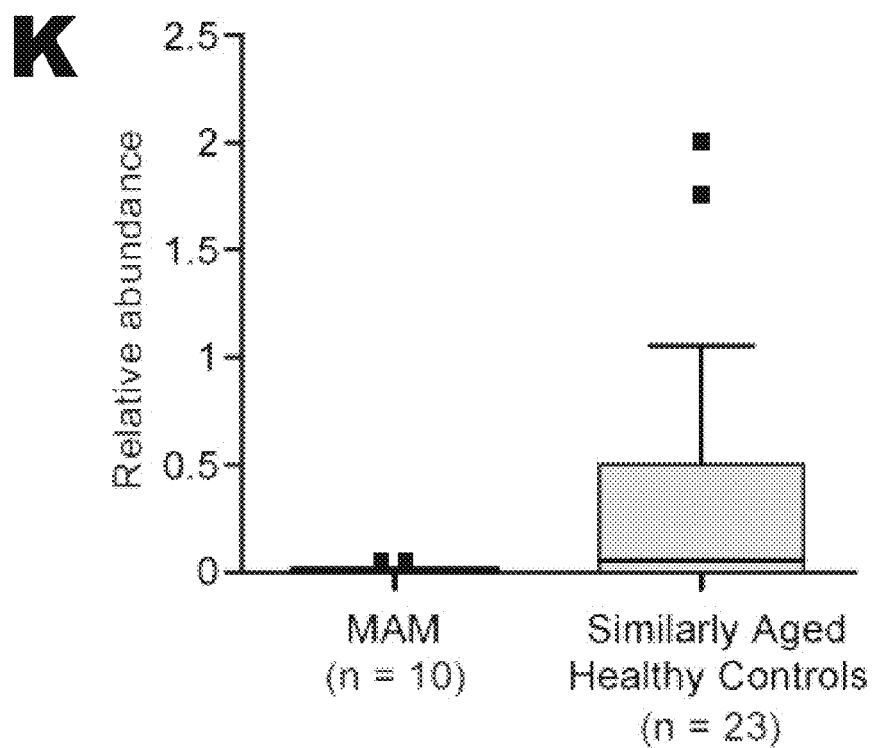
Figure 11:
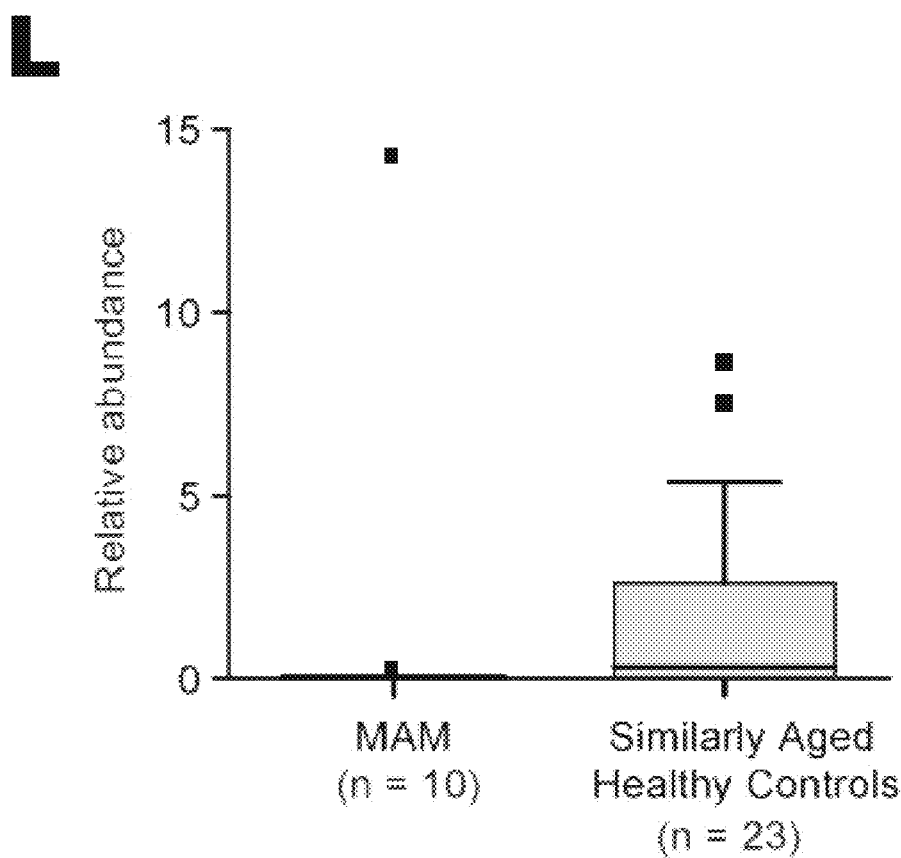

FIG. 11 graphically depicts the relative microbiota maturity and MAZ correlate with WHZ in children with MAM. (A-C) WHZ are significantly inversely correlated with relative microbiota maturity (A) and MAZ (B) in a cross-sectional analysis of 33 children at 18 months of age who were above and below the anthropometric threshold for MAM (Spearman's Rho=0.62 and 0.63, respectively; ***P<0.001). In contrast, there is no significant correlation between WHZ and microbiota diversity (C). (D-L), Relative abundances of age-discriminatory 97%-identity OTUs that are inputs to the Random Forests model that are significantly different in the faecal microbiota of children with MAM compared to age-matched 18-month-old healthy controls (Mann-Whitney U-test, P<0.05). Box plots represent the upper and lower quartiles (boxes), the median (middle horizontal line), and measurements that are beyond 1.5 times the interquartile range (whiskers) and above or below the 75th and 25th percentiles, respectively (points) (Tukey's method, PRISM software v6.0d). Taxa are presented in descending order of their importance to the Random Forests model. (D) *Faecalibacterium prauznitzii* 326792, (E) *Dorea longicatena* 191687, (F) *Lactobacillus mucosae* 15141, (G) *Catenibacterium mitsuokai* 287510, (H) *Dorea formicigenerans* 261912, (I) *Clostridium* sp. 181834, (J) *Bifidobacterium* sp. 469873, (K) *Clostridiales* sp. 185951, (L) *Ruminococcaceae* sp. 212619. See FIG. 10A,B.

Figure 12:
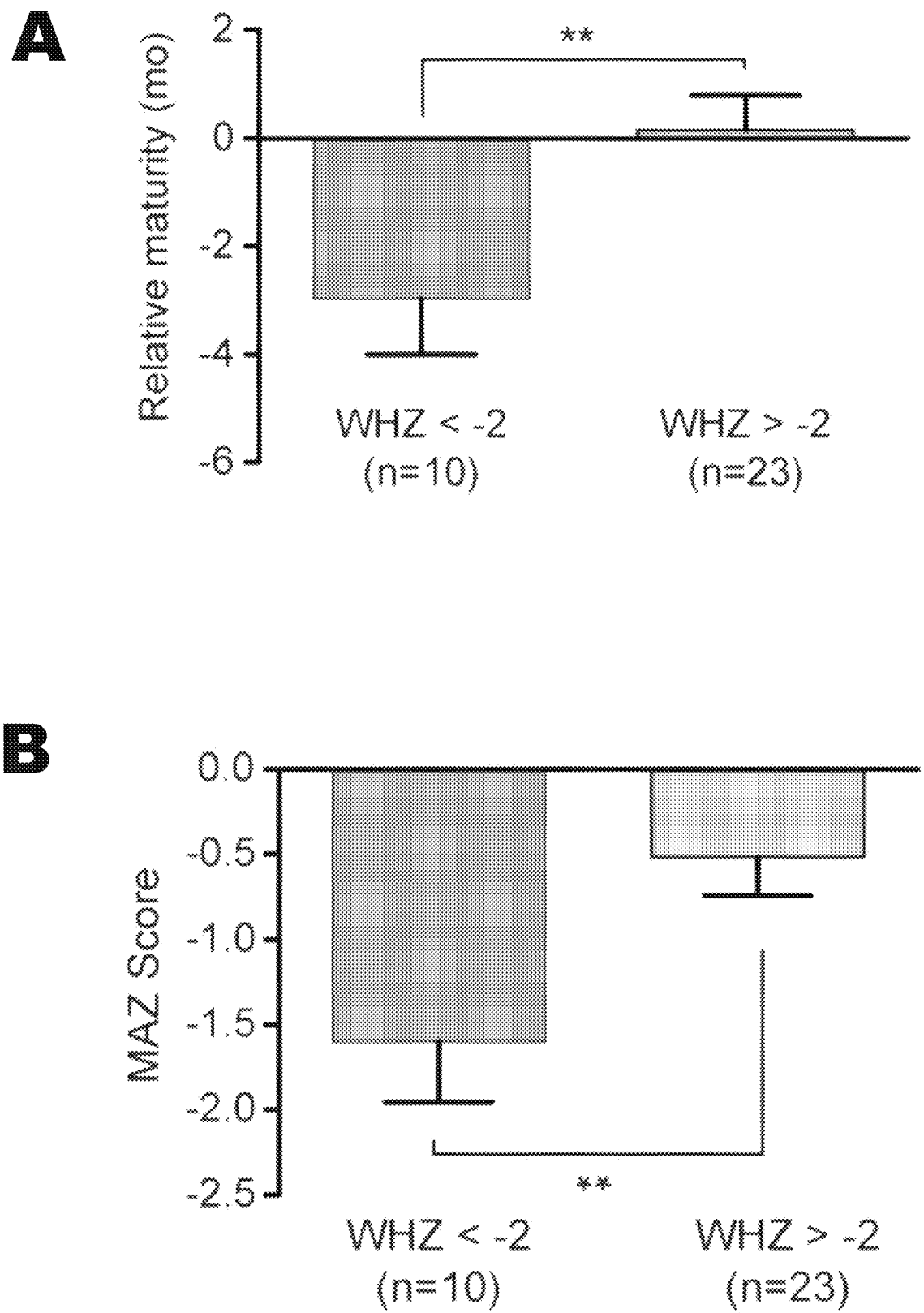

FIG. 12 depicts graphs and a schematic showing cross-sectional assessment of microbiota maturity at 18 months of age in Bangladeshi children with and without MAM, plus extension of the Bangladeshi-based model of microbiota maturity to Malawi. (A,B) Children with MAM (WHZ lower than −2 s.d.; grey) have significantly lower relative microbiota maturity (A) and MAZ (B) compared to healthy individuals (blue). Mean values±s.e.m. are plotted **P<0.01 (Mann-Whitney U-test). See FIG. 9 for correlations of metrics of microbiota maturation with WHZ and box-plots of age-discriminatory taxa whose relative abundances are significantly different in children with MAM relative to healthy reference controls. (C) Microbiota age predictions resulting from application of the Bangladeshi 24-taxon model to 47 faecal samples (brown circles) obtained from concordant healthy Malawian twins and triplets are plotted versus the chronologic age of the Malawian donor (collection occurred in individuals ranging from 0.4 to 25.1 months old). The results show the Bangladeshi model generalizes to this population, which is also at high risk for malnutrition (each circle represents an individual faecal sample collected during the course of a previous study[11]). (D) Spearman rho and significance of rank order correlations between the relative abundances of age-discriminatory taxa, and the chronologic age of all healthy Bangladeshi children described in the present study as well as concordant healthy Malawian twins and triplets. *P<0.05.

Figure 13:
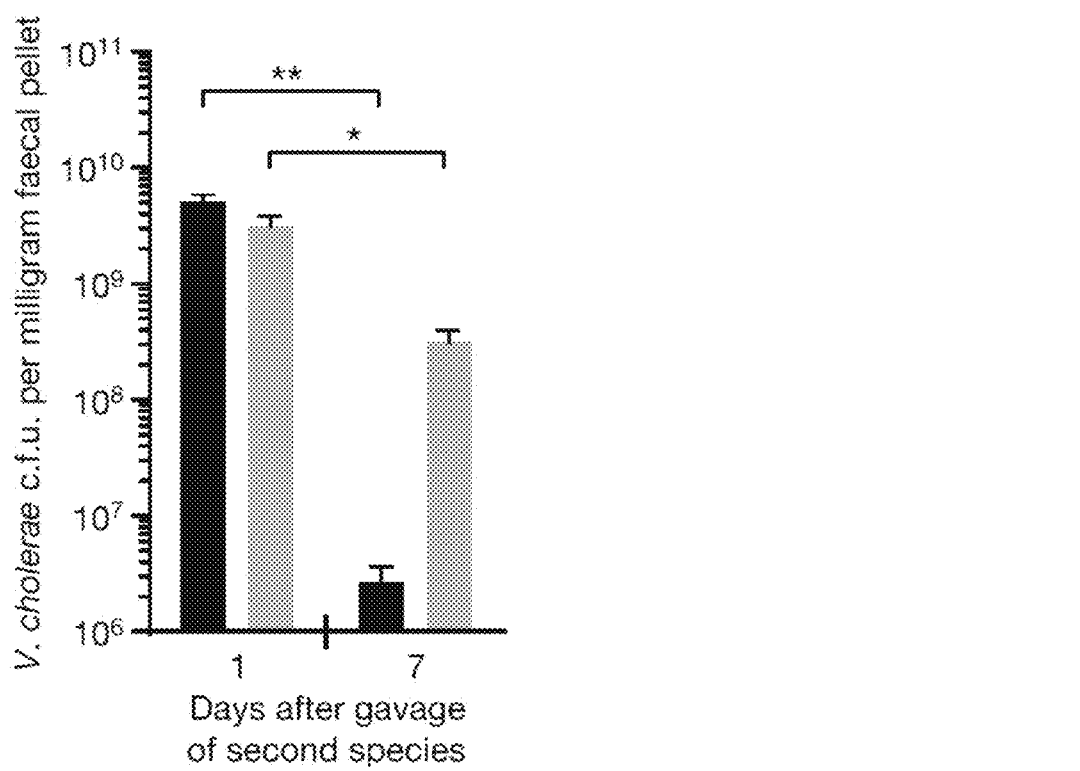
Figure 13:
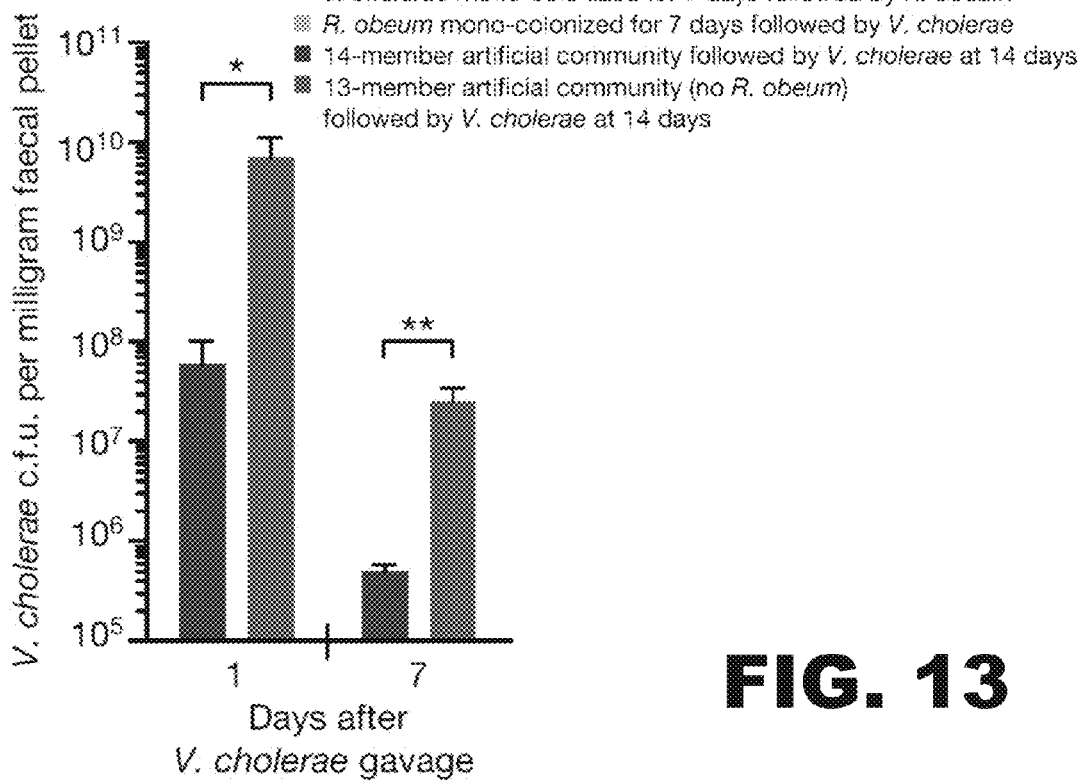

FIG. 13 graphically depicts that *R. obeum* restricts *V. cholerae* colonization in adult gnotobiotic mice. (A,B) *V. cholerae* levels in the faeces of mice colonized with the indicated human gut bacterial species (n=4-6 mice per group). (A) Days after gavage of second species and (B) Days after *V. cholerae* gavage. (C) Expression of *R. obeum* luxS AI-2 synthase in the 14-member community 4 days after introduction of $10^9$ c.f.u. of *V. cholerae* or no pathogen (n=5 mice per group). Note that *D. longicatena* levels fall precipitously after *V. cholerae* invasion (Table 25). Mean values±s.e.m. are shown. ND, not detected. *P<0.05, **P<0.01 (unpaired Mann-Whitney U-test).

Figure 14A:
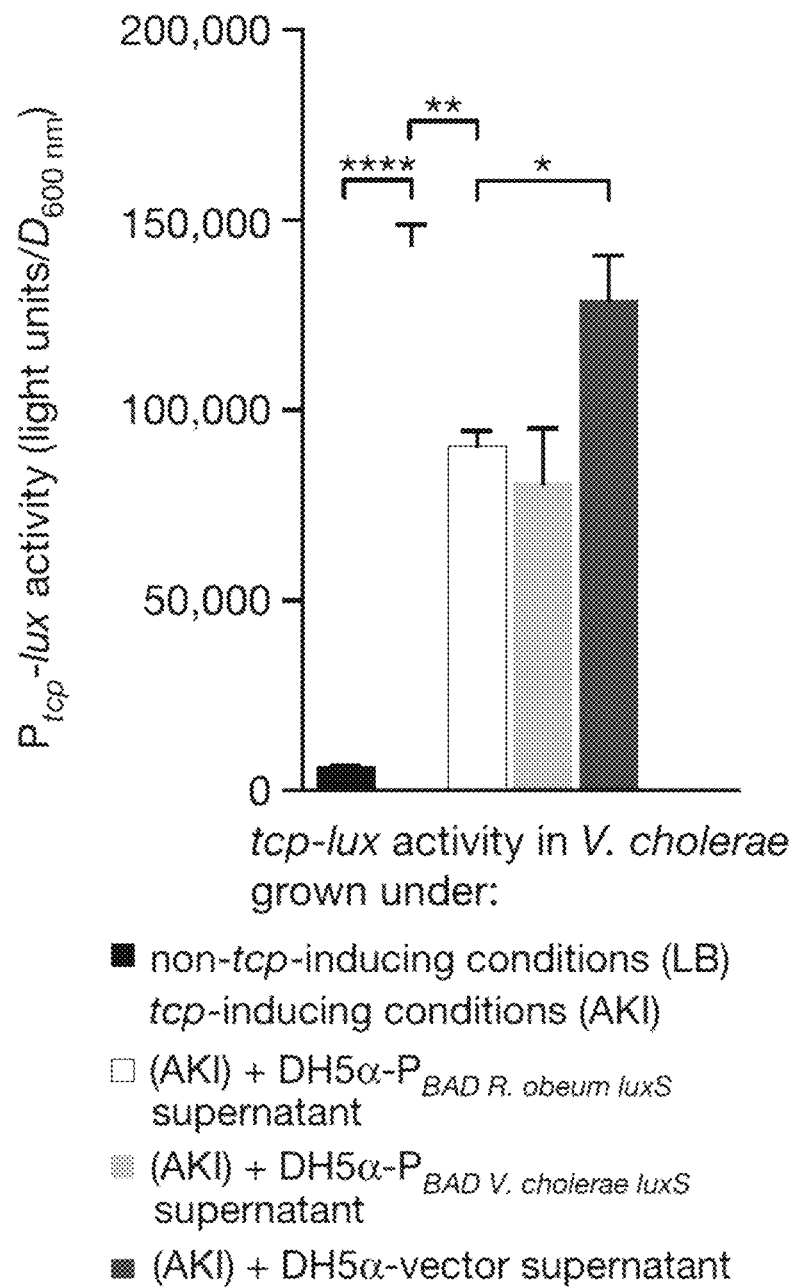
Figure 14:
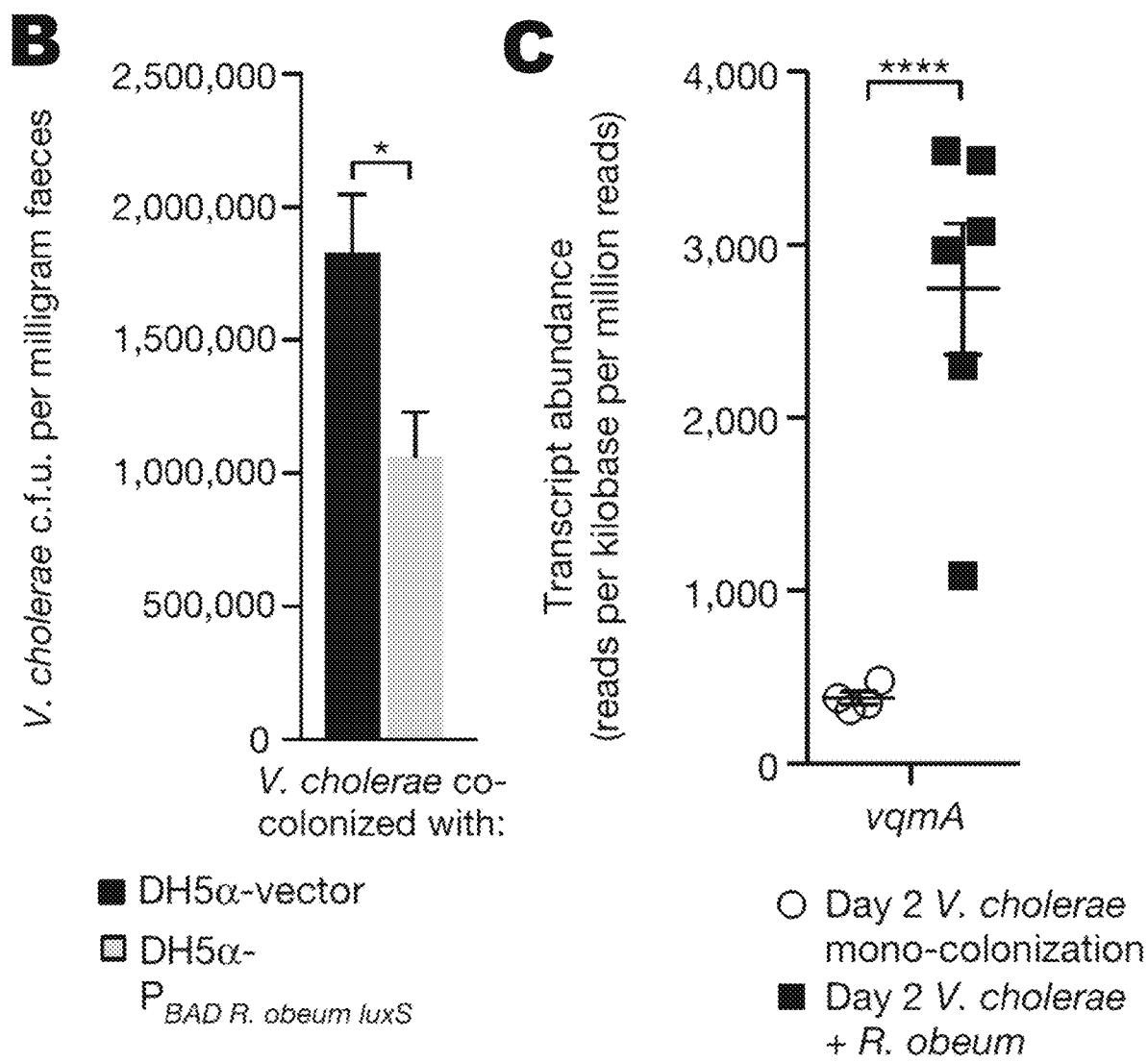

FIG. 14 graphically depicts that *R. obeum* AI-2 reduces *V. cholerae* colonization and virulence gene expression. (A) *R. obeum* AI-2 produced in *E. coli* represses the tcp promoter in *V. cholerae* (triplicate assays; results representative of four independent experiments). (B) Faecal *V. cholerae* levels in gnotobiotic mice 8 h after gavage with *V. cholerae* and an *E. coli* strain containing either the $P_{BAD}$-*R. obeum* luxS plasmid or vector control. (C) Faecal vqmA transcript abundance in mono- or co-colonized mice. (D) Competitive index of ΔvqmA versus wild-type *V. cholerae* during co-colonization with *R. obeum* (n=5 animals per group). Mean values±s.e.m. are shown. *P<0.05, P<0.01, **P<0.0001 (unpaired two-tailed Student's t-test).

Figure 15A:
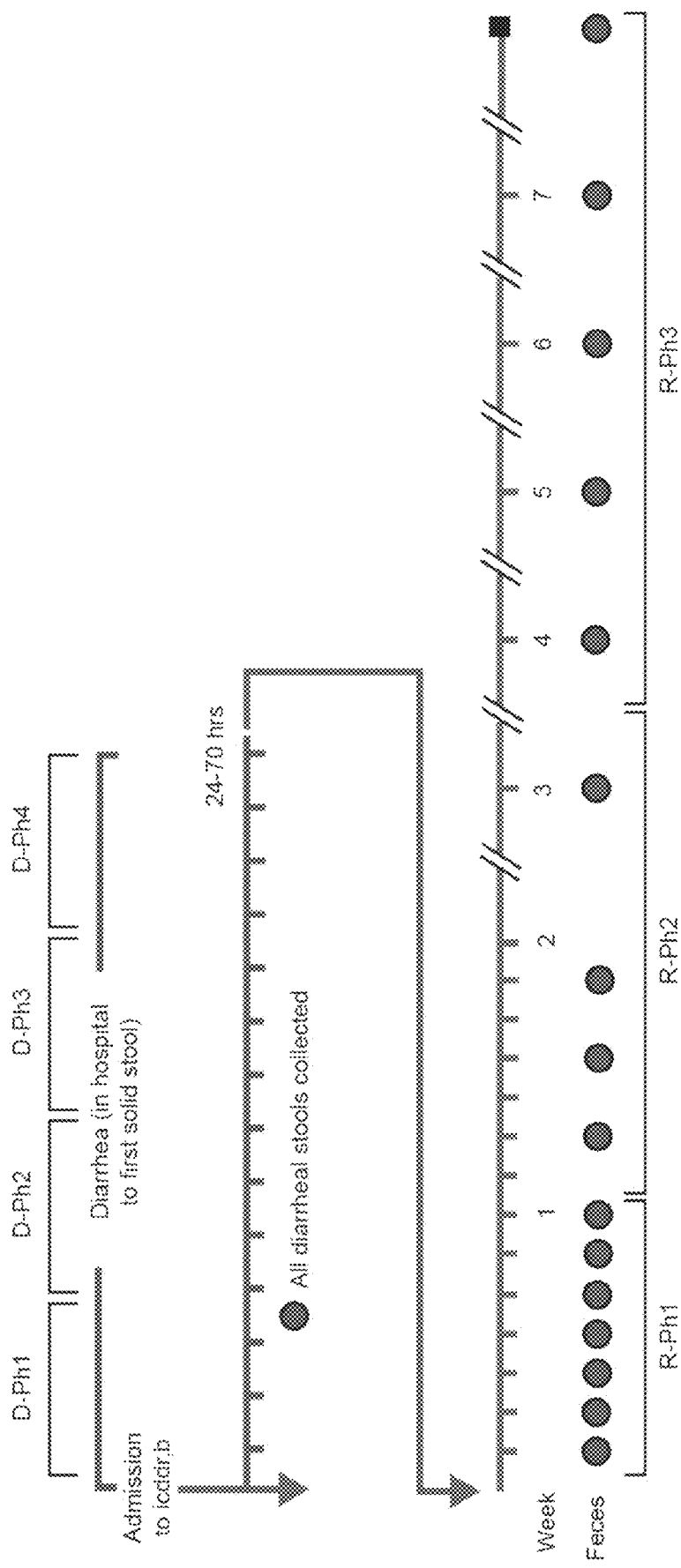
Figure 15:
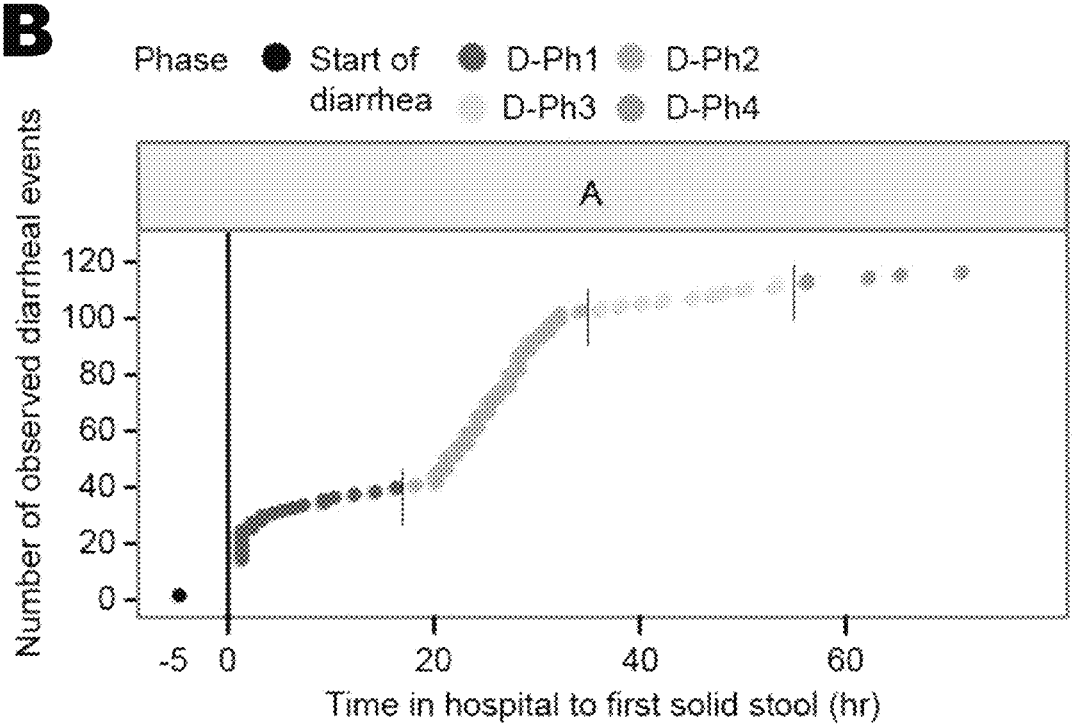
Figure 15:
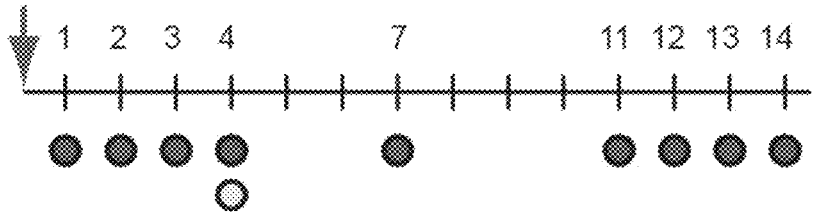
Figure 15:
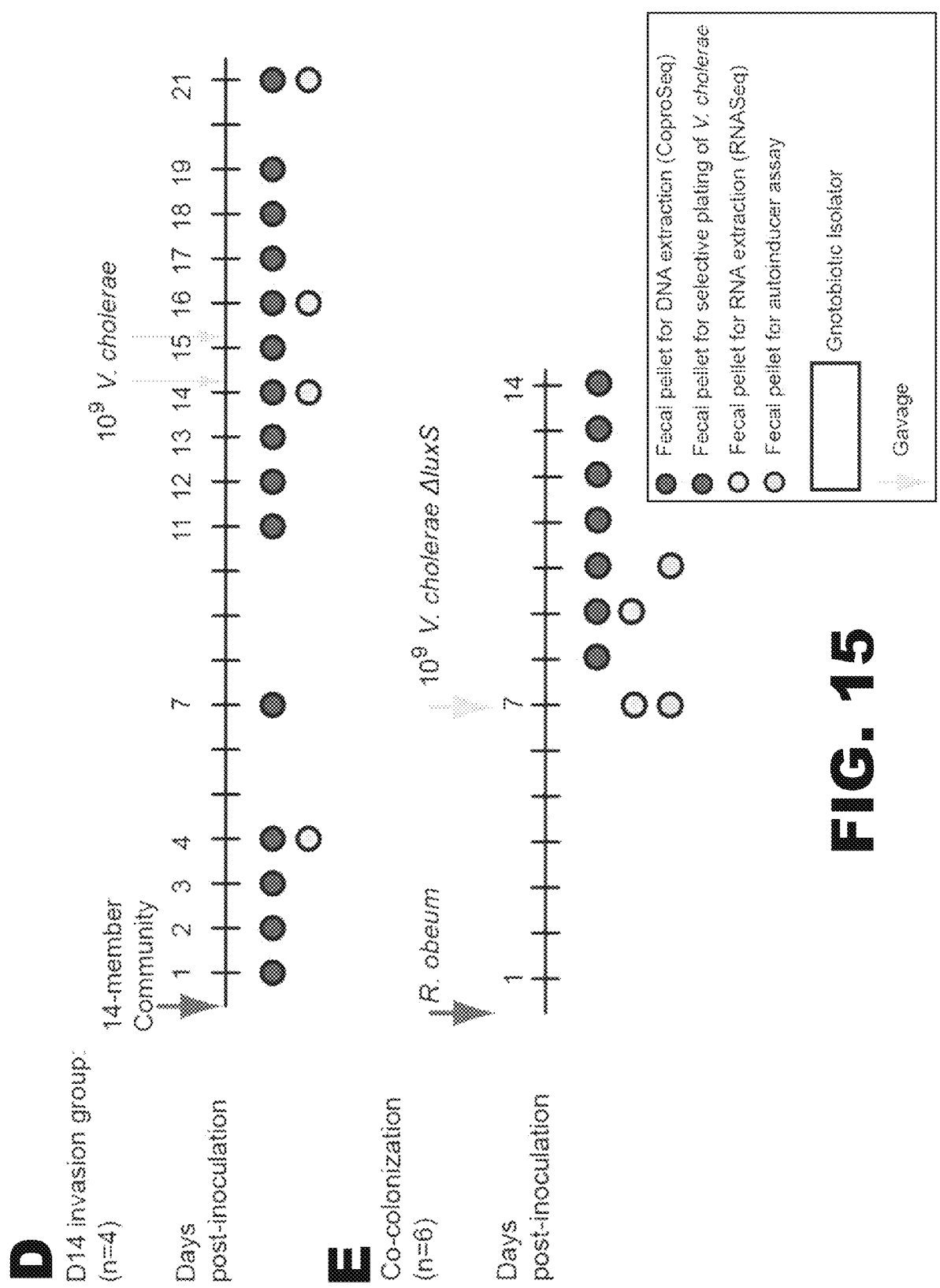
Figure 15:
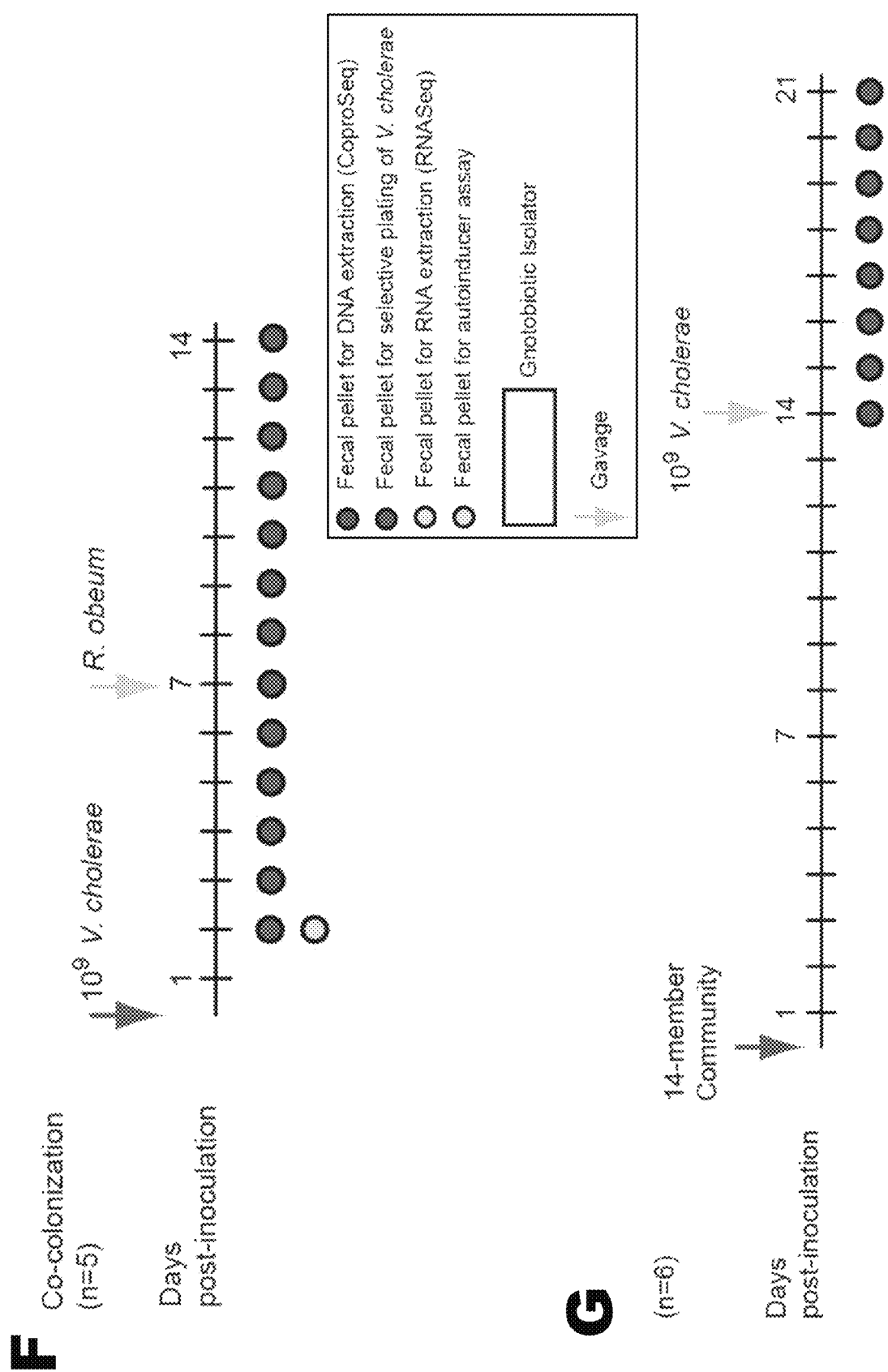
Figure 15H:
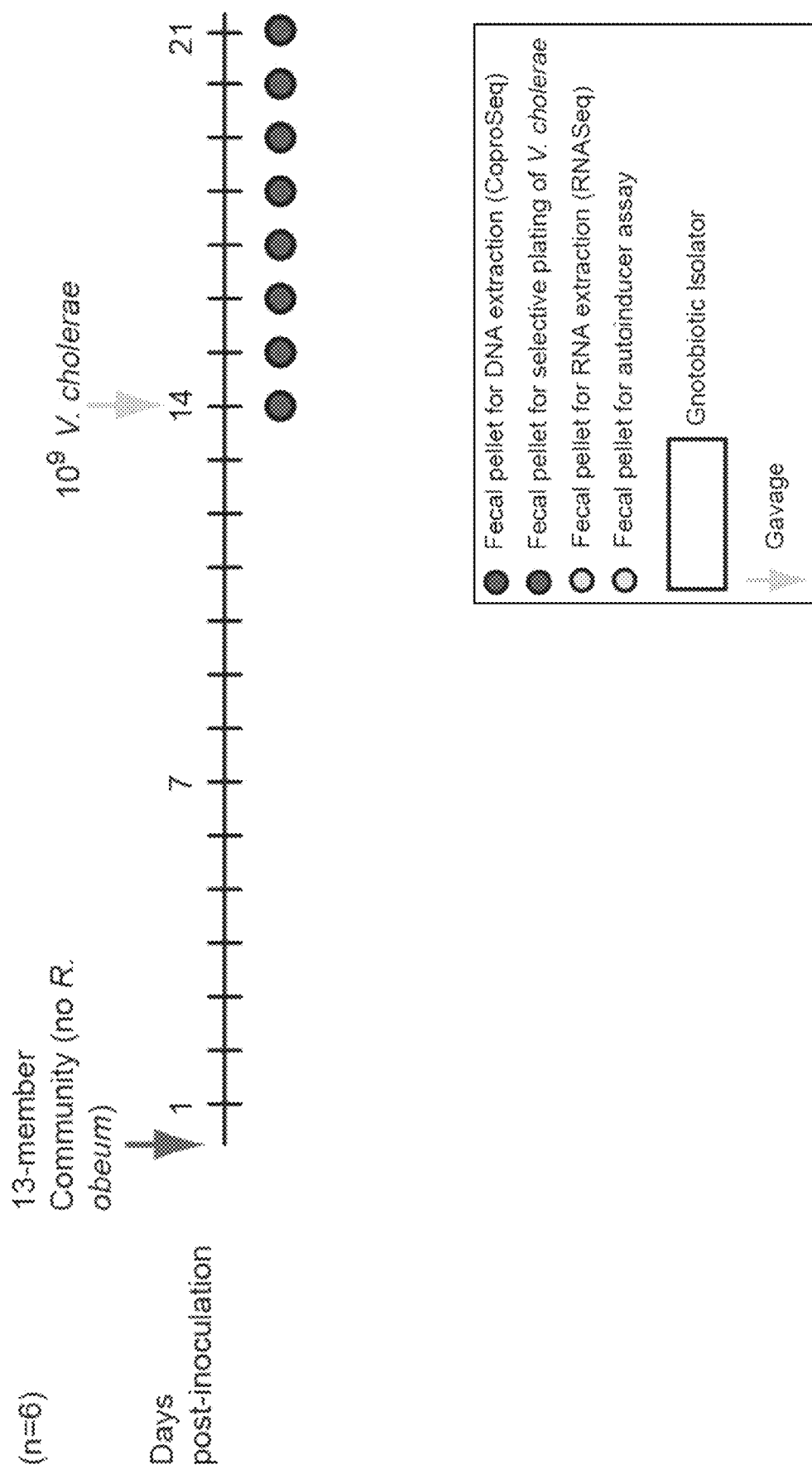

FIG. 15 depicts graphs and illustrations showing the experimental designs for clinical study and gnotobiotic mouse experiments. (A) Sampling schedule for human cholera study. (B) Frequency of diarrhoeal episodes over time for a representative participant (patient A). Initial time (black circle) represents beginning of diarrhoea. The long vertical line marks enrollment into the study. Colours and short vertical lines denote boundaries of study phases defined in (A). (C-H) Depict the various gnotobiotic mouse experimental designs. The number (n) of animals in each treatment group is shown.

Figure 16:
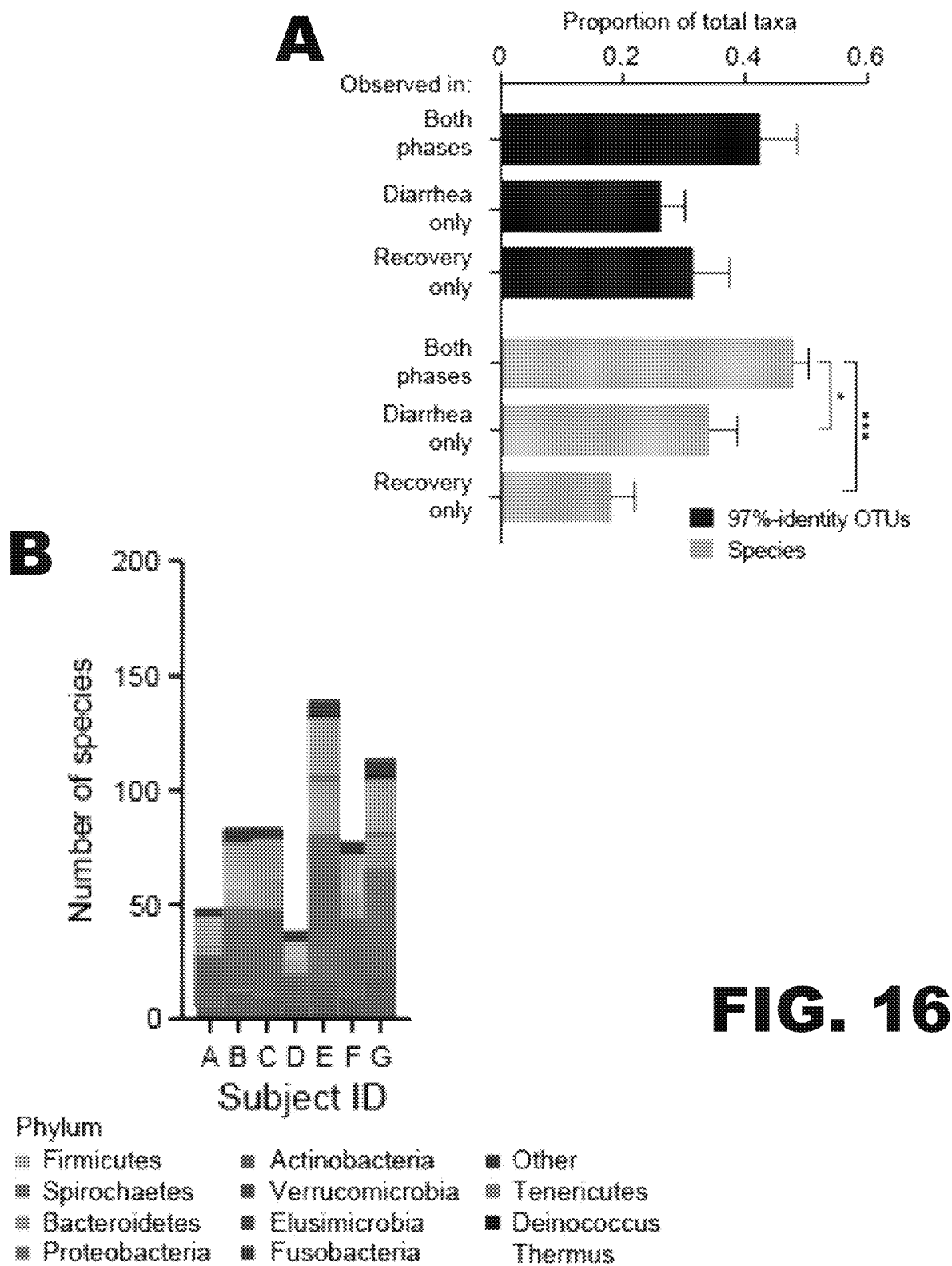
Figure 16:
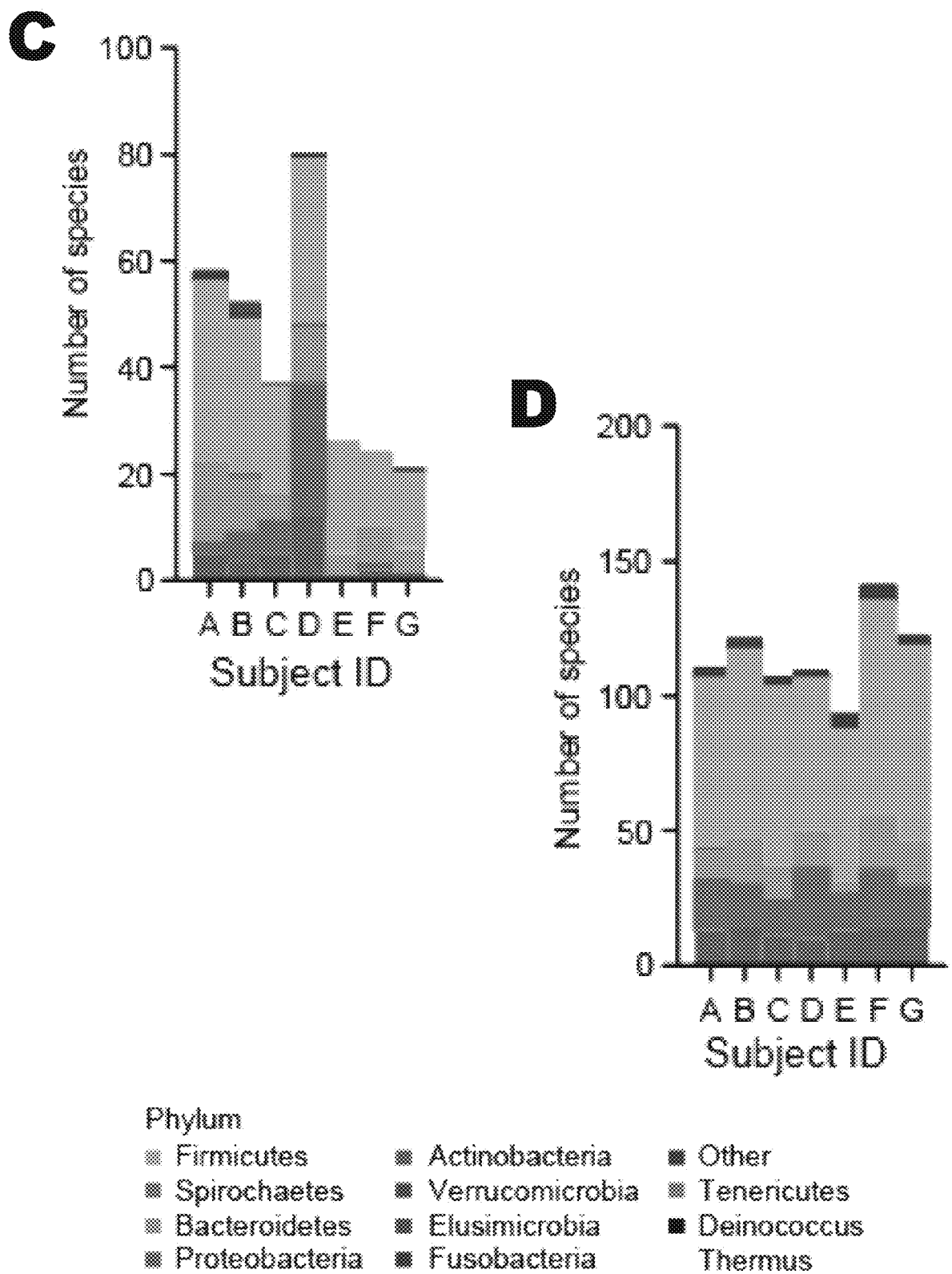

FIG. 16 depicts graphs and heatmaps showing the bacterial taxa associated with diarrhoeal and recovery phase. (A) Proportion of bacterial species-level taxa that were observed in both diarrhoeal and recovery phases, in D-Ph1 to D-Ph4 only, and in R-Ph1 to R-Ph3 only. Mean values±s.e.m. are plotted. *P<0.05, ***P<0.001 (unpaired Mann-Whitney U-test). (B-D) Phylum-level analysis. Mean values are plotted. (B) Diarrhea only, (C) Recovery only, and (D) Both phases. (E) Proportion of study participants having bacterial taxa associated by indicator species analysis with the diarrhoeal or recovery phase. The x axis shows species associated with each phase, ranked by proportion of subjects harbouring that species. For each species, 'representation in study participants' is the average presence/absence of all 97%-identity OTUs with that species taxonomic assignment. The OTU table was rarefied to 49,000 reads per sample. (F-N) Bacterial species identified by indicator analysis as indicative of diarrhoea or recovery phases in adult patients with cholera, and species identified by Random Forests analysis as discriminatory for different stages in the maturation of the gut microbiota of healthy Bangladeshi infants/children aged 1-24 months (denoted by the symbol †). (F-H) The heat map shows mean relative abundances of species across all individuals during D-Ph1 to D-Ph4, with each phase subdivided into four equal time bins. For recovery time points, columns represent the mean relative abundances for each sampling time point during R-Ph1 to R-Ph3. (I-K) Mean relative abundance values are also presented for these same species in the faecal microbiota of 50 healthy Bangladeshi children sampled from 1 to 2 years of age at monthly intervals. Unsupervised hierarchical clustering used relative abundances of species in the faecal microbiota of the patients with cholera. (F,G,I,J) The green portion of the tree encompasses species that are more abundant during recovery whereas (H,K) the red portion encompasses species that are more abundant during diarrhoea. (L-N) Indicator scores are presented in the right-hand portion of the panel, with 'score' for a given taxon defined as its indicator value for recovery minus its indicator value for diarrhoea (-1, highly diarrhoea-associated; +1, highly recovery-associated). Spearman's rank correlation coefficients of mean relative abundances of species by sample in the cholera study versus the mean sample-weighted UniFrac distance to healthy adult faecal microbiota are shown at the extreme right together with the statistical significance of correlations after Benjamini-Hochberg false discovery rate correction for multiple hypothesis testing (NS, not significant; *P<0.05; P<0.01; *P<0.001). Higher coefficients indicate increasing divergence from a healthy configuration with higher relative abundance of a given species. Species shown satisfied two or more of the following criteria: (1) presence among the list of the top 40 age-discriminatory species in the Random-Forests-based model of gut microbiota maturation in healthy infants and children; (2) indicator value score greater than 0.7; (3) significant correlation (Spearman'sr) between relative abundance in the faecal microbiota of patients with cholera and UniFrac distance to healthy adult faecal microbiota; and (4) inclusion in the artificial 14-member human gut community (species name highlighted in blue).

FIG. 17 depicts heatmaps showing the 97%-identity OTUs observed in both diarrhoeal and recovery phases. The proportion of 97%-identity OTUs with a given species-level taxonomic assignment that were present in both (A-D) diarrhoeal and (E-H) recovery phases is shown for each individual in the study. The number of 97%-identity OTUs with a given species assignment is shown in parentheses. Species are ordered based on their 'indicator scores' (defined as indicator value$_{recovery}$ minus indicator value$_{diarrhoea}$). Age-discriminatory bacterial species incorporated into a Random-Forests-based model for defining relative microbiota maturity and microbiota-for-age z-scores[3] in healthy Bangladeshi infants and children are marked with a '+' symbol. The 97%-identity OTUs were derived from data sets generated from all samples from adult patients with cholera; the OTU table was rarefied to 49,000 reads per sample.

FIG. 18 depicts heatmaps and graphs showing the pattern of appearance of age-discriminatory 97%-identity OTUs in the faecal microbiota of patients with cholera mirrors the normal age-dependent pattern in the faecal microbiota of healthy Bangladeshi infants and children. (A-C) Shows hierarchical clustering of relative abundance values for each of the top 60 most age-discriminatory 97%-identity OTUs in a Random-Forests-based model of normal maturation of the microbiota in healthy Bangladeshi infants/children (importance scores for the age-discriminatory taxa defined by Random Forests analysis are reported in ref. 3; these 60 97%-identity OTUs can be grouped into 40 species-level taxa). (D-I) Presents the mean relative abundances of these OTUs in samples obtained from patients with cholera during (D-F) D-Ph1 to D-Ph4, and (G-I) R-Ph1 to R-Ph3. The 97%-identity OTUs corresponding to species included in the artificial community that was introduced into gnotobiotic mice are highlighted in blue. (J) Relative abundance of *R. obeum* strains in the faecal microbiota of healthy Bangladeshi children sampled monthly through the first 3 years of life. Mean values±s.e.m. are plotted.

Figure 19:
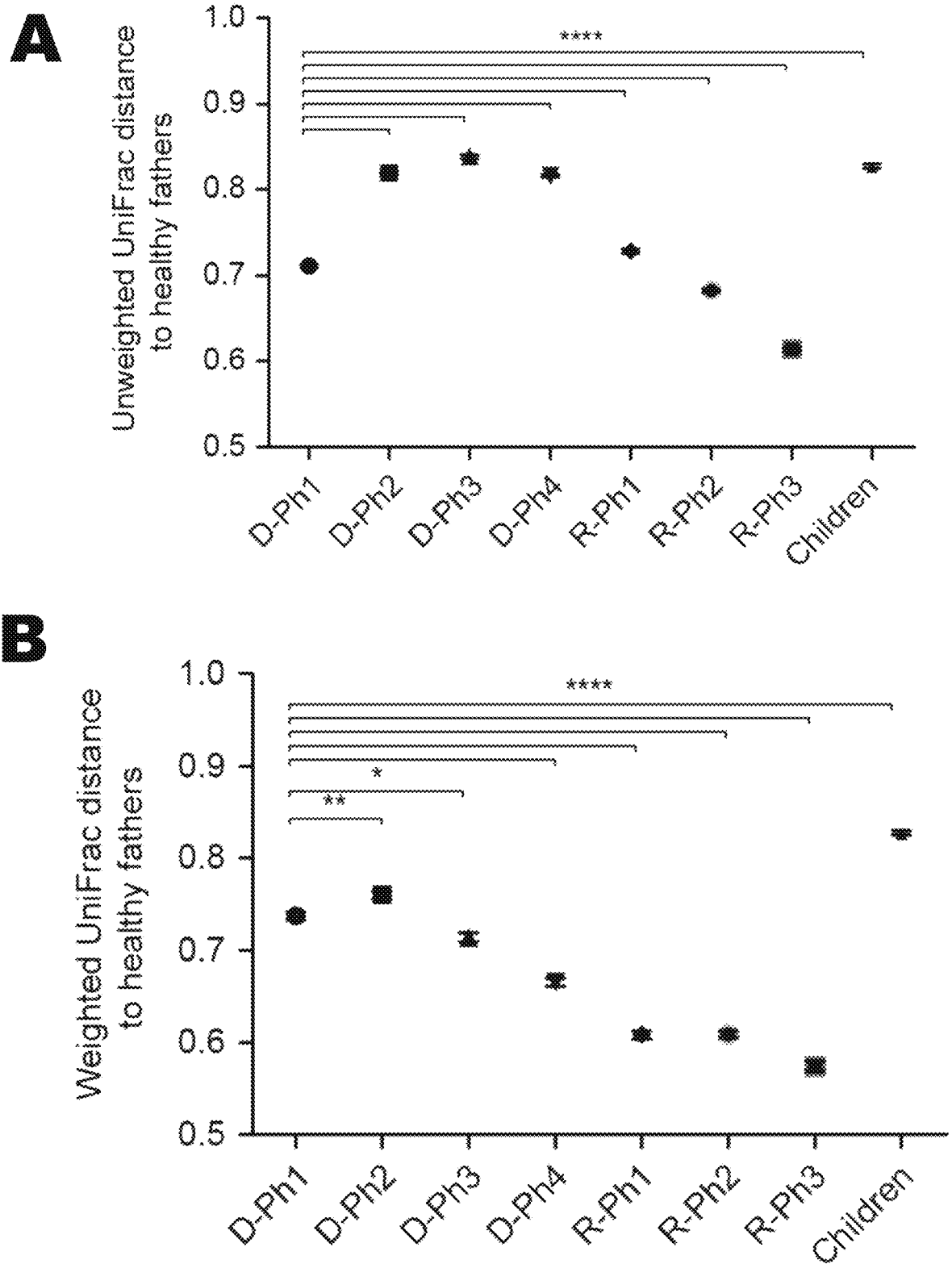
Figure 19:
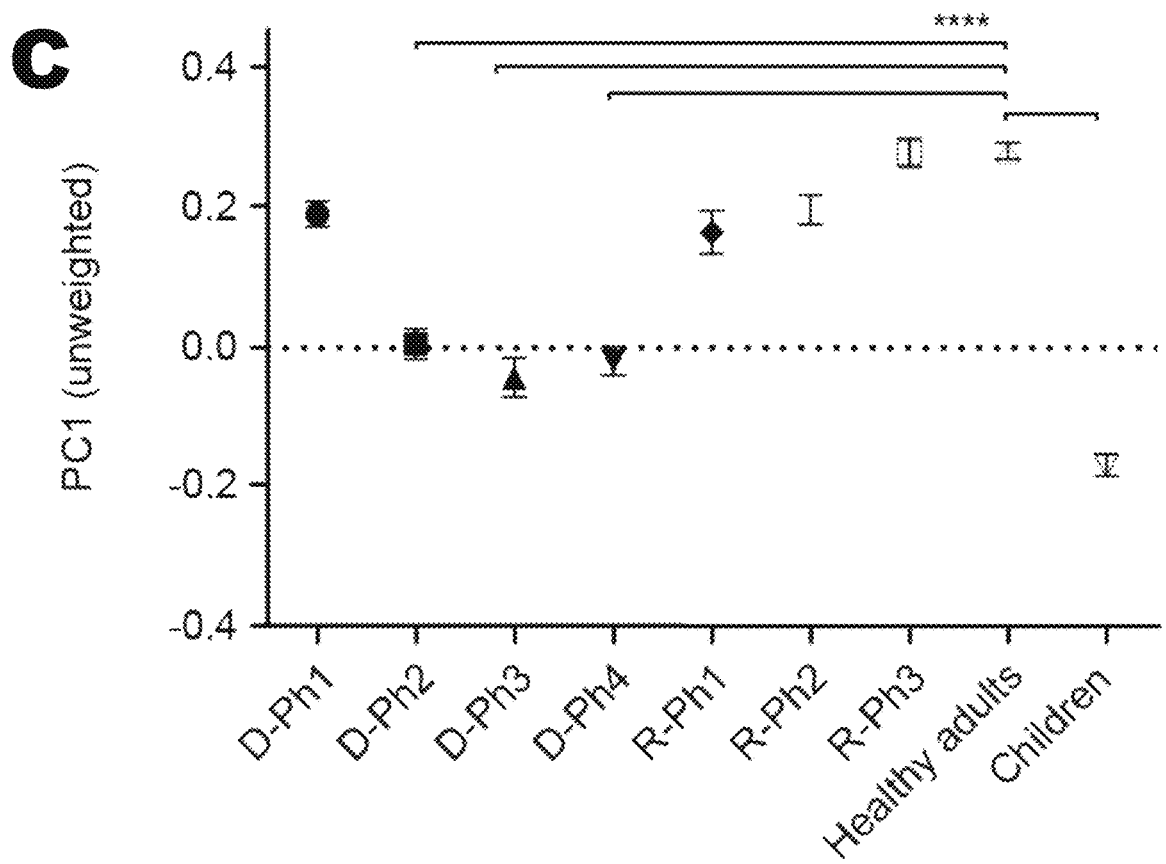
Figure 19:
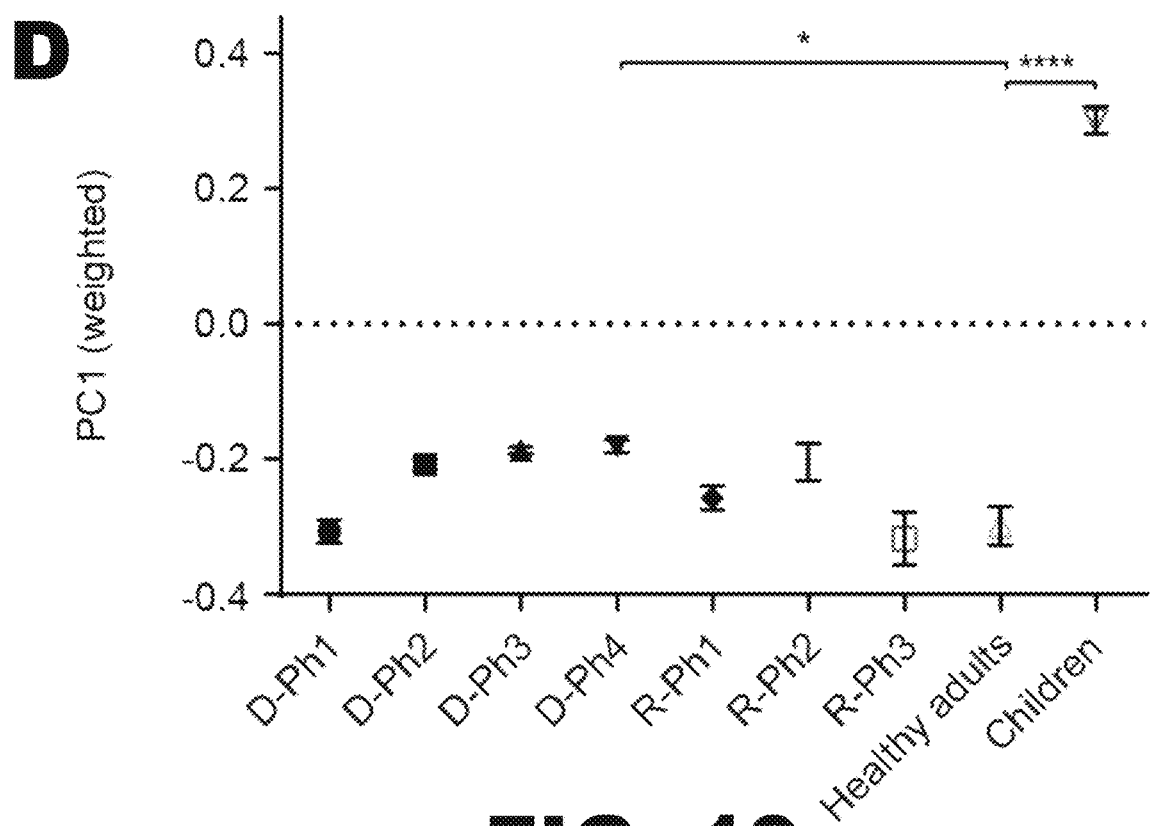

FIG. 19 graphically depicts the pattern of recovery of the gut microbiota in patients with cholera. (A,B) Mean unweighted (A) and weighted (B) UniFrac distances to healthy adult controls at each of the defined phases of diarrhoea and recovery. (C,D) Principal coordinates analysis of UniFrac distances between gut microbiota samples. Location along the principal axis of variation (PC1) shows how acute diarrhoeal communities first resemble those of healthy Bangladeshi children sampled during the first 2 years of life, then evolve their phylogenetic configurations during the recovery phase towards those of healthy Bangladeshi adults. PC1 accounts for 34.3% variation for weighted and 17.7% variation for unweighted UniFrac values. (E) Alpha diversity (whole-tree phylogenetic diversity) measurements of faecal microbial communities through all study phases. Mean values±s.e.m. are plotted. *P<0.05, P<0.01, **P<0.0001 (Kruskal-Wallis analysis of variance followed by multiple comparisons test).

FIG. 20 depicts heatmaps showing the proportional representation of genes encoding enzymes (classified according to Enzyme Commission number identifiers) in faecal microbiomes sampled during the diarrhoeal and recovery phases of cholera. Shotgun sequencing of faecal community DNA was performed (MiSeq 2000 instrument; 2×250 bp paired-end reads; 341,701±145,681 reads (mean±s.d. per sample)). Read pairs were assembled (SHERA software package[34]). Read counts were collapsed based on their assignment to Enzyme Commission (EC) number identifiers. The significance of differences in EC abundances compared with faecal microbiomes in healthy adult Bangladeshi controls was defined using ShotgunFunctionalizeR[39]. Unsupervised hierarchical clustering identifies groups of ECs that characterize the faecal microbiomes of patients with cholera at varying diarrhoeal and recovery phases. (A-E) The heat map shows the results of EC-based clustering by phase (diarrhoea/recovery). (F-J) The heat map presents the results of a global clustering of all time-points and study phases. Genes encoding 102 ECs were identified with (1) at least 0.1% average relative abundance across the study and (2) significant differences in their representation relative to healthy microbiomes in at least one comparison (adjusted P<0.00001 based on ShotgunFunctionalizeR). In each of the heat maps, z-scores for each EC across all samples are plotted. ECs are grouped by KEGG level 1 assignment and further annotated based on their KEGG Pathway assignments. Note that the majority of the 46 ECs that were more prominently represented in faecal microbiomes during diarrhoeal phases in study participants are related to carbohydrate metabolism. The faecal microbiomes of patients during recovery are enriched for genes involved in vitamin and cofactor metabolism (Table 24).

Figure 21:
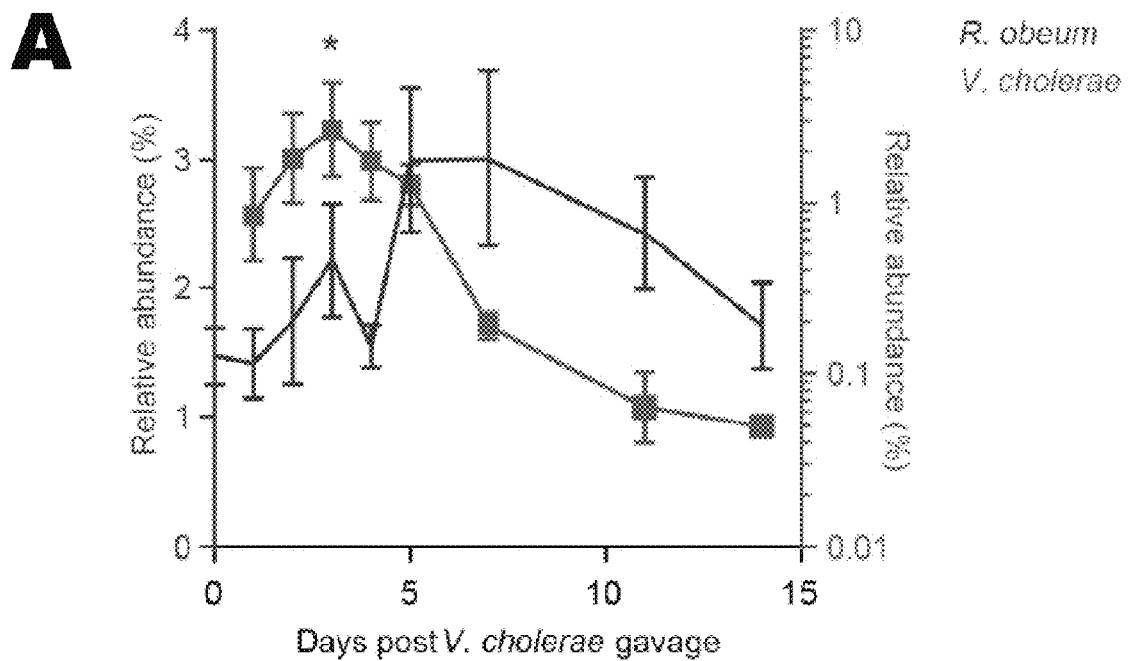
Figure 21:
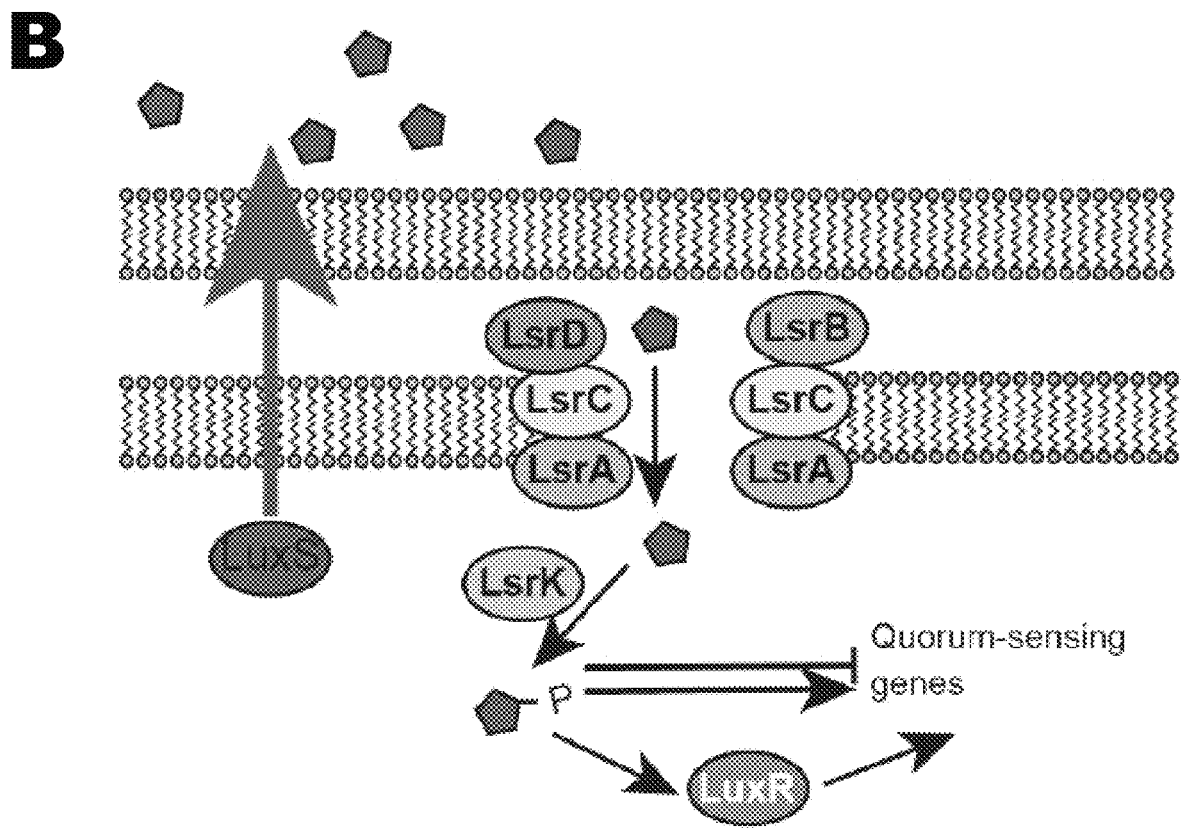
Figure 21C:
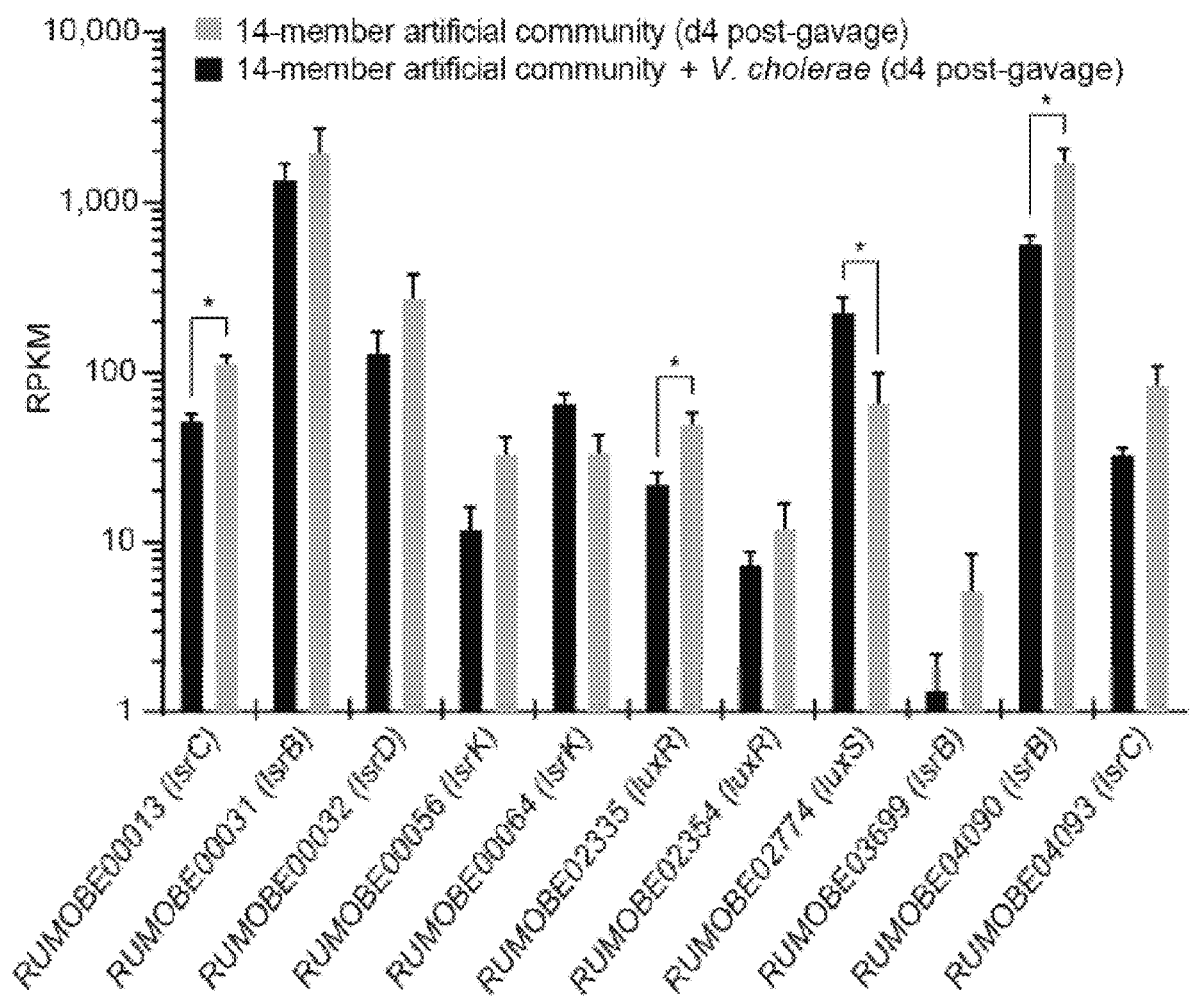

FIG. 21 depicts a schematic and graph showing that *R. obeum* encodes a functional AI-2 system, and *R. obeum* AI-2 production is stimulated by the presence of *V. cholerae*. (A) Relative abundances of *R. obeum* and *V. cholerae* in the faecal microbiota after introduction of *V. cholerae* into mice harbouring the artificial 14-member human gut community (D14invasion group, see FIG. 15C,D). 'Days post *V. cholerae* gavage' refers to the second of two daily gavages of $10^9$ c.f.u. *V. cholerae* into animals that had been colonized 14 days earlier with the 14-member community. Mean values±s.e.m. are shown (n=4 or 5 mice, *P<0.05, unpaired Student's t-test). (B) Shows AI-2 signalling pathway components represented in the *R. obeum* genome. (C) Plots changes in expression of these components as defined by microbial RNA-seq of faecal samples obtained (1) 4 days after colonization of mice with the 14-member community and (2) 4 days after gavage of mice with the 14-member community together with $10^9$ c.f.u. of *V. cholerae* (n=4-6 animals per group; one faecal sample analysed per animal). Mean values±s.e.m. are shown. *P<0.05 (Mann-Whitney U-test). (D) RNA-seq of faecal samples collected at the time points and treatment groups indicated reveals that *R. obeum* luxS transcription is directly correlated to *V. cholerae* abundance in the context of the 14-member community. **P<0.01 (F test). (E) *R. obeum* luxS expression. Mice were colonized first with *R. obeum* for 7 day. Faecal samples were collected for microbial RNA-seq analysis 1 day before gavage of $10^9$ c.f.u. of a *V. cholerae* ΔluxS mutant, and then 2 days post-gavage (d2pg). Mean values for relative *R. obeum* luxS transcript levels (±s.e.m.) are shown (n=5 or 6 animals per group per experiment, n=3 independent experiments; **P<0.01 unpaired Mann-Whitney U-test). (F) AI-2 levels in faecal samples, taken 1 day before and 3 days after gavage of the *V. cholerae* ΔluxS strain, from the same mice as those analysed in (A). AI-2 levels were measured based on induction of bioluminescence in *V. harveyi* BB170 using the same mass of input faecal sample for all assays. Mean values±s.e.m. are shown; ****P<0.0001 (unpaired Mann-Whitney U-test). (G) *R. obeum* produces AI-2 when co-cultured with *V. cholerae* in vitro. Aliquots of the supernatant from cultures containing *R. obeum* alone, or *R. obeum* plus the *V. cholerae* ΔluxS mutant, were assayed for their ability to induce *V. harveyi* bioluminescence. Mean values±s.e.m. are presented (n=4 independent experiments). LU, light units; RPKM, reads per kilobase per million reads. ****P<0.0001 (unpaired Mann-Whitney U-test). Note that (1) the number of *R. obeum* c.f.u. present in the samples obtained from mono-cultures of the organism was similar to the number in co-culture, as measured by selective plating, and (2) the *V. cholerae* ΔluxSmutant cultured alone produced levels of AI-2 signal that were not significantly different from that of *R. obeum* in mono-culture (data not shown).

Figure 22A:
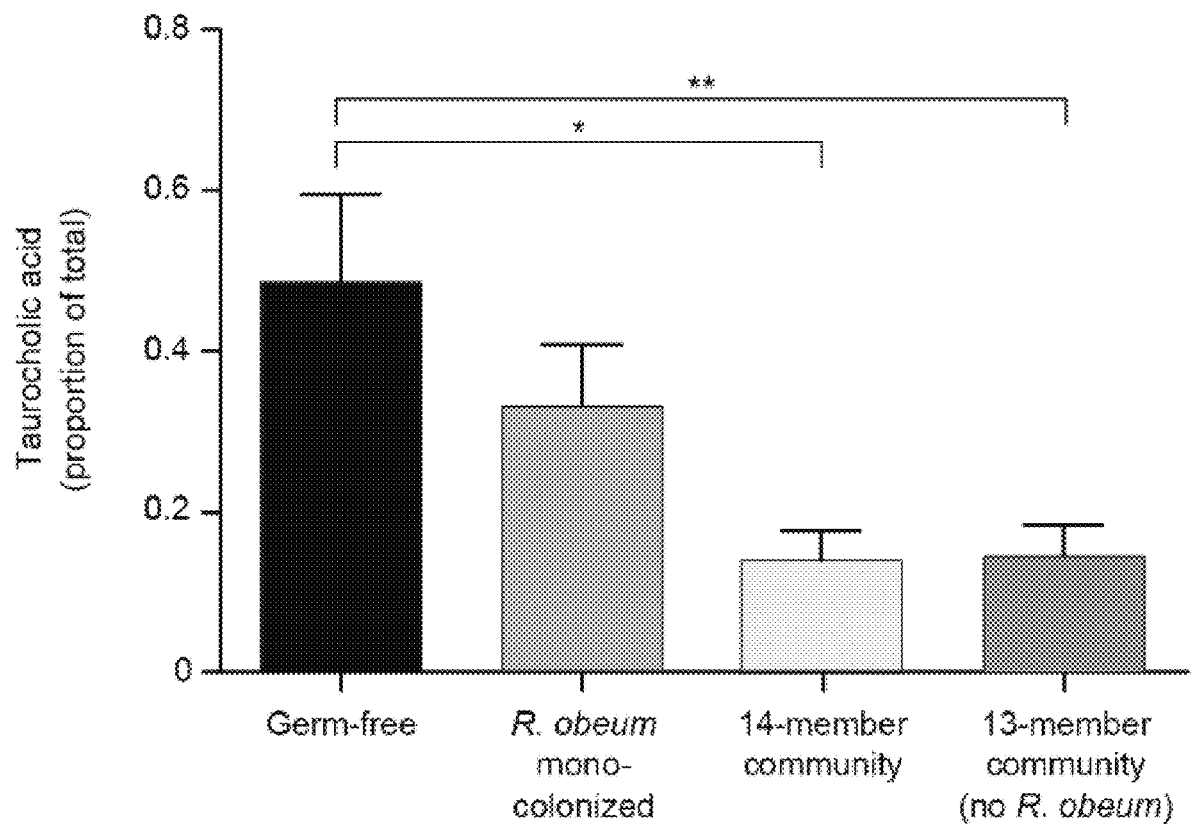
Figure 22B:
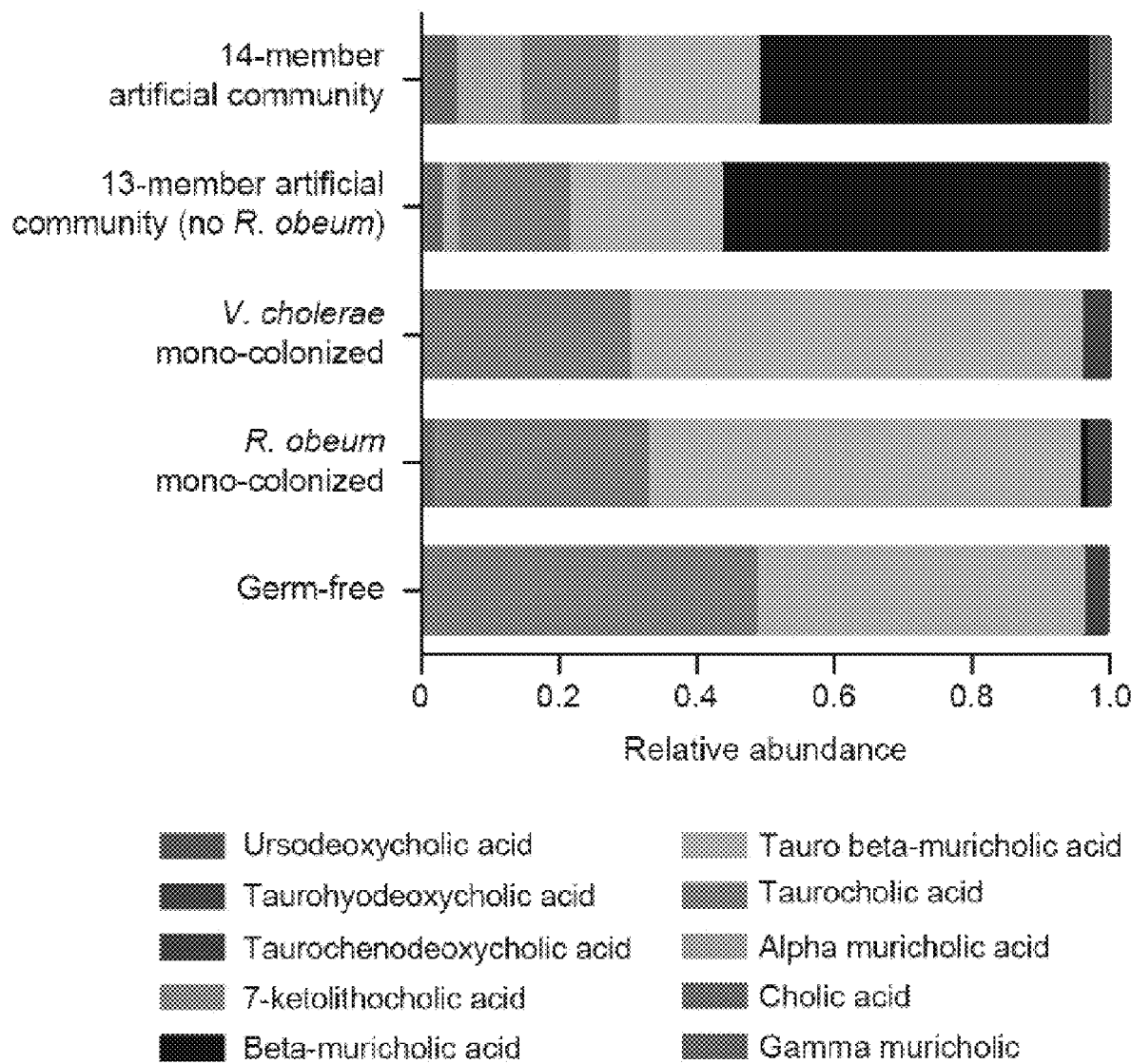

FIG. 22 graphically depicts UPLC-MS analysis of faecal bile acid profiles in gnotobiotic mice. Targeted UPLC-MS used methanol extracts of faecal pellets obtained from age- and gender-matched germ-free C57BL/6J mice and gnotobiotic mice colonized for 3 days with *R. obeum* alone, for 7 days with the 14-member community ('D1 invasion group'), and for 3 days with the 13-member community that lacked *R. obeum* (n=4-6 mice per treatment group; one faecal sample analysed per animal). (A) Faecal levels of taurocholic acid. Mean values±s.e.m. are plotted. *P<0.05, **P<0.01, Mann-Whitney U-test. (B) Mean relative abundance of ten bile acid species in faecal samples obtained from the mice shown in (A).

Figure 23A:
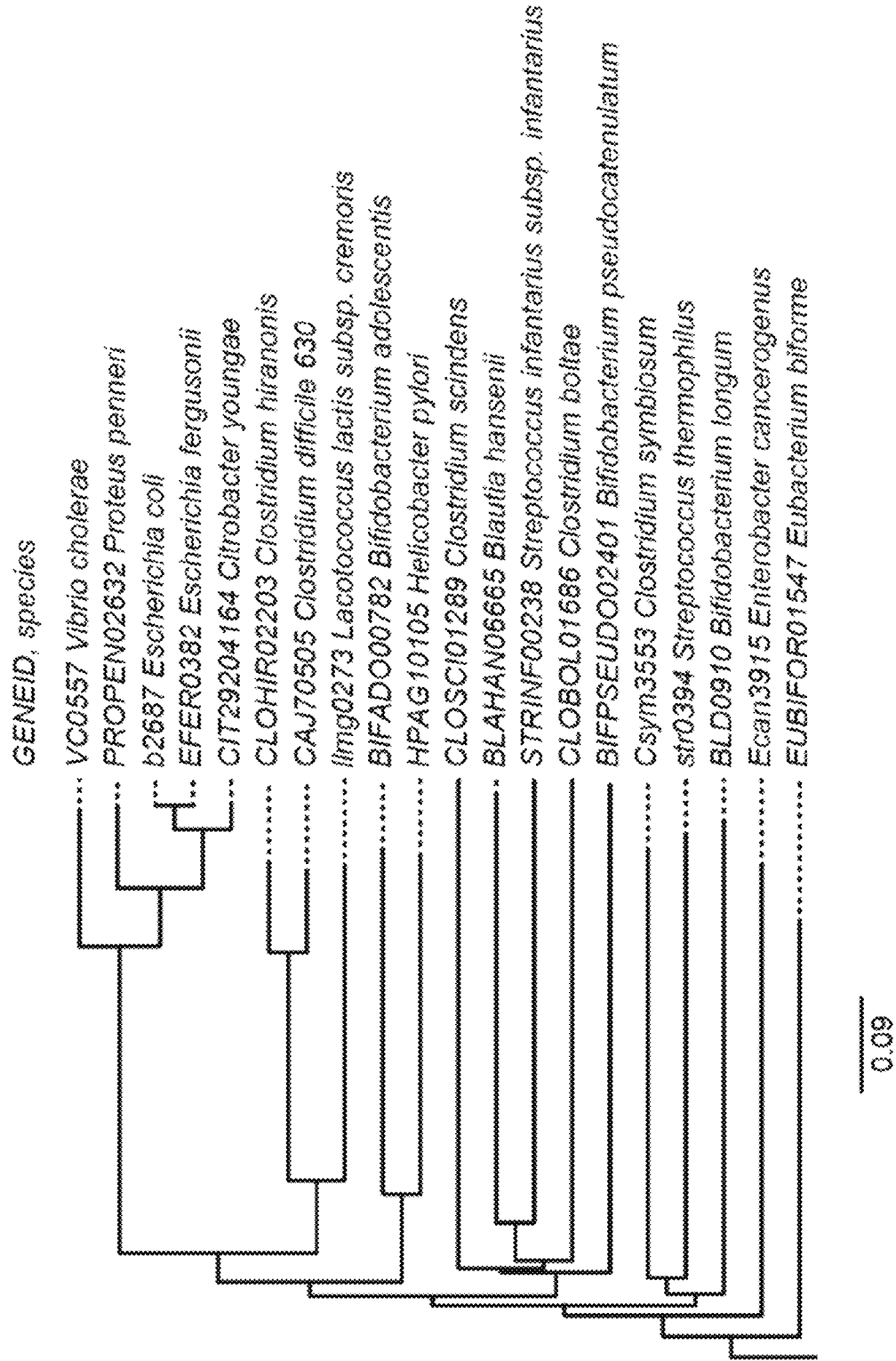
Figure 23B:
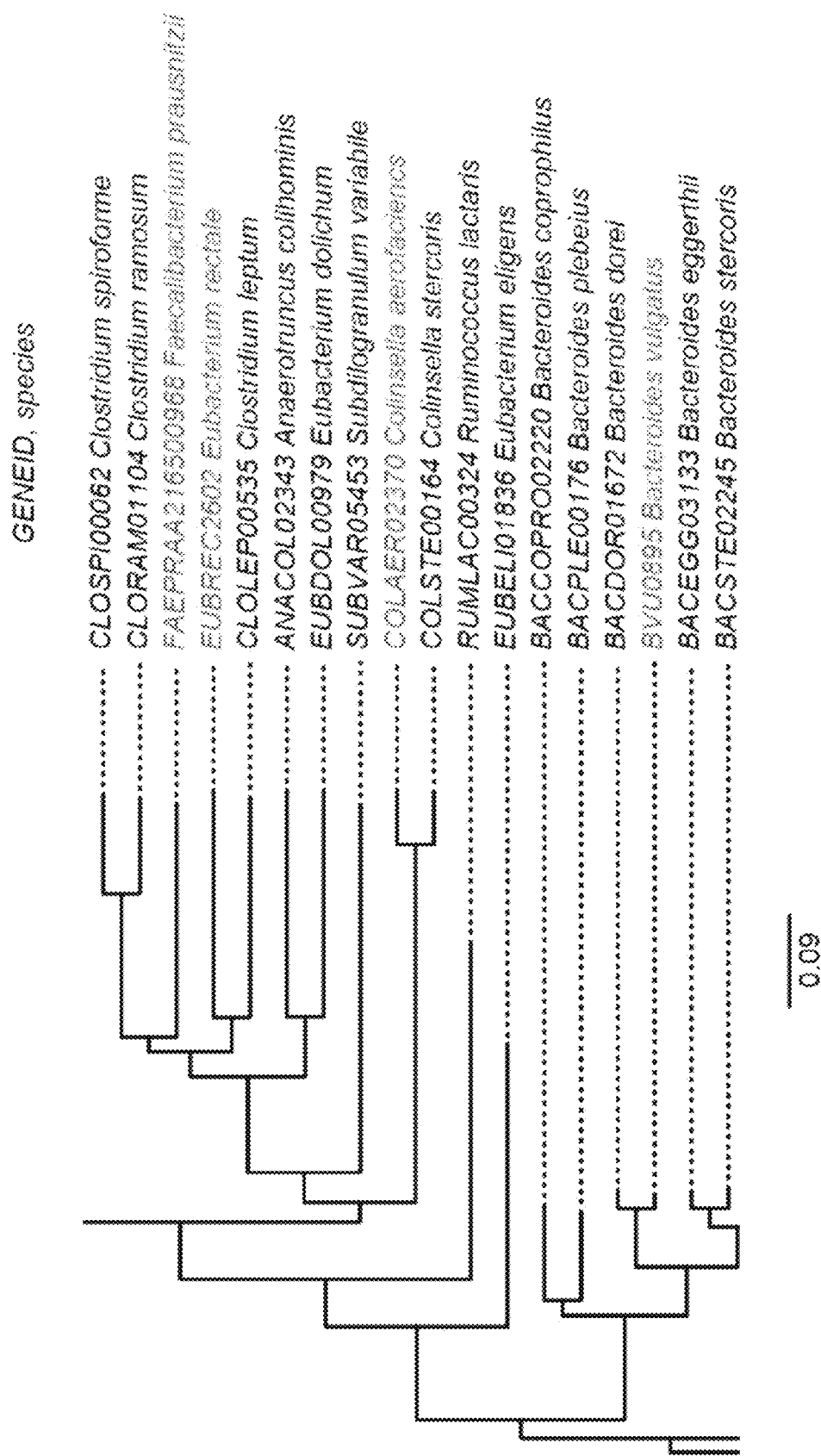
Figure 23C:
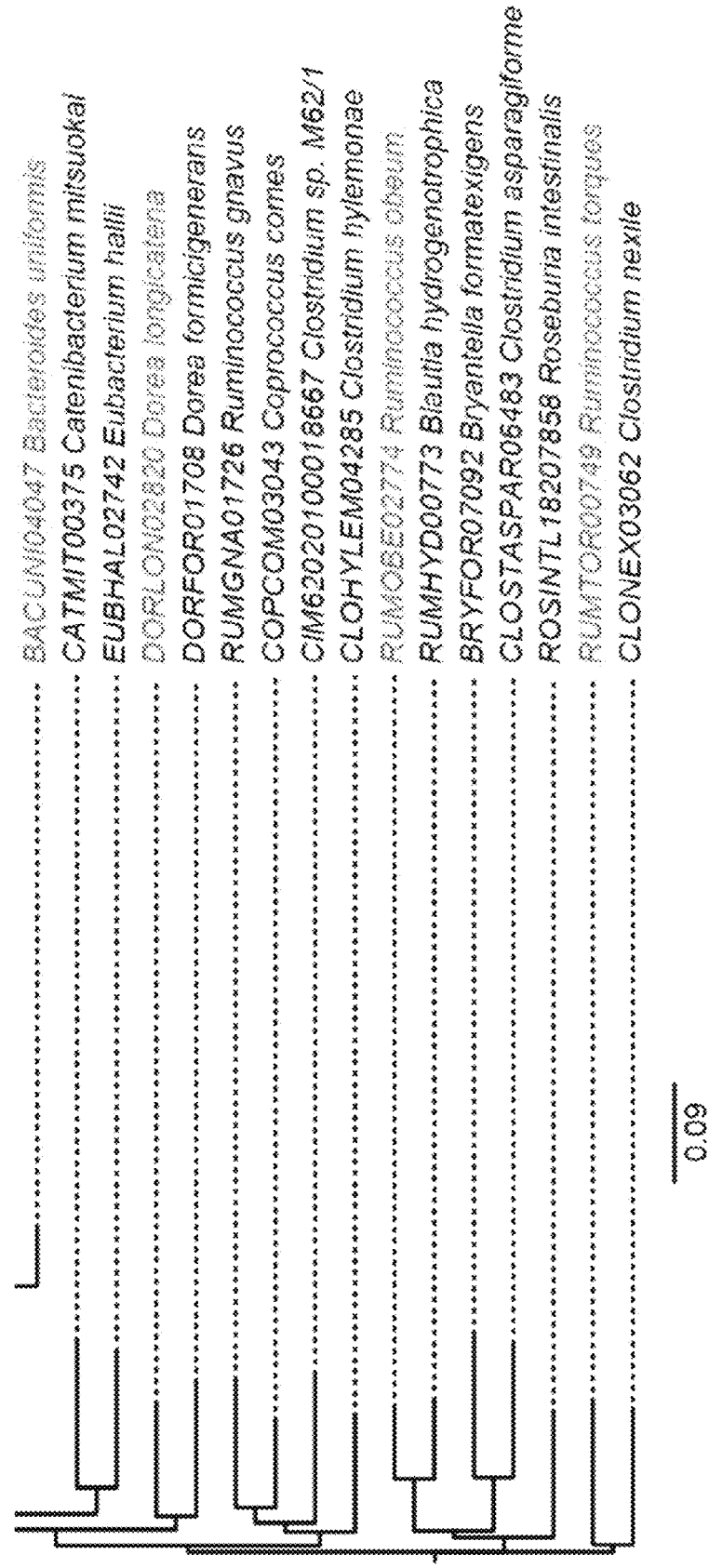

FIG. 23 depicts a phylogenetic tree of luxS genes present in human gut bacterial symbionts and enteropathogens. (A-C) The tree was constructed from amino-acid sequence alignments using Clustal X. Red type indicates that the homologue is represented in the genomes of members of the 14-member artificial human gut bacterial community.

Figure 24:
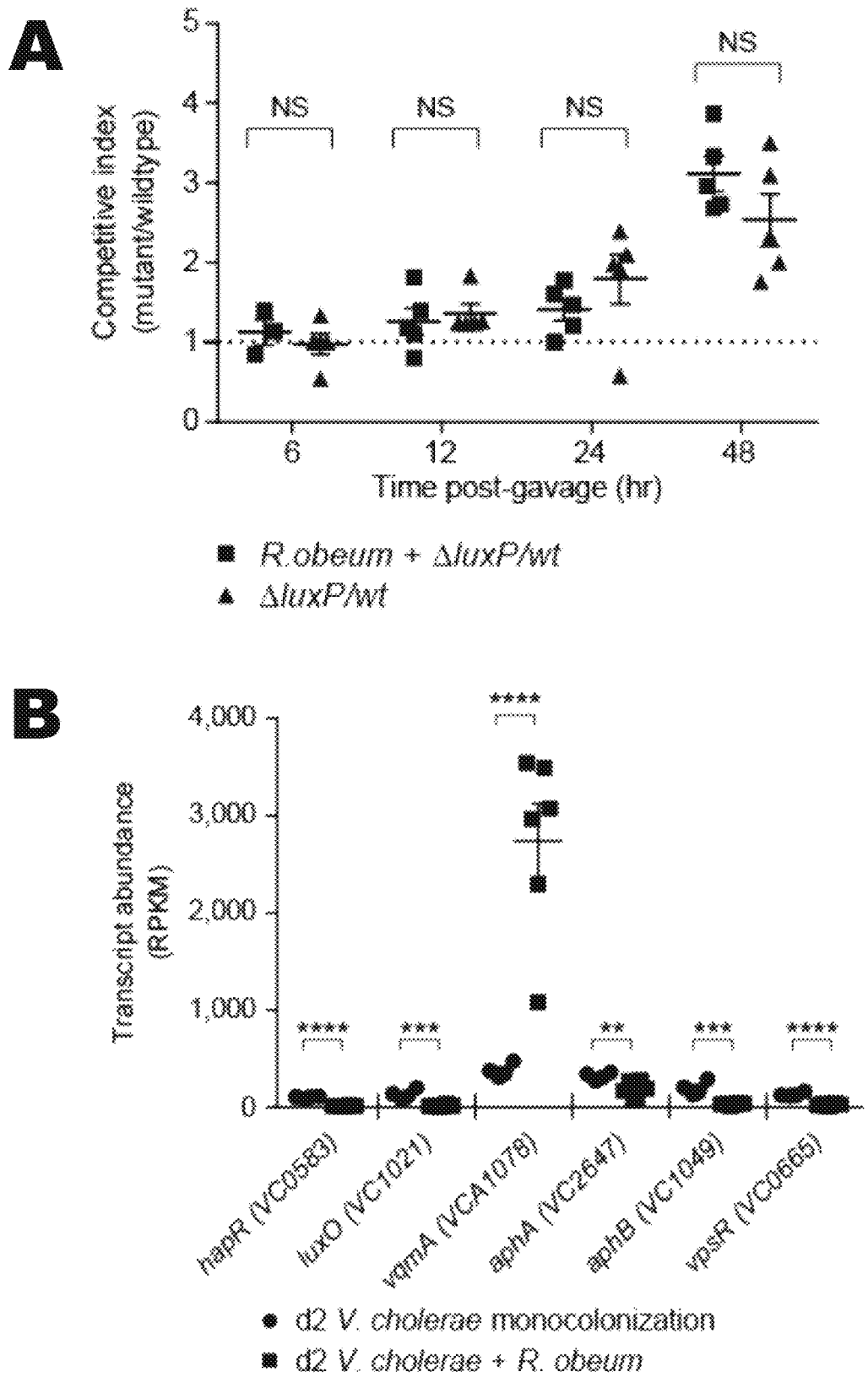

FIG. 24 graphically depicts in vivo tests of the effects of known quorum-sensing components on *R. obeum*-mediated reductions in *V. cholerae* colonization. (A) Competitive index of ΔluxP versus wild-type C6706 *V. cholerae* when colonized with or without *R. obeum* (n=4-6 animals per group). Horizontal bars, mean values. Data from individual animals are shown using the indicated symbols. (B) Transcript abundance (reads per kilobase per million reads) for selected quorum-sensing and virulence gene regulators in *V. cholerae*. Microbial RNA-seq was performed on faecal samples collected 2 days after mono-colonization of germ-free mice with *V. cholerae* (circles), or 2 days after *V. cholerae* was introduced into mice that had been monocolonized for 7 days with *R. obeum* (squares) (n=5 animals per group; NS, not significant (P≥0.05); P<0.01, *P<0.001, ****P<0.0001 (unpaired two-tailed Student's t-test)).

DETAILED DESCRIPTION

Applicants have discovered that maturation of the gut microbiota in healthy subjects (i.e. normal maturation of the gut microbiota) can be characterized or defined by a minimal number of bacterial taxa whose relative abundance changes over time. Accordingly, the present invention provides a method to identify a set of bacterial taxa that define normal maturation of the gut microbiota. The set of bacterial taxa can also be used to characterize the maturity of a test subject's gut microbiota. Determining whether the maturation of a test subject's gut microbiota corresponds to the test subject's chronological age may be used to guide treatment decisions (e.g. an immature state may indicate a need to initiate or continue therapy) or evaluate the effectiveness of a therapy (e.g. no improvement or a worsening would indicate the therapy is not effective).

Applicants have also discovered a set of bacterial taxa that strongly correlate with normal maturation of the gut microbiota in healthy children and recovery from diseases that perturb a normal/healthy configuration of the gut microbiota in adults. Accordingly, the present invention provides methods for preventing and/or treating a disease in a subject in need thereof by administering a composition comprising one or more of those bacterial taxa. Useful combinations of bacterial taxa are disclosed herein.

The term "subject," as used herein, refers to a mammal, including, but not limited to, a dog, a cat, a rat, a mouse, a hamster, a mouse, a cow, a horse, a goat, a sheep, a pig, a camel, a non-human primate, and a human. In a preferred embodiment, a subject is a human.

As used herein, a "healthy subject" is a subject with no known or diagnosed disease. The health of a subject may also be assessed by anthropometric measurements. For humans, the World Health Organization (WHO) Department of Nutrition for Health and Development has published a set of reference standards for individuals of about 19 years of age or less (WHO child growth standards growth velocity based on weight, length and head circumference: methods and development; World Health Organization, 2009; or current edition). Similar standards are known in the art for other subjects. The terms "healthy subject" and "normal subject" may be used interchangeably.

As used herein, a "subject in need of treatment" or a "subject in need thereof" is a subject in need of prophylaxis against, or treatment for, a disease, preferably a gastrointestinal disease. In some embodiments, a subject in need of treatment may be a healthy subject. For example, a healthy subject may have an increased risk of developing a disease relative to the population at large. In other embodiments, a subject in need of treatment may have a disease. In certain embodiments, a subject may have an immature microbiota and, therefore, may be in need of treatment. The phrase "microbiota immaturity" is described in detail in Section 1(C).

As used herein, the term "gut microbiota" refers to microbes that have colonized and inhabit the gastrointestinal tract of a subject. While various aspects of the present invention are exemplified with bacteria, the invention is applicable to all microbes including, but not limited to, archaea, bacteria, fungi, protists and viruses. A subject's gut microbiota may be naturally acquired or artificially established. Means by which a subject naturally acquires its gut microbiota are well known. Such examples may include, but are not limited to, exposure during birth, environmental exposure, consumption of foods, and coprophagy. Means by which a subject's gut microbiota may be artificially established are also well known. For example, artificially established gut microbial communities can be established in gnotobiotic animals by inoculating an animal with a defined or undefined consortium of microbes. Typically, a naturally acquired gut microbiota is comprised of both culturable and unculturable components. An artificially acquired gut microbiota may be similarly comprised of both culturable and unculturable components, or may consist of only culturable components. The phrase "culturable components" refers to the microbes comprising the gut microbiota that may be cultured in vitro using techniques known in the art. Culture collections of gut microbial communities are described in detail in PCT/US2012/028600, incorporated herein in its entirety by reference.

As used herein, the phrase "normal maturation of the gut microbiota" refers to the ordered change in the relative abundances of bacterial taxa in the gut microbiota over time, as determined from a group of healthy subjects.

As used herein, the phrase "chronological age of a subject" refers to the amount of time a subject has lived.

I. Normal Maturation of the Gut Microbiota

Applicants have discovered that the proportional representation of a minimal number of bacterial taxa defines a healthy gut microbiota as it assembles (i.e. matures). The changes in the relative abundance of these bacterial taxa over time are consistent across substantially all healthy subjects within the same age range. Accordingly, the present invention provides a method to accurately characterize the maturity of a subject's gut microbiota using a limited amount of information. This is exemplified in the Examples using a group of subjects between 0 and about 2 years of age. However, without wishing to be bound by theory, the gut microbiota of a human relatively stabilizes after about 2-3 years provided there are no insults. When there is an insult, the gut microbiota regresses to an immature state that can be discriminated using the relative abundances of these same bacterial taxa.

A. Methods to Define Normal Maturation of the Gut Microbiota Using a Limited Number of Bacterial Taxa In an aspect, the present invention provides a method to define normal maturation of the gut microbiota using a limited number of bacterial taxa found in the gut microbiota. The relative abundances of these limited number of bacterial taxa, referred to herein as "age-discriminatory bacterial taxa", in gut microbiota samples obtained from healthy subjects changes over time in a consistent way across substantially all healthy subjects within the same age range. Regressing the relative abundance of age-discriminatory taxa in their gut microbiota against the chronological age of each healthy subject at the time a sample of the gut microbiota was collected produces a regression model that may be used to characterize the maturity of another subject's gut microbiota to provide a measure of gastrointestinal health without having to query the whole microbiota.

A method for identifying a group of age-discriminatory taxa that define normal maturation of the gut microbiota is described in detail in the Examples. Briefly, a method for identifying a group of age-discriminatory bacterial taxa comprises (a) providing, for each healthy subject, a relative abundance for the bacterial taxa comprising the healthy subject's gut microbiota, wherein the relative abundance of the bacterial taxa in the subject's gut microbiome was determined from a plurality of gut microbiota samples obtained at intervals of time, (b) applying a regression analysis to model the relative abundance of the bacterial taxa comprising each healthy subject's gut microbiota against the amount of time the subject has lived (i.e. the chronological age of the healthy subject) at the time the gut microbiota sample was collected, and (c) selecting the minimum number of bacterial taxa needed for the model to predict gut microbiota age.

Methods for profiling the relative abundances of bacterial taxa in biological samples, including biological samples of gut microbiota, are well known in the art. Suitable methods may be sequencing-based or array-based. An exemplary method is detailed in the Examples. Briefly, the bacterial component of a gut microbiota sample is characterized by sequencing a nucleic acid suitable for taxonomic classification and assigning the sequencing reads to operational taxonomic units (OTUs) with ≥97% nucleotide sequence identity to a database of annotated and representative sequences. An example of such a database is Greengenes version 4feb2011; however any suitable database may be used. After OTUs are defined, a representative sequence from each OTU can be selected and compared to a reference set. If a match is identified in the reference set, that OTU can be given an identity. Relative abundance of a bacterial taxon may be defined by the number of sequencing reads that can be unambiguously assigned to each taxon after adjusting for genome uniqueness.

Generally speaking, a suitable nucleic acid used for taxonomic classification is universally distributed among the gut microbial population being queried allowing for the analysis of phylogenetic relationships among distant taxa, and has both a conserved region and at least one region subject to variation. The presence of at least one variable region allows sufficient diversification to provide a tool for classification, while the presence of conserved regions enables the design of suitable primers for amplification (if needed) and/or probes for hybridization for various taxa at different taxonomic levels ranging from individual strains to whole phyla. While any suitable nucleic acid known in the art may be used, one skilled in the art will appreciate that selection of a nucleic acid or region of a nucleic acid to amplify may differ by environment. In some embodiments, a nucleic acid queried is a small subunit ribosomal RNA gene. For bacterial and archaeal populations, at least the V1, V2, V3, V4, V5, V6, V7, V8 and/or V9 regions of the 16S rRNA gene are suitable, though other suitable regions are known in the art. Guidance for selecting a suitable 16S rRNA region to amplify can be found throughout the art, including Guo F et al. PLOS One 8(10) e76185, 2013; Soergel DAW et al. ISME Journal 6: 1440, 2012; and Hamady M et al. Genome Res. 19:1141, 2009, each hereby incorporated by reference in its entirety.

As used herein, "gut microbiota sample" refers to a biological sample comprising a plurality of heterogeneous nucleic acids produced by a subject's gut microbiota. Fecal samples are commonly used in the art to sample gut microbiota. Methods for obtaining a fecal sample from a subject are known in the art and include, but are not limited to, rectal swab and stool collection. Suitable fecal samples may be freshly obtained or may have been stored under appropriate temperatures and conditions known in the art. Methods for extracting nucleic acids from a fecal sample are also well known in the art. The extracted nucleic acids may or may not be amplified prior to being used as an input for profiling the relative abundances of bacterial taxa, depending upon the type and sensitivity of the downstream method. When amplification is desired, nucleic acids may be amplified via polymerase chain reaction (PCR). Methods for performing PCR are well known in the art. Selection of nucleic acids or regions of nucleic acids to amplify are discussed above. The nucleic acids comprising the nucleic acid sample may also be fluorescently or chemically labeled, fragmented, or otherwise modified prior to sequencing or hybridization to an array as is routinely performed in the art.

Gut microbiota samples may be obtained from a healthy subject at any suitable interval of time, varying from minutes to hours apart, days to weeks apart, or even weeks to months apart. Gut microbiota samples may be obtained multiple times a day, week, month or year. The duration of sampling can also vary. For example, the duration of sampling may be for about a month, about 6 months, about 1 year, about 2 years, about 3 years, about 4 years, about 5 years, about 6 years, about 7 years, about 8 years, about 9 years, about 10 years, about 11 years, about 12 years, about 13 years, about 14 years, about 15 years, about 16 years, about 17 years, about 18 years, about 19 years, about 20 years, about 30 years, or more.

The number of healthy subjects from which gut microbiota samples are obtained can and will vary. Generally, a suitable number is the number of healthy subjects needed to give the model produced by the regression analysis an acceptable degree of statistical significance. For example, the number of subject may be 3, 4, 5, 6, 7, 8, 9, 10, 11, 12 or more subjects.

Any suitable machine learning algorithm may be used to regress relative abundances of bacterial taxa against the amount of time the healthy subject has lived at the time the gut microbiota sample was collected. Preferably, the algorithm is able to detect both linear and nonlinear relationships between the bacterial taxa and chronologic age. In an exemplary embodiment, the Random Forests machine learning algorithm is used. The regression analysis produces a model that is a prediction of the gut microbiota age based on the microbial taxa present in the subject's gut microbiota sample.

Before selecting a minimal number of bacterial taxa required to discriminate different periods of post-natal life, the importance of the bacterial taxa are first determined. An "importance score" for the bacterial taxa may be an output of the learning algorithm. Generally, a ranked list of all bacterial taxa, in order of "age-discriminatory importance" may be determined by considering those taxa, whose relative abundance values when permuted leads to a meaningful increase in the error. Bacterial taxa ranked higher on the list (e.g. 1, 2, 3) have a larger increase in error than those lower on the list (e.g. 61, 62, 63). To select a minimal number of bacterial taxa, the predictive performance of sets comprising increasing numbers of the top-ranking bacterial taxa may be evaluated, and when minimal improvements in the predictive performance are observed after adding a new member to the set, then a minimal number of bacterial taxa have been identified. An example of a minimal improvement may be when the root mean-squared error of prediction remains below about 4 or aobut 5 months.

These steps produce a "sparse model" that is a prediction of the gut microbiota age based only on the relative abundance of age-discriminatory bacterial taxa present in a sample of the subject's gut microbiota. Additional bacterial taxa may be added to the sparse model to improve the model's performance, though the overall contribution of the additional bacterial taxa is usually minimal.

B. Useful Groups of Bacterial Taxa to Define Normal Maturation of the Gut Microbiota In another aspect, the present invention provides a group of bacterial taxa that define normal maturation of the gut microbiota (i.e. a group of age-discriminatory taxa). The phrase "normal maturation of the gut microbiota" is defined above. A group of bacterial taxa that define normal maturation of the gut microbiota can be used to characterize the maturity of a subject's gut microbiota. Stated another way, a group of bacterial taxa that define normal maturation of the gut microbiota can be used to determine whether the maturity of a subject's gut microbiota corresponds to what would be predicted by the subject's chronological age. Such information can be used to guide treatment decisions (e.g. an immature state may indicate a need to initiate or continue therapy) or evaluate the effectiveness of a therapy (e.g. no improvement or a worsening would indicate the therapy is not effective).

In some embodiments, a group of bacterial taxa that define normal maturation of the gut microbiota in may comprise at least 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or at least 59 of the bacterial taxa listed in Table A. In preferred embodiments, a group of bacterial taxa that define normal maturation of the gut microbiota in may comprise at least 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or at least 59 of the bacterial taxa listed in Table A. A bacterial isolate can be identified as belonging to a bacterial taxon listed in Table A if the V4 region of the 16S rRNA gene of the bacterial isolate has at least 97% sequence identity to any of SEQ ID NOs: 1-60. For example, the V4 region of the 16S rRNA gene of the bacterial isolate can have 97%, 97.5%, 98%, 98.5%, 99%, 99.5%, or 100% sequence identity to any of SEQ ID NOs: 1-60.

TABLE A

| ROW NO. | SEQ ID NO. | Bacterial Taxon |
|---|---|---|
| 1 | 1 | *Faecalibacterium prausnitzii* OTU ID 326792 |
| 2 | 2 | *Ruminococcus* sp. 5 1 39BFAA OTU ID 189827 |
| 3 | 3 | *Lactobacillus ruminis* OTU ID 470663 |
| 4 | 4 | *Dorea longicatena* OTU ID 191687 |
| 5 | 5 | *Bifidobacterium longum* OTU ID 72820 |
| 6 | 6 | *Ruminococcus* sp. 5 1 39BFAA OTU ID 194745 |
| 7 | 7 | *Lactobacillus mucosae* OTU ID 15141 |
| 8 | 8 | *Bifidobacterium* OTU ID 561483 |
| 9 | 9 | *Staphylococcus* OTU ID 217996 |
| 10 | 10 | *Ruminococcus* sp. 5 1 39BFAA OTU ID 364234 |
| 11 | 11 | *Catenibacterium mitsuokai* OTU ID 287510 |
| 12 | 12 | *Dorea formicigenerans* OTU ID 261912 |
| 13 | 13 | *Ruminococcus torques* OTU ID 361809 |
| 14 | 14 | *Streptococcus thermophilus* OTU ID 108747 |
| 15 | 15 | *Bifidobacterium* sp. OTU ID 533785 |
| 16 | 16 | *Haemophilus parainfluenzae* OTU ID 9514 |
| 17 | 17 | *Streptococcus* sp. OTU ID 561636 |
| 18 | 18 | *Clostridium* sp. OTU ID 312461 |
| 19 | 19 | *Clostridium ramosum* OTU ID 470139 |
| 20 | 20 | *Clostridium* sp. OTU ID 181834 |
| 21 | 21 | *Weissella cibaria* OTU ID 148099 |
| 22 | 22 | *Bifidobacterium* sp. OTU ID 469873 |
| 23 | 23 | *Clostridiales* sp. OTU ID 185951 |
| 24 | 24 | *Ruminococcaceae* sp. OTU ID 212619 |
| 25 | 25 | *Bifidobacterium bifidum* OTU ID 469852 |
| 26 | 26 | *Eubacterium desmolans* OTU ID 170124 |
| 27 | 27 | *Faecalibacterium prausnitzii* OTU ID 187010 |
| 28 | 28 | *Prevotella copri* OTU ID 303304 |
| 29 | 29 | *Lactobacillus reuteri* OTU ID 470527 |

TABLE A-continued

| ROW NO. | SEQ ID NO. | Bacterial Taxon |
|---|---|---|
| 30 | 30 | *Enterobacteriaceae* sp. OTU ID 210269 |
| 31 | 31 | *Clostridium glycolicum* OTU ID 182202 |
| 32 | 32 | *Ruminococcus obeum* OTU ID 178122 |
| 33 | 33 | *Enterococcus faecalis* OTU ID 540230 |
| 34 | 34 | *Prevotella copri* OTU ID 309068 |
| 35 | 35 | *Bifidobacterium* sp. OTU ID 24773 |
| 36 | 36 | *Enterococcus* sp. OTU ID 554755 |
| 37 | 37 | *Escherichia coli* OTU ID 305760 |
| 38 | 38 | *Prevotella* sp. OTU ID 268604 |
| 39 | 39 | *Faecalibacterium prausnitzii* OTU ID 188900 |
| 40 | 40 | *Eubacterium hallii* OTU ID 174256 |
| 41 | 41 | *Bacteroides fragilis* OTU ID 130663 |
| 42 | 42 | *Streptococcus* sp. OTU ID 292424 |
| 43 | 43 | *Staphylococcus* sp. OTU ID 269541 |
| 44 | 44 | *Ruminococcus* sp. 5 1 39BFAA OTU ID 191900 |
| 45 | 45 | *Dialister* sp. OTU ID 48207 |
| 46 | 46 | *Collinsella aerofaciens* OTU ID 186029 |
| 47 | 47 | *Clostridium bartlettii* OTU ID 325608 |
| 48 | 48 | *Lactobacillus* sp. OTU ID 252321 |
| 49 | 49 | *Prevotella* sp. OTU ID 195574 |
| 50 | 50 | *Ruminococcus* sp. 5 1 39BFAA OTU ID 365047 |
| 51 | 51 | *Lactobacillus ruminis* OTU ID 471308 |
| 52 | 52 | *Enterobacteriaceae* sp. OTU ID 307981 |
| 53 | 53 | *Streptococcus* sp. OTU ID 15382 |
| 54 | 54 | *Clostridium disporicum* OTU ID 302844 |
| 55 | 55 | *Streptococcus parasanguinis* OTU ID 528842 |
| 56 | 56 | *Bifidobacterium* sp. OTU ID 131391 |
| 57 | 57 | *Megamonas* sp. OTU ID 259261 |
| 58 | 58 | *Clostridium* sp. OTU ID 248563 |
| 59 | 59 | *Megasphaera* sp. OTU ID 162427 |
| 60 | 60 | *Lactobacillus* sp. OTU ID 545371 |

The SEQ ID NO can be used to identify the representative 16S rRNA sequence for the OTU ID (OTU ID = 16S rRNA OTU ID corresponding to Greengenes version 4 Feb. 2011).

In other embodiments, a group of bacterial taxa that define normal maturation of the gut microbiota comprises (a) at least 12 bacterial taxa listed in Table B; and (b) at least 12 bacterial taxa listed in Table C. In other embodiments, a group of bacterial taxa that define normal maturation of the gut microbiota comprises (a) at least 16 bacterial taxa listed in Table B; and (b) at least 8 bacterial taxa listed in Table C. In other embodiments, a group of bacterial taxa that define normal maturation of the gut microbiota comprises (a) at least 20 bacterial taxa listed in Table B; and (b) at least 4 bacterial taxa listed in Table C. In other embodiments, a group of bacterial taxa that define normal maturation of the gut microbiota comprises the bacterial taxa listed in Table B. In other embodiments, a group of bacterial taxa that define normal maturation of the gut microbiota consists of the bacterial taxa listed in Table B. A bacterial isolate can be identified as belonging to a bacterial taxon listed in Table B or Table C if the V4 region of the 16S rRNA gene of the bacterial isolate has at least 97% sequence identity to any of SEQ ID NOs: 1-24 (Table A), or 25-60 (Table B). For example, the V4 region of the 16S rRNA gene of the bacterial isolate can have 97%, 97.5%, 98%, 98.5%, 99%, 99.5%, or 100% sequence identity to any of SEQ ID NOs: 1-60.

TABLE B

| ROW NO. | SEQ ID NO. | Bacterial Taxon |
|---|---|---|
| 1 | 1 | *Faecalibacterium prausnitzii* OTU ID 326792 |
| 2 | 2 | *Ruminococcus* sp. 5 1 39BFAA OTU ID 189827 |
| 3 | 3 | *Lactobacillus ruminis* OTU ID 470663 |
| 4 | 4 | *Dorea longicatena* OTU ID 191687 |
| 5 | 5 | *Bifidobacterium longum* OTU ID 72820 |

TABLE B-continued

| ROW NO. | SEQ ID NO. | Bacterial Taxon |
|---|---|---|
| 6 | 6 | *Ruminococcus* sp. 5_1_39BFAA OTU ID 194745 |
| 7 | 7 | *Lactobacillus mucosae* OTU ID 15141 |
| 8 | 8 | *Bifidobacterium* OTU ID 561483 |
| 9 | 9 | *Staphylococcus* OTU ID 217996 |
| 10 | 10 | *Ruminococcus* sp. 5_1_39BFAA OTU ID 364234 |
| 11 | 11 | *Catenibacterium mitsuokai* OTU ID 287510 |
| 12 | 12 | *Dorea formicigenerans* OTU ID 261912 |
| 13 | 13 | *Ruminococcus torques* OTU ID 361809 |
| 14 | 14 | *Streptococcus thermophilus* OTU ID 108747 |
| 15 | 15 | *Bifidobacterium* sp. OTU ID 533785 |
| 16 | 16 | *Haemophilus parainfluenzae* OTU ID 9514 |
| 17 | 17 | *Streptococcus* sp. OTU ID 561636 |
| 18 | 18 | *Clostridium* sp. OTU ID 312461 |
| 19 | 19 | *Clostridium ramosum* OTU ID 470139 |
| 20 | 20 | *Clostridium* sp. OTU ID 181834 |
| 21 | 21 | *Weissella cibaria* OTU ID 148099 |
| 22 | 22 | *Bifidobacterium* sp. OTU ID 469873 |
| 23 | 23 | *Clostridiales* sp. OTU ID 185951 |
| 24 | 24 | *Ruminococcaceae* sp. OTU ID 212619 |

The SEQ ID NO can be used to identify the representative 16S rRNA sequence for the OTU ID (OTU ID = 16S rRNA OTU ID corresponding to Greengenes version 4 Feb. 2011).

TABLE C

| ROW NO. | SEQ ID NO. | Bacterial Taxon |
|---|---|---|
| 1 | 25 | *Bifidobacterium bifidum* OTU ID 469852 |
| 2 | 26 | *Eubacterium desmolans* OTU ID 170124 |
| 3 | 27 | *Faecalibacterium prausnitzii* OTU ID 187010 |
| 4 | 28 | *Prevotella copri* OTU ID 303304 |
| 5 | 29 | *Lactobacillus reuteri* OTU ID 470527 |
| 6 | 30 | *Enterobacteriaceae* sp. OTU ID 210269 |
| 7 | 31 | *Clostridium glycolicum* OTU ID 182202 |
| 8 | 32 | *Ruminococcus obeum* OTU ID 178122 |
| 9 | 33 | *Enterococcus faecalis* OTU ID 540230 |
| 10 | 34 | *Prevotella copri* OTU ID 309068 |
| 11 | 35 | *Bifidobacterium* sp. OTU ID 24773 |
| 12 | 36 | *Enterococcus* sp. OTU ID 554755 |
| 13 | 37 | *Escherichia coli* OTU ID 305760 |
| 14 | 38 | *Prevotella* sp. OTU ID 268604 |
| 15 | 39 | *Faecalibacterium prausnitzii* OTU ID 188900 |
| 16 | 40 | *Eubacterium hallii* OTU ID 174256 |
| 17 | 41 | *Bacteroides fragilis* OTU ID 130663 |
| 18 | 42 | *Streptococcus* sp. OTU ID 292424 |
| 19 | 43 | *Staphylococcus* sp. OTU ID 269541 |
| 20 | 44 | *Ruminococcus* sp. 5_1_39BFAA OTU ID 191900 |
| 21 | 45 | *Dialister* sp. OTU ID 48207 |
| 22 | 46 | *Collinsella aerofaciens* OTU ID 186029 |
| 23 | 47 | *Clostridium bartlettii* OTU ID 325608 |
| 24 | 48 | *Lactobacillus* sp. OTU ID 252321 |
| 25 | 49 | *Prevotella* sp. OTU ID 195574 |
| 26 | 50 | *Ruminococcus* sp. 5_1_39BFAA OTU ID 365047 |
| 27 | 51 | *Lactobacillus ruminis* OTU ID 471308 |
| 28 | 52 | *Enterobacteriaceae* sp. OTU ID 307981 |
| 29 | 53 | *Streptococcus* sp. OTU ID 15382 |
| 30 | 54 | *Clostridium disporicum* OTU ID 302844 |
| 31 | 55 | *Streptococcus parasanguinis* OTU ID 528842 |
| 32 | 56 | *Bifidobacterium* sp. OTU ID 131391 |
| 33 | 57 | *Megamonas* sp. OTU ID 259261 |
| 34 | 58 | *Clostridium* sp. OTU ID 248563 |
| 35 | 59 | *Megasphaera* sp. OTU ID 162427 |
| 36 | 60 | *Lactobacillus* sp. OTU ID 545371 |

The SEQ ID NO can be used to identify the representative 16S rRNA sequence for the OTU ID (OTU ID = 16S rRNA OTU ID corresponding to Greengenes version 4 Feb. 2011).

C. Method for Characterizing the Maturity of a Subject's Gut Microbiota

In another aspect, the present invention provides a method to determine the maturity of a subject's gut microbiota. The method may comprise: (a) calculating a relative abundance for each bacterial taxon in a group bacterial taxa, from a fecal sample obtained from the subject; (b) applying the relative abundances of the bacterial taxa from step (a) to a regression model to determine a microbiota age for the subject's gut microbiota, wherein the model regresses, for a group of healthy subjects, relative abundances of the same bacterial taxa, as determined from a plurality of gut microbiota samples obtained over time for each healthy subject in the group, against the chronological age of each healthy subject in the group at the time the gut microbiota sample was collected; and (c) calculating the maturity of the subject's gut microbiota using the subject's microbiota age. In some embodiments, the calculation for maturity is defined as relative maturity, and relative maturity=(microbiota age of the subject)−(microbiota age of a healthy subject of a similar chronological age). In other embodiments, the calculation for maturity is defined as a Microbiota-for-Age Z score (MAZ), wherein MAZ=((microbiota age of the subject)−(median microbiota age of a healthy subject of a similar chronological age))/(standard deviation of microbiota age of healthy subjects of the similar chronological age). In each embodiment above, the group of bacterial taxa can be a group described above in Section I(B), which are incorporated into this Section by reference. Alternatively, the group of bacterial taxa can be identified using a method described in Section I(A), which are incorporated into this Section by reference. Methods for calculating a relative abundance for a bacterial taxon are described in Section I(A). In a preferred embodiment, the subject is human that is about 2 years of age or less. In another preferred embodiment, the subject is a human that is about 5 years of age or less. In another preferred embodiment, the subject is a human that is about 10 years of age or less. In another preferred embodiment, the subject is a human that is about 20 years of age or less. In another preferred embodiment, the subject is a human that is about 30 years of age or less. In another preferred embodiment, the subject is a human that is about 40 years of age or less. In another preferred embodiment, the subject is a human that is about 50 years of age or less. In another preferred embodiment, the subject is a human that is about 60 years of age or less. In another preferred embodiment, the subject is a human that is about 70 years of age or less. In another preferred embodiment, the subject is a human that is about 80 years of age or less. In another preferred embodiment, the subject is a human that is about 90 years of age or less. In another preferred embodiment, the subject is a human that is about 100 years of age or less. In another preferred embodiment, the subject is a human that is about 110 years of age or less. In exemplary embodiments, the group of bacterial taxa is a group listed in Table A or Table B.

In another aspect, the present invention provides a method to classify a subject. For example, because the relative abundances of the age-discriminatory taxa change in a consistent way that corresponds to the chronological age of healthy subjects, it is also possible to classify the maturity of a subject's gut microbiota as perturbed if the abundances of the age-discriminatory taxa are not as predicted by the subject's chronological age. Within the classification of "perturbed maturation, a subject may an immature gut microbiota (i.e. the subject's microbiota age is less than predicted by chronological age alone), or a subject may have a gut microbiota that matured faster than normal (i.e. the subject's microbiota age is less than predicted by chronological age alone).

A method to classify a subject may comprise: (a) calculating a relative abundance for each bacterial taxon in a group bacterial taxa, from a fecal sample obtained from the subject; (b) applying the relative abundances of the bacterial taxa from step (a) to a regression model to determine a microbiota age for the subject's gut microbiota, wherein the model regresses, for a group of healthy subjects, relative abundances of the same bacterial taxa, as determined from a plurality of gut microbiota samples obtained over time for each healthy subject in the group, against the chronological age of each healthy subject in the group at the time the gut microbiota sample was collected; and (c) classifying the subject as having normal gut maturation when the microbiota age of the subject is substantially similar to the microbiota age of a healthy subject of a similar age. The group of bacterial taxa can be a group described above in Section I(B), which are incorporated into this Section by reference. Alternatively, the group of bacterial taxa can be identified using a method described in Section I(A), which are incorporated into this Section by reference. Methods for calculating a relative abundance for a bacterial taxon are described in Section I(A). In a preferred embodiment, the subject is human that is about 2 years of age or less. In another preferred embodiment, the subject is a human that is about 5 years of age or less. In another preferred embodiment, the subject is a human that is about 10 years of age or less. In another preferred embodiment, the subject is a human that is about 20 years of age or less. In another preferred embodiment, the subject is a human that is about 30 years of age or less. In another preferred embodiment, the subject is a human that is about 40 years of age or less. In another preferred embodiment, the subject is a human that is about 50 years of age or less. In another preferred embodiment, the subject is a human that is about 60 years of age or less. In another preferred embodiment, the subject is a human that is about 70 years of age or less. In another preferred embodiment, the subject is a human that is about 80 years of age or less. In another preferred embodiment, the subject is a human that is about 90 years of age or less. In another preferred embodiment, the subject is a human that is about 100 years of age or less. In another preferred embodiment, the subject is a human that is about 110 years of age or less. In exemplary embodiments, the group of bacterial taxa is a group listed in Table A or Table B.

Alternatively, a method to classify a subject may comprise: (a) calculating a relative abundance for each bacterial taxon in a group, from a fecal sample obtained from the subject; (b) using the relative abundances of the bacterial taxa from step (a) and chronologic age of the subject to indicate the health status of the subject's gut microbiota (e.g. healthy or unhealthy; normal maturation of the gut microbiota or perturbed maturation of the gut microbiota) using a classification model; wherein the classification model is trained on datasets comprising measurements obtained from a plurality of healthy subjects and a plurality undernourished subjects. For example, the datasets may contain measurements from at least 4, 5, 6, 7, 8, 9, 10, 11, 12, or more healthy subjects and at least 4, 5, 6, 7, 8, 9, 10, 11, 12, or more undernourished subjects. The undernourished subjects may be subjects with acute malnutrition, moderate acute malnutrition, or at risk for moderate acute malnutrition, as defined in Section II. The measurements may at least include relative abundances of the same bacterial taxa from step (a) above from samples of the health and undernourished subjects' gut microbiota obtained over time for each subject, and the chronological age of the subject at the time the gut microbiota sample was collected. Additional measurements may optionally include MUAC measurements (as defined in Section II), WHZ measurements ((as defined in Section II), and other anthropometric measurements, as well as measurements such as a response to therapy. The group of bacterial taxa can be a group described above in Section I(B), which are incorporated into this Section by reference. Alternatively, the group of bacterial taxa can be identified using a method described in Section I(A), which are incorporated into this Section by reference. Methods for calculating a relative abundance for bacterial taxon are described in Section I(A). In a preferred embodiment, the subject is human that is about 2 years of age or less. In another preferred embodiment, the subject is a human that is about 5 years of age or less. In another preferred embodiment, the subject is a human that is about 10 years of age or less. In another preferred embodiment, the subject is a human that is about 20 years of age or less. In exemplary embodiments, the group of bacterial taxa is a group listed in Table A or Table B.

D. Method for Identifying the Effect of a Therapy

In another aspect, the present invention provides a method for identifying an effect of a therapy.

In some embodiments, a method for identifying an effect of a therapy may comprise (a) calculating a relative abundance for each bacterial taxon in a group, from a fecal sample obtained from the subject before and after administration of the therapy; (b) applying the relative abundances of the bacterial taxa from step (a) to a regression model to determine a microbiota age for the subject's gut microbiota before and after therapy, wherein the model regresses, for a group of healthy subjects, relative abundances of the same bacterial taxa, as determined from a plurality of gut microbiota samples obtained over time for each healthy subject in the group, against the chronological age of each healthy subject in the group at the time the gut microbiota sample was collected; wherein the therapy has an effect when the microbiota age of the subject changes after therapy. When the effect is positive, the microbiota age of the subject increases. When the effect is negative, the microbiota age of the subject decreases. The group of bacterial taxa can be a group described above in Section I(B), which are incorporated into this Section by reference. Alternatively, the group of bacterial taxa can be identified using a method described in Section I(A), which are incorporated into this Section by reference. Methods for calculating a relative abundance for a bacterial taxon are described in Section I(A). In a preferred embodiment, the subject is human that is about 2 years of age or less. In another preferred embodiment, the subject is a human that is about 5 years of age or less. In another preferred embodiment, the subject is a human that is about 10 years of age or less. In another preferred embodiment, the subject is a human that is about 20 years of age or less. In another preferred embodiment, the subject is a human that is about 30 years of age or less. In another preferred embodiment, the subject is a human that is about 40 years of age or less. In another preferred embodiment, the subject is a human that is about 50 years of age or less. In another preferred embodiment, the subject is a human that is about 60 years of age or less. In another preferred embodiment, the subject is a human that is about 70 years of age or less. In another preferred embodiment, the subject is a human that is about 80 years of age or less. In another preferred embodiment, the subject is a human that is about 90 years of age or less. In another preferred embodiment, the subject is a human that is about 100 years of age or less. In another preferred embodiment, the subject is a human that is about 110 years of age or less. In exemplary embodiments, the group of bacterial taxa is a group listed in Table A or Table B.

In other embodiments, a method for identifying an effect of a therapy may comprise (a) identifying a set of age-discriminatory bacterial taxa within the bacterial taxa comprising the gut microbiota a group of healthy subject's gut microbiota, the method comprising (i) providing, for each healthy subject, a relative abundance for the bacterial taxa comprising the subject's gut microbiota, wherein the relative abundance of the bacterial taxa in the healthy subject's gut microbiota was determined from a plurality of gut microbiota samples obtained at intervals of time; (ii) regressing the relative abundances of the bacterial taxa comprising each healthy subject's gut microbiota against the chronological age of the healthy subject at the time the gut microbiota sample was collected, thereby producing a prediction of a gut microbiota age that is based only on the relative abundance of age-discriminatory bacterial taxa present in the subject's gut microbiota; and (iii) selecting the minimum number of bacterial taxa from step (ii) that is needed to produce a prediction that is substantially similar to or better than the prediction of step (ii); calculating a relative abundance for each bacterial taxon in the set of age-discriminatory taxa from step (a)(iii), using a fecal sample obtained from a subject before and after administration of the therapy; and applying the relative abundances from step (b) to the prediction of gut microbiota age from step (a)(iii) to determine the microbiota age of the subject's gut microbiota before and after therapy; wherein the therapy has an effect when the microbiota age of the subject changes after therapy. When the effect is positive, then the microbiota age of the subject increases. When the effect is negative, then the microbiota age of the subject decreases. Methods for calculating a relative abundance for a bacterial taxon are described in Section I(A). In a preferred embodiment, the subject is human that is about 2 years of age or less. In another preferred embodiment, the subject is a human that is about 5 years of age or less. In another preferred embodiment, the subject is a human that is about 10 years of age or less. In another preferred embodiment, the subject is a human that is about 20 years of age or less. In another preferred embodiment, the subject is a human that is about 30 years of age or less. In another preferred embodiment, the subject is a human that is about 40 years of age or less. In another preferred embodiment, the subject is a human that is about 50 years of age or less. In another preferred embodiment, the subject is a human that is about 60 years of age or less. In another preferred embodiment, the subject is a human that is about 70 years of age or less. In another preferred embodiment, the subject is a human that is about 80 years of age or less. In another preferred embodiment, the subject is a human that is about 90 years of age or less. In another preferred embodiment, the subject is a human that is about 100 years of age or less. In another preferred embodiment, the subject is a human that is about 110 years of age or less.

II. Method of Preventing and/or Treating a Disease

In another aspect, the present invention provides a method for preventing and/or treating a disease in a subject in need thereof. As described in detail in the Examples, Applicants have discovered that certain bacterial taxa associated with normal maturation of the gut microbiota in healthy subjects (i.e. age-discriminatory taxa) are also associated with repair of the gut microbiota (i.e. recovery-indicative taxa) in subjects whose gut communities have been affected by a variety of insults (e.g. malnutrition or gastrointestinal disease). Accordingly, a method for preventing and/or treating a disease in a subject in need thereof may comprise administering to the subject a therapeutically effective amount of one or more age-indicative taxa associated with repair of the gut microbiota.

As used herein, "preventing" a disease refers to reducing the onset of symptoms or complications of a disease, condition or disorder (collectively, a "disease"), or the disease itself. Preventing a disease may involve reducing in treated subjects (e.g. a normal subject) (1) the incidence, development or formation of disease, (2) the development, duration, and/or severity of symptoms of disease, (3) death rates, or (4) a combination thereof. In each embodiment, the amount of reduction may each be about 10%, 20%, 30%, 40%, 50%, 60%, 70%, 80%, 90%, 95% or about 100% in treated subjects, as compared to untreated subjects. For an infectious disease (e.g. enteropathogenic infection), preventing a disease may also involve increasing the median infectious disease dose ($ID_{50}$) by about 10%, 20%, 30%, 40%, 50%, 60%, 70%, 80%, 90%, 95%, 100%, or more. Preventing a disease may also involve increasing the (relative) microbiota maturity, increasing bacterial diversity, increasing MAZ score.

As used herein, "treating" describes the management and care of a patient for the purpose of combating a disease in a subject. Treating a disease may involve reducing in treated subjects (1) the infectious burden (e.g. viral, bacterial, patristic load), (2) the duration and/or severity of symptoms of disease, (3) death rates, or (4) a combination thereof. In each embodiment, the amount of reduction may each be about 10%, 20%, 30%, 40%, 50%, 60%, 70%, 80%, 90%, 95% or about 100% in treated subjects, as compared to untreated subjects. Treating a disease may also involve increasing the (relative) microbiota maturity, increasing bacterial diversity, increasing MAZ score.

As used herein, "therapeutically effective amount" means an amount of one or more bacterial taxa of the invention that will elicit a desired biological or medical response of a tissue, system, or subject that is being sought by a researcher or clinician. In one aspect, the biological or medical response is prevention or treatment of a gastrointestinal disease. In another aspect, the biological or medical response is prevention or treatment of a gastrointestinal disease caused by an enteropathogenic infection. In another aspect, the biological or medical response is treatment or prevention of acute malnutrition. In another aspect, the biological or medical response is treatment or prevention of acute diarrheal disease. In another aspect, the biological or medical response is treatment or prevention of acute diarrheal disease caused by an enteropathogenic infection. In another aspect, the biological or medical response is treatment or prevention of chronic diarrheal disease.

As used herein, the phrase "bacterial taxa of the invention" refers to age-discriminatory bacterial taxa associated with repair of the gut microbiota. Methods for identifying age-discriminatory bacterial taxa are described in detail in Section I. In some embodiments, one or more bacterial taxa of the invention are selected from the group listed in Table A. In other embodiments, one or more bacterial taxa of the invention are selected from the group listed in Table B. In other embodiments, one or more bacterial taxa of the invention are selected from the group listed in Table C. Preferred combinations of bacterial taxa of the invention include, but are not limited to the combinations listed in Table D, or further described in Section III. Preferred combinations of bacterial taxa of the invention may also be identified by testing for a therapeutic effect in an appropriate animal model. Combinations may also be selected by identifying bacterial taxa associated with repair of the gut microbiota that are under-represented in a subject's gut microbiota as compared to a healthy subject. Section III also describes in further detail formulations comprising bacterial taxa of the invention for administration to a subject. Bacterial taxa of the invention are preferably administered orally or rectally. A bacterial taxon administered to a subject is isolated and biologically pure. A bacterial isolate can be identified as belonging to a bacterial taxon listed in Tables A-D if the V4 region of the 16S rRNA gene of the bacterial isolate has at least 97% sequence identity to any of SEQ ID NOs: 1-60. For example, the V4 region of the 16S rRNA gene of the bacterial isolate can have 97%, 97.5%, 98%, 98.5%, 99%, 99.5%, or 100% sequence identity to any of SEQ ID NOs: 1-60. The duration of therapy can and will vary, depending at least in part upon the disease and the severity of the disease. In subjects with an immature gut microbiota, one or more bacterial taxa of the invention may be administered until the microbiota age of the subject is similar to the microbiota age of a healthy subject of the same chronological age.

As used herein, "gastrointestinal diseases" refer to diseases involving the gastrointestinal tract. In some embodiments, the disease is malnutrition. In other embodiments, the disease is an infection caused by an enteropathogen. Non-limiting examples of enteropathogens include *Escherichia coli* (e.g. enterotoxigenic *E. coli*, enteropathogenic *E. coli*, enteroinvasive *E. coli*, enterohemorrhagic *E. coli*, enteroaggregative *E. coli*, etc.), *Salmonella enterica*, *Shigella* sp. (e.g. *S. flexneri*, *S. sonnei*, *S. dysenteriae*, etc.), *Camplobacter* sp. (e.g. *C. jejuni*, *C. coli*, *C. upsaliensis*, etc.), *Yersinia* sp. (e.g. *Y. enterocolitica*, *Y. pseudotuberculosis*, etc.), *Vibrio* sp. (e.g. *Vibrio cholera*, *Vibrio parahaemolyticus*, etc.) *Clostridum* sp. (*C. difficile*), *Entamoeba* sp. (e.g. *Entamoeba histolytica*, *Entamoeba dispar*, etc.) *Endolimax nana*, *Iodamoeba butschii*, *Chilomastix mesnili*, *Blastocystis hominis*, *Trichomonas hominis*, Coccidian-like body, *Giardia* sp. (e.g. *Giardia intestinalis*, *Giardia lamblia*, etc.) *Cryptosporidium parvum*, *Isospora belli*, *Dientamoeba fragilis*, Microsporidia, *Strongyloides stercoralis*, *Angiostrongylus costaricensis*, *Schistosoma* sp. (e.g. *S. mansoni*, *S. japonicum*, etc.) *Cyclospora cayetanensis*, *Enterocytozoon* sp. (e.g. *Enterocytozoon bieneusi*, *Enterocytozoon helium*, etc.) *Encephalitozoon* sp. (e.g. *Encephalitozoon intestinalis*, *Encephalitozoon cuniculi*, etc.) *Ascaris lumbricoides*, *Trichuris tricuria*, *Ancylostoma duodenale*, *Necator americanus*, *Hymenolepsis nana*, rotaviruses, human caliciviruses (e.g. noroviruses and sapoviruses), astroviruses, cytolomegaloviruses. In other embodiments, the disease is ulcerative colitis, necrotizing enterocolitis, or Crohn's disease. In still other embodiments, the disease is traveler's diarrhea. In a preferred embodiment, the disease is acute malnutrition. In another preferred embodiment, the disease is an enteropathogen infection that has as a symptom acute diarrhea. In an exemplary embodiment, the disease is a *Vibrio cholerae* infection.

Acute malnutrition results from decreased food consumption and/or illness resulting in sudden weight loss. It is associated with greater risk of medical complications and infections, increased risk of death from illness and infections, and micronutrient deficiencies. Non-limiting examples of micronutrient deficiencies associated with acute malnutrition are iron deficiency, iodine deficiency, and vitamin A deficiency. The most common way to assess malnutrition, particularly in humans of about 19 years of age or less, is through anthropometric measurements. It is usually diagnosed in one of three ways: by weighing a subject and measuring the subject's height; by measuring the circumference of the subject's mid-upper arm (MUAC); and/or by checking for oedema in the subject's lower legs or feet. Acute malnutrition is divided into two types: severe acute malnutrition (SAM) and moderate acute malnutrition (MAM). A subject is classified as having SAM if the subject's weight-for-height Z-scores (WHZ) is below three standard deviations (−3 s.d.) from the median of the World Health Organization (WHO) reference growth standards. A subject with a WHZ between −2 s.d. and −3 s.d. from the median of the WHO reference growth standards is categorized as having MAM. If a subject is between about six months and about five years of age, a MUAC measurement of less than 12.5 cm also indicates that a subject is suffering from moderate acute malnutrition. Finally, the presence of oedema in both feet and lower legs of a subject is a sign of SAM. WHO reference growth standards are available from the WHO. See for example, World Health Organization Department of Nutrition for Health and Development: WHO child growth standards growth velocity based on weight, length and head circumference: methods and development; World Health Organization, 2009, or the current edition.

In some embodiments, the subject to be treated is a subject with acute malnutrition and a therapeutically effective amount of one or more bacterial taxa of the invention is administered to the subject. Treating acute malnutrition may involve reducing in treated subjects the duration and/or severity of symptoms of acute malnutrition, death rates associated with acute malnutrition, or a combination thereof. In each embodiment, the amount of reduction may each be about 10%, 20%, 30%, 40%, 50%, 60%, 70%, 80%, 90%, 95% or about 100% in treated subjects, as compared to untreated subjects. Treating acute malnutrition may also involve increasing a suitable anthropometric measurement in a treated subject including, but not limited to, a subject's WHZ or MUAC. For each aspect, the amount of increase may each be about 10%, 20%, 30%, 40%, 50%, 60%, 70%, 80%, 90%, 95% or about 100% in treated subjects, as compared to untreated subjects or as compared to the treated subject prior to administration of the combination of the invention. In certain embodiments, a subject's WHZ may improve to less than −3.0 s.d., less than −2.5 s.d., less than −2.0 s.d., less than −1.5 s.d., less than −1.0 s.d., or less than −0.5 s.d. from the median of the WHO reference growth standards. Treating acute malnutrition may also result in no worsening (i.e. decrease) in a subject's WHZ or MUAC. Treating acute malnutrition may also involve increasing the subject's relative gut microbiota maturity, MAZ score, gut microbiota diversity, or a combination thereof. The duration of treatment can and will vary. In certain embodiments, the duration of therapy is about 1, 2, 3, or 4 months. In other embodiments, the duration of therapy is about 1, 2, 3, 4, 5, 6, 7, or 8 weeks. In still other embodiments, the duration of therapy is about 4 to about 12 weeks, about 6 to about 10 weeks, or about 6 to about 8 weeks. Alternatively, a subject may be administered one or more bacterial taxa of the invention for as long as acute malnutrition persists. Useful combinations are described in further detail below. One or more bacterial taxa of the invention may be formulated for oral or rectal administration, and may be administered alone or with an additional therapeutic agent. Non-limiting examples of additional therapeutic agents include therapeutic foods, probiotics, antibiotics and vaccines. In exemplary embodiments, a subject with acute malnutrition is administered a therapeutically effective amount of one or more bacterial taxa of the invention and a therapeutic food. As used herein, "therapeutic food" refers to a food designed for specific, usually nutritional, therapeutic purposes as a form of dietary supplement. Therapeutic foods are usually made of a mixture of protein, carbohydrate, lipid and vitamins and minerals, and are usually produced by grinding all ingredients together, mixing them and packaging without water. The term "therapeutic foods" includes ready-to-use-therapeutic foods (RUTFs). Generally speaking, RUTFs are homogenous mixtures of lipid-rich and water-soluble foods. The lipids used in formulating RUTFs are in a viscous liquid form, and the other ingredients (e.g. protein, carbohydrate, vitamins, minerals) are mixed through the lipids. Non-limiting examples of therapeutic foods include F-75, F-100, K-Mix 2, Citadel spread, Plumpy'nut, Medika Mamba, Ensure, Fortisip, Energyzip, TwoCal, BP-100, and eeZee.

In other embodiments, the subject to be treated is a subject at risk for acute malnutrition and a therapeutically effective amount of one or more bacterial taxa of the invention is administered to the subject. A subject at risk for acute malnutrition may have limited access to nutritious foods and/or may have frequent exposure to infectious diseases. A subject at risk for acute malnutrition may also be a subject with a WHZ between 0 s.d. and −2 s.d., between −1 s.d and −2 s.d, or between −1.5 s.d and −2 s.d from the median of the WHO reference growth standards. Treating a subject at risk for acute malnutrition may prevent acute malnutrition in the subject. For example, preventing acute malnutrition may involve reducing in treated subjects (1) the incidence, development or formation of acute malnutrition, (2) the development, duration, and/or severity of symptoms of malnutrition, if malnutrition does develop, (3) death rates associated with acute malnutrition, or (4) a combination thereof. In each embodiment, the amount of reduction may each be about 10%, 20%, 30%, 40%, 50%, 60%, 70%, 80%, 90%, 95% or about 100% in treated subjects, as compared to untreated subjects. Preventing acute malnutrition may also involve increasing a suitable anthropometric measurement in a treated subject including, but not limited to, a subject's WHZ or MUAC. For each aspect, the amount of increase may each be about 10%, 20%, 30%, 40%, 50%, 60%, 70%, 80%, 90%, 95% or about 100% in treated subjects, as compared to untreated subjects or as compared to the treated subject prior to administration of the combination of the invention. In certain embodiments, a subject's WHZ may improve to less than −1.5 s.d., less than −1.0 s.d., or less than −1.5 s.d. from the median of the WHO reference growth standards. Preventing acute malnutrition may also result in no worsening (i.e. decrease) in a subject's WHZ or MUAC. Preventing acute malnutrition may also involve increasing the subject's relative gut microbiota maturity, MAZ score, gut microbiota diversity, or a combination thereof. The duration of treatment can and will vary. In certain embodiments, the duration of therapy is about 1, 2, 3, or 4 months. In other embodiments, the duration of therapy is about 1, 2, 3, 4, 5, 6, 7, or 8 weeks. In still other embodiments, the duration of therapy is about 4 to about 12 weeks, about 6 to about 10 weeks, or about 6 to about 8 weeks. Alternatively, a subject may be administered one or more bacterial taxa of the invention for as long as the subject remains at risk. Useful combinations are described in further detail below. One or more bacterial taxa of the invention may be formulated for oral or rectal administration, and may be administered alone or with an additional therapeutic agent. Non-limiting examples of additional therapeutic agents include therapeutic foods, antibiotics and/or vaccines.

As used herein, acute diarrhea is defined as three or more stools per day of decreased form (e.g. loose and/or water) from the normal, lasting for less than 14 days; persistent diarrhea is defined as three or more stools per day of decreased form from the normal, lasting for more than 14 days but less than 1 month; and chronic diarrhea is defined as three or more stools per day of decreased form from the normal, lasting for a month or more. Associated symptoms of acute diarrhea, persistent diarrhea, and chronic diarrhea may include abdominal cramps or pain, fever, nausea, vomiting, fatigue, urgency, weight loss, and/or malnutrition. Acute diarrhea, persistent diarrhea, and chronic diarrhea are themselves symptoms. Causes of acute diarrhea are well known in the art, and non-limiting examples include a food allergy, antibiotic use, an enteropathogen infection, and radiation therapy. Causes of persistent diarrhea are well known in the art, and non-limiting examples include a food allergy, antibiotic use, an enteropathogen infection, colon resection, colon cancer, ulcerative colitis, necrotizing enterocolitis, Crohn's disease and radiation therapy. Causes of chronic diarrhea are well known in the art, and non-limiting examples include a food allergy, use of a pharmacological agent, an enteropathogen infection, colon resection, colon cancer, ulcerative colitis, necrotizing enterocolitis, Crohn's disease, and radiation therapy. Pharmacological agents known to cause diarrhea are well known in the art and may include, but are not limited to, an antibiotic, an anti-TNF agent, chemotherapy agents, antacids, proton pump inhibitors, (e.g. asomeprazole, esomeprazole, lansoprazole, rabeprazole, patoprazole, cimetidine, ranitidine, naiziatidine), drugs that suppress the immne system (e.g. mycophenolate), antidepressants, blood pressure medications, digitalis, diuretics, cholesterol-lowering agents, lithium, theophylline, thyroid hormone, and colchicine.

In some embodiments, the subject to be treated is a subject with acute diarrhea and a therapeutically effective amount of one or more bacterial taxa of the invention is administered to the subject. Treating acute diarrhea may involve reducing in treated subjects the duration and/or severity of symptoms of acute diarrhea (e.g. fever, bloody stools, vomiting), death rates, or a combination thereof. For each aspect, the amount of reduction may each be about 10%, 20%, 30%, 40%, 50%, 60%, 70%, 80%, 90%, 95% or about 100% in treated subjects, as compared to untreated subjects. Treating an acute diarrhea may also involve reducing in treated subjects the number of stools per day of decreased form by about 10%, 20%, 30%, 40%, 50%, 60%, 70%, 80%, 90%, 95% or about 100% in treated subjects, as compared to untreated subjects. Treating an acute diarrhea may also involve reducing in treated subjects the number of stools per day of decreased form to less than 6, less than 5, less than 4, or less than 3. Treating acute diarrhea may also involve increasing the subject's relative gut microbiota maturity, MAZ score, gut microbiota diversity, or a combination thereof. The duration of treatment can and will vary. In certain embodiments, the duration of therapy is about 1 to about 4 weeks, about 1 to about 3 weeks, about 2 to about 3 weeks, about 1 to about 2 weeks, or about 10 to about 14 days. In other embodiments, the duration of therapy is about 1, 2, 3, or 4 weeks. In still other embodiments, the duration of therapy is about 10, 11, 12, 13, 14, 15, 16, or 17 days. In yet other embodiments, the duration of therapy is about 3, 4, 5, 6, 7, 8, 9, or 10 days. Alternatively, the duration of therapy may be a month or more. Useful combinations are described in further detail in Section III. One or more bacterial taxa of the invention may be formulated for oral or rectal administration, and may be administered alone or with an additional therapeutic agent. Non-limiting examples of additional therapeutic agents include antibiotics, antimotility agents (e.g. loperamide), antisecretory agents (e.g. racecadotril and other agents that reduce the amount of water that is released into the gut during an episode of diarrhea), bulk-forming agents (e.g. isphaghula husk, methylcellulose, sterculia, etc.)

prebiotics, probiotics, synbiotics, supplemental zinc therapy, nonsteroidal anti-inflammatory drugs, mucosal protectants and adsorbents (e.g. kaolin-pectin, activated charcoal, bismuth subsalicylate, etc.) and/or rehydration therapy. In exemplary embodiment, acute diarrhea is a symptom of a *Vibrio cholerae* infection.

In some embodiments, the subject to be treated is a subject with acute diarrhea and a therapeutically effective amount of a bacterial isolate that is a member of the taxon *Ruminococcus obeum* OTU ID 178122 is administered to the subject, optionally in combination with one or more additional bacterial taxa of the invention. In other embodiments, the subject to be treated is a subject with acute diarrhea and a therapeutically effective amount of *Ruminococcus obeum* ATCC29714 is administered to the subject, optionally in combination with one or more additional bacterial taxa of the invention. Treating acute diarrhea may involve reducing in treated subjects the duration and/or severity of symptoms of acute diarrhea (e.g. fever, bloody stools, vomiting), death rates, or a combination thereof. For each aspect, the amount of reduction may each be about 10%, 20%, 30%, 40%, 50%, 60%, 70%, 80%, 90%, 95% or about 100% in treated subjects, as compared to untreated subjects. Treating an acute diarrhea may also involve reducing in treated subjects the number of stools per day of decreased form by about 10%, 20%, 30%, 40%, 50%, 60%, 70%, 80%, 90%, 95% or about 100% in treated subjects, as compared to untreated subjects. Treating an acute diarrhea may also involve reducing in treated subjects the number of stools per day of decreased form to less than 6, less than 5, less than 4, or less than 3. Treating acute diarrhea may also involve increasing the subject's relative gut microbiota maturity, MAZ score, gut microbiota diversity, or a combination thereof. The duration of treatment can and will vary. In certain embodiments, the duration of therapy is about 1 to about 4 weeks, about 1 to about 3 weeks, about 2 to about 3 weeks, about 1 to about 2 weeks, or about 10 to about 14 days. In other embodiments, the duration of therapy is about 1, 2, 3, or 4 weeks. In still other embodiments, the duration of therapy is about 10, 11, 12, 13, 14, 15, 16, or 17 days. In yet other embodiments, the duration of therapy is about 3, 4, 5, 6, 7, 8, 9, or 10 days. Alternatively, the duration of therapy may be a month or more. Useful combinations comprising *Ruminococcus obeum* ATCC29714 or a bacterial isolate that is a member of the taxon *Ruminococcus obeum* OTU ID 178122 are described in further detail in Section III. A composition comprising *Ruminococcus obeum* ATCC29714 or a bacterial isolate that is a member of the taxon *Ruminococcus obeum* OTU ID 178122 may be formulated for oral or rectal administration, and may be administered alone or with an additional therapeutic agent. Non-limiting examples of additional therapeutic agents include antibiotics, antimotility agents (e.g. loperamide), antisecretory agents (e.g. racecadotril and other agents that reduce the amount of water that is released into the gut during an episode of diarrhea), bulk-forming agents (e.g. isphaghula husk, methylcellulose, sterculia, etc.) prebiotics, probiotics, synbiotics, supplemental zinc therapy, nonsteroidal anti-inflammatory drugs, mucosal protectants and adsorbents (e.g. kaolin-pectin, activated charcoal, bismuth subsalicylate, etc.) and/or rehydration therapy. In exemplary embodiment, acute diarrhea is a symptom of a *Vibrio cholerae* infection.

In some embodiments, the subject to be treated is a subject at risk for acute diarrhea and a therapeutically effective amount of one or more bacterial taxa of the invention is administered to the subject. A subject at risk for acute diarrhea may be a subject living in a geographic area with limited or no access to clean drinking water, a subject living in a geographic area that is experiencing a disease outbreak, or a subject that is exposed to others that have an acute diarrhea. A subject at risk for acute diarrhea may be a subject that is malnourished. Treating a subject at risk for acute diarrhea may prevent acute diarrhea in the subject. For example, preventing an acute diarrhea may involve reducing in treated subjects (1) the incidence, development or formation of the acute diarrhea, (2) the development, duration, and/or severity of symptoms of the acute diarrhea (e.g. fever, bloody stools, vomiting), if the disease does develop, (3) death rates associated with the acute diarrhea, or (4) a combination thereof. For each aspect, the amount of reduction may each be about 10%, 20%, 30%, 40%, 50%, 60%, 70%, 80%, 90%, 95% or about 100% in treated subjects, as compared to untreated subjects. Preventing an acute diarrhea may also involve result in a minimal change in the number of stools per day of decreased form in treated subjects. For example, the change in the number of stools per day of decreased form may be an increase of 3 or less, 2 or less, or 1 or less. Preventing acute diarrhea may also involve increasing the subject's relative gut microbiota maturity, MAZ score, gut microbiota diversity, or a combination thereof. The duration of treatment can and will vary. In certain embodiments, the duration of therapy is about 1 to about 4 weeks, 1 to about 3 weeks, about 2 to about 3 weeks, about 1 to about 2 weeks, or about 10 to about 14 days. In other embodiments, the duration of therapy is about 1, 2, 3, or 4 weeks. In still other embodiments, the duration of therapy is about 10, 11, 12, 13, 14, 15, 16, or 17 days. In yet other embodiments, the duration of therapy is about 3, 4, 5, 6, 7, 8, 9, or 10 days. Alternatively, the duration of therapy may be a month or more. Useful combinations are described in further detail in Section III. One or more bacterial taxa of the invention may be formulated for oral or rectal administration, and may be administered alone or with an additional therapeutic agent. Non-limiting examples of additional therapeutic agents include antibiotics, antimotility agents (e.g. loperamide), antisecretory agents (e.g. racecadotril and other agents that reduce the amount of water that is released into the gut during an episode of diarrhea), bulk-forming agents (e.g. isphaghula husk, methylcellulose, sterculia, etc.) prebiotics, probiotics, synbiotics, supplemental zinc therapy, nonsteroidal anti-inflammatory drugs, mucosal protectants and adsorbents (e.g. kaolin-pectin, activated charcoal, bismuth subsalicylate, etc.) and/or rehydration therapy. In exemplary embodiment, acute diarrhea is a symptom of a *Vibrio cholerae* infection.

In some embodiments, the subject to be treated is a subject with acute diarrhea and a therapeutically effective amount of a bacterial isolate that is a member of the taxon *Ruminococcus obeum* OTU ID 178122 is administered to the subject, optionally in combination with one or more additional bacterial taxa of the invention. In some embodiments, the subject to be treated is a subject at risk for acute diarrhea and a therapeutically effective amount of *Ruminococcus obeum* ATCC29714 is administered to the subject, optionally in combination with one or more additional bacterial taxa of the invention. A subject at risk for acute diarrhea may be a subject living in a geographic area with limited or no access to clean drinking water, a subject living in a geographic area that is experiencing a disease outbreak, or a subject that is exposed to others that have an acute diarrhea. A subject at risk for acute diarrhea may be a subject that is malnourished. Treating a subject at risk for acute diarrhea may prevent acute diarrhea in the subject. For example, preventing an acute diarrhea may involve reducing in treated subjects (1) the incidence, development or formation of the acute diarrhea, (2) the development, duration, and/or severity of symptoms of the acute diarrhea (e.g. fever, bloody stools, vomiting), if the disease does develop, (3) death rates associated with the acute diarrhea, or (4) a combination thereof. For each aspect, the amount of reduction may each be about 10%, 20%, 30%, 40%, 50%, 60%, 70%, 80%, 90%, 95% or about 100% in treated subjects, as compared to untreated subjects. Preventing an acute diarrhea may also involve result in a minimal change in the number of stools per day of decreased form in treated subjects. For example, the change in the number of stools per day of decreased form may be an increase of 3 or less, 2 or less, or 1 or less. Preventing acute diarrhea may also involve increasing the subject's relative gut microbiota maturity, MAZ score, gut microbiota diversity, or a combination thereof. The duration of treatment can and will vary. In certain embodiments, the duration of therapy is about 1 to about 4 weeks, 1 to about 3 weeks, about 2 to about 3 weeks, about 1 to about 2 weeks, or about 10 to about 14 days. In other embodiments, the duration of therapy is about 1, 2, 3, or 4 weeks. In still other embodiments, the duration of therapy is about 10, 11, 12, 13, 14, 15, 16, or 17 days. In yet other embodiments, the duration of therapy is about 3, 4, 5, 6, 7, 8, 9, or 10 days. Alternatively, the duration of therapy may be a month or more. Useful combinations comprising *Ruminococcus obeum* ATCC29714 or a bacterial isolate that is a member of the taxon *Ruminococcus obeum* OTU ID 178122 are described in further detail in Section III. A composition comprising *Ruminococcus obeum* ATCC29714 or a bacterial isolate that is a member of the taxon *Ruminococcus obeum* OTU ID 178122 may be formulated for oral or rectal administration, and may be administered alone or with an additional therapeutic agent. Non-limiting examples of additional therapeutic agents include antibiotics, antimotility agents (e.g. loperamide), antisecretory agents (e.g. racecadotril and other agents that reduce the amount of water that is released into the gut during an episode of diarrhea), bulk-forming agents (e.g. isphaghula husk, methylcellulose, sterculia, etc.) prebiotics, probiotics, synbiotics, supplemental zinc therapy, nonsteroidal anti-inflammatory drugs, mucosal protectants and adsorbents (e.g. kaolin-pectin, activated charcoal, bismuth subsalicylate, etc.) and/or rehydration therapy. In exemplary embodiment, acute diarrhea is a symptom of a *Vibrio cholerae* infection.

In some embodiments, the subject to be treated is a subject with chronic diarrhea and a therapeutically effective amount of one or more bacterial taxa of the invention is administered to the subject. Treating chronic diarrhea may involve reducing in treated subjects the duration and/or severity of symptoms of acute diarrhea (e.g. fever, bloody stools, vomiting), death rates, or a combination thereof. For each aspect, the amount of reduction may each be about 10%, 20%, 30%, 40%, 50%, 60%, 70%, 80%, 90%, 95% or about 100% in treated subjects, as compared to untreated subjects. Treating an chronic diarrhea may also involve reducing in treated subjects the number of stools per day of decreased form by about 10%, 20%, 30%, 40%, 50%, 60%, 70%, 80%, 90%, 95% or about 100% in treated subjects, as compared to untreated subjects. Treating an chronic diarrhea may also involve reducing in treated subjects the number of stools per day of decreased form to less than 6, less than 5, less than 4, or less than 3. Treating acute diarrhea may also involve increasing the subject's relative gut microbiota maturity, MAZ score, gut microbiota diversity, or a combination thereof. The duration of treatment can and will vary. In certain embodiments, the duration of therapy is about 1 to about 4 weeks, about 1 to about 3 weeks, about 2 to about 3 weeks, about 1 to about 2 weeks, or about 10 to about 14 days. In other embodiments, the duration of therapy is about 1, 2, 3, or 4 weeks. In still other embodiments, the duration of therapy is about 10, 11, 12, 13, 14, 15, 16, or 17 days. In yet other embodiments, the duration of therapy is about 3, 4, 5, 6, 7, 8, 9, or 10 days. Alternatively, the duration of therapy may be a month or more. Useful combinations are described in further detail in Section III. One or more bacterial taxa of the invention may be formulated for oral or rectal administration, and may be administered alone or with an additional therapeutic agent. Non-limiting examples of additional therapeutic agents include antibiotics, antimotility agents (e.g. loperamide), antisecretory agents (e.g. racecadotril and other agents that reduce the amount of water that is released into the gut during an episode of diarrhea), bulk-forming agents (e.g. isphaghula husk, methylcellulose, sterculia, etc.) prebiotics, probiotics, synbiotics, supplemental zinc therapy, nonsteroidal anti-inflammatory drugs, mucosal protectants and adsorbents (e.g. kaolin-pectin, activated charcoal, bismuth subsalicylate, etc.) and/or rehydration therapy. In exemplary embodiment, chronic diarrhea is a symptom of a *C. difficile* infection, Crohn's disease, ulcerative colitis, necrotizing enterocolitis, traveler's diarrhea, colon cancer, chemotherapy, radiation therapy, or use of pharmacological agent, including but not limited to an antibiotics, or an anti-TNF agent.

In some embodiments, the subject to be treated is a subject at risk for chronic diarrhea and a therapeutically effective amount of one or more bacterial taxa of the invention is administered to the subject. A subject at risk for chronic diarrhea may be a subject living in a geographic area with limited or no access to clean drinking water, a subject living in a geographic area that is experiencing a disease outbreak, or a subject that is exposed to others that have an acute diarrhea. A subject at risk for chronic diarrhea may be a subject that is malnourished. Treating a subject at risk for chronic diarrhea may prevent acute diarrhea in the subject. For example, preventing an chronic diarrhea may involve reducing in treated subjects (1) the incidence, development or formation of the acute diarrhea, (2) the development, duration, and/or severity of symptoms of the acute diarrhea (e.g. fever, bloody stools, vomiting), if the disease does develop, (3) death rates associated with the acute diarrhea, or (4) a combination thereof. For each aspect, the amount of reduction may each be about 10%, 20%, 30%, 40%, 50%, 60%, 70%, 80%, 90%, 95% or about 100% in treated subjects, as compared to untreated subjects. Preventing an chronic diarrhea may also involve result in a minimal change in the number of stools per day of decreased form in treated subjects. For example, the change in the number of stools per day of decreased form may be an increase of 3 or less, 2 or less, or 1 or less. Preventing chronic diarrhea may also involve increasing the subject's relative gut microbiota maturity, MAZ score, gut microbiota diversity, or a combination thereof. The duration of treatment can and will vary. In certain embodiments, the duration of therapy is about 1 to about 4 weeks, 1 to about 3 weeks, about 2 to about 3 weeks, about 1 to about 2 weeks, or about 10 to about 14 days. In other embodiments, the duration of therapy is about 1, 2, 3, or 4 weeks. In still other embodiments, the duration of therapy is about 10, 11, 12, 13, 14, 15, 16, or 17 days. In yet other embodiments, the duration of therapy is about 3, 4, 5, 6, 7, 8, 9, or 10 days. Alternatively, the duration of therapy may be a month or more. Useful combinations are described in further detail in Section III. One or more bacterial taxa of the invention may be formulated for oral or rectal administration, and may be administered alone or with an additional therapeutic agent. Non-limiting examples of additional therapeutic agents include antibiotics, antimotility agents (e.g. loperamide), antisecretory agents (e.g. racecadotril and other agents that reduce the amount of water that is released into the gut during an episode of diarrhea), bulk-forming agents (e.g. isphaghula husk, methylcellulose, sterculia, etc.) prebiotics, probiotics, synbiotics, supplemental zinc therapy, nonsteroidal anti-inflammatory drugs, mucosal protectants and adsorbents (e.g. kaolin-pectin, activated charcoal, bismuth subsalicylate, etc.) and/or rehydration therapy. In exemplary embodiment, chronic diarrhea is a symptom of a *C. difficile* infection, Crohn's disease, ulcerative colitis, necrotizing enterocolitis, traveler's diarrhea, colon cancer, radiation therapy, or use of pharmacological agent, including but not limited to an antibiotics, or an anti-TNF agent.

III. Compositions

In an aspect, the present invention provides a composition comprising 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 bacterial taxa selected from list provided in Table A, wherein each bacterial taxon present in the composition is isolated and biologically pure (i.e. ≥97% sequence identity to the SEQ ID NO. provided).

In another aspect, the present invention provides a combination comprising 2, 3, 4, 5, 6, 7, 8, 9, 10, 11, 12, 13, 14, 15, 16, 17, 18, 19, 20, 21, 22, 23, or 24 bacterial taxa selected from the bacterial taxa listed in Table B, wherein each bacterial taxon present in the composition is isolated and biologically pure (i.e. ≥97% sequence identity to the SEQ ID NO. provided).

In another aspect, the present invention provides a combination comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 bacterial taxa selected from the bacterial taxa listed in Table C, wherein each bacterial taxon present in the composition is isolated and biologically pure (i.e. ≥97% sequence identity to the SEQ ID NO. provided).

In another aspect, the present invention provides a combination identified below in Table D, wherein each bacterial taxon present in the composition is isolated and biologically pure (i.e. ≥97% sequence identity to the SEQ ID NO. provided).

TABLE D

| | BACTERIAL TAXON | | | | | | | | | | | | | | | | | | | | | | | |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| A | x | x | | | | | | | | | | | | | | | | | | | | | | |
| B | x | x | x | | | | | | | | | | | | | | | | | | | | | |
| C | x | x | x | x | | | | | | | | | | | | | | | | | | | | |
| D | x | x | x | x | x | | | | | | | | | | | | | | | | | | | |
| E | x | x | x | x | x | x | | | | | | | | | | | | | | | | | | |
| F | x | x | x | x | x | x | x | | | | | | | | | | | | | | | | | |
| G | x | x | x | x | x | x | x | x | | | | | | | | | | | | | | | | |
| H | x | x | x | x | x | x | x | x | x | | | | | | | | | | | | | | | |
| I | x | x | x | x | x | x | x | x | x | x | | | | | | | | | | | | | | |
| J | x | x | x | x | x | x | x | x | x | x | x | | | | | | | | | | | | | |
| K | x | x | x | x | x | x | x | x | x | x | x | x | | | | | | | | | | | | |
| L | x | x | x | x | x | x | x | x | x | x | x | x | x | | | | | | | | | | | |
| M | x | x | x | x | x | x | x | x | x | x | x | x | x | x | | | | | | | | | | |
| N | x | x | x | x | x | x | x | x | x | x | x | x | x | x | x | | | | | | | | | |
| O | x | x | x | x | x | x | x | x | x | x | x | x | x | x | x | x | | | | | | | | |
| P | x | x | x | x | x | x | x | x | x | x | x | x | x | x | x | x | x | | | | | | | |
| Q | x | x | x | x | x | x | x | x | x | x | x | x | x | x | x | x | x | x | | | | | | |
| R | x | x | x | x | x | x | x | x | x | x | x | x | x | x | x | x | x | x | x | | | | | |
| S | x | x | x | x | x | x | x | x | x | x | x | x | x | x | x | x | x | x | x | x | | | | |
| T | x | x | x | x | x | x | x | x | x | x | x | x | x | x | x | x | x | x | x | x | x | | | |
| U | x | x | x | x | x | x | x | x | x | x | x | x | x | x | x | x | x | x | x | x | x | x | | |
| V | x | x | x | x | x | x | x | x | x | x | x | x | x | x | x | x | x | x | x | x | x | x | x | |
| W | x | x | x | x | x | x | x | x | x | x | x | x | x | x | x | x | x | x | x | x | x | x | x | x |
| X | | x | x | | | | | | | | | | | | | | | | | | | | | |
| Y | | x | x | x | | | | | | | | | | | | | | | | | | | | |
| Z | | x | x | x | x | | | | | | | | | | | | | | | | | | | |
| AA | | x | x | x | x | x | | | | | | | | | | | | | | | | | | |
| AB | | x | x | x | x | x | x | | | | | | | | | | | | | | | | | |
| AC | | x | x | x | x | x | x | x | | | | | | | | | | | | | | | | |
| AD | | x | x | x | x | x | x | x | x | | | | | | | | | | | | | | | |
| AE | | x | x | x | x | x | x | x | x | x | | | | | | | | | | | | | | |
| AF | | x | x | x | x | x | x | x | x | x | x | | | | | | | | | | | | | |
| AG | | x | x | x | x | x | x | x | x | x | x | x | | | | | | | | | | | | |
| AH | | x | x | x | x | x | x | x | x | x | x | x | x | | | | | | | | | | | |
| AI | | x | x | x | x | x | x | x | x | x | x | x | x | x | | | | | | | | | | |
| AJ | | x | x | x | x | x | x | x | x | x | x | x | x | x | x | | | | | | | | | |
| AK | | x | x | x | x | x | x | x | x | x | x | x | x | x | x | x | | | | | | | | |
| AL | | x | x | x | x | x | x | x | x | x | x | x | x | x | x | x | x | | | | | | | |
| AM | | x | x | x | x | x | x | x | x | x | x | x | x | x | x | x | x | x | | | | | | |
| AN | | x | x | x | x | x | x | x | x | x | x | x | x | x | x | x | x | x | x | | | | | |
| AO | | x | x | x | x | x | x | x | x | x | x | x | x | x | x | x | x | x | x | x | | | | |
| AP | | x | x | x | x | x | x | x | x | x | x | x | x | x | x | x | x | x | x | x | x | | | |
| AQ | | x | x | x | x | x | x | x | x | x | x | x | x | x | x | x | x | x | x | x | x | x | | |
| AR | | x | x | x | x | x | x | x | x | x | x | x | x | x | x | x | x | x | x | x | x | x | x | |
| AS | | x | x | x | x | x | x | x | x | x | x | x | x | x | x | x | x | x | x | x | x | x | x | x |

TABLE D-continued

| | \multicolumn{24}{c}{BACTERIAL TAXON} |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| AT | | | x | x | | | | | | | | | | | | | | | | | | | | |
| AU | | | x | x | x | | | | | | | | | | | | | | | | | | | |
| AV | | | x | x | x | x | | | | | | | | | | | | | | | | | | |
| AW | | | x | x | x | x | x | | | | | | | | | | | | | | | | | |
| AX | | | x | x | x | x | x | x | | | | | | | | | | | | | | | | |
| AY | | | x | x | x | x | x | x | x | | | | | | | | | | | | | | | |
| AZ | | | x | x | x | x | x | x | x | x | | | | | | | | | | | | | | |
| AI | | | x | x | x | x | x | x | x | x | x | | | | | | | | | | | | | |
| AJ | | | x | x | x | x | x | x | x | x | x | x | | | | | | | | | | | | |
| AK | | | x | x | x | x | x | x | x | x | x | x | x | | | | | | | | | | | |
| AL | | | x | x | x | x | x | x | x | x | x | x | x | x | | | | | | | | | | |
| AM | | | x | x | x | x | x | x | x | x | x | x | x | x | x | | | | | | | | | |
| AN | | | x | x | x | x | x | x | x | x | x | x | x | x | x | x | | | | | | | | |
| AO | | | x | x | x | x | x | x | x | x | x | x | x | x | x | x | x | | | | | | | |
| AP | | | x | x | x | x | x | x | x | x | x | x | x | x | x | x | x | x | | | | | | |
| AQ | | | x | x | x | x | x | x | x | x | x | x | x | x | x | x | x | x | x | | | | | |
| AR | | | x | x | x | x | x | x | x | x | x | x | x | x | x | x | x | x | x | x | | | | |
| AS | | | x | x | x | x | x | x | x | x | x | x | x | x | x | x | x | x | x | x | x | | | |
| AT | | | x | x | x | x | x | x | x | x | x | x | x | x | x | x | x | x | x | x | x | x | | |
| AU | | | x | x | x | x | x | x | x | x | x | x | x | x | x | x | x | x | x | x | x | x | x | |
| AV | | | x | x | x | x | x | x | x | x | x | x | x | x | x | x | x | x | x | x | x | x | x | x |
| AW | x | | x | x | x | x | x | x | x | x | x | x | x | x | x | x | x | x | x | x | x | x | x | x |
| AX | | | | x | x | | | | | | | | | | | | | | | | | | | |
| AY | | | | x | x | x | | | | | | | | | | | | | | | | | | |
| AZ | | | | x | x | x | x | | | | | | | | | | | | | | | | | |
| BA | | | | x | x | x | x | x | | | | | | | | | | | | | | | | |
| BB | | | | x | x | x | x | x | x | | | | | | | | | | | | | | | |
| BC | | | | x | x | x | x | x | x | x | | | | | | | | | | | | | | |
| BD | | | | x | x | x | x | x | x | x | x | | | | | | | | | | | | | |
| BE | | | | x | x | x | x | x | x | x | x | x | | | | | | | | | | | | |
| BF | | | | x | x | x | x | x | x | x | x | x | x | | | | | | | | | | | |
| BG | | | | x | x | x | x | x | x | x | x | x | x | x | | | | | | | | | | |
| BH | | | | x | x | x | x | x | x | x | x | x | x | x | x | | | | | | | | | |
| BI | | | | x | x | x | x | x | x | x | x | x | x | x | x | x | | | | | | | | |
| BJ | | | | x | x | x | x | x | x | x | x | x | x | x | x | x | x | | | | | | | |
| BK | | | | x | x | x | x | x | x | x | x | x | x | x | x | x | x | x | | | | | | |
| BL | | | | x | x | x | x | x | x | x | x | x | x | x | x | x | x | x | x | | | | | |
| BM | | | | x | x | x | x | x | x | x | x | x | x | x | x | x | x | x | x | x | | | | |
| BN | | | | x | x | x | x | x | x | x | x | x | x | x | x | x | x | x | x | x | x | | | |
| BO | | | | x | x | x | x | x | x | x | x | x | x | x | x | x | x | x | x | x | x | x | | |
| BP | | | | x | x | x | x | x | x | x | x | x | x | x | x | x | x | x | x | x | x | x | x | |
| BQ | | | | x | x | x | x | x | x | x | x | x | x | x | x | x | x | x | x | x | x | x | x | x |
| BR | | | | | | x | x | | | | | | | | | | | | | | | | | |
| BS | | | | | | x | x | x | | | | | | | | | | | | | | | | |
| BT | | | | | | x | x | x | x | | | | | | | | | | | | | | | |
| BU | | | | | | x | x | x | x | x | | | | | | | | | | | | | | |
| BV | | | | | | x | x | x | x | x | x | | | | | | | | | | | | | |
| BW | | | | | | x | x | x | x | x | x | x | | | | | | | | | | | | |
| BX | | | | | | x | x | x | x | x | x | x | x | | | | | | | | | | | |
| BY | | | | | | x | x | x | x | x | x | x | x | x | | | | | | | | | | |
| BZ | | | | | | x | x | x | x | x | x | x | x | x | x | | | | | | | | | |
| CA | | | | | | x | x | x | x | x | x | x | x | x | x | x | | | | | | | | |
| CB | | | | | | x | x | x | x | x | x | x | x | x | x | x | x | | | | | | | |
| CC | | | | | | x | x | x | x | x | x | x | x | x | x | x | x | x | | | | | | |
| CD | | | | | | x | x | x | x | x | x | x | x | x | x | x | x | x | x | | | | | |
| CE | | | | | | x | x | x | x | x | x | x | x | x | x | x | x | x | x | x | | | | |
| CF | | | | | | x | x | x | x | x | x | x | x | x | x | x | x | x | x | x | x | | | |
| CG | | | | | | x | x | x | x | x | x | x | x | x | x | x | x | x | x | x | x | x | | |
| CH | | | | | | x | x | x | x | x | x | x | x | x | x | x | x | x | x | x | x | x | x | |
| CI | | | | | | x | x | x | x | x | x | x | x | x | x | x | x | x | x | x | x | x | x | x |
| CJ | | | | | | x | x | x | x | x | x | x | x | x | x | x | x | x | x | x | x | x | x | x |
| CK | x | | | | | x | x | x | x | x | x | x | x | x | x | x | x | x | x | x | x | x | x | x |
| CL | x | x | | | | x | x | x | x | x | x | x | x | x | x | x | x | x | x | x | x | x | x | x |
| CM | x | x | x | | | x | x | x | x | x | x | x | x | x | x | x | x | x | x | x | x | x | x | x |
| CN | | | | | | x | x | | | | | | | | | | | | | | | | | |
| CO | | | | | | x | x | x | | | | | | | | | | | | | | | | |
| CP | | | | | | x | x | x | x | | | | | | | | | | | | | | | |
| CQ | | | | | | x | x | x | x | x | | | | | | | | | | | | | | |
| CR | | | | | | x | x | x | x | x | x | | | | | | | | | | | | | |
| CS | | | | | | x | x | x | x | x | x | x | | | | | | | | | | | | |
| CT | | | | | | x | x | x | x | x | x | x | x | | | | | | | | | | | |
| CU | | | | | | x | x | x | x | x | x | x | x | x | | | | | | | | | | |
| CV | | | | | | x | x | x | x | x | x | x | x | x | x | | | | | | | | | |
| CW | | | | | | x | x | x | x | x | x | x | x | x | x | x | | | | | | | | |
| CX | | | | | | x | x | x | x | x | x | x | x | x | x | x | x | | | | | | | |
| CY | | | | | | x | x | x | x | x | x | x | x | x | x | x | x | x | | | | | | |

TABLE D-continued

| | \multicolumn{24}{c|}{BACTERIAL TAXON} |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| CZ | | | | | | x | x | x | x | x | x | x | x | x | x | x | x | x | x | | | | | |
| DA | | | | | | x | x | x | x | x | x | x | x | x | x | x | x | x | x | x | | | | |
| DB | | | | | | x | x | x | x | x | x | x | x | x | x | x | x | x | x | x | x | | | |
| DC | | | | | | x | x | x | x | x | x | x | x | x | x | x | x | x | x | x | x | x | | |
| DD | | | | | | x | x | x | x | x | x | x | x | x | x | x | x | x | x | x | x | x | x | |
| DE | | | | | | x | x | x | x | x | x | x | x | x | x | x | x | x | x | x | x | x | x | x |
| DF | x | | | | | x | x | x | x | x | x | x | x | x | x | x | x | x | x | x | x | x | x | x |
| DG | x | x | | | | x | x | x | x | x | x | x | x | x | x | x | x | x | x | x | x | x | x | x |
| DH | x | x | x | | | x | x | x | x | x | x | x | x | x | x | x | x | x | x | x | x | x | x | x |
| DI | x | x | x | x | | x | x | x | x | x | x | x | x | x | x | x | x | x | x | x | x | x | x | x |
| DJ | | | | | | | | x | x | | | | | | | | | | | | | | | |
| DK | | | | | | | | x | x | x | | | | | | | | | | | | | | |
| DL | | | | | | | | x | x | x | x | | | | | | | | | | | | | |
| DM | | | | | | | | x | x | x | x | x | | | | | | | | | | | | |
| DN | | | | | | | | x | x | x | x | x | x | | | | | | | | | | | |
| DO | | | | | | | | x | x | x | x | x | x | x | | | | | | | | | | |
| DP | | | | | | | | x | x | x | x | x | x | x | x | | | | | | | | | |
| DQ | | | | | | | | x | x | x | x | x | x | x | x | x | | | | | | | | |
| DR | | | | | | | | x | x | x | x | x | x | x | x | x | x | | | | | | | |
| DS | | | | | | | | x | x | x | x | x | x | x | x | x | x | x | | | | | | |
| DT | | | | | | | | x | x | x | x | x | x | x | x | x | x | x | x | | | | | |
| DU | | | | | | | | x | x | x | x | x | x | x | x | x | x | x | x | x | | | | |
| DV | | | | | | | | x | x | x | x | x | x | x | x | x | x | x | x | x | x | | | |
| DW | | | | | | | | x | x | x | x | x | x | x | x | x | x | x | x | x | x | x | | |
| DX | | | | | | | | x | x | x | x | x | x | x | x | x | x | x | x | x | x | x | x | |
| DY | | | | | | | | x | x | x | x | x | x | x | x | x | x | x | x | x | x | x | x | x |
| DZ | | | | | | | | x | x | x | x | x | x | x | x | x | x | x | x | x | x | x | x | x |
| EA | x | | | | | | | x | x | x | x | x | x | x | x | x | x | x | x | x | x | x | x | x |
| EB | x | x | | | | | | x | x | x | x | x | x | x | x | x | x | x | x | x | x | x | x | x |
| EC | x | x | x | | | | | x | x | x | x | x | x | x | x | x | x | x | x | x | x | x | x | x |
| ED | x | x | x | x | | | | x | x | x | x | x | x | x | x | x | x | x | x | x | x | x | x | x |
| EE | x | x | x | x | x | | | x | x | | | | | | | | | | | | | | | |
| EF | | | | | | | | x | x | x | | | | | | | | | | | | | | |
| EG | | | | | | | | x | x | x | x | | | | | | | | | | | | | |
| EH | | | | | | | | x | x | x | x | x | | | | | | | | | | | | |
| EI | | | | | | | | x | x | x | x | x | x | | | | | | | | | | | |
| EJ | | | | | | | | x | x | x | x | x | x | x | | | | | | | | | | |
| EK | | | | | | | | x | x | x | x | x | x | x | x | | | | | | | | | |
| EL | | | | | | | | x | x | x | x | x | x | x | x | x | | | | | | | | |
| EM | | | | | | | | x | x | x | x | x | x | x | x | x | x | | | | | | | |
| EN | | | | | | | | x | x | x | x | x | x | x | x | x | x | x | | | | | | |
| EO | | | | | | | | x | x | x | x | x | x | x | x | x | x | x | x | | | | | |
| EP | | | | | | | | x | x | x | x | x | x | x | x | x | x | x | x | x | | | | |
| EQ | | | | | | | | x | x | x | x | x | x | x | x | x | x | x | x | x | x | | | |
| ER | | | | | | | | x | x | x | x | x | x | x | x | x | x | x | x | x | x | x | | |
| ES | | | | | | | | x | x | x | x | x | x | x | x | x | x | x | x | x | x | x | x | |
| ET | | | | | | | | x | x | x | x | x | x | x | x | x | x | x | x | x | x | x | x | x |
| EU | x | | | | | | | x | x | x | x | x | x | x | x | x | x | x | x | x | x | x | x | x |
| EV | x | x | | | | | | x | x | x | x | x | x | x | x | x | x | x | x | x | x | x | x | x |
| EW | x | x | x | | | | | x | x | x | x | x | x | x | x | x | x | x | x | x | x | x | x | x |
| EX | x | x | x | x | | | | x | x | x | x | x | x | x | x | x | x | x | x | x | x | x | x | x |
| EY | x | x | x | x | x | | | x | x | x | x | x | x | x | x | x | x | x | x | x | x | x | x | x |
| EZ | x | x | x | x | x | x | | x | x | x | x | x | x | x | x | x | x | x | x | x | x | x | x | x |
| FA | | | | | | | | | x | x | | | | | | | | | | | | | | |
| FB | | | | | | | | | x | x | x | | | | | | | | | | | | | |
| FC | | | | | | | | | x | x | x | x | | | | | | | | | | | | |
| FD | | | | | | | | | x | x | x | x | x | | | | | | | | | | | |
| FE | | | | | | | | | x | x | x | x | x | x | | | | | | | | | | |
| FF | | | | | | | | | x | x | x | x | x | x | x | | | | | | | | | |
| FG | | | | | | | | | x | x | x | x | x | x | x | x | | | | | | | | |
| FH | | | | | | | | | x | x | x | x | x | x | x | x | x | | | | | | | |
| FI | | | | | | | | | x | x | x | x | x | x | x | x | x | x | | | | | | |
| FJ | | | | | | | | | x | x | x | x | x | x | x | x | x | x | x | | | | | |
| FK | | | | | | | | | x | x | x | x | x | x | x | x | x | x | x | x | | | | |
| FL | | | | | | | | | x | x | x | x | x | x | x | x | x | x | x | x | x | | | |
| FM | | | | | | | | | x | x | x | x | x | x | x | x | x | x | x | x | x | x | | |
| FN | | | | | | | | | x | x | x | x | x | x | x | x | x | x | x | x | x | x | x | |
| FO | | | | | | | | | x | x | x | x | x | x | x | x | x | x | x | x | x | x | x | x |
| FP | x | | | | | | | | x | x | x | x | x | x | x | x | x | x | x | x | x | x | x | x |
| FQ | x | x | | | | | | | x | x | x | x | x | x | x | x | x | x | x | x | x | x | x | x |
| FR | x | x | x | | | | | | x | x | x | x | x | x | x | x | x | x | x | x | x | x | x | x |
| FS | x | x | x | x | | | | | x | x | x | x | x | x | x | x | x | x | x | x | x | x | x | x |
| FT | x | x | x | x | x | | | | x | x | x | x | x | x | x | x | x | x | x | x | x | x | x | x |
| FU | x | x | x | x | x | x | | | x | x | x | x | x | x | x | x | x | x | x | x | x | x | x | x |
| FV | x | x | x | x | x | x | x | | x | x | x | x | x | x | x | x | x | x | x | x | x | x | x | x |
| FW | | | | | | | | | x | x | | | | | | | | | | | | | | |

TABLE D-continued

| | BACTERIAL TAXON | | | | | | | | | | | | | | | | | | | | | | | |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| FX | | | | | | | | | | x | x | x | | | | | | | | | | | | |
| FY | | | | | | | | | | x | x | x | x | | | | | | | | | | | |
| FZ | | | | | | | | | | x | x | x | x | x | | | | | | | | | | |
| GA | | | | | | | | | | x | x | x | x | x | x | | | | | | | | | |
| GB | | | | | | | | | | x | x | x | x | x | x | x | | | | | | | | |
| GC | | | | | | | | | | x | x | x | x | x | x | x | x | | | | | | | |
| GD | | | | | | | | | | x | x | x | x | x | x | x | x | x | | | | | | |
| GE | | | | | | | | | | x | x | x | x | x | x | x | x | x | x | | | | | |
| GF | | | | | | | | | | x | x | x | x | x | x | x | x | x | x | x | | | | |
| GG | | | | | | | | | | x | x | x | x | x | x | x | x | x | x | x | x | | | |
| GH | | | | | | | | | | x | x | x | x | x | x | x | x | x | x | x | x | x | | |
| GI | | | | | | | | | | x | x | x | x | x | x | x | x | x | x | x | x | x | x | |
| GJ | | | | | | | | | | x | x | x | x | x | x | x | x | x | x | x | x | x | x | x |
| GK | x | | | | | | | | | x | x | x | x | x | x | x | x | x | x | x | x | x | x | x |
| GL | x | x | | | | | | | | x | x | x | x | x | x | x | x | x | x | x | x | x | x | x |
| GM | x | x | x | | | | | | | x | x | x | x | x | x | x | x | x | x | x | x | x | x | x |
| GN | x | x | x | x | | | | | | x | x | x | x | x | x | x | x | x | x | x | x | x | x | x |
| GO | x | x | x | x | x | | | | | x | x | x | x | x | x | x | x | x | x | x | x | x | x | x |
| GP | x | x | x | x | x | x | | | | x | x | x | x | x | x | x | x | x | x | x | x | x | x | x |
| GQ | x | x | x | x | x | x | x | | | x | x | x | x | x | x | x | x | x | x | x | x | x | x | x |
| GR | x | x | x | x | x | x | x | x | | x | x | x | x | x | x | x | x | x | x | x | x | x | x | x |
| GR | | | | | | | | | | | | x | x | | | | | | | | | | | |
| GS | | | | | | | | | | | | x | x | x | | | | | | | | | | |
| GT | | | | | | | | | | | | x | x | x | x | | | | | | | | | |
| GU | | | | | | | | | | | | x | x | x | x | x | | | | | | | | |
| GV | | | | | | | | | | | | x | x | x | x | x | x | | | | | | | |
| GW | | | | | | | | | | | | x | x | x | x | x | x | x | | | | | | |
| GX | | | | | | | | | | | | x | x | x | x | x | x | x | x | | | | | |
| GY | | | | | | | | | | | | x | x | x | x | x | x | x | x | x | | | | |
| GZ | | | | | | | | | | | | x | x | x | x | x | x | x | x | x | x | | | |
| HA | | | | | | | | | | | | x | x | x | x | x | x | x | x | x | x | x | | |
| HB | | | | | | | | | | | | x | x | x | x | x | x | x | x | x | x | x | x | |
| HC | | | | | | | | | | | | x | x | x | x | x | x | x | x | x | x | x | x | |
| HD | | | | | | | | | | | | x | x | x | x | x | x | x | x | x | x | x | x | x |
| HE | x | | | | | | | | | | | x | x | x | x | x | x | x | x | x | x | x | x | x |
| HF | x | x | | | | | | | | | | x | x | x | x | x | x | x | x | x | x | x | x | x |
| HG | x | x | x | | | | | | | | | x | x | x | x | x | x | x | x | x | x | x | x | x |
| HH | x | x | x | x | | | | | | | | x | x | x | x | x | x | x | x | x | x | x | x | x |
| HI | x | x | x | x | x | | | | | | | x | x | x | x | x | x | x | x | x | x | x | x | x |
| HJ | x | x | x | x | x | x | | | | | | x | x | x | x | x | x | x | x | x | x | x | x | x |
| HK | x | x | x | x | x | | x | | | | | x | x | x | x | x | x | x | x | x | x | x | x | x |
| HL | x | x | x | x | x | x | x | | | | | x | x | x | x | x | x | x | x | x | x | x | x | x |
| HM | x | x | x | x | x | x | x | x | x | | | x | x | x | x | x | x | x | x | x | x | x | x | x |
| HN | | | | | | | | | | | | | x | x | | | | | | | | | | |
| HO | | | | | | | | | | | | | x | x | x | | | | | | | | | |
| HP | | | | | | | | | | | | | x | x | x | x | | | | | | | | |
| HQ | | | | | | | | | | | | | x | x | x | x | x | | | | | | | |
| HR | | | | | | | | | | | | | x | x | x | x | x | x | | | | | | |
| HS | | | | | | | | | | | | | x | x | x | x | x | x | x | | | | | |
| HT | | | | | | | | | | | | | x | x | x | x | x | x | x | x | | | | |
| HU | | | | | | | | | | | | | x | x | x | x | x | x | x | x | x | | | |
| HV | | | | | | | | | | | | | x | x | x | x | x | x | x | x | x | x | | |
| HW | | | | | | | | | | | | | x | x | x | x | x | x | x | x | x | x | x | |
| HX | | | | | | | | | | | | | x | x | x | x | x | x | x | x | x | x | x | |
| HY | | | | | | | | | | | | | x | x | x | x | x | x | x | x | x | x | x | x |
| HZ | x | | | | | | | | | | | | x | x | x | x | x | x | x | x | x | x | x | x |
| IA | x | x | | | | | | | | | | | x | x | x | x | x | x | x | x | x | x | x | x |
| IB | x | x | x | | | | | | | | | | x | x | x | x | x | x | x | x | x | x | x | x |
| IC | x | x | x | x | | | | | | | | | x | x | x | x | x | x | x | x | x | x | x | x |
| ID | x | x | x | x | x | | | | | | | | x | x | x | x | x | x | x | x | x | x | x | x |
| IE | x | x | x | x | x | x | | | | | | | x | x | x | x | x | x | x | x | x | x | x | x |
| IF | x | x | x | x | x | x | x | | | | | | x | x | x | x | x | x | x | x | x | x | x | x |
| IG | x | x | x | x | x | x | x | x | | | | | x | x | x | x | x | x | x | x | x | x | x | x |
| IH | x | x | x | x | x | x | x | x | x | | | | x | x | x | x | x | x | x | x | x | x | x | x |
| II | x | x | x | x | x | x | x | x | x | x | | | x | x | x | x | x | x | x | x | x | x | x | x |
| IJ | | | | | | | | | | | | | x | x | | | | | | | | | | |
| IK | | | | | | | | | | | | | x | x | x | | | | | | | | | |
| IL | | | | | | | | | | | | | x | x | x | x | | | | | | | | |
| IM | | | | | | | | | | | | | x | x | x | x | x | | | | | | | |
| IN | | | | | | | | | | | | | x | x | x | x | x | x | | | | | | |
| IO | | | | | | | | | | | | | x | x | x | x | x | x | x | | | | | |
| IP | | | | | | | | | | | | | x | x | x | x | x | x | x | x | | | | |
| IQ | | | | | | | | | | | | | x | x | x | x | x | x | x | x | x | | | |
| IR | | | | | | | | | | | | | x | x | x | x | x | x | x | x | x | x | | |
| IS | | | | | | | | | | | | | x | x | x | x | x | x | x | x | x | x | x | |
| IT | | | | | | | | | | | | | x | x | x | x | x | x | x | x | x | x | x | x |

TABLE D-continued

| | BACTERIAL TAXON | | | | | | | | | | | | | | | | | | | | | | | |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| IU | x | | | | | | | | | | | | | x | x | x | x | x | x | x | x | x | x | x |
| IV | x | x | | | | | | | | | | | | x | x | x | x | x | x | x | x | x | x | x |
| IC | x | x | x | | | | | | | | | | | x | x | x | x | x | x | x | x | x | x | x |
| ID | x | x | x | x | | | | | | | | | | x | x | x | x | x | x | x | x | x | x | x |
| IE | x | x | x | x | x | | | | | | | | | x | x | x | x | x | x | x | x | x | x | x |
| IF | x | x | x | x | x | x | | | | | | | | x | x | x | x | x | x | x | x | x | x | x |
| IG | x | x | x | x | x | x | x | | | | | | | x | x | x | x | x | x | x | x | x | x | x |
| IH | x | x | x | x | x | x | x | x | | | | | | x | x | x | x | x | x | x | x | x | x | x |
| II | x | x | x | x | x | x | x | x | x | | | | | x | x | x | x | x | x | x | x | x | x | x |
| IJ | x | x | x | x | x | x | x | x | x | x | | | | x | x | x | x | x | x | x | x | x | x | x |
| IK | x | x | x | x | x | x | x | x | x | x | x | | | x | x | x | x | x | x | x | x | x | x | x |
| IL | | | | | | | | | | | | | | x | x | | | | | | | | | |
| IM | | | | | | | | | | | | | | x | x | x | | | | | | | | |
| IN | | | | | | | | | | | | | | x | x | x | x | | | | | | | |
| IO | | | | | | | | | | | | | | x | x | x | x | x | | | | | | |
| IP | | | | | | | | | | | | | | x | x | x | x | x | x | | | | | |
| IQ | | | | | | | | | | | | | | x | x | x | x | x | x | x | | | | |
| IR | | | | | | | | | | | | | | x | x | x | x | x | x | x | x | | | |
| IS | | | | | | | | | | | | | | x | x | x | x | x | x | x | x | x | | |
| IT | | | | | | | | | | | | | | x | x | x | x | x | x | x | x | x | x | |
| IU | | | | | | | | | | | | | | x | x | x | x | x | x | x | x | x | x | x |
| IV | x | | | | | | | | | | | | | x | x | x | x | x | x | x | x | x | x | x |
| IW | x | x | | | | | | | | | | | | x | x | x | x | x | x | x | x | x | x | x |
| IX | x | x | x | | | | | | | | | | | x | x | x | x | x | x | x | x | x | x | x |
| IY | x | x | x | x | | | | | | | | | | x | x | x | x | x | x | x | x | x | x | x |
| IZ | x | x | x | x | x | | | | | | | | | x | x | x | x | x | x | x | x | x | x | x |
| JA | x | x | x | x | x | x | | | | | | | | x | x | x | x | x | x | x | x | x | x | x |
| JB | x | x | x | x | x | x | x | | | | | | | x | x | x | x | x | x | x | x | x | x | x |
| JC | x | x | x | x | x | x | x | x | | | | | | x | x | x | x | x | x | x | x | x | x | x |
| JD | x | x | x | x | x | x | x | x | x | | | | | x | x | x | x | x | x | x | x | x | x | x |
| JE | x | x | x | x | x | x | x | x | x | x | | | | x | x | x | x | x | x | x | x | x | x | x |
| JF | x | x | x | x | x | x | x | x | x | x | x | | | x | x | x | x | x | x | x | x | x | x | x |
| JK | x | x | x | x | x | x | x | x | x | x | x | x | | x | x | x | x | x | x | x | x | x | x | x |
| JL | | | | | | | | | | | | | | x | x | | | | | | | | | |
| JM | | | | | | | | | | | | | | x | x | x | | | | | | | | |
| JN | | | | | | | | | | | | | | x | x | x | x | | | | | | | |
| JO | | | | | | | | | | | | | | x | x | x | x | x | | | | | | |
| JP | | | | | | | | | | | | | | x | x | x | x | x | x | | | | | |
| JQ | | | | | | | | | | | | | | x | x | x | x | x | x | x | | | | |
| JR | | | | | | | | | | | | | | x | x | x | x | x | x | x | x | | | |
| JS | | | | | | | | | | | | | | x | x | x | x | x | x | x | x | x | | |
| JT | | | | | | | | | | | | | | x | x | x | x | x | x | x | x | x | x | x |
| JU | x | | | | | | | | | | | | | x | x | x | x | x | x | x | x | x | x | x |
| JV | x | x | | | | | | | | | | | | x | x | x | x | x | x | x | x | x | x | x |
| JW | x | x | x | | | | | | | | | | | x | x | x | x | x | x | x | x | x | x | x |
| JX | x | x | x | x | | | | | | | | | | x | x | x | x | x | x | x | x | x | x | x |
| JY | x | x | x | x | x | | | | | | | | | x | x | x | x | x | x | x | x | x | x | x |
| JZ | x | x | x | x | x | x | | | | | | | | x | x | x | x | x | x | x | x | x | x | x |
| KA | x | x | x | x | x | x | x | | | | | | | x | x | x | x | x | x | x | x | x | x | x |
| KB | x | x | x | x | x | x | x | x | | | | | | x | x | x | x | x | x | x | x | x | x | x |
| KC | x | x | x | x | x | x | x | x | x | | | | | x | x | x | x | x | x | x | x | x | x | x |
| KD | x | x | x | x | x | x | x | x | x | x | | | | x | x | x | x | x | x | x | x | x | x | x |
| KE | x | x | x | x | x | x | x | x | x | x | x | | | x | x | x | x | x | x | x | x | x | x | x |
| KF | x | x | x | x | x | x | x | x | x | x | x | x | | x | x | x | x | x | x | x | x | x | x | x |
| KG | x | x | x | x | x | x | x | x | x | x | x | x | x | x | x | x | x | x | x | x | x | x | x | x |
| KH | | | | | | | | | | | | | | | | x | x | | | | | | | |
| KI | | | | | | | | | | | | | | | | x | x | x | | | | | | |
| KJ | | | | | | | | | | | | | | | | x | x | x | x | | | | | |
| KK | | | | | | | | | | | | | | | | x | x | x | x | x | | | | |
| KL | | | | | | | | | | | | | | | | x | x | x | x | x | x | | | |
| KM | | | | | | | | | | | | | | | | x | x | x | x | x | x | x | | |
| KN | | | | | | | | | | | | | | | | x | x | x | x | x | x | x | x | |
| KO | | | | | | | | | | | | | | | | x | x | x | x | x | x | x | x | x |
| KP | x | | | | | | | | | | | | | | | x | x | x | x | x | x | x | x | x |
| KQ | x | x | | | | | | | | | | | | | | x | x | x | x | x | x | x | x | x |
| KR | x | x | x | | | | | | | | | | | | | x | x | x | x | x | x | x | x | x |
| KS | x | x | x | x | | | | | | | | | | | | x | x | x | x | x | x | x | x | x |
| KT | x | x | x | x | x | | | | | | | | | | | x | x | x | x | x | x | x | x | x |
| KU | x | x | x | x | x | x | | | | | | | | | | x | x | x | x | x | x | x | x | x |
| KV | x | x | x | x | x | x | x | | | | | | | | | x | x | x | x | x | x | x | x | x |
| KW | x | x | x | x | x | x | x | x | | | | | | | | x | x | x | x | x | x | x | x | x |
| KX | x | x | x | x | x | x | x | x | x | | | | | | | x | x | x | x | x | x | x | x | x |
| KY | x | x | x | x | x | x | x | x | x | x | | | | | | x | x | x | x | x | x | x | x | x |
| KZ | x | x | x | x | x | x | x | x | x | x | x | | | | | x | x | x | x | x | x | x | x | x |
| LA | x | x | x | x | x | x | x | x | x | x | x | x | | | | x | x | x | x | x | x | x | x | x |
| LB | x | x | x | x | x | x | x | x | x | x | x | x | x | | | x | x | x | x | x | x | x | x | x |

TABLE D-continued

| | \multicolumn{24}{c}{BACTERIAL TAXON} |
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| LC | x | x | x | x | x | x | x | x | x | x | x | x | x | | | x | x | x | x | x | x | x | x | x |
| LD | | | | | | | | | | | | | | | | | | x | x | | | | | |
| LE | | | | | | | | | | | | | | | | | | x | x | x | | | | |
| LF | | | | | | | | | | | | | | | | | | x | x | x | x | | | |
| LG | | | | | | | | | | | | | | | | | | x | x | x | x | x | | |
| LH | | | | | | | | | | | | | | | | | | x | x | x | x | x | x | |
| LI | | | | | | | | | | | | | | | | | | x | x | x | x | x | x | |
| LJ | | | | | | | | | | | | | | | | | | x | x | x | x | x | x | x |
| LK | x | | | | | | | | | | | | | | | | | x | x | x | x | x | x | x |
| LL | x | x | | | | | | | | | | | | | | | | x | x | x | x | x | x | x |
| LM | x | x | x | | | | | | | | | | | | | | | x | x | x | x | x | x | x |
| LN | x | x | x | x | | | | | | | | | | | | | | x | x | x | x | x | x | x |
| LO | x | x | x | x | x | | | | | | | | | | | | | x | x | x | x | x | x | x |
| LP | x | x | x | x | x | x | | | | | | | | | | | | x | x | x | x | x | x | x |
| LQ | x | x | x | x | x | x | x | | | | | | | | | | | x | x | x | x | x | x | x |
| LR | x | x | x | x | x | x | x | x | | | | | | | | | | x | x | x | x | x | x | x |
| LS | x | x | x | x | x | x | x | x | x | | | | | | | | | x | x | x | x | x | x | x |
| LT | x | x | x | x | x | x | x | x | x | x | | | | | | | | x | x | x | x | x | x | x |
| LU | x | x | x | x | x | x | x | x | x | x | x | | | | | | | x | x | x | x | x | x | x |
| LV | x | x | x | x | x | x | x | x | x | x | x | x | | | | | | x | x | x | x | x | x | x |
| LW | x | x | x | x | x | x | x | x | x | x | x | x | x | | | | | x | x | x | x | x | x | x |
| LX | x | x | x | x | x | x | x | x | x | x | x | x | x | x | | | | x | x | x | x | x | x | x |
| LY | x | x | x | x | x | x | x | x | x | x | x | x | x | x | x | | | x | x | x | x | x | x | x |
| LZ | | | | | | | | | | | | | | | | | | | x | x | | | | |
| MA | | | | | | | | | | | | | | | | | | | x | x | x | | | |
| MB | | | | | | | | | | | | | | | | | | | x | x | x | x | | | |
| MC | | | | | | | | | | | | | | | | | | | x | x | x | x | x | | |
| MD | | | | | | | | | | | | | | | | | | | x | x | x | x | x | x | |
| ME | | | | | | | | | | | | | | | | | | | x | x | x | x | x | x | x |
| MF | x | | | | | | | | | | | | | | | | | | x | x | x | x | x | x | x |
| MG | x | x | | | | | | | | | | | | | | | | | x | x | x | x | x | x | x |
| MH | x | x | x | | | | | | | | | | | | | | | | x | x | x | x | x | x | x |
| MI | x | x | x | x | | | | | | | | | | | | | | | x | x | x | x | x | x | x |
| MJ | x | x | x | x | x | | | | | | | | | | | | | | x | x | x | x | x | x | x |
| MK | x | x | x | x | x | x | | | | | | | | | | | | | x | x | x | x | x | x | x |
| ML | x | x | x | x | x | x | x | | | | | | | | | | | | x | x | x | x | x | x | x |
| MM | x | x | x | x | x | x | x | x | | | | | | | | | | | x | x | x | x | x | x | x |
| MN | x | x | x | x | x | x | x | x | x | | | | | | | | | | x | x | x | x | x | x | x |
| MO | x | x | x | x | x | x | x | x | x | x | | | | | | | | | x | x | x | x | x | x | x |
| MP | x | x | x | x | x | x | x | x | x | x | x | | | | | | | | x | x | x | x | x | x | x |
| MQ | x | x | x | x | x | x | x | x | x | x | x | x | | | | | | | x | x | x | x | x | x | x |
| MR | x | x | x | x | x | x | x | x | x | x | x | x | x | | | | | | x | x | x | x | x | x | x |
| MS | x | x | x | x | x | x | x | x | x | x | x | x | x | x | | | | | x | x | x | x | x | x | x |
| MT | x | x | x | x | x | x | x | x | x | x | x | x | x | x | x | | | | x | x | x | x | x | x | x |
| MU | x | x | x | x | x | x | x | x | x | x | x | x | x | x | x | x | | | x | x | x | x | x | x | x |
| MV | | | | | | | | | | | | | | | | | | | x | x | | | | |
| MW | | | | | | | | | | | | | | | | | | | x | x | x | | | | |
| MX | | | | | | | | | | | | | | | | | | | x | x | x | x | | | |
| MY | | | | | | | | | | | | | | | | | | | x | x | x | x | x | | |
| MZ | | | | | | | | | | | | | | | | | | | x | x | x | x | x | x | |
| NA | x | | | | | | | | | | | | | | | | | | x | x | x | x | x | x | x |
| NB | x | x | | | | | | | | | | | | | | | | | x | x | x | x | x | x | x |
| NC | x | x | x | | | | | | | | | | | | | | | | x | x | x | x | x | x | x |
| ND | x | x | x | x | | | | | | | | | | | | | | | x | x | x | x | x | x | x |
| NE | x | x | x | x | x | | | | | | | | | | | | | | x | x | x | x | x | x | x |
| NF | x | x | x | x | x | x | | | | | | | | | | | | | x | x | x | x | x | x | x |
| NG | x | x | x | x | x | x | x | | | | | | | | | | | | x | x | x | x | x | x | x |
| NH | x | x | x | x | x | x | x | x | | | | | | | | | | | x | x | x | x | x | x | x |
| NI | x | x | x | x | x | x | x | x | x | | | | | | | | | | x | x | x | x | x | x | x |
| NJ | x | x | x | x | x | x | x | x | x | x | | | | | | | | | x | x | x | x | x | x | x |
| NK | x | x | x | x | x | x | x | x | x | x | x | | | | | | | | x | x | x | x | x | x | x |
| NL | x | x | x | x | x | x | x | x | x | x | x | x | | | | | | | x | x | x | x | x | x | x |
| NM | x | x | x | x | x | x | x | x | x | x | x | x | x | | | | | | x | x | x | x | x | x | x |
| NN | x | x | x | x | x | x | x | x | x | x | x | x | x | x | | | | | x | x | x | x | x | x | x |

TABLE D-continued

| | BACTERIAL TAXON | | | | | | | | | | | | | | | | | | | | | | | |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| NO | x | x | x | x | x | x | x | x | x | x | x | x | x | x | | | | | | x | x | x | x | x | x |
| NP | x | x | x | x | x | x | x | x | x | x | x | x | x | x | x | | | | | x | x | x | x | x | x |
| NQ | x | x | x | x | x | x | x | x | x | x | x | x | x | x | x | x | | | | x | x | x | x | x | x |
| NR | | | | | | | | | | | | | | | | | | | | | x | x | | | |
| NS | | | | | | | | | | | | | | | | | | | | | x | x | x | | |
| NT | | | | | | | | | | | | | | | | | | | | | x | x | x | x | |
| NU | | | | | | | | | | | | | | | | | | | | | x | x | x | x | x |
| NV | x | | | | | | | | | | | | | | | | | | | | x | x | x | x | x |
| NW | x | x | | | | | | | | | | | | | | | | | | | x | x | x | x | x |
| NX | x | x | x | | | | | | | | | | | | | | | | | | x | x | x | x | x |
| NY | x | x | x | x | | | | | | | | | | | | | | | | | x | x | x | x | x |
| NZ | x | x | x | x | x | | | | | | | | | | | | | | | | x | x | x | x | x |
| OA | x | x | x | x | x | x | | | | | | | | | | | | | | | x | x | x | x | x |
| OB | x | x | x | x | x | x | x | | | | | | | | | | | | | | x | x | x | x | x |
| OC | x | x | x | x | x | x | x | x | | | | | | | | | | | | | x | x | x | x | x |
| OD | x | x | x | x | x | x | x | x | x | | | | | | | | | | | | x | x | x | x | x |
| OE | x | x | x | x | x | x | x | x | x | x | | | | | | | | | | | x | x | x | x | x |
| OF | x | x | x | x | x | x | x | x | x | x | x | | | | | | | | | | x | x | x | x | x |
| OG | x | x | x | x | x | x | x | x | x | x | x | x | | | | | | | | | x | x | x | x | x |
| OH | x | x | x | x | x | x | x | x | x | x | x | x | x | | | | | | | | x | x | x | x | x |
| OI | x | x | x | x | x | x | x | x | x | x | x | x | x | x | | | | | | | x | x | x | x | x |
| OJ | x | x | x | x | x | x | x | x | x | x | x | x | x | x | x | | | | | | x | x | x | x | x |
| OK | x | x | x | x | x | x | x | x | x | x | x | x | x | x | x | x | | | | | x | x | x | x | x |
| OL | x | x | x | x | x | x | x | x | x | x | x | x | x | x | x | x | x | | | | x | x | x | x | x |
| OM | x | x | x | x | x | x | x | x | x | x | x | x | x | x | x | x | x | x | | | x | x | x | x | x |
| ON | | | | | | | | | | | | | | | | | | | | | x | x | | | |
| OO | | | | | | | | | | | | | | | | | | | | | x | x | x | x | |
| OP | x | | | | | | | | | | | | | | | | | | | | x | x | x | x | |
| OQ | x | x | | | | | | | | | | | | | | | | | | | x | x | x | x | |
| OR | x | x | x | | | | | | | | | | | | | | | | | | x | x | x | x | |
| OS | x | x | x | x | | | | | | | | | | | | | | | | | x | x | x | x | |
| OT | x | x | x | x | x | | | | | | | | | | | | | | | | x | x | x | x | |
| OU | x | x | x | x | x | x | | | | | | | | | | | | | | | x | x | x | x | |
| OV | x | x | x | x | x | x | x | | | | | | | | | | | | | | x | x | x | x | |
| OW | x | x | x | x | x | x | x | x | | | | | | | | | | | | | x | x | x | x | |
| OX | x | x | x | x | x | x | x | x | x | | | | | | | | | | | | x | x | x | x | |
| OY | x | x | x | x | x | x | x | x | x | x | | | | | | | | | | | x | x | x | x | |
| OZ | x | x | x | x | x | x | x | x | x | x | x | | | | | | | | | | x | x | x | x | |
| PA | x | x | x | x | x | x | x | x | x | x | x | x | | | | | | | | | x | x | x | x | |
| PB | x | x | x | x | x | x | x | x | x | x | x | x | x | | | | | | | | x | x | x | x | |
| PC | x | x | x | x | x | x | x | x | x | x | x | x | x | x | | | | | | | x | x | x | x | |
| PD | x | x | x | x | x | x | x | x | x | x | x | x | x | x | x | | | | | | x | x | x | x | |
| PE | x | x | x | x | x | x | x | x | x | x | x | x | x | x | x | x | | | | | x | x | x | x | |
| PF | x | x | x | x | x | x | x | x | x | x | x | x | x | x | x | x | x | | | | x | x | x | x | |
| PG | x | x | x | x | x | x | x | x | x | x | x | x | x | x | x | x | x | x | | | x | x | x | x | |
| PH | x | x | x | x | x | x | x | x | x | x | x | x | x | x | x | x | x | x | x | | x | x | x | x | |
| PI | | | | | | | | | | | | | | | | | | | | | | | x | x | |
| PJ | | | | | | | | | | | | | | | | | | | | | | | x | x | x |
| PK | | | | | | | | | | | | | | | | | | | | | | | | x | x |
| PL | x | | | | | | | | | | | | | | | | | | | | | | | | x |
| PM | x | x | | | | | | | | | | | | | | | | | | | | | | | x |
| PN | x | x | x | | | | | | | | | | | | | | | | | | | | | | x |
| PO | x | x | x | x | | | | | | | | | | | | | | | | | | | | | x |
| PP | x | x | x | x | x | | | | | | | | | | | | | | | | | | | | x |
| PQ | x | x | x | x | x | x | | | | | | | | | | | | | | | | | | | x |
| PR | x | x | x | x | x | x | x | | | | | | | | | | | | | | | | | | x |
| PS | x | x | x | x | x | x | x | x | | | | | | | | | | | | | | | | | x |
| PT | x | x | x | x | x | x | x | x | x | | | | | | | | | | | | | | | | x |
| PU | x | x | x | x | x | x | x | x | x | x | | | | | | | | | | | | | | | x |
| PV | x | x | x | x | x | x | x | x | x | x | x | | | | | | | | | | | | | | x |
| PW | x | x | x | x | x | x | x | x | x | x | x | x | | | | | | | | | | | | | x |
| PX | x | x | x | x | x | x | x | x | x | x | x | x | x | | | | | | | | | | | | x |
| PY | x | x | x | x | x | x | x | x | x | x | x | x | x | x | | | | | | | | | | | x |
| PZ | x | x | x | x | x | x | x | x | x | x | x | x | x | x | x | | | | | | | | | | x |
| QA | x | x | x | x | x | x | x | x | x | x | x | x | x | x | x | | | | | | | | | | x |

TABLE D-continued

| | BACTERIAL TAXON | | | | | | | | | | | | | | | | | | | | | | | |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| QB | x | x | x | x | x | x | x | x | x | x | x | x | x | x | x | x | x | | | | | | | x |
| QC | x | x | x | x | x | x | x | x | x | x | x | x | x | x | x | x | x | x | | | | | | x |
| QD | x | x | x | x | x | x | x | x | x | x | x | x | x | x | x | x | x | x | x | | | | | x |
| QE | x | x | x | x | x | x | x | x | x | x | x | x | x | x | x | x | x | x | x | x | | | | x |
| QF | x | x | x | x | x | x | x | x | x | x | x | x | x | x | x | x | x | x | x | x | x | | | x |
| QG | x | x | x | x | x | x | x | x | x | x | x | x | x | x | x | x | x | x | x | x | x | x | | x |

Strain 1: *Faecalibacterium prausnitzii* OTU ID 326792,
Strain 2: *Ruminococcus* sp. 5 1 39BFAA OTU ID 189827,
Strain 3: *Lactobacillus ruminis* OTU ID 470663,
Strain 4: *Dorea longicatena* OTU ID 191687,
Strain 5: *Bifidobacterium longum* OTU ID 72820,
Strain 6: *Ruminococcus* sp. 5 1 39BFAA OTU ID 194745,
Strain 7: *Lactobacillus mucosae* OTU ID 15141,
Strain 8: *Bifidobacterium* sp. OTU ID 561483,
Strain 9: *Staphylococcus* sp. OTU ID 217996,
Strain 10: *Ruminococcus* sp. 5 1 39BFAA OTU ID 364234,
Strain 11: *Catenibacterium mitsuokai* OTU ID 287510,
Strain 12: *Dorea formicigenerans* OTU ID 261912,
Strain 13: *Ruminococcus torques* OTU ID 361809,
Strain 14: *Streptococcus thermophilus* OTU ID 108747,
Strain 15: *Bifidobacterium* sp. OTU ID 533785,
Strain 16: *Haemophilus parainfluenzae* OTU ID 9514,
Strain 17: *Streptococcus* sp. OTU ID 561636,
Strain 18: *Clostridium* sp. OTU ID 312461,
Strain 19: *Clostridium ramosum* OTU ID 470139,
Strain 20: *Clostridium* sp. OTU ID 181834,
Strain 21: *Weissella cibaria* OTU ID 148099,
Strain 22: *Bifidobacterium* sp. OTU ID 469873,
Strain 23: Clostridiales sp. OTU ID 185951,
Strain 24: Ruminococcaceae sp. OTU ID 212619.
Additional information about these bacterial taxa may be found in Table B.

A bacterial taxon of the invention, or a combination of bacterial taxa of the invention, is formulated to maintain a suitable level of viable cells during the formulation's shelf life and upon administration to a subject. Each bacterial taxon may be present in a wide range of amounts provided that the composition or combination delivers the effect described. The total amount of bacteria per unit dose is dependent, in part, upon the dosage form and excipients. Non-limiting examples of suitable amounts include from about $10^2$ to about $10^{12}$ colony forming units (cfu) of each bacterial strain per unit dose. In some embodiments, the amount of each bacterial strain is between about $10^5$ and about $10^{12}$ cfu per unit dose, between about $10^6$ and about $10^{12}$ cfu per unit dose, between about $10^7$ and about $10^{12}$ cfu per unit dose, or between about $10^8$ and about $10^{12}$ cfu per unit dose. In other embodiments, the amount of each bacterial strain is between about $10^5$ and about $10^{11}$ cfu per unit dose, between about 106 and about $10^{11}$ cfu per unit dose, between about $10^7$ and about $10^{11}$ cfu per unit dose, or between about 108 and about $10^{11}$ cfu per unit dose. In other embodiments, the amount of each bacterial strain is between about $10^5$ and about $10^{10}$ cfu per unit dose, between about 106 and about $10^{10}$ cfu per unit dose, between about $10^7$ and about $10^{10}$ cfu per unit dose, or between about $10^8$ and about $10^{10}$ cfu per unit dose. In other embodiments, the amount of each bacterial taxon is between about $10^5$ and about $10^9$ cfu per unit dose, between about $10^6$ and about $10^9$ cfu per unit dose, between about $10^7$ and about $10^9$ cfu per unit dose, or between about $10^8$ and about $10^9$ cfu per unit dose. Generally, a bacterial strain may be provided as a frozen or freeze-dried culture, or as bacterial spores.

A bacterial taxon of the invention, or a combination of bacterial taxa of the invention, may be formulated into a formulation for oral or rectal administration comprising one or more bacterial taxa of the invention and one more excipients. Non-limiting examples of excipients include binders, diluents, fillers, disintegrants, effervescent disintegration agents, preservatives, antioxidants, flavor-modifying agents, lubricants and glidants, dispersants, coloring agents, pH modifiers, chelating agents, and release-controlling polymers. Bacterial taxa of the invention, or a combination of bacterial taxa of the invention, may be formulated in unit dosage form as a solid, semi-solid, liquid, capsule, or powder. These formulations are a further aspect of the invention. Usually the amount of a bacterial taxon of the invention, or a combination of bacterial taxa of the invention, is between 0.1-95% by weight of the formulation, or between 1 and 50% by weight of the formulation. Methods of formulating compositions are discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

In the preparation of formulations in dosage units for oral administration, a bacterial taxon of the invention, or a combination of bacterial taxa of the invention, may be mixed with a solid, powdered carrier, e.g. lactose, saccharose, sorbitol, mannitol, starch, amylopectin, cellulose derivatives or gelatin, and optionally with lubricants (e.g. magnesium stearate, calcium stearate, sodium steryl fumarate and polyethylene glycol waxes), release-controlling polymers and other excipients. The mixture is then processed into granules or pressed into tablets. Since the viability of the a bacterial strain may be negatively impacted by acidic media, the above-mentioned granules or tablets may be coated with an enteric coating which protects the combination of the invention from acid degradation as long as the dosage form remains in the stomach. The enteric coating is chosen among pharmaceutically acceptable enteric-coating materials e.g. beeswax, shellac or anionic film-forming polymers such as cellulose acetate phthalate, hydroxypropyl methylcellulose phthalate, partly methyl esterified methacrylic acid polymers and the like, if preferred in combination with a suitable plasticizer. To this coating various dyes may be added in order to distinguish among tablets or granules with different combinations or with different amounts of the combination present.

Alternatively, the pharmaceutical compositions may be incorporated into a food product or powder for mixing with a liquid, or administered orally after only mixing with a non-foodstuff liquid.

Soft gelatine capsules may also be prepared with capsules comprising a combination of the invention and vegetable oil, fat, or other suitable vehicle for soft gelatine capsules. Soft gelatine capsules are preferably enteric coated as described above. Hard gelatine capsules may contain enteric-coated granules of a combination of the invention. Hard gelatine capsules may also contain a combination of the invention in combination with a solid powdered carrier e.g. lactose, saccharose, sorbitol, mannitol, potato starch, corn starch, amylopectin, cellulose derivatives or gelatine; the hard gelatine capsules are preferably enteric coated as described above.

Dosage units for rectal administration may be prepared in the form of suppositories which comprise a bacterial taxon of the invention, or a combination of bacterial taxa of the invention, mixed with a non-irritating excipient that is solid at room temperature but liquid at rectal temperature and therefore will melt in the rectum to release the drug. Non-limiting examples of suitable excipients for rectal suppository embodiments include cocoa butter, beeswax, and polyethylene glycols. Alternatively, a dosage unit for rectal administration may be prepared in the form of a gelatine rectal capsule which comprises a bacterial taxon of the invention, or a combination of bacterial taxa of the invention, in a mixture with a vegetable oil, paraffin oil or other suitable vehicle for gelatine rectal capsules. In yet another alternative, a bacterial taxon of the invention, or a combination of bacterial taxa of the invention, may be prepared in the form of a ready-made enema, or in the form of a dry enema formulation to be reconstituted in a suitable solvent just prior to administration.

Liquid preparations for oral administration may be prepared in the form of syrups or suspensions, e.g. solutions or suspensions containing from 0.2% to 20% by weight of a bacterial taxon of the invention, or a combination of bacterial taxa of the invention, and the remainder consisting of sugar or sugar alcohols and a mixture of ethanol, water, glycerol, propylene glycol and polyethylene glycol. If desired, such liquid preparations may contain colouring agents, flavouring agents, saccharine and carboxymethyl cellulose and thickening agent. Liquid preparations for oral administration may also be prepared in the form of a dry powder to be reconstituted with a suitable solvent prior to use.

The dosing regimen involving compositions in accordance with the present disclosure can be varied to achieve a desired result, such as may be determined empirically for a given individual subject, or by extrapolation from data obtained from administering a composition of the invention to a clinical or other test population. The desired dose may be presented in multiple (e.g., two, three, four, five, six, or more) sub-doses administered at appropriate intervals throughout the day.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that changes may be made in the specific embodiments that are disclosed and still obtain a like or similar result without departing from the spirit and scope of the invention. Therefore, all matter set forth or shown in the accompanying drawings is to be interpreted as illustrative and not in a limiting sense.

EXAMPLES

The following examples illustrate various iterations of the invention.

Severe acute malnutrition and moderate acute malnutrition (MAM) are typically defined by anthropometric measurements: children are classified as having SAM if their weight-for-height Z-scores (WHZ)[3] are below three standard deviations (—3 s.d.) from the median of the World Health Organization (WHO) reference growth standards, whereas those with WHZ between—2 and—3 s.d. are categorized as having MAM. SAM and MAM typically develop between 3 and 24 months after birth[4]. A standardized treatment protocol for SAM and its complications has been developed in Bangladesh[1]. The result has been a reduction in mortality rate, although the extent to which this protocol results in long-term restoration of normal growth and development needs to be ascertained through longitudinal studies[5,6]. There is similar lack of clarity about the long-term efficacy of nutritional interventions for MAM[7,8].

Food is a major factor that shapes the proportional representation of organisms present in the gut microbial community (microbiota), and its gene content (microbiome). The microbiota and microbiome in turn have an important role in extracting and metabolizing dietary ingredients[9-14]. To investigate the hypothesis that healthy postnatal development (maturation) of the gut microbiota is perturbed in malnutrition[12], we monitored 50 healthy Bangladeshi children monthly during the first 2 years after birth (25 singletons, 11 twin pairs, 1 set of triplets; 996 faecal samples collected monthly; see Methods for Examples 1-9 and Tables 1 and 2). By identifying bacterial taxa that discriminate the microbiota of healthy children at different chronologic ages, we were able to test our hypothesis by studying 6 to 20-month-old children presenting with SAM, just before, during, and after treatment with two very different types of food intervention, as well as children with MAM. The results provide a different perspective about malnutrition; one involving disruption of a microbial facet of our normal human postnatal development.

To characterize gut microbiota maturation across unrelated healthy Bangladeshi children living in separate households, faecal samples were collected at monthly intervals up to 23.4±0.5 months of age in a training set of 12 children who exhibited consistently healthy anthropometric scores (WHZ, —0.32±0.98 (mean±s.d.) 22.7±1.5 faecal samples per child; Table 3a). The bacterial component of their faecal microbiota samples was characterized by V4-16S rRNA sequencing (Table 4) and assigning the resulting reads to operational taxonomic units (OTUs) sharing 97% nucleotide sequence identity (see Methods for Examples 1-9; a 97%-identity OTU is commonly construed as representing a species-level taxon). The relative abundances of 1,222 97%-identity OTUs that passed our filtering criterion[15] were regressed against the chronologic age of each child at the time of faecal sample collection using the Random Forests machine learning algorithm[16]. The regression explained 73% of the variance related to chronologic age. The significance of the fit was established by comparing fitted to null models in which age labels of samples were randomly permuted with respect to their 16S rRNA microbiota profiles (P=0.0001, 9,999 permutations). Ranked lists of all bacterial taxa, in order of 'age-discriminatory importance', were determined by considering those taxa, whose relative abundance values when permuted have a larger marginal increase in mean squared error, to be more important (see Methods for Examples 1-9). Tenfold cross-validation was used to estimate age-discriminatory performance as a function of the number of top-ranking taxa according to their feature importance scores. Minimal improvement in predictive performance was observed when including taxa beyond the top 24 (see Table 5 for the top 60). The 24 most age-discriminatory taxa identified by Random Forests are shown in FIG. 1A in rank order of their contribution to the predictive accuracy of the model and were selected as inputs to a sparse 24-taxon model.

To test the extent to which this sparse model could be applied, we applied it, with no further parameter optimization, to additional monthly faecal samples collected from two other healthy groups of children: 13 singletons (WHZ, —0.4±0.8 (mean±s.d.)) and 25 children from a birth-cohort study of twins and triplets, (WHZ, —0.5±0.7 (mean±s.d.)), all born and raised in Mirpur, Bangladesh (Table 3b,c). We found that the model could be applied to both groups ($r^2$=0.71 and 0.68, respectively), supporting the consistency of the observed taxonomic signature of microbiota maturation across different healthy children living in this geographic locale (FIGS. 1B-D and F-H).

Two metrics of microbiota maturation were defined by applying the sparse model to the 13 healthy singletons and 25 members of twin pairs and triplets that had been used for model validation. The first metric, relative microbiota maturity, was calculated as follows:

relative microbiota maturity=(microbiota age of child)−(microbiota age of healthy children of similar chronologic age)

where microbiota age values for healthy children were interpolated across the first 2 years of life using a spline fit (FIG. 1B-D). The second metric, microbiota-for-age Z score, was calculated as follows:

$MAZ$=(microbiota age−median microbiota age of healthy children of same chronologic age)

(s.d. of microbiota age of healthy children of the same chronologic age) where MAZ is the microbiota-for-age Z-score, and median and s.d. of microbiota age were computed for each month up to 24 months. The MAZ accounts for the variance of predictions of microbiota age as a function of different host age ranges (when considered in discrete monthly bins) (see FIG. 3 for the calculation of each metric, and Example 8 for discussion of how this approach defines immaturity as a specific recognizable state rather than as a lack of maturity).

To study the influences of genetic and environmental factors on these microbiota maturation indices, we examined their distribution in healthy Bangladeshi twins and triplets. Monozygotic twins were not significantly more correlated in their maturity profiles compared to dizygotic twins, and within the set of triplets, the two monozygotic siblings were not more correlated than their fraternal sibling (monozygotic pairs, 0.1±0.5 (Spear-man's Rho±s.d.); dizygotic pairs, 0.33±0.3; in the case of the triplets, values for the monozygotic pair and fraternal sibling were 0.1; and 0.24±0.3, respectively). Maturity was significantly decreased in faecal samples obtained during and 1 month after diarrhoeal episodes (P<0.001 and P<0.01, respectively) but not beyond that period (FIG. 4). There was no discernible effect of recent antibiotic usage (1 week before sampling) on relative microbiota maturity, whereas intake of infant formula was associated with significantly higher maturity values (Table 6). Family membership explained 29% of the total variance in relative microbiota maturity measurements (log-likelihood ratio=102.1,P<0.0001; linear mixed model) (see Example 3, Tables 7 and 8, and FIG. 5 for analyses of faecal microbiota variation in mother-infant dyads and fathers).

To investigate the effects of SAM on microbiota maturity, 64 children with SAM who had been admitted to the Nutritional Rehabilitation Unit of the International Centre for Diarrhoeal Disease Research, Bangladesh (ICDDR,B), Dhaka Hospital, were enrolled in a study to investigate the configuration of their faecal microbiota before, during and after treatment with either an imported, internationally used ready-to-use therapeutic food (RUTF; Plumpy'Nut) or a locally produced, lower-cost nutritional food combination (Khichuri-Halwa). Children ranged in age from 6 to 20 months of age at the time of enrollment and were randomly assigned to either of the treatment arms. At enrollment, WHZ averaged—4.2±0.7 (mean±s.d.) (see Tables 9 and 10 for patient metadata and FIG. 2A for study design). In the initial 'acute phase' of treatment, infection control was achieved with parenteral administration of ampicillin and gentamicin for 2 and 7 days, respectively, and oral amoxicillin for 5 days (from days 3 to 7 of the antibiotic treatment protocol). Children with SAM were initially stabilized by being fed the milk-based gruel, 'suji', followed by randomization to either an imported peanut-based RUTF intervention or an intervention with locally produced, rice-and-lentil-based therapeutic foods (Khichuri and Halwa; see Methods for Examples 1-9 and Table 11 for compositions of all foods used during nutritional rehabilitation). During this second 'nutritional rehabilitation phase' (1.3±0.7 weeks long) children received 150-250 kcal $kg^{-1}$ body weight per day of RUTF or Khichuri-Halwa (3-5 g protein $kg^{-1}$ per day), plus micronutrients including iron. Children were discharged from the hospital after the completion of this second phase; during the 'post-intervention phase', periodic follow-up examinations were performed to monitor health status. Faecal samples were obtained during the acute phase before treatment with Khichuri-Halwa or RUTF, then every 3 days during the nutritional rehabilitation phase, and monthly thereafter during the post-intervention follow-up period.

There was no significant difference in the rate of weight gain between the RUTF and Khichuri-Halwa groups (10.9±4.6 versus 10.4±5.4 g $kg^{-1}$ body weight per day (mean±s.d.); Student's t-test, P=0.7). The mean WHZ at the completion of nutritional rehabilitation was significantly improved in both treatment groups (−3.1±0.7(mean±s.d.) RUTF, P<0.001; and −2.7±1.6 Khichuri-Halwa, P<0.0001), but not significantly different between groups (P=0.15). During follow-up, WHZ remained significantly lower compared to healthy children (−2.1±1.2, Khichuri-Halwa; −2.4±0.8 RUTF versus −0.5±1.1 for healthy, P<0.0001; FIG. 6A). Children in both treatment arms also remained markedly below normal height and severely underweight throughout the follow-up period (FIG. 6B,C).

The Random Forests model derived from healthy children was used to define relative microbiota maturity for children with SAM at the time of enrollment, during treatment, at the end of either nutritional intervention, and during the months of follow-up. The results revealed that compared to healthy children, children with SAM had significant microbiota immaturity at the time that nutritional rehabilitation was initiated and at cessation of treatment (Dunnett's post-hoc test, P<0.0001 for both groups; FIG. 2B). Within 1 month of follow-up, both groups had improved significantly. However, improvement in this metric was short-lived for the RUTF and Khichuri-Halwa groups, with regression to significant immaturity relative to healthy children beyond 4 months after treatment was stopped (FIG. 2B and Table 12). MAZ, like relative microbiota maturity, indicated a transient improvement after RUTF intervention that was not durable beyond 4 months. In the Khichuri-Halwa group, relative microbiota maturity and MAZ improved following treatment, but subsequently regressed, exhibiting significant differences relative to healthy children at 2-3 months, and >4 months after cessation of treatment (FIG. 2B and Table 12).

Both food interventions had non-durable effects on other microbiota parameters. The reduced bacterial diversity associated with SAM persisted after Khichuri-Halwa and only transiently improved with RUTF (FIG. 7 and Table 12). We identified a total of 220 bacterial taxa that were significantly different in their proportional representation in the faecal microbiota of children with SAM compared to healthy children; 165 of these 220 97%-identity OTUs were significantly diminished in the microbiota of children with SAM during the longer term follow-up period in both treatment groups (FIGS. 8 and 9 and Table 13).

Figure 10E:
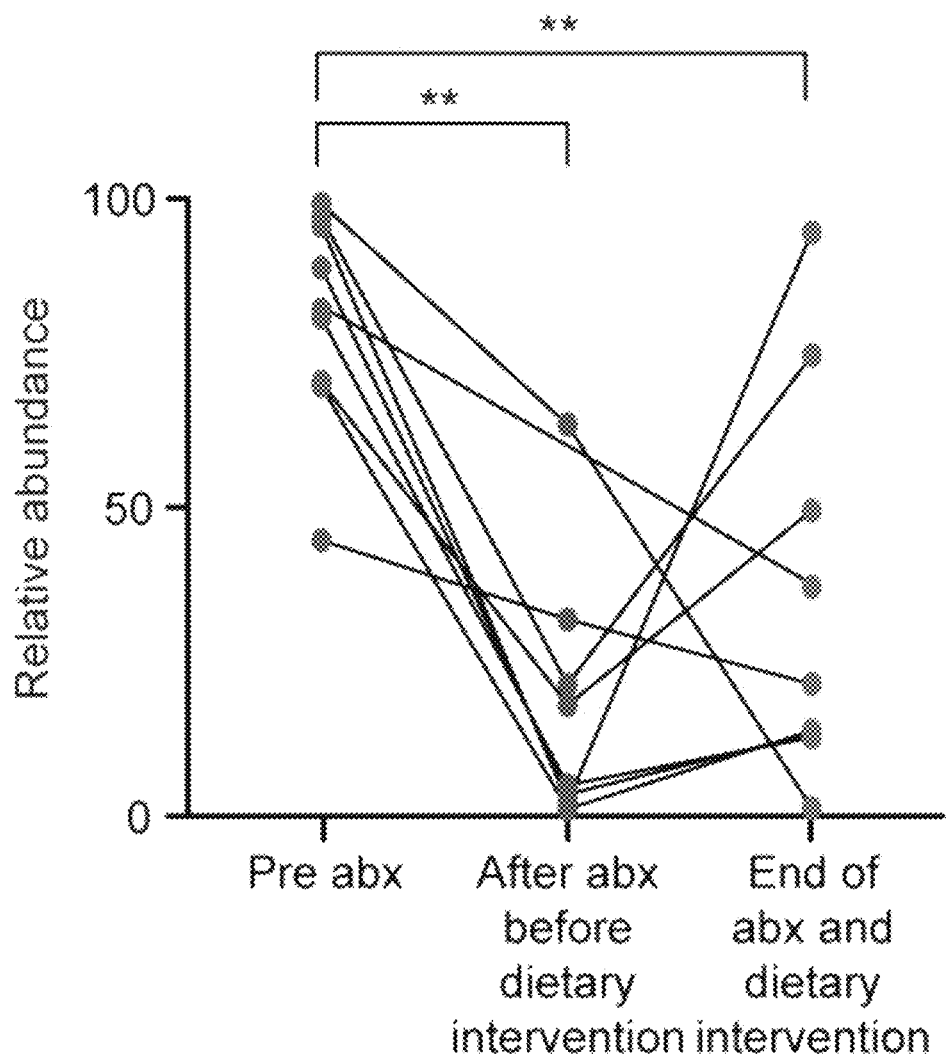
Figure 10F:
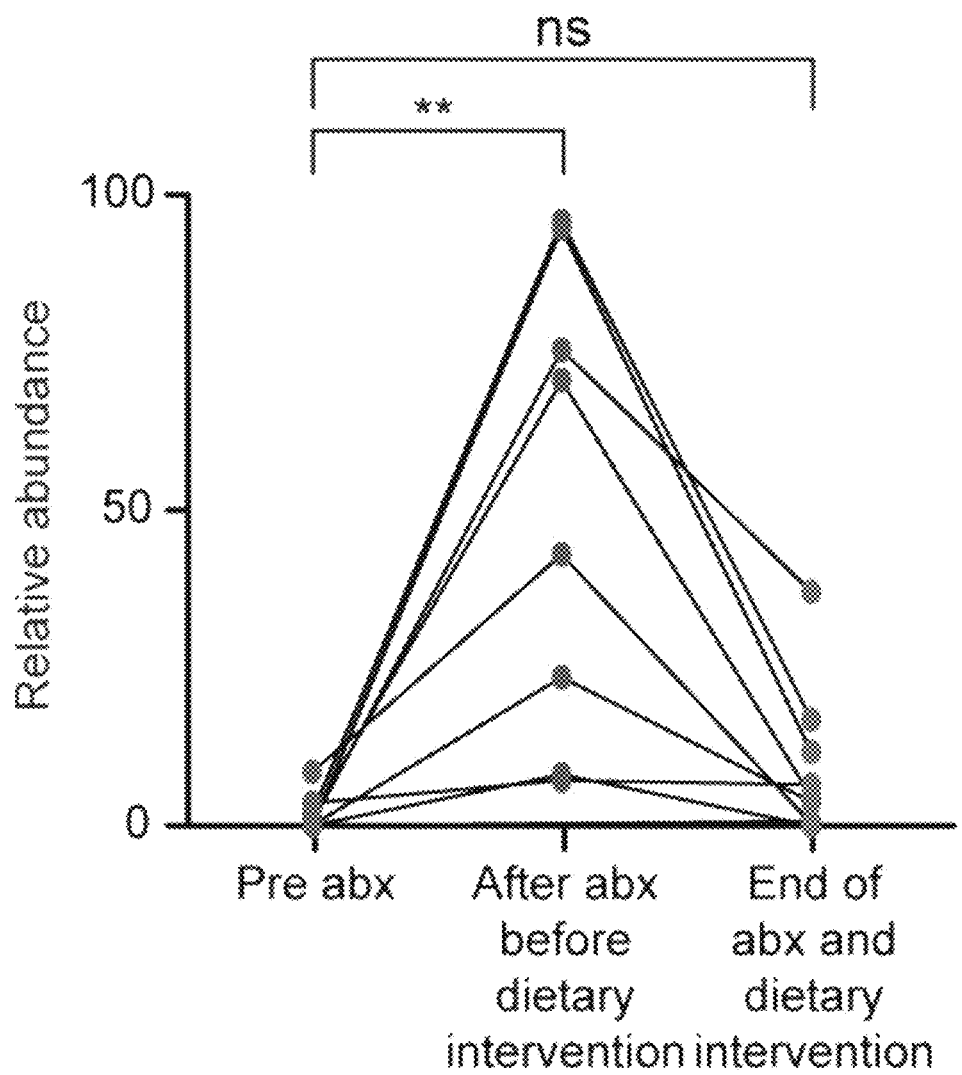

Although the majority of children in both treatment arms of the SAM study were unable to provide faecal samples before the initiation of antibiotic treatment due to the severity of the illness, a subset of nine children each provided one or two faecal samples (n=12) before administration of parenteral ampicillin and gentamicin, and oral amoxicillin. Microbiota immaturity was manifest at this early time-point before antibiotics in these nine children (relative microbiota maturity: −5.15±0.9 months versus −0.03±0.1 for the 38 reference healthy controls; Mann-Whitney, P<0.0001). Sampling these nine children after treatment with parenteral and oral antibiotics but before initiation of RUTF or Khichuri-Halwa (6±3.6 days after hospital admission) showed that there was no significant effect on microbiota maturity (Wilcoxon matched-pairs rank test, P=1). When pre-antibiotic faecal samples from these nine children were compared to samples collected at the end of all treatment interventions (dietary and antibiotic, 20±9 days after admission), no significant differences in relative microbiota maturity (Wilcoxon, P=0.7), MAZ, bacterial diversity (or WHZ) were found (FIG. 10A-D). This is not to say that these interventions were without effects on overall community composition: opposing changes in the relative abundance of Streptococcaceae and Enterobacteriaceae were readily apparent (FIG. 10E,F; note that the Random Forests model classified both the microbiota of children with SAM sampled before and at the conclusion of all treatment interventions as immature, indicating lack of a generic immature state). Although these findings indicate that the relative microbiota immaturity associated with SAM was not solely attributable to the antibiotics used to treat these children, we could not, in cases where children were unable to provide pre-intervention faecal samples, measure the effects of other antibiotics, consumed singly or in various combinations during the acute infection control and nutritional rehabilitation phases, on their metrics of microbiota maturation (see Example 7 and Table 14 for further evidence indicating antibiotic use in the follow-up period did not correlate with the persistence of microbiota immaturity in children with SAM).

SAM affects approximately 4% of children in developing countries. MAM is more prevalent, particularly in South Central Asia, where it affects approximately 19% (30 million children)[7]. Epidemiological studies indicate that periods of MAM are associated with progression to SAM, and with stunting which affects >40% of children under the age of five in Bangladesh[17]. Therefore, we extended our study to children from the singleton cohort at 18 months of age, when all had transitioned to solid foods (n=10 children with WHZ lower than −2 s.d., the threshold for MAM; 23 children with healthy WHZ; Table 15). The relationship between relative microbiota maturity, MAZ and WHZ was significant (Spearman's Rho=0.62 and 0.63, P<0.001, respectively; FIG. 11A,B). Comparing children with MAM to those defined as healthy revealed significantly lower relative microbiota maturity, MAZ and differences in the relative abundances of age-discriminatory taxa in the malnourished group (FIGS. 11D-L and FIGS. 12A,B). These results suggest that microbiota immaturity may be an additional pathophysiological component of moderately malnourished states.

In conclusion, definition of microbiota maturity using bacterial taxonomic biomarkers that are highly discriminatory for age in healthy children has provided a way to characterize malnourished states, including whether responses to food interventions endure for prolonged periods of time beyond the immediate period of treatment. RUTF and Khichuri-Halwa produced improvements in microbiota maturity indices that were not sustained. Addressing the question of how to achieve durable responses in children with varying degrees of malnutrition may involve extending the period of administration of existing or new types of food interventions[7]. One testable hypothesis is that a population's microbiota conditioned for generations on a diet will respond more favourably to nutrient supplementation based on food groups represented in that diet. Next-generation probiotics using gut-derived taxa may also be required in addition to food-based interventions. The functional roles (niches) of the age-discriminatory taxa identified by our Random Forests model need to be clarified since they themselves maybe therapeutic candidates and/or form the basis for low cost field-based diagnostic assessments.

Figure 12C:
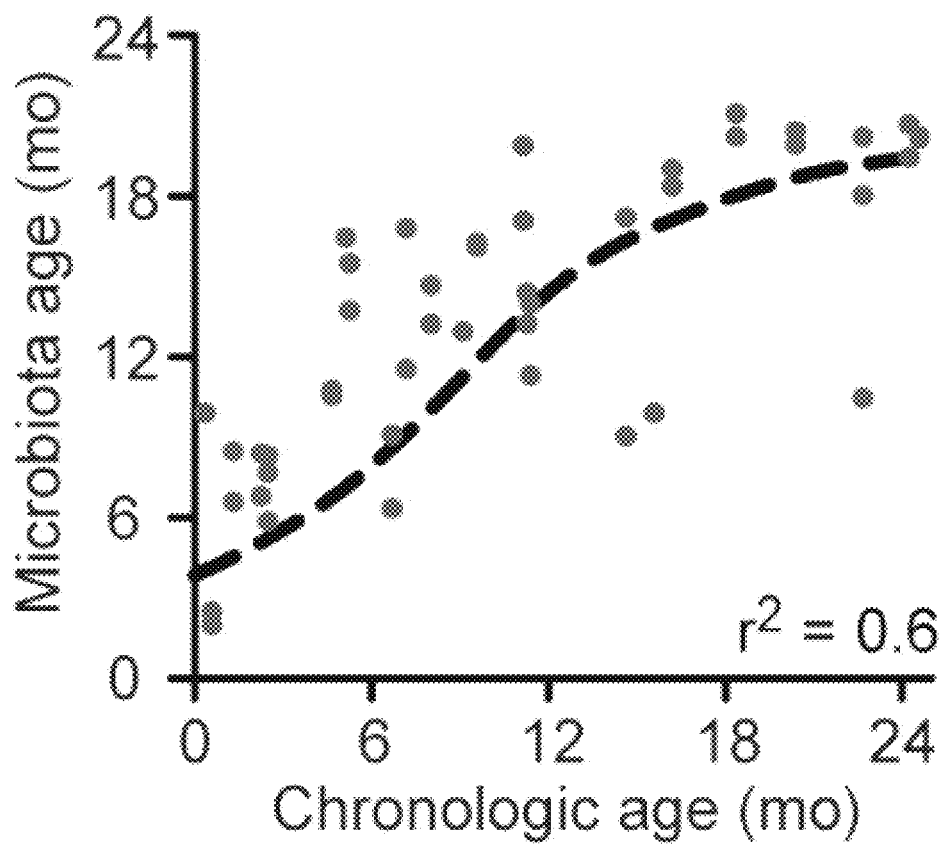
Figure 12D:
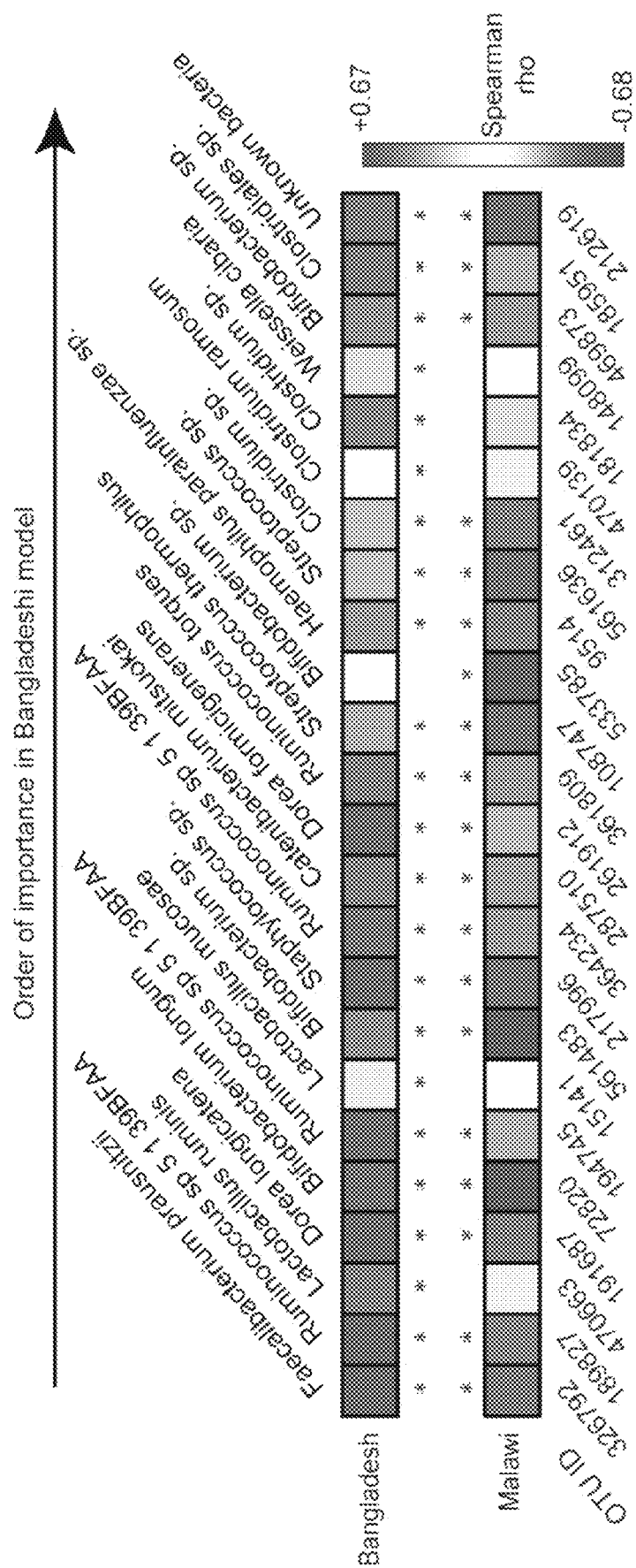

Systematic analyses of microbiota maturation in different healthy and malnourished populations living in different locales, representing different lifestyles andculturaltraditions[11,18], may yield a taxonomy-based model that is generally applicable to many countries and types of diagnostic and therapeutic assessments. Alternatively, these analyses may demonstrate a need for geographic specificity when constructing such models (and diagnostic tests or therapeutic regimens). Two observations are notable in this regard. First, expansion of our sparse model from 24 to 60 taxa yielded similar results regarding the effects of diarrhoea in healthy individuals, MAM and SAM (and its treatment with RUTF and Khichuri-Halwa) on microbiota maturity (see Example 8). Second, we applied the model that we used for Bangladeshi children to healthy children in another population at high risk for malnutrition. The results show that the model generalizes ($r^2$=0.6) to a cohort of 47 Malawian twins and triplets, aged 0.4-25.1 months, who were concordant for healthy status in a previous study[11] (WHZ, −0.23±0.97 (mean±s.d.); Table 16). Age-discriminatory taxa identified in healthy Bangladeshi children show similar age-dependent changes in their representation in the microbiota of healthy Malawian children, as assessed by the Spearman rank correlation metric (FIG. 12C,D).

The question of whether microbiota immaturity associated with SAM and MAM is maintained during and beyond childhood also underscores the need to determine the physiologic, metabolic and immunologic consequences of this immaturity, and how they might contribute to the associated morbidities and sequelae of malnutrition, including increased risk for diarrhoeal disease, stunting, impaired vaccine responses, and cognitive abnormalities[2,19]. Our study raises a testable hypothesis: namely, that assessments of microbiota maturation, including in the context of the maternal-infant dyad, will provide a more comprehensive view of normal human development and of developmental disorders, and generate new directions for preventive medicine. Testing this hypothesis will require many additional clinical studies but answers may also arise from analyses of gut microbiota samples that have already been stored from previous studies.

Example 2

Anthropologic Assessment

The study population resided in the Mirpur slum of Dhaka, Bangladesh (23.8042° N 90.3667° E) in a catchment area consisting of 9,250 households. Most of the homes in this community consist of one main room (~220 square feet), composed of concrete floors and tin roofs with bamboo, metal, and in a few cases cement walls. The average number of household members ranges from 4-10 people, and average monthly family income is 4,000-10,000 Bangladeshi Taka (50 to 130 USD). Infants do not wear diapers, nor do they typically wear any clothing on the bottom halves of their bodies. The importance of hand washing before eating or child feeding is widely understood but rarely practiced due to lack of access to clean water. Families prepare food either on the floor or on a ground-level cement slab located at the entrance of the home; this slab typically straddles an open drain containing wastewater running along the street. Since few families have refrigerators, most food is stored on shelves or under the bed. Households may consist of more than one biological family: in these cases all individuals in the household share a gas stove and cooking area immediately outside the main room, although food, cooking pots and utensils are used separately by each biological family. All individuals share a common 'bathroom,' a small space containing a latrine, and sometimes the water pump, located next to the main room. The common practice is to wash the perianal area by hand with water contained in a small, special container called bodna in Bangla.

Example 3

Fecal Microbiota Variation within and Between Family Members During the First Year of Postnatal Life There are few reports of time-series studies charting assembly of the gut microbiota in healthy USA infants and even fewer studies in infants from non-Western populations. The results published to date have revealed pronounced intra—as well as interpersonal variation during the first year of life[11,29-31]. In contrast, the gut microbiota of healthy USA adults is quite stable over time, with signatures of within-individual and within-family similarity evident throughout sampling periods[15].

To obtain a view of gut microbiota development in Bangladeshi infants and children as a function of time after birth and family structure, we collected monthly fecal samples from 11 twin pairs and 1 set of triplets and their parents. The first fecal sample was obtained from infants at the time of their enrollment (4±3 days of age). Monthly samples were subsequently obtained from each of these 25 infants and from their mothers while samples were collected from their fathers every three months. Families were followed for a total of 520±159 days (mean±SD). The duration of exclusive breastfeeding was 28±23 days (mean±SD). Diarrhoea occurred for 11±12 days (2±3% of the total number of days followed during the study).

Distances (degree of similarity) between all pairs of fecal microbiota samples in this birth cohort were computed using the Hellinger metric, an abundance-based ecological metric, as well as the phylogeny-based unweighted UniFrac metric where distance is calculated based on the degree to which any two communities share branch length on a bacterial tree of life[32]. In the case of triplets, we performed all possible pairwise comparisons (self-self; all three possible pairwise comparisons among siblings; each sibling against unrelated age-matched individuals; each sibling against their mother or father).

We had previously noted that genetically unrelated cohabiting adults in the USA have more similar overall bacterial phylogenetic configurations in their fecal microbiota than unrelated adults living separately[11]. Comparing the difference (distance) of a Bangladeshi mother's microbiota during her first month post-partum to her microbiota three months later revealed a larger shift in overall structure compared to fathers sampled during the same three-month interval [P=0.01 (Hellinger); P=0.04 (unweighted UniFrac); FIG. 5C,D], thus obscuring a microbial manifestation of their co-habitation. This signature of co-habitation emerged 10 months postpartum, at a time when the preceding marked temporal variation of the mother's microbiota had diminished (P=0.006 for difference between co-habiting spouses at 10 months postpartum versus non-co-habiting adults in the cohort as measured by the abundance based Hellinger metric; P=0.08 using the presence/absence unweighted UniFrac phylogenetic metric; see FIG. 5E,F).

Figure 5I:
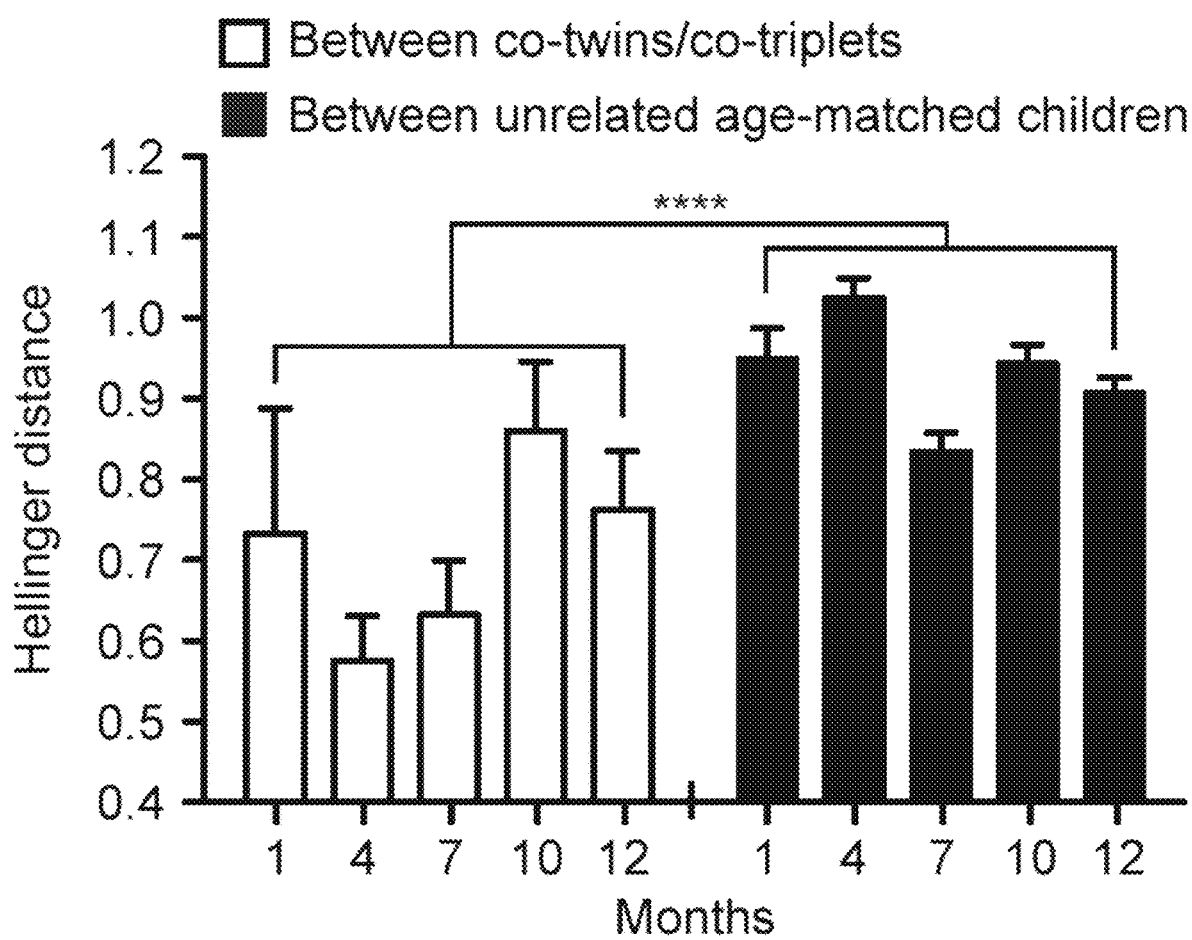
Figure 5J:
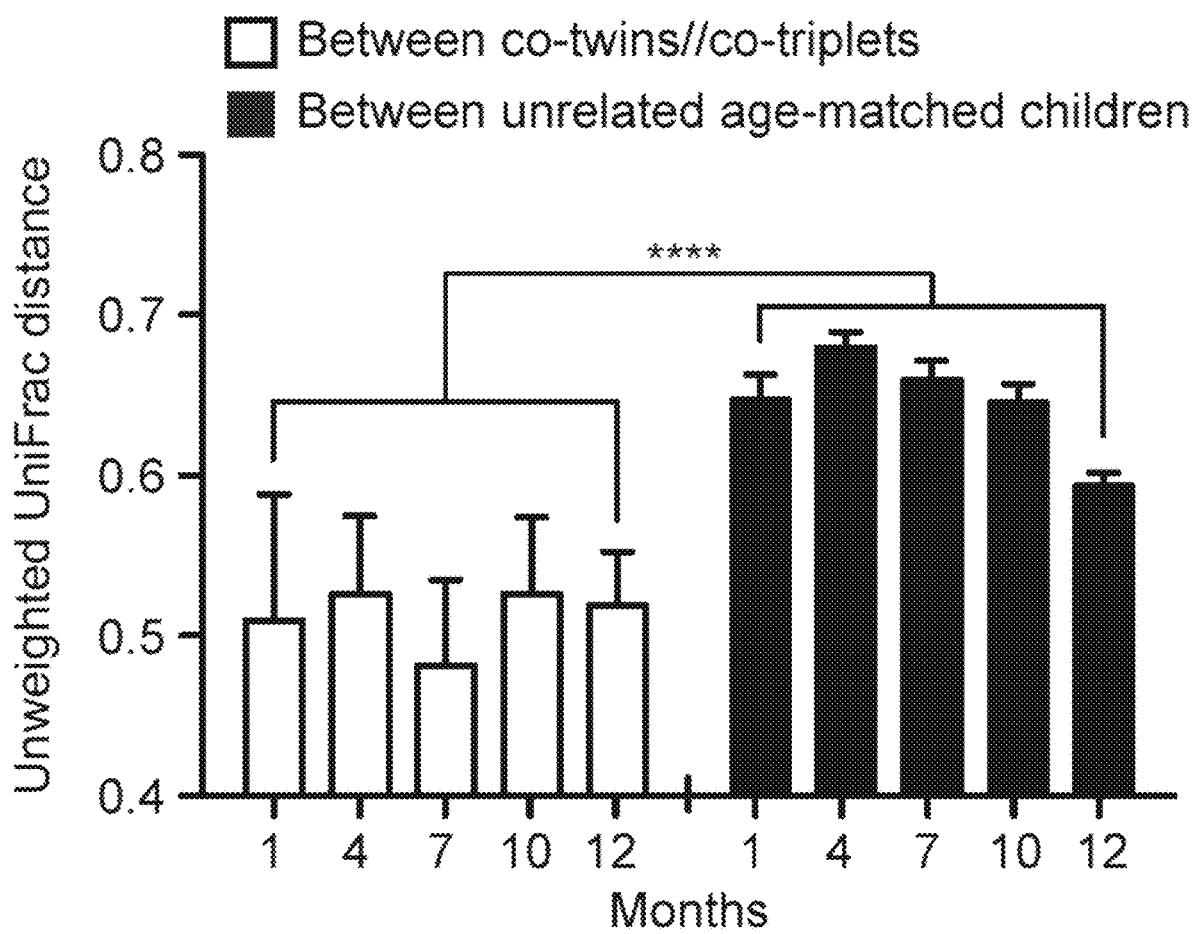

During the first postnatal month, the bacterial configuration of the fecal microbiota of infants was more similar to mothers compared to fathers (P<0.001 Hellinger metric; P=0.07 with unweighted UniFrac; FIG. 5G,H). Co-twins were more similar to one another than unrelated age-matched twins during the first postpartum year (P<0.001 Kruskall-Wallis; FIG. 5I,J). An analysis of sources of variation in the microbiota of the twins and triplets over the course of the entire study revealed that age alone captured 19% and 37.7% of variance (Hellinger and unweighted UniFrac metrics, respectively) in contrast to dietary factors (presence/absence of 'breast milk', 'formula', 'solid foods') which explained only 2.5% and 3.8%, respectively (see Table 7 for partitioning of variance by metric and metadata; PERMANOVA as implemented with adonis function in R package vegan)[33].

We identified increases in the proportional representation of 97%-identity OTUs in the microbiota of mothers during the perinatal period, including a number of the age-discriminatory taxonomic biomarkers, notably Bifidobacteria in FIGS. 5A,B and Table 8. This latter feature is not unique to Bangladesh: a recent study of 80 Finnish mother-infant pairs sampled at 1 and 6 months post-partum demonstrated that if a mother was positive for *B. bifidum* 1 month following delivery, the likelihood of her child being colonized was significantly higher[34]).

Example 4

Transient Reduction of Gut Microbiota Diversity in Healthy Twins and Triplets Associated with Diarrhea In addition to changes in the relative proportions of specific bacterial taxa incorporated into our Random Forests model-derived MAZ and relative microbiota maturity metrics, the developing gut microbiota of infants/children is also characterized by an increase in total community bacterial diversity as judged by the Shannon Diversity Index (SDI). SDI is an ecological measure of within-sample (alpha) diversity that incorporates both the concept of total community size as well as the evenness of the abundance of its members. Across the 50 healthy Bangladeshi children sampled, SDI increased linearly with age (0.11 units per month of life with an intercept of 1.6±0.1 units at birth; mixed model; $P<0.0001$). In twins and triplets, diarrhoea (n=36 episodes) was the only significant clinical parameter associated with a reduction in SDI (−0.44±0.1; $P<0.01$). This reduction showed a similar time course of recovery as relative microbiota maturity, persisting for one month (−0.35±0.2 SDI; $P<0.05$) followed by subsequent recovery (FIG. 4; Table 6c).

Example 5

Persistent Reductions in Diversity Associated with SAM

As with measurements of microbiota maturity, the RUTF group showed significant improvement in SDI values between 1-3 months following cessation of treatment, followed by regression to a persistent lower than healthy SDI beyond 3 months. In the case of Khichuri-Halwa, improvement in SDI was only significant at 3-4 months of follow-up. SAM children in both treatment groups exhibited significant reductions in diversity compared to healthy Bangladeshi children at all phases of treatment and recovery, except for 1-3 months post-RUTF and 3-4 months post-Khichuri-Halwa (FIG. 7; Table 12).

Example 6

Two Hundred and Twenty Bacterial Taxa that are Significantly Different in their Proportional Representation in Microbiota of Children with SAM Compared to Healthy at Multiple Treatment Phases Across Both Groups During the acute phase, prior to nutritional rehabilitation, 116 97%-identity OTUs were significantly altered in SAM. The majority were lower in relative abundance compared to healthy children. The four 97% identity OTUs with the largest reductions in abundance during the acute phase included three classified as belonging to the genus *Bifidobacterium* (*B. longum*, two unassigned to a species) and *Faecalibacterium prausnitzii*, of which two are age-discriminatory taxa (FDR-corrected $P<0.05$). Taxa that were enriched in children diagnosed with SAM compared to healthy children included those belonging to the family Enterobacteriaceae (genera *Escherichia* and *Klebsiella*) as well as *Enterococcus faecalis* (FDR-corrected $P<0.05$).

In children with SAM, taxa that remain depleted throughout the follow-up period included members of the bacterial families Ruminococcaceae, Veillonellaceae and Prevotellaceae. Taxa enriched in the microbiota of children with SAM after the therapeutic food interventions belonged predominantly to the genus *Streptococcus*, including 97% ID OTUs identified as *Streptococcus* lutentiensis, *Streptococcus thermophilus* (also age-discriminatory) and other as yet unknown *Streptococcus* species (FDR-corrected $P<0.01$; see FIG. 8 and FIG. 9 for a heatmap depiction of all 97% ID OTUs whose representation in the fecal microbiota is significantly altered in SAM relative to healthy before, during and after the nutritional rehabilitation period; also see Table 13).

Example 7

Assessing the Effects of Antibiotics on Microbiota Maturity During the Follow-Up Period in Children with SAM As noted in Example 1, we compared antibiotic use during the post-intervention periods for the two treatment arms. The results indicate that (i) the frequency of antibiotic consumption during this period was comparable to that of healthy children in our training and validation sets ($P=0.5$, one-way ANOVA); (ii) there was no significant difference in antibiotic use between treatment arms ($P=1$; Fisher's exact test; Table 10); (iii) there was no significant association between recent antibiotic intake (defined as occurring seven or fewer days before collection of a fecal sample) and relative microbiota maturity values [difference in maturity values for samples with versus those without recent antibiotic intake: −0.37±0.8 (mean±SEM) $P=0.6$ (ANOVA of linear mixed model; n=100 samples for the 22 children in the post RUTF arm); +0.17±0.9; $P=0.9$ (n=103 samples, 25 children in the Khichuri-Halwa arm)]. Similarly, we found that diarrhoea was not significantly associated with differences in maturity values in either arm during the post-intervention period (Table 14).

Example 8

Expanding the Sparse Random Forests-Based Model from 24 to 60 Taxa

It is logical to ask the following questions about our approach for defining microbiota maturity. First, are we defining "immaturity" entirely as a lack of maturity, rather than a specific, recognizable state in and of itself. Ours is a 'positive' composition-based classification. For example, the *Bifidobacterium longum* OTU in FIG. 1A ranks $5^{th}$ in terms of its feature importance score in the 24-taxon Random Forests model. In samples from healthy infants less than 6 months old, this OTU is highly represented [relative abundance=52.7±30% (mean±SD); >1% in 94% of samples from the training and validation sets). The remaining seven 97%-identity OTUs that comprise the cluster of early age-discriminatory taxa shown in FIG. F-H together represent 6.35±8% of the microbiota and are present at >1% abundance in 84% of samples.

Second, was there an outlet for samples containing very few or none the 24 taxa selected by the model? For example, were they deemed unclassifiable, or classified as "other", or were all samples "forced" onto the maturity scale? How were samples with low feature signal having few to no age-discriminant taxa classified? Only one of the 589 fecal samples in the SAM study had undetectable levels of the 24 age-discriminatory taxa. In the SAM cohort, only 10% of fecal samples (60/589) had an aggregate relative abundance of the 24 age-discriminatory taxa that was less than 10%. In healthy children, this was true for 36/960 samples.

When we expanded our model to include the top 60 age-discriminatory taxa, we found that <1% of SAM samples and none of the healthy samples had an aggregate relative abundance of the 60 age-discriminatory taxa that was less than 10%. Note that in expanding the model, we excluded OTUs that were deemed chimeric when using default BLAST thresholds to the Greengenes reference as implemented in QIIME. The performance of the 24 and 60 taxa models were similar. Predictions made by the two models when they were applied to the healthy validation datasets (all 724 samples considered), and when they were applied to the SAM datasets (all 589 samples considered), showed a strong correlation ($r^2$=0.98 and 0.93, respectively). Both yielded similar results for our analysis of (i) the effects of diarrhoea in healthy twins/triplets (microbiota immaturity was transient), (ii) the SAM trial (the effects of RUTF and Khichuri-Halwa produced transient non-durable improvements compared to healthy controls; antibiotics did not have a significant effect on microbiota maturity measurements either during the acute phase or during the post-intervention; note that the top 60 model includes Enterobacteriaceae and Streptococcaceae OTUs that are highly enriched in children with SAM relative to healthy); and (iii) the MAM study (a significant difference was observed between 18 month old healthy controls versus children with MAM) (data not shown).

Example 9

Processed 16S rRNA Datasets

Processed 16S rRNA datasets are available here, http://gordonlab.wustl.edu/Subramanian_6_14/Nature_2014_Processed_16 S_rRNA_da tasets.html, as a BIOM-formatted OTU table, along with split libraries of data generated from faecal samples and 'Mock' communities, mapping file, and an augmented reference sequence set (Greengenes version 4feb2011 plus de novo OTUs picked from sequences generated in the present study).

Methods for Examples 1-9

Summary

All subjects lived in Dhaka, Bangladesh (see Anthropologic Study below and Example 2 for anthropologic assessment of Mirpur, an urban slum in Bangladesh, where most subjects resided). Informed consent was obtained and studies were conducted using protocols approved by the ICDDR, B, Washington University, and University of Virginia institutional review boards (IRBs). Linear mixed models were applied to test hypotheses in repeated measurements of relative abundance of 97%-identity OTUs and maturation metrics in time-series profiling of faecal microbiota[20]. To account for similarity between observations from repeated sampling of the same individuals and families, we fit random intercepts for each subject in the case of adults and singletons, nested these intercepts within each family in the case of twins and triplets, and included age as a fixed-effect covariate, while testing the significance of associations between the microbiota and specified host and environmental factors. Differences between microbiota maturation metrics in each treatment phase of SAM were compared to values at enrollment in each treatment group, and to healthy children within the same age range (excluding samples from children used to train the Random Forests model), using analysis of variance (ANOVA) of linear mixed models followed by Dunnett's post-hoc comparisons.

Singleton Birth Cohort.

Full details of the design of this now-complete birth cohort study have been described previously[21]. Faecal microbiota samples were profiled from 25 children who had consistently healthy anthropometric measures based on quarterly (every 3 months) measurements (Table 1). The WHZ threshold used for 'healthy' (on average above −2 s.d.) was based on median weight and height measurements obtained from age- and gender-matched infants and children by the Multi-Centre Growth Reference study of the World Health Organization[3]. Clinical parameters, including diarrhoeal episodes and antibiotic consumption associated with each of their faecal samples are provided in Supplementary Table 2 of Subramanian et al, Nature 2014; S10:417-421, which is hereby incorporated by reference in its entirety.

A second group studied from this singleton cohort consisted of 33 children sampled cross-sectionally at 18 months, including those who were incorporated as healthy reference controls, and those with a WHZ <−2 who were classified with MAM (Table 15).

Twins and Triplets Birth Cohort.

Mothers with multiple pregnancy, identified by routine clinical and sonographic assessment at the Radda Maternal Child Health and Family Planning (MCH-FP) Clinic in Dhaka, were enrolled in a prospective longitudinal study (n=11 mothers with twins, 1 mother with triplets). The zygosity of twin pairs and triplets was determined using plasma DNA and a panel of 96 polymorphic single-nucleotide polymorphisms (SNPs) (Center for Inherited Disease Research, Johns Hopkins University). Four twin pairs were monozygotic, six were dizygotic, and the set of triplets consisted of a monozygotic pair plus one fraternal sibling (Table 1; note that one of the 11 twin pairs could not be tested for zygosity because plasma samples were not available). Information about samples from healthy twins, triplets and their parents, including clinical parameters associated with each faecal sample, is provided in Table 2 and in Supplementary Table 2 of Subramanian et al, Nature 2014; S10:417-421, which is hereby incorporated by reference in its entirety.

The three healthy Bangladeshi groups used for model training and validation had the following WHZ scores: −0.32 6 1 (mean 6 s.d.; 12 singletons randomized to the training set), −0.4460.8 (13 singletons randomized to one of the two validation sets), and −0.466 0.7 (twins and triplets in the other validation set) (Table 3). The average number of diarrhoeal episodes in the singleton training set, the singleton validation set, and the twin and triplet validation set (4, 4.6 and 1.7, respectively) was comparable to values reported in previous surveys of another cohort of 0-2-year-old Bangladeshi children (4.25 per child per year)[22].

There were no significant differences in the number of diarrheal episodes per year per child and the number of diarrheal days per year per child between the singleton training and validation sets (Student's t-test, P 5 0.5). Moreover, across all training and validation sets, neither of these diarrheal parameters correlated with mean age-adjusted Shannon diversity indices (Spearman's Rho, −0.18 and −0.12, P 5 0.22 and 0.4, respectively). The fraction of faecal samples collected from each child where oral antibiotics had been consumed within the prior 7 days was not significantly different between the training and two validation sets (one-way ANOVA, P 5 0.14; see Table 3).

Severe Acute Malnutrition Study.

Sixty-four children in the Nutritional Rehabilitation Unit of ICDDR,B, Dhaka Hospital suffering from SAM (defined as having a WHZ less than −3 s.d. and/or bilateral pedal oedema) were enrolled in a randomized interventional trial to compare an imported peanut-based RUTF, Plumpy'Nut (Nutriset Plumpyfield, India) and locally produced Khichuri-Halwa (clinical trial NCT01331044). Initially, children were stabilized by rehydration and feeding 'suji', which contains whole bovine milk powder, rice powder, sugar and soybean oil (approximately 100 kcal $kg^{-1}$ body weight per day, including 1.5 g protein $kg^{-1}$ per day). Children were then randomized to the Khichuri-Halwa or RUTF groups. Khichuri consists of rice, lentils, green leafy vegetables and soybean oil; Halwa consists of wheat flour (atta), lentils, molasses and soybean oil. Children randomized to the Khichuri-Halwa treatment arm also received milk suji '100' during their nutritional rehabilitation phase (a form of suji with a higher contribution of calories from milk powder compared to suji provided during the acute phase). RUTF is a ready-to-use paste that does not need to be mixed with water; it consists of peanut paste mixed with dried skimmed milk, vitamins and minerals (energy density, 5.4 $kcalg^{-1}$). Khichuri and Halwa are less energy-dense than RUTF (1.45 kcal g-1 and 2.4 kcal $g^{-1}$, respectively, see Table 11 for a list of ingredients for all foods used during nutritional rehabilitation).

The primary outcome measurement, rate of weight gain (g $kg^{-1}$ per day), along with improvement in WHZ after nutritional rehabilitation are reported by child in Table 9. Faecal samples were collected before randomization to the RUTF and Khichuri-Halwa treatment arms, every 3 days during nutritional rehabilitation and once a month during the follow-up period (information associated with each faecal sample is provided in Supplementary Table 11 of Subramanian et al, Nature 2014; S10:417-421, which is hereby incorporated by reference in its entirety).

Anthropologic Study.

To obtain additional information about household practices in the Mirpur slum of Dhaka, in-depth semi-structured interviews and observations were conducted over the course of 1 month in nine households (n=30 individuals). This survey, approved by the Washington University and ICDDR,B IRBs, involved three ICDDR,B field research assistants, and three senior scientific staff in the ICDDR,B Centre for Nutrition and Food Security, plus two anthropologists affiliated with Washington University in St. Louis. Parameters that might affect interpretation of metagenomic analyses of gut microbial-community structure were noted, including information about daily food preparation, food storage, personal hygiene and childcare practices.

Characterization of the Bacterial Component of the Gut Microbiota by V4-16S rRNA Sequencing.

Faecal samples were frozen at −20° C. within 30 min of their collection and subsequently stored at −80° C. before extraction of DNA. DNA was isolated by bead-beating in phenol and chloroform, purified further (QIAquick column), quantified (Qubit) and subjected to polymerase chain reaction (PCR) using primers directed at variable region 4 (V4) of bacterial 16S rRNA genes. Bacterial V4-16S rRNA data sets were generated by multiplex sequencing of amplicons prepared from 1,897 faecal DNA samples (26,580 6 26,312 (mean 6 s.d.) reads per sample, paired-end 162- or 250- nucleotide reads; Illumina MiSeq platform; Table 4). Reads of 250 nucleotides in length were trimmed to 162 nucleotides, then all reads were processed using previously described custom scripts, and overlapped to 253-nucleotide fragments spanning the entire V4 amplicon[15]. 'Mock' communities, consisting of mixtures of DNAs isolated from 48 sequenced bacterial members of the human gut microbiota combined in one equivalent and two intentionally varied combinations, were included as internal controls in the Illumina MiSeq runs. Data from the mock communities were used for diversity and precision-sensitivity analyses employing methods described previously[15,23].

Reads with ≥97% nucleotide sequence identity (97%-identity) across all studies were binned into operational taxonomic units (OTUs) using QIIME (v 1.5.0), and matched to entries in the Greengenes reference database (version 4feb2011)[24,25]. Reads that did not map to the Greengenes database were clustered de novo with UCLUST at 97%-identity and retained in further analysis. A total of 1,222 97%-identity OTUs were found to be present at or above a level of confident detection (0.1% relative abundance) in at least two faecal samples from all studies. Taxonomy was assigned based on the naive Bayesian RDP classifier version 2.4 using 0.8 as the minimum confidence threshold for assigning a level of taxonomic classification to each 97%-identity OTU.

Definition of Gut-Microbiota Maturation in Healthy Children Using Random Forests.

Random Forests regression was used to regress relative abundances of OTUs in the time-series profiling of the microbiota of healthy singletons against their chronologic age using default parameters of the R implementation of the algorithm (R package 'randomForest', ntree 5 10,000, using default mtry of p/3 where p is the number of input 97%-identity OTUs (features))[26]. The Random Forests algorithm, due to its non-parametric assumptions, was applied and used to detect both linear and nonlinear relationships between OTUs and chronologic age, thereby identifying taxa that discriminate different periods of postnatal life in healthy children. A rarefied OTU table at 2,000 sequences per sample served as input data. Ranked lists of taxa in order of Random Forests reported 'feature importance' were determined over 100 iterations of the algorithm. To estimate the minimal number of top ranking age-discriminatory taxa required for prediction, the rfcv function implemented in the 'randomForest' package was applied over 100 iterations. A sparse model consisting of the top 24 taxa was then trained on the training set of 12 healthy singletons (272 faecal samples). Without any further parameter optimization, this model was validated in other healthy children (13 singletons, 25 twins and triplets) and then applied to samples from children with SAM and MAM. A smoothing spline function was fit between microbiota age and chronologic age of the host (at the time of faecal sample collection) for healthy children in the validation sets to which the sparse model was applied.

Alpha Diversity Comparisons.

Estimates of within-sample diversity were made at a rarefaction depth of 2,000 reads per sample. A linear regression was fit between the Shannon diversity index (SDI) and postnatal age in the 50 healthy children using a mixed model (see the additional details regarding statistical methods, below). An estimate of the coefficient for the slope of SDI with age and intercept was extracted, residuals of this regression were defined as a DSDI metric, and associations of this metric with clinical parameters were tested in the cohort of healthy twins and triplets. To test for differences in SDI as a function of health status and chronologic age in malnourished children, we compared the distribution of age-adjusted ΔSDIs in children with SAM between treatment phases.

Detection of Associations of Bacterial Taxa with Nutritional Status and Other Parameters.

Relative abundances of 97%-identity OTUs were used in linear mixed models as response variables to test for associations with clinical metadata as predictors. For each comparison, we restricted our analysis to 97%-identity OTUs and bacterial families whose relative abundance values reached a level of confident detection (0.1%) in a minimum of 1% of samples in each comparison. Pseudocounts of 1 were added to 97%-identity OTUs to account for variable depth of sequencing between samples, and relative abundances were arcs in-square-root-transformed to approximate homoscedasticity when applying linear models. P values of associations of factors with the relative abundances of bacterial taxa were computed using ANOVA type III (tests of fixed effects), subjected to Benjamini-Hochberg false discovery rate (FDR) correction.

Enteropathogen Testing.

Clinical microscopy was performed for all faecal samples collected at monthly intervals from the singleton birth cohort and from healthy twins and triplets, and screened for *Entamoeba histolytica, Entamoeba dispar, Escherichia coli, Blastocystis hominis, Trichomonas hominis, Blastocystis hominis*, Coccidian-like bodies, *Giardia lamblia, Ascaris lumbricoides, Trichuris Tricuria, Ancylostoma duodenale/ Necator americanus, Hymenolepsis nana, Endolimax nana, lodamoebabutschlii* and *Chilomastixmesnili*. The effects of enteropathogens, detected by microscopy on relative microbiota maturity, MAZ and SDI were included in our analysis of multiple environmental factors in FIG. 4 and Table 6. In cases in which children presented with SAM plus diarrhoea, faecal samples collected before nutritional rehabilitation were cultured for *Vibrio cholerae, Shigella flexneri, Shigella boydi, Shigella sonnei, Salmonella enterica, Aeromonas hydrophila* and *Hafnia alvae*. See Tables 9 and 17 for results of enteropathogen testing.

Additional Details Regarding Statistical Methods.

Linear mixed models were applied to test for associations of microbiota metrics (relative microbiota maturity, MAZ and SDI) with genetic and environmental factors in twins and triplets. Log-likelihood ratio tests and F tests were used to perform backward elimination of non-significant random and fixed effects[27]. Relative microbiota maturity, MAZ and SDI were defined at different phases of treatment and at defined periods of follow-up (<1 month, 1-2, 3-4 and >4 months after completion of the RUTF or Khichuri-Halwa nutritional intervention) in children with SAM relative to healthy children. 'Treatment phase' was specified as a categorical multi-level factor in a univariate mixed model with random by-child intercepts. Dunnett's post-hoc comparison procedure was performed to compare each treatment phase relative to healthy controls and relative to samples collected at enrollment in each food intervention group.

REFERENCES FOR EXAMPLES 1-9

1. Ahmed, T. et al. Mortality in severely malnourished children with diarrhoea and use of a standardised management protocol. *Lancet* 353, 1919-1922 (1999).
2. Ashraf, H. et al. A follow-up experience of 6 months after treatment of children with severe acute malnutrition in Dhaka, Bangladesh. *J. Trop. Pediatr.* 58, 253-257 (2012).
3. World Health Organization Department of Nutrition for Health and Development. WHO child growth standards growth velocity based on weight, length and head circumference: methods and development. (World Health Organization, 2009).
4. Victora, C. G., de Onis, M., Hallal, P. C., Blo¨ssner, M. & Shrimpton, R. Worldwide timing of growth faltering: revisiting implications for interventions. *Pediatrics* 125, e473-e480 (2010).
5. Ahmed, T. & Begum, B. Badiuzzaman, Ali, M. & Fuchs, G. Management of severe malnutrition and diarrhea. *Indian J. Pediatr.* 68, 45-51 (2001).
6. Ahmed, T. et al. P0580 Use of a standardized protocol based on local diet results in satisfactory rates of weight gain of severely malnourished children undergoing nutritional rehabilitation. *J. Pediatr. Gastroenterol. Nutr.* 39, S277 (2004).
7. Lazzerini, M., Rubert, L. & Pani, P. Specially formulated foods for treating children with moderate acute malnutrition in low- and middle-income countries. *Cochrane Database Syst. Rev.* CD009584 (2013).
8. Prentice, A. M. et al. Critical windows for nutritional interventions against stunting. *Am. J. Clin. Nutr.* 97, 911-918 (2013).
9. Muegge, B. D. et al. Diet drives convergence in gut microbiome functions across mammalian phylogeny and within humans. *Science* 332, 970-974 (2011).
10. Wu, G. D. et al. Linking long-term dietary patterns with gut microbial enterotypes. *Science* 334, 105-108 (2011).
11. Yatsunenko, T. et al. Human gut microbiome viewed across age and geography. *Nature* 486, 222-227 (2012).
12. Smith, M. I. et al. Gut microbiomes of Malawian twin pairs discordant for kwashiorkor. *Science* 339, 548-554 (2013).
13. David, L. A. et al. Diet rapidly and reproducibly alters the human gut microbiome. *Nature* 505, 559-563 (2014).
14. Tang, W. H. W. et al. Intestinal microbial metabolism of phosphatidylcholine and cardiovascular risk. *N. Engl. J. Med.* 368, 1575-1584 (2013).
15. Faith, J. J. et al. The long-term stability of the human gut microbiota. *Science* 341 (2013).
16. Breiman, L. Random Forests. *Mach. Learn.* 45, 5-32 (2001).
17. Dewey, K. G. et al. Infant weight-for-length is positively associated with subsequent linear growth across four different populations. *Matern. Child Nutr.* 1, 11-20 (2005).
18. Lin, A. et al. Distinct distal gut microbiome diversity and composition in healthy children from Bangladesh and the United States. *PLoS ONE* 8, e53838 (2013).
19. Nahar, B. et al. Effects of a community-based approach of food and psychosocial stimulation on growth and development of severely malnourished children in Bangladesh: a randomised trial. *Eur. J. Clin. Nutr.* 66, 701-709 (2012).
20. Bates, D., Maechler, M. & Bolker, B. lme4: Linear mixed-effects models using S4 classes. http://CRAN.R-projectorg/package=lme4 (2011).
21. Mondal, D. et al. Contribution of enteric infection, altered intestinal barrier function, and maternal malnutrition to infant malnutrition in Bangladesh. *Clin. Infect. Dis.* 54, 185-192 (2012).
22. Pathela, P. et al. Diarrheal illness in a cohort of children 0-2 years of age in rural Bangladesh: I. Incidence and risk factors. *Acta Paediatr.* 95, 430-437 (2006).

23. Bokulich, N. A. et al. Quality-filtering vastly improves diversity estimates from Illumina amplicon sequencing. *Nature Meth.* 10, 57-59 (2013).
24. Caparaso, J. G. et al. QIIME allows analysis of high-throughput community sequencing data. *Nature Meth.* 7, 335-336 (2010).
25. McDonald, D. et al. An improved Greengenes taxonomy with explicit ranks for ecological and evolutionaryanalyses of bacteria and archaea. *ISMEJ.* 6, 610-618 (2012).
26. Liaw, A. & Weiner, M. Classification and regression by randomForest. R package version 4.6-7. *R News* 2, 18-22 (2002).
27. Kuznetsova, A., Brockhoff, P. B. & Christensen, R. H. B. lmerTest: tests for random and fixed effects for linear mixed effect models (lmer objects of lme4 package). http://CRAN.R-projectorg/package=lmerTest (2013).
28. National Institute of Population Research and Training (NIPORT), Mitra and Associates, and ICF International. Bangladesh Demographic and Health Survey 2011. Dhaka, Bangladesh and Calverton, Maryland, USA: NIPORT, Mitra and Associates, and ICF International (2013).
29. Palmer, C., Bik, E. M., DiGiulio, D. B., Reiman, D. A. & Brown, P. O. Development of the Human Infant Intestinal Microbiota. *PLoS Biol.* 5, e177 (2007).
30. Koenig, J. E. et al. Succession of microbial consortia in the developing infant gut microbiome. *Proc. Natl. Acad. Sci. U.S.A.* 108 Suppl 1, 4578-4585 (2011).
31. White, R. A. et al. Novel Developmental Analyses Identify Longitudinal Patterns of Early Gut Microbiota that Affect Infant Growth. *PLoS Comput. Biol.* 9, e1003042 (2013).
32. Lozupone, C. & Knight, R. UniFrac: a New Phylogenetic Method for Comparing Microbial Communities. *Appl. Environ. Microbiol.* 71, 8228-8235 (2005).
33. Oksanen, J. et al. vegan: Community Ecology Package. R package version 2.0-7. http://CRAN.R-projectorg/package=vegan (2013).
34. Grönlund, M.-M., Grześkowiak, Ł., Isolauri, E. & Salminen, S. Influence of mother's intestinal microbiota on gut colonization in the infant. Gut Microbes 2, 227-233 (2011).

Example 10

Members of the Human Gut Microbiota Involved in Recovery from *Vibrio cholerae* Infection We used an approved protocol for recruiting Bangladeshi adults living in Dhaka Municipal Corporation area for this study. Of the 1,153 patients with acute diarrhoea who were screened, seven passed all entry criteria (Methods for Examples 10-17) and were enrolled (Tables 18 and 19). Faecal samples collected at monthly intervals during the first 2 postnatal years from 50 healthy children living in the Mirpur area of Dhaka city, plus samples obtained at approximately 3-month intervals over a 1-year period from 12 healthy adult males also living Mirpur, allowed us to compare recovery of the microbiota from cholera with the normal process of assembly of the gut community in infants and children, and with unperturbed communities from healthy adult controls.

Using the standard treatment protocol of the International Centre for Diarrhoeal Disease Research, Bangladesh, study participants with acute cholera received a single oral dose of azithromycin and were given oral rehydration therapy for the duration of their hospital stay. Patients were discharged after their first solid stool. We divided the diarrhoeal period (from the first diarrhoeal stool after admission to the first solid stool) into four proportionately equal time bins: diarrhoeal phase 1 (D-Ph1) to D-Ph4. Every diarrhoeal stool was collected from every participant. Faecal samples were also collected every day for the first week after discharge (recovery phase 1, R-Ph1), weekly during the next 3 weeks (R-Ph2), and monthly for the next 2 months (R-Ph3). For each individual, we selected a subset of samples from D-Ph1 to D-Ph3 (Methods for Examples 10-17), plus all samples from D-Ph4 to R-Ph3, for analysis of bacterial composition by sequencing PCR amplicons generated from variable region 4 (V4) of the 16S ribosomal RNA (rRNA) gene (FIG. 15A and Supplementary Table 3 of Hsiao et al, *Nature* 2014; Epub, which is hereby incorporated by reference in its entirety). Reads sharing 97% nucleotide sequence identity were grouped into operational taxonomic units (97%-identity OTUs; Methods for Example 10-17).

We identified a total of 1,733 97%-identity OTUs assigned to 343 different species after filtering and rarefaction (Methods for Example 10-17). *V. cholerae* dominated the microbiota of the seven patients with cholera during D-Ph1 (mean maximum relative abundance 55.6%), declining markedly within hours after initiation of oral rehydration therapy. The microbiota then became dominated by either an unidentified *Streptococcus* species (maximum relative abundance 56.2-98.6%) or by *Fusobacterium* species (19.4-65.1% in patients B-E). In patient G, dominance of the community passed from a *Campylobacter* species (58.6% maximum) to a *Streptococcus* species (98.6% maximum) (Table 20 and Supplementary Table 4 of Hsiao et al, *Nature* 2014; Epub, which is hereby incorporated by reference in its entirety). Of the 343 species, 47.9±6.6% (mean±s.d.) were observed throughout both the diarrhoeal and recovery phases, suggesting that microbiota composition during the recovery phase may reflect an outgrowth from reservoirs of bacteria retained during disruption by diarrhoea (FIG. 16).

Indicator species analysis[4] (Methods for Example 10-17) was used to identify 260 bacterial species consistently associated with the diarrhoeal or recovery phases across members of the study group, and in a separate analysis for each subject (Table 21). The relative abundance of each of the discriminatory species in each faecal sample was compared with the mean weighted phylogenetic (UniFrac) distance between that microbiota sample and all microbiota samples collected from the reference cohort of healthy Bangladeshi adults. The results revealed 219 species with significant indicator value assignments to diarrhoeal or recovery phases, and relative abundances with statistically significant Spearman's rank correlation values to community UniFrac distance to healthy control microbiota (Table 22 and FIG. 16F-N). Not surprisingly, the abundance of *V. cholerae* directly correlated with increased distance to a healthy microbiota. *Streptococcus* and *Fusobacterium* species, which bloomed during the early phases of diarrhoea, were also significantly and positively correlated with distance from a healthy adult microbiota. Increases in the relative abundances of species in the genera *Bacteroides, Prevotella,Ruminococcus/Blautia*, and *Faecalibacterium* (for example, *Bacteroides vulgatus, Prevotella copri, R obeum*, and *Faecalibacterium prausnitzii*) were strongly correlated with a shift in community structure towards a healthy adult configuration (FIGS. 16F-N and Table 22).

Previously we used Random Forests, a machine-learning algorithm, to identify a collection of age-discriminatory bacterial taxa that together define different stages in the postnatal assembly/maturation of the gut microbiota in healthy Bangladeshi children living in the same area as the adult patients with cholera[3]. Of those 60 most age-discriminatory 97%-identity OTUs representing 40 different species, 31 species were present in adult patients with cholera. Intriguingly, they followed a similar progression of changing representation during diarrhoea to recovery as they do during normal maturation of the healthy infant gut microbiota (FIG. 16F-N). Twenty-seven of the 31 species were significantly associated with recovery from diarrhoea by indicator species analysis (see FIG. 17, 18, 19 for OTU-level and community-wide analyses). These 27 species, which serve as indicators and are potential mediators of restoration of the gut microbiota after cholera, guided construction of a gnotobiotic mouse model that examined the molecular mechanisms by which some of these taxa might affect *V. cholerae* infection and promote restoration.

We assembled an artificial community of 14 sequenced human gut bacterial species (Table 23) that included (1) five species that directly correlated with gut microbiota recovery from cholera and with normal maturation of the infant gut microbiota (*R. obeum, Ruminococcus torques, F. prausnitzii, Dorea longicatena, Collinsella aerofaciens*), (2) six species significantly associated with recovery from cholera by indicator species analysis (*Bacteroides ovatus, Bacteroides vulgatus, Bacteroides caccae, Bacteroides uniformis, Parabacteroides distasonis, Eubacterium rectale*), and (3) three prominent members of the adult human gut microbiota that have known capacity to process dietary and host glycans (*Bacteroides cellulosilyticus, Bacteroides thetaiotaomicron, Clostridium scindens*[6,7,8]; as noted in FIG. 20 and Table 24 and Supplementary Table 8 of Hsiao et al, Nature 2014; Epub, which is hereby incorporated by reference in its entirety, shotgun sequencing of diarrhoeal- and recovery-phase human faecal DNA samples revealed that genes encoding enzymes involved in carbohydrate metabolism were the largest category of identified genes specifying known enzymes that changed in relative abundance within the faecal microbiome during the course of cholera). One group of mice was directly inoculated with approximately $10^9$ colony-forming units (c.f.u.) of *V. cholerae* at the same time they received the 14-member community to simulate the rapidly expanding *V. cholerae* population during diarrhoea ('D1 invasion' group). A separate group was gavaged with the community alone and then invaded 14 days later with *V. cholerae* ('D14invasion' group) (FIG. 15C,D).

*V. cholerae* levels remained at a high level in the D1 invasion group over the first week (maximum 46.3% relative abundance), and then declined rapidly to low levels (<1%). Introduction of *V. cholerae* into the established 14-member community produced much lower levels of V. cho/eraeinfection (range of mean abundances measured daily over the 3 days after gavage of the enteropathogen, 1.2-2.7%; Table 25). Control experiments demonstrated that *V. cholerae* was able to colonize at high levels for at least 7 days when it was introduced alone into germ-free recipients ($10^9$-$10^{10}$ c.f.u. per milligram wet weight of faeces; FIG. 13A,B). Together, these data suggest that a member or members of the artificial human gut microbiota had the ability to restrict *V. cholerae* colonization.

Figure 18A:
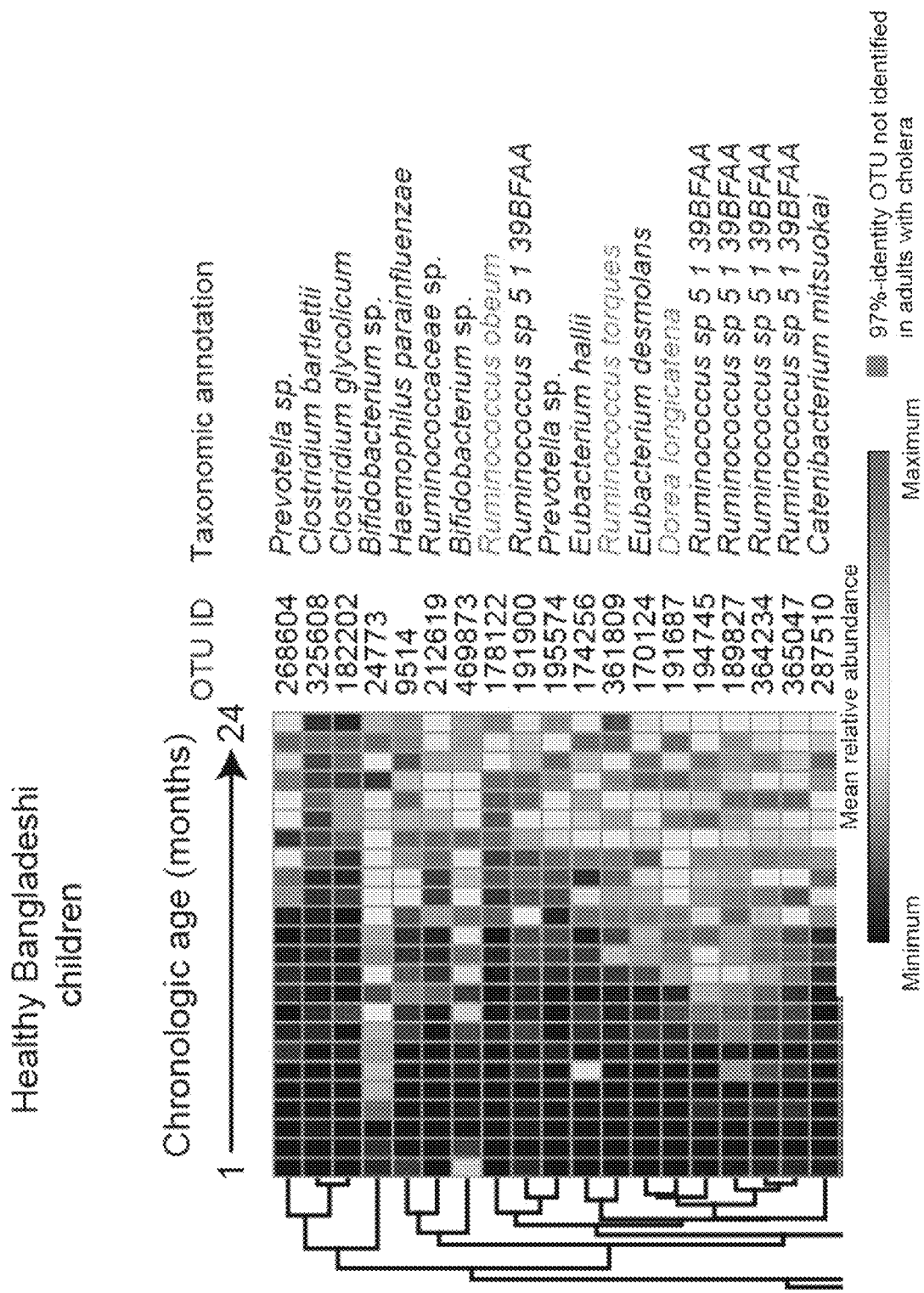
Figure 18B:
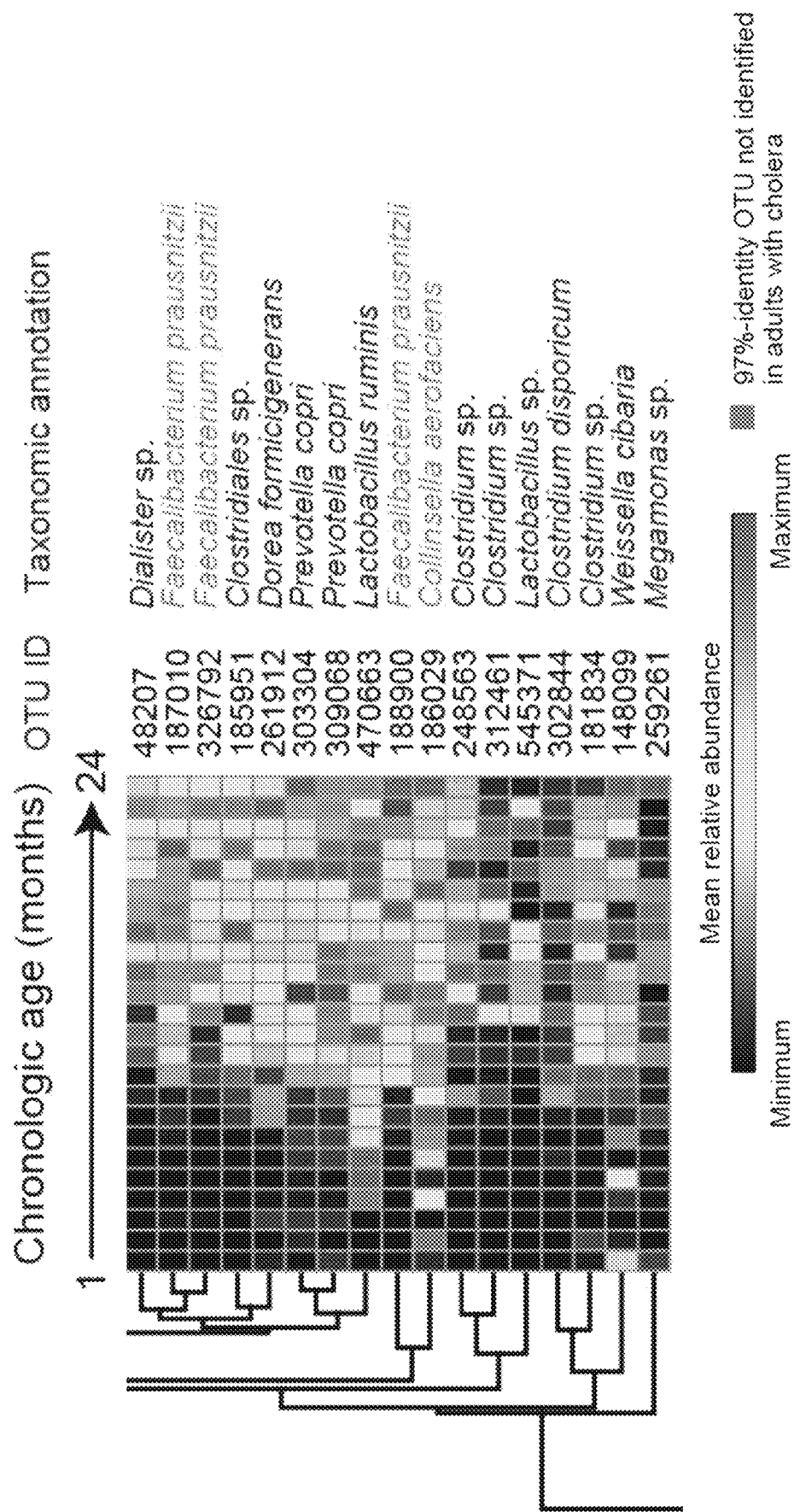
Figure 18C:
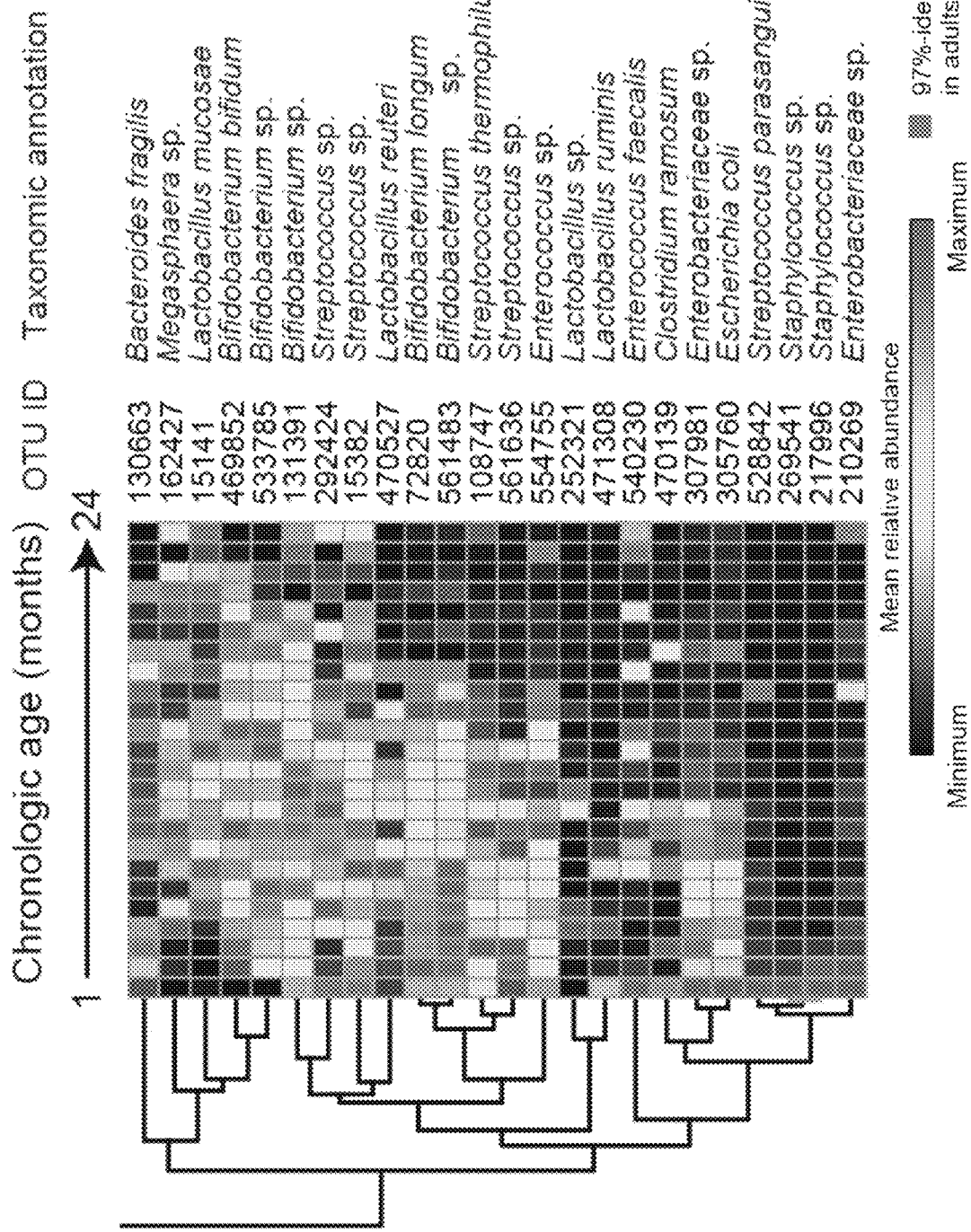
Figure 18D:
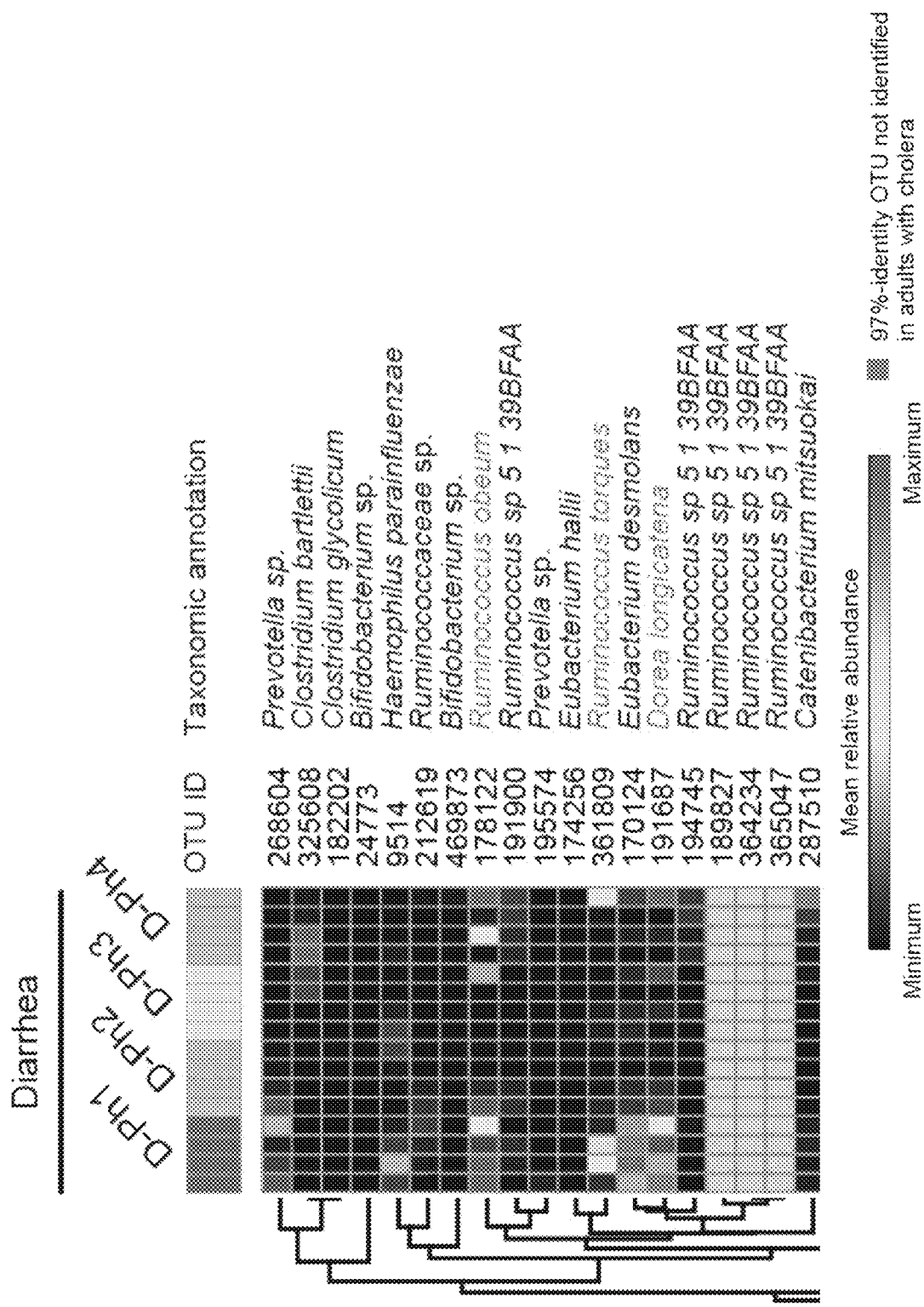
Figure 18E:
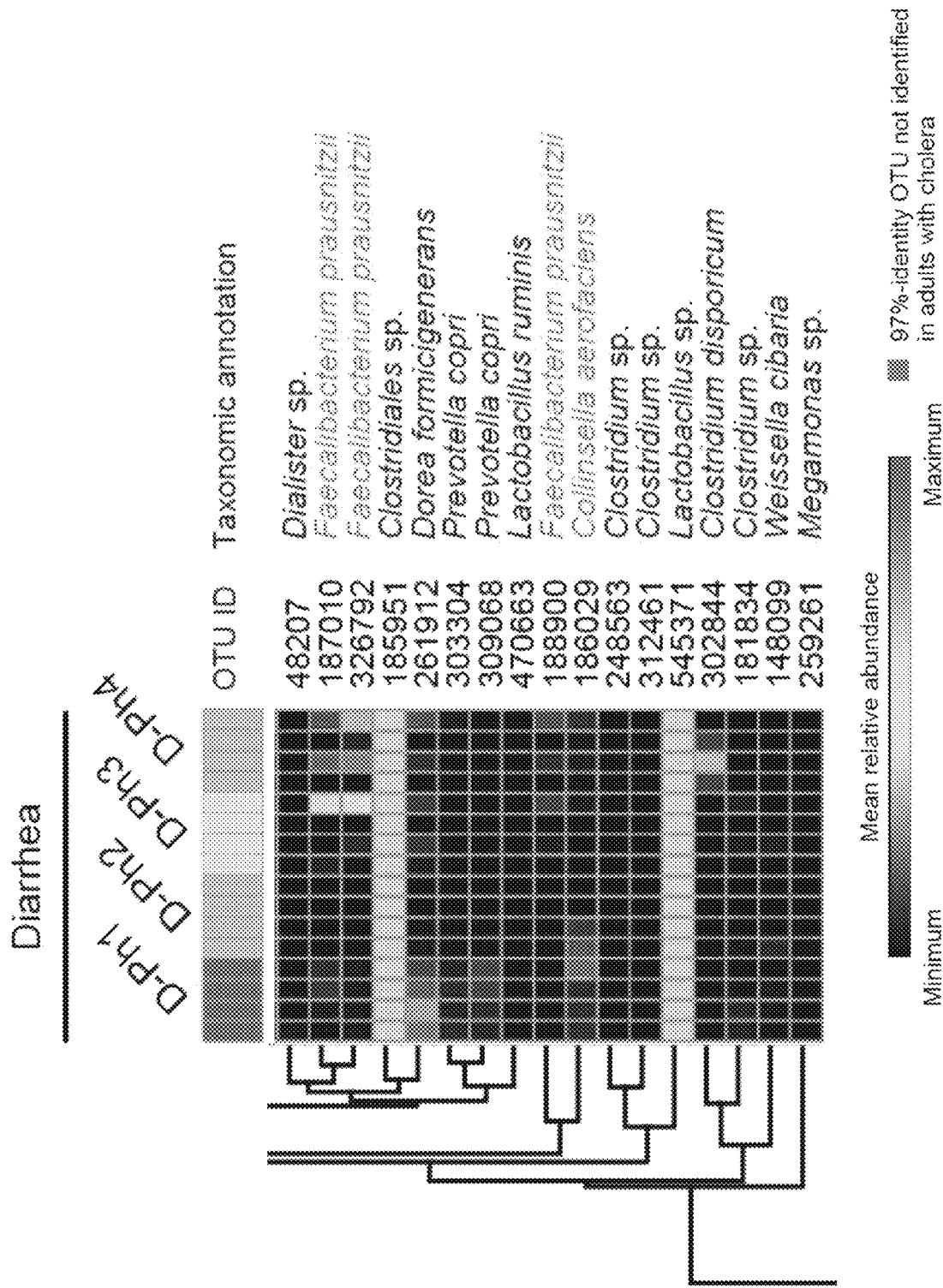
Figure 18F:
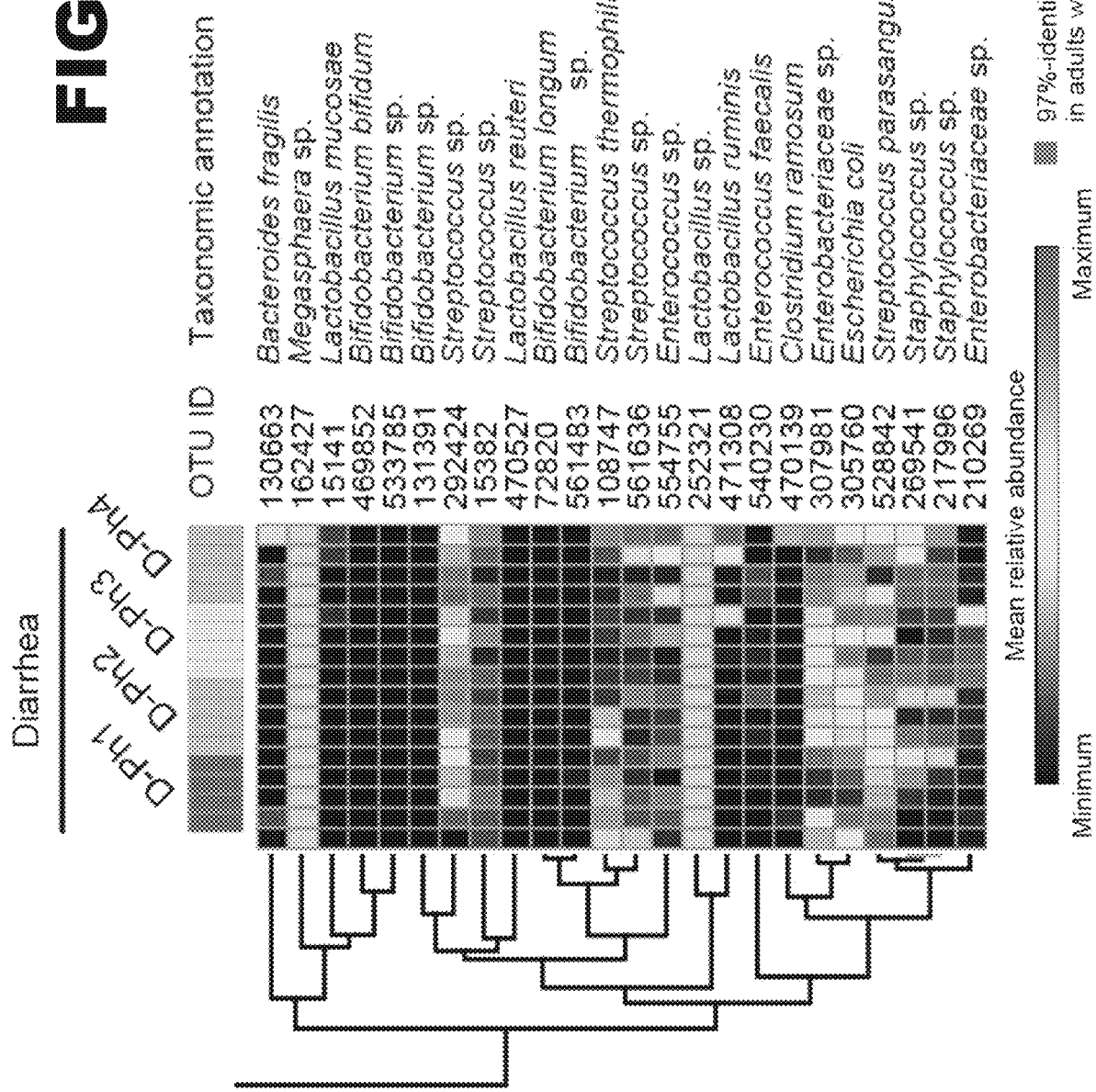
Figure 18G:
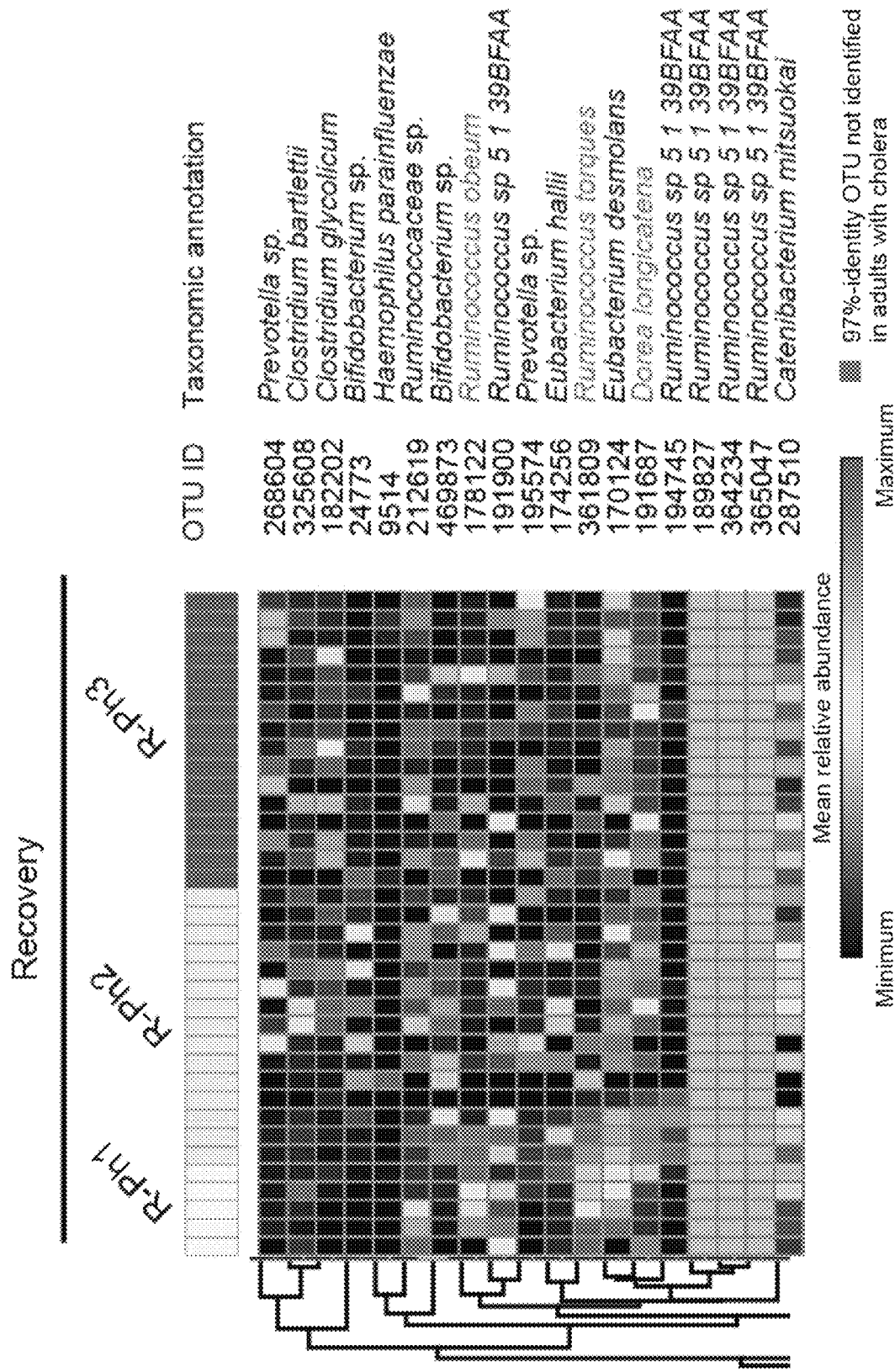
Figure 18H:
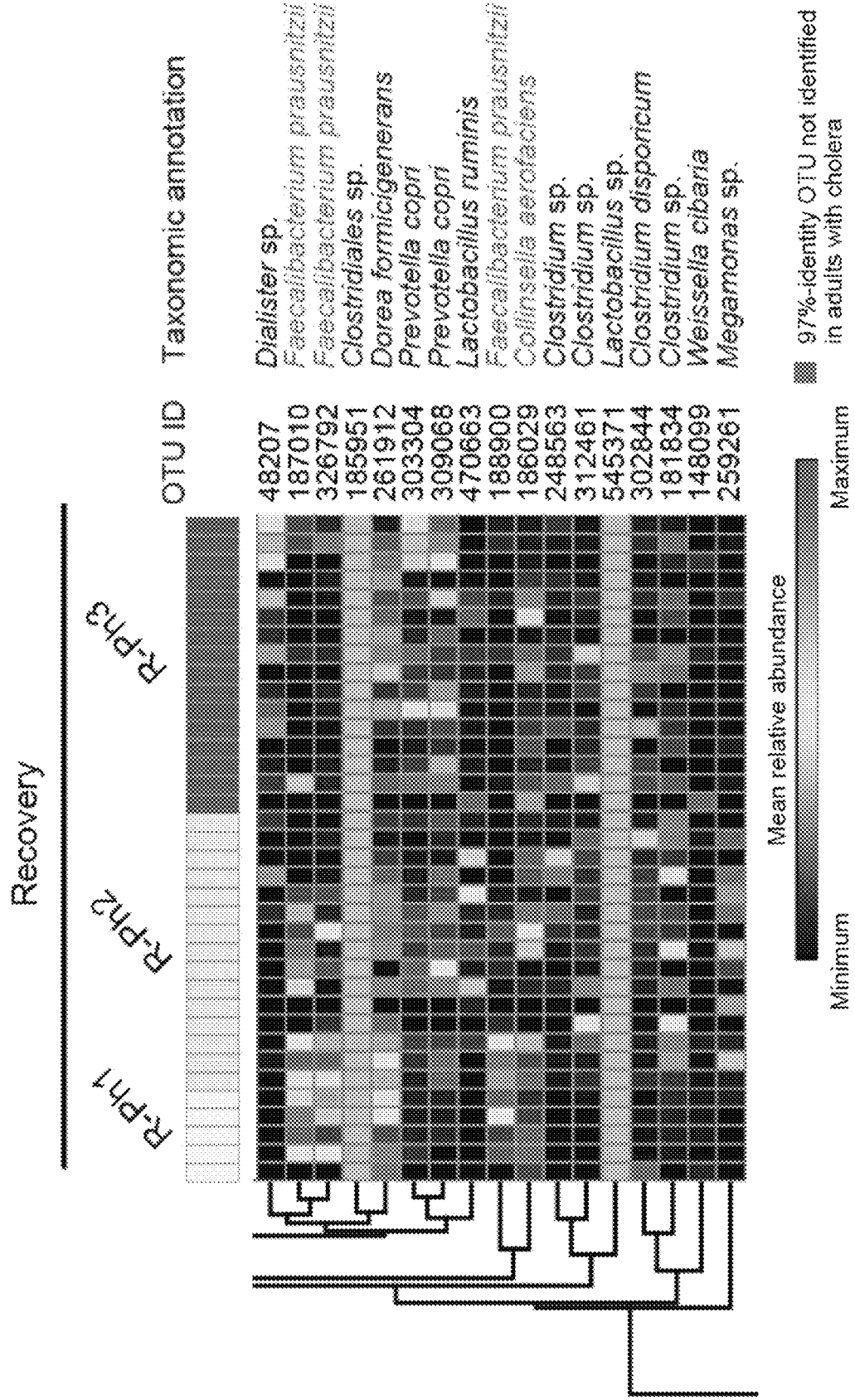
Figure 18I:
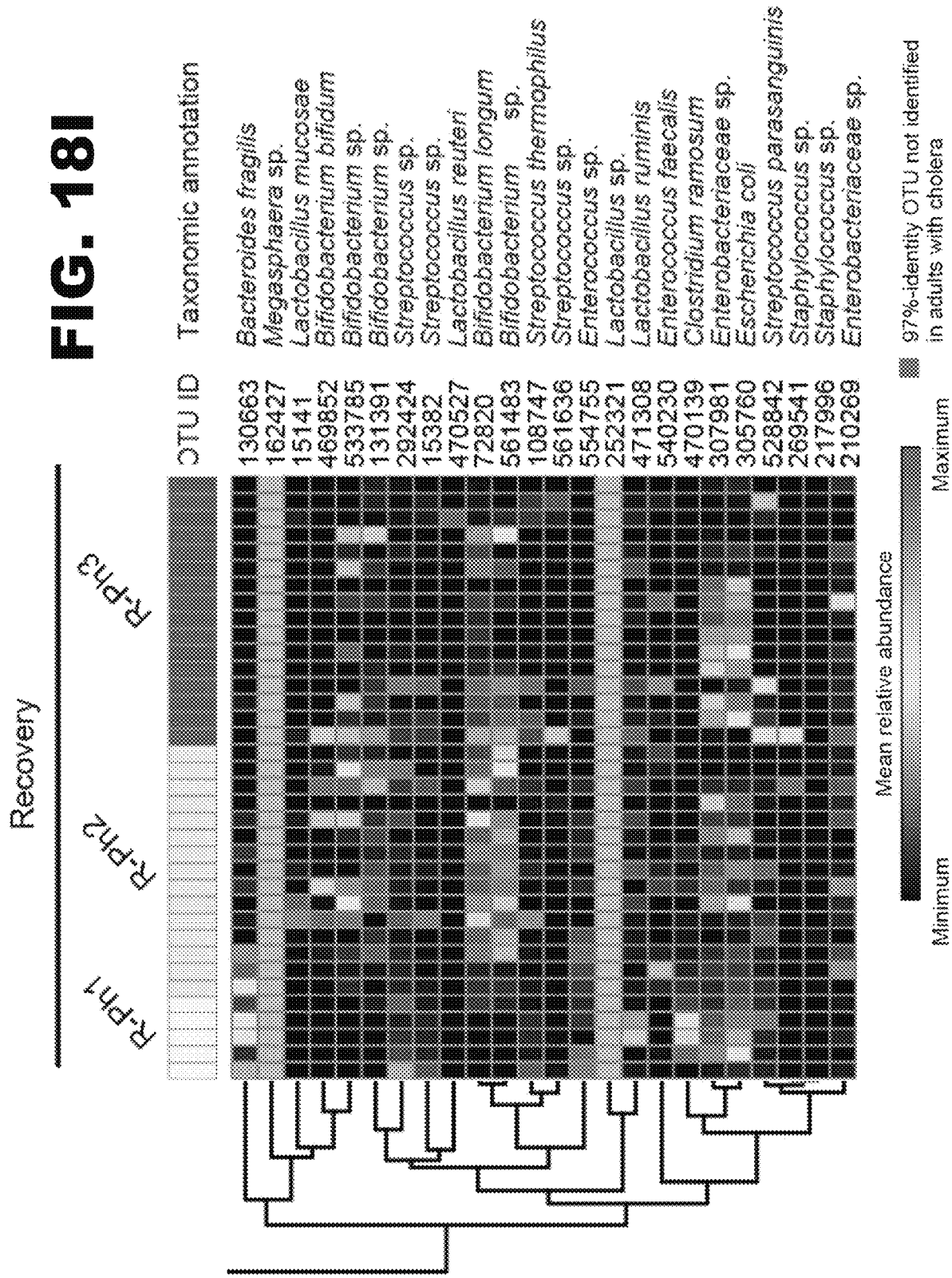
Figure 18J:
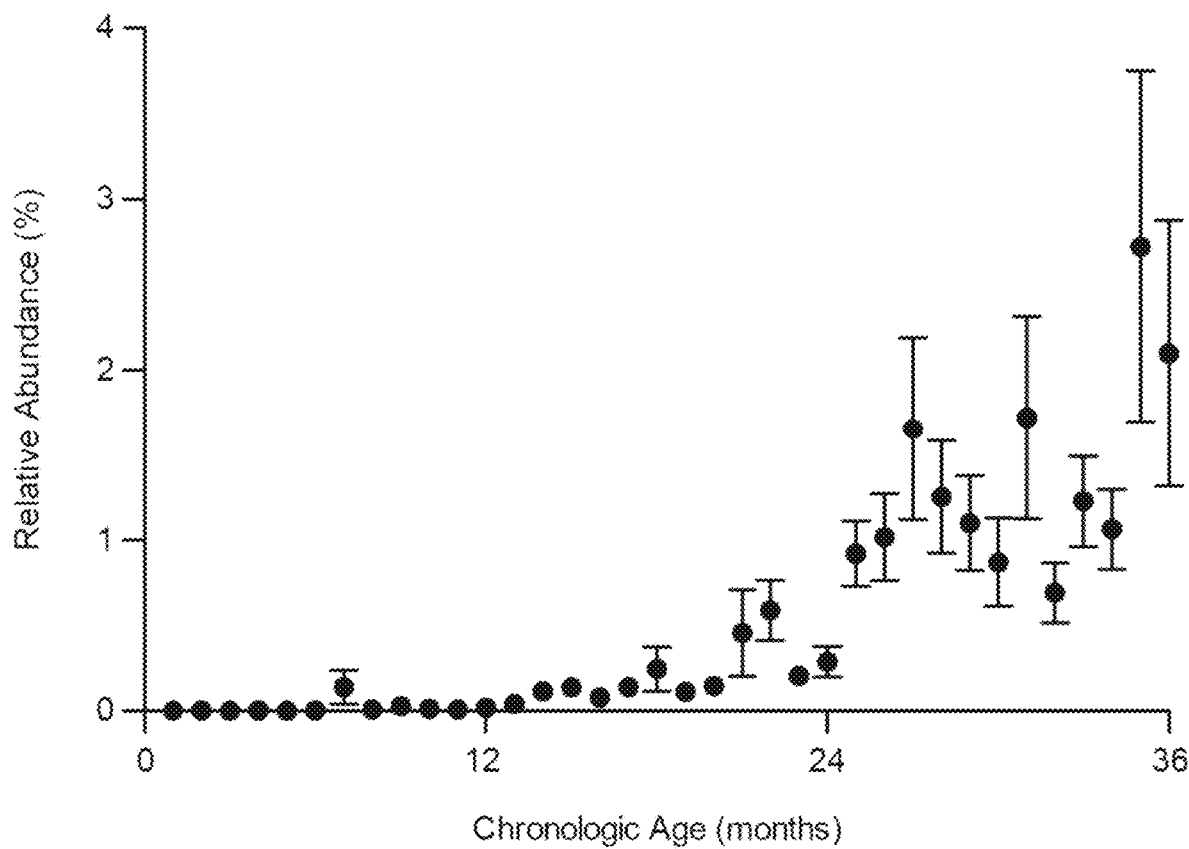

Changes in relative abundances of the 14 community members in faecal samples in response to *V. cholerae* were consistent for most species across the D1 invasion and D14invasion mice (Table 25). We focused on one member, *R. obeum*, because its relative abundance increased significantly after introduction of *V. cholerae* in both the D1 invasion and D14invasion groups (FIG. 21A and Table 25) and because it is a prominent age-discriminatory taxon in the Random Forests model of gut microbiota maturation in healthy Bangladeshi children[3] (FIG. 18J). Mice were mono-colonized with either *R. obeum* or *V. cholerae* for 7 days and then the other species was introduced (FIG. 15E,F). When *R. obeum* was present, *V. cholerae* levels declined by 1-3 logs (FIG. 13A,B). Germ-free mice were also colonized with the defined 14-member community or the same community without *R. obeum* for 2 weeks, and *V. cholerae* was then introduced by gavage (FIG. 15G,H). V. choleraelevels 1 day after gavage were 100-fold higher in the community that lacked *R. obeum*; these differences were sustained over time (50-fold higher after 7 days; P<0.01, unpaired Mann-Whitney U-test; FIG. 13A,B).

Having established that *R. obeum* restricts *V. cholerae* colonization, we used microbial RNA sequencing (RNA-seq) of faecal RNAs to determine the effect of *R. obeum* on expression of known *V. cholerae* virulence factors in mono- and co-colonized mice. Co-colonization led to reduced expression of tcpA (a primary colonization factor in humans[9,10]), rtxA and hlyA (encode accessory toxins[11,12]), and VC1447-VC1448 (RtxA transporters) (threefold to fivefold changes; P<0.05 compared with *V. cholerae* mono-colonized controls, Mann-Whitney U-test; see Table 26 for other regulated genes that could impact colonization, plus FIG. 22 for an ultra-performance liquid chromatography mass spectrometry (UPLC-MS) analysis of bile acids reported to effect *V. cholerae* gene regulation[13]).

Figure 13C:
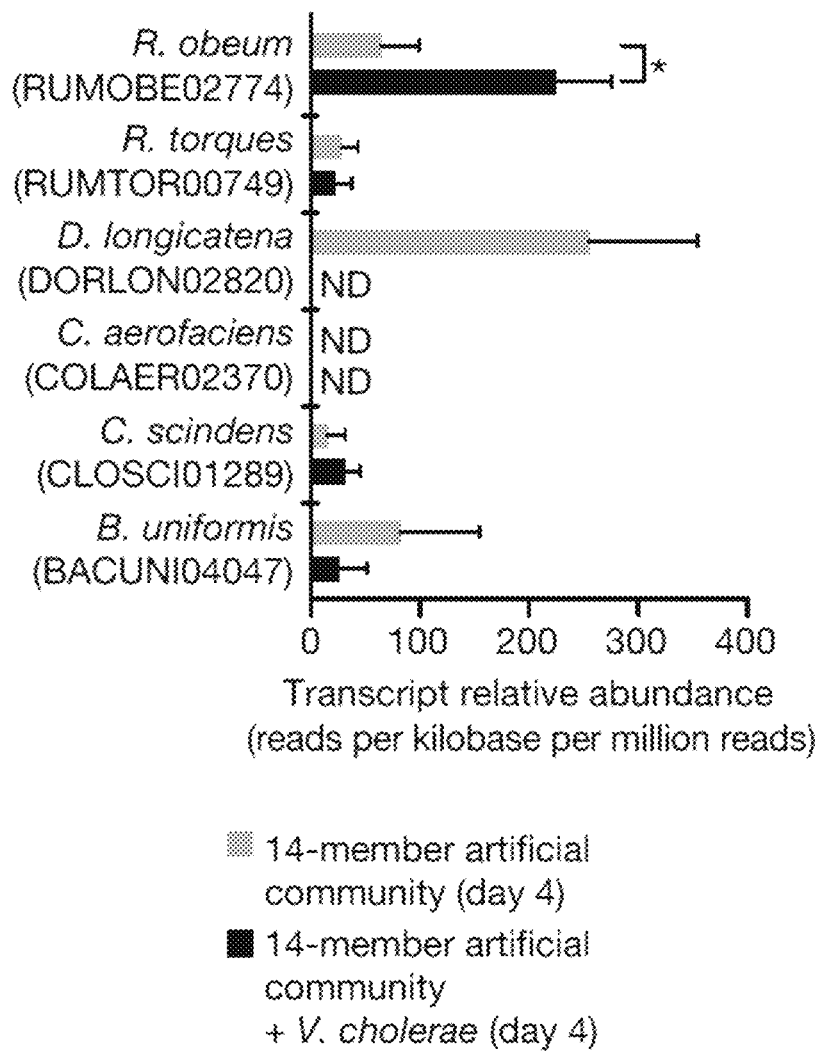
Figure 21D:
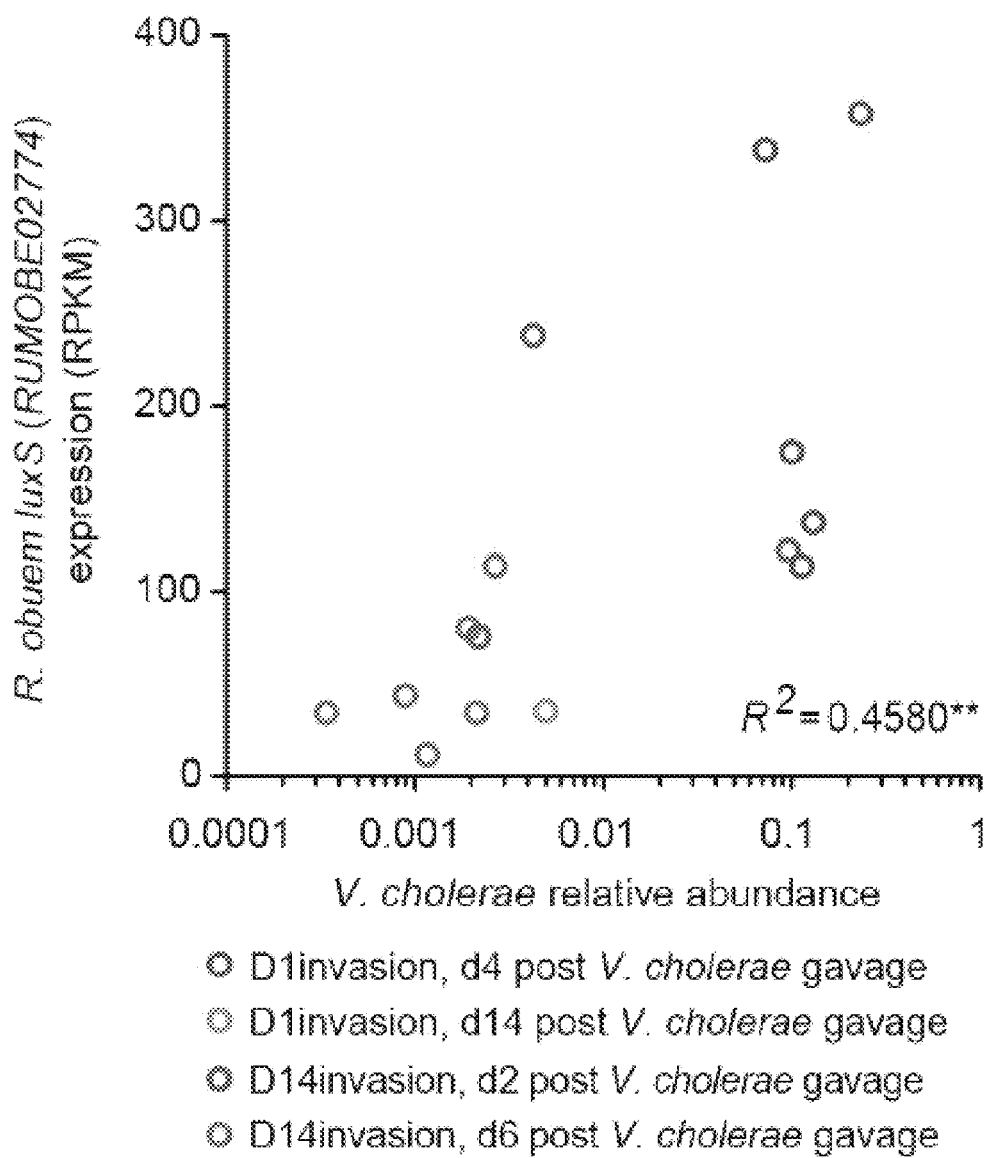
Figure 21:
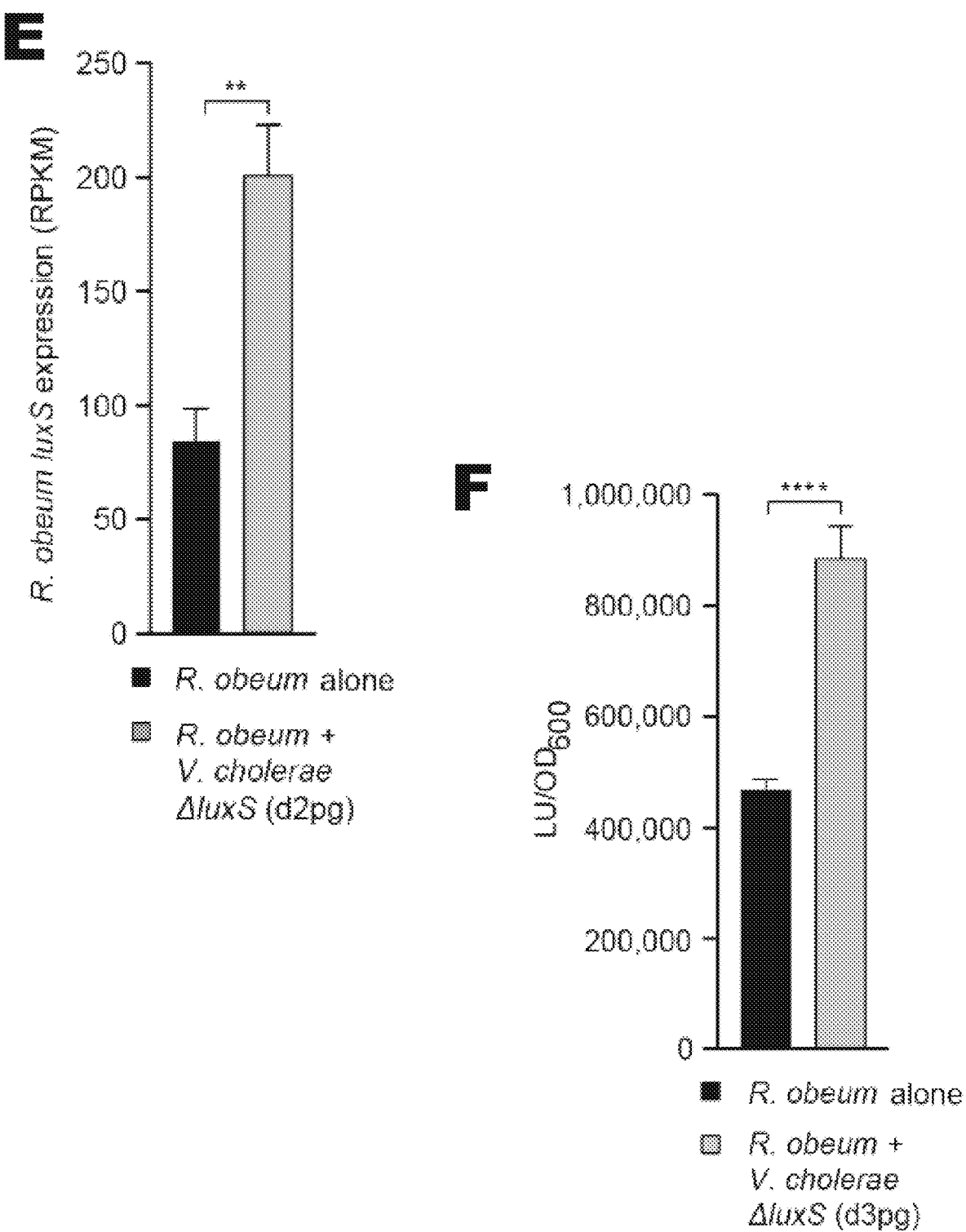

Two quorum-sensing pathways are known to regulate *V. cholerae* colonization/virulence[14,15,16,17]: an intra-species mechanism involving cholera autoinducer-1, and an inter-species mechanism involving autoinducer-2[18,19]. Quorum sensing disrupts expression of *V. cholerae* virulence determinants through a signalling pathway that culminates in production of the LuxR-family regulator HapR[15,16]. Repression of quorum sensing in *V. cholerae* is important for virulence factor expression and infection[20,21,22]. The luxS gene encodes the S-ribosylhomocysteine lyase responsible for Al-2 synthesis. Homologues of luxS are widely distributed among bacteria[18,19], including 8 of the 14 species in the artificial human gut community (Table 27 and FIG. 23). RNA-seq of the faecal meta-transcriptomes of D1 invasion mice colonized with the 14-member artificial community plus *V. cholerae*, and mice harbouring the 14-member consortium without *V. cholerae*, revealed that of predicted luxS homologues in the community, only expression of *R. obeum* luxS (RUMOBE02774) increased significantly in response to *V. cholerae*(P<0.05, Mann-Whitney U-test; FIG. 13C). Moreover, *R. obeum* luxS transcript levels directly correlated with *V. cholerae* levels (FIG. 21D).

In addition to luxS, the *R. obeum* strain represented in the artificial community contains homologues of IsrABCK that are responsible for import and phosphorylation of Al-2 in Gram-negative bacteria[23], as well as homologues of two genes, luxR and luxQ, that play a role in Al-2 sensing and downstream signalling in other organisms[24]. Expression of all these *R. obeum* genes was detected in vivo, consistent with *R. obeum* having a functional Al-2 signalling system (FIG. 21B,C). (See Example 17 for results showing that *R. obeum* Al-2 production is stimulated by *V. cholerae* in vitro and in co-colonized animals (FIG. 21E-G), plus (1) a genome-wide analysis of the effects of *V. cholerae* on *R. obeum* transcription in co-colonized mice (Table 26c) and (2) a community-wide view of the transcriptional responses of the 14-member consortium to *V. cholerae* (Table 28).)

Quorum sensing downregulates the *V. cholerae* tcp operon that encodes components of the toxin co-regulated pilus (TCP) biosynthesis pathway required for infection of humans[9,10]. To confirm that *R. obeum* LuxS could signal through Al-2 pathways, we cloned *R. obeum* and *V. cholerae* luxS downstream of the arabinose-inducible $P_{BAD}$ promoter in plasmids that were maintained in an *Escherichia coli* strain unable to produce its own Al-2 (DH5a)[25]. High tcp expression can be induced in *V. cholerae* after slow growth in AKI medium without agitation followed by rapid growth under aerobic conditions[26]. Addition of culture supernatants harvested from the *E. coli* strains expressing *R. obeum* or *V. cholerae* luxS caused a two- to threefold reduction in tcp induction in *V. cholerae* (P<0.05, unpaired Student's t-test; replicated in four independent experiments). Supernatants from a control *E. coli* strain with the plasmid vector lacking luxS had no effect (FIG. 14A). These findings are consistent with our in vivo RNA-seq results and provide direct evidence that *R. obeum* Al-2 regulates expression of *V. cholerae* virulence factor.

Germ-free mice were then colonized with *V. cholerae* and *E. coli* bearing either the $P_{BAD}$-*R. obeum* luxS plasmid or the vector control. Mice that received *E. coli* expressing *R. obeum* luxS showed a significantly lower level of *V. cholerae* colonization 8 h after gavage than mice that received *E. coli* with vector alone (FIG. 14B; there was no statistically significant difference in levels of *E. coli* between the two groups (data not shown)). Together, these results establish a direct causal relationship between *R. obeum*-mediated restriction of *V. cholerae* colonization and *R. obeum* Al-2 synthesis.

Several *V. cholerae* mutants were used to determine whether known *V. cholerae* Al-2 signalling pathways are required for the observed effects of *R. obeum* on *V. cholerae* colonization. LuxP is critical for sensing Al-2 in *V. cholerae*. Co-colonization experiments in gnotobiotic mice revealed that levels of isogenic ΔluxP or wild-type luxP⁺ *V. cholerae* strains were not significantly different as a function of the presence of *R. obeum* (FIG. 24), suggesting that *R. obeum* modulates *V. cholerae* levels through other quorum-sensing regulatory genes. The luxO and hapRgenes encode central regulators linking known *V. cholerae* quorum-signalling and virulence regulatory pathways. Deletion of luxO typically results in increased hapR expression[15]. However, our RNA-seq analysis had shown that both luxO and hapR are repressed in the presence of *R. obeum* (six- to sevenfold, P<0.0001; Mann-Whitney U-test), as are two important downstream activators of virulence repressed by HapR[16], encoded by aphA and aphB. These findings provide additional evidence that *R. obeum* operates to regulate virulence through a novel regulatory pathway.

Figure 14D:
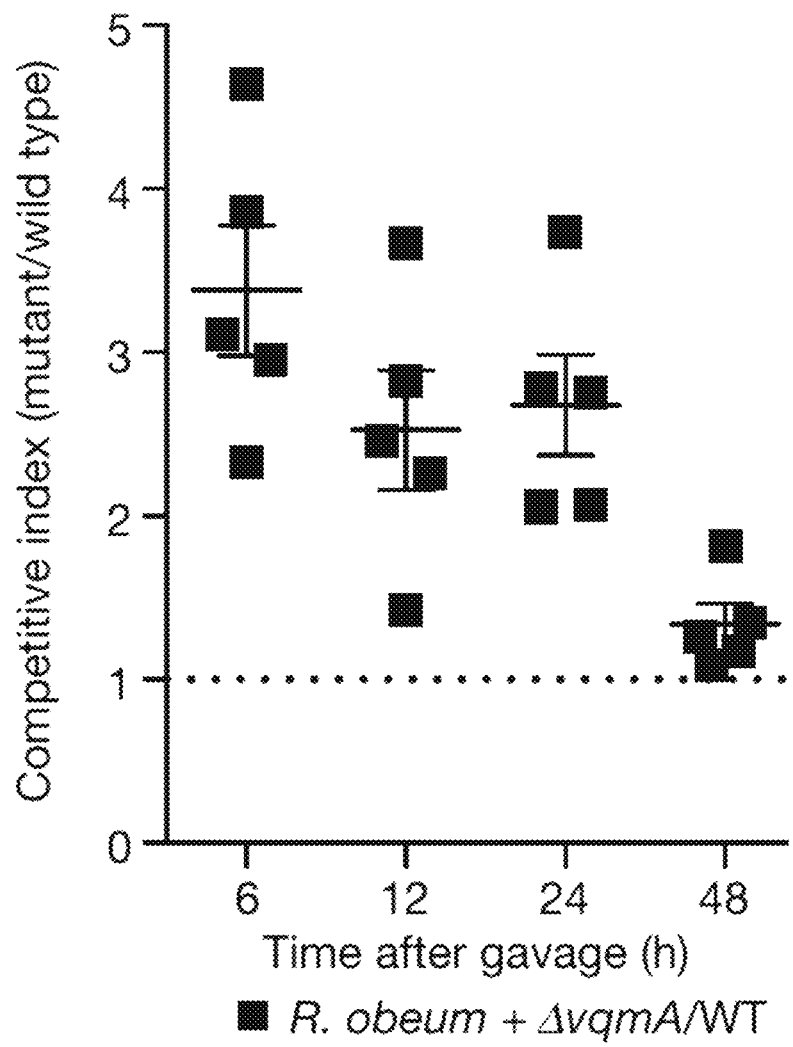

The quorum-sensing transcriptional regulator VqmA was upregulated more than 25-fold when *V. cholerae* was introduced into mice mono-colonized with *R. obeum* (FIG. 14C and Table 26). When germ-free mice were gavaged with *R. obeum* and a mixture of ΔvqmA (ΔlacZ)[27] and wild-type *V. cholerae* (lacZ+) strains, the ΔvqmA mutant exhibited an early competitive advantage (FIG. 14D), suggesting that *R. obeum* may be able to affect early colonization of *V. cholerae* through VqmA. VqmA is able to bind to and activate the hapR promoter directly[27]. Since RNA-seq showed that hapR activation did not occur in gnotobiotic mice despite high levels of vqmAexpression (FIG. 24B and Table 26), we postulate that the role played by VqmA in *R. obeum* modulation of *Vibrio* virulence genes involves an uncharacterized mechanism rather than the known pathway passing through HapR.

We have identified a set of bacterial species that strongly correlate with a process in which the perturbed gut bacterial community in adult patients with cholera is restored to a configuration found in healthy Bangladeshi adults. Several of these species are also associated with the normal assembly/maturation of the gut microbiota in Bangladeshi infants and children, raising the possibility that some of these taxa may be useful for 'repair' of the gut microbiota in individuals whose gut communities have been 'wounded' through a variety of insults, including enteropathogen infections. Translating these observations to a gnotobiotic mouse model containing an artificial human gut microbiota composed of recovery- and age-indicative taxa established that one of these species, *R. obeum*, reduces *V. cholerae* colonization. As an entrenched member of the gut microbiota in Bangladeshi individuals, *R. obeum* could function to increase median infectious dose ($ID_{50}$) for *V. cholerae* in humans and thus help to determine whether exposure to a given dose of this enteropathogen results in diarrhoeal illness. The modest effects of *R. obeum* Al-2 on *V. cholerae* virulence gene expression in our adult gnotobiotic mouse model may reflect the possibility that we have only identified a small fraction of the microbiota's full repertoire of virulence-suppressing mechanisms. Culture collections generated from the faecal microbiota of Bangladeshi subjects are a logical starting point for 'second-generation' artificial communities containing *R. obeum* isolates that have evolved in this population, and for testing whether the observed effects of *R. obeum* generalize across many different strains from different populations. Moreover, the strategy described in this report could be used to mine the gut microbiota of Bangladeshi or other populations where diarrhoeal disease is endemic for additional species that use quorum-related and/or other mechanisms to limit colonization by *V. cholerae* and potentially other enteropathogens.

Example 11

Patient Selection

Of the 1153 patients screened (Table 18), 796 (69%) were disqualified because of immediate prior antibiotic usage. Another 100 were disqualified because their diarrhea began more than 24 h before enrollment, while 132 were excluded due to lack of a permanent address for follow-up. Of the 11 adults (all males) who entered the study, four could not be contacted by staff after discharge from the hospital; their samples were not included in our analysis, leaving a total of seven individuals (A-G; see Table 19 for clinical metadata). The seven patients included in the study experienced diarrhea for 8.0±2.6 hours (mean±SD) prior to hospital admission and for 41.5±16.7 hours during their hospital stay. They had an average of 1.5±1.0 diarrheal stools per hour (Table 19).

For ethical reasons, we could not withhold treatment with azithromycin (or for that matter oral rehydration therapy). Therefore, our study design did not allow us to isolate the nature and effect sizes of various elements of the treatment protocol on the temporal patterns of change in the gut microbiota during the acute and recovery phases of infection, versus those produced by the diarrheal disease per se.

Example 12

Identifying Community-Wide Changes in Representation of 97%-Identity OTU and Species During Diarrhea and Recovery Phases Across all seven individuals, 58.6% of 97%-identity OTUs with a species-level taxonomic assignment associated with recovery (see below) were also detected during both diarrhea and recovery phases (FIG. 15, 16). For individuals C and E, where higher time-resolution analysis was performed, 41.1% and 29.9% of species-level taxa were identified in both diarrhea and recovery samples respectively, with 6.9% and 11.1% of the identified species detected only in recovery phase samples (see Supplementary Table 4c of Hsiao et al, Nature 2014; Epub, which is hereby incorporated by reference in its entirety).

Figure 19E:
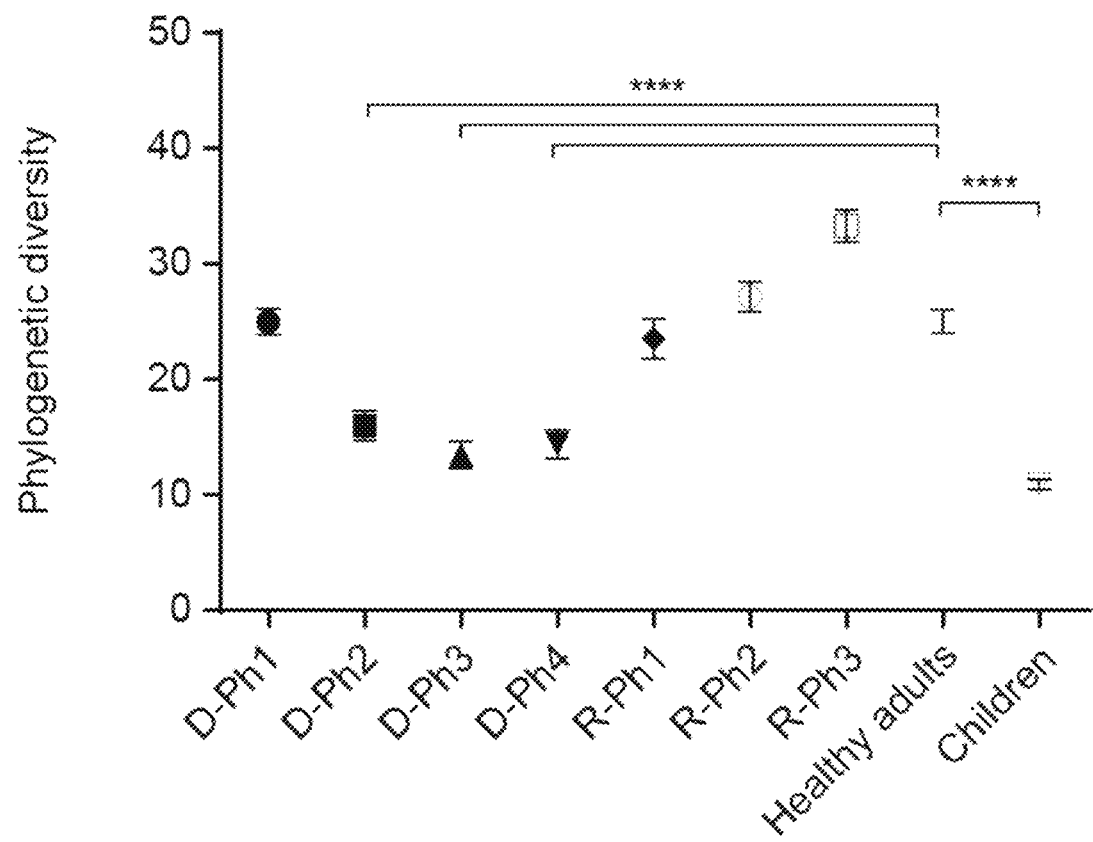
Figure 20A:
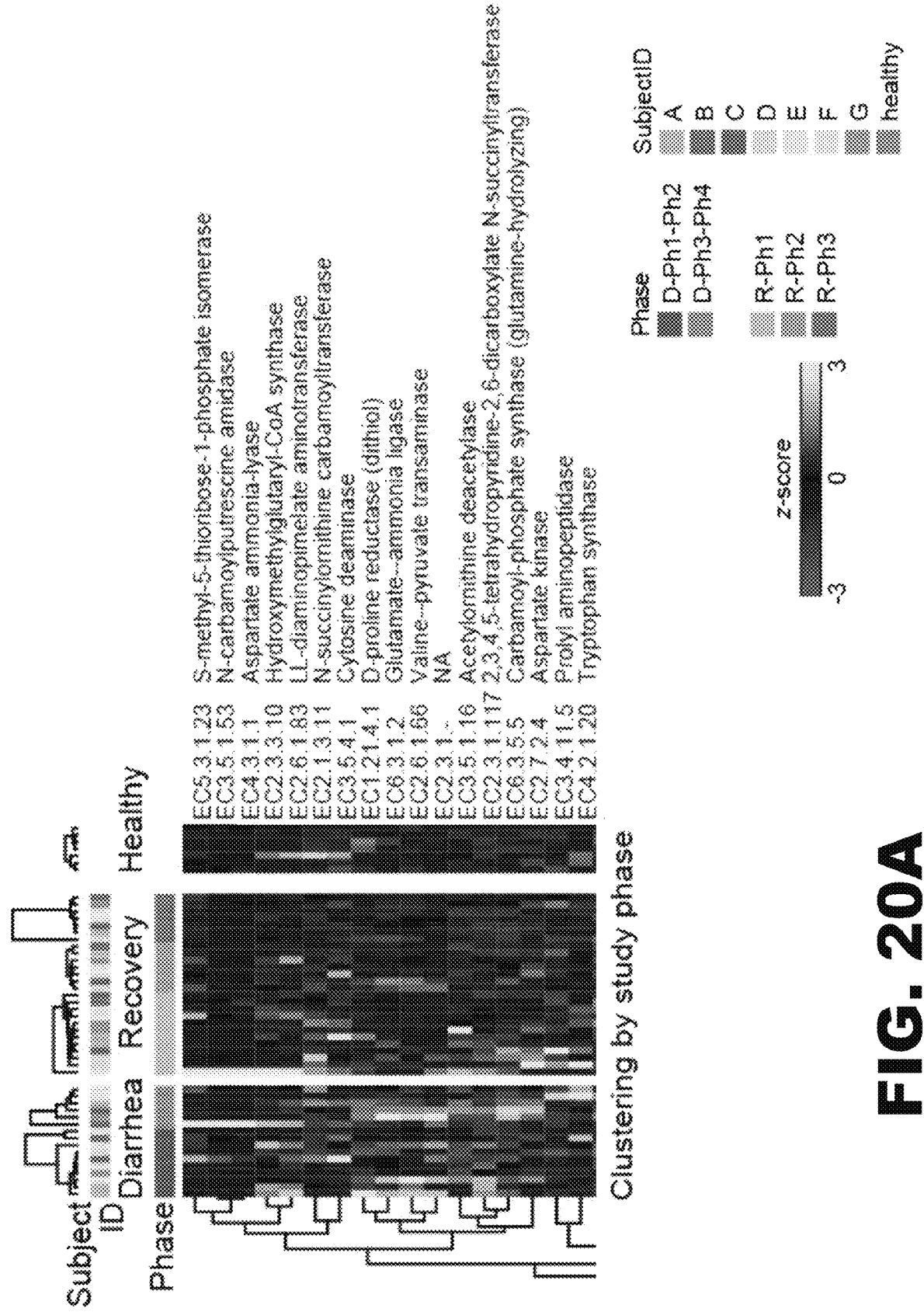
Figure 20B:
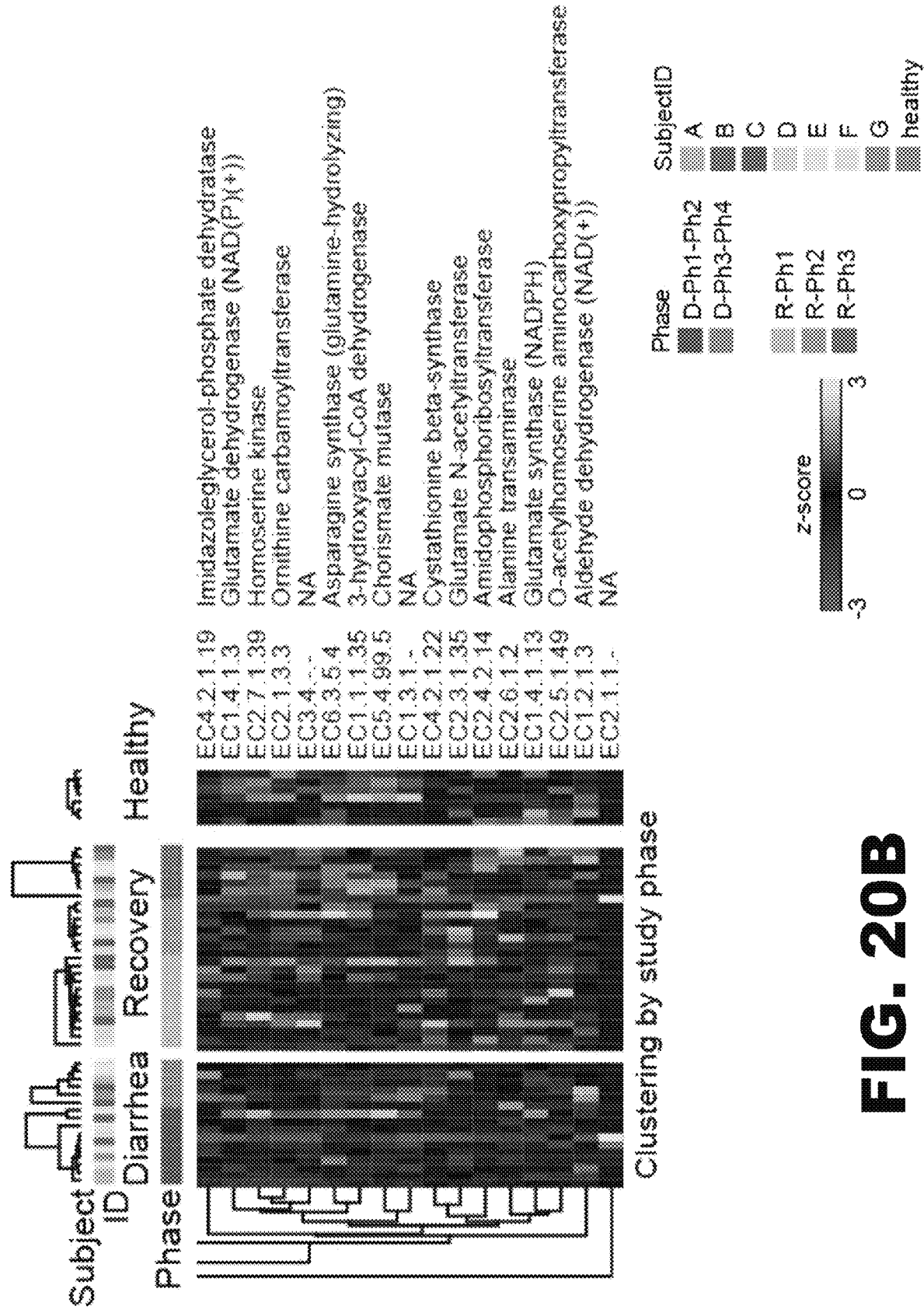
Figure 20C:
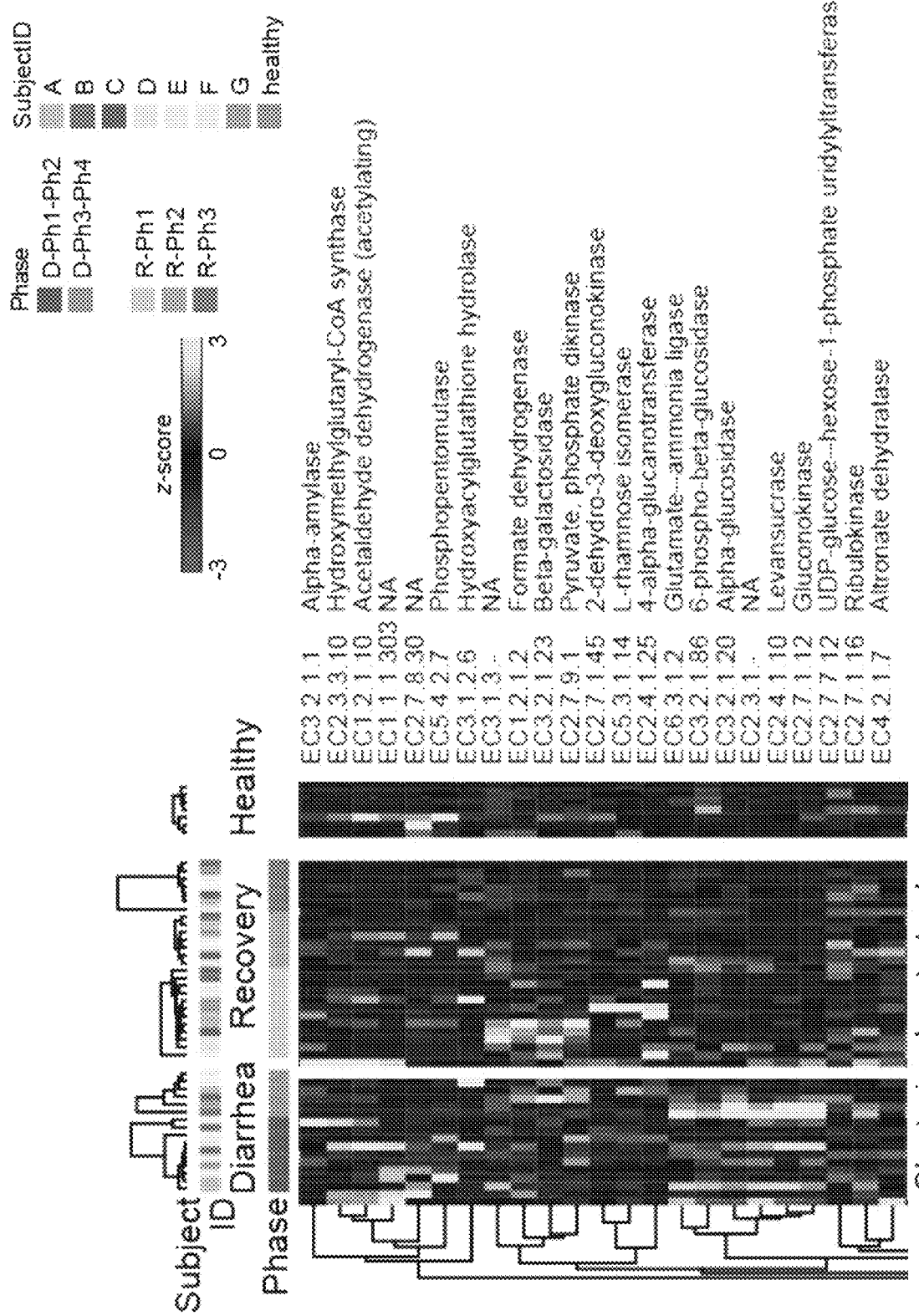
Figure 20D:
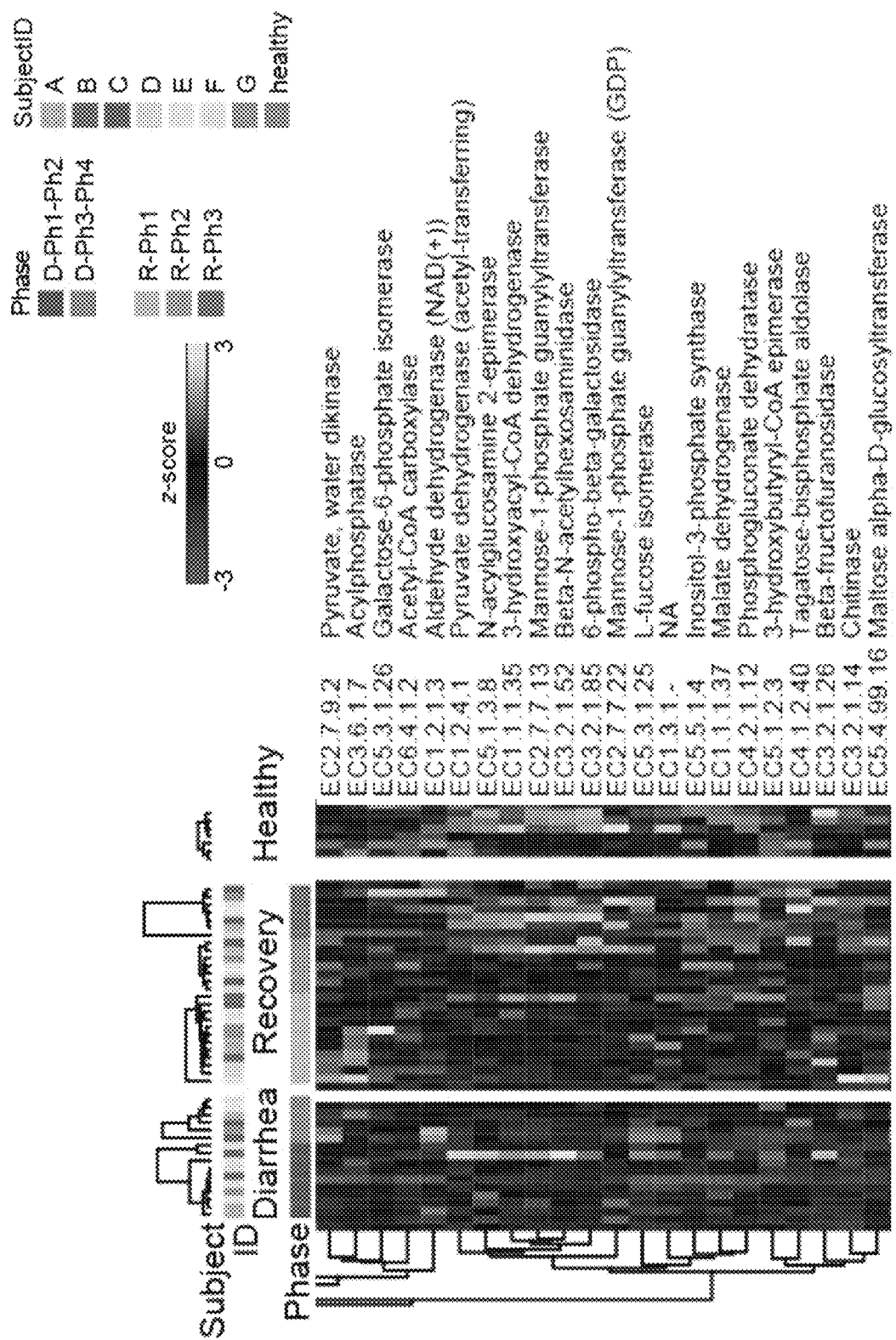
Figure 20E:
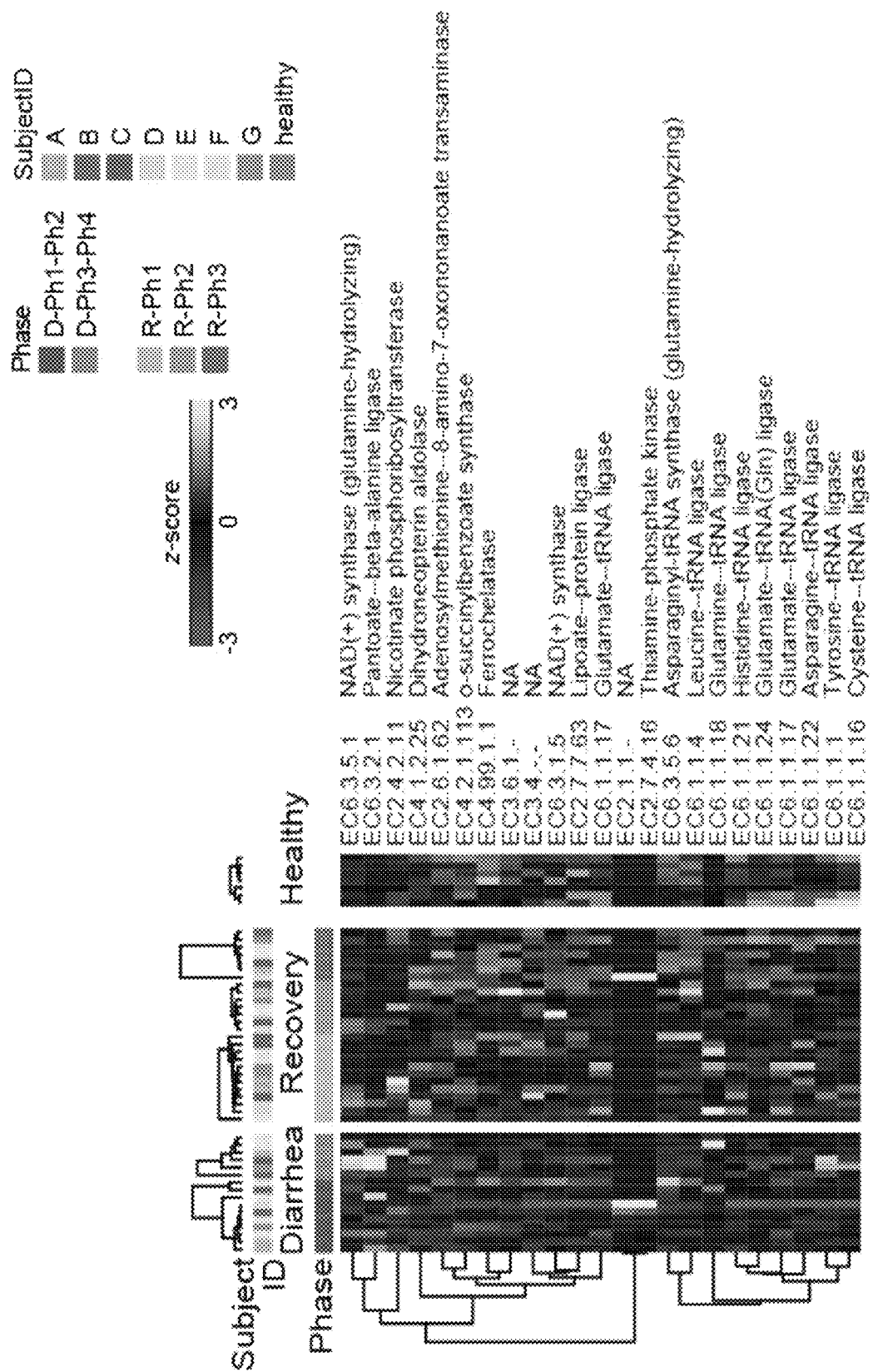
Figure 20F:
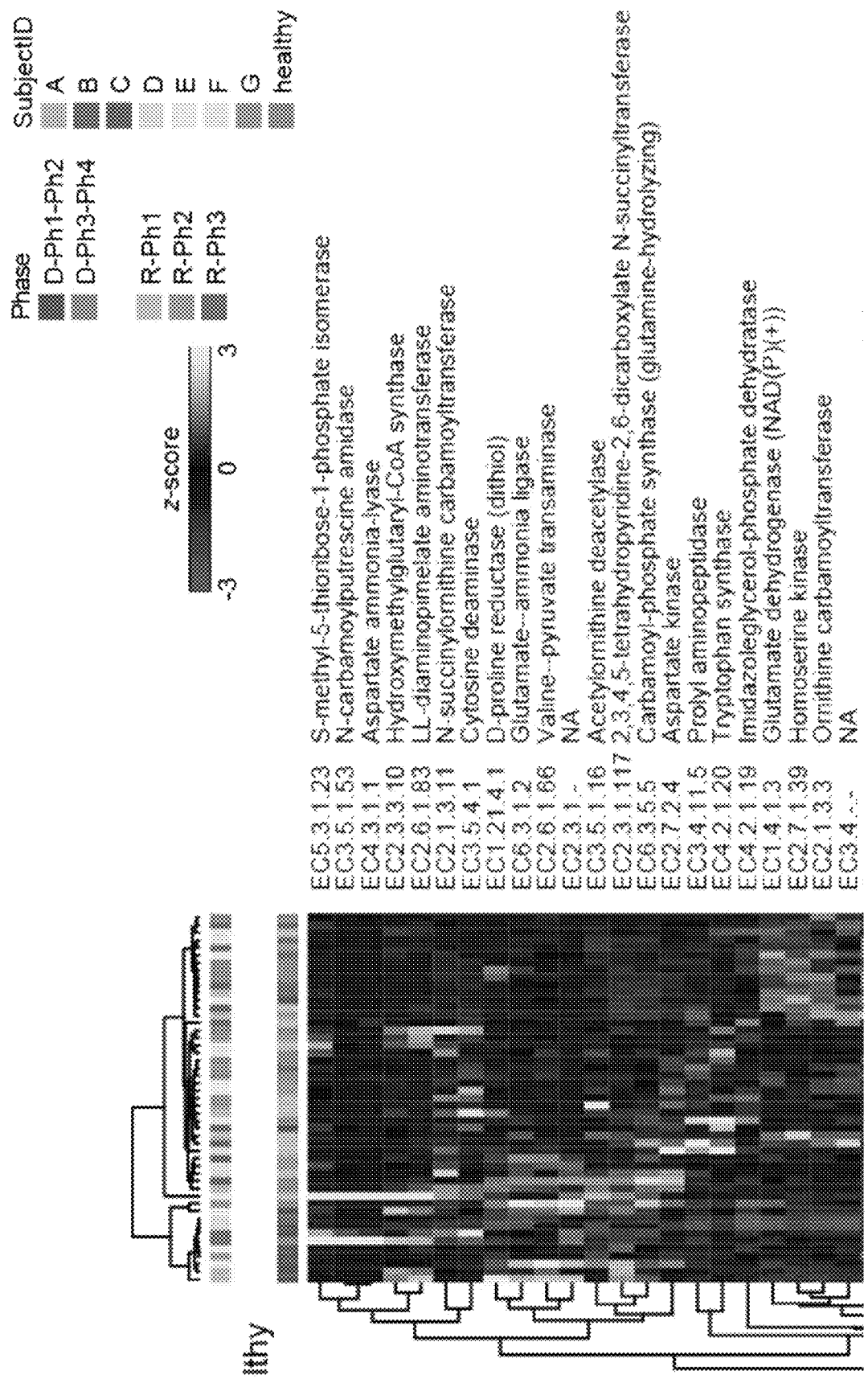
Figure 20G:
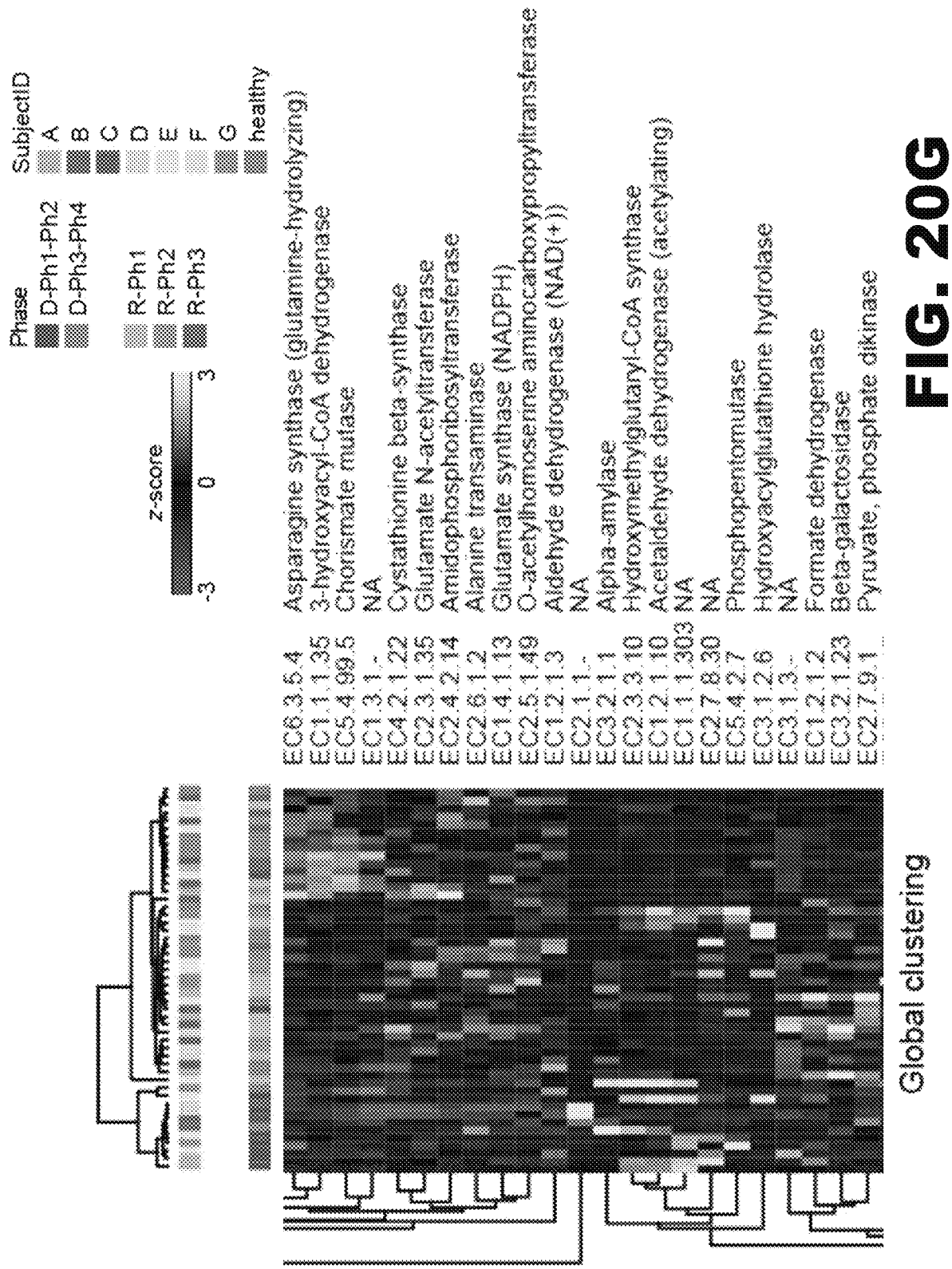
Figure 20H:
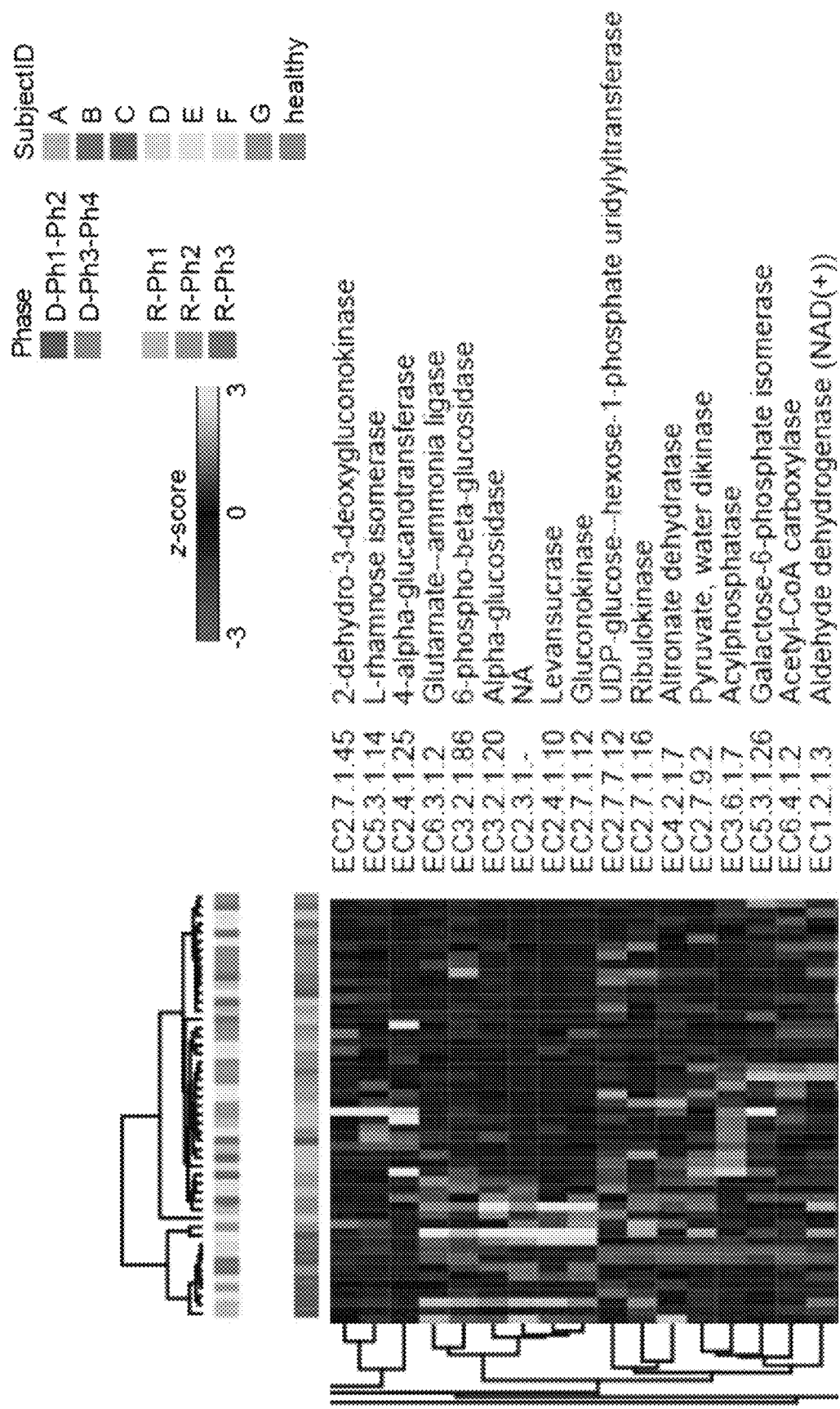
Figure 20I:
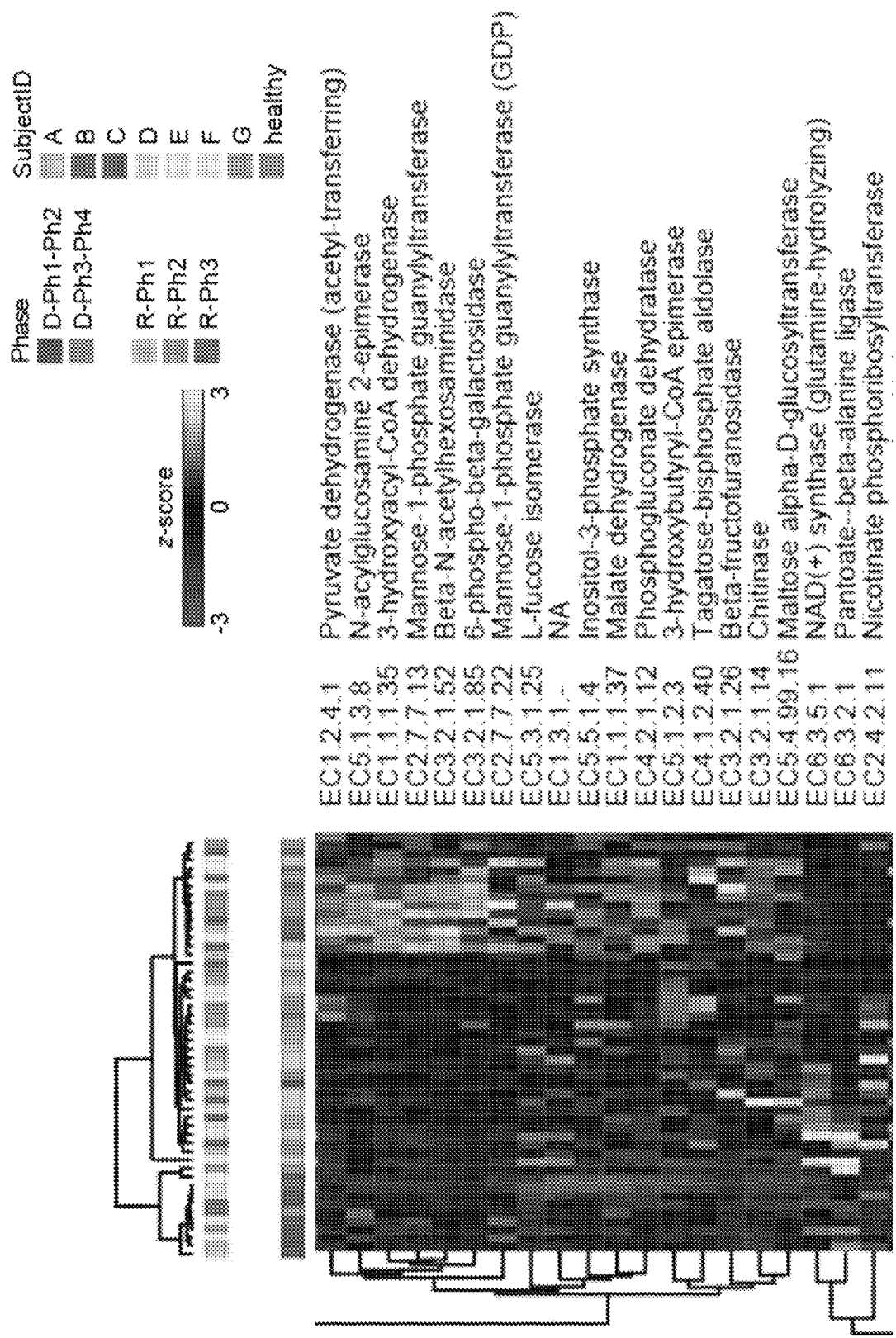
Figure 20J:
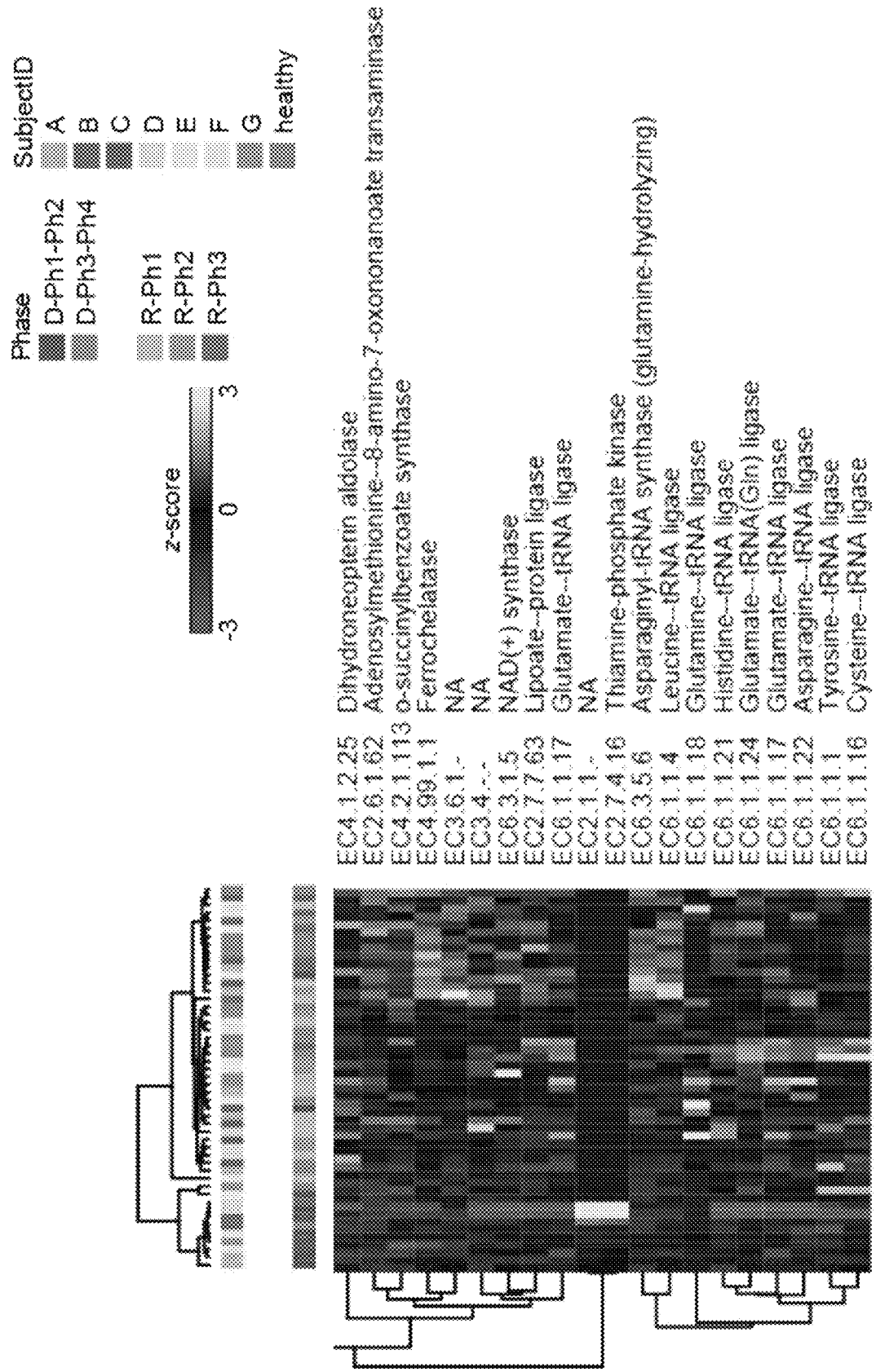

Phylogenetic diversity (PD) of the cholera fecal microbiota decreased markedly during D-Ph2/D-Ph3, approaching the PD of healthy Bangladeshi children, before rising during R-Ph1-R-Ph3 in a temporal pattern that paralleled the UniFrac measurements of similarity to reference healthy adult controls (FIG. 19E).

Figure 16E:
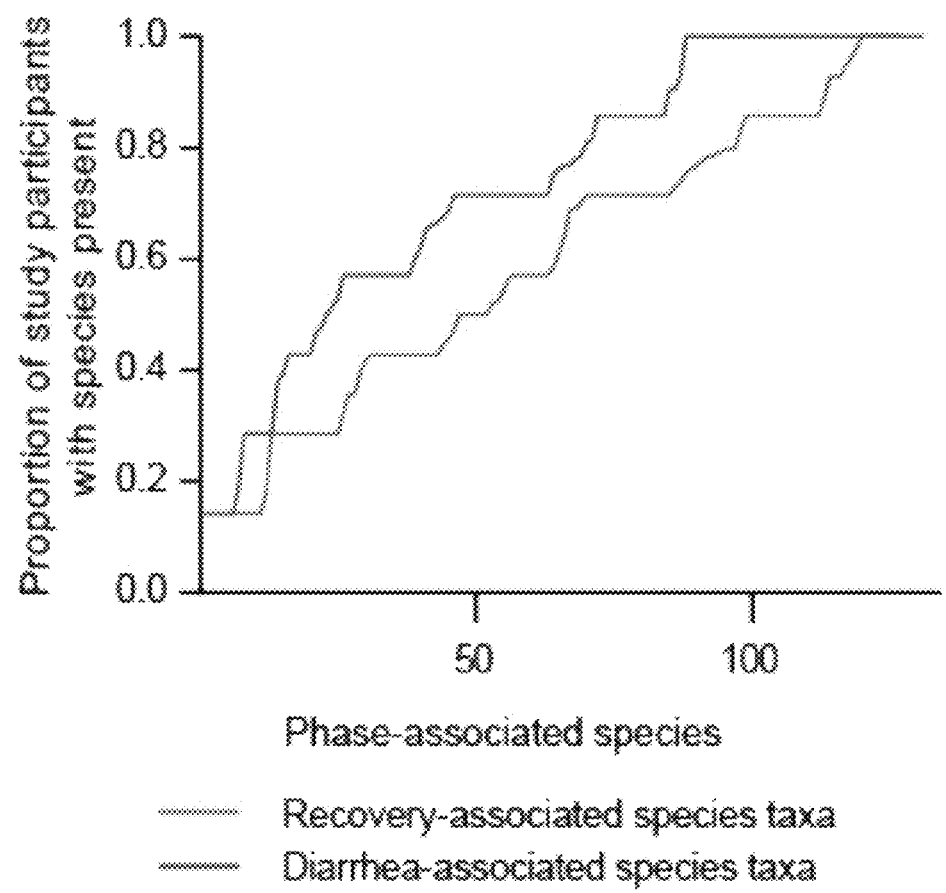
Figure 16F:
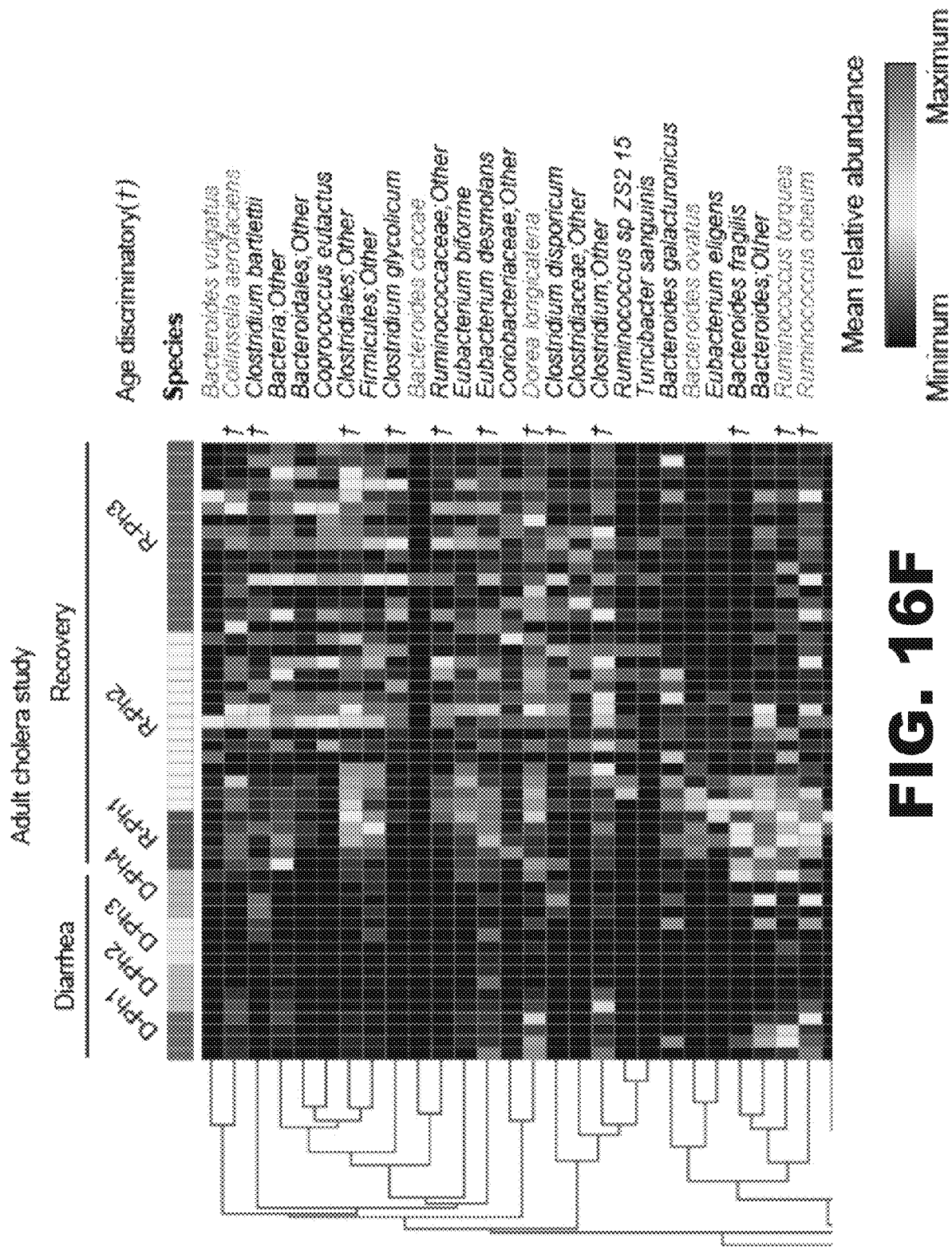
Figure 16G:
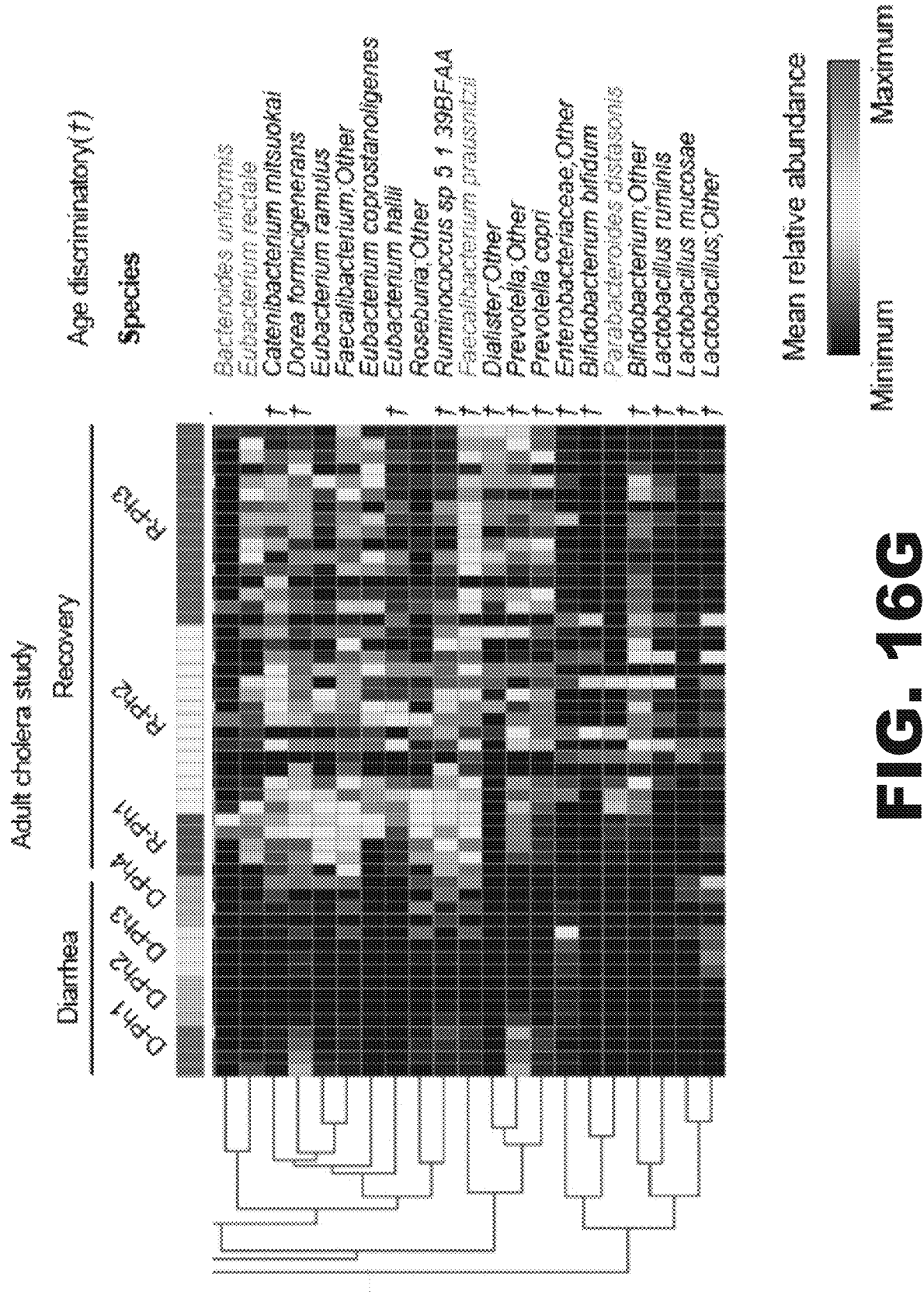
Figure 16H:
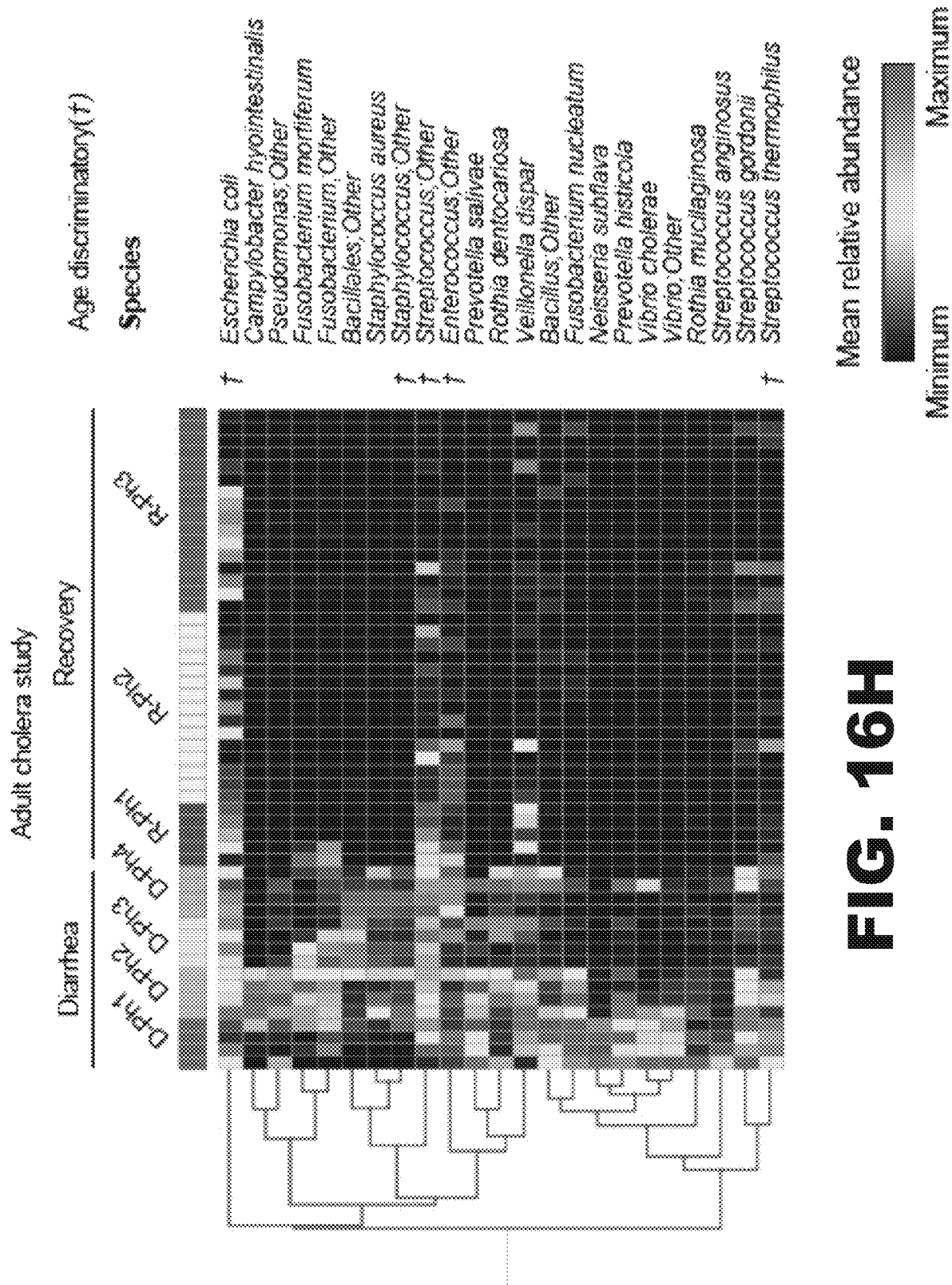
Figure 16I:
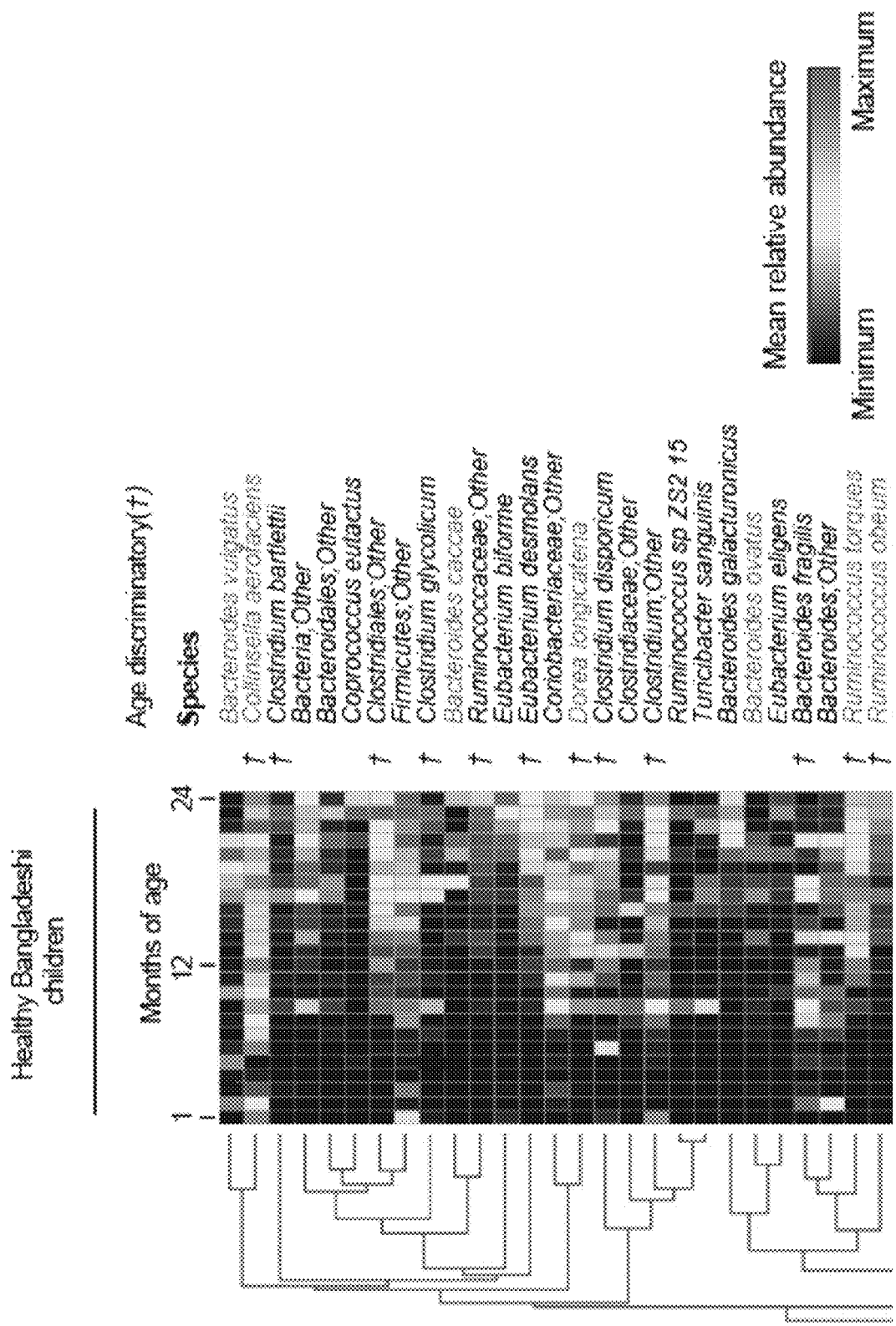
Figure 16J:
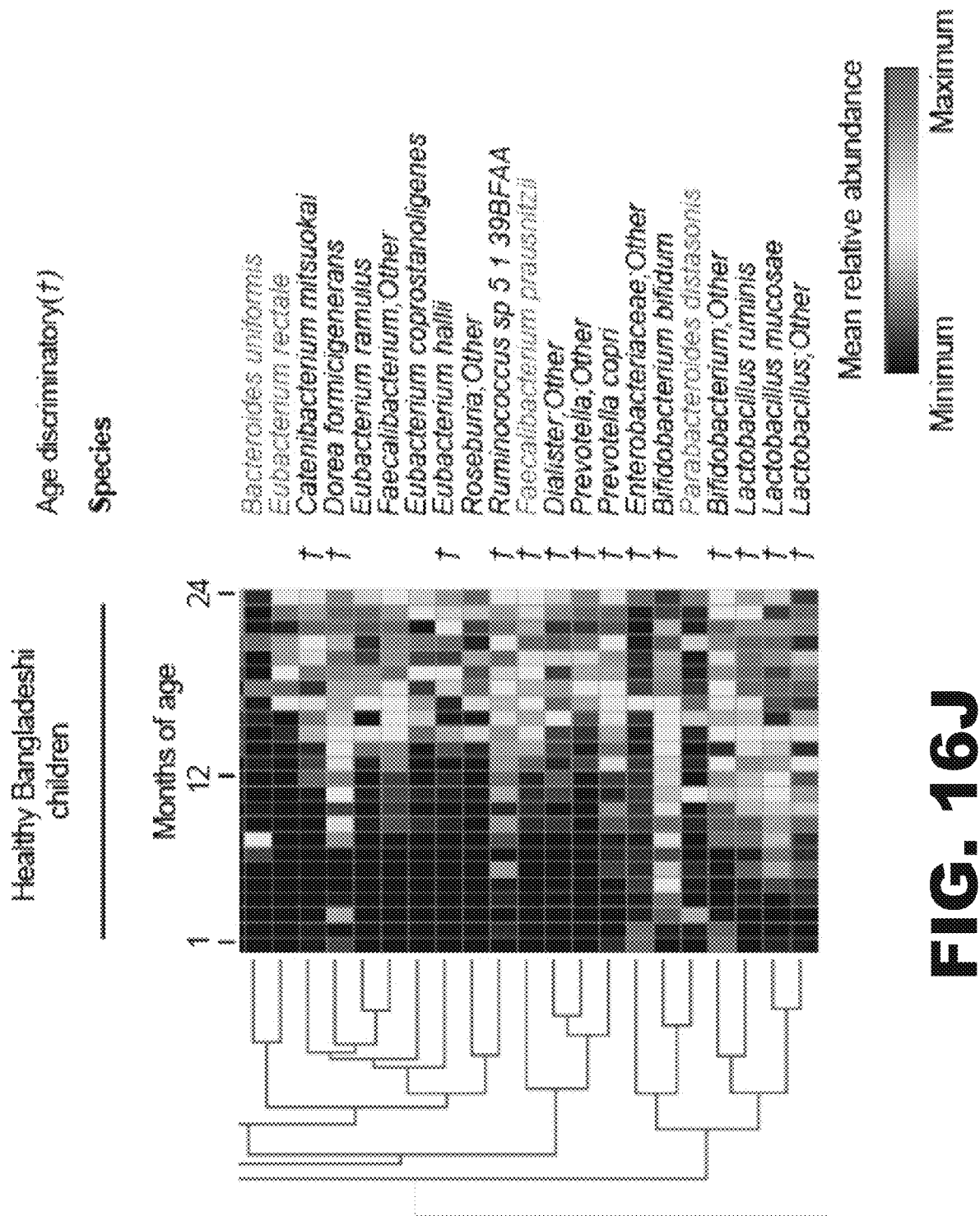
Figure 16K:
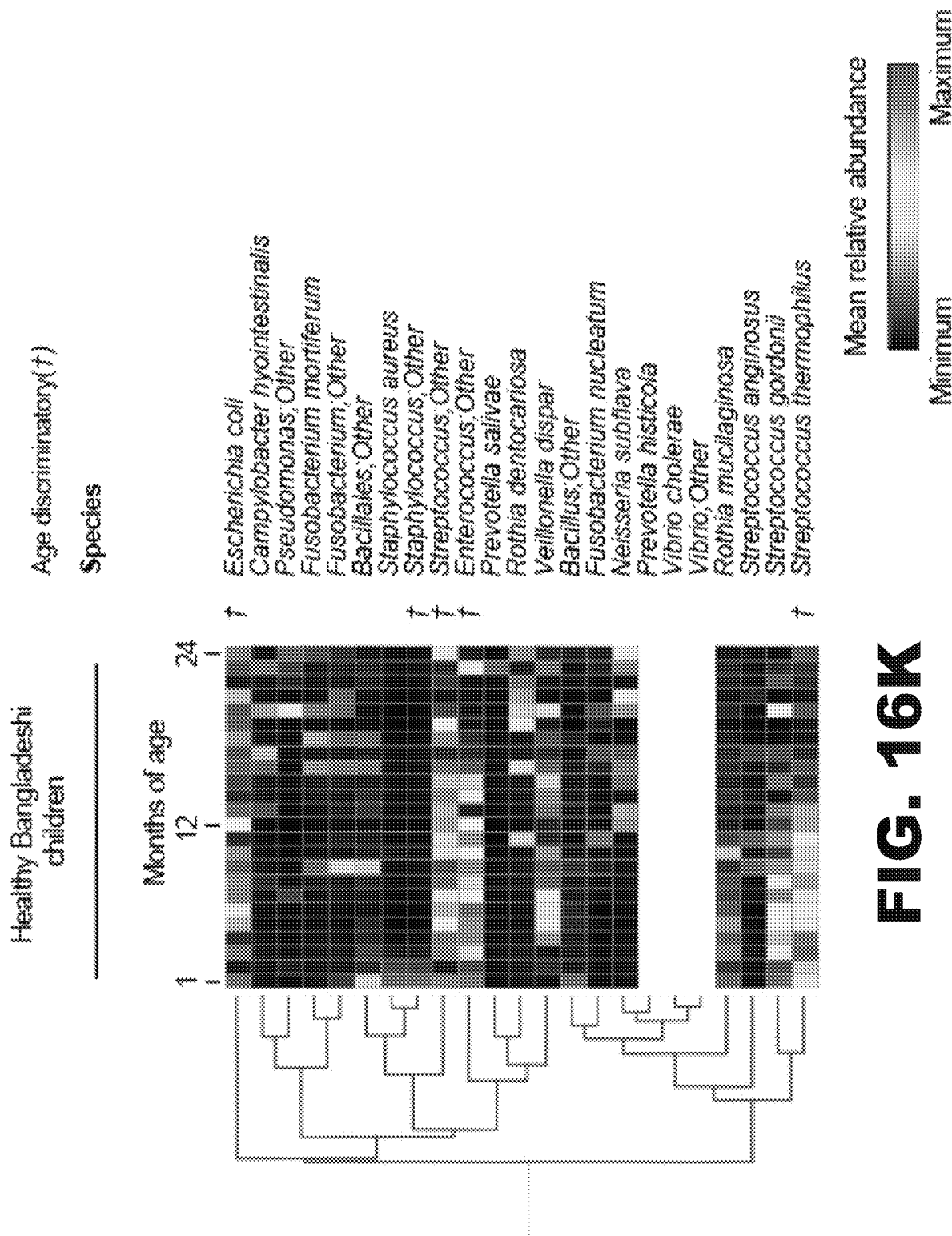
Figure 16L:
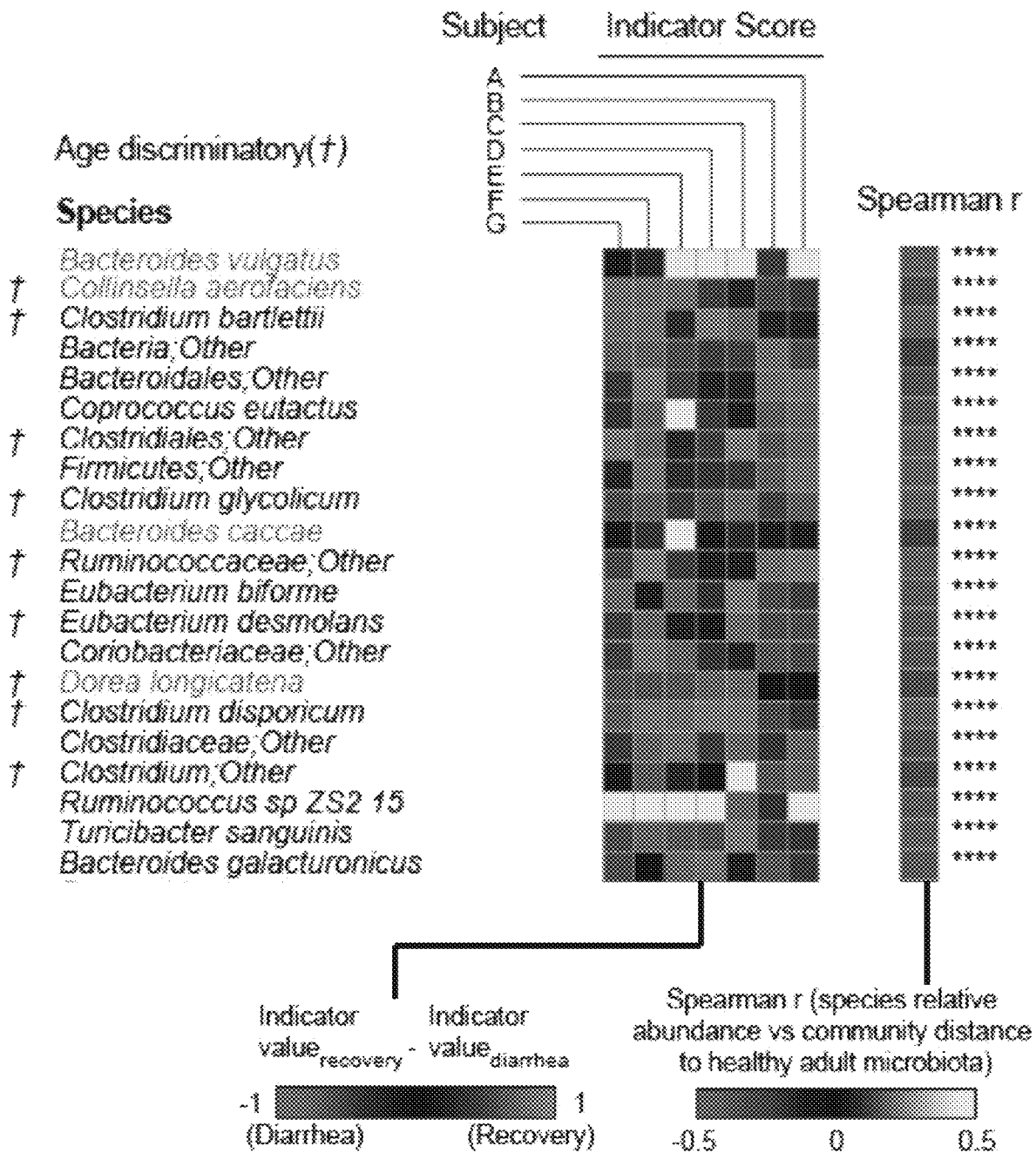
Figure 16M:
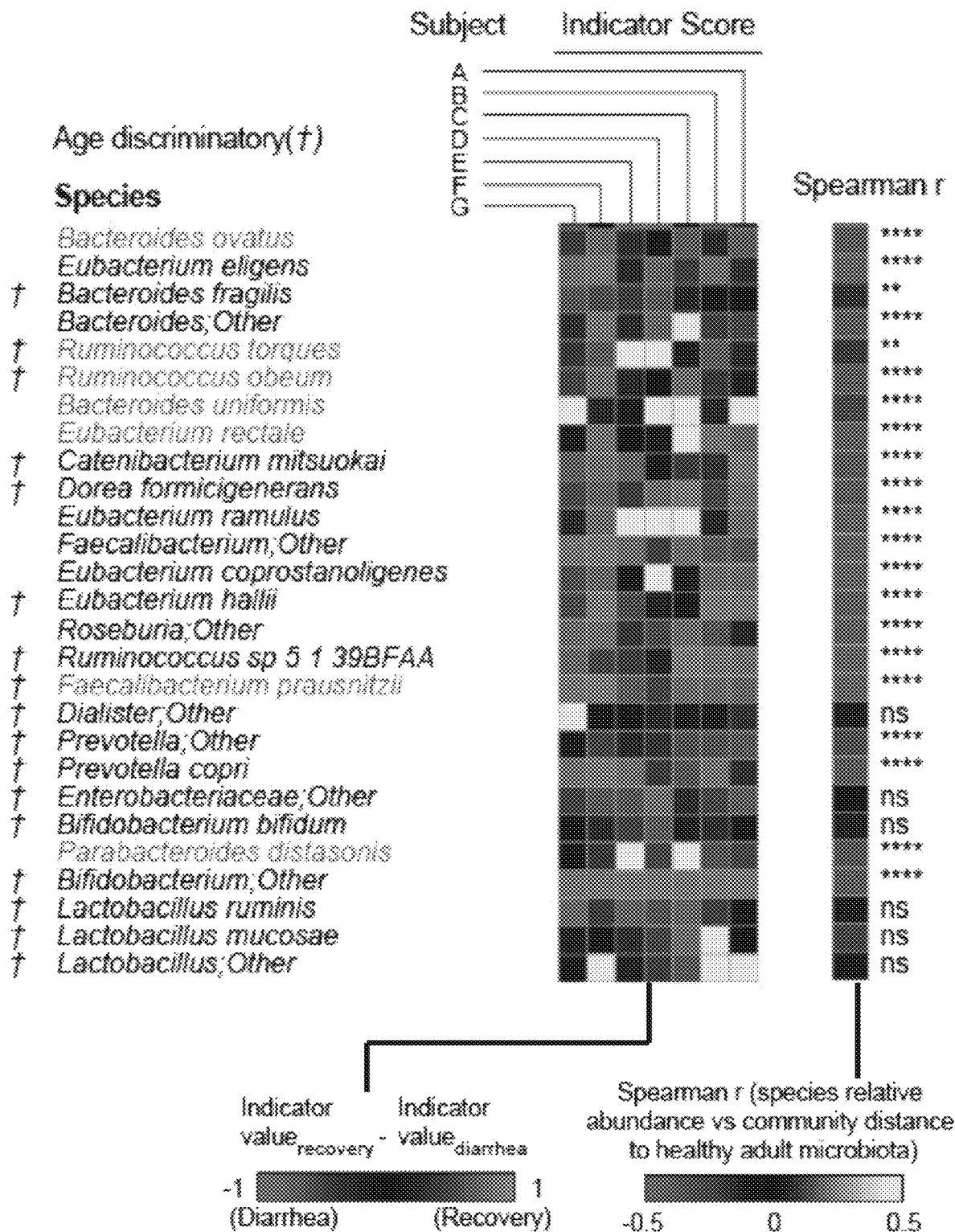
Figure 16N:
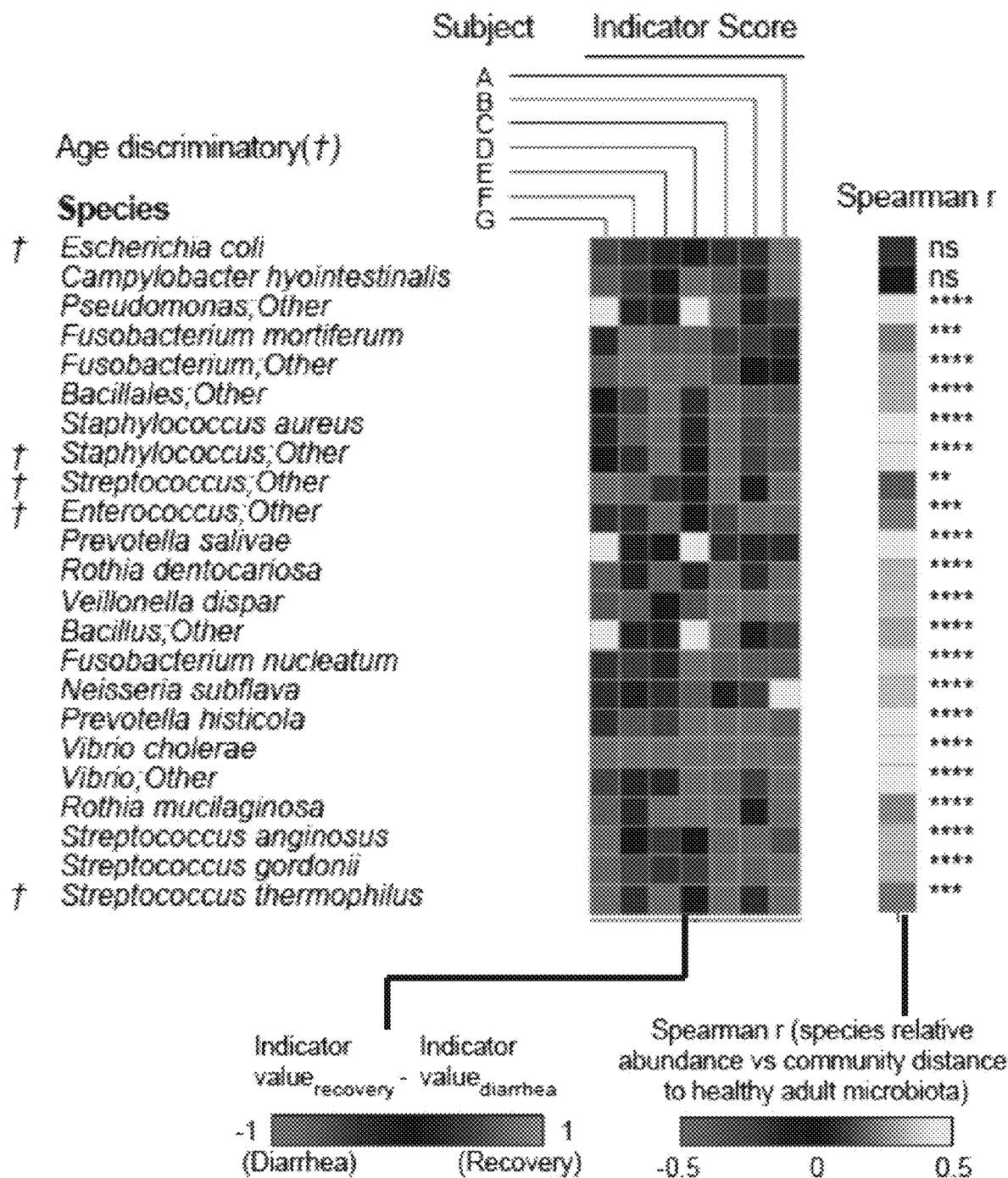
Figure 17A:
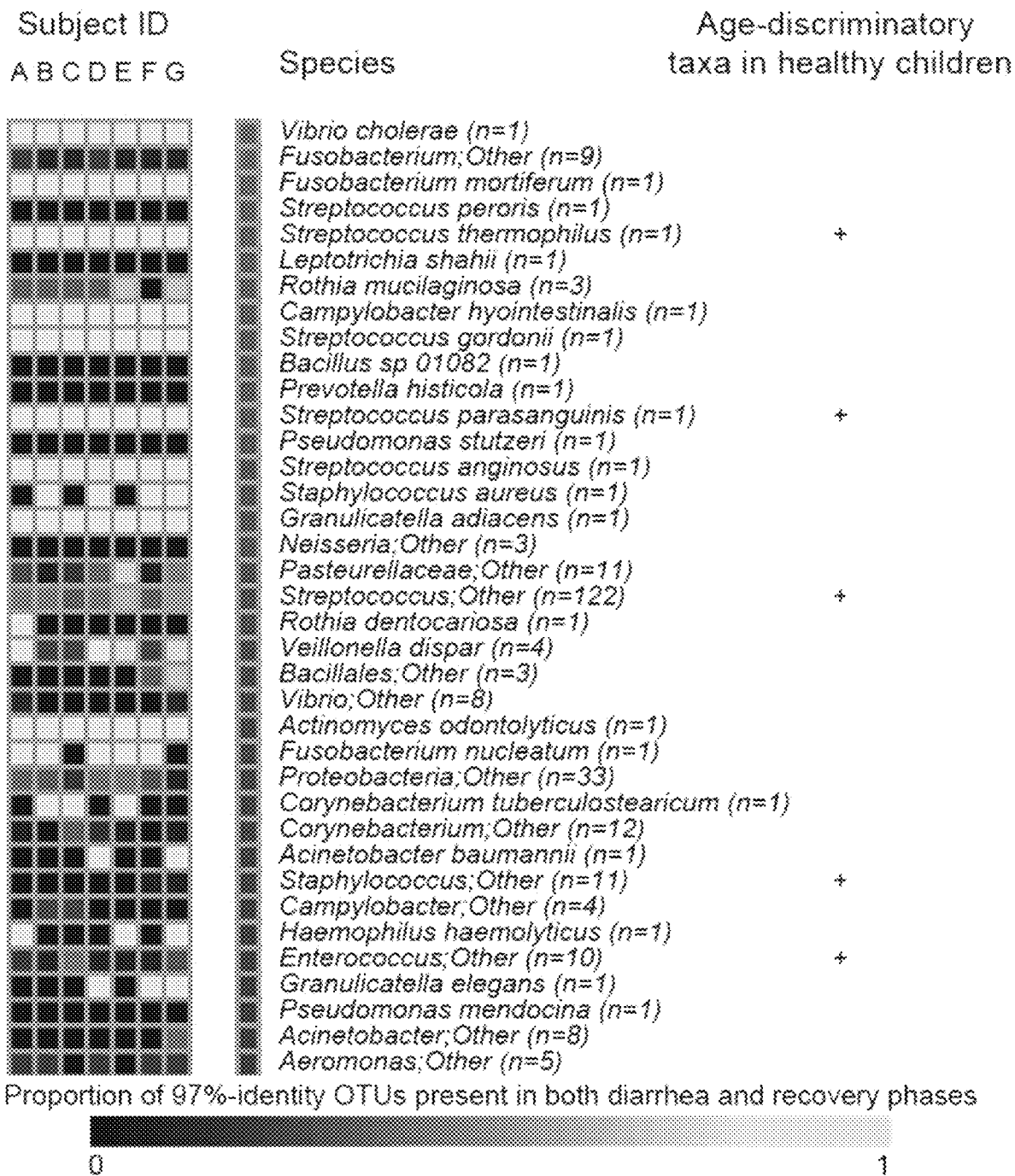
Figure 17B:
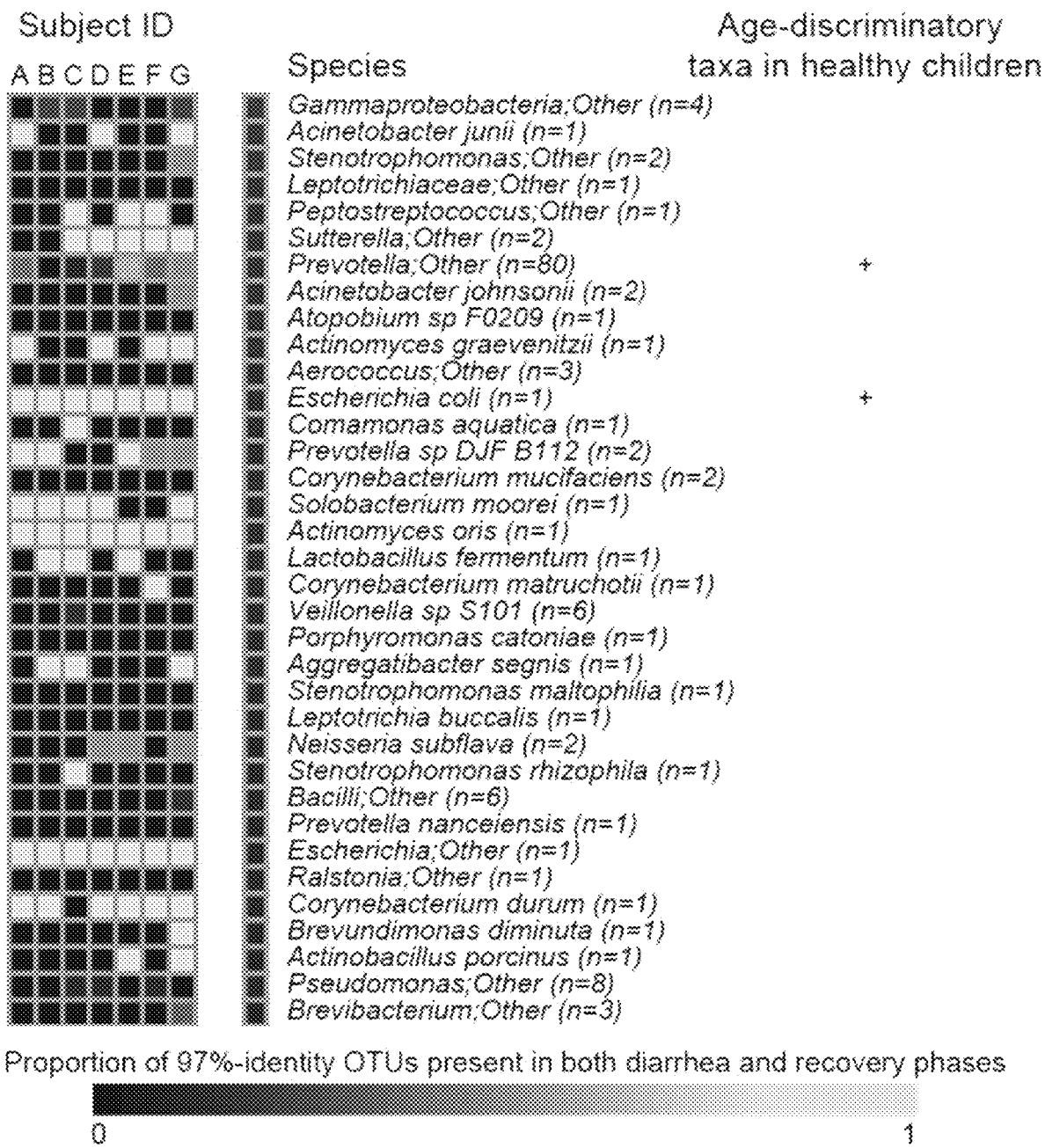
Figure 17C:
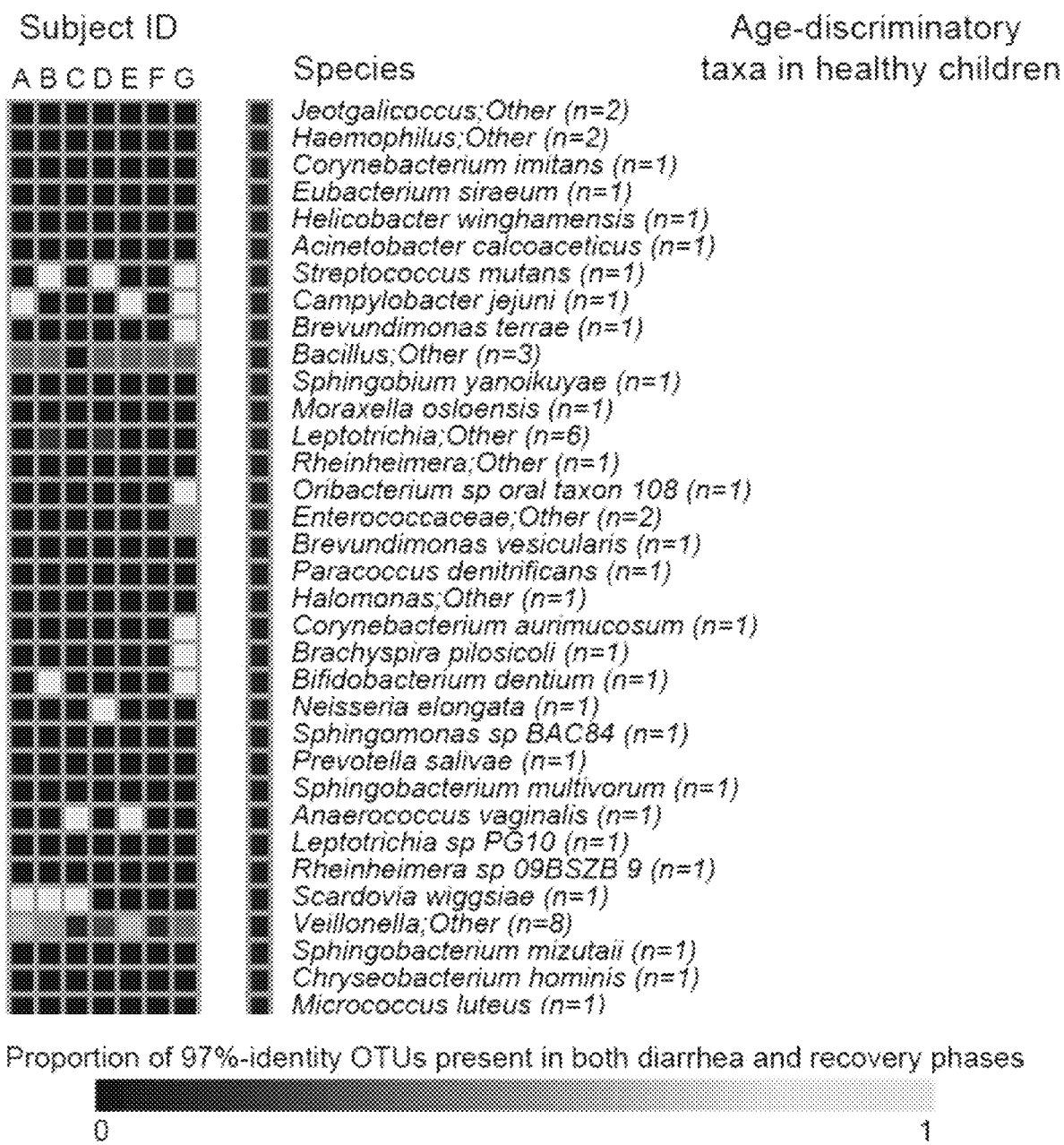
Figure 17D:
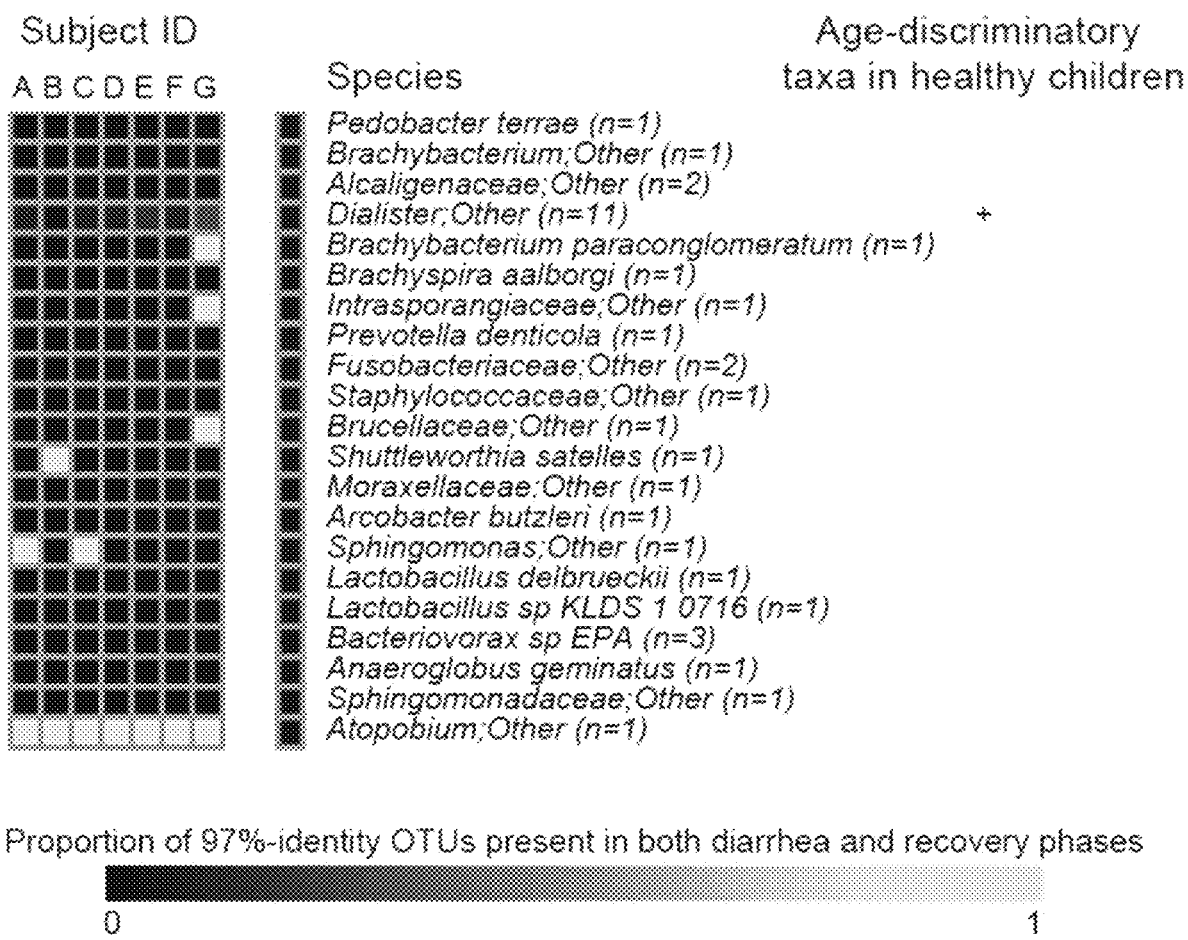
Figure 17E:
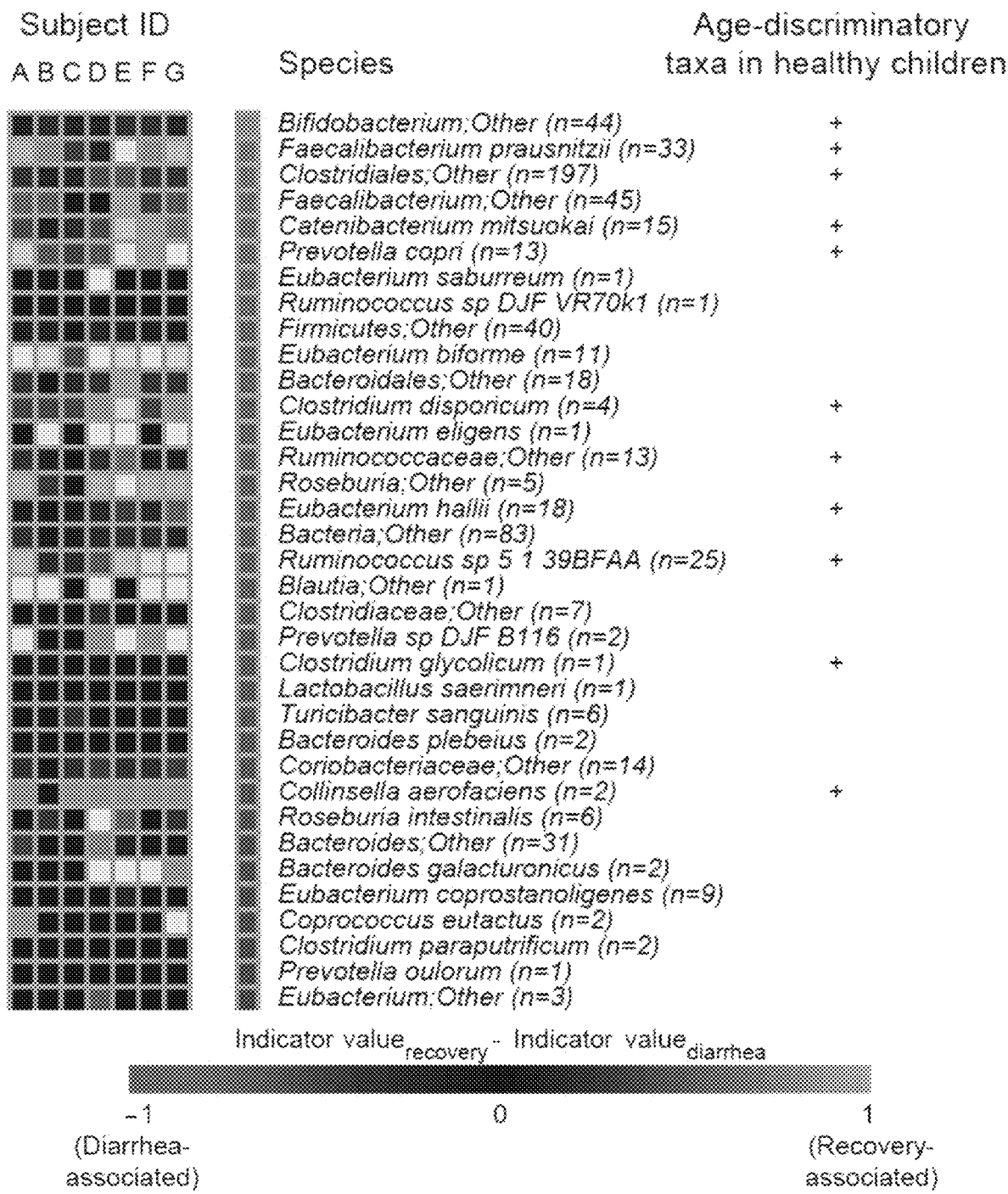
Figure 17F:
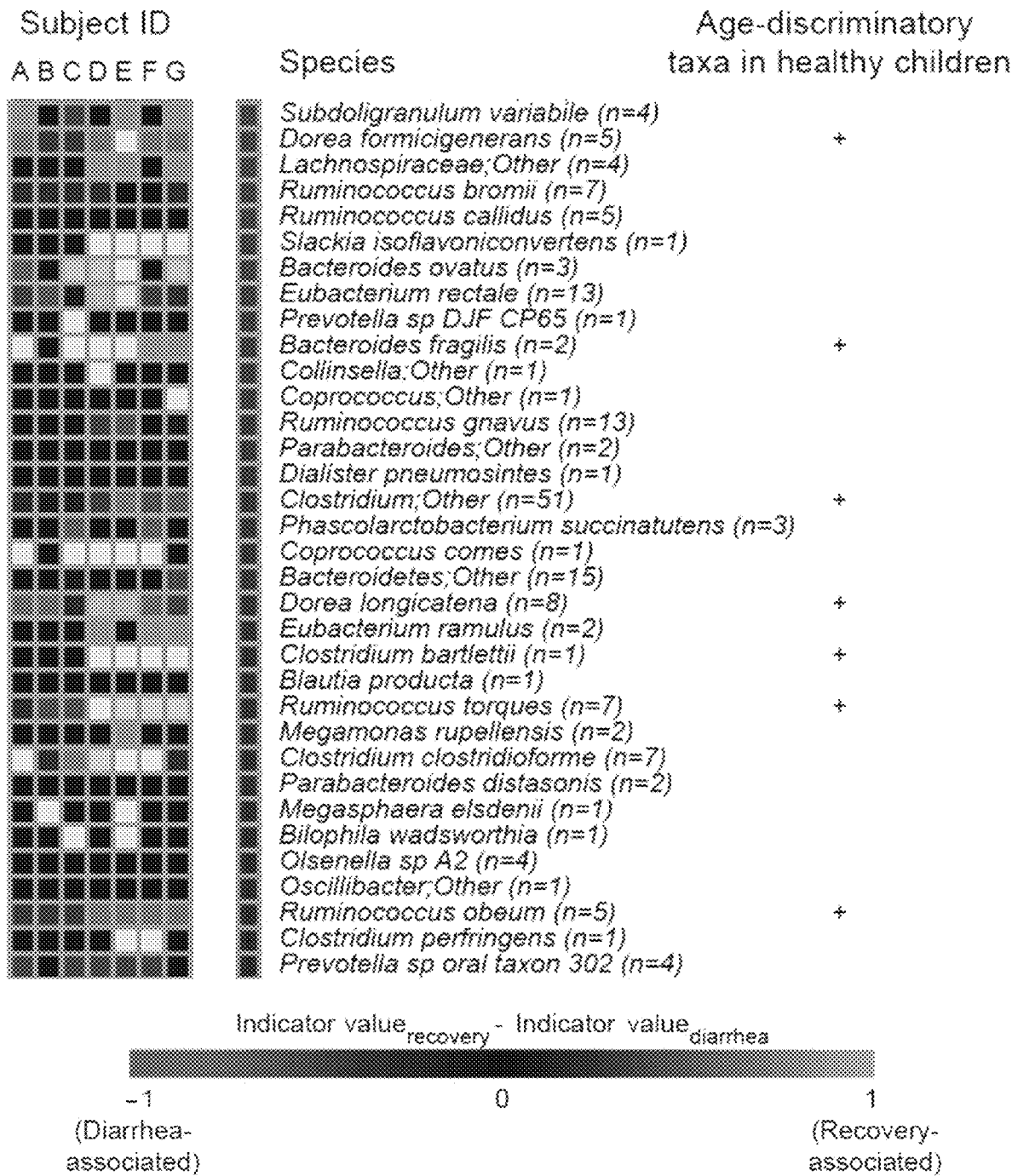
Figure 17G:
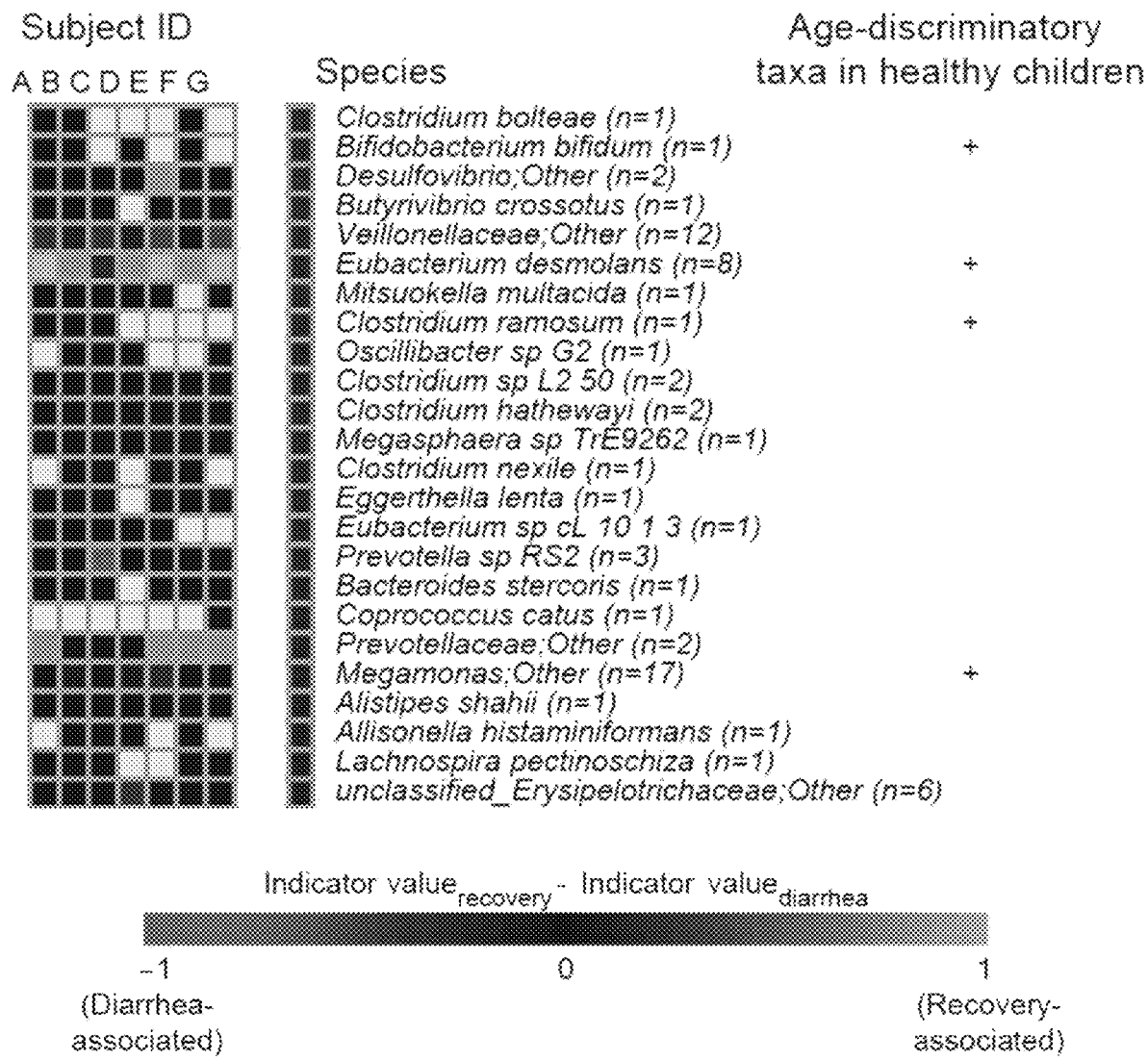
Figure 17H:
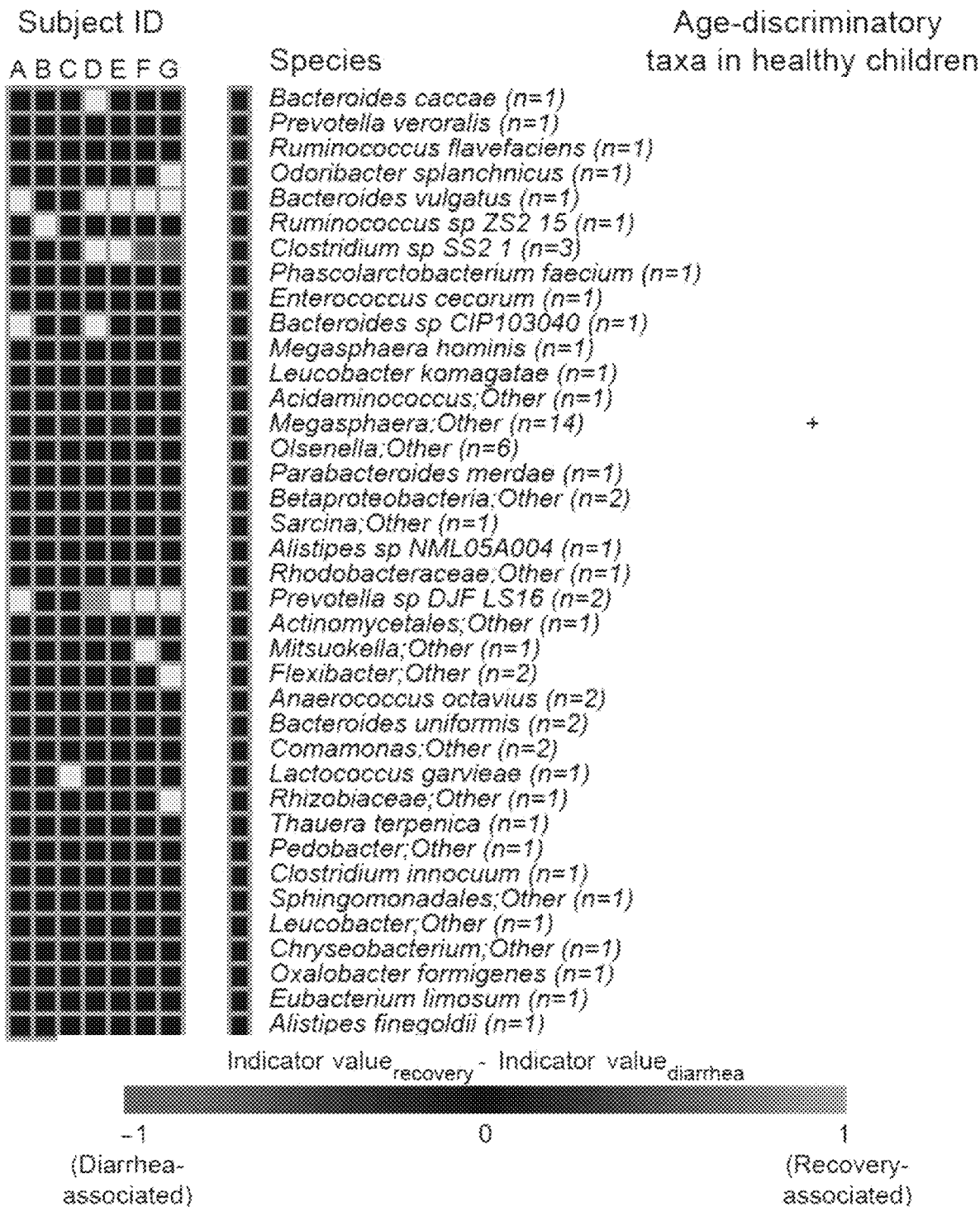

Indicator species analysis was performed on the set of 236 fecal specimens selected from the diarrheal and recovery phases of subjects A-G. The statistical significance of associations was defined using permutation tests in which permutations were constrained within subjects: a bacterial species was considered significantly associated if it had a FDR-adjusted P<0.05. This approach identified 260 bacterial species consistently associated with either the diarrheal or recovery phases. 219 of these 260 species also had a significant correlation to community UniFrac distance to healthy control microbiota (FDR-adjusted P<0.05; Tables 21, 22, FIG. 16F-N). For species with positive correlations, higher relative abundances in a given microbiota state correlated to an increased difference to healthy fecal microbiota. Interpersonal differences in the distribution of 97%-identity OTUs comprising these species were also evident (FIGS. 16E, 17).

Of the 31 age-discriminatory species-level bacterial taxa in the developing gut microbiota of healthy Bangladeshi children, 24 including R. obeum and F. prausnitzii, also had a significant Spearman rank correlation value between their relative abundance in each fecal sample and the mean weighted UniFrac distance between that sample and all healthy adult Bangladeshi microbiota (Tables 21, 22, see FIGS. 16, 17, 18) for 97%-identity OTU analysis). In addition, Spearman rank correlations revealed that (i) 23 of the 27 species had relative abundances that significantly correlated with chronologic age in healthy children and with time following onset of acute diarrhea, and (ii) the direction of change (increase or decrease) was concordant between the two datasets for all 23 species (Table 20).

Example 13

Changes in Relative Abundance of Genes Encoding ECs in Fecal Microbiomes Sampled During Diarrhea and Recovery Shotgun sequencing of DNA prepared from diarrhea and recovery phase human fecal samples, followed by binning reads into assignable KEGG Enzyme Commission numbers (ECs), revealed that genes encoding enzymes involved in carbohydrate metabolism comprised the largest category of ECs that changed in relative abundance within the fecal microbiome during the course of cholera (see FIG. 20 and Table 24 and Supplementary Table 8 of Hsiao et al, Nature 2014; Epub, which is hereby incorporated by reference in its entirety for EC-based abundance analysis, including Spearman rank correlations of EC abundance as a function of time across D-Ph1 through R-Ph3). These results led us to include Bacteroides cellulosilyticus, Bacteroides thetaiotaomicron, and Clostridium scindens in the artificial community of human gut symbionts, even though they did not satisfy the criteria described above as recovery phase-indicative or significantly correlated to normal maturation of the Bangladeshi infant microbiota.

Example 14

Genome-Wide Analysis of how V. cholerae Influences the R. obeum Transcriptome In Vivo Mice were first mono-colonized with R. obeum or V. cholerae for 7 days, followed by introduction of the other organism (FIG. 15C,D). RNA-Seq was performed using fecal samples collected from both groups of mice on the day prior to and 2 days after co-colonization (Table 28). An analysis of changes across the entire R. obeum transcriptome 2d after introduction of V. cholerae revealed few (n=7) functionally annotated transcripts with significant differences in expression (P<0.05 after multiple-hypothesis testing in DESee; see Table 26c). LuxS serves a dual role: production of the precursor AI-2 molecule [(S)-4,5-dihydroxyl-2,3-pentanedione] and participation in the pathway that re-generates homocysteine for use in the activated methyl cycle; in the absence of luxS, homocysteine is produced via oxaloacetate involving aspartate and glutamate as intermediates[41,42] Consistent with this, three R. obeum genes encoding ECs involved in glutamate biosynthesis were significantly down-regulated after introduction of V. cholerae.

Example 15

Genome-Wide Analysis of how R. obeum Influences the V. cholerae Transcriptome In Vivo R. obeum increased the expression of several V. cholerae genes whose functions could impact its colonization, including five that encode products involved in iron acquisition and transport [VCO365 (bacterioferritin), VCO364 (bacterioferritin-associated ferredoxin), VC0608 (iron(III) transporter), VC0750 (hesB family protein)] plus five genes thought to be involved in cell wall modification (VCO246, VCO247, VCO245, VCO259, VCO249 in Table 26b; modifications in V. cholerae LPS have been reported to be important in colonization of mice[17]). Cholera toxin gene (ctxA, ctxB) expression was below the limits of reliable detection in each of the V. cholerae treatment groups, consistent with previous reports that it is not required for colonization of adult mice[11-12].

Example 16

Bile Acids and Regulation of Virulence Genes

V. cholerae senses host signals, including bile acids, in order to coordinately up-regulate expression of colonization factor genes[13,43-47] and down-regulate expression of anti-colonization factors such as the mannose-sensitive hemagglutinin pilus[48]. The gut microbiota could, in principle, affect colonization by modulating levels of host-derived signals that impact V. cholerae, or the microbiota could produce signaling molecules that directly modulate V. cholerae pathogenesis. To explore these possibilities, we used ultra-performance liquid chromatography-mass spectroscopy (UPLC-MS) to characterize the representation of bile acid species in fecal samples collected from mice colonized with the 14-member community and this community minus

*R. obeum*, (n=5-6 animals/group). We detected 10 bile acid species, and expressed each of their levels as a proportion of the aggregate levels of all 10 bile acids. Comparing fecal samples collected from mice after colonization with the 14- and 13-member communities, we found that the presence or absence of *R. obeum* did not have a statistically significant effect on levels of the primary bile acids taurocholic acid, tauro-beta-muricholic acid, and beta-muricholic acid that together comprise >80% of the measured pool (P>0.05, unpaired Mann-Whitney U test). One primary bile acid, alpha muricholic acid, and a secondary bile acid, urosodeoxycholic acid, were affected, but in aggregate they represent minor constituents (<11%) of the measured pool (FIG. 22). While we could not rule out that the effect of *R. obeum* on these minor bile acid species impacts *V. cholerae* colonization/virulence, given the observed lack of change in the predominant bile acid species, we turned our attention to classes of microbial factors known to affect virulence (see Example 10).

Example 17

Figure 21G:
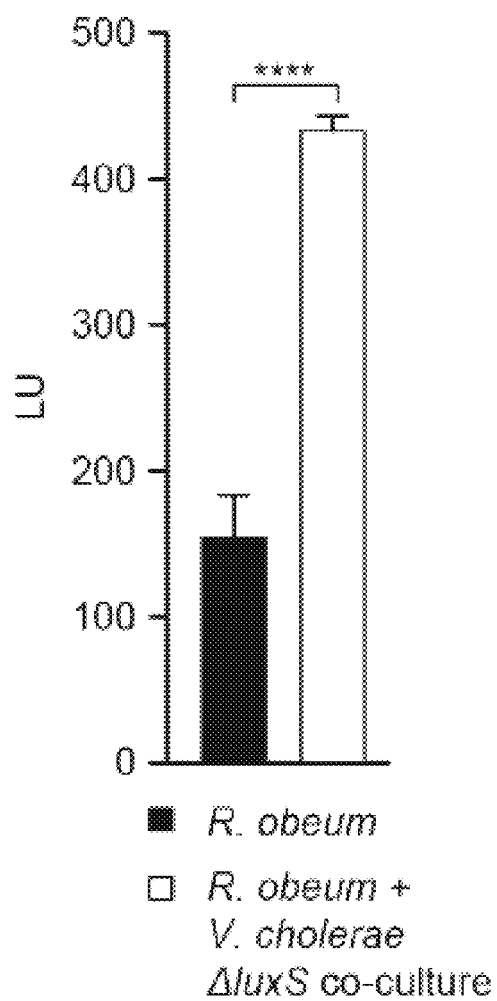

*R. obeum* Al-2 Production is Stimulated by *V. cholerae* In Vitro and in Co-Colonized Animals In mice initially mono-colonized with *R. obeum* for 7d, *R. obeum* luxS expression increased more than 2-fold 2d following introduction of *V. cholerae* (P<0.01, unpaired Mann-Whitney U test; FIG. 21E). Using the BB170 Al-2 assay[24], we measured fecal Al-2 levels from mice mono-colonized with *R. obeum* or co-colonized with *R. obeum* and ΔluxS *V. cholerae* (MM883)[14], and confirmed that Al-2 levels were modestly but significantly higher in the co-colonized group (FIG. 21F). When these bacteria were co-cultured in vitro under anaerobic conditions, *R. obeum* Al-2 signal increased significantly [2.8±0.1-fold (mean±SEM), P<0.01, unpaired Mann-Whitney; FIG. 21G]. Furthermore, we induced expression of cloned *R. obeum* and *V. cholerae* luxS genes using an arabinose-inducible PBAD promoter in an Al-2-deficient *E. coli* strain (DH5a)[25] and observed that supernatants from these strains were able to induce increased BB170 bioluminescence over vector controls [7.2±1.1 and 8.8±2.4-fold (mean±SEM), respectively].

Methods for Examples 10-17

Human Studies

Subject recruitment. Protocols for recruitment, enrollment, and consent, procedures for sampling the faecal microbiota of healthy Bangladeshi adults and children, and the faecal microbiota of adults during and after cholera infection, plus the subsequent de-identification of these samples, were approved by the Human Studies Committees of the International Centre for Diarrhoeal Disease Research, Bangladesh, and Washington University School of Medicine in St. Louis.

Enrollment into the adult cholera study was based on the following criteria: residency in the Dhaka Municipal Corporation area, a positive stool test for *V. cholerae* as judged by dark-field microscopy, diarrhoea for no more than 24 h before enrollment, and a permanent address that allowed follow-up faecal sampling after discharge from Dhaka Hospital (International Centre for Diarrhoeal Disease Research, Bangladesh). Non-prescription antibiotic usage is prevalent in Bangladesh[28,29]. Since a history of previous antibiotic consumption could be a confounder when interpreting the effects of cholera on the gut microbiota, we excluded individuals if they had received antibiotics in the 7 days preceding admission to the hospital. Since this was an observational study with no experimental treatment arm, blinding for study inclusion was not necessary. See Table 18 for the number of individuals screened for inclusion in the study, the number of potential subjects excluded from the study and the reasons for their exclusion, and the number of subjects enrolled who satisfied all criteria for inclusion.

The healthy adults were fathers in a cohort of healthy twins, triplets, and their parents living in Mirpur that is described in ref. 3. Fathers were sampled every 3 months during the first 2 years of their offspring's postnatal life. Histories of diarrhoea and antibiotic use were not available for these fathers. However, histories of diarrhoea and antibiotic use in their healthy children were known: 46 of the 49 paternal faecal samples used were obtained during periods when none of their children had diarrhoea; 36 of these 49 samples were collected at a time when there had been no antibiotic use by their children in the preceding 7 days.

DNA extraction from human faecal samples, sequencing, and analysis. All diarrhoeal stools were collected from each participant (one sterilized bowl per sample), frozen immediately at −80° C., then subjected to the same bead beating and phenol chloroform extraction procedure for DNA purification that was applied to the formed frozen faecal samples collected from these individuals during the recovery phases (and previously to a wide range of samples collected from individuals representing different ages, cultural traditions, geographical locations, and physiological and disease states[3,30]).

DNA was isolated from all frozen faecal samples from D-Ph1 to D-Ph4, from the period of frequent sampling during the first week following discharge (recovery phase 1; R-Ph1), the period of less frequent sampling during weeks 2-3 (R-Ph2), and from weeks 4 to 12 of recovery (R-Ph3) (n=1,053 samples in total). For analyses involving healthy adult and child control groups, samples were excluded from our analysis where antibiotic use or diarrhoea was known to have occurred in the 7 days before sample collection.

For each participant in the cholera study, we selected one sample with high DNA yield (≥2 μg) from each 2-hour period during D-Ph1 to D-Ph3. An additional 7±2 samples (mean±s.d.) that had been collected during the approximately 5-h period before the rate of diarrhoea began to decrease at the beginning of D-Ph3 were included. All faecal samples collected after this time point (that is, from the remainder of D-Ph3 to R-Ph3), were also included in our analysis (n=19.7±7.4 total samples (mean±s.d.) per individual in the diarrhoeal phase, and 14±3.3 total samples per individual in the recovery phase). Two patients (C and E) were chosen for additional sequencing of all their diarrhoeal samples (n=100 and 50, respectively; see Supplementary Table 3b of Hsiao et al, *Nature* 2014; Epub, which is hereby incorporated by reference in its entirety).

The V4 region of bacterial 16S rRNA genes represented in each selected faecal microbiota sample was amplified by PCR using primers containing sample-specific barcode identifiers. Amplicons were purified, pooled, and paired-end sequenced with an Illumina MiSeq instrument (250 nucleotide paired-end reads; 86,315±2,043 (mean±s.e.m.) assembled reads per sample; see Supplementary Table 3 of Hsiao et al, *Nature* 2014; Epub, which is hereby incorporated by reference in its entirety). Healthy control samples were analysed using the same sequencing platform and chemistry (n=293 total samples).

Sequences were assembled, then de-multiplexed and analysed using the QIIME software package[31] and custom Perl scripts. For analysis of diarrhoeal and recovery phase samples, rarefaction was performed to 49,000 reads per sample. For analyses including samples from healthy adults and children, samples were rarefied to 7,900 reads per sample. Reads sharing 97% nucleotide sequence identity were grouped into operational taxonomic units (97%-identity OTUs). To ensure that we retained less abundant bacterial taxa in our analysis of the faecal samples of patients with cholera, a 97%-identity OTU was called 'distinct and reliable' if it appeared at 0.1% relative abundance in at least one faecal sample. Taxonomic assignments of OTUs to species level were made using the Ribosomal Database Project version 2.4 classifier[32] and a manually curated Greengenes database[33].

Indicator species analysis[4] was used to classify bacterial species as highly associated with either diarrhoeal phases or recovery. This approach is used in studies of macroecosystems to identify species that associate with different environmental groupings; it assigns for each species an indicator value that is a product of two components: (1) the species' specificity, which is the probability that a sample in which the species is found came from a given group; and (2) the species' fidelity, which is the proportion of samples from a given group that contains the species. We performed indicator species analysis in the set of 236 faecal specimens, selected from the seven patients according to the subsampling scheme described above, to identify bacterial species consistently associated with the diarrhoeal or recovery phases across members of the study group; statistical significance was defined using permutation tests in which permutations were constrained within subjects. We also conducted a separate indicator species analysis for each subject, using each individual's replicate diarrhoeal and recovery phase samples as the groupings.

For analyses of variation across communities, we used UniFrac[5], a metric that measures the overall degree of phylogenetic similarity of any two communities based on the degree to which they share branch length on a bacterial tree of life; low pairwise UniFrac distance values indicate that communities are more similar to one another. Unifrac distances were calculated using the QIIME software package[31].

The gut microbiomes of study participants were characterized by paired-end 2×250 nucleotide shotgun sequencing of faecal DNA using an Illumina MiSeq instrument (mean 216,698 reads per sample; Supplementary Table 3 of Hsiao et al, Nature 2014; Epub, which is hereby incorporated by reference in its entirety). Paired sequences were assembled into single reads using the SHERA software package[34], and annotated by mapping to version 58 of the Kyoto Encyclopedia of Genes and Genomes (KEGG) database[35] using UBLAST[36].

Gnotobiotic Mouse Experiments.

All experiments involving animals used protocols approved by the Washington University Animal Studies Committee. Germ-free male C57BL/6J mice were maintained in flexible plastic film gnotobiotic isolators and fed an autoclaved, low-fat, plant polysaccharide-rich mouse chow (B&K, catalogue number 7378000, Zeigler Bros) ad libitum. Mice were 5-8 weeks old at time of gavage. The number of mice used in each experiment is reported in the text, relevant figure legends, and summarized in FIG. 15.

Bacterial strains and plasmids. Table 23 lists the sequenced human gut-derived bacterial strains used to generate the artificial communities and their sources. Since all Bangladeshi faecal samples were devoted to DNA extraction, we were unable to utilize strains that originated from culture collections generated from study participants' faecal biospecimens. Thus, the strains incorporated into the artificial community were from public repositories, represented multiple individuals, and were typically not accompanied by information about donor health status or living conditions.

A $P_{tcp}$-lux reporter strain was constructed by introducing $P_{tcp}$-lux (pJZ376) into V. cholerae C6706 via conjugation from SM10λpir. $P_{BAD}$-luxS expression vectors were produced by first amplifying the luxS sequences of V. cholerae C6706 and R. obeum ATCC2917 using PCR and the primers described in Table 29. Amplicons were then cloned into pBAD202 (TOPO TA Expression Kit; Life Technologies), and introduced into E. coli DH5a by electroporation.

All cultures of V. cholerae C6706, the isogenic ΔluxS mutant (MM883), and E. coli strains containing luxS expression vectors were grown aerobically in Luria Broth (LB) medium with appropriate antibiotics (Table 29). All members of the 14-member artificial human gut microbiota, including R. obeum ATCC29174, were propagated anaerobically in MegaMedium[37].

Colonization of gnotobiotic mice. All animal experiments involved administration of known consortia of bacterial species; as such, no blinding to group allocation was performed. The order of administration of microbial species to given groups of recipient mice was intentionally varied, as described in FIG. 15C-H.

Mono-colonized animals received either 200 μl of overnight cultures of R. obeum strain ATCC29174 or V. cholerae strain C6706. All V. cholerae colonization studies in mice used the current pandemic El Tor biotype (strain C6706). Mice receiving the defined 13- or 14-member communities of sequenced human bacterial symbionts were gavaged with 200 μl of an equivalent mixture of bacteria assembled from overnight monocultures of each strain ($D_{600\ nm}$≈0.4 per strain; grown in MegaMedium). In the case of mice that received mixtures of V. cholerae and E. coli strains with R. obeum luxS-expressing plasmids (or vector controls), the E. coli strains were first grown overnight in LB medium containing 50 μg ml$^{-1}$ kanamycin. Two millilitres of the culture were removed and cell pellets were obtained by centrifugation, washed three times with 2 ml LB medium to remove antibiotics, and re-suspended in 6 ml LB medium containing 0.1% arabinose. The suspension of E. coli cells was then incubated at 37° C. for 90 min, and mixed with V. cholerae C6706 such that each mouse was gavaged with ~50 μl and ~2.5 μl of overnight cultures of each organism, respectively. All gavages involving V. cholerae were preceded by a gavage of 100 μl sterile 1 M sodium bicarbonate to neutralize gastric pH. Colonization levels of V. cholerae were determined by serial dilution plating of faecal homogenates on selective medium.

Competitive index assays were performed with mice gavaged with 50 μl aliquots of cultures of mutant and wild-type V. cholerae C6706 strains that had been grown to $D_{600\ nm}$=0.3. For experiments involving competitive index calculations as a function of the presence of R. obeum, 100 μl of an overnight R. obeum culture was co-inoculated with the mixture of V. cholerae strains. Faecal samples from recipient gnotobiotic mice were subjected to dilution plating and aerobic growth on LB agar with the LacZ substrate Xgal; blue-white screening was used to determine colonization levels of the individual V. cholerae strains.

Community profiling by shotgun sequencing (COPROseq). Shotgun sequencing of faecal community DNA was used to define the relative abundance of species in the artificial communities; experimental and computational tools for COPRO-seq have been described previously[8].

Microbial RNA-seq analysis of faecal samples collected from mice colonized with the 14-member artificial community with and without *V. cholerae*. Faecal samples were collected from colonized gnotobiotic mice and immediately snap-frozen in liquid nitrogen. RNA was extracted using bead-beating in phenol/chloroform/isoamyl alcohol followed by further purification using MEGAClear (Life Technologies). Purified RNA was depleted of 16S rRNA, 5S rRNA, and transfer RNA as previously described[8] or by using a RiboZero kit (Epicentre). Complementary DNA (cDNA) libraries were generated and sequenced (50 nucleotide unidirectional reads; Illumina GA-llx, HiSeq 2000 or MiSeq instruments; see Supplementary Table 3 of Hsiao et al, Nature 2014; Epub, which is hereby incorporated by reference in its entirety). Reads were mapped to the genomes of members of the artificial community using Bowtie[38].

To profile transcriptional responses to *V. cholerae*, all cDNA reads that mapped to the genomes of the 14 consortium members were binned based on enzyme classification level annotations from KEGG. ShotgunFunctionalizeR[39] was then used compare the faecal meta-transcriptomes of 'D14invasion' animals sampled 4 days after gavage of the 14-member community to the faecal meta-transcriptomes of D1 invasion mice sampled 4 days after gavage of the 14-member community plus *V. cholerae*. A mean twofold or greater difference in expression between the conditions, with an adjusted P value less than 0.0001 (ShotgunFunctionalizeR) was considered significant. This approach of binning to enzyme classifications mitigates issues with low-abundance transcripts being insufficiently profiled owing to limitations in sequencing depth[8].

Owing to the higher sequencing depth achieved for *R. obeum* and *V. cholerae* in mono- and co-colonization experiments, reads were mapped to reference genomes using Bowtie, and changes at the single transcript level were analysed using DESeq[40] (Table 27). Transcripts that satisfied the criteria of (1) having greater than twofold differential expression after DESeq normalization, (2) an adjusted P value less than 0.05, and (3) a minimum mean count value more than 10 were retained.

AI-2 assays. Previously frozen faecal pellets from gnotobiotic mice were re-suspended in AB medium[24] by agitation with a rotary bead-beater (25 mg faecal pellet per millilitre of medium). AI-2 assays were performed using the *V. harveyi* BB170 bioassay strain[24], with reported results representative of at least two independent experiments, each with five technical repeats. *V. harveyi* BB170 cultures were grown aerobically overnight in AB medium, and diluted 1:500 in this medium for use in the AI-2 bioassay[24]. Luminescence was measured using a BioTek Synergy 2 instrument after 4 h of growth at 30° C. with agitation (300 r.p.m. using a rotatory incubator).

For in vitro measurements of *R. obeum* AI-2 production, a 100 µl aliquot from an overnight monoculture of the bacterium grown in MegaMedium without glucose was diluted 1:20 in fresh MegaMedium without glucose. In addition, cells pelleted from 100 µl of an overnight culture of *V. cholerae* ΔluxS (MM883 (ref. 14)) grown in LB medium were added to *R. obeum* that had also been diluted 1:20 in MegaMedium without glucose. The resulting mono- and co-cultures were incubated anaerobically at 37° C. for 16 h. Cells were pelleted by centrifugation, and supernatants were harvested and then added to *V. harveyi* BB170 cultures for AI-2 bioassay.

UPLC-MS. Procedures for UPLC-MS of bile acids have been described in ref. 37.

REFERENCES FOR EXAMPLES 10-17

1. World Health Organization Cholera, 2013. *Wkly Epidemiol. Rec.* 89, 345-356 (2014).
2. Chowdhury, F. et al. Impact of rapid urbanization on the rates of infection by *Vibrio cholerae* O1 and enterotoxigenic *Escherichia coli* in Dhaka, Bangladesh. *PLoS Negl Trop. Dis.* 5, e999 (2011).
3. Subramanian, S. et al. Persistent gut microbiota immaturity in malnourished Bangladeshi children. *Nature* 510, 417-421 (2014).
4. Dufrene, M. & Legendre, P. Species assemblages and indicator species: the need for a flexible asymmetrical approach. *Ecol. Monogr.* 67, 345-366 (1997).
5. Lozupone, C. & Knight, R. UniFrac: a new phylogenetic method for comparing microbial communities. *Appl. Environ. Microbiol.* 71, 8228-8235 (2005).
6. Martens, E. C. et al. Recognition and degradation of plant cell wall polysaccharides by two human gut symbionts. *PLoS Biol.* 9, e1001221 (2011).
7. McNulty, N. P. et al. Effects of diet on resource utilization by a model human gut microbiota containing *Bacteroides cellulosilyticus* WH2, a symbiont with an extensive glycobiome. *PLoS Biol.* 11, e1001637 (2013).
8. McNulty, N. P. et al. The impact of a consortium of fermented milk strains on the gut microbiome of gnotobiotic mice and monozygotic twins. *Sci. Translat. Med.* 3, 106ra106 (2011).
9. Taylor, R. K., Miller, V. L., Furlong, D. B.& Mekalanos, J. J. UseofphoAgenefusionsto identify a pilus colonization factor coordinately regulated with cholera toxin. *Proc. Natl Acad. Sci. USA* 84, 2833-2837 (1987).
10. Herrington, D. A. et al. Toxin, toxin-coregulated pili, and the toxR regulon are essential for *Vibrio cholerae* pathogenesis in humans. *J. Exp. Med.* 168, 1487-1492 (1988).
11. Olivier, V., Salzman, N. H. & Satchell, K. J. Prolonged colonization of mice by *Vibrio cholerae* El Tor O1 depends on accessory toxins. *Infect. Immun.* 75, 5043-5051 (2007).
12. Olivier, V., Haines, G. K., Ill, Tan, Y. & Satchell, K. J. Hemolysin and the multifunctional autoprocessing RTX toxin are virulence factors during intestinal infection of mice with *Vibrio cholerae* El Tor O1 strains. *Infect. Immun.* 75, 5035-5042 (2007).
13. Yang, M. et al. Bile salt-induced intermolecular disulfide bond formation activates *Vibrio cholerae* virulence. *Proc. Natl Acad. Sci. USA* 110, 2348-2353 (2013).
14. Miller, M. B., Skorupski, K., Lenz, D. H., Taylor, R. K. & Bassler, B. L. Parallel quorum sensing systems converge to regulate virulence in *Vibrio cholerae*. *Cell* 110, 303-314 (2002).
15. Zhu, J. et al. Quorum-sensing regulators control virulence gene expression in *Vibrio cholerae*. *Proc. Natl Acad. Sci. USA* 99, 3129-3134 (2002).
16. Kovacikova, G. & Skorupski, K. Regulation of virulence gene expression in *Vibrio cholerae* by quorum sensing: HapRfunctions atthe aphA promoter. *Mol. Microbiol.* 46, 1135-1147 (2002).
17. Higgins, D. A. et al. The major *Vibrio cholerae* autoinducer and its role in virulence factor production. *Nature* 450, 883-886 (2007).
18. Pereira, C. S., Thompson, J. A. & Xavier, K. B. AI-2-mediated signalling in bacteria. *FEMS Microbiol. Rev.* 37, 156-181 (2013).

19. Sun, J., Daniel, R., Wagner-Dobler, I. & Zeng, A. P. Isautoinducer-2 a universal signal for interspecies communication: a comparative genomic and phylogenetic analysis of the synthesis and signal transduction pathways. *BMC Evol. Biol.* 4, 36 (2004).
20. Duan, F. & March, J. C. Engineered bacterial communication prevents *Vibrio cholerae* virulence in an infant mouse model. *Proc. Natl Acad. Sci. USA* 107, 11260-11264 (2010).
21. Liu, Z. et al. Mucosal penetration primes *Vibrio cholerae* for host colonization by repressing quorum sensing. *Proc. Natl Acad. Sci. USA* 105, 9769-9774 (2008).
22. Liu, Z., Stirling, F. R. & Zhu, J. Temporal quorum-sensing induction regulates *Vibrio cholerae* biofilm architecture. *Infect. Immun.* 75, 122-126 (2007).
23. Taga, M. E., Semmelhack, J. L. & Bassler, B. L. The LuxS-dependent autoinducer AI-2 controls the expression of an ABC transporter that functions in AI-2 uptake in *Salmonella typhimurium*. *Mol. Microbiol.* 42, 777-793 (2001).
24. Bassler, B. L., Wright, M. & Silverman, M. R. Multiple signalling systems controlling expression of luminescence in *Vibrio harveyi*: sequence and function of genes encoding a second sensory pathway. *Mol. Microbiol.* 13, 273-286 (1994).
25. Surette, M. G., Miller, M. B. & Bassler, B. L. Quorum sensing in *Escherichia coli, Salmonella typhimurium*, and *Vibrio harveyi*: a new family of genes responsible for autoinducer production. *Proc. Natl Acad. Sci. USA* 96, 1639-1644 (1999).
26. Iwanaga, M. et al. Culture conditions for stimulating cholera toxin production by *Vibrio cholerae* 01 El Tor. *MicrobioL ImmunoL* 30, 1075-1083 (1986).
27. Liu, Z., Hsiao, A., Joelsson, A. & Zhu, J. Thetranscriptional regulator VqmAincreases expression of the quorum-sensing activator HapR in *Vibrio cholerae*. *J. Bacteriol.* 188, 2446-2453 (2006).
28. Faiz, M. A. & Basher, A. Antimicrobial resistance: Bangladesh experience. *Reg. Health Forum* 15, 1-18 (2011).
29. Morgan, D. J., Okeke, I. N., Laxminarayan, R., Perencevich, E. N. & Weisenberg, S. Non-prescription antimicrobial use worldwide: a systematic review. *Lancet Infect. Dis.* 11, 692-701 (2011).
30. Yatsunenko, T. et al. Human gut microbiome viewed across age and geography. *Nature* 486, 222-227 (2012).
31. Caporaso, J. G. et al. QIIME allows analysis of high-throughput community sequencing data. *Nature Methods* 7, 335-336 (2010).
32. Cole, J. R. et al. The ribosomal database project(RDP-II): introducingmyRDPspace and quality controlled public data. *Nucleic Acids Res.* 35, D169-D172 (2007).
33. DeSantis, T. Z. et al. Greengenes, a chimera-checked 16S rRNA gene database and workbench compatible with ARB. *Appl. Environ. Microbiol.* 72, 5069-5072 (2006).
34. Rodrigue, S. et al. Unlocking short read sequencing for metagenomics. *PLoS ONE* 5, e11840 (2010).
35. Kanehisa, M. & Goto, S. KEGG: Kyoto Encyclopedia of Genes and Genomes. *Nucleic Acids Res.* 28, 27-30 (2000).
36. Edgar, R. C. Search and clustering orders of magnitude faster than BLAST. *Bioinformatics* 26, 2460-2461 (2010).
37. Ridaura, V. K. et al. Gut microbiota from twins discordant for obesity modulate metabolism in mice. *Science* 341, 1241214 (2013).
38. Langmead, B., Trapnell, C., Pop, M. & Salzberg, S. L. Ultrafastand memory-efficient alignment of short DNA sequences to the human genome. *Genome Biol.* 10, R25 (2009).
39. Kristiansson, E., Hugenholtz, P. & Dalevi, D. Shotgun-FunctionalizeR: an R-package for functional comparison of metagenomes. *Bioinformatics* 25, 2737-2738 (2009).
40. Anders, S. & Huber, W. Differential expression analysis for sequence count data. *Genome Biol.* 11, R106 (2010).
41. Schauder, S., Shokat, K., Surette, M. G. & Bassler, B. L. The LuxS family of bacterial autoinducers: biosynthesis of a novel quorum-sensing signal molecule. *Mol. Microbiol.* 41, 463476 (2001).
42. Walters, M., Sircili, M. P. & Sperandio, V. AI-3 synthesis is not dependent on luxS in *Escherichia coli*. *J. Bacteriol.* 188, 5668-5681, doi:10.1128/JB.00648-06 (2006). doi: 10.1007/s12223-008-0030-1 (2008).
43. Miller, V. L., Di Rita, V. J. & Mekalanos, J. J. Identification of toxS, a regulatory gene whose product enhances toxR-mediated activation of the cholera toxin promoter. *J. Bacteriol.* 171, 1288-1293 (1989).
44. Higgins, D. E., Nazareno, E. & Di Rita, V. J. The virulence gene activator ToxT from *Vibrio cholerae* is a member of the AraC family of transcriptional activators. *J. Bacteriol.* 174, 6974-6980 (1992).
45. Di Rita, V. J. Co-ordinate expression of virulence genes by ToxR in *Vibrio cholerae*. *Mol. Microbiol.* 6, 451-458 (1992).
46. Higgins, D. E. & Di Rita, V. J. Transcriptional control of toxT, a regulatory gene in the ToxR regulon of *Vibrio cholerae*. *Mol. Microbiol.* 14, 17-29 (1994).
47. Lee, S. H., Hava, D. L., Waldor, M. K. & Camilli, A. Regulation and temporal expression patterns of *Vibrio cholerae* virulence genes during infection. *Cell* 99, 625-634 (1999).
48. Hsiao, A., Liu, Z., Joelsson, A. & Zhu, J. *Vibrio cholerae* virulence regulator-coordinated evasion of host immunity. *Proc. Natl. Acad. Sci. USA* 103, 14542-14547, doi: 10.1073/pnas.0604650103 (2006).
49. Larkin M. A. et al. Clustal W and Clustal X version 2.0. *Bioinformatics* 21, 2947-2948, doi:10.1093/bioinformatics/btm404 (2007).
50. Eckburg, P. B. et al. Diversity of the human intestinal microbial flora. *Science* 308, 1635-1638, doi:10.1126/science.1110591 (2005).

TABLE 1

Metadata for 50 healthy Bangladeshi children sampled monthly during the first two years of life.

| Child ID | Family ID | Birth Cohort | Gender | Zygosity | WHZ | WAZ | HAZ |
|---|---|---|---|---|---|---|---|
| Bgsng7035 | Bgsng7035 | Healthy Singleton Birth Cohort | Male | NA | $-0.5 \pm 0.5$ | $-1.7 \pm 0.2$ | $-1.7 \pm 0.2$ |
| Bgsng7106 | Bgsng7106 | Healthy Singleton Birth Cohort | Male | NA | $-0.4 \pm 0.6$ | $-0.9 \pm 0.9$ | $-0.9 \pm 0.9$ |
| Bgsng7115 | Bgsng7115 | Healthy Singleton Birth Cohort | Male | NA | $-1.6 \pm 0.5$ | $0.2 \pm 0.4$ | $0.2 \pm 0.4$ |
| Bgsng7128 | Bgsng7128 | Healthy Singleton Birth Cohort | Female | NA | $-1.4 \pm 0.7$ | $-1.3 \pm 0.6$ | $-1.3 \pm 0.6$ |
| Bgsng7150 | Bgsng7150 | Healthy Singleton Birth Cohort | Male | NA | $0.0 \pm 1.2$ | $0.0 \pm 0.8$ | $0.0 \pm 0.8$ |
| Bgsng7155 | Bgsng7155 | Healthy Singleton Birth Cohort | Female | NA | $-1.5 \pm 1.3$ | $-1.0 \pm 1.3$ | $-1.0 \pm 1.3$ |

TABLE 1-continued

Metadata for 50 healthy Bangladeshi children sampled monthly during the first two years of life.

| | | | | | | | |
|---|---|---|---|---|---|---|---|
| Bgsng7177 | Bgsng7177 | Healthy Singleton Birth Cohort | Female | NA | 0.9 ± 0.6 | −0.9 ± 1.0 | −0.9 ± 1.0 |
| Bgsng7192 | Bgsng7192 | Healthy Singleton Birth Cohort | Female | NA | 0.0 ± 0.8 | −1.6 ± 0.7 | −1.6 ± 0.7 |
| Bgsng7202 | Bgsng7202 | Healthy Singleton Birth Cohort | Female | NA | −0.4 ± 1.8 | 0.1 ± 0.6 | 0.1 ± 0.6 |
| Bgsng7204 | Bgsng7204 | Healthy Singleton Birth Cohort | Male | NA | −0.7 ± 1.7 | −0.1 ± 0.6 | −0.1 ± 0.6 |
| Bgsng8064 | Bgsng8064 | Healthy Singleton Birth Cohort | Male | NA | 0.9 ± 0.7 | 1.7 ± 0.7 | 1.7 ± 0.7 |
| Bgsng8169 | Bgsng8169 | Healthy Singleton Birth Cohort | Male | NA | 0.9 ± 1.5 | 1.1 ± 0.5 | 1.1 ± 0.5 |
| Bgsng7018 | Bgsng7018 | Healthy Singleton Birth Cohort | Male | NA | −0.7 ± 0.7 | −0.4 ± 0.9 | −0.4 ± 0.9 |
| Bgsng7052 | Bgsng7052 | Healthy Singleton Birth Cohort | Male | NA | 0.0 ± 1.1 | −0.3 ± 1.2 | −0.3 ± 1.2 |
| Bgsng7063 | Bgsng7063 | Healthy Singleton Birth Cohort | Male | NA | −0.4 ± 0.7 | 0.0 ± 0.9 | 0.0 ± 0.9 |
| Bgsng7071 | Bgsng7071 | Healthy Singleton Birth Cohort | Male | NA | 0.5 ± 0.8 | 0.6 ± 0.7 | 0.6 ± 0.7 |
| Bgsng7082 | Bgsng7082 | Healthy Singleton Birth Cohort | Female | NA | −0.9 ± 1.4 | −0.8 ± 0.7 | −0.8 ± 0.7 |
| Bgsng7090 | Bgsng7090 | Healthy Singleton Birth Cohort | Male | NA | −0.4 ± 0.5 | −0.3 ± 0.7 | −0.3 ± 0.7 |
| Bgsng7096 | Bgsng7096 | Healthy Singleton Birth Cohort | Female | NA | −0.5 ± 0.4 | −1.1 ± 0.6 | −1.1 ± 0.6 |
| Bgsng7114 | Bgsng7114 | Healthy Singleton Birth Cohort | Male | NA | −0.9 ± 0.3 | −0.7 ± 0.2 | −0.7 ± 0.2 |
| Bgsng7131 | Bgsng7131 | Healthy Singleton Birth Cohort | Male | NA | −0.9 ± 0.5 | −1.3 ± 0.8 | −1.3 ± 0.8 |
| Bgsng7142 | Bgsng7142 | Healthy Singleton Birth Cohort | Male | NA | −0.7 ± 1.5 | −0.8 ± 1.5 | −0.8 ± 1.5 |
| Bgsng7149 | Bgsng7149 | Healthy Singleton Birth Cohort | Female | NA | −1.0 ± 0.4 | −0.3 ± 0.4 | −0.3 ± 0.4 |
| Bgsng7173 | Bgsng7173 | Healthy Singleton Birth Cohort | Male | NA | −0.5 ± 0.5 | −1.2 ± 0.6 | −1.2 ± 0.6 |
| Bgsng7178 | Bgsng7178 | Healthy Singleton Birth Cohort | Female | NA | 0.6 ± 1.4 | −0.9 ± 0.6 | −0.9 ± 0.6 |
| Bgtw1.T1 | Bgtw1 | Healthy Twins & Triplets | Female | MZ | −0.5 ± 0.7 | −2.3 ± 0.5 | −3.1 ± 0.7 |
| Bgtw1.T2 | Bgtw1 | Healthy Twins & Triplets | Female | MZ | −1.3 ± 0.8 | −3.0 ± 0.3 | −3.4 ± 0.7 |
| Bgtw2.T1 | Bgtw2 | Healthy Twins & Triplets | Male | DZ | −1.2 ± 0.8 | −3.8 ± 0.9 | −4.7 ± 0.7 |
| Bgtw2.T2 | Bgtw2 | Healthy Twins & Triplets | Female | DZ | −0.8 ± 1.0 | −3.3 ± 0.9 | −4.2 ± 0.4 |
| Bgtw3.T1 | Bgtw3 | Healthy Twins & Triplets | Male | MZ | −0.6 ± 0.4 | −1.4 ± 0.5 | −1.6 ± 0.3 |
| Bgtw3.T2 | Bgtw3 | Healthy Twins & Triplets | Male | MZ | −0.6 ± 0.5 | −1.8 ± 0.6 | −2.1 ± 0.6 |
| Bgtw4.T1 | Bgtw4 | Healthy Twins & Triplets | Female | MZ co-twin in set of triplets | −0.2 ± 0.8 | −2.4 ± 0.6 | −3.4 ± 0.5 |
| Bgtw4.T2 | Bgtw4 | Healthy Twins & Triplets | Female | MZ co-twin in set of triplets | −0.1 ± 0.8 | −2.2 ± 0.9 | −3.4 ± 0.6 |
| Bgtw4.T3 | Bgtw4 | Healthy Twins & Triplets | Female | Fraternal co-twin in set of triplets | −1.7 ± 0.9 | −2.9 ± 0.7 | −2.6 ± 0.6 |
| Bgtw5.T1 | Bgtw5 | Healthy Twins & Triplets | Male | DZ | −0.5 ± 0.8 | −3.1 ± 0.9 | −4.3 ± 0.8 |
| Bgtw5.T2 | Bgtw5 | Healthy Twins & Triplets | Female | DZ | −0.1 ± 0.5 | −2.5 ± 0.4 | −4.0 ± 0.5 |
| Bgtw6.T1 | Bgtw6 | Healthy Twins & Triplets | Male | DZ | −0.2 ± 0.6 | −1.5 ± 1.8 | −1.6 ± 1.7 |
| Bgtw6.T2 | Bgtw6 | Healthy Twins & Triplets | Male | DZ | −0.6 ± 0.6 | −2.5 ± 1.2 | −2.6 ± 1.7 |
| Bgtw7.T1 | Bgtw7 | Healthy Twins & Triplets | Female | DZ | 0.5 ± 1.7 | −2.3 ± 0.5 | −3.8 ± 0.4 |
| Bgtw7.T2 | Bgtw7 | Healthy Twins & Triplets | Female | DZ | 0.5 ± 1.7 | −2.8 ± 0.8 | −4.3 ± 0.2 |
| Bgtw8.T1 | Bgtw8 | Healthy Twins & Triplets | Female | DZ | −0.9 ± 0.7 | −1.6 ± 0.3 | −1.4 ± 0.4 |
| Bgtw8.T2 | Bgtw8 | Healthy Twins & Triplets | Female | DZ | −1.4 ± 0.8 | −2.6 ± 0.5 | −2.3 ± 0.6 |
| Bgtw9.T1 | Bgtw9 | Healthy Twins & Triplets | Female | MZ | 0.1 ± 1.2 | −3.1 ± 0.5 | −4.0 ± 0.7 |
| Bgtw9.T2 | Bgtw9 | Healthy Twins & Triplets | Female | MZ | 0.8 ± 1.2 | −2.6 ± 0.6 | −4.0 ± 0.9 |
| Bgtw10.T1 | Bgtw10 | Healthy Twins & Triplets | Female | MZ | −1.5 ± 0.8 | −2.7 ± 0.5 | −2.4 ± 0.4 |
| Bgtw10.T2 | Bgtw10 | Healthy Twins & Triplets | Female | MZ | −1.0 ± 1.1 | −2.8 ± 0.3 | −2.8 ± 0.5 |
| Bgtw11.T1 | Bgtw11 | Healthy Twins & Triplets | Female | not tested | −0.2 ± 0.3 | −2.9 ± 0.4 | −3.7 ± 0.4 |
| Bgtw11.T2 | Bgtw11 | Healthy Twins & Triplets | Female | not tested | −0.7 ± 0.9 | −2.6 ± 0.4 | −2.9 ± 0.3 |
| Bgtw12.T1 | Bgtw12 | Healthy Twins & Triplets | Male | DZ | 1.2 ± 1.3 | −2.3 ± 1.1 | −4.4 ± 1.2 |
| Bgtw12.T2 | Bgtw12 | Healthy Twins & Triplets | Female | DZ | −0.6 ± 2.0 | −2.9 ± 1.2 | −3.6 ± 0.9 |

| Child ID | Age at first fecal sample collection (days) | Age at last fecal sample collection (days) | Number of fecal samples collected | Sampling interval (days) mean ± SD | Months of exclusive breast-feeding | Age at first introduction of solid food (months) | Number of diarrhoeal episodes/yr | % Days with diarrhoea during sampling period | Fraction of samples collected where antibiotics had been consumed within prior 7 days | Training-Validation Set Subject Allocation |
|---|---|---|---|---|---|---|---|---|---|---|
| Bgsng7035 | 5 | 701 | 23 | 32 ± 11 | 0.0 | 1.2 | 3.6 | 1.9 | 0.2 | Training |
| Bgsng7106 | 9 | 738 | 19 | 41 ± 19 | 4.4 | 9.4 | 4.0 | 3.9 | 0.1 | Training |
| Bgsng7115 | 5 | 706 | 21 | 35 ± 19 | 0.9 | 6.2 | 5.2 | 5.9 | 0.1 | Training |
| Bgsng7128 | 4 | 735 | 23 | 33 ± 12 | 3.3 | 9.8 | 4.5 | 5.0 | 0.1 | Training |
| Bgsng7150 | 5 | 701 | 22 | 33 ± 14 | 5.9 | 8.2 | 2.1 | 3.0 | 0.4 | Training |
| Bgsng7155 | 5 | 701 | 24 | 30 ± 5 | 1.2 | 4.3 | 1.6 | 1.6 | 0.3 | Training |
| Bgsng7177 | 8 | 700 | 23 | 31 ± 6 | 6.4 | 7.3 | 3.7 | 4.3 | 0.2 | Training |
| Bgsng7192 | 4 | 704 | 24 | 30 ± 8 | 5.4 | 6.3 | 5.2 | 4.4 | 0.4 | Training |
| Bgsng7202 | 6 | 714 | 23 | 32 ± 11 | 5.4 | 6.2 | 3.1 | 3.1 | 0.1 | Training |
| Bgsng7204 | 5 | 708 | 24 | 31 ± 10 | 0.2 | 4.5 | 8.8 | 7.2 | 0.4 | Training |
| Bgsng8064 | 6 | 700 | 24 | 30 ± 4 | 3.0 | 6.0 | 3.1 | 3.6 | 0.1 | Training |
| Bgsng8169 | 6 | 737 | 22 | 35 ± 18 | 3.0 | 5.6 | 3.0 | 2.3 | 0.0 | Training |
| Bgsng7018 | 3 | 710 | 21 | 35 ± 24 | 7.3 | 9.6 | 4.6 | 3.5 | 0.3 | Validation |
| Bgsng7052 | 7 | 715 | 20 | 37 ± 22 | 6.6 | 7.3 | 4.1 | 4.8 | 0.1 | Validation |
| Bgsng7063 | 5 | 700 | 20 | 37 ± 17 | 0.2 | 9.2 | 2.1 | 1.6 | 0.0 | Validation |
| Bgsng7071 | 4 | 704 | 18 | 41 ± 11 | 6.3 | 8.4 | 8.8 | 8.0 | 0.3 | Validation |
| Bgsng7082 | 5 | 724 | 18 | 42 ± 28 | 4.4 | 5.8 | 3.5 | 3.0 | 0.3 | Validation |
| Bgsng7090 | 5 | 703 | 23 | 32 ± 12 | 3.4 | 4.7 | 7.3 | 5.1 | 0.4 | Validation |
| Bgsng7096 | 15 | 706 | 23 | 31 ± 10 | 3.2 | 7.2 | 2.6 | 2.7 | 0.2 | Validation |
| Bgsng7114 | 4 | 702 | 18 | 41 ± 18 | 3.1 | 4.3 | 0.5 | 0.1 | 0.0 | Validation |

TABLE 1-continued

Metadata for 50 healthy Bangladeshi children sampled monthly during the first two years of life.

| | | | | | | | | | |
|---|---|---|---|---|---|---|---|---|---|
| Bgsng7131 | 10 | 717 | 23 | 32 ± 10 | 2.2 | 3.1 | 4.1 | 4.3 | 0.3 | Validation |
| Bgsng7142 | 12 | 728 | 22 | 34 ± 13 | 0.4 | 4.6 | 3.0 | 4.1 | 0.3 | Validation |
| Bgsng7149 | 5 | 704 | 22 | 33 ± 11 | 3.4 | 9.4 | 6.2 | 3.7 | 0.2 | Validation |
| Bgsng7173 | 8 | 702 | 24 | 30 ± 9 | 1.6 | 4.0 | 7.8 | 10.8 | 0.5 | Validation |
| Bgsng7178 | 8 | 700 | 24 | 30 ± 6 | 5.3 | 6.3 | 4.7 | 4.3 | 0.3 | Validation |
| Bgtw1.T1 | 35 | 730 | 26 | 28 ± 7 | 0.0 | 4.1 | 2.0 | 2.7 | 0.4 | Validation - Twins & Triplets |
| Bgtw1.T2 | 34 | 729 | 24 | 30 ± 9 | 0.0 | 4.1 | 2.0 | 2.7 | 0.3 | Validation - Twins & Triplets |
| Bgtw2.T1 | 31 | 701 | 25 | 28 ± 8 | 1.0 | 3.1 | 0.5 | 0.7 | 0.1 | Validation - Twins & Triplets |
| Bgtw2.T2 | 31 | 701 | 25 | 28 ± 7 | 2.0 | 7.9 | 1.0 | 1.0 | 0.1 | Validation - Twins & Triplets |
| Bgtw3.T1 | 8 | 638 | 24 | 27 ± 12 | 0.0 | 7.1 | 2.9 | 5.0 | 0.0 | Validation - Twins & Triplets |
| Bgtw3.T2 | 8 | 639 | 26 | 25 ± 12 | 0.0 | 7.9 | 1.7 | 4.7 | 0.1 | Validation - Twins & Triplets |
| Bgtw4.T1 | 1 | 575 | 21 | 29 ± 10 | 0.0 | 9.1 | 1.3 | 0.3 | 0.1 | Validation - Twins & Triplets |
| Bgtw4.T2 | 1 | 581 | 19 | 32 ± 7 | 0.0 | 8.9 | 1.9 | 0.7 | 0.1 | Validation - Twins & Triplets |
| Bgtw4.T3 | 7 | 575 | 22 | 27 ± 9 | 0.0 | 8.9 | 3.8 | 3.8 | 0.1 | Validation - Twins & Triplets |
| Bgtw5.T1 | 31 | 638 | 21 | 30 ± 3 | 1.0 | 8.0 | 0.6 | 0.2 | 0.0 | Validation - Twins & Triplets |
| Bgtw5.T2 | 4 | 638 | 21 | 32 ± 7 | 0.1 | 7.0 | 1.7 | 1.1 | 0.0 | Validation - Twins & Triplets |
| Bgtw6.T1 | 6 | 286 | 9 | 35 ± 25 | 0.2 | 7.9 | 1.3 | 1.7 | 0.1 | Validation - Twins & Triplets |
| Bgtw6.T2 | 6 | 286 | 10 | 35 ± 11 | 0.2 | 9.4 | 0.0 | 0.3 | 0.1 | Validation - Twins & Triplets |
| Bgtw7.T1 | 14 | 455 | 18 | 26 ± 8 | 0.0 | 9.0 | 0.8 | 0.4 | 0.2 | Validation - Twins & Triplets |
| Bgtw7.T2 | 12 | 455 | 18 | 26 ± 7 | 0.4 | 9.1 | 3.2 | 2.0 | 0.2 | Validation - Twins & Triplets |
| Bgtw8.T1 | 15 | 364 | 14 | 27 ± 8 | 1.0 | 6.1 | 1.0 | 1.9 | 0.2 | Validation - Twins & Triplets |
| Bgtw8.T2 | 15 | 366 | 13 | 29 ± 5 | 1.0 | 6.1 | 0.0 | 0.0 | 0.5 | Validation - Twins & Triplets |
| Bgtw9.T1 | 37 | 368 | 12 | 30 ± 3 | 2.1 | 6.9 | 3.0 | 1.4 | 0.3 | Validation - Twins & Triplets |
| Bgtw9.T2 | 8 | 368 | 14 | 28 ± 7 | 2.3 | 6.9 | 2.0 | 2.2 | 0.1 | Validation - Twins & Triplets |
| Bgtw10.T1 | 4 | 366 | 17 | 23 ± 10 | 1.0 | 6.9 | 5.0 | 9.6 | 0.1 | Validation - Twins & Triplets |
| Bgtw10.T2 | 4 | 365 | 17 | 23 ± 11 | 1.1 | 6.9 | 4.0 | 9.3 | 0.1 | Validation - Twins & Triplets |
| Bgtw11.T1 | 1 | 336 | 12 | 30 ± 5 | 0.9 | 3.9 | 0.0 | 0.0 | 0.1 | Validation - Twins & Triplets |
| Bgtw11.T2 | 5 | 368 | 13 | 30 ± 11 | 1.1 | 4.0 | 0.0 | 0.0 | 0.0 | Validation - Twins & Triplets |

TABLE 1-continued

Metadata for 50 healthy Bangladeshi children sampled monthly during the first two years of life.

| Bgtw12.T1 | 6 | 372 | 14 | 28 ± 6 | 1.0 | 8.5 | 1.0 | 1.6 | 0.4 | Validation - Twins & Triplets |
| Bgtw12.T2 | 6 | 372 | 13 | 31 ± 5 | 1.0 | 8.0 | 1.0 | 0.5 | 0.1 | Validation - Twins & Triplets |

NA, not applicable

TABLE 2

Information associated with fecal samples collected from parents in twins and triplets birth cohort

| Family ID | Person ID | Family membership | Fecal Sample ID | Age of subject at time of fecal sample collection, years | Age of subject's children at the time of subject's fecal sample collection, months | Age of subject's children at the time of subject's fecal sample collection, days | Number of high quality V4-16S rRNA sequences | 16S rRNA Sequencing Run ID |
|---|---|---|---|---|---|---|---|---|
| Bgtw1 | Bgtw1.F | Father | Bgtw1.F.m1 | 33.0 | 1 | 5 | 17,266 | TCP2 (runs 1 and 2) |
| Bgtw1 | Bgtw1.F | Father | Bgtw1.F.m4 | 33.3 | 4 | 93 | 13,599 | T12 |
| Bgtw1 | Bgtw1.F | Father | Bgtw1.F.m7 | 33.5 | 7 | 184 | 18,411 | T12 |
| Bgtw1 | Bgtw1.F | Father | Bgtw1.F.m10 | 33.8 | 10 | 274 | 18,354 | T12 |
| Bgtw1 | Bgtw1.F | Father | Bgtw1.F.m12 | 34.0 | 12 | 369 | 33,506 | T12 |
| Bgtw1 | Bgtw1.F | Father | Bgtw1.F.m16 | 34.3 | 16 | 459 | 22,406 | T12 |
| Bgtw2 | Bgtw2.F | Father | Bgtw2.F.m4 | 26.3 | 4 | 95 | 14,837 | T34 |
| Bgtw2 | Bgtw2.F | Father | Bgtw2.F.m10 | 26.5 | 10 | 276 | 9,185 | T34 |
| Bgtw3 | Bgtw3.F | Father | Bgtw3.F.m1 | 40.0 | 1 | 8 | 11,154 | T12 |
| Bgtw3 | Bgtw3.F | Father | Bgtw3.F.m4 | 40.3 | 4 | 92 | 10,854 | T34 |
| Bgtw3 | Bgtw3.F | Father | Bgtw3.F.m7 | 40.5 | 7 | 179 | 34,147 | T78 |
| Bgtw3 | Bgtw3.F | Father | Bgtw3.F.m10 | 40.8 | 10 | 274 | 15,316 | TCP2 (runs 1 and 2) |
| Bgtw3 | Bgtw3.F | Father | Bgtw3.F.m13 | 41.0 | 13 | 367 | 22,178 | T12 |
| Bgtw3 | Bgtw3.F | Father | Bgtw3.F.m16 | 41.3 | 16 | 458 | 30,845 | TCP2 (runs 1 and 2) |
| Bgtw4 | Bgtw4.F | Father | Bgtw4.F.m1 | 23.0 | 1 | 5 | 27,558 | T12 |
| Bgtw4 | Bgtw4.F | Father | Bgtw4.F.m4 | 23.3 | 4 | 92 | 18,137 | T34 |
| Bgtw4 | Bgtw4.F | Father | Bgtw4.F.m7 | 23.5 | 7 | 187 | 18,674 | T34 |
| Bgtw4 | Bgtw4.F | Father | Bgtw4.F.m10 | 23.8 | 10 | 272 | 23,417 | T56 (runs 1 and 2) |
| Bgtw4 | Bgtw4.F | Father | Bgtw4.F.m13 | 24.0 | 13 | 365 | 23,890 | T56 (runs 1 and 2) |
| Bgtw5 | Bgtw5.F | Father | Bgtw5.F.m1 | 38.0 | 1 | 4 | 18,085 | T12 |
| Bgtw5 | Bgtw5.F | Father | Bgtw5.F.m4 | 38.3 | 4 | 94 | 25,138 | T56 (runs 1 and 2) |
| Bgtw5 | Bgtw5.F | Father | Bgtw5.F.m7 | 38.5 | 7 | 195 | 14,529 | T34 |
| Bgtw5 | Bgtw5.F | Father | Bgtw5.F.m10 | 38.8 | 10 | 274 | 15,468 | T12 |
| Bgtw5 | Bgtw5.F | Father | Bgtw5.F.m13 | 39.0 | 13 | 366 | 17,789 | T34 |
| Bgtw6 | Bgtw6.F | Father | Bgtw6.F.m1 | 29.0 | 1 | 2 | 14,873 | T34 |
| Bgtw6 | Bgtw6.F | Father | Bgtw6.F.m4 | 29.3 | 4 | 92 | 19,520 | TCP2 (runs 1 and 2) |
| Bgtw6 | Bgtw6.F | Father | Bgtw6.F.m7 | 29.5 | 7 | 181 | 16,345 | TCP2 (runs 1 and 2) |
| Bgtw6 | Bgtw6.F | Father | Bgtw6.F.m10 | 29.8 | 10 | 286 | 9,139 | T12 |
| Bgtw7 | Bgtw7.F | Father | Bgtw7.F.m1 | 38.0 | 1 | 14 | 21,791 | T34 |
| Bgtw7 | Bgtw7.F | Father | Bgtw7.F.m4 | 38.3 | 4 | 91 | 12,730 | TCP2 (runs 1 and 2) |
| Bgtw7 | Bgtw7.F | Father | Bgtw7.F.m7 | 38.5 | 7 | 190 | 13,123 | T12 |
| Bgtw8 | Bgtw8.F | Father | Bgtw8.F.m1 | 40.0 | 1 | 18 | 14,289 | TCP2 (runs 1 and 2) |
| Bgtw8 | Bgtw8.F | Father | Bgtw8.F.m4 | 40.3 | 4 | 92 | 18,075 | TCP2 (runs 1 and 2) |
| Bgtw8 | Bgtw8.F | Father | Bgtw8.F.m7 | 40.5 | 7 | 185 | 29,674 | TCP2 (runs 1 and 2) |
| Bgtw8 | Bgtw8.F | Father | Bgtw8.F.m13 | 41.0 | 13 | 374 | 29,593 | TCP2 (runs 1 and 2) |
| Bgtw9 | Bgtw9.F | Father | Bgtw9.F.m1 | 28.0 | 1 | 8 | 16,769 | T34 |
| Bgtw9 | Bgtw9.F | Father | Bgtw9.F.m4 | 28.3 | 4 | 93 | 8,311 | T12 |
| Bgtw9 | Bgtw9.F | Father | Bgtw9.F.m7 | 28.5 | 7 | 185 | 25,311 | T56 (runs 1 and 2) |
| Bgtw9 | Bgtw9.F | Father | Bgtw9.F.m10 | 28.8 | 10 | 278 | 20,809 | T56 (runs 1 and 2) |
| Bgtw9 | Bgtw9.F | Father | Bgtw9.F.m13 | 29.0 | 13 | 367 | 26,044 | T56 (runs 1 and 2) |
| Bgtw10 | Bgtw10.F | Father | Bgtw10.F.m1 | 32.0 | 1 | 2 | 20,923 | T12 |
| Bgtw10 | Bgtw10.F | Father | Bgtw10.F.m4 | 32.3 | 4 | 92 | 14,148 | T34 |
| Bgtw10 | Bgtw10.F | Father | Bgtw10.F.m7 | 32.5 | 7 | 191 | 14,161 | TCP2 (runs 1 and 2) |
| Bgtw10 | Bgtw10.F | Father | Bgtw10.F.m10 | 32.8 | 10 | 275 | 25,813 | T56 (runs 1 and 2) |
| Bgtw10 | Bgtw10.F | Father | Bgtw10.F.m13 | 33.0 | 13 | 365 | 38,175 | T56 (runs 1 and 2) |
| Bgtw11 | Bgtw11.F | Father | Bgtw11.F.m1 | 26.0 | 1 | 4 | 23,237 | TCP2 (runs 1 and 2) |
| Bgtw11 | Bgtw11.F | Father | Bgtw11.F.m4 | 26.3 | 4 | 88 | 28,777 | T56 (runs 1 and 2) |
| Bgtw12 | Bgtw12.F | Father | Bgtw12.F.m1 | 25.0 | 1 | 7 | 23,115 | TCP2 (runs 1 and 2) |
| Bgtw12 | Bgtw12.F | Father | Bgtw12.F.m4 | 25.3 | 4 | 94 | 22,396 | T56 (runs 1 and 2) |
| Bgtw1 | Bgtw1.M | Mother | Bgtw1.M.m1 | 25.0 | 1 | 5 | 12,057 | T34 |
| Bgtw1 | Bgtw1.M | Mother | Bgtw1.M.m3 | 25.2 | 3 | 64 | 15,500 | T34 |
| Bgtw1 | Bgtw1.M | Mother | Bgtw1.M.m4 | 25.3 | 4 | 92 | 22,699 | T34 |
| Bgtw1 | Bgtw1.M | Mother | Bgtw1.M.m5 | 25.3 | 5 | 124 | 14,512 | T34 |
| Bgtw1 | Bgtw1.M | Mother | Bgtw1.M.m6 | 25.5 | 6 | 167 | 15,921 | T34 |
| Bgtw1 | Bgtw1.M | Mother | Bgtw1.M.m7 | 25.5 | 7 | 188 | 19,137 | T12 |
| Bgtw1 | Bgtw1.M | Mother | Bgtw1.M.m8 | 25.6 | 8 | 216 | 37,309 | T56 (runs 1 and 2) |
| Bgtw1 | Bgtw1.M | Mother | Bgtw1.M.m9 | 25.7 | 9 | 243 | 18,428 | T34 |

TABLE 2-continued

Information associated with fecal samples collected from parents in twins and triplets birth cohort

| Family ID | Person ID | Family membership | Fecal Sample ID | Age of subject at time of fecal sample collection, years | Age of subject's children at the time of subject's fecal sample collection, months | Age of subject's children at the time of subject's fecal sample collection, days | Number of high quality V4-16S rRNA sequences | 16S rRNA Sequencing Run ID |
|---|---|---|---|---|---|---|---|---|
| Bgtw1 | Bgtw1.M | Mother | Bgtw1.M.m10 | 25.8 | 10 | 274 | 15,102 | T34 |
| Bgtw1 | Bgtw1.M | Mother | Bgtw1.M.m11 | 25.8 | 11 | 305 | 13,393 | T34 |
| Bgtw1 | Bgtw1.M | Mother | Bgtw1.M.m12 | 25.9 | 12 | 338 | 19,050 | T34 |
| Bgtw1 | Bgtw1.M | Mother | Bgtw1.M.m13 | 26.0 | 13 | 365 | 19,374 | T12 |
| Bgtw1 | Bgtw1.M | Mother | Bgtw1.M.m14 | 26.1 | 14 | 397 | 19,439 | T12 |
| Bgtw1 | Bgtw1.M | Mother | Bgtw1.M.m15 | 26.2 | 15 | 426 | 22,949 | TCP2 (runs 1 and 2) |
| Bgtw1 | Bgtw1.M | Mother | Bgtw1.M.m16 | 26.2 | 16 | 456 | 10,227 | T12 |
| Bgtw1 | Bgtw1.M | Mother | Bgtw1.M.m17 | 26.3 | 17 | 488 | 23,442 | T12 |
| Bgtw1 | Bgtw1.M | Mother | Bgtw1.M.m18 | 26.4 | 18 | 519 | 18,496 | T12 |
| Bgtw1 | Bgtw1.M | Mother | Bgtw1.M.m19 | 26.5 | 19 | 551 | 18,563 | T78 |
| Bgtw1 | Bgtw1.M | Mother | Bgtw1.M.m20 | 26.6 | 20 | 579 | 20,085 | T78 |
| Bgtw1 | Bgtw1.M | Mother | Bgtw1.M.m21 | 26.7 | 21 | 610 | 18,046 | T78 |
| Bgtw1 | Bgtw1.M | Mother | Bgtw1.M.m22 | 26.8 | 22 | 639 | 16,539 | T78 |
| Bgtw1 | Bgtw1.M | Mother | Bgtw1.M.m23 | 26.8 | 23 | 669 | 14,823 | T78 |
| Bgtw1 | Bgtw1.M | Mother | Bgtw1.M.m24 | 26.9 | 24 | 700 | 15,480 | T56 (runs 1 and 2) |
| Bgtw1 | Bgtw1.M | Mother | Bgtw1.M.m25 | 27.0 | 25 | 730 | 35,842 | T56 (runs 1 and 2) |
| Bgtw2 | Bgtw2.M | Mother | Bgtw2.M.m1 | 22.0 | 1 | 1 | 14,645 | TRX |
| Bgtw2 | Bgtw2.M | Mother | Bgtw2.M.m2 | 22.1 | 2 | 31 | 20,841 | T34 |
| Bgtw2 | Bgtw2.M | Mother | Bgtw2.M.m3 | 22.2 | 3 | 60 | 15,540 | T12 |
| Bgtw2 | Bgtw2.M | Mother | Bgtw2.M.m4 | 22.3 | 4 | 94 | 12,088 | T12 |
| Bgtw2 | Bgtw2.M | Mother | Bgtw2.M.m5 | 22.3 | 5 | 123 | 17,342 | T34 |
| Bgtw2 | Bgtw2.M | Mother | Bgtw2.M.m6 | 22.4 | 6 | 154 | 12,497 | T34 |
| Bgtw2 | Bgtw2.M | Mother | Bgtw2.M.m7 | 22.5 | 7 | 184 | 33,721 | T56 (runs 1 and 2) |
| Bgtw2 | Bgtw2.M | Mother | Bgtw2.M.m8 | 22.6 | 8 | 214 | 13,669 | T34 |
| Bgtw2 | Bgtw2.M | Mother | Bgtw2.M.m9 | 22.7 | 9 | 240 | 35,256 | T56 (runs 1 and 2) |
| Bgtw2 | Bgtw2.M | Mother | Bgtw2.M.m10 | 22.8 | 10 | 275 | 14,594 | T34 |
| Bgtw2 | Bgtw2.M | Mother | Bgtw2.M.m11 | 22.8 | 11 | 302 | 13,499 | T34 |
| Bgtw2 | Bgtw2.M | Mother | Bgtw2.M.m12 | 22.9 | 12 | 333 | 13,956 | T34 |
| Bgtw2 | Bgtw2.M | Mother | Bgtw2.M.m13 | 23.0 | 13 | 367 | 11,822 | T34 |
| Bgtw2 | Bgtw2.M | Mother | Bgtw2.M.m14 | 23.1 | 14 | 399 | 14,283 | T34 |
| Bgtw2 | Bgtw2.M | Mother | Bgtw2.M.m15 | 23.2 | 15 | 426 | 21,608 | T12 |
| Bgtw2 | Bgtw2.M | Mother | Bgtw2.M.m16 | 23.3 | 16 | 458 | 20,707 | T34 |
| Bgtw2 | Bgtw2.M | Mother | Bgtw2.M.m17 | 23.3 | 17 | 491 | 21,304 | T56 (runs 1 and 2) |
| Bgtw2 | Bgtw2.M | Mother | Bgtw2.M.m18 | 23.4 | 18 | 518 | 18,054 | TCP2 (runs 1 and 2) |
| Bgtw2 | Bgtw2.M | Mother | Bgtw2.M.m19 | 23.5 | 19 | 547 | 21,550 | T56 (runs 1 and 2) |
| Bgtw2 | Bgtw2.M | Mother | Bgtw2.M.m20 | 23.6 | 20 | 581 | 24,239 | T56 (runs 1 and 2) |
| Bgtw2 | Bgtw2.M | Mother | Bgtw2.M.m21 | 23.7 | 21 | 609 | 18,456 | T78 |
| Bgtw2 | Bgtw2.M | Mother | Bgtw2.M.m22 | 23.8 | 22 | 639 | 23,139 | T56 (runs 1 and 2) |
| Bgtw2 | Bgtw2.M | Mother | Bgtw2.M.m23 | 23.8 | 23 | 668 | 18,401 | T78 |
| Bgtw2 | Bgtw2.M | Mother | Bgtw2.M.m24 | 23.9 | 24 | 702 | 22,541 | T56 (runs 1 and 2) |
| Bgtw3 | Bgtw3.M | Mother | Bgtw3.M.m1 | 30.0 | 1 | 8 | 18,168 | T56 (runs 1 and 2) |
| Bgtw3 | Bgtw3.M | Mother | Bgtw3.M.m2 | 30.1 | 2 | 32 | 15,001 | T34 |
| Bgtw3 | Bgtw3.M | Mother | Bgtw3.M.m3 | 30.2 | 3 | 61 | 12,832 | T34 |
| Bgtw3 | Bgtw3.M | Mother | Bgtw3.M.m4 | 30.3 | 4 | 92 | 15,985 | T34 |
| Bgtw3 | Bgtw3.M | Mother | Bgtw3.M.m5 | 30.3 | 5 | 123 | 17,652 | T34 |
| Bgtw3 | Bgtw3.M | Mother | Bgtw3.M.m6 | 30.4 | 6 | 151 | 17,953 | TCP2 (runs 1 and 2) |
| Bgtw3 | Bgtw3.M | Mother | Bgtw3.M.m7 | 30.5 | 7 | 178 | 17,506 | T34 |
| Bgtw3 | Bgtw3.M | Mother | Bgtw3.M.m8 | 30.6 | 8 | 213 | 7,341 | T12 |
| Bgtw3 | Bgtw3.M | Mother | Bgtw3.M.m9 | 30.7 | 9 | 240 | 16,599 | T34 |
| Bgtw3 | Bgtw3.M | Mother | Bgtw3.M.m10 | 30.8 | 10 | 274 | 24,901 | T56 (runs 1 and 2) |
| Bgtw3 | Bgtw3.M | Mother | Bgtw3.M.m11 | 30.8 | 11 | 304 | 19,920 | T34 |
| Bgtw3 | Bgtw3.M | Mother | Bgtw3.M.m12 | 30.9 | 12 | 341 | 15,278 | TCP2 (runs 1 and 2) |
| Bgtw3 | Bgtw3.M | Mother | Bgtw3.M.m13 | 31.0 | 13 | 367 | 30,379 | TCP2 (runs 1 and 2) |
| Bgtw3 | Bgtw3.M | Mother | Bgtw3.M.m14 | 31.1 | 14 | 400 | 26,537 | TCP2 (runs 1 and 2) |
| Bgtw3 | Bgtw3.M | Mother | Bgtw3.M.m15 | 31.2 | 15 | 430 | 14,244 | T12 |
| Bgtw3 | Bgtw3.M | Mother | Bgtw3.M.m16 | 31.3 | 16 | 459 | 22,655 | T12 |
| Bgtw3 | Bgtw3.M | Mother | Bgtw3.M.m17 | 31.3 | 17 | 487 | 32,562 | T56 (runs 1 and 2) |
| Bgtw3 | Bgtw3.M | Mother | Bgtw3.M.m19 | 31.5 | 19 | 549 | 29,619 | T56 (runs 1 and 2) |
| Bgtw3 | Bgtw3.M | Mother | Bgtw3.M.m20 | 31.6 | 20 | 579 | 15,865 | TCP2 (runs 1 and 2) |
| Bgtw3 | Bgtw3.M | Mother | Bgtw3.M.m21 | 31.7 | 21 | 609 | 17,611 | TCP2 (runs 1 and 2) |
| Bgtw3 | Bgtw3.M | Mother | Bgtw3.M.m22 | 31.7 | 22 | 638 | 15,611 | TCP2 (runs 1 and 2) |
| Bgtw4 | Bgtw4.M | Mother | Bgtw4.M.m1 | 20.0 | 1 | 5 | 20,006 | T34 |
| Bgtw4 | Bgtw4.M | Mother | Bgtw4.M.m2 | 20.1 | 2 | 32 | 16,042 | T34 |
| Bgtw4 | Bgtw4.M | Mother | Bgtw4.M.m3 | 20.2 | 3 | 61 | 15,325 | T34 |
| Bgtw4 | Bgtw4.M | Mother | Bgtw4.M.m4 | 20.3 | 4 | 92 | 22,921 | T12 |
| Bgtw4 | Bgtw4.M | Mother | Bgtw4.M.m5 | 20.3 | 5 | 123 | 13,727 | T34 |
| Bgtw4 | Bgtw4.M | Mother | Bgtw4.M.m6 | 20.4 | 6 | 151 | 25,198 | T56 (runs 1 and 2) |
| Bgtw4 | Bgtw4.M | Mother | Bgtw4.M.m7 | 20.5 | 7 | 181 | 20,259 | T34 |
| Bgtw4 | Bgtw4.M | Mother | Bgtw4.M.m8 | 20.6 | 8 | 211 | 15,493 | T34 |
| Bgtw4 | Bgtw4.M | Mother | Bgtw4.M.m9 | 20.7 | 9 | 251 | 14,538 | T34 |
| Bgtw4 | Bgtw4.M | Mother | Bgtw4.M.m10 | 20.8 | 10 | 277 | 16,851 | T34 |
| Bgtw4 | Bgtw4.M | Mother | Bgtw4.M.m11 | 20.8 | 11 | 305 | 11,467 | T34 |

TABLE 2-continued

Information associated with fecal samples collected from parents in twins and triplets birth cohort

| Family ID | Person ID | Family membership | Fecal Sample ID | Age of subject at time of fecal sample collection, years | Age of subject's children at the time of subject's fecal sample collection, months | Age of subject's children at the time of subject's fecal sample collection, days | Number of high quality V4-16S rRNA sequences | 16S rRNA Sequencing Run ID |
|---|---|---|---|---|---|---|---|---|
| Bgtw4 | Bgtw4.M | Mother | Bgtw4.M.m12 | 20.9 | 12 | 334 | 32,997 | T56 (runs 1 and 2) |
| Bgtw4 | Bgtw4.M | Mother | Bgtw4.M.m13 | 21.0 | 13 | 364 | 20,722 | T12 |
| Bgtw4 | Bgtw4.M | Mother | Bgtw4.M.m14 | 21.1 | 14 | 395 | 13,616 | T12 |
| Bgtw4 | Bgtw4.M | Mother | Bgtw4.M.m15 | 21.2 | 15 | 425 | 21,943 | T12 |
| Bgtw4 | Bgtw4.M | Mother | Bgtw4.M.m16 | 21.3 | 16 | 458 | 22,991 | T78 |
| Bgtw4 | Bgtw4.M | Mother | Bgtw4.M.m17 | 21.3 | 17 | 487 | 17,381 | T78 |
| Bgtw4 | Bgtw4.M | Mother | Bgtw4.M.m18 | 21.4 | 18 | 517 | 34,752 | T56 (runs 1 and 2) |
| Bgtw4 | Bgtw4.M | Mother | Bgtw4.M.m19 | 21.5 | 19 | 547 | 24,521 | T56 (runs 1 and 2) |
| Bgtw4 | Bgtw4.M | Mother | Bgtw4.M.m20 | 21.6 | 20 | 575 | 44,125 | T56 (runs 1 and 2) |
| Bgtw5 | Bgtw5.M | Mother | Bgtw5.M.m1 | 29.0 | 1 | 4 | 9,540 | T34 |
| Bgtw5 | Bgtw5.M | Mother | Bgtw5.M.m2 | 29.1 | 2 | 33 | 16,280 | T34 |
| Bgtw5 | Bgtw5.M | Mother | Bgtw5.M.m3 | 29.2 | 3 | 61 | 23,552 | TCP2 (runs 1 and 2) |
| Bgtw5 | Bgtw5.M | Mother | Bgtw5.M.m4 | 29.3 | 4 | 95 | 25,903 | T12 |
| Bgtw5 | Bgtw5.M | Mother | Bgtw5.M.m5 | 29.3 | 5 | 123 | 15,880 | T34 |
| Bgtw5 | Bgtw5.M | Mother | Bgtw5.M.m6 | 29.4 | 6 | 152 | 16,214 | T34 |
| Bgtw5 | Bgtw5.M | Mother | Bgtw5.M.m7 | 29.5 | 7 | 181 | 20,984 | T56 (runs 1 and 2) |
| Bgtw5 | Bgtw5.M | Mother | Bgtw5.M.m8 | 29.6 | 8 | 218 | 13,008 | T34 |
| Bgtw5 | Bgtw5.M | Mother | Bgtw5.M.m9 | 29.7 | 9 | 248 | 21,653 | T34 |
| Bgtw5 | Bgtw5.M | Mother | Bgtw5.M.m10 | 29.8 | 10 | 277 | 13,582 | T34 |
| Bgtw5 | Bgtw5.M | Mother | Bgtw5.M.m11 | 29.8 | 11 | 310 | 14,621 | T12 |
| Bgtw5 | Bgtw5.M | Mother | Bgtw5.M.m12 | 29.9 | 12 | 341 | 18,744 | T34 |
| Bgtw5 | Bgtw5.M | Mother | Bgtw5.M.m13 | 30.0 | 13 | 365 | 15,753 | T34 |
| Bgtw5 | Bgtw5.M | Mother | Bgtw5.M.m14 | 30.1 | 14 | 396 | 21,882 | T56 (runs 1 and 2) |
| Bgtw5 | Bgtw5.M | Mother | Bgtw5.M.m15 | 30.2 | 15 | 429 | 17,027 | T12 |
| Bgtw5 | Bgtw5.M | Mother | Bgtw5.M.m16 | 30.3 | 16 | 458 | 14,496 | T78 |
| Bgtw5 | Bgtw5.M | Mother | Bgtw5.M.m17 | 30.4 | 17 | 493 | 14,010 | T78 |
| Bgtw5 | Bgtw5.M | Mother | Bgtw5.M.m18 | 30.4 | 18 | 514 | 18,506 | T78 |
| Bgtw5 | Bgtw5.M | Mother | Bgtw5.M.m19 | 30.5 | 19 | 548 | 19,202 | T56 (runs 1 and 2) |
| Bgtw5 | Bgtw5.M | Mother | Bgtw5.M.m20 | 30.6 | 20 | 578 | 22,358 | T56 (runs 1 and 2) |
| Bgtw5 | Bgtw5.M | Mother | Bgtw5.M.m21 | 30.7 | 21 | 613 | 41,854 | T56 (runs 1 and 2) |
| Bgtw5 | Bgtw5.M | Mother | Bgtw5.M.m22 | 30.8 | 22 | 640 | 14,899 | T78 |
| Bgtw6 | Bgtw6.M | Mother | Bgtw6.M.m1 | 18.0 | 1 | 6 | 21,134 | T12 |
| Bgtw6 | Bgtw6.M | Mother | Bgtw6.M.m2 | 18.1 | 2 | 35 | 22,561 | TCP2 (runs 1 and 2) |
| Bgtw6 | Bgtw6.M | Mother | Bgtw6.M.m3 | 18.2 | 3 | 63 | 12,071 | TCP2 (runs 1 and 2) |
| Bgtw6 | Bgtw6.M | Mother | Bgtw6.M.m4 | 18.3 | 4 | 92 | 15,084 | T12 |
| Bgtw6 | Bgtw6.M | Mother | Bgtw6.M.m6 | 18.4 | 6 | 152 | 8,105 | T12 |
| Bgtw6 | Bgtw6.M | Mother | Bgtw6.M.m7 | 18.5 | 7 | 182 | 24,708 | TCP2 (runs 1 and 2) |
| Bgtw6 | Bgtw6.M | Mother | Bgtw6.M.m8 | 18.6 | 8 | 212 | 25,775 | T56 (runs 1 and 2) |
| Bgtw6 | Bgtw6.M | Mother | Bgtw6.M.m9 | 18.7 | 9 | 246 | 31,301 | TCP2 (runs 1 and 2) |
| Bgtw6 | Bgtw6.M | Mother | Bgtw6.M.m10 | 18.8 | 10 | 286 | 22,264 | TCP2 (runs 1 and 2) |
| Bgtw7 | Bgtw7.M | Mother | Bgtw7.M.m1 | 32.0 | 1 | 12 | 12,620 | T34 |
| Bgtw7 | Bgtw7.M | Mother | Bgtw7.M.m2 | 32.1 | 2 | 32 | 12,895 | T34 |
| Bgtw7 | Bgtw7.M | Mother | Bgtw7.M.m3 | 32.2 | 3 | 61 | 14,622 | T34 |
| Bgtw7 | Bgtw7.M | Mother | Bgtw7.M.m4 | 32.2 | 4 | 90 | 15,904 | T12 |
| Bgtw7 | Bgtw7.M | Mother | Bgtw7.M.m5 | 32.3 | 5 | 125 | 13,728 | T34 |
| Bgtw7 | Bgtw7.M | Mother | Bgtw7.M.m6 | 32.5 | 6 | 167 | 25,899 | TCP2 (runs 1 and 2) |
| Bgtw7 | Bgtw7.M | Mother | Bgtw7.M.m7 | 32.5 | 7 | 189 | 16,171 | TCP2 (runs 1 and 2) |
| Bgtw7 | Bgtw7.M | Mother | Bgtw7.M.m8 | 32.6 | 8 | 214 | 21,054 | TCP2 (runs 1 and 2) |
| Bgtw7 | Bgtw7.M | Mother | Bgtw7.M.m9 | 32.7 | 9 | 244 | 16,054 | TCP2 (runs 1 and 2) |
| Bgtw7 | Bgtw7.M | Mother | Bgtw7.M.m10 | 32.8 | 10 | 275 | 16,972 | T78 |
| Bgtw7 | Bgtw7.M | Mother | Bgtw7.M.m11 | 32.8 | 11 | 307 | 18,622 | T78 |
| Bgtw7 | Bgtw7.M | Mother | Bgtw7.M.m12 | 32.9 | 12 | 336 | 17,114 | T56 (runs 1 and 2) |
| Bgtw7 | Bgtw7.M | Mother | Bgtw7.M.m13 | 33.0 | 13 | 364 | 24,908 | TCP2 (runs 1 and 2) |
| Bgtw7 | Bgtw7.M | Mother | Bgtw7.M.m14 | 33.1 | 14 | 397 | 25,642 | T56 (runs 1 and 2) |
| Bgtw7 | Bgtw7.M | Mother | Bgtw7.M.m15 | 33.2 | 15 | 427 | 34,912 | T56 (runs 1 and 2) |
| Bgtw7 | Bgtw7.M | Mother | Bgtw7.M.m16 | 33.2 | 16 | 455 | 26,763 | T56 (runs 1 and 2) |
| Bgtw8 | Bgtw8.M | Mother | Bgtw8.M.m2 | 35.1 | 2 | 35 | 14,743 | T34 |
| Bgtw8 | Bgtw8.M | Mother | Bgtw8.M.m3 | 35.2 | 3 | 64 | 12,586 | T34 |
| Bgtw8 | Bgtw8.M | Mother | Bgtw8.M.m4 | 35.2 | 4 | 90 | 15,905 | T12 |
| Bgtw8 | Bgtw8.M | Mother | Bgtw8.M.m5 | 35.3 | 5 | 122 | 22,094 | T56 (runs 1 and 2) |
| Bgtw8 | Bgtw8.M | Mother | Bgtw8.M.m6 | 35.4 | 6 | 157 | 11,955 | T12 |
| Bgtw8 | Bgtw8.M | Mother | Bgtw8.M.m7 | 35.5 | 7 | 185 | 12,986 | T12 |
| Bgtw8 | Bgtw8.M | Mother | Bgtw8.M.m8 | 35.6 | 8 | 212 | 24,345 | T56 (runs 1 and 2) |
| Bgtw8 | Bgtw8.M | Mother | Bgtw8.M.m9 | 35.7 | 9 | 247 | 24,921 | T56 (runs 1 and 2) |

TABLE 2-continued

Information associated with fecal samples collected from parents in twins and triplets birth cohort

| Family ID | Person ID | Family membership | Fecal Sample ID | Age of subject at time of fecal sample collection, years | Age of subject's children at the time of subject's fecal sample collection, months | Age of subject's children at the time of subject's fecal sample collection, days | Number of high quality V4-16S rRNA sequences | 16S rRNA Sequencing Run ID |
|---|---|---|---|---|---|---|---|---|
| Bgtw8 | Bgtw8.M | Mother | Bgtw8.M.m11 | 35.8 | 11 | 305 | 18,724 | T56 (runs 1 and 2) |
| Bgtw8 | Bgtw8.M | Mother | Bgtw8.M.m12 | 35.9 | 12 | 333 | 22,064 | T56 (runs 1 and 2) |
| Bgtw8 | Bgtw8.M | Mother | Bgtw8.M.m13 | 36.0 | 13 | 364 | 22,114 | T78 |
| Bgtw9 | Bgtw9.M | Mother | Bgtw9.M.m2 | 20.1 | 2 | 38 | 21,305 | TCP2 (runs 1 and 2) |
| Bgtw9 | Bgtw9.M | Mother | Bgtw9.M.m3 | 20.2 | 3 | 65 | 11,004 | T12 |
| Bgtw9 | Bgtw9.M | Mother | Bgtw9.M.m4 | 20.3 | 4 | 93 | 17,898 | T12 |
| Bgtw9 | Bgtw9.M | Mother | Bgtw9.M.m5 | 20.3 | 5 | 120 | 12,883 | T12 |
| Bgtw9 | Bgtw9.M | Mother | Bgtw9.M.m7 | 20.5 | 7 | 185 | 22,936 | TCP2 (runs 1 and 2) |
| Bgtw9 | Bgtw9.M | Mother | Bgtw9.M.m8 | 20.6 | 8 | 218 | 18,803 | T78 |
| Bgtw9 | Bgtw9.M | Mother | Bgtw9.M.m10 | 20.7 | 10 | 273 | 16,732 | TCP2 (runs 1 and 2) |
| Bgtw9 | Bgtw9.M | Mother | Bgtw9.M.m12 | 20.9 | 12 | 336 | 29,995 | T56 (runs 1 and 2) |
| Bgtw9 | Bgtw9.M | Mother | Bgtw9.M.m13 | 21.0 | 13 | 368 | 19,398 | T56 (runs 1 and 2) |
| Bgtw10 | Bgtw10.M | Mother | Bgtw10.M.m1 | 30.0 | 1 | 3 | 22,263 | TCP2 (runs 1 and 2) |
| Bgtw10 | Bgtw10.M | Mother | Bgtw10.M.m2 | 30.1 | 2 | 33 | 18,615 | T12 |
| Bgtw10 | Bgtw10.M | Mother | Bgtw10.M.m3 | 30.2 | 3 | 60 | 22,139 | T12 |
| Bgtw10 | Bgtw10.M | Mother | Bgtw10.M.m4 | 30.3 | 4 | 93 | 19,762 | TRX |
| Bgtw10 | Bgtw10.M | Mother | Bgtw10.M.m5 | 30.3 | 5 | 123 | 15,019 | T78 |
| Bgtw10 | Bgtw10.M | Mother | Bgtw10.M.m6 | 30.4 | 6 | 154 | 24,658 | T56 (runs 1 and 2) |
| Bgtw10 | Bgtw10.M | Mother | Bgtw10.M.m7 | 30.5 | 7 | 184 | 18,035 | T78 |
| Bgtw10 | Bgtw10.M | Mother | Bgtw10.M.m8 | 30.6 | 8 | 212 | 19,391 | T56 (runs 1 and 2) |
| Bgtw10 | Bgtw10.M | Mother | Bgtw10.M.m9 | 30.7 | 9 | 245 | 38,351 | T56 (runs 1 and 2) |
| Bgtw10 | Bgtw10.M | Mother | Bgtw10.M.m10 | 30.7 | 10 | 271 | 26,347 | T56 (runs 1 and 2) |
| Bgtw10 | Bgtw10.M | Mother | Bgtw10.M.m11 | 30.8 | 11 | 303 | 31,076 | T56 (runs 1 and 2) |
| Bgtw10 | Bgtw10.M | Mother | Bgtw10.M.m12 | 30.9 | 12 | 332 | 27,492 | T56 (runs 1 and 2) |
| Bgtw10 | Bgtw10.M | Mother | Bgtw10.M.m13 | 31.0 | 13 | 365 | 13,612 | T78 |
| Bgtw11 | Bgtw11.M | Mother | Bgtw11.M.m1 | 21.0 | 1 | 3 | 26,161 | T56 (runs 1 and 2) |
| Bgtw11 | Bgtw11.M | Mother | Bgtw11.M.m2 | 21.1 | 2 | 27 | 33,396 | T56 (runs 1 and 2) |
| Bgtw11 | Bgtw11.M | Mother | Bgtw11.M.m3 | 21.2 | 3 | 60 | 38,371 | T56 (runs 1 and 2) |
| Bgtw11 | Bgtw11.M | Mother | Bgtw11.M.m4 | 21.2 | 4 | 88 | 18,784 | T78 |
| Bgtw11 | Bgtw11.M | Mother | Bgtw11.M.m5 | 21.3 | 5 | 120 | 31,702 | T56 (runs 1 and 2) |
| Bgtw11 | Bgtw11.M | Mother | Bgtw11.M.m6 | 21.4 | 6 | 151 | 27,234 | TCP2 (runs 1 and 2) |
| Bgtw11 | Bgtw11.M | Mother | Bgtw11.M.m7 | 21.5 | 7 | 192 | 18,199 | TCP2 (runs 1 and 2) |
| Bgtw11 | Bgtw11.M | Mother | Bgtw11.M.m8 | 21.6 | 8 | 216 | 41,854 | T56 (runs 1 and 2) |
| Bgtw11 | Bgtw11.M | Mother | Bgtw11.M.m9 | 21.7 | 9 | 243 | 19,865 | T56 (runs 1 and 2) |
| Bgtw11 | Bgtw11.M | Mother | Bgtw11.M.m10 | 21.8 | 10 | 279 | 16,839 | T78 |
| Bgtw11 | Bgtw11.M | Mother | Bgtw11.M.m11 | 21.8 | 11 | 306 | 20,396 | T78 |
| Bgtw11 | Bgtw11.M | Mother | Bgtw11.M.m12 | 21.9 | 12 | 334 | 17,489 | T78 |
| Bgtw12 | Bgtw12.M | Mother | Bgtw12.M.m1 | 22.0 | 1 | 7 | 18,105 | T56 (runs 1 and 2) |
| Bgtw12 | Bgtw12.M | Mother | Bgtw12.M.m2 | 22.1 | 2 | 31 | 38,175 | T56 (runs 1 and 2) |
| Bgtw12 | Bgtw12.M | Mother | Bgtw12.M.m3 | 22.2 | 3 | 60 | 16,379 | T78 |
| Bgtw12 | Bgtw12.M | Mother | Bgtw12.M.m4 | 22.2 | 4 | 91 | 40,446 | T56 (runs 1 and 2) |
| Bgtw12 | Bgtw12.M | Mother | Bgtw12.M.m5 | 22.3 | 5 | 125 | 12,674 | T78 |
| Bgtw12 | Bgtw12.M | Mother | Bgtw12.M.m6 | 22.4 | 6 | 158 | 41,746 | T56 (runs 1 and 2) |
| Bgtw12 | Bgtw12.M | Mother | Bgtw12.M.m7 | 22.5 | 7 | 187 | 21,437 | T56 (runs 1 and 2) |
| Bgtw12 | Bgtw12.M | Mother | Bgtw12.M.m8 | 22.6 | 8 | 216 | 36,976 | T56 (runs 1 and 2) |
| Bgtw12 | Bgtw12.M | Mother | Bgtw12.M.m9 | 22.7 | 9 | 245 | 15,573 | T78 |
| Bgtw12 | Bgtw12.M | Mother | Bgtw12.M.m10 | 22.8 | 10 | 280 | 16,713 | T78 |
| Bgtw12 | Bgtw12.M | Mother | Bgtw12.M.m11 | 22.9 | 11 | 314 | 16,498 | T78 |
| Bgtw12 | Bgtw12.M | Mother | Bgtw12.M.m12 | 22.9 | 12 | 341 | 15,881 | TRX |
| Bgtw12 | Bgtw12.M | Mother | Bgtw12.M.m13 | 23.0 | 13 | 372 | 17,612 | TRX |

TABLE 3

Characteristics of children in training and validation sets used for Random Forests age-discriminatory model (a) Training Set

| Characteristics | Training |
|---|---|
| Weight-for-Height Z score | −0.32 ± 1 |
| Male/Female | 7/5 |
| Number of fecal samples collected per child | 22.7 ± 1.5 |
| Age at first fecal sample collection (days) | 6 ± 1 |
| Age at last fecal sample collection (days) | 712 ± 15 |
| Mean sampling interval (days) | 33 ± 3.0 |
| Months of exclusive breastfeeding | 3.2 ± 2.3 |
| Age of first introduction of solid food (months) | 6.3 ± 2.3 |
| Number of diarrhoeal episodes per year | 4.0 ± 1.9 |
| % Days with diarrhoea during sampling period | 3.9 ± 1.7 |
| Fraction of samples collected where antibiotics had been consumed within prior 7 days | 0.2 ± 0.1 |

(b) Validation

| Characteristics | Validation |
|---|---|
| Weight-for-Height Z score | −0.44 ± 0.8 |
| Male/Female | 9/4 |
| Number of fecal samples collected per child | 21.2 ± 2.2 |
| Age at first fecal sample collection (days) | 7 ± 4 |
| Age at last fecal sample collection (days) | 709 ± 9 |

TABLE 3-continued

Characteristics of children in training and validation sets used for Random Forests age-discriminatory model

| | |
|---|---|
| Mean sampling interval (days) | 35.1 ± 4.3 |
| Months of exclusive breastfeeding | 3.6 ± 2.3 |
| Age of first introduction of solid food (months) | 6.4 ± 6.4 |
| Number of diarrhoeal episodes per year | 4.6 ± 2.4 |
| % Days with diarrhoea during sampling period | 4.3 ± 2.7 |
| Fraction of samples collected where antibiotics had been consumed within prior 7 days | 0.2 ± 0.2 |

(c) Validation - Twins & Triplets

| Characteristics | Validation - Twins & Triplets |
|---|---|
| Weight-for-Height Z score | −0.46 ± 0.7 |
| Male/Female | 7/18 |
| Number of fecal samples collected per child | 17.9 ± 5.3 |
| Age at first fecal sample collection (days) | 13 ± 12 |
| Age at last fecal sample collection (days) | 497 ± 147 |
| Mean sampling interval (days) | 29 ± 3.1 |
| Months of exclusive breastfeeding | 0.7 ± 2.3 |
| Age of first introduction of solid food (months) | 7.0 ± 1.9 |
| Number of diarrhoeal episodes per year | 1.7 ± 1.3 |
| % Days with diarrhoea during sampling period | 2.2 ± 2.6 |
| Fraction of samples collected where antibiotics had been consumed within prior 7 days | 0.1 ± 0.1 |

Mean values ± SD are shown

TABLE 4

Bacterial V4-16S rRNA sequencing statistics

| Study Subjects | V4-16S rRNA reads per sample (mean ± SD) | Number of fecal samples | Total number of high quality reads |
|---|---|---|---|
| 50 Healthy Children (Singletons, Twins and Triplets) | 25,288 ± 13,990 | 996 | 25,187,256 |
| Mothers & Fathers | 20,233 ± 7,120 | 243 | 4,916,630 |
| Severe Acute Malnutrition Randomized Clinical Trial | 21,545 ± 15,731 | 589 | 12,689,785 |
| Moderate Acute Malnutrition Cross-Sectional Analysis | 22,964 ± 8,713 | 22 | 505,207 |
| Concordant Healthy Malawian Twins and Triplets | 151,578 ± 65,521 | 47 | 7,124,158 |
| | | 1897 | 50,423,036 |

TABLE 5

16S rRNA sequences and annotation of age-discriminatory bacterial taxa in order of feature importance

| Rank Order / SEQ ID NO | 16S rRNA OTU ID (as shown in FIG. 1) | Age discriminatory feature importance score (mean ± SD) | RDP 2.4 Taxonomic Annotation (Phylum; Class; Order; Family; Genus; Species) | Representative 16S rRNA Sequence of the 97% ID OTU cluster |
|---|---|---|---|---|
| 1 | 326792 | 9.64 ± 0.29 | Firmicutes; Clostridia; Clostridiales; Ruminococcaceae; Faecalibacterium; Faecalibacterium_prausnitzii | AACGTAGTCACAAGCGTTGTCCGGAATTACTGGGTGTAAAGGG AGCGCAGGCGGGAGAACAAGTTGGAAGTGAAATCCATGGGCTC AACCCATGAACTGCTTTCAAAACTGTTTTTCTTGAGTAGTGCAGA GGTAGGCGGAATTCCCGTGTAGCGGTGGAATGCGTAGATATC GGGAGGAACACCAGTGGCGAAGGCGGCCTACTGGCACCAAC TGACGCTGAGGCTCGAAAGTGTGGGTAGCAAACAGG |
| 2 | 189827 | 7.21 ± 0.38 | Firmicutes; Clostridia; Clostridiales; Ruminococcaceae; Ruminococcus; Ruminococcus_sp_5_1_39BFAA | TACGTAGGGGCAAGCGTTATCCGGAATTTACTGGGTGTAAAGG GAGCGTAGACGGTGTGGCAAGTCTGATGTGAAAGGCATGGGCT CAACCTGTGGACTGCATTGGAAACTGTCATACTTGAGTGCCGA GGGGTAAGCGGAATTCCTAGTGTAGCGGTGAAATGCGTAGATAT TAGGAGGAACACCAGTGGCGAAGGCGGCTTACTGGACGGTAAC TGACGTTGAGGCTCGAAAGCGTGGGAGCAAACAGG |
| 3 | 470663 | 3.89 ± 0.22 | Firmicutes; Bacilli; Lactobacillales; Lactobacillaceae; Lactobacillus; Lactobacillus_ruminis | TACGTAGGTGGCGAGCGTTGTCCGGATTTATTGGGCGTAAAGG GAACGCAGGCGGTCTTTTAAGTCTGATGTGAAAGCCTTCGGCTT AACCGAAGTAGTGCATTGGAAACTGGAAGACTTGAGTGCAGAAG AGGAGAGTGGAACTCCATGTGTAGCGGTGAAATGCGTAGATATA TGGAAGAACACCAGTGGCGAAAGCGGCTCTCTGGTCTGTAACT GACGCTGAGGTTCGAAAGCGTGGGTAGCAAACAGG |
| 4 | 191687 | 3.27 ± 0.23 | Firmicutes; Clostridia; Clostridiales; Lachnospiraceae; Dorea; Dorea_longicatena | TACGTAGGGGGCAAGCGTTATCCGGAATTTACTGGGTGTAAAGG GAGCGTAGACGGCACGGCAAGCCAGATGTGAAAGCCCGGGGC TCAACCCCGGGACTGCATTTGGAACTGCTGAGCTAGAGTGTCG GAGAGGCAAGTGGAATTCCTAGTGTAGCGGTGAAATGCGTAGAT ATTAGGAGGAACACCAGTGGCGAAGGCGGCTTCTGGACGATG ACTGACGTTGAGGCTCGGGAGCGAAAGCGTGGGGAGCAAACAGG |
| 5 | 72820 | 2.86 ± 0.14 | Actinobacteria; 1760; Bifidobacteriales; Bifidobacteriaceae; Bifidobacterium; Bifidobacterium_longum | TACGTAGGGTGCAAGCGTTATCCGGAATTATTGGGCGTAAAGG CTCGTAGGCGGTTCGTCGCGTCCGGTGTGAAAGTCCATCGCTT AACGGTGGATCGCGCCGGGTACGGCGGGCTTGAGTGCGGT AGGGGAGACTGGAATTCCCGGTGTAACGGTGGAATGTGTAGAT ATCGGGAAGAACACCAATGGCGAAGGCAGGTCTCTGGGCCGTT ACTGACGCTGAGGAGCGAAAGCGTGGGGAGCGAACAGG |
| 6 | 194745 | 2.43 ± 0.19 | Firmicutes; Clostridia; Clostridiales; Ruminococcaceae; Ruminococcus; Ruminococcus_sp_5_1_39BFAA | TACGTAGGGGCAAGCGTTATCCGGATTTACTGGGTGTAAAGG GAGCGTAGACGGTGTGGCAAGTCTGATGTGAAAGGCATGGGCT CAACCCGTGGACTGCATTGGAAACTGTCATACTTGAGTGCCGA GGGGTAAGCGGAATTCCTAGTGTAGCGGTGAAATGCGTAGATAT TAGGAGGAACACCAGTGGCGAAGGCGGCTTACTGGACGGTAAC TGACGTTGAGGCTCGAAAGCGTGGGAGCAAACAGG |

TABLE 5-continued 16S rRNA sequences and annotation of age-discriminatory bacterial taxa in order of feature importance

| Rank Order / SEQ ID NO | 16S rRNA OTU ID (as shown in FIG. 1) | Age discriminatory feature importance score (mean ± SD) | RDP 2.4 Taxonomic Annotation (Phylum; Class; Order; Family; Genus; Species) | Representative 16S rRNA Sequence of the 97% ID OTU cluster |
|---|---|---|---|---|
| 7 | 15141 | 1.98 ± 0.12 | Firmicutes; Bacilli; Lactobacillales; Lactobacillaceae; Lactobacillus; Lactobacillus_mucosae | TACGTAGGTGGCAAGCGTTATCCGGAATTTATTGGGCGTAAAGCG AGCGCAGGCGGTTTGATAAGTCTGATGTGAAAGCCTTTGGCTTA ACCAAAGAAGTGCATCGGAAACTGTCAGACTTGAGTGCAGAAGA GGAGAGTGGAACTCCATGTGTAGCGGTGGAATGCGTAGATATAT GGAAGAACACCAGTGGCGAAGGCGGCTCTCTGGTCTGCAACTG ACGCTGAGGCTCGAAAGCATGGTAGCGAACAGG |
| 8 | 561483 | 1.59 ± 0.10 | Actinobacteria; 1760; Bifidobacteriales; Bifidobacteriaceae; Bifidobacterium | TACGTAGGGTGCAAGCGTTATCCGGAATTATTGGGCGTAAAGGG CTCGTAGGCGGTTCGTCGCGTCCGCTGTGAAAGTCCATCGCTT AACGGTGATCCGCGCGGGTACGGCGGCTTGAGTGCGT AGGGGAGACTGGAATTCCCGGTGTAACGGTGGAATGTGTAGAT ATCGGAAGAACACCAATGGCGAAGGCAGGTCTCTGGGCCGTT ACTGACGCTGAGGAGCCGAAGCGTGGGGAGCGAACAGG |
| 9 | 217996 | 0.99 ± 0.06 | Firmicutes; Bacilli; Bacillales Staphylococcaceae; Staphylococcus | TACGTAGGTGGCAAGCGTTATCCGGAATTATTGGGCGTAAAGCG CGCGTAGGCGGTTTTTAAGTCTGATGTGAAAGCCCACGGCTCA ACCGTGAGGGTCATTGGAAACTGGAAAACTTGAGTGCAGAAG AGGAAAGTGGAATTCCATGTGTAGCGGTGAGATGCCAGAGAT ATGGAGGAACACCAGTGCGAAGGCGACTTTCTGGTCTGTAACT GACGCTGATGTGCGAAAGCGTGGGGATCAAACAGG |
| 10 | 364234 | 0.95 ± 0.12 | Firmicutes; Clostridia; Clostridiales; Ruminococcaceae; Ruminococcus; Ruminococcus_sp_5_1_39BFAA | TACGTAGGTGCAAGCGTTATCCGGATTTACTGGGTGTAAAGGG AGCGTAGACGGTGTGCAAGTCTGATGTGAAAGGCATGGGCTC AACCTGTGACTGCATTGGAAACTGTCATACTTGAGTGCCGAG GGGTAAGCGGAATTCCTAGTGTAGCGGTGAAATGCGTAGATATT AGGAGGAACACCAGTGGCGAAGGCGGCTTACTGGACGGTAACT GACGTTGAGGCTCGAAAGCGTGGGGAGCAAACAGG |
| 11 | 287510 | 0.92 ± 0.08 | Firmicutes; Erysipelotrichi; Erysipelotrichales; Erysipelotrichaceae; Catenibacterium; Catenibacterium_mitsuokai | TACGTAGGTGGCAGCGTTATCCGAATCATTGGGCGTAAAGA GGGAGCAGGCGGCCCAAGGGTCTGTGTGAAAGACCCAAGC TAAACTTCGGTAAGCCATGGAAACCGGGCGGCTAGAGTGCGGA AGAGGATCGTGGAATTCCATGTGTAGCGGTGAAATGCGTAGATA TATGGAGGAACACCAGTGGCGAAGGCGGCGTCTGGGCCGCAA CTGACGCTCATTCCCGAAAGCGTGGGGAGCAAATAGG |
| 12 | 261912 | 0.88 ± 0.10 | Firmicutes; Clostridia; Clostridiales; Lachnospia; Dorea; Dorea_formicigeneans | TACGTAGGGGGCAAGCGTTATCCGGATTTACTGGGTGTAAAGG GAGCGTAGACGGCTGTCAAGTCTGTGAAGGCATGGGCT CAACCTGTGACTGCTTTGGAAACTGTCAGCTAGAGTGTCGA GAGGTAAGTGGAATTCCTAGTGTAGCGGTGAAATGCGTAGATAT TAGGAGGAACACCAGTGCGAAGGCGGCTTACTGGACGATGAC TGACGTTGAGGCTCGAAAGCGTGGGAGCAAACAGG |

TABLE 5-continued 16S rRNA sequences and annotation of age-discriminatory bacterial taxa in order of feature importance

| Rank Order / SEQ ID NO | 16S rRNA OTU ID (as shown in FIG. 1) | Age discriminatory feature importance score (mean ± SD) | RDP 2.4 Taxonomic Annotation (Phylum; Class; Order; Family; Genus; Species) | Representative 16S rRNA Sequence of the 97% ID OTU cluster |
|---|---|---|---|---|
| 13 | 361809 | 0.61 ± 0.11 | Firmicutes; Clostridia; Clostridiales; Ruminococcaceae; Ruminococcus; Ruminococcus_torques | TACGTATGGTGCAAGCGTTATCCGGATTTACTGGGTGTAAAGGG AGCGTAGACGGAGTGGCAAGTCTGATGTGAAAACCCGGGGCTC AACCCCGGGACTGCATTGGAAACTGTCAATCTAGAGTACCGAG AGTAAGCGGAATTCCTAGTGTAGCGGTGAAATGCGTAGATATT AGGAGGAACACCAGTGGCGAAGGCGGCTACTGGACCGTAACT GACGTTGAGGCTCGAAAGCGTGGGAGCAAACAGG |
| 14 | 108747 | 0.52 ± 0.05 | Firmicutes; Bacilli; Lactobacillales; Streptococcaceae; Streptococcus; Streptococcus_thermophilus | TACGTAGGTCCCCGAGCGTTGTCCGGATTTATTGGGCGTAAAGCG AGCGCAGGCGGTTTGATAAGTCTGAAGTTAAAGGCTGTGGCTCA ACCATAGTTCGCTTTGGAAACTGTCAAACTTGAGTGCAGAAGGG GAGAGTGGAATTCCATGTGTAGCGGTGAAATGCGTAGATATATG GAGGAACACCGGTGGCGAAAGCGGCTCTCTGGTCTGTAACTGA CGCTGAGGCTCGAAAGCGTGGGAGCGAACAGG |
| 15 | 533785 | 0.51 ± 0.05 | Actinobacteria; 1760; Bifidobacteriales; Bifidobacteriaceae; Bifidobacterium | TACGTAGGGCGCAAGCGTTATCCGGATTTATTGGGCGTAAAGG GCTCGTAGGCGGTTCGTCGCGTCCGGTGTGAAAGTCCATCGCT TAACGGTTGGATCCGCCGCCGGGTACGGGCCTTGAGTGCGG TAGGGGAGACTGGAATTCCCGGTGTAACGGTGGCTTGAGTGCGG TATCGGGAAGAACACCAATGGCGAAGGCAGGTCTCTGGGCCGT TACTGACGCTGAGGAGCGAAAGCGTGGGGAGCGAACAGG |
| 16 | 9514 | 0.46 ± 0.06 | Proteobacteria; Gammaproteobacteria; Pasteurellales; Pasteurellaceae; Haemophilus; Haemophilus_parainfluenzae | TACGGAGGGTGCGAGCGTTAATCGGAATAACTGGGCGTAAAGG GCACGCAGGCGGTGACTTAAGTGAGGTGTGAAAGCCCCGGGCT TAACCTGGGAATTGCATTTCATACTGGGTCGTAGAGTACTTTAG GGAGGGGTAGAATTCCACGTGTAGCGGTGAAATGCGTAGAGAT GTGGAGGAATACCGAAGGCGAAGGCAGCCCCTTGGAATGTAC TGACGCTCATGTGCGAAAGCGTGGGAGCAAACAGG |
| 17 | 561636 | 0.42 ± 0.05 | Firmicutes; Bacilli; Lactobacillales; Streptococcaceae; Streptococcus | TACGTAGGTCCCCGAGCGTTATCCGGATTTATTGGGCGTAAAGCG AGCGCAGGCGGTTAGATAAGTCTGAAGTTAAAGGCTGTGGCTTA ACCATAGTACGCTTTGGAAACTGTTTAACTTGAGTGCAAGAGGG GAGAGTGGAATTCCATGTGTAGCGGTGAAATGCGTAGATATATG GAGGAACACCGGTGGCGAAAGCGGCTCTCTGGCTTGTAACTGA CGCTGAGGCTCGAAAGCGTGGGGAGCAAACAGG |
| 18 | 312461 | 0.42 ± 0.04 | Firmicutes; Clostridia; Clostridiales; Clostridiaceae; Clostridium | TACGTAGGGGGCTAGCGTTATCCGGAATTACTGGGCGTAAAGG GTGCGTAGGTGGTTTCTTAAGTCAGAGGTGAAAGGCTACGGCTC AACCTAGTAAGCCTTTGAAACTTGGAAACTTGAGTGCCAGGAGA GGAGAGTGGAATTCCTAGTGTAGCGGTGAAATGCGTAGATATTA GGAGGAACACCAGTTGCGAAGGCGCTCTCTGGACTGTAACTG ACACTGAGGCACGAAAGCGTGGGGAGCAAACAGG |

TABLE 5-continued 16S rRNA sequences and annotation of age-discriminatory bacterial taxa in order of feature importance

| Rank Order / SEQ ID NO | 16S rRNA OTU ID (as shown in FIG. 1) | Age discriminatory feature importance score (mean ± SD) | RDP 2.4 Taxonomic Annotation (Phylum; Class; Order; Family; Genus; Species) | Representative 16S rRNA Sequence of the 97% ID OTU cluster |
|---|---|---|---|---|
| 19 | 470139 | 0.40 ± 0.05 | Firmicutes; Erysipelotrichi; Erysipelotrichales; Erysipelotrichaceae; unclassified_ Erysipelotrichaceae; Clostridium_ ramosum | TACGTAGTGGCAAGCGTTATCCGGAATTATTGGGCGTAAAGAG GGAGCAGGCGGCAGCAAGGGTCTGTGTGAAAGCCTGAAGCTT AACTTCAGTAAGCCATAGAAACCAGGCAGCTAGAGTCAGGAGA GGATCGTGGAATTCCATGTGTAGCGGTGAAATGCGTAGATATAT GGAGGAACACCAGTGGCGAAGGCGACGATCTGCCTGCAACTG ACCGTCAGTCCCGAAAGCGTGGGAGCAAATAGG |
| 20 | 181834 | 0.38 ± 0.08 | Firmicutes; Clostridia; Clostridiales; Clostridiaceae; Clostridium | TACGTAGGGGGCAAGCGTTATCCGGATTTACTGGGTGTAAAGG GAGCGCAGACGGCGATGCAAGTCTGAAGTGAAAGCCCGGGGCT CAACCCCCGGACTGCTTTTGGAAACTGTATGGCTAGAGTGCTGG AGAGGCAAGCGGAATTCCTAGTGTAGCGGTGAAATGCGTAGATA TTAGGAAGAACACCAGTGGCGAAGGCGGCTTGCTGGACAGTAA CTGACGTTCAGCTCGAAAGCGTGGGGAGCACAGG |
| 21 | 148099 | 0.38 ± 0.05 | Firmicutes; Bacilli; Lactobacillales; Leuconostocaceae; Weissella; Weissella_cibaria | TACGTATGTTCCAAGCGTTATCCGGATTTATTGGGCGTAAAGCG AGCGCAGACGGTTATTTAAGTCTGATGTGAAAGCCCTCAGCTCA ACTGAGGAATTGCTTTGCAAACTGGATGACTTGAGTGCAGTAGA GGAAAGTGGAACTCCATGTGTAGCGGTGAAATGCGTAGATATAT GGAAGAACACCAGTGGCGAAGGCGGCTTTCTGGACTGTAACTG ACGTTGAGGCTCGAAAGTGTGGGTAGCAACAGG |
| 22 | 469873 | 0.36 ± 0.05 | Actinobacteria; 1760; Bifidobacteriales; Bifidobacteriaceae; Bifidobacterium | TACGTAGGGTGCAAGCGTTATCCGGAATTATTGGGCGTAAAGGG CTCGTAGGCGGTTCGTCCGCGTCCGGTGTGAAAGTCCATCGCTT AACGGTGATCTGCGCCGGGTACGGGCGGGCTGGAGTGCGGT AGGGGAGACTGGAATTCCCGGTGTAACGGTGGAATGTGTAGAT ATCGGGAAGAACACCAATGCGAAGGCAGGTCTCTGGGCCGTT ACTGACGCTGAGGAGCGAAAGCGTGGGGAGCGAACAGG |
| 23 | 185951 | 0.35 ± 0.06 | Firmicutes; Clostridia; Clostridiales | TACGTAGGGGGCAAGCGTTATCCGGATTTACTGGGTGTAAAGG GAGCGTAGACGGATGGACAAGTCTGAAGTGAAAGGCTGGGGCT CAACCCCCGGACTGCTTCATTGGAAACTGCCCCGTCTTGAGTGCCGG AGAGGTAAGCGGAATTCCTAGTGTAGCGGTGAAATGCGTAGATA TTAGGAGGAACACCAGTGGCGAAGGCGGCTTACTGGACGGTAA CTGACGTTGAGGCTCGAAAGCGTGGGGAGCAAACAGG |
| 24 | 212619 | 0.31 ± 0.04 | Firmicutes; Clostridia; Clostridiales; Ruminococcaceae | AACGTAGGGTGCAAGCGTTGTCCGGAATTACTGGGTGTAAAGG GAGCGCAGGCGGACCGGCAAGTTGGAAGTGAAAACTATGGGCT CAACCCATAAATTGCTTTCAAAACTGCTGGCCTTGAGTGAGTGCA GAGGTAGGTGGAATTCCCGGTGTAGCGGTGAATGCGTAGATA TCGGGAGGAACACCAGTGGCGAAGGCGACCTACTGGGCACCAA CTGACGCTGAGGCTCGAAAGCATGGGTAGCAACAGG |

TABLE 5-continued 16S rRNA sequences and annotation of age-discriminatory bacterial taxa in order of feature importance

| Rank Order / SEQ ID NO | 16S rRNA OTU ID (as shown in FIG. 1) | Age discriminatory feature importance score (mean ± SD) | RDP 2.4 Taxonomic Annotation (Phylum; Class; Order; Family; Genus; Species) | Representative 16S rRNA Sequence of the 97% ID OTU cluster |
|---|---|---|---|---|
| 25 | 469852 | 0.29 ± 0.05 | Actinobacteria; 1760; Bifidobacteriales; Bifidobacteriaceae; Bifidobacterium; Bifidobacterium_bifidum | TACGTAGGGCGCAAGCGTTATCCGGATTTATTGGGCGTAAAGG GCTCGTAGGCGGCTCGTCCGTCCGGTGTGAAAGTCCATCGCT TAACGGTGGATTTGCGCCGGGTACGGGCGGGCTGGAGTGCGG TAGGGGAGACTGGAATTCCCGGTGTAACGGTGAATGTGTAGA TATCGGGAAGAACACCGATGGCGAAGGCAGGTCTCTGGCCGT CACTGACCCTGAGGAGCGAAAGCGTGGGGAGCGAACAGG |
| 26 | 170124 | 0.28 ± 0.06 | Firmicutes; Clostridia; Clostridiales; Eubacteriaceae; Eubacterium; Eubacterium_desmolans | TACGTGGGGAGCAAGCGTTATCCGGATTTACTGGGTGTAAAGGG CGCGCAGGCGGGCCGGCAAGTTGGAAGTGAAAATCTATGGGCTT AACCCATAAACTGCTTTCAAAACTGCTGCTCTTTGAGTGATGGAG AGCAGGCGGAATTCCGTGTGTAGCGGTGAAATGCGTAGATAT AGGAGGAACACCAGTGCGAAGGCGGCCTGCTGGACATTAAC TGACGCTGAGGCGCGAAAGCGTGGGGAGCAAACAGG |
| 27 | 187010 | 0.28 ± 0.06 | Firmicutes; Clostridia; Clostridiales; Ruminococcaceae; Faecalibacterium; Faecalibacterium_prausnitzii | TACGTAGGTCACAAGCGTTGTCCGGAATTACTGGGTGTAAAGGG AGCGCAGGCGGGAGAGCAAGTTGGAAGTGAAATCCATGGGCTC AACCCATGAACTGCTTTCAAAACTGTTTTCTTGAGTAGTGCAGA GGTAGGCGGAATTCCCGGTGTAGCGGTGAAATGCGTAGATATC GGAGGAACACCAGTGCGCAAGGCGGCCTACTGGGCACCAAC TGACGCTGAGGCTCGAAAGTGTGGGTAGCAAACAGG |
| 28 | 303304 | 0.27 ± 0.05 | Bacteroidetes; Bacteroidia; Bacteroidales; Prevotellaceae; Prevotella; Prevotella_copri | TACGGAAGGTCCCGGCGTTATCCGGATTTATTGGGTTTAAAGGG AGCGTAGGCCGGAGATTAAGCGTGTTGTGAAATGTAGACGCTCA ACGTCTGCACTGCAGCCGCGAACTGTTTCTTGAGTACGCACAA AGTGGGCGGAATTCGTGGTGTAGCGGTGAAATGCTTAGATATCA CGAAGAACTCCGATTGCGAAGGCAGCTCACTGAGCGCAACTG ACCCTGAAGCTCGAAAGTGCGGGTATCGAACAG |
| 29 | 470527 | 0.26 ± 0.03 | Firmicutes; Bacilli; Lactobacillales; Lactobacillaceae; Lactobacillus; Lactobacillus_reuteri | TACGTAGTGGCAAGCGTTATCCGGATTTATTGGGCGTAAAGCG AGCGCAGGCGGTTCTTAGGTCTGATGTGAAAGCCTTCGGCTTA ACCGAAGAAGTGCATCGGAAACCGGGCGACTTGAGTGCAGAAG AGGACAGTGGAACTCCATGTGTAGCGGTGAATGCGTAGATATA TGGAAGAACACCAGTGGCGAAGGCGGCTGTCTGGTCTGCAACT GACGCTGAGGCTCGAAAGCATGGTAGCGAACAGG |
| 30 | 210269 | 0.25 ± 0.04 | Proteobacteria; Gammaproteobacteria; Enterobacteriales; Enterobacteriaceae | TACGGAGGGTGCAAGCGTTAATCGGAATTACTGGGCGTAAAGC GCAACCAGGCCGGTCGTCAAGTCGGATGTGAAATCCCCGGGCT CAACCTGGGAACTGCATTCGAAACTGGCAGGCTAGAGTCTTGTA GAGGGGTAGAATTCCAGGTGTAGCGGTGAAATGCGTAGAGA TCTGGAGGAATACCGGTGGCGAAGGCGGCCCCCTGGACAAAGA CTGACGCTCAGGTGCGAAAGCGTGGGGAGCAAACAGG |

TABLE 5-continued 16S rRNA sequences and annotation of age-discriminatory bacterial taxa in order of feature importance

| Rank Order / SEQ ID NO | 16S rRNA OTU ID (as shown in FIG. 1) | Age discriminatory feature importance score (mean ± SD) | RDP 2.4 Taxonomic Annotation (Phylum; Class; Order; Family; Genus; Species) | Representative 16S rRNA Sequence of the 97% ID OTU cluster |
|---|---|---|---|---|
| 31 | 182202 | 0.24 ± 0.03 | Firmicutes; Clostridia; Clostridiales; Clostridiaceae; Clostridium; Clostridium_glycolicum | TACGTAGGGGGCTAGCGTTATCCGGATTTACTGGGCGTAAAGG GTGCGTAGGTGGTTTCTTAAGTCAGGAGTGAAAGGCTACGGCTC AACCGTAGTAAGCTCTTGAAACTTGGGAAACTTGAGTGCAGGAGA GGAAAGTGGAATTCCTAGTGTAGCGGTGAAATGCGTAGATATTA GGAGGAACACCAGTGGCGAAGGCGCTTTCTGACTGTAACTG ACACTGAGGCACCGAAAGCGTGGGAGCAAACAGG |
| 32 | 178122 | 0.23 ± 0.06 | Firmicutes; Clostridia; Clostridiales; Ruminococcaceae; Ruminococcus; Ruminococcus_obeum | TACGTAGGGGGCAAGCGTTATCCGGATTTACTGGGTGTAAAGG GAGCGTAGACGACTGGCAAGTCTGATGTGAAAGGCGGGGGCT CAACCCCTGGACTGCATTGGAAACTGTTAGTCTTGAGTGCCGGA GAGGTAAGCGGAATTCCTAGTGTAGCGGTGAAATGCGTAGATAT TAGGAGGAACACCAGTGGCGAAGGCGGCTTACTGGACGGTAAC TGACGTTGAGGCTCGAAAGCGTGGGGAGCAAACAGG |
| 33 | 540230 | 0.21 ± 0.04 | Firmicutes; Bacilli; Lactobacillales; Enterococcaceae; Enterococcus; Enterococcus_faecalis | TACGTAGGTGGCAAGCGTTGTCCGGATTTATTGGGCGTAAAGCG AGCGCAGGCGGTTTCTTAAGTCTGATGTGAAAGCCCCCGGCTC AACCGGGAGAGGGTCATTGGAAACTGGGAGACTTGAGTGCAGAA GAGGAGAGTGGAATTCCATGTGTAGCGGTGAAATGCGTAGATAT ATGGAGGAACACCAGTGGCGAAGGCGGCTCTCTGGTCTGTAAC TGACGCTGAGGCTCGAAAGCGTGGGGAGCAAACAGG |
| 34 | 309068 | 0.18 ± 0.04 | Bacteroidetes; Bacteroidia; Bacteroidales; Prevotellaceae; Prevotella; Prevotella_copri | TACGGAAGGTCCGGGCGTTATCCGGATTTATTGGGTTTAAAGGG AGCGTAGGCCGGAGATTAAGCGTGTTGTGAAATGTAGATGCTCA ACATCTGCACTGCAGCGCGAACTGGTTTCTTGAGTACGCACAA AGTGGGCGGAATTCGTGGTGTAGCGGTGAAATGCTTAGATATCA CGAAGAACTCCGATTGCGAAGGCAGCTCACTGAGCGCAACTG ACGCTGAAGCTCGAAAGTGCGGGTATCGAACTG |
| 35 | 24773 | 0.16 ± 0.03 | Actinobacteria; 1760; Bifidobacteriales; Bifidobacteriaceae; Bifidobacterium | TACGGAGGGTGCAAGCGTTATCCGGAATTATTGGGCGTAAAGGG CTCGTAGGCGGTTCGTCGCGTCCGGTGTGAAAGTCCATCGCTT AACGGTGATCTGCGCCGGGTACGGGCGGCTGAGTGCGGT AGGGGAGACTGGAATTCCCGGTGTAACGGTGGAATGTGTAGAT ATCGGGAAGAACACCGATGGCGAAGGCAGGTCTCTGGGCCGTC ACTGACGCTGAGGAGCGAAAGCGTGGGGAGCGAACAGG |
| 36 | 554755 | 0.16 ± 0.03 | Firmicutes; Bacilli; Lactobacillales; Enterococcaceae; Enterococcus | TACGTAGGTGGCAAGCGTTATCCGGATTTATTGGGCGTAAAGCG AGCGCAGGCGGTTTCTTAAGTCTGATGTGAAAGCCCCCGGCTC AACCGGGAGAGGGTCATTGGAAACTTGAGTGCAGAA GAGGAGAGTGGAATTCCATGTGTAGCGGTGAAATGCGTAGATAT ATGGAGGAACACCAGTGGCGAAGGCGGCTCTCTGGTCTGTAAC TGACGCTGAGGTTCGAAAGCGTGGGTAGCAAACAGG |

TABLE 5-continued 16S rRNA sequences and annotation of age-discriminatory bacterial taxa in order of feature importance

| Rank Order / SEQ ID NO | 16S rRNA OTU ID (as shown in FIG. 1) | Age discriminatory feature importance score (mean ± SD) | RDP 2.4 Taxonomic Annotation (Phylum; Class; Order; Family; Genus; Species) | Representative 16S rRNA Sequence of the 97% ID OTU cluster |
|---|---|---|---|---|
| 37 | 305760 | 0.15 ± 0.04 | Proteobacteria; Gammaproteobacteria; Enterobacteriales; Enterobacteriaceae; Escherichia; Escherichia_coli | TACGGAGGGTGCAAGCGTTAATCGGAATTACTGGGCGTAAAGC GCACGCAGGCGGTTTGTTAAGTCAGATGTGAAATCCCCGGGCT CAACCTGGGAACTGCATCTGATACTGCAAGCTTGAGTCTCGTA GAGGGGGTAGAATTCCAGGTGTAGCGGTGAAATGCGTAGAGA TCTGGAGGAATACCGGTGGCGAAGGCGGCCCCCTGGACGAAG ACTGACGCTCAGGTGCGAAAGCGTGGGGAGCAAACAGG |
| 38 | 268604 | 0.15 ± 0.03 | Bacteroidetes; Bacteroidia; Bacteroidales; Prevotellaceae; Prevotella | TACGGAAGGTCCGGGCGTTATCCGGATTTATTGGGTTTAAAGGG AGCGCAGGCGGACCTTTAAGTCAGCTGTGAAAATACGGCGGCTC AACCGTCGAACTGCAGTTGATACTGGAGGTCTTGAGTGCACACA GGGATGCTGGAATTCATGGTGTAGCGGTGAAATGCTCAGATATC ATGAAGAACTCCGATCCGAAGGCAGGCATCCGGGGTGCAACT GACGCTGAGGCTCGAAAGTGCGGGTATCAAACAGG |
| 39 | 188900 | 0.15 ± 0.04 | Firmicutes; Clostridia; Clostridiales; Ruminococcaceae; Faecalibacterium; Faecalibacterium_prausnitzii | AACGTAGTCACAAGCGTTGTCCGGAATTACTGGGCGTAAAGGG AGCGCAGGCGGGAGAACAAGTTGGAAGTGAAATCCATGGCTC AACCCATGAACTGCTTTCAAAACTGTTTTCTTGAGTAGTGCAGA GGTAGGCGGAATTCCCGGTGTAGCGGTGAAATGCGTAGATATC GGGAGGAACACCAGTGCGAAGGCGGCCTACTGGGCACCAAC TGACGCTGAGGCTCGAAAGTGTGGGTAGCAAACAGG |
| 40 | 174256 | 0.14 ± 0.03 | Firmicutes; Clostridia; Clostridiales; Eubacteriaceae; Eubacterium; Eubacterium_hallii | TACGTATGGAGCAAGCGTTATCCGGATTTACTGGGTGTAAAGGG TGCGTAGGTGGCAGTGCAAGTCAGATGTGAAAGGCCGGGGCTC AACCCCGGAGCTGCATTTGAAACTGCTCGCTAGAGTACAGGA GAGGCAGGCGGAATTCCTAGTGTAGCGGTGAAATGCGTAGATA TTAGGAGGAACACCAGTGGCGAAGGCGGCCTGCTGGACTGTTA CTGACACTGAGGCACGAAAGCGTGGGGAGCAAACAGG |
| 41 | 130663 | 0.14 ± 0.03 | Bacteroidetes; Bacteroidia; Bacteroidales; Bacteroidaceae; Bacteroides; Bacteroides_fragilis | TACGGAGGATCCGAGCGTTATCCGGATTTATTGGGTTTAAAGGG AGCGTAGGTGGACTGGTAAGTCAGTTGTGAAAGTTTGCGGCTCA ACCGTAAAATTGCAGTTGATACTGTCAGTCTTGAGTACAGTAGA GGTGGGCGGAATTCGTGGTGTAGCGGTGAAATGCTTAGATATCA CGAAGAACTCCGATTGCGAAGGCAGCTCACTGACTGCAACTG ACACTGATGCTCGAAAGTGTGGGTATCAAACAGG |
| 42 | 292424 | 0.14 ± 0.04 | Firmicutes; Bacilli; Lactobacillales; Streptococcaceae; Streptococcus | TACGTAGTCCCGAGCGTTGTCCGGATTTATTGGGCGTAAAGCG AGCGCAGGCGGTTTAATAAGTCTGAAGTTAAAGGCAGTGGCTTA ACCATTGTTCGCTTTGGAAACTGTTAGACTTGAGTGCAGAAGGG GAGAGTGGAATTCCATGTGTAGCGGTGAAATGCGTAGATATATG GAGGAACACCGGTGGCGAAAGCGGCTCTCTGGTCTGTAACTGA CGCTGAGGCTCGAAAGCGTGGGGAGCAAACAGG |

TABLE 5-continued 16S rRNA sequences and annotation of age-discriminatory bacterial taxa in order of feature importance

| Rank Order / SEQ ID NO | 16S rRNA OTU ID (as shown in FIG. 1) | Age discriminatory feature importance score (mean ± SD) | RDP 2.4 Taxonomic Annotation (Phylum; Class; Order; Family; Genus; Species) | Representative 16S rRNA Sequence of the 97% ID OTU cluster |
|---|---|---|---|---|
| 43 | 269541 | 0.14 ± 0.03 | Firmicutes; Bacilli; Bacillales Staphylococcaceae; Staphylococcus | TACGTAGTGGCAAGCGTTATCCGGAATTATTGGGCGTAAAGCG CGCGTAGGCGGTTTTTAAGTCTGATGTGAAAGCCCACGGCTCA ACCGTGGAGGGTCATTGGAAACTGGAAACTTGAGTGCAGAAG AGGAAAGTGGAATTCCATGTGTAGCGGTGAAATGCGCAGAGATA TGGAGGAACACCAGTGGCGAAGGCGACTTTCTGGTCTGTAACT GACGCTGATATGCGAAAGCGTGGGGATCAAACAGG |
| 44 | 191900 | 0.13 ± 0.03 | Firmicutes; Clostridia; Clostridiales; Ruminococcaceae; Ruminococcus; Ruminococcus_sp_5_1_39BFAA | TACGTAGGGGGCAAGCGTTATCCGGATTTACTGGGTGTAAAGG GAGCGTAGACGTGCGCAAGTCTGATGTGAAAGGCATGGGCT CAACCCTGTGGACTGCATTGGAAACTGTCATACTTGAGTGCCGGA GGGTAAGCGGAATTCCTAGTGTAGCGGTGAAATGCGTAGATAT TAGGAGGAACACCAGTGGCGAAGGCGGCTTACTGGACGGCAAC TGACGTTGAGGCTCGAAAGCGTGGGGAGCAAACAGG |
| 45 | 48207 | 0.13 ± 0.03 | Firmicutes; Negativicutes; Selenomonadales; Veillonellaceae; Dialister | TACGTAGTGGCAAGCGTTGTCCGGAATTATTGGGCGTAAAGC GCGCGCAGGCGGCTTCTTAAGTCCATCTTAAAAGTGCGGGCT TAACCCCGTGATGGATGGAAACTGAAGAGCTGGAGTATCGGA GAGGAAAGTGGAATTCCTAGTGTAGCGGTGAAATGCGTAGAGAT TAGGAAGAACACCCGTGGCGAAGGCGACTTTCTGGACGACAAC TGACGCTGAGGCGCGAAAGCGTGGGGAGCAAACAGG |
| 46 | 186029 | 0.12 ± 0.03 | Actinobacteria; 1760; Coriobacteriales; Coriobacteriaceae; Collinsella; Collinsella_aerofaciens | TACGTAGGGGCGAGCGTTATCCGGATTCATTGGGCGTAAAGC GCCGTAGGCGGCCCCGGAAGCCCGCAGGCCGGGTCGAAGCGGGGG CTCAACCCCCGAAGCCCCCGAACCTCCGCGCTTGGTCCG GTAGGGAGGGTGGAACACCCGGTGTAGCGGTGAATGCGCA GATATCGGGTGGAACACCGGTGCGAAGGCGGCCCTCTGGGC CGAGACCCACGCTGAGGCGCGAAAGCTGGGGAGCGAACAGG |
| 47 | 325608 | 0.11 ± 0.04 | Firmicutes; Clostridia; Clostridiales; Clostridiaceae; Clostridium; Clostridium_bartlettii | TACGTAGGGGCTAGCGTTATCCGGATTTACTGGGCGTAAAGG GTGCGTAGGCGGTCTTTTAAGTCAGGAGTGAAAGGCTACGGCT CAACCGTAGTAAGCTCTTGAAACTGGAAGACTTGAGTGCAGGAG AGGAGAGTGGAATTCCTAGTGTAGCGGTGAAATGCGTAGATATT AGGAGGAACACCAGTAGCGAAGGCGGCTCTCTGGACTGTAACT GACGCTGAGGCACGAAAGCGTGGGGAGCAAACAGG |
| 48 | 252321 | 0.11 ± 0.02 | Firmicutes; Bacilli; Lactobacillales; Lactobacillaceae; Lactobacillus | TACGTAGGTGCAAGCGTTGTCCGGATTTATTGGGCGTAAAGCG AGCGCAGGCGGAAGAATAAGTCTGATGTGAAAGCCCTCGGCTT AACCGAGGAACTGCATCGGAAACTGTTTTCTTGAGTGCAGAAG AGAGAATGGAACTCCATGTGTAGCGGTGGAATGCGTAGATATA TGGAAGAACACCAGTGCGAAGGCGCCTCTCTGGTCTGCAACT GACGCTGAGGCTCGAAAGCATGGTAGCGAACAGG |

TABLE 5-continued 16S rRNA sequences and annotation of age-discriminatory bacterial taxa in order of feature importance

| Rank Order / SEQ ID NO | 16S rRNA OTU ID (as shown in FIG. 1) | Age discriminatory feature importance score (mean ± SD) | RDP 2.4 Taxonomic Annotation (Phylum; Class; Order; Family; Genus; Species) | Representative 16S rRNA Sequence of the 97% ID OTU cluster |
|---|---|---|---|---|
| 49 | 195574 | 0.10 ± 0.02 | Bacteroidetes; Bacteroidia; Gacteroidales; Prevotellaceae; Prevotella | TACGGAAGGTCCGGGCGTTATCCGGATTTATTGGGTTTAAAGGG AGCGTAGGCCGGAGATTAAGCGTGTTGTGAAATGTAGAGGCTC AACCTCTGCACTGCAGCGCGAACTGGTCTTCTTGAGTACGCACA ACTGGGCGGAATTCGTGGTGTAGCGGTGAAATGCTTAGATATC ACGAAGAACTCCGATTGCGAAGGCAGCTCACGGAGCGCAACT GACGCTGAAGCTCGAAAGTGCGGGTATCGAACAGG |
| 50 | 365047 | 0.10 ± 0.03 | Firmicutes; Clostridia; Clostridiales; Ruminococcaceae; Ruminococcus; Ruminococcus_sp_5_1_39BFAA | TACGTAGGGGGCAAGCGTTATCCGGATTTACTGGGTGTAAAGG GAGCGTAGACGGTGTGCAAGTCTGAAGTGAAAGGCATGGGCT CAACCTGTGGACTGCATTGGAAACTGTCATACTTGAGTGCCGGA GGGTAAGCGGAATTCCTAGTGTAGCGGTGAAATGCTAGATAT TAGGAGGAACACCAGTGGCGAAGGCGGCTTACTGGACGGTAAC TGACGTTGAGGCTCGAAAGCGTGGGTAGCAAACAGG |
| 51 | 471308 | 0.09 ± 0.03 | Firmicutes; Bacilli; Lactobacillales; Lactobacillaceae; Lactobacillus; Lactobacillus_ruminis | TACGTAGTGGCAGGCGTTGTCCGGATTTATTGGGCGTAAAGG GAACCAGGCGGTCTTTTAAGTCTGATGTGAAAGCCTTCGGCTT AACCGAAGTAGTGCATTGGAAACTGGAAGACTTGAGTGCAGAAG AGGAGAGTGGAGTCCATGTGTAGCGGTGAAATGCGTAGATATA TGGAAGAACACCAGTGGCGAAAGCGGCTCTCTGGTCTGTAACT GACGCTGAGGTTCGAAAGCGTGGGTAGCAAACAGG |
| 52 | 307981 | 0.09 ± 0.03 | Proteobacteria; Gammaproteobacteria; Enterobacteriales; Enterobacteriaceae | TACGGAGGGTGCAAGCGTTAATCGGAATTACTGGGCGTAAAGC GCACGCAGGCGGTTTGTTAAGTCAGATGTGAAATCCCCGGGCT CAACCTGGGAACTGCATCTGATACTGGCAAGCTTGAGTCTCGTA GAGGGGGTAGAATTCCAGGTGTAGCGGTGAAATGCGTAGAGA TCTGGAGGAATACCGGTGGCGAAGGCGGCCCCCTGGACAAGA CTGACGCTCAGTGCGAAAGCGTGGGGAGCAAACAGG |
| 53 | 15382 | 0.08 ± 0.02 | Firmicutes; Bacilli; Lactobacillales; Streptococcaceae; Streptococcus | TACGTAGGTCCCGAGCGTTGTCCGGATTTATTGGGCGTAAAGCG AGCGCAGGCGGTTTGATAAGTCTGAAGTTAAAGGCTGTGGCTCA ACCATAGTTCGCTTTGGAAACTGTCAAACTTGAGTGCAGAAGGG GAGAGTGGAATTCCATGTGTAGCGGTGAAATGCGTAGATATATG GAGGAACACCGGTGGCGAAAGCGGCTCTCTGGTCTGTAACTGA CGCTGAGGCTCGAAAGCGTGGGGAGCAAACAGG |
| 54 | 302844 | 0.08 ± 0.02 | Firmicutes; Clostridia; Clostridiales; Clostridiaceae; Clostridium; Clostridium_disporicum | TACGTAGTGGGCAGCGTTGTCCGGATTTACTGGGCGTAAAGG GAGCGTAGGCGGACTTTTTAAGTGAGATGTGAAATACCCGGGCT CAACTTGGGTGCTGCATTTCAAACTGGAAGTCTAGAGTGCAGGA GAGGAGAATGGAATTCCTAGTGTAGCGGTGAAATGCGTAGAGAT TAGGAAGAACACCAGTGGCGAAGGCGGATTCTCTGGACTGTAACT GACGCTGAGGCTCGAAAGCGTGGGAGCAAACAGG |

TABLE 5-continued 16S rRNA sequences and annotation of age-discriminatory bacterial taxa in order of feature importance

| Rank Order / SEQ ID NO | 16S rRNA OTU ID (as shown in FIG. 1) | Age discriminatory feature importance score (mean ± SD) | RDP 2.4 Taxonomic Annotation (Phylum; Class; Order; Family; Genus; Species) | Representative 16S rRNA Sequence of the 97% ID OTU cluster |
|---|---|---|---|---|
| 55 | 528842 | 0.08 ± 0.02 | Firmicutes; Bacilli; Lactobacillales; Streptococcaceae; Streptococcus; Streptococcus_parasanguinis | TACGTAGTCCCGAGCGTTATCCGGATTTATTGGGCGTAAAGCG AGCGCAGGCGGTTAGATAAGTCTGAAGTTAAAGGCTGTGGCTTA ACCATAGTACGCTTTGAAACTGTTTAACTTGAGTGCAGAAGGG GAGAGTGGAATTCCATGTGTAGCGGTGAAATGCGTAGATATATG GAGGAACACCGGTGGCGAAAGCGGCTCTCTGGTCTGTAACTGA CGCTGAGGCTCGAAAGCGTGGGGAGCAAACAGG |
| 56 | 131391 | 0.08 ± 0.03 | Actinobacteria; 1760; Bifidobacteriales; Bifidobacteriaceae; Bifidobacterium | TACGTAGTCCCGAGCGTTGTCCGGATTTATTGGGCGTAAAGG GCTCGTAGGCGGTTCGTCCGCGTCCGGTGTGAAAGTCCATCGCT TAACGGTGATCCGCGCGGGTACGGGCGGGCTTGAGTGCGG TAGGGGAGACTGGAATTCCCGGTGTAACGGTGGAATGTGTAGA TATCGGGAAGAACACCAATGGCGAAGGCAGGTCTCTGGGCCGT TACTGACGCTGAGGAGCGAAAGCGTGGGAGCGAACAGG |
| 57 | 259261 | 0.08 ± 0.02 | Firmicutes; Negativicutes; Selenomonadales; Veillonellaceae; Megamonas | TACGTAGGCGGCAAGCGTTGTCCGGAATTATTGGGCGTAAAGG GAGCCAGGCGGCAAATTAAGCGGATCTTAAAGTGCGGGGCT CAACCCCGTGATGGGTCCGAACTGTTTTCTTGAGTGCAGGA GAGGAAAGCGGAATTCCCAGTGTAGCGGTGAAATGCGTAGATAT TGGGAAGAACACCAGTGGCGAAGGCGCTTTCTGGACTGTAAC TGACGCTGAGGCTCGAAAGCTAGGGTAGCGAACGGG |
| 58 | 248563 | 0.08 ± 0.02 | Firmicutes; Clostridia; Clostridiales; Clostridiaceae; Clostridium | TACGTAGTGGCGAGCGTTGTCCGGATTTACTGGGCGTAAAGG GAGCGTAGGCGGATTTTTAAGTGAGATGTGAAATACTCGGCTT AACCTGAGTGCTGCATTTCAAACTGGAAGTCTAGAGTGCAGGAG AGGAGAGGGAATTCCTAGTGTAGCGGTGAAATGCGTAGAGATT AGGAGAACACCAGTGGCGAAGGCGCTCTCTGGACTGTAACT GACGCTGAGGCTCGAAAGCGTGGGGAGCAAACAGG |
| 59 | 162427 | 0.08 ± 0.02 | Firmicutes; Negativicutes; Selenomonadales; Veillonellaceae; Megasphaera | TACGTAGTGGCAAGCGTTGTCCGGAATTATTGGGCGTAAAGG GCGCGCAGGCGGCATCGCAAGTCGTCTTAAAAGTGCGGGGCT TAACCCCCGTGAGGGGACCGAAACTGTGAAGCTCGAGTGTCGA GAGGAAAGCGGAATTCCTAGTGTAGCGGTGAAATGCGTAGATAT TAGGAGGAACACCAGTGGCGAAAGCGGCTTTCTGGACGACAAC TGACGCTGAGGCGCGAAAGCCAGGGGAGCAAACGGG |
| 60 | 545371 | 0.07 ± 0.01 | Firmicutes; Bacilli; Lactobacillales; Lactobacillaceae; Lactobacillus | TACGTAGTGGCAAGCGTTGTCCGGATTTATTGGGCGTAAAGCG CAGGCGGAAGAATAAGTCTGAAGTGAAAGCCCCGGCTT AACCGGGAACTGCTTCGGAAACTGTTCTTCTTGAGTGCAGAAG AGAGAGTGGAACTCCATGTGTAGCGGTGAAATGCGTAGATATA TGGAAGAACACCAGTGCGAAGGCGGCTCTCTGGTCTGTCAACT GACGCTGAGGCTCGAAAGCATGGGTAGCGAACAGG |

The larger the age-discriminatory importance score the more important the indicated taxon is for age discrimination (determined by permutation using unscaled feature importance scores)

TABLE 6

Associations between relative microbiota maturity, Microbiota-for-Age Z-score and age-adjusted Shannon Diversity Index (SDI) with clinical and dietary parameters in the healthy twins and triplets birth cohort (a) Relative microbiota maturity

| Factor | Effect size on relative microbiota maturity | Standard Error | p-value |
|---|---|---|---|
| diarrhoea | −1.98 | 0.51 | 0.0001 |
| Month following diarrhoea | −1.55 | 0.56 | 0.01 |
| Formula | +0.75 | 0.34 | 0.03 |
| Antibiotics | −0.42 | 0.39 | 0.27 |
| Chronologic Age (months) | −0.05 | 0.02 | 0.06 |

| | Log-likelihood ratio | Degrees of Freedom | p-value |
|---|---|---|---|
| random by-family intercepts | 102.1 | 1 | p < 0.0001 |
| nested random by-child intercepts within family-intercepts | 3.29E−07 | 1 | 0.9995 |

(b) MAZ score

| Factor | Effect size on MAZ | Standard Error | p-value |
|---|---|---|---|
| diarrhoea | −0.60 | 0.16 | 0.0002 |
| Month following diarrhoea | −0.42 | 0.18 | 0.02 |
| Formula | +0.22 | 0.11 | 0.04 |
| Antibiotics | −0.08 | 0.12 | 0.52 |
| Chronologic Age (months) | −0.04 | 0.01 | <0.001 |

| | Log-likelihood ratio | Degrees of Freedom | p-value |
|---|---|---|---|
| random by-family intercepts | 102.1 | 1 | <0.0001 |
| nested random by-child intercepts within family-intercepts | 3.29E−07 | 1 | 0.9995 |

(c) Age-adjusted Shannon Diversity Index

| Factor | Effect size on ΔSDI | Standard Error | p-value |
|---|---|---|---|
| diarrhoea | −0.44 | 0.15 | 0.0028 |
| Month following diarrhoea | −0.37 | 0.16 | 0.0247 |
| Formula | +0.11 | 0.10 | 0.2796 |
| Antibiotics | −0.08 | 0.11 | 0.3987 |
| Chronologic Age (months) | +0.01 | 0.01 | 0.296 |

| | Log-likelihood ratio | Degrees of Freedom | p-value |
|---|---|---|---|
| random by-family intercepts | 53.8 | 1 | <.0001 |
| nested random by-child intercepts within family-intercepts | 1.31 | 1 | 0.2515 |

TABLE 7

Identification of factors affecting variance in fecal microbiota configuration of healthy twins and triplets

| | | Hellinger Distance Metric | | | | | Unweighted UniFrac Distance Metric | | | | |
|---|---|---|---|---|---|---|---|---|---|---|---|
| Factor | | SumsOf Sqs | MeanSqs | F. Model | R² | p-value | SumsOf Sqs | MeanSqs | F. Model | R² | p-value |
| Chronologic Age | | 0.6212 | 0.6212 | 108.364 | 0.19033 | 0.001 | 0.79963 | 0.79963 | 290.79 | 0.37721 | 0.001 |
| Diet at time of fecal sample collection | Breastmilk | 0.0549 | 0.0549 | 9.568 | 0.01681 | 0.001 | 0.03117 | 0.03117 | 11.336 | 0.01471 | 0.052 |
| | Formula | 0.0049 | 0.0049 | 0.848 | 0.00149 | 0.88 | 0.00939 | 0.00939 | 3.415 | 0.00443 | 0.184 |
| | Solid foods | 0.0205 | 0.0205 | 3.584 | 0.00629 | 0.08 | 0.03922 | 0.03922 | 14.263 | 0.0185 | 0.001 |
| diarrhoea | | 0.01 | 0.01 | 1.681 | 0.00295 | 0.18 | 0.01255 | 0.01255 | 4.563 | 0.00592 | 0.006 |
| Antibiotic Usage | | 0.002 | 0.002 | 0.294 | 0.00052 | 0.88 | 0.00421 | 0.00421 | 1.533 | 0.00199 | 0.154 |

PERMANOVA was implemented using the R vegan package's 'adonis function'. We tested for significant associations in a linear model between microbiota variation (as measured by Hellinger or unweighted Unifrac metrics) and the indicated factors. Permutations were constrained within each twin-pair and the set of triplets and interactions between factors were not considered.

TABLE 8

Bacterial taxa enriched in the gut microbiota of Bangladeshi mothers during the first post-partum month compared to subsequent months 2-12

| 16S rRNA OTU ID (as shown in FIG. 2B) | Relative abundance (%) during first month post-partum[1] | Relative abundance (%) during subsequent months | FDR-corrected p value | Beta Coefficient[2] | Rank order of importance in Random Forests-based age-discriminatory model | RDP 2.4 Taxonomic Annotation (Phylum; Class; Order; Family; Genus; Species) |
|---|---|---|---|---|---|---|
| 469873 | 12.27 ± 4.91 | 2.08 ± 0.45 | 0.033 | +0.148 | 22 | Actinobacteria; 1760; Bifidobacteriales; Bifidobacteriaceae; *Bifidobacterium* |
| 72820 | 7.70 ± 3.33 | 0.64 ± 0.14 | 0.001 | +0.13 | 5 | Actinobacteria; 1760; Bifidobacteriales; Bifidobacteriaceae; *Bifidobacterium*; Bifidobacterium_longum |
| 348374 | 0.62 ± 0.60 | 0.00 ± 0.00 | 0.012 | +0.028 | | Bacteroidetes; Bacteroidia; Bacteroidales; Bacteroidaceae; *Bacteroides*; Bacteroides_thetaiotaomicron |
| 158660 | 0.54 ± 0.46 | 0.02 ± 0.01 | 0.037 | +0.025 | | Bacteroidetes; Bacteroidia; Bacteroidales; Bacteroidaceae; *Bacteroides* |

TABLE 8-continued

Bacterial taxa enriched in the gut microbiota of Bangladeshi mothers during the first post-partum month compared to subsequent months 2-12

| 16S rRNA OTU ID (as shown in FIG. 2B) | Relative abundance (%) during first month post-partum[1] | Relative abundance (%) during subsequent months | FDR-corrected p value | Beta Coefficient[2] | Rank order of importance in Random Forests-based age-discriminatory model | RDP 2.4 Taxonomic Annotation (Phylum; Class; Order; Family; Genus; Species) |
|---|---|---|---|---|---|---|
| 194648 | 0.40 ± 0.13 | 0.11 ± 0.01 | 0.020 | +0.024 | | Firmicutes; Clostridia; Clostridiales; unclassified_Clostridiales; *Blautia*; Blautia_sp_M25 |
| 528842 | 0.29 ± 0.26 | 0.02 ± 0.00 | 0.006 | +0.023 | | Firmicutes; Bacilli; Lactobacillales; Streptococcaceae; *Streptococcus*; Streptococcus_parasanguinis |
| 561483 | 0.15 ± 0.07 | 0.01 ± 0.00 | <0.0001 | +0.019 | 8 | Actinobacteria; 1760; Bifidobacteriales; Bifidobacteriaceae; *Bifidobacterium* |
| 113558 | 0.19 ± 0.12 | 0.02 ± 0.00 | 0.027 | +0.018 | | Proteobacteria; Gammaproteobacteria; Enterobacteriales; Enterobacteriaceae |
| 122816 | 0.16 ± 0.15 | 0.00 ± 0.00 | 0.007 | +0.014 | | Proteobacteria; Gammaproteobacteria; Enterobacteriales; Enterobacteriaceae; *Morganella*; Morganella_morganii |
| 259130 | 0.10 ± 0.09 | 0.00 ± 0.00 | 0.012 | +0.011 | | Firmicutes; Clostridia; Clostridiales; Eubacteriaceae; *Eubacterium*; Eubacterium_limosum |
| 259422 | 0.06 ± 0.05 | 0.00 ± 0.00 | 0.012 | +0.008 | | Firmicutes; Bacilli; Lactobacillales; Lactobacillaceae; *Lactobacillus* |
| 192132 | 0.04 ± 0.03 | 0.00 ± 0.00 | 0.024 | +0.007 | | Proteobacteria; Deltaproteobacteria; Desulfovibrionales; Desulfovibrionaceae; *Bilophila*; Bilophila_wadsworthia |
| 44126 | 0.03 ± 0.02 | 0.00 ± 0.00 | 0.012 | +0.007 | | Firmicutes; Bacilli; Lactobacillales; Enterococcaceae; *Enterococcus* |

[1]Mean values ± SEM are shown
[2]Beta-coefficient is the measure of effect size in linear mixed models used to identify maternally-enriched taxa during the first post-partum month

TABLE 9

Metadata for Bangladeshi children with SAM in a randomized clinical trial of RUTF versus Khichuri-Halwa

| Child ID | Gender | WHZ at enrollment | Food Intervention Assignment | Age at beginning of intervention (months) | Duration of food intervention (days)[1] | WHZ at end of food intervention phase | Rate of weight gain (g/kg body weight/day) | Enteropathogens detected at enrollment | Months followed during post intervention period |
|---|---|---|---|---|---|---|---|---|---|
| Bgmal1 | Male | −5.22 | RUTF | 7.43 | 28 | −2.97 | 2.12 | none detected | 5.53 |
| Bgmal5 | Male | edema | RUTF | 10.87 | 21 | −4.18 | 8.07 | none detected | 5.97 |
| Bgmal6 | Male | −4 | RUTF | 11.7 | 17 | −2.75 | 10.69 | none detected | lost to follow-up |
| Bgmal7 | Female | −3.92 | RUTF | 10.3 | 27 | −2.72 | 12.47 | none detected | 3.04 |
| Bgmal9 | Female | −3.76 | RUTF | 11.27 | 8 | −3.02 | 5.18 | not done | lost to follow-up |
| Bgmal13 | Female | −3.51 | RUTF | 6.67 | 3 (LAMA) | −3.78 | 4.63 | none detected | lost to follow-up |
| Bgmal14 | Male | −4.17 | RUTF | 14.2 | 17 | −2.79 | 8.31 | *Vibrio cholerae* | lost to follow-up |
| Bgmal15 | Male | −4.03 | RUTF | 17.37 | 8 | −2.49 | 17.23 | none detected | 2 |
| Bgmal18 | Male | −4.6 | RUTF | 14.97 | 17 | −3.67 | 4.76 | none detected | 1.1 |
| Bgmal20 | Female | −3.38 | RUTF | 10.67 | 9 (LAMA) | −3.32 | 11.13 | *Shigella flexneri* | lost to follow-up |
| Bgmal22 | Male | −3.35 | RUTF | 9.27 | 8 | −3.31 | 4.75 | not done | 6.17 |
| Bgmal25 | Male | −3.38 | RUTF | 6.77 | 18 | −2.25 | 7.82 | none detected | 6 |
| Bgmal26 | Male | −4.97 | RUTF | NA | 3 (LAMA) | −5.23 | 16.2 | none detected | lost to follow-up |
| Bgmal27 | Male | −4.91 | RUTF | 9.07 | 16 | −3.75 | 15.98 | none detected | lost to follow-up |
| Bgmal29 | Male | −4.07 | RUTF | 10.47 | 8 | −2.63 | 16.87 | none detected | 0.13 |
| Bgmal33 | Female | −4.86 | RUTF | 8.33 | 21 | −3.23 | 11.6 | none detected | 3.93 |
| Bgmal34 | Male | −4.73 | RUTF | 16.6 | 17 | −3.3 | 14.7 | none detected | 3.04 |
| Bgmal35 | Male | −5.28 | RUTF | 7.87 | 15 | −3.92 | 12.3 | not done | 4.9 |
| Bgmal38 | Male | −4.66 | RUTF | 14.13 | 1 (LAMA) | −4.66 | no weight gain | none detected | lost to follow-up |
| Bgmal41 | Female | −3.39 | RUTF | 18.8 | 17 | −2.33 | 8.6 | *Shigella boydi* | 4.87 |
| Bgmal42 | Female | −3.4 | RUTF | 14.6 | 13 | −2.58 | 10.7 | *Hafnia alvae* | lost to follow-up |
| Bgmal43 | Male | −5.3 | RUTF | 7.13 | 14 | −4.07 | 15.3 | none detected | 5.9 |
| Bgmal44 | Male | −3.45 | RUTF | 7.77 | 14 | −2.63 | 10.1 | not done | 5.9 |
| Bgmal48 | Male | −3.3 | RUTF | 16.1 | 13 | −1.99 | 8.6 | *Vibrio cholerae* | 1.54 |
| Bgmal49 | Male | −4.09 | RUTF | 8.73 | 4 (LAMA) | −3.81 | 15.9 | none detected | lost to follow-up |
| Bgmal52 | Male | −5.3 | RUTF | 12.57 | 12 (LAMA) | −4.24 | 4.5 | not done | lost to follow-up |
| Bgmal54 | Female | −3.91 | RUTF | 10.53 | 14 | −3.1 | 7.4 | not done | 2.93 |
| Bgmal57 | Male | −4.24 | RUTF | 17.33 | 12 | −2.57 | 13.8 | not done | 6 |
| Bgmal58 | Male | −4.29 | RUTF | 11.07 | 11 | −2.13 | 17.1 | not done | 7.27 |
| Bgmal59 | Male | −4.54 | RUTF | 14.77 | 9 | −2.75 | 16.2 | not done | 6.06 |
| Bgmal61 | Male | −4.44 | RUTF | 14.27 | 13 | −3.31 | 16.69 | not done | 0.54 |
| Bgmal62 | Male | −3.51 | RUTF | 7.33 | 20 | −2.34 | 6.92 | not done | 1.5 |

TABLE 9-continued

Metadata for Bangladeshi children with SAM in a randomized clinical trial of RUTF versus Khichuri-Halwa

| Child ID | Gender | WHZ at enrollment | Food Intervention Assignment | Age at beginning of intervention (months) | Duration of food intervention (days)[1] | WHZ at end of food intervention phase | Rate of weight gain (g/kg body weight/day) | Enteropathogens detected at enrollment | Months followed during post intervention period |
|---|---|---|---|---|---|---|---|---|---|
| Bgmal2  | Female | −4.21  | Khichuri-Halwa | 12.13 | 21       | −2.72 | 10.62 | none detected            | lost to follow-up |
| Bgmal3  | Male   | −4.4   | Khichuri-Halwa | 9.23  | 17       | −3.09 | 10.1  | Vibrio cholerae          | 3.76 |
| Bgmal4  | Male   | −4.35  | Khichuri-Halwa | 9.13  | 29       | −3.53 | 4.85  | none detected            | 1.03 |
| Bgmal8  | Female | −3.29  | Khichuri-Halwa | 17.9  | 18       | −1.7  | 8.57  | none detected            | 2.07 |
| Bgmal10 | Male   | −5.45  | Khichuri-Halwa | 15.57 | 13       | −3.69 | 16.48 | none detected            | 1.97 |
| Bgmal11 | Male   | −3.84  | Khichuri-Halwa | 15.07 | 16       | −3.13 | 1.95  | none detected            | lost to follow-up |
| Bgmal12 | Female | −3.48  | Khichuri-Halwa | 19.77 | 9        | −1.67 | 13.91 | none detected            | 0.56 |
| Bgmal16 | Female | −3.94  | Khichuri-Halwa | 12.73 | 8        | −2.12 | 16.42 | none detected            | 0.16 |
| Bgmal17 | Male   | −4.2   | Khichuri-Halwa | na    | 2 (LAMA) | −4.16 | 3.78  | none detected            | lost to follow-up |
| Bgmal19 | Male   | edema  | Khichuri-Halwa | 7.8   | 25       | −0.09 | 7.06  | Aeromona hydrophila      | 1.17 |
| Bgmal21 | Male   | −4.76  | Khichuri-Halwa | 8.83  | 22       | −3.89 | 3.31  | none detected            | 2.74 |
| Bgmal23 | Male   | −3.15  | Khichuri-Halwa | 9.97  | 6 (LAMA) | −3.1  | 4     | not done                 | lost to follow-up |
| Bgmal24 | Male   | −4.63  | Khichuri-Halwa | 8.43  | 14       | −3.94 | 4.81  | Shigella sonnei          | 0.46 |
| Bgmal28 | Female | −3.56  | Khichuri-Halwa | 15.87 | 18       | −2.26 | 8.89  | Shigella flexneri        | 5.94 |
| Bgmal30 | Female | −3.35  | Khichuri-Halwa | 9.2   | 13       | −2.13 | 11.31 | none detected            | lost to follow-up |
| Bgmal31 | Male   | −4.47  | Khichuri-Halwa | 13.9  | 13       | −3    | 12.5  | none detected            | 5.67 |
| Bgmal32 | Male   | −4.54  | Khichuri-Halwa | 19.9  | 15       | −3.05 | 11.4  | none detected            | 5.9 |
| Bgmal36 | Male   | −3.96  | Khichuri-Halwa | 15.37 | 27       | −2.61 | 5.9   | none detected            | 3.4 |
| Bgmal37 | Male   | −3.37  | Khichuri-Halwa | 13.13 | 26       | 3.01  | 2.6   | none detected            | 5.43 |
| Bgmal39 | Female | −5.59  | Khichuri-Halwa | 14.13 | 10       | −4.93 | 15.9  | Salmonella enterica group C1 | 9.1 |
| Bgmal40 | Female | −4.21  | Khichuri-Halwa | 10.1  | 27       | −3.76 | 3.3   | not done                 | 5.57 |
| Bgmal45 | Male   | −5.32  | Khichuri-Halwa | 8.6   | 26       | −4.58 | 5.6   | none detected            | 5.9 |
| Bgmal46 | Female | −5.4   | Khichuri-Halwa | 18.5  | 15       | −4.03 | 12.3  | none detected            | 3.87 |
| Bgmal47 | Female | −4.76  | Khichuri-Halwa | 12.33 | 10       | −3.91 | 10.8  | Shigella flexneri        | 5.9 |
| Bgmal50 | Male   | −3.79  | Khichuri-Halwa | 13.97 | 13       | −2.23 | 12.9  | not done                 | 6.03 |
| Bgmal51 | Male   | −4.03  | Khichuri-Halwa | 14.93 | 10       | −2.22 | 14.7  | Vibrio cholerae          | 1.96 |
| Bgmal53 | Male   | −4.54  | Khichuri-Halwa | 14.53 | 11       | −2.76 | 16.1  | not done                 | lost to follow-up |
| Bgmal55 | Male   | −5.58  | Khichuri-Halwa | 8.4   | 4 (LAMA) | −4.9  | 23.2  | not done                 | lost to follow-up |
| Bgmal56 | Male   | −3.35  | Khichuri-Halwa | 9     | 11       | −1.87 | 13.5  | not done                 | 7.3 |
| Bgmal60 | Male   | edema  | Khichuri-Halwa | 8.97  | 15       | −0.71 | 11.7  | not done                 | 5.9 |
| Bgmal63 | Male   | −3.02  | Khichuri-Halwa | 8.47  | 12       | −1.59 | 14.74 | not done                 | 6 |
| Bgmal64 | Female | −3.1   | Khichuri-Halwa | 11.17 | 8        | −1.55 | 19.77 | not done                 | 4.5 |

[1]LAMA—left against medical advice

TABLE 10

Contingency tables relating gender and antibiotics to food-intervention arms in the SAM trial (a) 'Gender by Food-intervention'

| Gender | RUTF | Khichuri-Halwa | Total | p value |
|---|---|---|---|---|
| Male   | 24 | 21 | 45 | |
| Female | 8  | 11 | 19 | |
| Total  | 32 | 32 | 64 | 0.59 |

| Antibiotics | RUTF | Khichuri-Halwa | Total | p value |
|---|---|---|---|---|

(b) 'Antibiotics by Food-intervention' during nutritional rehabilitation

| | | | | |
|---|---|---|---|---|
| Yes   | 84  | 79  | 163 | |
| No    | 55  | 90  | 145 | |
| Total | 139 | 169 | 308 | 0.02 |

(c) 'Antibiotics by Food-intervention' during the post-intervention follow-up period

| | | | | |
|---|---|---|---|---|
| Yes   | 22  | 23  | 45  | |
| No    | 78  | 80  | 158 | |
| Total | 100 | 103 | 203 | 1 |

Fisher's Exact test (two-sided) p-value are presented

TABLE 11

Ingredients of foods used during nutritional rehabilitation of children with SAM (a) Khichuri

| Ingredient | Amount in 1 kg khichuri |
|---|---|
| Rice | 120 g |
| Lentils (mashur dal) | 60 g |
| Oil (soya) | 70 ml |
| Potato | 100 g |
| Pumpkin | 100 g |
| Leafy vegetable (shak) | 80 g |
| Onion (2 medium size) | 50 g |
| Spices (ginger, garlic, turmeric and coriander powder) | 50 g |
| Water | 1000 ml |
| Total energy/kg | 1,442 kcal |
| Total protein/kg | 29.6 g |

(b) Halwa

| Ingredient | Amount in 1 kg halwa |
|---|---|
| Wheat flour (atta) | 200 g |
| Lentils (mashur dal) | 100 g |
| Oil (soya) | 100 ml |
| Molasses (brown sugar or gur) | 125 g |
| Water (to make a thick paste) | 600 ml |

TABLE 11-continued

Ingredients of foods used during nutritional rehabilitation of children with SAM

| Total energy/kg | 2,404 kcal |
| Total protein/kg | 50.5 g |

(c) Milk suji & Milk suji '100'

| Ingredient | Amount in 1 L Milk Suji | Amount in 1 L Milk Suji '100' |
| --- | --- | --- |
| Whole milk powder (g) | 40 | 80 |
| Rice powder (g) | 40 | 50 |
| Sugar (g) | 25 | 50 |
| Soya oil (g) | 25 | 25 |
| $MgCl_2$ (g) | 0.5 | 0.5 |
| KCl (g) | 1 | 1 |
| Calcium lactate/calcium carbonate (g) | 2 | 2 |
| Total energy/L | 670 kcal | 1000 kcal |
| Total protein/L | 14 g | 26 g |

(d) RUTF (Plumpy Nut)[1]

| Ingredient | Amount in 1 kg RUTF |
| --- | --- |
| Skimmed milk powder | 300 g |
| Sugar | 280 g |
| Vegetable oil | 154 g |
| Peanut paste | 250 g |
| Mineral vitamin mix | 16 g |
| Total energy/kg | 5300-5450 kcal |
| Total protein/kg | 136 g |

[1]Formulation complies with the WHO macro- and micronutrient profile requirements for RUTF.

TABLE 12

Relative microbiota maturity, Microbiota-for-Age Z-score and Age-adjusted Shannon Diversity Index comparisons in each treatment phase of each intervention arm in the SAM trial (compared to healthy controls and to values at enrollment)

|  | Intervention Arm | Estimate | Std. Error | p value |
| --- | --- | --- | --- | --- |

(a) Effect size and significance of differences in microbiota maturation metrics between each treatment phase relative to healthy children Relative microbiota maturity

| Enrollment | RUTF | −5.62 | 0.78 | <0.001 |
| During | | −5.09 | 0.68 | <0.001 |
| End of Intervention | | −4.75 | 0.82 | <0.001 |
| <1 month | | −2.85 | 0.83 | <0.01 |
| 1-2 months | | −2.19 | 0.87 | 0.07 |
| 2-3 months | | −0.31 | 1.03 | 1.00 |
| 3-4 months | | −1.96 | 1.11 | 0.35 |
| >4 months | | −3.43 | 0.96 | <0.01 |
| Enrollment | Khichuri-Halwa | −6.55 | 0.67 | <0.001 |
| During | | −5.88 | 0.53 | <0.001 |
| End of Intervention | | −5.63 | 0.72 | <0.001 |
| <1 month | | −3.98 | 0.74 | <0.001 |
| 1-2 months | | −1.72 | 0.79 | 0.18 |
| 2-3 months | | −2.67 | 0.89 | 0.02 |
| 3-4 months | | −1.58 | 1.05 | 0.59 |
| >4 months | | −2.29 | 0.82 | 0.04 |

Microbiota-for-Age Z-score

| Enrollment | RUTF | −1.63 | 0.26 | <0.001 |
| During | | −1.49 | 0.23 | <0.001 |
| End of Intervention | | −1.39 | 0.27 | <0.001 |
| <1 month | | −0.84 | 0.27 | 0.01 |
| 1-2 months | | −0.75 | 0.28 | 0.04 |
| 2-3 months | | −0.42 | 0.33 | 0.68 |
| 3-4 months | | −0.73 | 0.35 | 0.19 |
| >4 months | | −1.43 | 0.31 | <0.001 |
| Enrollment | Khichuri-Halwa | −1.80 | 0.23 | <0.001 |
| During | | −1.68 | 0.19 | <0.001 |
| End of Intervention | | −1.66 | 0.24 | <0.001 |
| <1 month | | −1.30 | 0.25 | <0.001 |
| 1-2 months | | −0.69 | 0.26 | 0.06 |
| 2-3 months | | −1.05 | 0.29 | <0.01 |
| 3-4 months | | −0.56 | 0.34 | 0.46 |
| >4 months | | −0.96 | 0.27 | <0.01 |

Age-Adjusted Shannon Diversity Index

| Enrollment | RUTF | −1.18 | 0.16 | <0.001 |
| During | | −0.82 | 0.12 | <0.001 |
| End of Intervention | | −0.89 | 0.17 | <0.001 |
| <1 month | | −0.56 | 0.18 | 0.01 |
| 1-2 months | | −0.30 | 0.19 | 0.55 |
| 2-3 months | | −0.46 | 0.24 | 0.32 |
| 3-4 months | | −1.18 | 0.26 | <0.001 |
| >4 months | | −0.79 | 0.22 | <0.01 |
| Enrollment | Khichuri-Halwa | −1.03 | 0.15 | <0.001 |
| During | | −0.95 | 0.11 | <0.001 |
| End of Intervention | | −0.90 | 0.16 | <0.001 |
| <1 month | | −0.83 | 0.17 | <0.001 |
| 1-2 months | | −0.89 | 0.18 | <0.001 |
| 2-3 months | | −0.73 | 0.21 | <0.01 |
| 3-4 months | | −0.41 | 0.25 | 0.54 |
| >4 months | | −0.58 | 0.19 | 0.02 |

(b) Effect size and significance of differences in microbiota maturation metrics between each treatment phase relative to enrollment Relative microbiota maturity

| Healthy | RUTF | 5.62 | 0.78 | <0.001 |
| During | | 0.53 | 0.57 | 0.93 |
| End of Intervention | | 0.87 | 0.73 | 0.80 |
| <1 month | | 2.77 | 0.74 | <0.01 |
| 1-2 months | | 3.44 | 0.78 | <0.001 |
| 2-3 months | | 5.31 | 0.96 | <0.001 |
| 3-4 months | | 3.67 | 1.05 | <0.01 |
| >4 months | | 2.20 | 0.88 | 0.08 |
| Healthy | Khichuri-Halwa | 6.55 | 0.67 | <0.001 |
| During | | 0.67 | 0.56 | 0.79 |
| End of Intervention | | 0.92 | 0.74 | 0.76 |
| <1 month | | 2.58 | 0.76 | <0.01 |
| 1-2 months | | 4.83 | 0.81 | <0.001 |
| 2-3 months | | 3.88 | 0.91 | <0.001 |
| 3-4 months | | 4.97 | 1.07 | <0.001 |
| >4 months | | 4.27 | 0.84 | <0.001 |

Microbiota-for-Age Z-score

| Healthy | RUTF | 1.63 | 0.26 | <0.001 |
| During | | 0.13 | 0.17 | 0.98 |
| End of Intervention | | 0.24 | 0.22 | 0.88 |
| <1 month | | 0.79 | 0.23 | <0.01 |
| 1-2 months | | 0.88 | 0.24 | <0.01 |
| 2-3 months | | 1.21 | 0.30 | <0.001 |
| 3-4 months | | 0.90 | 0.32 | 0.036 |
| >4 months | | 0.20 | 0.27 | 0.98 |
| Healthy | Khichuri-Halwa | 1.80 | 0.23 | <0.001 |
| During | | 0.12 | 0.17 | 0.99 |
| End of Intervention | | 0.14 | 0.23 | 0.99 |
| <1 month | | 0.50 | 0.24 | 0.20 |
| 1-2 months | | 1.11 | 0.25 | <0.001 |
| 2-3 months | | 0.75 | 0.28 | 0.05 |

TABLE 12-continued

Relative microbiota maturity, Microbiota-for-Age Z-score and Age-adjusted Shannon Diversity Index comparisons in each treatment phase of each intervention arm in the SAM trial (compared to healthy controls and to values at enrollment)

| | Intervention Arm | Estimate | Std. Error | p value |
|---|---|---|---|---|
| 3-4 months | | 1.24 | 0.33 | 0.001 |
| >4 months | | 0.84 | 0.26 | 0.01 |
| Age-adjusted Shannon Diversity Index | | | | |
| Healthy | RUTF | 1.18 | 0.16 | <0.001 |
| During | | 0.36 | 0.15 | 0.11 |
| End of Intervention | | 0.29 | 0.19 | 0.56 |
| <1 month | | 0.62 | 0.20 | 0.01 |
| 1-2 months | | 0.88 | 0.21 | <0.001 |
| 2-3 months | | 0.72 | 0.26 | 0.03 |
| 3-4 months | | 0.00 | 0.28 | 1.00 |
| >4 months | | 0.39 | 0.23 | 0.46 |
| Healthy | Khichuri-Halwa | 1.03 | 0.15 | <0.001 |
| During | | 0.07 | 0.14 | 1.00 |
| End of Intervention | | 0.12 | 0.18 | 0.99 |
| <1 month | | 0.19 | 0.19 | 0.89 |
| 1-2 months | | 0.13 | 0.20 | 0.99 |
| 2-3 months | | 0.30 | 0.23 | 0.70 |
| 3-4 months | | 0.62 | 0.27 | 0.12 |
| >4 months | | 0.45 | 0.21 | 0.18 |

Estimates of beta coefficients, standard error and p-values from Dunnett's post-hoc comparisons between treatment phases for each intervention arm of linear mixed models with random by-child intercepts
Samples associated with diarrhoea in healthy reference controls were not considered as suitable controls and excluded from comparisons

TABLE 13

220 bacterial taxa whose abundances are significantly altered in the microbiota of children with SAM compared to similarly aged healthy children

| 16S rRNA OTU ID (as shown in FIG. 8 & 9) | Unabbreviated OTU ID in deposited OTU table | FDR-corrected p value | Beta Coefficient | Rank order of importance in Random Forests-based age-discriminatory model | RDP 2.4 Taxonomic Annotation (Phylum; Class; Order; Family; Genus; Species) |
|---|---|---|---|---|---|
| (a) Taxa altered in children with SAM relative to healthy controls at enrollment prior to intervention phase ||||||
| 142054 | 142054 | 0.000 | 0.0286 | | Proteobacteria; Gammaproteobacteria; Enterobacteriales; Enterobacteriaceae |
| 210269 | 210269 | 0.000 | 0.0278 | | Proteobacteria; Gammaproteobacteria; Enterobacteriales; Enterobacteriaceae |
| 9715 | 9715 | 0.000 | 0.0263 | | Proteobacteria; Gammaproteobacteria; Enterobacteriales; Enterobacteriaceae |
| 563485 | 563485 | 0.002 | 0.0236 | | Proteobacteria; Gammaproteobacteria; Enterobacteriales; Enterobacteriaceae |
| 436723 | 436723 | 0.000 | 0.0232 | | Proteobacteria; Gammaproteobacteria; Enterobacteriales; Enterobacteriaceae |
| 512914 | 512914 | 0.000 | 0.0215 | | Proteobacteria; Gammaproteobacteria; Enterobacteriales; Enterobacteriaceae |
| 310265 | 310265 | 0.000 | 0.0207 | | Proteobacteria; Gammaproteobacteria; Enterobacteriales; Enterobacteriaceae |
| 307981 | 307981 | 0.000 | 0.0174 | | Proteobacteria; Gammaproteobacteria; Enterobacteriales; Enterobacteriaceae |
| 307080 | 307080 | 0.000 | 0.0152 | | Proteobacteria; Gammaproteobacteria; Enterobacteriales; Enterobacteriaceae; *Escherichia* |
| 305760 | 305760 | 0.000 | 0.0131 | | Proteobacteria; Gammaproteobacteria; Enterobacteriales; Enterobacteriaceae; *Escherichia*; Escherichia_coli |
| 113558 | 113558 | 0.000 | 0.0115 | | Proteobacteria; Gammaproteobacteria; Enterobacteriales; Enterobacteriaceae |
| 280706 | 280706 | 0.000 | 0.0090 | | Proteobacteria; Gammaproteobacteria; Enterobacteriales; Enterobacteriaceae |
| 540230 | 540230 | 0.002 | 0.0079 | | Firmicutes; Bacilli; Lactobacillales; Enterococcaceae; *Enterococcus*; Enterococcus_faecalis |
| 15382 | 15382 | 0.027 | 0.0068 | | Firmicutes; Bacilli; Lactobacillales; Streptococcaceae; *Streptococcus* |
| 249155.c0 | New.0.CleanUp.ReferenceOTU249155 | 0.027 | 0.0067 | | Firmicutes; Bacilli; Lactobacillales; Leuconostocaceae; *Leuconostoc* |
| 316587 | 316587 | 0.007 | 0.0063 | | Firmicutes; Bacilli; Lactobacillales; Streptococcaceae; *Streptococcus*; Streptococcus_gallolyticus |
| 469852 | 469852 | 0.000 | −0.0163 | | Actinobacteria; 1760; Bifidobacteriales; Bifidobacteriaceae; *Bifidobacterium*; Bifidobacterium_bifidum |
| 533785 | 533785 | 0.000 | −0.0146 | 15 | Actinobacteria; 1760; Bifidobacteriales; Bifidobacteriaceae; *Bifidobacterium* |
| 24773 | 24773 | 0.000 | −0.0137 | | Actinobacteria; 1760; Bifidobacteriales; Bifidobacteriaceae; *Bifidobacterium* |
| 326792 | 326792 | 0.000 | −0.0118 | 1 | Firmicutes; Clostridia; Clostridiales; Ruminococcaceae; *Faecalibacterium*; Faecalibacterium_prausnitzii |
| 301004 | 301004 | 0.001 | −0.0115 | | Actinobacteria; 1760; Coriobacteriales; Coriobacteriaceae; *Olsenella* |
| 181834 | 181834 | 0.000 | −0.0112 | 20 | Firmicutes; Clostridia; Clostridiales; Clostridiaceae; *Clostridium* |
| 261912 | 261912 | 0.000 | −0.0109 | 12 | Firmicutes; Clostridia; Clostridiales; Lachnospiraceae; *Dorea*; Dorea_formicigenerans |
| 13823 | 13823 | 0.005 | −0.0104 | | Firmicutes; Negativicutes; Selenomonadales; Veillonellaceae; *Veillonella*; Veillonella_ratti |
| 188900 | 188900 | 0.000 | −0.0103 | | Firmicutes; Clostridia; Clostridiales; Ruminococcaceae; *Faecalibacterium*; Faecalibacterium_prausnitzii |
| 187010 | 187010 | 0.000 | −0.0102 | | Firmicutes; Clostridia; Clostridiales; Ruminococcaceae; *Faecalibacterium*; Faecalibacterium_prausnitzii |
| 131391 | 131391 | 0.000 | −0.0098 | | Actinobacteria; 1760; Bifidobacteriales; Bifidobacteriaceae; *Bifidobacterium* |
| 576.d0 | New.0.ReferenceOTU576 | 0.001 | −0.0097 | | Actinobacteria; 1760; Coriobacteriales; Coriobacteriaceae |

TABLE 13-continued 220 bacterial taxa whose abundances are significantly altered in the microbiota of children with SAM compared to similarly aged healthy children

| 16S rRNA OTU ID (as shown in FIG. 8 & 9) | Unabbreviated OTU ID in deposited OTU table | FDR-corrected p value | Beta Coefficient | Rank order of importance in Random Forests-based age-discriminatory model | RDP 2.4 Taxonomic Annotation (Phylum; Class; Order; Family; Genus; Species) |
|---|---|---|---|---|---|
| 162427 | 162427 | 0.020 | −0.0096 | | Firmicutes; Negativicutes; Selenomonadales; Veillonellaceae; *Megasphaera* |
| 303304 | 303304 | 0.000 | −0.0094 | | Bacteroidetes; Bacteroidia; Bacteroidales; Prevotellaceae; *Prevotella*; Prevotella_copri |
| 470663 | 470663 | 0.000 | −0.0094 | 3 | Firmicutes; Bacilli; Lactobacillales; Lactobacillaceae; *Lactobacillus*; Lactobacillus_ruminis |
| 309068 | 309068 | 0.000 | −0.0093 | | Bacteroidetes; Bacteroidia; Bacteroidales; Prevotellaceae; *Prevotella*; Prevotella_copri |
| 186029 | 186029 | 0.000 | −0.0092 | | Actinobacteria; 1760; Coriobacteriales; Coriobacteriaceae; *Collinsella*; Collinsella_aerofaciens |
| 145149 | 145149 | 0.001 | −0.0090 | | Firmicutes; Negativicutes; Selenomonadales; Veillonellaceae; *Veillonella* |
| 130663 | 130663 | 0.020 | −0.0088 | | Bacteroidetes; Bacteroidia; Bacteroidales; Bacteroidaceae; *Bacteroides*; Bacteroides_fragilis |
| 194745 | 194745 | 0.000 | −0.0088 | 6 | Firmicutes; Clostridia; Clostridiales; Ruminococcaceae; *Ruminococcus*; Ruminococcus_sp_5_1_39BFAA |
| 212503 | 212503 | 0.000 | −0.0088 | | Firmicutes; Clostridia; Clostridiales; Clostridiaceae; *Clostridium* |
| 184464 | 184464 | 0.001 | −0.0085 | | Bacteroidetes; Bacteroidia; Bacteroidales; Prevotellaceae; *Prevotella*; Prevotella_copri |
| 89679.c0 | New.0.CleanUp.ReferenceOTU89679 | 0.007 | −0.0085 | | Actinobacteria; 1760; Coriobacteriales; Coriobacteriaceae; *Collinsella*; Collinsella_aerofaciens |
| 274208 | 274208 | 0.014 | −0.0084 | | Firmicutes; Negativicutes; Selenomonadales; Veillonellaceae; *Megasphaera*; Megasphaera_elsdenii |
| 469873 | 469873 | 0.000 | −0.0081 | 22 | Actinobacteria; 1760; Bifidobacteriales; Bifidobacteriaceae; *Bifidobacterium* |
| 139221 | 139221 | 0.017 | −0.0080 | | Actinobacteria; 1760; Coriobacteriales; Coriobacteriaceae |
| 15141 | 15141 | 0.016 | −0.0079 | 7 | Firmicutes; Bacilli; Lactobacillales; Lactobacillaceae; *Lactobacillus*; Lactobacillus_mucosae |
| 364234 | 364234 | 0.000 | −0.0077 | 10 | Firmicutes; Clostridia; Clostridiales; Ruminococcaceae; *Ruminococcus*; Ruminococcus_sp_5_1_39BFAA |
| 198251 | 198251 | 0.022 | −0.0077 | | Firmicutes; Clostridia; Clostridiales; Ruminococcaceae; *Ruminococcus*; Ruminococcus_gnavus |
| 259261 | 259261 | 0.011 | −0.0077 | | Firmicutes; Negativicutes; Selenomonadales; Veillonellaceae; *Megamonas* |
| 191687 | 191687 | 0.000 | −0.0076 | 4 | Firmicutes; Clostridia; Clostridiales; Lachnospiraceae; *Dorea*; Dorea_longicatena |
| 189827 | 189827 | 0.000 | −0.0073 | 2 | Firmicutes; Clostridia; Clostridiales; Ruminococcaceae; *Ruminococcus*; Ruminococcus_sp_5_1_39BFAA |
| 292302 | 292302 | 0.002 | −0.0072 | | Firmicutes; Bacilli; Lactobacillales; Lactobacillaceae; *Lactobacillus* |
| 365047 | 365047 | 0.000 | −0.0072 | | Firmicutes; Clostridia; Clostridiales; Ruminococcaceae; *Ruminococcus*; Ruminococcus_sp_5_1_39BFAA |
| 250395 | 250395 | 0.000 | −0.0072 | | Firmicutes; Bacilli; Lactobacillales; Lactobacillaceae; *Lactobacillus* |
| 258806.c0 | New.0.CleanUp.ReferenceOTU258806 | 0.005 | −0.0071 | | Actinobacteria; 1760; Coriobacteriales; Coriobacteriaceae |
| 326977 | 326977 | 0.000 | −0.0070 | | Actinobacteria; 1760; Bifidobacteriales; Bifidobacteriaceae; *Bifidobacterium* |
| 165261 | 165261 | 0.005 | −0.0069 | | Firmicutes; Clostridia; Clostridiales; Clostridiaceae; *Clostridium* |
| 370431 | 370431 | 0.003 | −0.0068 | | Actinobacteria; 1760; Actinomycetales; Actinomycetaceae; *Actinomyces*; Actinomyces_odontolyticus |
| 2000 | 2000 | 0.038 | −0.0068 | | Bacteroidetes; Bacteroidia; Bacteroidales; Bacteroidaceae; *Bacteroides*; Bacteroides_fragilis |
| 561483 | 561483 | 0.006 | −0.0067 | 8 | Actinobacteria; 1760; Bifidobacteriales; Bifidobacteriaceae; *Bifidobacterium* |
| 177351 | 177351 | 0.004 | −0.0064 | | Bacteroidetes; Bacteroidia; Bacteroidales; Prevotellaceae; *Prevotella* |
| 72820 | 72820 | 0.005 | −0.0064 | 5 | Actinobacteria; 1760; Bifidobacteriales; Bifidobacteriaceae; *Bifidobacterium*; Bifidobacterium_longum |
| 58262 | 58262 | 0.012 | −0.0064 | | Firmicutes; Negativicutes; Selenomonadales; Veillonellaceae; *Allisonella*; Allisonella_histaminiformans |
| 212619 | 212619 | 0.000 | −0.0063 | 24 | Firmicutes; Clostridia; Clostridiales; Ruminococcaceae |
| 142448 | 142448 | 0.006 | −0.0060 | | Firmicutes; Bacilli; Lactobacillales; Lactobacillaceae; *Lactobacillus* |
| 48207 | 48207 | 0.001 | −0.0060 | | Firmicutes; Negativicutes; Selenomonadales; Veillonellaceae; *Dialister* |
| 158660 | 158660 | 0.038 | −0.0059 | | Bacteroidetes; Bacteroidia; Bacteroidales; Bacteroidaceae; *Bacteroides* |
| 195574 | 195574 | 0.005 | −0.0059 | | Bacteroidetes; Bacteroidia; Bacteroidales; Prevotellaceae; *Prevotella* |
| 28727 | 28727 | 0.009 | −0.0059 | | Firmicutes; Bacilli; Lactobacillales; Lactobacillaceae; *Lactobacillus* |
| 170124 | 170124 | 0.000 | −0.0057 | | Firmicutes; Clostridia; Clostridiales; Eubacteriaceae; *Eubacterium*; Eubacterium_desmolans |
| 11372 | 11372 | 0.019 | −0.0057 | | Actinobacteria; 1760; Coriobacteriales; Coriobacteriaceae; *Eggerthella*; Eggerthella_lenta |
| 365758 | 365758 | 0.003 | −0.0057 | | Bacteroidetes; Bacteroidia; Bacteroidales; Prevotellaceae; *Prevotella* |
| 361809 | 361809 | 0.000 | −0.0056 | 13 | Firmicutes; Clostridia; Clostridiales; Ruminococcaceae; *Ruminococcus*; Ruminococcus_torques |
| 287510 | 287510 | 0.000 | −0.0055 | 11 | Firmicutes; Erysipelotrichi; Erysipelotrichales; Erysipelotrichaceae; *Catenibacterium*; Catenibacterium_mitsuokai |

TABLE 13-continued 220 bacterial taxa whose abundances are significantly altered in the microbiota of children with SAM compared to similarly aged healthy children

| 16S rRNA OTU ID (as shown in FIG. 8 & 9) | Unabbreviated OTU ID in deposited OTU table | FDR-corrected p value | Beta Coefficient | Rank order of importance in Random Forests-based age-discriminatory model | RDP 2.4 Taxonomic Annotation (Phylum; Class; Order; Family; Genus; Species) |
|---|---|---|---|---|---|
| 177005 | 177005 | 0.000 | −0.0054 | | Firmicutes; Clostridia; Clostridiales |
| 185951 | 185951 | 0.000 | −0.0054 | 23 | Firmicutes; Clostridia; Clostridiales |
| 73.d0 | New.0.ReferenceOTU73 | 0.026 | −0.0054 | | Firmicutes; Bacilli; Lactobacillales; Lactobacillaceae |
| 155355.c0 | New.0.CleanUp.ReferenceOTU155355 | 0.045 | −0.0052 | | Firmicutes; Clostridia; Clostridiales; Ruminococcaceae; *Faecalibacterium* |
| 325969 | 325969 | 0.002 | −0.0051 | | Firmicutes; Clostridia; Clostridiales; Clostridiaceae; *Clostridium*; Clostridium_sp_SS2_1 |
| 268604 | 268604 | 0.016 | −0.0050 | | Bacteroidetes; Bacteroidia; Bacteroidales; Prevotellaceae; *Prevotella* |
| 182804 | 182804 | 0.000 | −0.0050 | | Actinobacteria; 1760; Coriobacteriales; Coriobacteriaceae |
| 71685 | 71685 | 0.006 | −0.0049 | | Firmicutes; Clostridia; Clostridiales; Ruminococcaceae; *Ruminococcus*; Ruminococcus_torques |
| 181003 | 181003 | 0.001 | −0.0048 | | Firmicutes; Clostridia; Clostridiales; Ruminococcaceae; *Ruminococcus* |
| 266274 | 266274 | 0.007 | −0.0047 | | Firmicutes; Clostridia; Clostridiales |
| 198941 | 198941 | 0.004 | −0.0045 | | Firmicutes; Clostridia; Clostridiales; Eubacteriaceae; *Eubacterium*; Eubacterium_desmolans |
| 470477 | 470477 | 0.009 | −0.0044 | | Firmicutes; Bacilli; Lactobacillales; Carnobacteriaceae; *Granulicatella*; Granulicatella_adiacens |
| 184037 | 184037 | 0.004 | −0.0044 | | Firmicutes; Clostridia; Clostridiales; Clostridiaceae; *Clostridium*; Clostridium_sp_SS2_1 |
| 325608 | 325608 | 0.003 | −0.0044 | | Firmicutes; Clostridia; Clostridiales; Clostridiaceae; *Clostridium*; Clostridium_bartlettii |
| 367433 | 367433 | 0.009 | −0.0044 | | Firmicutes; Clostridia; Clostridiales; Ruminococcaceae; *Faecalibacterium*; Faecalibacterium_prausnitzii |
| 517331 | 517331 | 0.006 | −0.0043 | | Bacteroidetes; Bacteroidia; Bacteroidales; Prevotellaceae; *Prevotella* |
| 302844 | 302844 | 0.015 | −0.0042 | | Firmicutes; Clostridia; Clostridiales; Clostridiaceae; *Clostridium*; Clostridium_disporicum |
| 189396 | 189396 | 0.019 | −0.0042 | | Firmicutes; Clostridia; Clostridiales; Lachnospiraceae; *Coprococcus*; Coprococcus_comes |
| 24916 | 24916 | 0.019 | −0.0042 | | Bacteroidetes; Bacteroidia; Bacteroidales; Prevotellaceae; *Prevotella* |
| 369164 | 369164 | 0.007 | −0.0040 | | Firmicutes; Clostridia; Clostridiales |
| 191306 | 191306 | 0.003 | −0.0039 | | Firmicutes; Clostridia; Clostridiales; Ruminococcaceae; *Ruminococcus*; Ruminococcus_sp_5_1_39BFAA |
| 9514 | 9514 | 0.011 | −0.0038 | 16 | Proteobacteria; Gammaproteobacteria; Pasteurellales; Pasteurellaceae; *Haemophilus*; Haemophilus_parainfluenzae |
| 470369 | 470369 | 0.009 | −0.0038 | | Firmicutes; Erysipelotrichi; Erysipelotrichales; Erysipelotrichaceae; unclassified_Erysipelotrichaceae; Eubacterium_biforme |
| 295024 | 295024 | 0.009 | −0.0037 | | Firmicutes; Erysipelotrichi; Erysipelotrichales; Erysipelotrichaceae; unclassified_Erysipelotrichaceae; Eubacterium_biforme |
| 185281 | 185281 | 0.009 | −0.0037 | | Firmicutes; Clostridia; Clostridiales |
| 579564 | 579564 | 0.039 | −0.0036 | | Firmicutes; Clostridia; Clostridiales; Clostridiaceae; *Clostridium*; Clostridium_disporicum |
| 178146 | 178146 | 0.019 | −0.0034 | | Firmicutes; Clostridia; Clostridiales; Eubacteriaceae; *Eubacterium*; Eubacterium_hallii |
| 199293 | 199293 | 0.005 | −0.0033 | | Firmicutes; Clostridia; Clostridiales; Ruminococcaceae; *Faecalibacterium*; Faecalibacterium_prausnitzii |
| 177772 | 177772 | 0.009 | −0.0032 | | Firmicutes; Clostridia; Clostridiales; Eubacteriaceae; *Eubacterium*; Eubacterium_rectale |
| 174256 | 174256 | 0.016 | −0.0031 | | Firmicutes; Clostridia; Clostridiales; Eubacteriaceae; *Eubacterium*; Eubacterium_hallii |
| 182994 | 182994 | 0.034 | −0.0031 | | Firmicutes; Clostridia; Clostridiales; Eubacteriaceae; *Eubacterium*; Eubacterium_rectale |
| 179460 | 179460 | 0.042 | −0.0030 | | Firmicutes; Clostridia; Clostridiales; Clostridiaceae; *Clostridium* |
| 212304 | 212304 | 0.017 | −0.0029 | | Firmicutes; Clostridia; Clostridiales |
| 594084 | 594084 | 0.001 | −0.0029 | | Actinobacteria; 1760; Coriobacteriales; Coriobacteriaceae; *Slackia*; Slackia_isoflavoniconvertens |
| 175682 | 175682 | 0.019 | −0.0028 | | Firmicutes; Clostridia; Clostridiales; Eubacteriaceae; *Eubacterium*; Eubacterium_rectale |
| 325738 | 325738 | 0.049 | −0.0027 | | Bacteroidetes; Bacteroidia; Bacteroidales; Bacteroidaceae; *Bacteroides*; Bacteroides_galacturonicus |
| 178122 | 178122 | 0.007 | −0.0027 | | Firmicutes; Clostridia; Clostridiales; Ruminococcaceae; *Ruminococcus*; Ruminococcus_obeum |
| 182202 | 182202 | 0.036 | −0.0026 | | Firmicutes; Clostridia; Clostridiales; Clostridiaceae; *Clostridium*; Clostridium_glycolicum |
| 168716 | 168716 | 0.025 | −0.0026 | | Firmicutes; Clostridia; Clostridiales |
| 206931 | 206931 | 0.014 | −0.0025 | | Firmicutes; Clostridia; Clostridiales |
| 560141 | 560141 | 0.011 | −0.0023 | | Actinobacteria; 1760; Coriobacteriales; Coriobacteriaceae |
| 212787 | 212787 | 0.030 | −0.0022 | | Firmicutes; Clostridia; Clostridiales |
| 100258 | 100258 | 0.026 | −0.0021 | | Firmicutes; Clostridia; Clostridiales; Eubacteriaceae; *Eubacterium*; Eubacterium_sp_cL_10_1_3 |

TABLE 13-continued 220 bacterial taxa whose abundances are significantly altered in the microbiota of children with SAM compared to similarly aged healthy children

| 16S rRNA OTU ID (as shown in FIG. 8 & 9) | Unabbreviated OTU ID in deposited OTU table | FDR-corrected p value | Beta Coefficient | Rank order of importance in Random Forests-based age-discriminatory model | RDP 2.4 Taxonomic Annotation (Phylum; Class; Order; Family; Genus; Species) |
|---|---|---|---|---|---|
| 194648 | 194648 | 0.038 | −0.0018 | | Firmicutes; Clostridia; Clostridiales; unclassified_Clostridiales; *Blautia*; Blautia_sp_M25 |
| 471180 | 471180 | 0.027 | −0.0017 | | Actinobacteria; 1760; Bifidobacteriales; Bifidobacteriaceae; *Bifidobacterium* |
| (b) Taxa altered in children with SAM relative to healthy controls during the post-intervention period | | | | | |
| 292424 | 292424 | 0.0000 | 0.0105 | | Firmicutes; Bacilli; Lactobacillales; Streptococcaceae; *Streptococcus* |
| 148099 | 148099 | 0.0000 | 0.0101 | 21 | Firmicutes; Bacilli; Lactobacillales; Leuconostocaceae; *Weissella*; Weissella_cibaria |
| 249155.c0 | New.0.CleanUp.ReferenceOTU249155 | 0.0035 | 0.0100 | | Firmicutes; Bacilli; Lactobacillales; Leuconostocaceae; *Leuconostoc* |
| 15382 | 15382 | 0.0001 | 0.0096 | | Firmicutes; Bacilli; Lactobacillales; Streptococcaceae; *Streptococcus* |
| 628.d0 | New.0.ReferenceOTU628 | 0.0011 | 0.0080 | | Firmicutes; Bacilli; Lactobacillales; Streptococcaceae; *Streptococcus* |
| 239.d0 | New.0.ReferenceOTU239 | 0.0045 | 0.0065 | | Firmicutes; Bacilli; Lactobacillales; Lactobacillaceae; *Lactobacillus* |
| 282068/c0 | New.0.CleanUp.ReferenceOTU282068 | 0.0051 | 0.0063 | | Firmicutes; Bacilli; Lactobacillales; Lactobacillaceae; *Lactobacillus* |
| 528842 | 528842 | 0.0029 | 0.0059 | | Firmicutes; Bacilli; Lactobacillales; Streptococcaceae; *Streptococcus*; Streptococcus_parasanguinis |
| 108747 | 108747 | 0.0018 | 0.0057 | 14 | Firmicutes; Bacilli; Lactobacillales; Streptococcaceae; *Streptococcus*; Streptococcus_thermophilus |
| 340.d0 | New.0.ReferenceOTU340 | 0.0043 | 0.0055 | | Actinobacteria; 1760; Bifidobacteriales; Bifidobacteriaceae; *Bifidobacterium* |
| 73.d0 | New.0.ReferenceOTU73 | 0.0417 | 0.0054 | | Firmicutes; Bacilli; Lactobacillales; Lactobacillaceae |
| 294794 | 294794 | 0.0173 | 0.0045 | | Firmicutes; Bacilli; Lactobacillales; Streptococcaceae; *Streptococcus* |
| 233573 | 233573 | 0.0172 | 0.0006 | | Firmicutes; Erysipelotrichi; Erysipelotrichales; Erysipelotrichaceae |
| 326792 | 326792 | 0.0000 | −0.0136 | 1 | Firmicutes; Clostridia; Clostridiales; Ruminococcaceae; *Faecalibacterium*; Faecalibacterium_prausnitzii |
| 181834 | 181834 | 0.0000 | −0.0126 | 20 | Firmicutes; Clostridia; Clostridiales; Clostridiaceae; *Clostridium* |
| 187010 | 187010 | 0.0000 | −0.0114 | | Firmicutes; Clostridia; Clostridiales; Ruminococcaceae; *Faecalibacterium*; Faecalibacterium_prausnitzii |
| 188900 | 188900 | 0.0000 | −0.0106 | | Firmicutes; Clostridia; Clostridiales; Ruminococcaceae; *Faecalibacterium*; Faecalibacterium_prausnitzii |
| 162427 | 162427 | 0.0008 | −0.0095 | | Firmicutes; Negativicutes; Selenomonadales; Veillonellaceae; *Megasphaera* |
| 533785 | 533785 | 0.0008 | −0.0093 | 15 | Actinobacteria; 1760; Bifidobacteriales; Bifidobacteriaceae; *Bifidobacterium* |
| 576.d0 | New.0.ReferenceOTU576 | 0.0002 | −0.0090 | | Actinobacteria; 1760; Coriobacteriales; Coriobacteriaceae |
| 417.d0 | New.0.ReferenceOTU417 | 0.0000 | −0.0090 | | Actinobacteria; 1760; Bifidobacteriales; Bifidobacteriaceae; *Bifidobacterium* |
| 469852 | 469852 | 0.0000 | −0.0090 | | Actinobacteria; 1760; Bifidobacteriales; Bifidobacteriaceae; *Bifidobacterium*; Bifidobacterium_bifidum |
| 212503 | 212503 | 0.0000 | −0.0089 | | Firmicutes; Clostridia; Clostridiales; Clostridiaceae; *Clostridium* |
| 261912 | 261912 | 0.0000 | −0.0088 | 12 | Firmicutes; Clostridia; Clostridiales; Lachnospiraceae; *Dorea*; Dorea_formicigenerans |
| 309068 | 309068 | 0.0000 | −0.0086 | | Bacteroidetes; Bacteroidia; Bacteroidales; Prevotellaceae; *Prevotella*; Prevotella_copri |
| 301004 | 301004 | 0.0034 | −0.0084 | | Actinobacteria; 1760; Coriobacteriales; Coriobacteriaceae; *Olsenella* |
| 184464 | 184464 | 0.0000 | −0.0083 | | Bacteroidetes; Bacteroidia; Bacteroidales; Prevotellaceae; *Prevotella*; Prevotella_copri |
| 177351 | 177351 | 0.0000 | −0.0082 | | Bacteroidetes; Bacteroidia; Bacteroidales; Prevotellaceae; *Prevotella* |
| 303304 | 303304 | 0.0000 | −0.0081 | | Bacteroidetes; Bacteroidia; Bacteroidales; Prevotellaceae; *Prevotella*; Prevotella_copri |
| 48207 | 48207 | 0.0000 | −0.0081 | | Firmicutes; Negativicutes; Selenomonadales; Veillonellaceae; *Dialister* |
| 13823 | 13823 | 0.0024 | −0.0079 | | Firmicutes; Negativicutes; Selenomonadales; Veillonellaceae; *Veillonella*; Veillonella_ratti |
| 130663 | 130663 | 0.0017 | −0.0079 | | Bacteroidetes; Bacteroidia; Bacteroidales; Bacteroidaceae; *Bacteroides*; Bacteroides_fragilis |
| 58262 | 58262 | 0.0000 | −0.0076 | | Firmicutes; Negativicutes; Selenomonadales; Veillonellaceae; *Allisonella*; Allisonella_histaminiformans |
| 195574 | 195574 | 0.0000 | −0.0076 | | Bacteroidetes; Bacteroidia; Bacteroidales; Prevotellaceae; *Prevotella* |
| 259261 | 259261 | 0.0001 | −0.0075 | | Firmicutes; Negativicutes; Selenomonadales; Veillonellaceae; *Megamonas* |
| 365758 | 365758 | 0.0000 | −0.0072 | | Bacteroidetes; Bacteroidia; Bacteroidales; Prevotellaceae; *Prevotella* |
| 165261 | 165261 | 0.0000 | −0.0072 | | Firmicutes; Clostridia; Clostridiales; Clostridiaceae; *Clostridium* |
| 212619 | 212619 | 0.0000 | −0.0069 | 24 | Firmicutes; Clostridia; Clostridiales; Ruminococcaceae |
| 196757 | 196757 | 0.0092 | −0.0067 | | Bacteroidetes; Bacteroidia; Bacteroidales; Bacteroidaceae; *Bacteroides*; Bacteroides_ovatus |

TABLE 13-continued 220 bacterial taxa whose abundances are significantly altered in the microbiota of children with SAM compared to similarly aged healthy children

| 16S rRNA OTU ID (as shown in FIG. 8 & 9) | Unabbreviated OTU ID in deposited OTU table | FDR-corrected p value | Beta Coefficient | Rank order of importance in Random Forests-based age-discriminatory model | RDP 2.4 Taxonomic Annotation (Phylum; Class; Order; Family; Genus; Species) |
|---|---|---|---|---|---|
| 181330 | 181330 | 0.0000 | −0.0067 | | Firmicutes; Clostridia; Clostridiales; Ruminococcaceae; *Ruminococcus*; Ruminococcus_sp_5_1_39BFAA |
| 170124 | 170124 | 0.0000 | −0.0067 | | Firmicutes; Clostridia; Clostridiales; Eubacteriaceae; *Eubacterium*; Eubacterium_desmolans |
| 194745 | 194745 | 0.0001 | −0.0066 | 6 | Firmicutes; Clostridia; Clostridiales; Ruminococcaceae; *Ruminococcus*; Ruminococcus_sp_5_1_39BFAA |
| 189862 | 189862 | 0.0046 | −0.0066 | | Bacteroidetes; Bacteroidia; Bacteroidales; Prevotellaceae; *Prevotella*; Prevotella_sp_DJF_B116 |
| 191687 | 191687 | 0.0000 | −0.0066 | 4 | Firmicutes; Clostridia; Clostridiales; Lachnospiraceae; *Dorea*; Dorea_longicatena |
| 158660 | 158660 | 0.0006 | −0.0064 | | Bacteroidetes; Bacteroidia; Bacteroidales; Bacteroidaceae; *Bacteroides* |
| 268604 | 268604 | 0.0000 | −0.0064 | | Bacteroidetes; Bacteroidia; Bacteroidales; Prevotellaceae; *Prevotella* |
| 192132 | 192132 | 0.0006 | −0.0063 | | Proteobacteria; Deltaproteobacteria; Desulfovibrionales; Desulfovibrionaceae; *Bilophila*; Bilophila_wadsworthia |
| 274208 | 274208 | 0.0172 | −0.0062 | | Firmicutes; Negativicutes; Selenomonadales; Veillonellaceae; *Megasphaera*; Megasphaera_elsdenii |
| 155355.c0 | New.0.CleanUp.ReferenceOTU155355 | 0.0008 | −0.0062 | | Firmicutes; Clostridia; Clostridiales; Ruminococcaceae; *Faecalibacterium* |
| 266274 | 266274 | 0.0000 | −0.0061 | | Firmicutes; Clostridia; Clostridiales |
| 2000 | 2000 | 0.0059 | −0.0059 | | Bacteroidetes; Bacteroidia; Bacteroidales; Bacteroidaceae; *Bacteroides*; Bacteroides_fragilis |
| 331820 | 331820 | 0.0043 | −0.0058 | | Bacteroidetes; Bacteroidia; Bacteroidales; Bacteroidaceae; *Bacteroides*; Bacteroides_vulgatus |
| 364234 | 364234 | 0.0000 | −0.0057 | 10 | Firmicutes; Clostridia; Clostridiales; Ruminococcaceae; *Ruminococcus*; Ruminococcus_sp_5_1_39BFAA |
| 11.d0 | New.0.ReferenceOTU11 | 0.0305 | −0.0057 | | Firmicutes; Negativicutes; Selenomonadales; Veillonellaceae |
| 198941 | 198941 | 0.0000 | −0.0057 | | Firmicutes; Clostridia; Clostridiales; Eubacteriaceae; *Eubacterium*; Eubacterium_desmolans |
| 365047 | 365047 | 0.0000 | −0.0057 | | Firmicutes; Clostridia; Clostridiales; Ruminococcaceae; *Ruminococcus*; Ruminococcus_sp_5_1_39BFAA |
| 258806.c0 | New.0.CleanUp.ReferenceOTU258806 | 0.0051 | −0.0056 | | Actinobacteria; 1760; Coriobacteriales; Coriobacteriaceae |
| 298533 | 298533 | 0.0012 | −0.0055 | | Bacteroidetes; Bacteroidia; Bacteroidales; Prevotellaceae; *Prevotella* |
| 367433 | 367433 | 0.0000 | −0.0053 | | Firmicutes; Clostridia; Clostridiales; Ruminococcaceae; *Faecalibacterium*; Faecalibacterium_prausnitzii |
| 11372 | 11372 | 0.0052 | −0.0053 | | Actinobacteria; 1760; Coriobacteriales; Coriobacteriaceae; *Eggerthella*; Eggerthella_lenta |
| 189396 | 189396 | 0.0000 | −0.0052 | | Firmicutes; Clostridia; Clostridiales; Lachnospiraceae; *Coprococcus*; Coprococcus_comes |
| 24916 | 24916 | 0.0000 | −0.0052 | | Bacteroidetes; Bacteroidia; Bacteroidales; Prevotellaceae; *Prevotella* |
| 348374 | 348374 | 0.0089 | −0.0052 | | Bacteroidetes; Bacteroidia; Bacteroidales; Bacteroidaceae; *Bacteroides*; Bacteroides_thetaiotaomicron |
| 517331 | 517331 | 0.0000 | −0.0052 | | Bacteroidetes; Bacteroidia; Bacteroidales; Prevotellaceae; *Prevotella* |
| 574.d0 | New.0.ReferenceOTU574 | 0.0356 | −0.0049 | | Actinobacteria; 1760; Coriobacteriales; Coriobacteriaceae |
| 189827 | 189827 | 0.0002 | −0.0049 | 2 | Firmicutes; Clostridia; Clostridiales; Ruminococcaceae; *Ruminococcus*; Ruminococcus_sp_5_1_39BFAA |
| 235476.c0 | New.0.CleanUp.ReferenceOTU235476 | 0.0449 | −0.0049 | | Actinobacteria; 1760; Coriobacteriales; Coriobacteriaceae |
| 294710 | 294710 | 0.0002 | −0.0048 | | Firmicutes; Clostridia; Clostridiales; Clostridiaceae; *Clostridium* |
| 369164 | 369164 | 0.0000 | −0.0047 | | Firmicutes; Clostridia; Clostridiales |
| 145149 | 145149 | 0.0335 | −0.0046 | | Firmicutes; Negativicutes; Selenomonadales; Veillonellaceae; *Veillonella* |
| 369502 | 369502 | 0.0025 | −0.0043 | | Firmicutes; Clostridia; Clostridiales; Lachnospiraceae; *Coprococcus*; Coprococcus_catus |
| 199293 | 199293 | 0.0000 | −0.0042 | | Firmicutes; Clostridia; Clostridiales; Ruminococcaceae; *Faecalibacterium*; Faecalibacterium_prausnitzii |
| 209122 | 209122 | 0.0001 | −0.0041 | | Firmicutes; Clostridia; Clostridiales |
| 184037 | 184037 | 0.0003 | −0.0041 | | Firmicutes; Clostridia; Clostridiales; Clostridiaceae; *Clostridium*; Clostridium_sp_SS2_1 |
| 174902 | 174902 | 0.0021 | −0.0041 | | Firmicutes; Clostridia; Clostridiales; Ruminococcaceae; *Faecalibacterium*; Faecalibacterium_prausnitzii |
| 177772 | 177772 | 0.0000 | −0.0041 | | Firmicutes; Clostridia; Clostridiales; Eubacteriaceae; *Eubacterium*; Eubacterium_rectale |
| 185281 | 185281 | 0.0000 | −0.0041 | | Firmicutes; Clostridia; Clostridiales |
| 305760 | 305760 | 0.0087 | −0.0040 | | Proteobacteria; Gammaproteobacteria; Enterobacteriales; Enterobacteriaceae; *Escherichia*; Escherichia_coli |

TABLE 13-continued 220 bacterial taxa whose abundances are significantly altered in the microbiota of children with SAM compared to similarly aged healthy children

| 16S rRNA OTU ID (as shown in FIG. 8 & 9) | Unabbreviated OTU ID in deposited OTU table | FDR-corrected p value | Beta Coefficient | Rank order of importance in Random Forests-based age-discriminatory model | RDP 2.4 Taxonomic Annotation (Phylum; Class; Order; Family; Genus; Species) |
|---|---|---|---|---|---|
| 179460 | 179460 | 0.0001 | −0.0040 | | Firmicutes; Clostridia; Clostridiales; Clostridiaceae; *Clostridium* |
| 198161 | 198161 | 0.0001 | −0.0040 | | Bacteroidetes; Bacteroidia; Bacteroidales |
| 182994 | 182994 | 0.0000 | −0.0039 | | Firmicutes; Clostridia; Clostridiales; Eubacteriaceae; *Eubacterium*; Eubacterium_rectale |
| 179287 | 179287 | 0.0006 | −0.0038 | | Firmicutes; Clostridia; Clostridiales; Ruminococcaceae; *Faecalibacterium*; Faecalibacterium_prausnitzii |
| 294196 | 294196 | 0.0000 | −0.0037 | | Bacteroidetes; Bacteroidia; Bacteroidales; Prevotellaceae; *Prevotella*; Prevotella_copri |
| 208539 | 208539 | 0.0002 | −0.0037 | | Firmicutes; Clostridia; Clostridiales; Eubacteriaceae; *Eubacterium* |
| 177005 | 177005 | 0.0017 | −0.0037 | | Firmicutes; Clostridia; Clostridiales |
| 191306 | 191306 | 0.0001 | −0.0037 | | Firmicutes; Clostridia; Clostridiales; Ruminococcaceae; *Ruminococcus*; Ruminococcus_sp_5_1_39BFAA |
| 195493 | 195493 | 0.0023 | −0.0037 | | Firmicutes; Clostridia; Clostridiales; Lachnospiraceae; *Roseburia*; Roseburia_intestinalis |
| 177495 | 177495 | 0.0002 | −0.0037 | | Firmicutes; Clostridia; Clostridiales; Ruminococcaceae; *Subdoligranulum*; Subdoligranulum_variabile |
| 325608 | 325608 | 0.0009 | −0.0036 | | Firmicutes; Clostridia; Clostridiales; Clostridiaceae; *Clostridium*; Clostridium_bartlettii |
| 168716 | 168716 | 0.0000 | −0.0036 | | Firmicutes; Clostridia; Clostridiales |
| 325969 | 325969 | 0.0110 | −0.0036 | | Firmicutes; Clostridia; Clostridiales; Clostridiaceae; *Clostridium*; Clostridium_sp_SS2_1 |
| 181170 | 181170 | 0.0007 | −0.0035 | | Firmicutes; Clostridia; Clostridiales |
| 541301 | 541301 | 0.0035 | −0.0035 | | Bacteroidetes; Bacteroidia; Bacteroidales; Porphyromonadaceae; *Parabacteroides*; Parabacteroides_merdae |
| 340615 | 340615 | 0.0110 | −0.0035 | | Firmicutes; Clostridia; Clostridiales; Eubacteriaceae; *Eubacterium*; Eubacterium_hallii |
| 204593 | 204593 | 0.0049 | −0.0035 | | Firmicutes; Clostridia; Clostridiales; Eubacteriaceae; *Eubacterium*; Eubacterium_coprostanoligenes |
| 193067 | 193067 | 0.0000 | −0.0034 | | Firmicutes; Clostridia; Clostridiales; Eubacteriaceae; *Eubacterium*; Eubacterium_rectale |
| 181003 | 181003 | 0.0017 | −0.0034 | | Firmicutes; Clostridia; Clostridiales; Ruminococcaceae; *Ruminococcus* |
| 172962 | 172962 | 0.0042 | −0.0034 | | Bacteroidetes; Bacteroidia; Bacteroidales; Prevotellaceae; *Prevotella* |
| 363400 | 363400 | 0.0108 | −0.0034 | | Firmicutes; Clostridia; Clostridiales; Clostridiaceae; *Clostridium*; Clostridium_clostridioforme |
| 171.d0 | New.0.ReferenceOTU171 | 0.0367 | −0.0034 | | Proteobacteria |
| 172274 | 172274 | 0.0042 | −0.0034 | | Firmicutes; Clostridia; Clostridiales; Ruminococcaceae; *Faecalibacterium*; Faecalibacterium_prausnitzii |
| 212304 | 212304 | 0.0001 | −0.0034 | | Firmicutes; Clostridia; Clostridiales |
| 175682 | 175682 | 0.0000 | −0.0034 | | Firmicutes; Clostridia; Clostridiales; Eubacteriaceae; *Eubacterium*; Eubacterium_rectale |
| 361809 | 361809 | 0.0093 | −0.0034 | 13 | Firmicutes; Clostridia; Clostridiales; Ruminococcaceae; *Ruminococcus*; Ruminococcus_torques |
| 316732 | 316732 | 0.0022 | −0.0034 | | Firmicutes; Clostridia; Clostridiales |
| 111135 | 111135 | 0.0069 | −0.0034 | | Proteobacteria; Betaproteobacteria; Burkholderiales; Sutterellaceae; *Sutterella*; Sutterella_wadsworthensis |
| 528303 | 528303 | 0.0000 | −0.0033 | | Bacteroidetes; Bacteroidia; Bacteroidales; Prevotellaceae; *Prevotella* |
| 182087 | 182087 | 0.0033 | −0.0032 | | Firmicutes; Clostridia; Clostridiales; Ruminococcaceae; *Faecalibacterium*; Faecalibacterium_prausnitzii |
| 210269 | 210269 | 0.0489 | −0.0031 | | Proteobacteria; Gammaproteobacteria; Enterobacteriales; Enterobacteriaceae |
| 188.d1 | New.1.ReferenceOTU188 | 0.0372 | −0.0031 | | Firmicutes; Negativicutes; Selenomonadales; Veillonellaceae; *Megamonas* |
| 71685 | 71685 | 0.0262 | −0.0031 | | Firmicutes; Clostridia; Clostridiales; Ruminococcaceae; *Ruminococcus*; Ruminococcus_torques |
| 162623 | 162623 | 0.0002 | −0.0031 | | Firmicutes; Clostridia; Clostridiales |
| 185951 | 185951 | 0.0108 | −0.0031 | 23 | Firmicutes; Clostridia; Clostridiales |
| 203590 | 203590 | 0.0110 | −0.0030 | | Firmicutes; Clostridia; Clostridiales; Clostridiaceae; *Clostridium* |
| 291266 | 291266 | 0.0000 | −0.0030 | | Firmicutes; Clostridia; Clostridiales; Ruminococcaceae; *Subdoligranulum*; Subdoligranulum_variabile |
| 184511 | 184511 | 0.0112 | −0.0030 | | Firmicutes; Clostridia; Clostridiales; Ruminococcaceae; *Faecalibacterium*; Faecalibacterium_prausnitzii |
| 188236 | 188236 | 0.0002 | −0.0030 | | Firmicutes; Clostridia; Clostridiales; Ruminococcaceae; *Faecalibacterium*; Faecalibacterium_prausnitzii |
| 263461 | 263461 | 0.0223 | −0.0029 | | Firmicutes; Clostridia; Clostridiales |
| 181139 | 181139 | 0.0001 | −0.0029 | | Firmicutes; Clostridia; Clostridiales; Ruminococcaceae; *Faecalibacterium*; Faecalibacterium_prausnitzii |
| 442.d0 | New.0.ReferenceOTU442 | 0.0051 | −0.0029 | | Bacteroidetes |

TABLE 13-continued 220 bacterial taxa whose abundances are significantly altered in the microbiota of children with SAM compared to similarly aged healthy children

| 16S rRNA OTU ID (as shown in FIG. 8 & 9) | Unabbreviated OTU ID in deposited OTU table | FDR-corrected p value | Beta Coefficient | Rank order of importance in Random Forests-based age-discriminatory model | RDP 2.4 Taxonomic Annotation (Phylum; Class; Order; Family; Genus; Species) |
|---|---|---|---|---|---|
| 352304 | 352304 | 0.0035 | −0.0029 | | Firmicutes; Clostridia; Clostridiales; Lachnospiraceae; *Roseburia* |
| 178146 | 178146 | 0.0075 | −0.0029 | | Firmicutes; Clostridia; Clostridiales; Eubacteriaceae; *Eubacterium*; Eubacterium_hallii |
| 181882 | 181882 | 0.0002 | −0.0029 | | Firmicutes; Clostridia; Clostridiales |
| 323253 | 323253 | 0.0298 | −0.0028 | | Unknown bacteria |
| 207570 | 207570 | 0.0015 | −0.0028 | | Firmicutes; Clostridia; Clostridiales; Clostridiaceae; *Clostridium*; Clostridium_lactatifermentans |
| 9514 | 9514 | 0.0335 | −0.0028 | 16 | Proteobacteria; Gammaproteobacteria; Pasteurellales; Pasteurellaceae; *Haemophilus*; Haemophilus_parainfluenzae |
| 174256 | 174256 | 0.0039 | −0.0028 | | Firmicutes; Clostridia; Clostridiales; Eubacteriaceae; *Eubacterium*; Eubacterium_hallii |
| 206931 | 206931 | 0.0001 | −0.0028 | | Firmicutes; Clostridia; Clostridiales |
| 212787 | 212787 | 0.0000 | −0.0027 | | Firmicutes; Clostridia; Clostridiales |
| 173135 | 173135 | 0.0018 | −0.0027 | | Firmicutes; Clostridia; Clostridiales; Ruminococcaceae; *Faecalibacterium*; Faecalibacterium_prausnitzii |
| 203620 | 203620 | 0.0060 | −0.0026 | | Firmicutes; Clostridia; Clostridiales |
| 354737 | 354737 | 0.0017 | −0.0026 | | Firmicutes; Clostridia; Clostridiales; Ruminococcaceae; *Subdoligranulum*; Subdoligranulum_variabile |
| 69909 | 69909 | 0.0107 | −0.0026 | | Firmicutes; Clostridia; Clostridiales; Eubacteriaceae; *Eubacterium*; Eubacterium_ramulus |
| 555326 | 555326 | 0.0190 | −0.0026 | | Firmicutes; Negativicutes; Selenomonadales; Acidaminococcaceae; *Phascolarctobacterium*; Phascolarctobacterium_succinatutens |
| 16054 | 16054 | 0.0092 | −0.0026 | | Firmicutes; Clostridia; Clostridiales; Ruminococcaceae; *Ruminococcus*; Ruminococcus_callidus |
| 325738 | 325738 | 0.0043 | −0.0025 | | Bacteroidetes; Bacteroidia; Bacteroidales; Bacteroidaceae; *Bacteroides*; Bacteroides_galacturonicus |
| 329096 | 329096 | 0.0335 | −0.0025 | | Proteobacteria; Gammaproteobacteria; Enterobacteriales; Enterobacteriaceae |
| 287510 | 287510 | 0.0338 | −0.0025 | 11 | Firmicutes; Erysipelotrichi; Erysipelotrichales; Erysipelotrichaceae; *Catenibacterium*; Catenibacterium_mitsuokai |
| 175537 | 175537 | 0.0001 | −0.0025 | | Firmicutes; Clostridia; Clostridiales |
| 187846 | 187846 | 0.0022 | −0.0025 | | Firmicutes; Clostridia; Clostridiales; Eubacteriaceae; *Eubacterium*; Eubacterium_desmolans |
| 183879 | 183879 | 0.0312 | −0.0024 | | Firmicutes; Clostridia; Clostridiales |
| 179795 | 179795 | 0.0017 | −0.0024 | | Firmicutes; Clostridia; Clostridiales; Clostridiaceae; *Clostridium* |
| 191547 | 191547 | 0.0013 | −0.0023 | | Firmicutes; Clostridia; Clostridiales; Ruminococcaceae; *Faecalibacterium*; Faecalibacterium_prausnitzii |
| 260352 | 260352 | 0.0301 | −0.0023 | | Firmicutes; Clostridia; Clostridiales; Eubacteriaceae; *Eubacterium*; Eubacterium_coprostanoligenes |
| 329728 | 329728 | 0.0071 | −0.0023 | | Bacteroidetes; Bacteroidia; Bacteroidales; Prevotellaceae; *Prevotella* |
| 205408 | 205408 | 0.0335 | −0.0023 | | Proteobacteria; Gammaproteobacteria; Aeromonadales; Succinivibrionaceae; *Succinivibrio*; Succinivibrio_dextrinosolvens |
| 293221 | 293221 | 0.0223 | −0.0022 | | Firmicutes; Clostridia; Clostridiales; Lachnospiraceae; *Roseburia*; Roseburia_intestinalis |
| 293896 | 293896 | 0.0087 | −0.0022 | | Firmicutes; Clostridia; Clostridiales |
| 113909 | 113909 | 0.0007 | −0.0022 | | Firmicutes; Clostridia; Clostridiales; Eubacteriaceae; *Eubacterium*; Eubacterium_rectale |
| 338889 | 338889 | 0.0291 | −0.0021 | | Bacteroidetes; Bacteroidia; Bacteroidales; Prevotellaceae; *Prevotella* |
| 259959 | 259959 | 0.0293 | −0.0021 | | Bacteroidetes; Bacteroidia; Bacteroidales; Prevotellaceae; *Prevotella*; Prevotella_sp_oral_taxon_302 |
| 193632 | 193632 | 0.0013 | −0.0021 | | Firmicutes; Clostridia; Clostridiales; Oscillospiraceae; *Oscillibacter*; Oscillibacter_sp_G2 |
| 186640 | 186640 | 0.0015 | −0.0020 | | Firmicutes; Clostridia; Clostridiales |
| 529733 | 529733 | 0.0307 | −0.0020 | | Bacteroidetes; Bacteroidia; Bacteroidales; Prevotellaceae; *Prevotella* |
| 321016 | 321016 | 0.0135 | −0.0019 | | Firmicutes; Clostridia; Clostridiales |
| 16076 | 16076 | 0.0335 | −0.0018 | | Firmicutes; Clostridia; Clostridiales; Ruminococcaceae; *Ruminococcus*; Ruminococcus_bromii |
| 209578 | 209578 | 0.0092 | −0.0018 | | Firmicutes; Clostridia; Clostridiales; Ruminococcaceae; *Ruminococcus* |
| 215433 | 215433 | 0.0489 | −0.0017 | | Firmicutes; Clostridia; Clostridiales |
| 192252 | 192252 | 0.0054 | −0.0017 | | Firmicutes; Clostridia; Clostridiales; Eubacteriaceae; *Eubacterium*; Eubacterium_rectale |
| 196225.c0 | New.0.CleanUp.ReferenceOTU196225 | 0.0449 | −0.0016 | | Bacteroidetes; Bacteroidia; Bacteroidales; Prevotellaceae; *Prevotella* |
| 194648 | 194648 | 0.0136 | −0.0015 | | Firmicutes; Clostridia; Clostridiales; unclassified_Clostridiales; *Blautia*; Blautia_sp_M25 |
| 560141 | 560141 | 0.0356 | −0.0015 | | Actinobacteria; 1760; Coriobacteriales; Coriobacteriaceae |
| 172603 | 172603 | 0.0219 | −0.0014 | | Firmicutes; Clostridia; Clostridiales; Eubacteriaceae; *Eubacterium*; Eubacterium_hallii |
| 187524 | 187524 | 0.0027 | −0.0014 | | Firmicutes; Clostridia; Clostridiales |
| 195102 | 195102 | 0.0060 | −0.0013 | | Firmicutes; Clostridia; Clostridiales |
| 343985 | 343985 | 0.0032 | −0.0013 | | Firmicutes |

TABLE 13-continued 220 bacterial taxa whose abundances are significantly altered in the microbiota of children with SAM compared to similarly aged healthy children

| 16S rRNA OTU ID (as shown in FIG. 8 & 9) | Unabbreviated OTU ID in deposited OTU table | FDR-corrected p value | Beta Coefficient | Rank order of importance in Random Forests-based age-discriminatory model | RDP 2.4 Taxonomic Annotation (Phylum; Class; Order; Family; Genus; Species) |
|---|---|---|---|---|---|
| 207065 | 207065 | 0.0108 | −0.0013 | | Firmicutes; Clostridia; Clostridiales |
| 189047 | 189047 | 0.0177 | −0.0013 | | Firmicutes; Clostridia; Clostridiales; Ruminococcaceae |
| 310301 | 310301 | 0.0075 | −0.0013 | | Firmicutes; Clostridia; Clostridiales; Ruminococcaceae; *Faecalibacterium*; Faecalibacterium_prausnitzii |
| 364261 | 364261 | 0.0244 | −0.0013 | | Firmicutes; Clostridia; Clostridiales |
| 516022 | 516022 | 0.0276 | −0.0012 | | Firmicutes |
| 190572 | 190572 | 0.0018 | −0.0012 | | Firmicutes; Clostridia; Clostridiales; Ruminococcaceae; *Faecalibacterium*; Faecalibacterium_prausnitzii |
| 571220 | 571220 | 0.0194 | −0.0012 | | Firmicutes; Clostridia; Clostridiales |
| 293360 | 293360 | 0.0414 | −0.0009 | | Firmicutes; Clostridia; Clostridiales |
| 298079 | 298079 | 0.0383 | −0.0007 | | Firmicutes; Clostridia; Clostridiales |
| 179291 | 179291 | 0.0299 | −0.0007 | | Firmicutes; Clostridia; Clostridiales; Ruminococcaceae; *Faecalibacterium*; Faecalibacterium_prausnitzii |
| 54730 | 54730 | 0.0394 | −0.0007 | | Unknown bacteria |
| 352215 | 352215 | 0.0298 | −0.0007 | | Firmicutes; Clostridia; Clostridiales |
| 43267 | 43267 | 0.0258 | −0.0006 | | Firmicutes; Clostridia; Clostridiales |
| 312816.c0 | New.0.CleanUp.ReferenceOTU312816 | 0.0449 | −0.0005 | | Firmicutes; Clostridia; Clostridiales; Clostridiaceae |

TABLE 14

Relative microbiota maturity, Microbiota-for-Age Z-score and age-adjusted Shannon Diversity Index in relation to antibiotic usage and diarrhoea during the post-intervention follow-up period

| | Intervention Arm | Estimate | Std. Error | p value |
|---|---|---|---|---|
| Relative microbiota maturity | | | | |
| Antibiotics | RUTF | −0.37 | 0.81 | 0.65 |
| diarrhoea | | −0.92 | 2.03 | 0.65 |
| Chronologic Age | | −0.18 | 0.12 | 0.13 |
| Antibiotics | Khichuri-Halwa | 0.17 | 0.92 | 0.85 |
| diarrhoea | | 0.31 | 1.57 | 0.84 |
| Chronologic Age | | 0.11 | 0.13 | 0.41 |
| Microbiota-for-Age Z score | | | | |
| Antibiotics | RUTF | 0.15 | 0.31 | 0.64 |
| diarrhoea | | 0.27 | 0.53 | 0.61 |
| Chronologic Age | | −0.03 | 0.04 | 0.43 |
| Antibiotics | Khichuri-Halwa | 0.07 | 0.25 | 0.77 |
| diarrhoea | | −0.42 | 0.61 | 0.49 |
| Chronologic Age | | −0.12 | 0.03 | <0.001 |
| Age-adjusted Shannon Diversity Index | | | | |
| Antibiotics | RUTF | 0.02 | 0.22 | 0.91 |
| diarrhoea | | 0.07 | 0.47 | 0.88 |
| Chronologic Age | | −0.05 | 0.02 | 0.03 |
| Antibiotics | Khichuri-Halwa | −0.32 | 0.19 | 0.09 |
| diarrhoea | | −0.49 | 0.32 | 0.13 |
| Chronologic Age | | 0.00 | 0.02 | 0.89 |

Estimates of beta coefficients, standard error and p-values from linear mixed models with random by-child intercepts and chronologic age as a fixed effect covariate for each intervention arm

TABLE 15

Metadata associated with individual fecal samples collected from 33 children in singleton cohort with and without MAM

| Child ID | Fecal Sample ID | Gender | Threshold for MAM Diagnosis | Age, days | Age, months | WHZ | HAZ | WAZ |
|---|---|---|---|---|---|---|---|---|
| Bgsng7001 | Bgsng7001.m19 | Male | MAM | 552 | 18.1 | −2.87 | −2.9 | −3.38 |
| Bgsng7013 | Bgsng7013.m19 | Male | MAM | 547 | 18.0 | −2.54 | −3.16 | −3.31 |
| Bgsng7031 | Bgsng7031.m19 | Female | MAM | 557 | 18.3 | −2.08 | −2.67 | −2.86 |
| Bgsng7082 | Bgsng7082.m19 | Female | MAM | 551 | 18.1 | −3.7 | −0.83 | −3.11 |
| Bgsng7094 | Bgsng7094.m19 | Female | MAM | 562 | 18.5 | −2.1 | −2.49 | −2.78 |
| Bgsng7109 | Bgsng7109.m18 | Male | MAM | 548 | 18.0 | −2.62 | −4 | −3.78 |
| Bgsng7110 | Bgsng7110.m18 | Female | MAM | 552 | 18.1 | −2.72 | −2.07 | −3 |
| Bgsng7116 | Bgsng7116.m19 | Male | MAM | 553 | 18.2 | −2.7 | −2.41 | −3.05 |
| Bgsng7123 | Bgsng7123.m18 | Female | MAM | 548 | 18.0 | −2.95 | −2.67 | −3.46 |
| Bgsng7148 | Bgsng7148.m19 | Female | MAM | 551 | 18.1 | −3.69 | −2.32 | −3.79 |
| Bgsng7004 | Bgsng7004.m19 | Male | Not MAM | 557 | 18.3 | −1.68 | −3.63 | −2.99 |
| Bgsng7018 | Bgsng7018.m19 | Male | Not MAM | 551 | 18.1 | −1.6 | −1.29 | −1.78 |
| Bgsng7040 | Bgsng7040.m19 | Female | Not MAM | 551 | 18.1 | −0.1 | −3.01 | −1.56 |
| Bgsng7050 | Bgsng7050.m19 | Female | Not MAM | 555 | 18.2 | −0.2 | −2.54 | −1.37 |
| Bgsng7052 | Bgsng7052.m19 | Male | Not MAM | 552 | 18.1 | −1.05 | −0.87 | −1.2 |

TABLE 15-continued

Metadata associated with individual fecal samples collected from 33 children in singleton cohort with and without MAM

| | | | | | | | | | |
|---|---|---|---|---|---|---|---|---|---|
| Bgsng7063 | Bgsng7063.m19 | Male | Not MAM | 553 | 18.2 | −0.87 | −0.85 | −1.06 | |
| Bgsng7071 | Bgsng7071.m19 | Male | Not MAM | 554 | 18.2 | −0.04 | 0.02 | −0.07 | |
| Bgsng7074 | Bgsng7074.m19 | Male | Not MAM | 556 | 18.3 | −1.82 | −3.47 | −2.99 | |
| Bgsng7081 | Bgsng7081.m19 | Female | Not MAM | 551 | 18.1 | −0.73 | −2.25 | −1.62 | |
| Bgsng7087 | Bgsng7087.m19 | Female | Not MAM | 551 | 18.1 | −1.63 | −2.5 | −2.43 | |
| Bgsng7090 | Bgsng7090.m19 | Male | Not MAM | 552 | 18.1 | −0.71 | −0.75 | −0.9 | |
| Bgsng7096 | Bgsng7096.m19 | Female | Not MAM | 560 | 18.4 | −0.68 | −1.98 | −1.44 | |
| Bgsng7108 | Bgsng7108.m18 | Male | Not MAM | 548 | 18.0 | −1.32 | −2.51 | −2.14 | |
| Bgsng7130 | Bgsng7130.m19 | Male | Not MAM | 544 | 17.9 | −1.89 | −4.18 | −3.43 | |
| Bgsng7131 | Bgsng7131.m19 | Male | Not MAM | 570 | 18.7 | −1.63 | −1.9 | −2.07 | |
| Bgsng7133 | Bgsng7133.m19 | Female | Not MAM | 558 | 18.3 | −1.64 | −2.3 | −2.33 | |
| Bgsng7135 | Bgsng7135.m19 | Female | Not MAM | 549 | 18.0 | −0.96 | −2.34 | −1.84 | |
| Bgsng7145 | Bgsng7145.m19 | Male | Not MAM | 549 | 18.0 | 1.38 | −4.18 | −1.08 | |
| Bgsng7149 | Bgsng7149.m19 | Female | Not MAM | 565 | 18.6 | −1.05 | −0.84 | −1.16 | |
| Bgsng7152 | Bgsng7152.m19 | Male | Not MAM | 554 | 18.2 | −1.5 | −1.96 | −2 | |
| Bgsng7173 | Bgsng7173.m19 | Male | Not MAM | 556 | 18.3 | 0.14 | −1.58 | −0.63 | |
| Bgsng7178 | Bgsng7178.m19 | Female | Not MAM | 560 | 18.4 | 0.72 | −0.91 | 0.11 | |
| Bgsng7203 | Bgsng7203.m19 | Male | Not MAM | 551 | 18.1 | 0.16 | −3.44 | −1.55 | |

| Child ID | Diet at time of fecal sample collection | | | diarrhoea at the time of sample collection | Antibiotics within 7 days prior to sample collection | Medications (Antibiotics and other) | Number of high quality V4-16S rRNA sequences | 16S rRNA Sequencing Run ID |
|---|---|---|---|---|---|---|---|---|
| | Breast Milk | Solid Foods | Formula | | | | | |
| Bgsng7001 | Yes | Yes | No | No | No | Chlorpheniramine Maleate, Paracetamol | 18,860 | 7 |
| Bgsng7013 | Yes | Yes | No | Yes | No | | 18,634 | 7 |
| Bgsng7031 | Yes | Yes | No | No | No | | 15,771 | 7 |
| Bgsng7082 | Yes | Yes | No | No | No | | 46,439 | 4 |
| Bgsng7094 | Yes | Yes | No | No | No | | 21,799 | 5 |
| Bgsng7109 | Yes | Yes | No | No | No | | 25,516 | 6 |
| Bgsng7110 | Yes | Yes | No | No | No | | 21,546 | 6 |
| Bgsng7116 | Yes | Yes | No | No | Yes | Flucloxacillin Sodium, Chlorpheniramine Maleate, Multi Vitamin | 20,166 | 5 |
| Bgsng7123 | Yes | Yes | No | No | No | | 27,214 | 7 |
| Bgsng7148 | Yes | Yes | No | No | No | | 44,754 | 4 |
| Bgsng7004 | Yes | Yes | No | No | No | | 23,688 | 4 |
| Bgsng7018 | Yes | Yes | No | No | Yes | Flucloxacillin Sodium | 25,765 | 7 |
| Bgsng7040 | Yes | Yes | No | No | No | | 49,576 | 7 |
| Bgsng7050 | Yes | Yes | No | No | No | Chlorpheniramine Maleate, Multi Vitamin | 13,988 | 5 |
| Bgsng7052 | Yes | Yes | No | No | No | | 25,364 | 5 |
| Bgsng7063 | Yes | Yes | No | No | No | | 23,878 | 7 |
| Bgsng7071 | Yes | Yes | No | No | No | Paracetamol | 21,695 | 5 |
| Bgsng7074 | Yes | Yes | No | Yes | No | Oral rehydration saline, Multi Vitamin | 15,006 | 5 |
| Bgsng7081 | Yes | Yes | No | No | No | | 17,264 | 5 |
| Bgsng7087 | Yes | Yes | No | No | No | | 19,084 | 5 |
| Bgsng7090 | Yes | Yes | No | No | Yes | Amoxycillin trihydrate, Sulbutamol | 20,562 | 5 |
| Bgsng7096 | Yes | Yes | No | No | No | | 27,208 | 5 |
| Bgsng7108 | Yes | Yes | No | No | No | | 21,247 | 6 |
| Bgsng7130 | Yes | Yes | No | No | No | | 26,268 | 5 |
| Bgsng7131 | Yes | Yes | No | No | No | | 39,288 | 5 |
| Bgsng7133 | Yes | Yes | No | Yes | Yes | Azithromycin Dihydrate, Oral rehydration saline, Chlorpheniramine Maleate | 23,886 | 5 |
| Bgsng7135 | Yes | Yes | No | No | No | | 18,644 | 5 |
| Bgsng7145 | Yes | Yes | No | No | No | | 24,350 | 4 |
| Bgsng7149 | Yes | Yes | No | No | No | | 21,384 | 4 |
| Bgsng7152 | Yes | Yes | No | No | No | | 22,772 | 4 |
| Bgsng7173 | Yes | Yes | No | No | Yes | Amoxicillin trihydrate + Clavulanic acid, Chloramphenicol, Sulbutamol | 22,652 | 9 |
| Bgsng7178 | Yes | Yes | No | No | No | | 26,494 | 9 |
| Bgsng7203 | Yes | Yes | No | No | No | | 15,174 | 7 |

TABLE 16

Metadata associated with individual fecal samples from concordant healthy Malawian twins and triplets

| Family ID | Child ID | Gender | Zygosity | Fecal Sample ID | Age, months | WHZ | Number of high quality V4-16S rRNA sequences | 16S rRNA Sequencing Run ID |
|---|---|---|---|---|---|---|---|---|
| h208 | h208A | female | MZ | h208A.1 | 0.4 | −1.73 | 133,515 | Malawi89 |
| h301 | h301A | male | DZ | h301A.1 | 0.6 | 0.2 | 101,465 | Malawi89 |
| h301 | h301B | male | DZ | h301B.1 | 0.6 | −0.33 | 135,737 | Malawi89 |
| h257 | h257A | male | MZ | h257A.1 | 2.3 | −0.62 | 117,949 | Malawi89 |
| h257 | h257B | male | MZ | h257B.1 | 2.3 | 0.47 | 121,595 | Malawi89 |
| h181 | h181A | male | DZ | h181A.1 | 2.6 | 0.36 | 221,464 | Malawi7 |
| h181 | h181B | male | MZ | h181B.1 | 2.6 | −0.25 | 229,814 | Malawi7 |
| h181 | h181C | male | MZ | h181C.1 | 2.6 | −0.99 | 216,056 | Malawi7 |
| h259 | h259A | female | MZ | h259A.2 | 3.2 | 1.86 | 197,189 | Malawi7 |
| h259 | h259B | female | MZ | h259B.2 | 3.2 | 1.53 | 200,122 | Malawi7 |
| h305 | h305B | male | DZ | h305B.2 | 4.7 | −1 | 131,898 | Malawi89 |
| h305 | h305C | female | DZ | h305C.2 | 4.7 | −0.42 | 111,403 | Malawi89 |
| h121 | h121B | male | MZ | h121B.1 | 5.2 | 2.58 | 122,051 | Malawi89 |
| h165 | h165A | male | MZ | h165A.1 | 5.3 | −0.58 | 230,639 | Malawi7 |
| h165 | h165B | male | MZ | h165B.1 | 5.3 | −0.38 | 236,422 | Malawi7 |
| h209 | h209A | female | MZ | h209A.2 | 6.8 | −0.18 | 101,469 | Malawi89 |
| h209 | h209B | female | MZ | h209B.2 | 6.8 | −0.83 | 80,917 | Malawi89 |
| h47 | h47A | male | MZ | h47A.1 | 7.2 | −0.93 | 64,752 | Malawi6 |
| h47 | h47B | male | MZ | h47B.1 | 7.2 | −2.26 | 99,204 | Malawi7 |
| h235 | h235A | male | MZ | h235A.1 | 8.0 | −1.09 | 118,988 | Malawi89 |
| h235 | h235B | male | MZ | h235B.1 | 8.0 | −0.31 | 108,240 | Malawi89 |
| h128 | h128A | male | MZ | h128A.1 | 9.1 | −1.31 | 177,426 | Malawi7 |
| h264 | h264A | female | MZ | h264A.2 | 9.6 | 0.01 | 122,455 | Malawi89 |
| h264 | h264B | female | MZ | h264B.2 | 9.6 | −0.33 | 246,575 | Malawi7 |
| h273 | h273A | female | MZ | h273A.2 | 11.1 | 0.48 | 245,101 | Malawi7 |
| h273 | h273B | female | MZ | h273B.2 | 11.1 | 0.81 | 245,319 | Malawi7 |
| h37 | h37A | female | DZ | h37A.2 | 11.2 | −1.07 | 141,448 | Malawi89 |
| h37 | h37B | female | DZ | h37B.2 | 11.2 | −0.27 | 142,827 | Malawi89 |
| h279 | h279A | male | MZ | h279A.2 | 11.4 | 0.96 | 106,307 | Malawi89 |
| h279 | h279B | male | MZ | h279B.2 | 11.4 | −1.01 | 110,396 | Malawi89 |
| h144 | h144A | male | MZ | h144A.1 | 14.6 | −0.74 | 230,465 | Malawi7 |
| h144 | h144B | male | MZ | h144B.1 | 14.6 | −1.96 | 289,895 | Malawi7 |
| h10 | h10A | female | DZ | h10A.2 | 16.1 | −0.32 | 130,876 | Malawi89 |
| h18 | h18A | female | MZ | h18A.4 | 16.2 | 0.51 | 76,375 | Malawi6 |
| h18 | h18B | female | MZ | h18B.4 | 16.2 | 0.08 | 70,390 | Malawi6 |
| h68 | h68A | male | DZ | h68A.4 | 20.4 | −0.09 | 267,547 | Malawi3 |
| h68 | h68B | male | DZ | h68B.4 | 20.4 | 0 | 70,403 | Malawi3 |
| h35 | h35A | male | MZ | h35A.3 | 22.7 | −2.16 | 46,022 | Malawi6 |
| h78 | h78A | male | DZ | h78A.4 | 22.7 | −0.7 | 241,999 | Malawi3 |
| h78 | h78B | male | DZ | h78B.4 | 22.7 | 0.95 | 216,988 | Malawi3 |
| h186 | h186A | male | MZ | h186A.1 | 24.2 | 0.09 | 120,553 | Malawi89 |
| h186 | h186B | female | DZ | h186B.1 | 24.2 | 1.36 | 62,791 | Malawi7 |
| h186 | h186C | male | MZ | h186C.1 | 24.2 | −0.07 | 121,883 | Malawi89 |
| h60 | h60A | female | MZ | h60A.2 | 24.5 | 0.04 | 232,045 | Malawi7 |
| h60 | h60B | female | MZ | h60B.2 | 24.5 | −0.29 | 93,313 | Malawi89 |
| h101 | h101A | female | MZ | h101A.3 | 25.1 | −0.55 | 111,821 | Malawi89 |
| h101 | h101B | female | MZ | h101B.3 | 25.1 | −0.16 | 122,049 | Malawi89 |

TABLE 17

Results of clinical microscopy of fecal samples obtained from healthy Bangladeshi children and those with MAM

| | | Enteropathogens detected | | |
|---|---|---|---|---|
| Fecal Sample ID | Study Group | *Giardia lamblia* | *Ascaris lumbricoides* | *Trichuris Tricuria* |

The following enteropathogens were not detected in any sample: *Entamoeba histolytica/Entamoeba dispar*, *Escherichia coli*, *Endolimax nana*, *Iodamoeba butschlii*, *Chilomastix mesnili*, *Blastocystis hominia*, Coccidian-like body (CLB), *Ancylostoma duodenale/Necator americanus*, or *Hymenolepsis nana*

| Fecal Sample ID | Study Group | *Giardia lamblia* | *Ascaris lumbricoides* | *Trichuris Tricuria* |
|---|---|---|---|---|
| Bgsng7035.m23 | Healthy Singleton Birth Cohort | − | + | − |
| Bgsng7106.m12 | Healthy Singleton Birth Cohort | + | − | − |
| Bgsng7106.m16 | Healthy Singleton Birth Cohort | + | − | − |
| Bgsng7106.m24 | Healthy Singleton Birth Cohort | + | − | − |
| Bgsng7128.m11 | Healthy Singleton Birth Cohort | + | − | − |
| Bgsng7128.m12 | Healthy Singleton Birth Cohort | + | − | − |
| Bgsng7128.m18 | Healthy Singleton Birth Cohort | + | + | − |
| Bgsng7128.m19 | Healthy Singleton Birth Cohort | − | + | − |
| Bgsng7177.m19 | Healthy Singleton Birth Cohort | + | − | − |
| Bgsng7177.m20 | Healthy Singleton Birth Cohort | + | − | − |

TABLE 17-continued

Results of clinical microscopy of fecal samples obtained from healthy Bangladeshi children and those with MAM

| | | Enteropathogens detected | | |
|---|---|---|---|---|
| Fecal Sample ID | Study Group | Giardia lamblia | Ascaris lumbricoides | Trichuris Tricuria |
| Bgsng7192.m19 | Healthy Singleton Birth Cohort | + | − | − |
| Bgsng7204.m17 | Healthy Singleton Birth Cohort | − | + | − |
| Bgsng7204.m19 | Healthy Singleton Birth Cohort | − | + | − |
| Bgsng7204.m20 | Healthy Singleton Birth Cohort | − | + | − |
| Bgsng7204.m22 | Healthy Singleton Birth Cohort | − | + | − |
| Bgsng7204.m23 | Healthy Singleton Birth Cohort | − | + | − |
| Bgsng8169.m17 | Healthy Singleton Birth Cohort | − | + | − |
| Bgsng8169.m18 | Healthy Singleton Birth Cohort | − | + | − |
| Bgsng8169.m19 | Healthy Singleton Birth Cohort | − | + | − |
| Bgsng8169.m22 | Healthy Singleton Birth Cohort | − | + | − |
| Bgsng8169.m23 | Healthy Singleton Birth Cohort | − | + | − |
| Bgsng8169.m24 | Healthy Singleton Birth Cohort | − | + | − |
| Bgsng7052.m15 | Healthy Singleton Birth Cohort | + | − | − |
| Bgsng7052.m17 | Healthy Singleton Birth Cohort | + | − | − |
| Bgsng7052.m24 | Healthy Singleton Birth Cohort | + | − | − |
| Bgsng7071.m18 | Healthy Singleton Birth Cohort | − | + | − |
| Bgsng7082.m17 | Healthy Singleton Birth Cohort | − | + | − |
| Bgsng7096.m9 | Healthy Singleton Birth Cohort | + | − | − |
| Bgsng7096.m13 | Healthy Singleton Birth Cohort | + | − | − |
| Bgsng7096.m16 | Healthy Singleton Birth Cohort | + | − | − |
| Bgsng7096.m19 | Healthy Singleton Birth Cohort | + | − | − |
| Bgsng7096.m21 | Healthy Singleton Birth Cohort | + | − | − |
| Bgsng7096.m22 | Healthy Singleton Birth Cohort | + | − | − |
| Bgsng7096.m24 | Healthy Singleton Birth Cohort | + | − | − |
| Bgsng7142.m18 | Healthy Singleton Birth Cohort | + | − | − |
| Bgsng7142.m20 | Healthy Singleton Birth Cohort | + | − | − |
| Bgsng7142.m24 | Healthy Singleton Birth Cohort | + | − | − |
| Bgsng7149.m14 | Healthy Singleton Birth Cohort | − | + | − |
| Bgsng7149.m15 | Healthy Singleton Birth Cohort | − | + | − |
| Bgsng7149.m16 | Healthy Singleton Birth Cohort | − | + | − |
| Bgsng7149.m18 | Healthy Singleton Birth Cohort | − | + | − |
| Bgsng7149.m19 | Healthy Singleton Birth Cohort | − | + | − |
| Bgsng7149.m21 | Healthy Singleton Birth Cohort | − | + | + |
| Bgsng7149.m24 | Healthy Singleton Birth Cohort | − | + | − |
| Bgsng7173.m12 | Healthy Singleton Birth Cohort | − | + | − |
| Bgsng7173.m22 | Healthy Singleton Birth Cohort | − | + | − |
| Bgsng7173.m24 | Healthy Singleton Birth Cohort | + | − | − |
| Bgsng7178.m14 | Healthy Singleton Birth Cohort | − | + | − |
| Bgsng7178.m18 | Healthy Singleton Birth Cohort | − | + | − |
| Bgsng7178.m23 | Healthy Singleton Birth Cohort | − | + | − |
| Bgtw1.T1.m18 | Healthy Twins & Triplets | − | + | − |
| Bgtw2.T1.m21 | Healthy Twins & Triplets | − | + | − |
| Bgtw2.T1.m22 | Healthy Twins & Triplets | − | + | − |
| Bgtw5.T1.m3 | Healthy Twins & Triplets | + | − | − |
| Bgtw11.T1.m1 | Healthy Twins & Triplets | − | + | − |
| Bgtw1.T2.m21 | Healthy Twins & Triplets | − | + | − |
| Bgtw2.T2.m21 | Healthy Twins & Triplets | − | + | − |
| Bgtw5.T2.m3 | Healthy Twins & Triplets | − | − | + |
| Bgtw8.T2.m7 | Healthy Twins & Triplets | − | + | + |
| Bgsng7013.m19 | Additional singletons sampled with and without MAM at 18 months | + | − | − |
| Bgsng7040.m19 | Additional singletons sampled with and without MAM at 18 months | − | + | − |
| Bgsng7148.m19 | Additional singletons sampled with and without MAM at 18 months | − | + | − |

Samples for which the enteropathogens tested for were not detected:

| | | | | |
|---|---|---|---|---|
| Bgsng7035.m1 | Bgsng7202.m21 | Bgsng7096.m15 | Bgtw4.T1.m5 | Bgtw4.T2.m4 |
| Bgsng7035.m2 | Bgsng7202.m22 | Bgsng7096.m17 | Bgtw4.T1.m6 | Bgtw4.T2.m5 |
| Bgsng7035.m3 | Bgsng7202.m23 | Bgsng7096.m20 | Bgtw4.T1.m7 | Bgtw4.T2.m6 |
| Bgsng7035.m4 | Bgsng7202.m24 | Bgsng7096.m23 | Bgtw4.T1.m8 | Bgtw4.T2.m8 |
| Bgsng7035.m5 | Bgsng7204.m1 | Bgsng7114.m1 | Bgtw4.T1.m9 | Bgtw4.T2.m9 |
| Bgsng7035.m6 | Bgsng7204.m2 | Bgsng7114.m2 | Bgtw4.T1.m10 | Bgtw4.T2.m10 |
| Bgsng7035.m7 | Bgsng7204.m3 | Bgsng7114.m3 | Bgtw4.T1.m11 | Bgtw4.T2.m11 |
| Bgsng7035.m8 | Bgsng7204.m4 | Bgsng7114.m4 | Bgtw4.T1.m12 | Bgtw4.T2.m12 |
| Bgsng7035.m9 | Bgsng7204.m5 | Bgsng7114.m5 | Bgtw4.T1.m13 | Bgtw4.T2.m13 |
| Bgsng7035.m10 | Bgsng7204.m6 | Bgsng7114.m6 | Bgtw4.T1.m14 | Bgtw4.T2.m14 |
| Bgsng7035.m11 | Bgsng7204.m7 | Bgsng7114.m7 | Bgtw4.T1.m15 | Bgtw4.T2.m15 |
| Bgsng7035.m12 | Bgsng7204.m8 | Bgsng7114.m8 | Bgtw4.T1.m16 | Bgtw4.T2.m15.dr |
| Bgsng7035.m13 | Bgsng7204.m9 | Bgsng7114.m10 | Bgtw4.T1.m18 | Bgtw4.T2.m17 |
| Bgsng7035.m14 | Bgsng7204.m10 | Bgsng7114.m11 | Bgtw4.T1.m18.drb | Bgtw4.T2.m18 |
| Bgsng7035.m15 | Bgsng7204.m11 | Bgsng7114.m12 | Bgtw4.T1.m18.drc | Bgtw4.T2.m19 |
| Bgsng7035.m16 | Bgsng7204.m12 | Bgsng7114.m13 | Bgtw4.T1.m20 | Bgtw5.T2.m1 |
| Bgsng7035.m17 | Bgsng7204.m13 | Bgsng7114.m16 | Bgtw5.T1.m2 | Bgtw5.T2.m2 |

TABLE 17-continued

Results of clinical microscopy of fecal samples obtained from healthy Bangladeshi children and those with MAM

|  |  | Enteropathogens detected | | |
| --- | --- | --- | --- | --- |
| Fecal Sample ID | Study Group | *Giardia lamblia* | *Ascaris lumbricoides* | *Trichuris Tricuria* |
| Bgsng7035.m19 | Bgsng7204.m14 | Bgsng7114.m17 | Bgtw5.T1.m4 | Bgtw5.T2.m4 |
| Bgsng7035.m20 | Bgsng7204.m15 | Bgsng7114.m18 | Bgtw5.T1.m5 | Bgtw5.T2.m5 |
| Bgsng7035.m21 | Bgsng7204.m16 | Bgsng7114.m20 | Bgtw5.T1.m6 | Bgtw5.T2.m6 |
| Bgsng7035.m22 | Bgsng7204.m18 | Bgsng7114.m22 | Bgtw5.T1.m7 | Bgtw5.T2.m8 |
| Bgsng7035.m24 | Bgsng7204.m21 | Bgsng7114.m24 | Bgtw5.T1.m8 | Bgtw5.T2.m9 |
| Bgsng7106.m1 | Bgsng7204.m24 | Bgsng7131.m1 | Bgtw5.T1.m9 | Bgtw5.T2.m10 |
| Bgsng7106.m2 | Bgsng8064.m1 | Bgsng7131.m2 | Bgtw5.T1.m10 | Bgtw5.T2.m11 |
| Bgsng7106.m3 | Bgsng8064.m2 | Bgsng7131.m3 | Bgtw5.T1.m11 | Bgtw5.T2.m12 |
| Bgsng7106.m4 | Bgsng8064.m3 | Bgsng7131.m4 | Bgtw5.T1.m12 | Bgtw5.T2.m13 |
| Bgsng7106.m5 | Bgsng8064.m4 | Bgsng7131.m5 | Bgtw5.T1.m13 | Bgtw5.T2.m14 |
| Bgsng7106.m6 | Bgsng8064.m5 | Bgsng7131.m6 | Bgtw5.T1.m14 | Bgtw5.T2.m15 |
| Bgsng7106.m9 | Bgsng8064.m6 | Bgsng7131.m7 | Bgtw5.T1.m15 | Bgtw5.T2.m16 |
| Bgsng7106.m10 | Bgsng8064.m7 | Bgsng7131.m8 | Bgtw5.T1.m16 | Bgtw5.T2.m17 |
| Bgsng7106.m11 | Bgsng8064.m8 | Bgsng7131.m9 | Bgtw5.T1.m17 | Bgtw5.T2.m18 |
| Bgsng7106.m14 | Bgsng8064.m9 | Bgsng7131.m10 | Bgtw5.T1.m18 | Bgtw5.T2.m19 |
| Bgsng7106.m18 | Bgsng8064.m10 | Bgsng7131.m11 | Bgtw5.T1.m19 | Bgtw5.T2.m20 |
| Bgsng7106.m19 | Bgsng8064.m11 | Bgsng7131.m12 | Bgtw5.T1.m20 | Bgtw5.T2.m21 |
| Bgsng7106.m20 | Bgsng8064.m12 | Bgsng7131.m13 | Bgtw5.T1.m21 | Bgtw5.T2.m22 |
| Bgsng7106.m21 | Bgsng8064.m13 | Bgsng7131.m15 | Bgtw5.T1.m22 | Bgtw6.T2.m1 |
| Bgsng7106.m22 | Bgsng8064.m14 | Bgsng7131.m16 | Bgtw6.T1.m1 | Bgtw6.T2.m2 |
| Bgsng7106.m23 | Bgsng8064.m15 | Bgsng7131.m17 | Bgtw6.T1.m2 | Bgtw6.T2.m3 |
| Bgsng7115.m1 | Bgsng8064.m16 | Bgsng7131.m18 | Bgtw6.T1.m3 | Bgtw6.T2.m4 |
| Bgsng7115.m2 | Bgsng8064.m17 | Bgsng7131.m19 | Bgtw6.T1.m4 | Bgtw6.T2.m6 |
| Bgsng7115.m3 | Bgsng8064.m18 | Bgsng7131.m20 | Bgtw6.T1.m7 | Bgtw6.T2.m7 |
| Bgsng7115.m4 | Bgsng8064.m19 | Bgsng7131.m21 | Bgtw6.T1.m8 | Bgtw6.T2.m8 |
| Bgsng7115.m5 | Bgsng8064.m20 | Bgsng7131.m22 | Bgtw6.T1.m9 | Bgtw6.T2.m9 |
| Bgsng7115.m6 | Bgsng8064.m21 | Bgsng7131.m23 | Bgtw6.T1.m10 | Bgtw6.T2.m10 |
| Bgsng7115.m7 | Bgsng8064.m22 | Bgsng7131.m24 | Bgtw7.T1.m1 | Bgtw6.T2.m15.dr |
| Bgsng7115.m8 | Bgsng8064.m23 | Bgsng7142.m1 | Bgtw7.T1.m2 | Bgtw7.T2.m1 |
| Bgsng7115.m9 | Bgsng8064.m24 | Bgsng7142.m2 | Bgtw7.T1.m3 | Bgtw7.T2.m2 |
| Bgsng7115.m10 | Bgsng8169.m1 | Bgsng7142.m3 | Bgtw7.T1.m4 | Bgtw7.T2.m3 |
| Bgsng7115.m11 | Bgsng8169.m3 | Bgsng7142.m4 | Bgtw7.T1.m5 | Bgtw7.T2.m4 |
| Bgsng7115.m12 | Bgsng8169.m5 | Bgsng7142.m5 | Bgtw7.T1.m6 | Bgtw7.T2.m5 |
| Bgsng7115.m13 | Bgsng8169.m6 | Bgsng7142.m6 | Bgtw7.T1.m6.dra | Bgtw7.T2.m6 |
| Bgsng7115.m14 | Bgsng8169.m7 | Bgsng7142.m7 | Bgtw7.T1.m6.drb | Bgtw7.T2.m6.dra |
| Bgsng7115.m15 | Bgsng8169.m8 | Bgsng7142.m8 | Bgtw7.T1.m7 | Bgtw7.T2.m6.drb |
| Bgsng7115.m16 | Bgsng8169.m9 | Bgsng7142.m9 | Bgtw7.T1.m8 | Bgtw7.T2.m8 |
| Bgsng7115.m17 | Bgsng8169.m10 | Bgsng7142.m11 | Bgtw7.T1.m9 | Bgtw7.T2.m9 |
| Bgsng7115.m18 | Bgsng8169.m11 | Bgsng7142.m12 | Bgtw7.T1.m10 | Bgtw7.T2.m10 |
| Bgsng7115.m20 | Bgsng8169.m12 | Bgsng7142.m13 | Bgtw7.T1.m11 | Bgtw7.T2.m11 |
| Bgsng7115.m23 | Bgsng8169.m13 | Bgsng7142.m14 | Bgtw7.T1.m12 | Bgtw7.T2.m12 |
| Bgsng7115.m24 | Bgsng8169.m14 | Bgsng7142.m15 | Bgtw7.T1.m13 | Bgtw7.T2.m13 |
| Bgsng7128.m1 | Bgsng8169.m15 | Bgsng7142.m16 | Bgtw7.T1.m14 | Bgtw7.T2.m14 |
| Bgsng7128.m2 | Bgsng8169.m16 | Bgsng7142.m17 | Bgtw7.T1.m15 | Bgtw7.T2.m15 |
| Bgsng7128.m3 | Bgsng8169.m20 | Bgsng7142.m21 | Bgtw7.T1.m16 | Bgtw7.T2.m16 |
| Bgsng7128.m4 | Bgsng8169.m21 | Bgsng7142.m22 | Bgtw8.T1.m1 | Bgtw8.T2.m1 |
| Bgsng7128.m5 | Bgsng7018.m1 | Bgsng7142.m23 | Bgtw8.T1.m2 | Bgtw8.T2.m2 |
| Bgsng7128.m6 | Bgsng7018.m2 | Bgsng7149.m1 | Bgtw8.T1.m3 | Bgtw8.T2.m3 |
| Bgsng7128.m7 | Bgsng7018.m3 | Bgsng7149.m2 | Bgtw8.T1.m4 | Bgtw8.T2.m4 |
| Bgsng7128.m8 | Bgsng7018.m4 | Bgsng7149.m3 | Bgtw8.T1.m5 | Bgtw8.T2.m5 |
| Bgsng7128.m9 | Bgsng7018.m5 | Bgsng7149.m4 | Bgtw8.T1.m6 | Bgtw8.T2.m6 |
| Bgsng7128.m10 | Bgsng7018.m6 | Bgsng7149.m5 | Bgtw8.T1.m7 | Bgtw8.T2.m8 |
| Bgsng7128.m13 | Bgsng7018.m7 | Bgsng7149.m6 | Bgtw8.T1.m8 | Bgtw8.T2.m9 |
| Bgsng7128.m14 | Bgsng7018.m8 | Bgsng7149.m7 | Bgtw8.T1.m9 | Bgtw8.T2.m10 |
| Bgsng7128.m16 | Bgsng7018.m9 | Bgsng7149.m8 | Bgtw8.T1.m10 | Bgtw8.T2.m11 |
| Bgsng7128.m17 | Bgsng7018.m10 | Bgsng7149.m9 | Bgtw8.T1.m11 | Bgtw8.T2.m12 |
| Bgsng7128.m20 | Bgsng7018.m11 | Bgsng7149.m10 | Bgtw8.T1.m12 | Bgtw8.T2.m13 |
| Bgsng7128.m21 | Bgsng7018.m12 | Bgsng7149.m11 | Bgtw8.T1.m13 | Bgtw9.T2.m1 |
| Bgsng7128.m22 | Bgsng7018.m13 | Bgsng7149.m12 | Bgtw9.T1.m2 | Bgtw9.T2.m2 |
| Bgsng7128.m23 | Bgsng7018.m14 | Bgsng7149.m13 | Bgtw9.T1.m3 | Bgtw9.T2.m3 |
| Bgsng7128.m24 | Bgsng7018.m15 | Bgsng7149.m17 | Bgtw9.T1.m4 | Bgtw9.T2.m4 |
| Bgsng7150.m1 | Bgsng7018.m16 | Bgsng7149.m23 | Bgtw9.T1.m5 | Bgtw9.T2.m5 |
| Bgsng7150.m2 | Bgsng7018.m17 | Bgsng7173.m1 | Bgtw9.T1.m6 | Bgtw9.T2.m6 |
| Bgsng7150.m3 | Bgsng7018.m18 | Bgsng7173.m2 | Bgtw9.T1.m8 | Bgtw9.T2.m8 |
| Bgsng7150.m4 | Bgsng7018.m19 | Bgsng7173.m3 | Bgtw9.T1.m9 | Bgtw9.T2.m9 |
| Bgsng7150.m5 | Bgsng7018.m20 | Bgsng7173.m4 | Bgtw9.T1.m10 | Bgtw9.T2.m10 |
| Bgsng7150.m6 | Bgsng7018.m24 | Bgsng7173.m5 | Bgtw9.T1.m11 | Bgtw9.T2.m11 |
| Bgsng7150.m7 | Bgsng7052.m1 | Bgsng7173.m6 | Bgtw9.T1.m12 | Bgtw9.T2.m12 |
| Bgsng7150.m8 | Bgsng7052.m2 | Bgsng7173.m7 | Bgtw9.T1.m13 | Bgtw9.T2.m13 |
| Bgsng7150.m9 | Bgsng7052.m3 | Bgsng7173.m8 | Bgtw10.T1.m1 | Bgtw10.T2.m1 |
| Bgsng7150.m10 | Bgsng7052.m4 | Bgsng7173.m9 | Bgtw10.T1.m2 | Bgtw10.T2.m2 |
| Bgsng7150.m11 | Bgsng7052.m5 | Bgsng7173.m10 | Bgtw10.T1.m4 | Bgtw10.T2.m4 |
| Bgsng7150.m12 | Bgsng7052.m6 | Bgsng7173.m11 | Bgtw10.T1.m5 | Bgtw10.T2.m5 |
| Bgsng7150.m13 | Bgsng7052.m7 | Bgsng7173.m13 | Bgtw10.T1.m6 | Bgtw10.T2.m6 |

TABLE 17-continued

Results of clinical microscopy of fecal samples obtained from healthy Bangladeshi children and those with MAM

|  |  | Enteropathogens detected | | |
| --- | --- | --- | --- | --- |
| Fecal Sample ID | Study Group | *Giardia lamblia* | *Ascaris lumbricoides* | *Trichuris Tricuria* |
| Bgsng7150.m14 | Bgsng7052.m8 | Bgsng7173.m14 | Bgtw10.T1.m8 | Bgtw10.T2.m7 |
| Bgsng7150.m15 | Bgsng7052.m9 | Bgsng7173.m15 | Bgtw10.T1.m9 | Bgtw10.T2.m8 |
| Bgsng7150.m16 | Bgsng7052.m10 | Bgsng7173.m16 | Bgtw10.T1.m10 | Bgtw10.T2.m9 |
| Bgsng7150.m17 | Bgsng7052.m11 | Bgsng7173.m17 | Bgtw10.T1.m11 | Bgtw10.T2.m10 |
| Bgsng7150.m18 | Bgsng7052.m12 | Bgsng7173.m18 | Bgtw10.T1.m12 | Bgtw10.T2.m11 |
| Bgsng7150.m19 | Bgsng7052.m14 | Bgsng7173.m19 | Bgtw10.T1.m13 | Bgtw10.T2.m12 |
| Bgsng7150.m20 | Bgsng7052.m16 | Bgsng7173.m20 | Bgtw11.T1.m2 | Bgtw10.T2.m13 |
| Bgsng7150.m21 | Bgsng7052.m18 | Bgsng7173.m21 | Bgtw11.T1.m3 | Bgtw11.T2.m1 |
| Bgsng7150.m24 | Bgsng7052.m19 | Bgsng7173.m23 | Bgtw11.T1.m4 | Bgtw11.T2.m2 |
| Bgsng7155.m1 | Bgsng7052.m20 | Bgsng7178.m1 | Bgtw11.T1.m5 | Bgtw11.T2.m3 |
| Bgsng7155.m2 | Bgsng7063.m1 | Bgsng7178.m2 | Bgtw11.T1.m6 | Bgtw11.T2.m4 |
| Bgsng7155.m3 | Bgsng7063.m2 | Bgsng7178.m3 | Bgtw11.T1.m7 | Bgtw11.T2.m5 |
| Bgsng7155.m4 | Bgsng7063.m3 | Bgsng7178.m4 | Bgtw11.T1.m8 | Bgtw11.T2.m6 |
| Bgsng7155.m5 | Bgsng7063.m4 | Bgsng7178.m5 | Bgtw11.T1.m9 | Bgtw11.T2.m6.dr |
| Bgsng7155.m6 | Bgsng7063.m5 | Bgsng7178.m6 | Bgtw11.T1.m10 | Bgtw11.T2.m7 |
| Bgsng7155.m7 | Bgsng7063.m6 | Bgsng7178.m7 | Bgtw11.T1.m11 | Bgtw11.T2.m8 |
| Bgsng7155.m8 | Bgsng7063.m7 | Bgsng7178.m8 | Bgtw11.T1.m12 | Bgtw11.T2.m9 |
| Bgsng7155.m9 | Bgsng7063.m8 | Bgsng7178.m9 | Bgtw12.T1.m1 | Bgtw11.T2.m10 |
| Bgsng7155.m10 | Bgsng7063.m10 | Bgsng7178.m10 | Bgtw12.T1.m2 | Bgtw11.T2.m12 |
| Bgsng7155.m11 | Bgsng7063.m11 | Bgsng7178.m11 | Bgtw12.T1.m3 | Bgtw11.T2.m12.dr |
| Bgsng7155.m12 | Bgsng7063.m12 | Bgsng7178.m12 | Bgtw12.T1.m4 | Bgtw12.T2.m1 |
| Bgsng7155.m13 | Bgsng7063.m15 | Bgsng7178.m13 | Bgtw12.T1.m5 | Bgtw12.T2.m2 |
| Bgsng7155.m14 | Bgsng7063.m16 | Bgsng7178.m15 | Bgtw12.T1.m6 | Bgtw12.T2.m3 |
| Bgsng7155.m15 | Bgsng7063.m17 | Bgsng7178.m16 | Bgtw12.T1.m7 | Bgtw12.T2.m4 |
| Bgsng7155.m16 | Bgsng7063.m18 | Bgsng7178.m17 | Bgtw12.T1.m8 | Bgtw12.T2.m5 |
| Bgsng7155.m17 | Bgsng7063.m19 | Bgsng7178.m19 | Bgtw12.T1.m9 | Bgtw12.T2.m6 |
| Bgsng7155.m18 | Bgsng7063.m20 | Bgsng7178.m20 | Bgtw12.T1.m10 | Bgtw12.T2.m7 |
| Bgsng7155.m19 | Bgsng7063.m21 | Bgsng7178.m21 | Bgtw12.T1.m11 | Bgtw12.T2.m8 |
| Bgsng7155.m20 | Bgsng7063.m22 | Bgsng7178.m22 | Bgtw12.T1.m12 | Bgtw12.T2.m9 |
| Bgsng7155.m21 | Bgsng7063.m24 | Bgsng7178.m24 | Bgtw12.T1.m13 | Bgtw12.T2.m10 |
| Bgsng7155.m22 | Bgsng7071.m1 | Bgtw1.T1.m2 | Bgtw1.T2.m2 | Bgtw12.T2.m11 |
| Bgsng7155.m23 | Bgsng7071.m2 | Bgtw1.T1.m3 | Bgtw1.T2.m3 | Bgtw12.T2.m12 |
| Bgsng7155.m24 | Bgsng7071.m4 | Bgtw1.T1.m4 | Bgtw1.T2.m4 | Bgtw12.T2.m13 |
| Bgsng7177.m1 | Bgsng7071.m5 | Bgtw1.T1.m5 | Bgtw1.T2.m5 | Bgtw4.T3.m1 |
| Bgsng7177.m2 | Bgsng7071.m6 | Bgtw1.T1.m6 | Bgtw1.T2.m6 | Bgtw4.T3.m2 |
| Bgsng7177.m3 | Bgsng7071.m7 | Bgtw1.T1.m6.dr | Bgtw1.T2.m7 | Bgtw4.T3.m3 |
| Bgsng7177.m4 | Bgsng7071.m9 | Bgtw1.T1.m7 | Bgtw1.T2.m8 | Bgtw4.T3.m4 |
| Bgsng7177.m5 | Bgsng7071.m10 | Bgtw1.T1.m8 | Bgtw1.T2.m9 | Bgtw4.T3.m5 |
| Bgsng7177.m6 | Bgsng7071.m12 | Bgtw1.T1.m9 | Bgtw1.T2.m10 | Bgtw4.T3.m6 |
| Bgsng7177.m7 | Bgsng7071.m14 | Bgtw1.T1.m10 | Bgtw1.T2.m11 | Bgtw4.T3.m8 |
| Bgsng7177.m8 | Bgsng7071.m15 | Bgtw1.T1.m11 | Bgtw1.T2.m12 | Bgtw4.T3.m8.dr |
| Bgsng7177.m9 | Bgsng7071.m16 | Bgtw1.T1.m12 | Bgtw1.T2.m13 | Bgtw4.T3.m9 |
| Bgsng7177.m11 | Bgsng7071.m19 | Bgtw1.T1.m13 | Bgtw1.T2.m14 | Bgtw4.T3.m10 |
| Bgsng7177.m12 | Bgsng7071.m20 | Bgtw1.T1.m14 | Bgtw1.T2.m15 | Bgtw4.T3.m11 |
| Bgsng7177.m13 | Bgsng7071.m22 | Bgtw1.T1.m15 | Bgtw1.T2.m16 | Bgtw4.T3.m12 |
| Bgsng7177.m14 | Bgsng7071.m23 | Bgtw1.T1.m16 | Bgtw1.T2.m18 | Bgtw4.T3.m13 |
| Bgsng7177.m15 | Bgsng7071.m24 | Bgtw1.T1.m19 | Bgtw1.T2.m19 | Bgtw4.T3.m14 |
| Bgsng7177.m16 | Bgsng7082.m1 | Bgtw1.T1.m20 | Bgtw1.T2.m22 | Bgtw4.T3.m15 |
| Bgsng7177.m17 | Bgsng7082.m2 | Bgtw1.T1.m21 | Bgtw1.T2.m23 | Bgtw4.T3.m16 |
| Bgsng7177.m18 | Bgsng7082.m3 | Bgtw1.T1.m22 | Bgtw1.T2.m24 | Bgtw4.T3.m17 |
| Bgsng7177.m21 | Bgsng7082.m4 | Bgtw1.T1.m23 | Bgtw1.T2.m25 | Bgtw4.T3.m18 |
| Bgsng7177.m22 | Bgsng7082.m5 | Bgtw1.T1.m24 | Bgtw2.T2.m2 | Bgtw4.T3.m19 |
| Bgsng7177.m23 | Bgsng7082.m6 | Bgtw1.T1.m24.dr | Bgtw2.T2.m2.dr | Bgtw4.T3.m20 |
| Bgsng7177.m24 | Bgsng7082.m7 | Bgtw1.T1.m25 | Bgtw2.T2.m3 | Bgtw1.T1.m17 |
| Bgsng7192.m1 | Bgsng7082.m8 | Bgtw2.T1.m2 | Bgtw2.T2.m4 | Bgtw2.T1.m6.dr |
| Bgsng7192.m2 | Bgsng7082.m9 | Bgtw2.T1.m2.dr | Bgtw2.T2.m5 | Bgtw3.T1.m4.dr |
| Bgsng7192.m3 | Bgsng7082.m10 | Bgtw2.T1.m3 | Bgtw2.T2.m6 | Bgtw3.T1.m5.dr |
| Bgsng7192.m4 | Bgsng7082.m11 | Bgtw2.T1.m4 | Bgtw2.T2.m7 | Bgtw3.T1.m9.dr |
| Bgsng7192.m5 | Bgsng7082.m12 | Bgtw2.T1.m5 | Bgtw2.T2.m8 | Bgtw3.T1.m10 |
| Bgsng7192.m6 | Bgsng7082.m15 | Bgtw2.T1.m6 | Bgtw2.T2.m9 | Bgtw3.T1.m18.dr |
| Bgsng7192.m7 | Bgsng7082.m18 | Bgtw2.T1.m7 | Bgtw2.T2.m10 | Bgtw4.T1.m18.dra |
| Bgsng7192.m8 | Bgsng7082.m19 | Bgtw2.T1.m8 | Bgtw2.T2.m11 | Bgtw6.T1.m8.dr |
| Bgsng7192.m9 | Bgsng7082.m20 | Bgtw2.T1.m9 | Bgtw2.T2.m12 | Bgtw8.T1.m5.dr |
| Bgsng7192.m10 | Bgsng7082.m24 | Bgtw2.T1.m10 | Bgtw2.T2.m13 | Bgtw9.T1.m7 |
| Bgsng7192.m11 | Bgsng7090.m1 | Bgtw2.T1.m11 | Bgtw2.T2.m14 | Bgtw10.T1.m2.dr |
| Bgsng7192.m12 | Bgsng7090.m2 | Bgtw2.T1.m12 | Bgtw2.T2.m15 | Bgtw10.T1.m3 |
| Bgsng7192.m13 | Bgsng7090.m3 | Bgtw2.T1.m13 | Bgtw2.T2.m16 | Bgtw10.T1.m4.dra |
| Bgsng7192.m14 | Bgsng7090.m4 | Bgtw2.T1.m14 | Bgtw2.T2.m17 | Bgtw10.T1.m4.drb |
| Bgsng7192.m15 | Bgsng7090.m5 | Bgtw2.T1.m15 | Bgtw2.T2.m18 | Bgtw10.T1.m7 |
| Bgsng7192.m16 | Bgsng7090.m6 | Bgtw2.T1.m16 | Bgtw2.T2.m19 | Bgtw10.T1.m8.dr |
| Bgsng7192.m17 | Bgsng7090.m7 | Bgtw2.T1.m17 | Bgtw2.T2.m20 | Bgtw12.T1.m9.dr |
| Bgsng7192.m18 | Bgsng7090.m8 | Bgtw2.T1.m18 | Bgtw2.T2.m22 | Bgtw1.T2.m16.dr |
| Bgsng7192.m20 | Bgsng7090.m9 | Bgtw2.T1.m19 | Bgtw2.T2.m23 | Bgtw1.T2.m17 |
| Bgsng7192.m21 | Bgsng7090.m10 | Bgtw2.T1.m20 | Bgtw2.T2.m24 | Bgtw2.T2.m6.dr |

TABLE 17-continued

Results of clinical microscopy of fecal samples obtained from healthy Bangladeshi children and those with MAM

| | | Enteropathogens detected | | |
|---|---|---|---|---|
| Fecal Sample ID | Study Group | Giardia lamblia | Ascaris lumbricoides | Trichuris Tricuria |
| Bgsng7192.m22 | Bgsng7090.m11 | Bgtw2.T1.m23 | Bgtw3.T2.m1 | Bgtw3.T2.m4.dr |
| Bgsng7192.m23 | Bgsng7090.m12 | Bgtw2.T1.m24 | Bgtw3.T2.m2 | Bgtw3.T2.m5.dra |
| Bgsng7192.m24 | Bgsng7090.m13 | Bgtw3.T1.m1 | Bgtw3.T2.m3 | Bgtw3.T2.m5.drb |
| Bgsng7202.m1 | Bgsng7090.m14 | Bgtw3.T1.m3 | Bgtw3.T2.m4 | Bgtw3.T2.m11.dr |
| Bgsng7202.m2 | Bgsng7090.m15 | Bgtw3.T1.m4 | Bgtw3.T2.m5 | Bgtw4.T2.m19.dr |
| Bgsng7202.m3 | Bgsng7090.m16 | Bgtw3.T1.m5 | Bgtw3.T2.m6 | Bgtw7.T2.m12.dr |
| Bgsng7202.m4 | Bgsng7090.m17 | Bgtw3.T1.m6 | Bgtw3.T2.m7 | Bgtw9.T2.m2.dr |
| Bgsng7202.m5 | Bgsng7090.m18 | Bgtw3.T1.m7 | Bgtw3.T2.m8 | Bgtw9.T2.m7 |
| Bgsng7202.m6 | Bgsng7090.m19 | Bgtw3.T1.m8 | Bgtw3.T2.m9 | Bgtw10.T2.m2.dr |
| Bgsng7202.m7 | Bgsng7090.m20 | Bgtw3.T1.m9 | Bgtw3.T2.m9.dr | Bgtw10.T2.m3 |
| Bgsng7202.m8 | Bgsng7090.m22 | Bgtw3.T1.m11 | Bgtw3.T2.m10 | Bgtw10.T2.m4.dra |
| Bgsng7202.m9 | Bgsng7090.m23 | Bgtw3.T1.m12 | Bgtw3.T2.m11 | Bgtw10.T2.m4.drb |
| Bgsng7202.m10 | Bgsng7090.m24 | Bgtw3.T1.m13 | Bgtw3.T2.m12 | Bgtw10.T2.m9.dr |
| Bgsng7202.m11 | Bgsng7096.m1 | Bgtw3.T1.m14 | Bgtw3.T2.m13 | Bgtw4.T3.m5.dr |
| Bgsng7202.m12 | Bgsng7096.m2 | Bgtw3.T1.m15 | Bgtw3.T2.m14 | Bgtw4.T3.m10.dr |
| Bgsng7202.m13 | Bgsng7096.m3 | Bgtw3.T1.m16 | Bgtw3.T2.m15 | Bgsng7001.m19 |
| Bgsng7202.m14 | Bgsng7096.m4 | Bgtw3.T1.m17 | Bgtw3.T2.m16 | Bgsng7004.m19 |
| Bgsng7202.m15 | Bgsng7096.m5 | Bgtw3.T1.m19 | Bgtw3.T2.m17 | Bgsng7031.m19 |
| Bgsng7202.m16 | Bgsng7096.m6 | Bgtw3.T1.m20 | Bgtw3.T2.m19 | Bgsng7050.m19 |
| Bgsng7202.m17 | Bgsng7096.m7 | Bgtw3.T1.m21 | Bgtw3.T2.m20 | Bgsng7074.m19 |
| Bgsng7202.m18 | Bgsng7096.m8 | Bgtw3.T1.m22 | Bgtw3.T2.m21 | Bgsng7081.m19 |
| Bgsng7202.m20 | Bgsng7096.m10 | Bgtw4.T1.m1 | Bgtw3.T2.m22 | Bgsng7087.m19 |
| Bgsng7145.m19 | Bgsng7096.m11 | Bgtw4.T1.m2 | Bgtw4.T2.m1 | Bgsng7094.m19 |
| Bgsng7152.m19 | Bgsng7096.m12 | Bgtw4.T1.m3 | Bgtw4.T2.m2 | Bgsng7108.m18 |
| Bgsng7203.m19 | Bgsng7096.m14 | Bgtw4.T1.m4 | Bgtw4.T2.m3 | Bgsng7109.m18 |
| Bgsng7133.m19 | Bgsng7123.m18 | | | Bgsng7110.m18 |
| Bgsng7135.m19 | Bgsng7130.m19 | | | Bgsng7116.m19 |

TABLE 18

History of recruitment for patients for cholera study

| | | Reason for Exclusion: | | | | |
|---|---|---|---|---|---|---|
| Date | Total screened | No permanent address | History of antibiotic usage ≤1 week prior to presentation | Negative Dark Field test for V. cholerae | Residence outside of Dhaka | Presentation >24 h after initiation of diarrhea | Number of individuals satisfying enrollment criteria |
| July, 2010 | 30 | 7 | 11 | 1 | 7 | 3 | 1 |
| August, 2010 | 38 | 6 | 19 | 3 | 5 | 3 | 2 |
| September, 2010 | 30 | 4 | 10 | 4 | 8 | 4 | 0 |
| October, 2010 | 94 | 11 | 55 | 7 | 7 | 7 | 7 |
| November, 2010 | 163 | 9 | 141 | 0 | 7 | 5 | 1 |
| December, 2010 | 50 | 6 | 36 | 0 | 4 | 4 | 0 |
| January, 2011 | 49 | 4 | 38 | 0 | 5 | 2 | 0 |
| February, 2011 | 51 | 7 | 37 | 0 | 3 | 4 | 0 |
| March, 2011 | 59 | 4 | 47 | 0 | 3 | 5 | 0 |
| April, 2011 | 94 | 6 | 77 | 0 | 7 | 4 | 0 |
| May, 2011 | 84 | 9 | 65 | 0 | 5 | 5 | 0 |
| June, 2011 | 96 | 11 | 76 | 0 | 4 | 5 | 0 |
| July, 2011 | 116 | 17 | 82 | 0 | 9 | 8 | 0 |
| August, 2011 | 199 | 31 | 102 | 0 | 25 | 41 | 0 |
| Total | 1153 | 132 | 796 | 15 | 99 | 100 | 11* |

*4 individuals lost to follow-up after hospital phase

TABLE 19

Summary of fecal samples collected for study

| PatientID | First diarrheal stool (hours before admission)* | Time in Hospital (h) | Total number of fecal samples collected | Total Diarrhea time (h) | Average number of samples/h in hospital |
|---|---|---|---|---|---|
| A | 5 | 70 | 103 | 76 | 1.5 |
| B | 11 | 49 | 57 | 60 | 1.2 |
| C | 6 | 33 | 114 | 39 | 3.5 |
| D | 11 | 27 | 21 | 38 | 0.8 |
| E | 5 | 34 | 69 | 39 | 2.0 |
| F | 9 | 54 | 35 | 62 | 0.7 |
| G | 9 | 24 | 29 | 33 | 1.2 |

*Sample not collected

TABLE 20

Correlation of relative abundance of species in fecal samples to time in healthy Bangladeshi children and adults with cholera

| Species | Spearman r (relative abundance versus time after enrollment in study) in adults with cholera | Spearman r (relative abundance versus chronological age) in healthy Bangladeshi children | p-value (Benjamini-Hochberg corrected, cholera dataset) | p-value (Benjamini-Hochberg corrected, healthy children dataset) |
|---|---|---|---|---|
| *Streptococcus parasanguinis* | −0.512511796 | −0.050103401 | 2.26E−16 | 1.73E−01 |
| *Streptococcus*; Other | −0.456793856 | −0.023206263 | 5.12E−13 | 5.24E−01 |
| *Staphylococcus*; Other | −0.370912336 | −0.427410828 | 1.02E−08 | 1.34E−34 |
| *Streptococcus thermophilus* | −0.342273555 | −0.302003888 | 1.50E−07 | 3.50E−17 |
| *Haemophilus parainfluenzae* | −0.341788561 | 0.485691395 | 1.50E−07 | 1.61E−45 |
| *Enterococcus*; Other | −0.101226118 | −0.101736034 | 1.34E−01 | 5.41E−03 |
| *Escherichia coli* | −0.051171255 | −0.291290688 | 4.50E−01 | 4.81E−16 |
| *Weissella cibaria* | −0.050569847 | 0.267047127 | 4.50E−01 | 1.22E−13 |
| *Ruminococcus torques* | −0.011293356 | 0.576732028 | 8.63E−01 | 2.16E−67 |
| *Enterococcus faecalis* | 0.067644949 | −0.105616125 | 3.24E−01 | 3.97E−03 |
| *Lactobacillus reuteri* | 0.108009698 | −0.122581566 | 1.11E−01 | 8.19E−04 |
| *Clostridium ramosum* | 0.14039172 | 0.124957472 | 3.61E−02 | 6.62E−04 |
| *Dialister*; Other | 0.145288932 | 0.525226374 | 3.07E−02 | 3.07E−54 |
| Enterobacteriaceae; Other | 0.165007089 | −0.279516196 | 1.37E−02 | 7.58E−15 |
| *Lactobacillus mucosae* | 0.175748083 | 0.205831988 | 8.62E−03 | 1.53E−08 |
| *Dorea longicatena* | 0.1847875 | 0.644770498 | 5.75E−03 | 6.07E−89 |
| *Bacteroides fragilis* | 0.202115079 | 0.167168648 | 2.43E−03 | 4.69E−06 |
| *Dorea formicigenerans* | 0.207317889 | 0.642324047 | 1.90E−03 | 3.69E−88 |
| *Prevotella*; Other | 0.239978967 | 0.529655297 | 2.84E−04 | 2.90E−55 |
| *Eubacterium desmolans* | 0.256993011 | 0.6126782 | 9.63E−05 | 3.55E−78 |
| *Ruminococcus obeum* | 0.272979694 | 0.538363585 | 3.25E−05 | 2.60E−57 |
| *Megamonas*; Other | 0.280339656 | 0.262466461 | 1.97E−05 | 3.20E−13 |
| *Bifidobacterium bifidum* | 0.304172965 | 0.202363768 | 3.18E−06 | 2.62E−08 |
| *Collinsella aerofaciens* | 0.307743017 | 0.432321119 | 2.48E−06 | 1.97E−35 |
| *Prevotella copri* | 0.316303623 | 0.544177019 | 1.26E−06 | 1.02E−58 |
| *Megasphaera*; Other | 0.333802576 | 0.164470597 | 2.83E−07 | 6.53E−06 |
| *Lactobacillus ruminis* | 0.333863734 | 0.535215561 | 2.83E−07 | 1.41E−56 |
| *Ruminococcus sp 5 1 39BFAA* | 0.354025816 | 0.661928886 | 5.24E−08 | 3.15E−95 |
| *Catenibacterium mitsuokai* | 0.384683801 | 0.50376204 | 2.54E−09 | 2.24E−49 |
| *Lactobacillus*; Other | 0.400088891 | 0.171080853 | 4.91E−10 | 2.84E−06 |
| *Eubacterium hallii* | 0.443162269 | 0.442782454 | 2.68E−12 | 3.19E−37 |
| Ruminococcaceae; Other | 0.449971243 | 0.433092184 | 1.18E−12 | 1.52E−35 |
| *Clostridium*; Other | 0.474086343 | 0.504843768 | 4.91E−14 | 1.39E−49 |
| *Faecalibacterium prausnitzii* | 0.481962341 | 0.710727898 | 1.73E−14 | 1.54E−115 |
| *Clostridium bartlettii* | 0.502239897 | 0.441173741 | 8.58E−16 | 5.88E−37 |
| Clostridiales; Other | 0.502335879 | 0.697003842 | 8.58E−16 | 1.44E−109 |
| *Clostridium disporicum* | 0.562421244 | 0.366422526 | 3.61E−20 | 3.64E−25 |
| *Bifidobacterium longum* | 0.614285922 | −0.455197243 | 7.47E−25 | 1.72E−39 |
| *Clostridium glycolicum* | 0.621583288 | 0.335500578 | 2.00E−25 | 4.26E−21 |
| *Bifidobacterium*; Other | 0.683619978 | 0.368987869 | 2.18E−32 | 1.66E−25 |

TABLE 21

Indicator value analysis results

| | Indicator value(Recovery) - Indicator value(Diarrhea)* Subject | | | | | | | |
|---|---|---|---|---|---|---|---|---|
| Species | A | B | C | D | E | F | G | Combined (not differentiated by subject) |
| *Acidaminococcus intestini* | NA | NA | NA | NA | NA | NA | NA | NA |
| *Acidaminococcus*; Other | 0.438 | NA | NA | NA | NA | NA | NA | 0.099 |
| *Acidovorax avenae* | NA | NA | NA | NA | NA | NA | NA | NA |
| *Acinetobacter baumannii* | NA | NA | NA | −0.765 | −0.929 | −0.691 | −0.588 | −0.478 |
| *Acinetobacter calcoaceticus* | NA | NA | NA | NA | NA | NA | −0.529 | −0.210 |
| *Acinetobacter johnsonii* | NA | −0.333 | NA | NA | −0.786 | NA | −0.588 | −0.388 |
| *Acinetobacter junii* | NA | NA | NA | NA | −0.857 | −0.695 | −0.706 | −0.428 |
| *Acinetobacter*; Other | NA | NA | NA | NA | −0.929 | −0.481 | −0.765 | −0.449 |
| *Actinobacillus porcinus* | NA | NA | NA | −0.552 | NA | −0.333 | NA | −0.230 |
| *Actinomyces georgiae* | NA | NA | NA | NA | NA | NA | NA | NA |
| *Actinomyces graevenitzii* | NA | NA | NA | NA | −0.857 | NA | −0.703 | −0.380 |
| *Actinomyces odontolyticus* | NA | NA | NA | NA | NA | NA | −0.917 | −0.512 |
| *Actinomyces oris* | NA | NA | NA | NA | NA | NA | −0.702 | −0.315 |
| Actinomycetales; Other | NA | NA | NA | NA | NA | NA | NA | 0.092 |
| *Aerococcus*; Other | NA | −0.444 | −0.565 | NA | −0.857 | NA | −0.529 | −0.348 |
| *Aeromonas*; Other | NA | NA | NA | NA | −1.000 | −0.687 | −0.814 | −0.442 |
| *Afipia* genosp 9 | NA | NA | NA | NA | NA | NA | NA | NA |
| *Aggregatibacter segnis* | NA | NA | NA | −0.881 | NA | −0.593 | NA | −0.288 |
| *Agrobacterium tumefaciens* | NA | NA | NA | NA | −0.929 | NA | −0.353 | NA |
| Alcaligenaceae; Other | NA | NA | NA | NA | NA | NA | NA | −0.111 |
| *Alistipes finegoldii* | NA | NA | NA | NA | NA | 0.250 | NA | 0.041 |
| *Alistipes shahii* | NA | NA | NA | NA | NA | 0.250 | 0.563 | 0.184 |
| *Alistipes* sp NML05A004 | NA | NA | NA | NA | NA | 0.375 | NA | 0.092 |
| *Allisonella histaminiformans* | 0.438 | NA | NA | NA | NA | NA | NA | 0.177 |
| *Anaerobiospirillum succiniciproducens* | NA | NA | NA | NA | NA | NA | NA | NA |
| *Anaerococcus octavius* | NA | 0.561 | NA | NA | NA | NA | NA | 0.088 |
| *Anaerococcus vaginalis* | NA | NA | NA | NA | NA | NA | −0.412 | −0.130 |
| *Anaeroglobus geminatus* | NA | NA | NA | NA | NA | NA | NA | −0.064 |
| *Arcobacter butzleri* | NA | NA | NA | NA | NA | NA | −0.471 | −0.072 |
| *Atopobium* sp F0209 | NA | NA | NA | NA | −0.750 | NA | −0.757 | −0.387 |
| *Atopobium*; Other | NA | NA | NA | NA | NA | NA | NA | −0.051 |
| *Azospirillum*; Other | NA | NA | NA | NA | NA | NA | NA | NA |
| Bacillaceae; Other | NA | NA | NA | NA | NA | NA | NA | NA |
| Bacillales; Other | NA | −0.500 | −1.000 | NA | −0.857 | −0.593 | −0.572 | −0.529 |
| Bacilli; Other | NA | NA | NA | NA | NA | −0.667 | NA | −0.274 |
| *Bacillus* sp 01082 | NA | NA | NA | −0.949 | NA | −0.962 | −0.877 | −0.667 |
| *Bacillus*; Other | NA | NA | NA | NA | NA | NA | −0.471 | −0.196 |
| Bacteria; Other | 0.803 | 0.786 | 0.574 | NA | NA | 0.875 | 0.567 | 0.672 |
| *Bacteriovorax* sp EPA | NA | NA | NA | NA | NA | NA | NA | −0.065 |
| *Bacteriovorax* sp F2 | NA | NA | NA | NA | NA | NA | NA | NA |
| Bacteroidales; Other | 0.422 | 0.999 | 0.500 | NA | NA | 0.911 | 0.920 | 0.700 |
| *Bacteroides caccae* | NA | NA | NA | NA | NA | NA | NA | 0.143 |
| *Bacteroides fragilis* | 0.625 | NA | 0.440 | 0.676 | NA | NA | NA | 0.445 |
| *Bacteroides galacturonicus* | 0.563 | NA | 0.834 | 0.929 | NA | 0.674 | 0.421 | 0.547 |
| *Bacteroides ovatus* | 0.438 | 0.833 | NA | NA | 0.712 | NA | 0.736 | 0.460 |
| *Bacteroides plebeius* | 0.250 | 0.431 | NA | 0.784 | 0.713 | 0.830 | 0.937 | 0.600 |
| *Bacteroides* sp CIP103040 | NA | NA | NA | NA | NA | 0.496 | NA | 0.112 |
| *Bacteroides stercoris* | 0.250 | NA | NA | NA | 0.571 | NA | NA | 0.208 |
| *Bacteroides uniformis* | NA | NA | NA | NA | NA | 0.250 | NA | 0.087 |
| *Bacteroides vulgatus* | NA | NA | NA | NA | NA | 0.450 | NA | 0.127 |
| *Bacteroides*; Other | 0.302 | 0.937 | NA | 0.784 | NA | NA | 0.498 | 0.549 |
| Bacteroidetes; Other | NA | 0.938 | NA | NA | NA | NA | 0.618 | 0.377 |
| Betaproteobacteria; Other | NA | NA | NA | NA | NA | NA | NA | 0.092 |
| Bifidobacteriaceae; Other | NA | NA | NA | NA | NA | NA | NA | NA |
| *Bifidobacterium bifidum* | NA | NA | 0.462 | 0.714 | NA | 0.301 | NA | 0.275 |
| *Bifidobacterium dentium* | NA | NA | NA | NA | −0.923 | NA | NA | −0.158 |
| *Bifidobacterium*; Other | 0.954 | 0.981 | 0.995 | 0.999 | 0.981 | 0.985 | 0.998 | 0.987 |
| *Bilophila wadsworthia* | NA | 0.938 | NA | NA | NA | NA | 0.735 | 0.312 |
| *Blautia producta* | NA | 0.571 | NA | NA | 0.857 | 0.313 | NA | 0.337 |
| *Blautia* sp M25 | NA | NA | NA | NA | NA | NA | −0.353 | NA |
| *Blautia*; Other | 0.537 | 0.676 | −0.845 | 0.848 | 0.857 | 0.890 | NA | 0.669 |
| *Brachybacterium paraconglomeratum* | NA | NA | NA | NA | NA | NA | NA | −0.109 |
| *Brachybacterium*; Other | NA | NA | NA | NA | NA | NA | NA | −0.114 |
| *Brachyspira aalborgi* | NA | NA | NA | NA | −1.000 | NA | NA | −0.101 |
| *Brachyspira pilosicoli* | NA | NA | NA | NA | −0.857 | NA | −0.588 | −0.158 |
| Bradyrhizobiaceae; Other | NA | NA | NA | NA | NA | NA | NA | NA |
| *Brevibacterium*; Other | NA | NA | NA | NA | NA | NA | −0.529 | −0.221 |
| *Brevundimonas diminuta* | NA | NA | NA | NA | NA | NA | −0.588 | −0.241 |
| *Brevundimonas terrae* | NA | NA | NA | NA | NA | NA | −0.647 | −0.202 |
| *Brevundimonas vesicularis* | NA | NA | NA | NA | NA | NA | NA | −0.167 |
| Brucellaceae; Other | NA | NA | NA | NA | NA | NA | NA | −0.086 |

TABLE 21-continued

| Indicator value analysis results | | | | | | | | |
|---|---|---|---|---|---|---|---|---|
| *Butyrivibrio crossotus* | NA | 0.840 | NA | NA | NA | NA | NA | 0.273 |
| *Campylobacter hyointestinalis* | 0.737 | NA | NA | −0.887 | NA | NA | −0.999 | −0.686 |
| *Campylobacter jejuni* | NA | NA | NA | −0.889 | NA | −0.481 | NA | −0.203 |
| *Campylobacter*; Other | −0.940 | NA | NA | −0.778 | NA | NA | −0.706 | −0.476 |
| *Catenibacterium mitsuokai* | 0.745 | 0.895 | 0.776 | NA | NA | NA | 0.994 | 0.791 |
| *Cerasicoccus arenae* | NA | NA | NA | NA | NA | NA | NA | NA |
| *Cetobacterium somerae* | 0.625 | NA | NA | NA | NA | −0.684 | NA | NA |
| *Chryseobacterium hominis* | NA | NA | NA | NA | NA | NA | NA | −0.123 |
| *Chryseobacterium*; Other | NA | NA | NA | NA | NA | NA | NA | 0.061 |
| Clostridiaceae; Other | 0.431 | 0.805 | 0.923 | NA | 0.857 | 0.373 | 0.812 | 0.641 |
| Clostridiales; Other | 0.972 | 0.825 | NA | NA | 0.996 | 0.695 | 0.852 | 0.832 |
| *Clostridium bartlettii* | 0.875 | 0.903 | NA | 1.000 | 0.857 | NA | NA | 0.341 |
| *Clostridium bifermentans* | NA | NA | NA | NA | NA | NA | NA | NA |
| *Clostridium bolteae* | NA | NA | NA | NA | NA | NA | 0.796 | 0.278 |
| *Clostridium clostridioforme* | 0.496 | 0.553 | NA | −0.888 | 0.857 | NA | 0.963 | 0.334 |
| *Clostridium disporicum* | 0.749 | 0.966 | 0.923 | 0.999 | 0.999 | 0.551 | NA | 0.699 |
| *Clostridium glycolicum* | 0.563 | 0.750 | 0.462 | 0.643 | 0.857 | 0.500 | 0.750 | 0.633 |
| *Clostridium glycyrrhizinilyticum* | NA | NA | −0.680 | NA | 0.714 | 0.489 | NA | NA |
| *Clostridium hathewayi* | NA | 0.374 | NA | NA | NA | NA | 0.875 | 0.234 |
| *Clostridium hylemonae* | NA | NA | NA | NA | NA | NA | NA | NA |
| *Clostridium innocuum* | NA | NA | NA | NA | NA | NA | NA | 0.061 |
| *Clostridium neonatale* | NA | NA | NA | NA | NA | NA | NA | NA |
| *Clostridium nexile* | 0.250 | NA | NA | NA | NA | NA | NA | 0.233 |
| *Clostridium paraputrificum* | 0.983 | NA | 0.874 | NA | 0.999 | 0.472 | NA | 0.521 |
| *Clostridium perfringens* | NA | 0.313 | NA | 0.714 | NA | NA | NA | 0.286 |
| *Clostridium ramosum* | 0.250 | NA | NA | 0.786 | NA | NA | NA | 0.247 |
| *Clostridium* sp L2 50 | NA | NA | NA | 0.786 | NA | NA | NA | 0.242 |
| *Clostridium* sp SS2 1 | NA | 0.563 | NA | NA | NA | NA | NA | 0.122 |
| *Clostridium*; Other | NA | 0.681 | NA | NA | NA | 0.681 | 0.820 | 0.387 |
| *Collinsella aerofaciens* | 0.918 | 0.883 | 0.890 | NA | NA | 0.525 | NA | 0.584 |
| *Collinsella*; Other | 0.438 | 0.703 | 0.538 | NA | NA | NA | 0.920 | 0.438 |
| Comamonadaceae; Other | NA | NA | NA | NA | NA | −0.704 | −0.824 | NA |
| *Comamonas aquatica* | NA | NA | NA | NA | NA | −0.370 | −0.765 | −0.343 |
| *Comamonas*; Other | NA | NA | NA | NA | NA | NA | NA | 0.082 |
| *Coprococcus catus* | NA | 0.950 | NA | −0.778 | 0.835 | NA | 0.772 | 0.199 |
| *Coprococcus comes* | NA | 0.627 | NA | −0.778 | NA | 0.652 | 0.745 | 0.378 |
| *Coprococcus eutactus* | 0.375 | 0.812 | NA | NA | NA | 0.747 | 0.851 | 0.526 |
| *Coprococcus*; Other | 0.250 | 0.625 | NA | NA | NA | 0.625 | 0.869 | 0.438 |
| Coriobacteriaceae; Other | 0.499 | 0.956 | 0.799 | NA | NA | 0.631 | 0.545 | 0.600 |
| *Corynebacterium aurimucosum* | NA | NA | NA | NA | NA | NA | NA | −0.164 |
| *Corynebacterium durum* | NA | NA | NA | NA | NA | NA | −0.584 | −0.245 |
| *Corynebacterium imitans* | NA | NA | NA | NA | NA | NA | −0.412 | −0.217 |
| *Corynebacterium matruchotii* | NA | NA | NA | NA | NA | NA | −0.641 | −0.311 |
| *Corynebacterium mucifaciens* | NA | NA | NA | NA | NA | −0.519 | NA | −0.326 |
| *Corynebacterium tuberculostearicum* | NA | NA | NA | NA | NA | NA | −0.647 | −0.492 |
| *Corynebacterium*; Other | −0.300 | NA | −0.695 | NA | NA | −0.481 | −0.706 | −0.488 |
| Deltaproteobacteria; Other | NA | NA | NA | NA | NA | NA | NA | NA |
| *Desulfovibrio*; Other | 0.438 | NA | NA | NA | NA | NA | 0.860 | 0.274 |
| *Dialister invisus* | NA | NA | NA | NA | NA | NA | NA | NA |
| *Dialister pneumosintes* | 0.749 | NA | NA | NA | NA | 0.551 | NA | 0.400 |
| *Dialister*; Other | NA | NA | NA | NA | NA | NA | −0.353 | −0.109 |
| *Dolosigranulum pigrum* | NA | NA | NA | NA | NA | NA | NA | NA |
| *Dorea formicigenerans* | 0.522 | 0.765 | NA | −0.836 | 0.998 | 0.513 | 0.909 | 0.494 |
| *Dorea longicatena* | 0.656 | 0.624 | 0.702 | −0.751 | 0.855 | NA | NA | 0.358 |
| *Edwardsiella ictaluri* | NA | NA | NA | NA | NA | NA | NA | NA |
| *Eggerthella lenta* | NA | NA | NA | NA | NA | NA | 0.500 | 0.227 |
| *Elusimicrobium minutum* | NA | NA | NA | NA | NA | NA | −0.706 | NA |
| Enterobacteriaceae; Other | 0.470 | NA | NA | NA | NA | −0.510 | 0.737 | NA |
| Enterococcaceae; Other | NA | NA | NA | NA | NA | NA | NA | −0.177 |
| *Enterococcus cecorum* | NA | 0.629 | NA | NA | NA | NA | NA | 0.116 |
| *Enterococcus faecalis* | NA | NA | NA | NA | NA | NA | NA | NA |
| *Enterococcus*; Other | NA | NA | −0.753 | NA | −0.525 | −0.765 | −0.750 | −0.460 |
| Erysipelotrichaceae; Other | NA | NA | NA | NA | NA | NA | NA | NA |
| *Escherichia albertii* | NA | NA | NA | NA | NA | NA | NA | NA |
| *Escherichia coli* | −0.518 | −0.409 | NA | NA | NA | −0.361 | 0.951 | −0.345 |
| *Escherichia*; Other | NA | NA | NA | NA | NA | −0.428 | 0.890 | −0.256 |
| *Eubacterium biforme* | 0.864 | NA | 0.774 | NA | 0.996 | 0.583 | 0.459 | 0.712 |
| *Eubacterium coprostanoligenes* | 0.563 | 0.812 | NA | NA | NA | 0.873 | 0.874 | 0.530 |
| *Eubacterium desmolans* | NA | 0.819 | NA | NA | 0.856 | 0.589 | 0.591 | 0.258 |
| *Eubacterium eligens* | 0.875 | 0.981 | NA | 0.786 | 0.429 | 0.845 | NA | 0.696 |
| *Eubacterium hallii* | 0.548 | 0.993 | NA | NA | NA | 0.989 | 0.969 | 0.673 |
| *Eubacterium limosum* | NA | NA | NA | NA | NA | NA | NA | 0.041 |
| *Eubacterium ramulus* | 0.250 | 0.872 | NA | NA | NA | NA | 0.844 | 0.353 |
| *Eubacterium rectale* | NA | 0.919 | NA | NA | NA | 0.929 | 0.830 | 0.457 |
| *Eubacterium saburreum* | 0.962 | 0.952 | NA | NA | NA | 0.891 | 0.944 | 0.769 |
| *Eubacterium siraeum* | NA | NA | NA | NA | NA | NA | −0.529 | −0.216 |
| *Eubacterium* sp cL 10 1 3 | NA | 0.435 | NA | NA | NA | NA | 0.869 | 0.223 |
| *Eubacterium*; Other | 0.500 | 0.438 | 0.686 | NA | NA | 0.625 | 0.931 | 0.508 |

TABLE 21-continued

Indicator value analysis results

| | | | | | | | | |
|---|---|---|---|---|---|---|---|---|
| *Faecalibacterium prausnitzii* | 0.972 | 1.000 | NA | NA | 0.857 | 0.835 | 0.801 | 0.860 |
| *Faecalibacterium*; Other | 0.953 | 0.999 | 0.876 | NA | NA | 0.697 | 0.660 | 0.819 |
| *Finegoldia magna* | NA | NA | NA | NA | NA | NA | NA | NA |
| *Firmicutes*; Other | NA | 0.902 | NA | NA | 0.748 | 0.947 | NA | 0.725 |
| Flavobacteriaceae; Other | NA | NA | NA | NA | NA | NA | NA | NA |
| Flavobacteriales; Other | NA | NA | NA | NA | NA | NA | NA | NA |
| *Flavobacterium*; Other | NA | NA | NA | NA | NA | NA | NA | NA |
| *Flexibacter*; Other | NA | NA | NA | NA | NA | NA | NA | 0.091 |
| Fusobacteriaceae; Other | NA | NA | NA | NA | NA | −0.481 | NA | −0.094 |
| *Fusobacterium mortiferum* | NA | −0.996 | NA | NA | NA | NA | NA | −0.786 |
| *Fusobacterium nucleatum* | NA | −0.444 | NA | −1.000 | NA | −0.641 | −0.641 | −0.511 |
| *Fusobacterium*; Other | NA | −0.996 | −0.981 | −0.836 | NA | NA | NA | −0.879 |
| Gammaproteobacteria; Other | NA | −0.943 | NA | NA | −0.820 | NA | −0.412 | −0.439 |
| *Granulicatella adiacens* | NA | NA | −0.746 | NA | NA | −0.705 | −0.925 | −0.615 |
| *Granulicatella elegans* | NA | NA | NA | −0.742 | −0.923 | −0.838 | NA | −0.452 |
| *Haemophilus haemolyticus* | NA | NA | NA | −0.965 | NA | −0.852 | NA | −0.463 |
| *Haemophilus*; Other | NA | NA | NA | NA | NA | −0.667 | NA | −0.217 |
| *Halomonas*; Other | NA | −0.333 | NA | NA | NA | NA | −0.353 | −0.167 |
| *Helicobacter cinaedi* | NA | NA | NA | NA | NA | NA | NA | NA |
| *Helicobacter winghamensis* | NA | NA | NA | NA | NA | −0.556 | NA | −0.210 |
| *Helicobacter*; Other | NA | NA | NA | NA | NA | NA | NA | NA |
| Intrasporangiaceae; Other | NA | NA | NA | NA | NA | NA | −0.706 | −0.101 |
| *Jeotgalicoccus*; Other | NA | −0.444 | NA | NA | NA | NA | NA | −0.217 |
| *Kocuria marina* | NA | NA | NA | NA | NA | NA | NA | NA |
| *Lachnospira pectinoschiza* | NA | 0.582 | NA | NA | NA | NA | NA | 0.176 |
| Lachnospiraceae; Other | 0.563 | 0.755 | NA | NA | NA | 0.708 | 0.460 | 0.492 |
| Lactobacillaceae; Other | NA | NA | NA | NA | NA | NA | NA | NA |
| Lactobacillales; Other | NA | NA | NA | NA | NA | NA | NA | NA |
| *Lactobacillus delbrueckii* | NA | NA | NA | NA | NA | NA | NA | −0.072 |
| *Lactobacillus fermentum* | −0.832 | NA | NA | NA | NA | NA | NA | −0.311 |
| *Lactobacillus mucosae* | NA | NA | 0.308 | NA | NA | NA | NA | NA |
| *Lactobacillus ruminis* | −0.823 | NA | 0.769 | NA | NA | NA | NA | NA |
| *Lactobacillus saerimneri* | NA | NA | 0.846 | NA | NA | NA | NA | 0.619 |
| *Lactobacillus* sp Atm5 | NA | NA | NA | NA | NA | NA | NA | NA |
| *Lactobacillus* sp KLDS 1 0716 | NA | NA | NA | NA | NA | NA | NA | −0.065 |
| *Lactobacillus*; Other | NA | NA | NA | NA | NA | NA | NA | NA |
| *Lactococcus garvieae* | NA | NA | NA | NA | NA | NA | NA | 0.082 |
| *Leptotrichia* 591114 | NA | NA | NA | NA | NA | NA | NA | −0.109 |
| *Leptotrichia buccalis* | NA | NA | NA | NA | −0.481 | NA | NA | −0.283 |
| *Leptotrichia shahii* | −0.667 | −0.389 | −0.609 | −0.889 | −0.928 | −0.908 | −0.706 | −0.716 |
| *Leptotrichia* sp PG10 | NA | NA | NA | NA | NA | NA | −0.471 | −0.130 |
| *Leptotrichia*; Other | NA | NA | NA | NA | −0.857 | NA | NA | −0.188 |
| Leptotrichiaceae; Other | NA | NA | NA | NA | −0.929 | −0.741 | NA | −0.399 |
| *Leucobacter komagatae* | NA | NA | NA | NA | NA | NA | NA | 0.102 |
| *Leucobacter*; Other | NA | NA | NA | NA | NA | NA | NA | 0.061 |
| *Leuconostoc*; Other | NA | NA | NA | NA | NA | NA | NA | NA |
| *Luteimonas*; Other | NA | NA | NA | NA | NA | NA | −0.647 | NA |
| *Megamonas rupellensis* | NA | NA | 0.921 | 0.786 | NA | 0.310 | NA | 0.336 |
| *Megamonas*; Other | NA | NA | 0.762 | NA | NA | NA | NA | 0.192 |
| *Megasphaera elsdenii* | 0.687 | NA | 0.919 | NA | NA | −0.333 | NA | 0.315 |
| *Megasphaera hominis* | NA | NA | 0.538 | NA | NA | NA | NA | 0.102 |
| *Megasphaera* sp TrE9262 | 0.437 | NA | 0.846 | NA | NA | NA | NA | 0.234 |
| *Megasphaera*; Other | 0.313 | NA | NA | NA | NA | NA | NA | 0.092 |
| *Micrococcus luteus* | NA | NA | NA | NA | NA | NA | NA | −0.123 |
| *Mitsuokella multacida* | 0.625 | 0.563 | NA | NA | NA | NA | NA | 0.255 |
| *Mitsuokella*; Other | 0.375 | NA | NA | NA | NA | NA | NA | 0.091 |
| *Mogibacterium neglectum* | NA | NA | NA | NA | NA | NA | −0.412 | NA |
| *Moraxella osloensis* | NA | NA | NA | NA | NA | NA | NA | −0.188 |
| Moraxellaceae; Other | NA | NA | NA | NA | NA | NA | NA | −0.080 |
| *Morganella morganii* | NA | NA | NA | NA | NA | NA | NA | NA |
| *Neisseria elongata* | NA | NA | NA | NA | NA | NA | NA | −0.158 |
| *Neisseria subflava* | NA | NA | NA | −0.667 | NA | −0.444 | NA | −0.275 |
| *Neisseria*; Other | −0.633 | −0.444 | −0.564 | −0.994 | NA | −0.660 | −0.412 | −0.613 |
| *Nevskia*; Other | NA | NA | NA | NA | NA | NA | NA | NA |
| *Novosphingobium*; Other | NA | NA | NA | NA | NA | NA | NA | NA |
| *Odoribacter splanchnicus* | NA | NA | NA | NA | NA | NA | 0.419 | 0.129 |
| *Olsenella* sp A2 | 0.500 | 0.995 | NA | NA | NA | NA | NA | 0.306 |
| *Olsenella*; Other | 0.500 | NA | NA | NA | NA | NA | NA | 0.092 |
| *Oribacterium* sp oral taxon 108 | NA | NA | NA | NA | NA | NA | −0.353 | −0.180 |
| *Oscillibacter* sp G2 | NA | 0.563 | NA | NA | NA | NA | 0.681 | 0.244 |
| *Oscillibacter*; Other | NA | 0.938 | NA | −0.667 | NA | 0.791 | NA | 0.304 |
| *Oxalobacter formigenes* | NA | NA | NA | NA | NA | NA | NA | 0.051 |
| *Pantoea ananatis* | NA | NA | NA | NA | NA | NA | NA | NA |
| *Parabacteroides distasonis* | NA | 0.375 | NA | NA | NA | 0.616 | 0.500 | 0.326 |
| *Parabacteroides merdae* | NA | NA | NA | NA | 0.375 | NA | NA | 0.092 |
| *Parabacteroides*; Other | 0.438 | 0.688 | NA | NA | NA | 0.500 | 0.938 | 0.429 |
| *Paracoccus denitrificans* | NA | NA | NA | NA | −0.786 | NA | −0.471 | −0.167 |
| *Paracoccus*; Other | NA | NA | NA | NA | NA | NA | NA | NA |

TABLE 21-continued

| Indicator value analysis results | | | | | | | | |
|---|---|---|---|---|---|---|---|---|
| Pasteurellaceae; Other | NA | NA | −0.770 | NA | NA | −0.870 | −0.689 | −0.568 |
| Pediococcus; Other | NA | NA | NA | NA | NA | NA | NA | NA |
| Pedobacter terrae | NA | NA | NA | NA | NA | NA | NA | −0.116 |
| Pedobacter; Other | NA | NA | NA | NA | NA | NA | NA | 0.071 |
| Peptoniphilus harei | NA | NA | NA | NA | NA | NA | NA | NA |
| Peptostreptococcus stomatis | NA | NA | NA | NA | NA | NA | NA | NA |
| Peptostreptococcus; Other | NA | NA | NA | −0.889 | NA | −0.543 | −0.647 | −0.396 |
| Peredibacter starrii | NA | NA | NA | NA | NA | NA | NA | NA |
| Phascolarctobacterium faecium | NA | NA | NA | NA | NA | 0.313 | 0.419 | 0.122 |
| Phascolarctobacterium succinatutens | NA | 0.998 | 0.615 | −0.667 | NA | NA | NA | 0.383 |
| Porphyromonas catoniae | NA | NA | NA | −0.778 | NA | NA | NA | −0.290 |
| Prevotella buccae | NA | NA | NA | NA | NA | NA | NA | NA |
| Prevotella copri | 0.920 | 0.994 | 0.900 | NA | NA | 0.925 | NA | 0.776 |
| Prevotella denticola | NA | NA | NA | NA | NA | NA | NA | −0.094 |
| Prevotella histicola | NA | −0.611 | −0.478 | −1.000 | −0.929 | −0.963 | −0.706 | −0.667 |
| Prevotella nanceiensis | NA | NA | NA | −0.889 | NA | −0.519 | NA | −0.268 |
| Prevotella oulorum | 0.966 | 0.969 | NA | NA | NA | 0.742 | NA | 0.520 |
| Prevotella salivae | NA | NA | NA | NA | NA | NA | NA | −0.145 |
| Prevotella sp DJF B112 | NA | −0.389 | NA | NA | NA | −0.630 | −0.588 | −0.341 |
| Prevotella sp DJF B116 | 0.560 | 0.938 | 0.754 | −0.540 | NA | 0.915 | 0.726 | 0.633 |
| Prevotella sp DJF CP65 | 0.492 | 0.927 | NA | −0.641 | NA | 0.789 | 0.481 | 0.453 |
| Prevotella sp DJF LS16 | 0.500 | NA | NA | NA | NA | NA | NA | 0.092 |
| Prevotella sp oral taxon 302 | 0.531 | 0.426 | NA | −0.674 | NA | 0.857 | NA | 0.280 |
| Prevotella sp RS2 | 0.312 | 0.937 | NA | NA | NA | NA | NA | 0.214 |
| Prevotella stercorea | NA | 0.976 | NA | −0.889 | NA | 0.788 | −0.684 | NA |
| Prevotella veroralis | NA | NA | NA | NA | NA | NA | NA | 0.139 |
| Prevotella; Other | NA | −0.500 | NA | NA | NA | −0.593 | −0.647 | −0.391 |
| Prevotellaceae; Other | NA | 0.500 | NA | NA | NA | NA | NA | 0.199 |
| Prosthecobacter; Other | NA | NA | NA | NA | NA | NA | NA | NA |
| Proteobacteria; Other | −0.691 | −0.450 | NA | NA | NA | −0.634 | 0.911 | −0.501 |
| Proteus mirabilis | NA | NA | NA | NA | NA | NA | NA | NA |
| Pseudomonas mendocina | NA | −0.778 | NA | NA | −0.857 | NA | −0.647 | −0.449 |
| Pseudomonas stutzeri | −0.400 | −0.888 | −0.565 | NA | −1.000 | −0.601 | −0.913 | −0.653 |
| Pseudomonas; Other | NA | NA | NA | NA | −0.786 | NA | −0.471 | −0.225 |
| Ralstonia; Other | NA | −0.611 | NA | NA | −0.786 | NA | NA | −0.246 |
| Rheinheimera sp 09BSZB 9 | NA | NA | NA | NA | NA | NA | NA | −0.130 |
| Rheinheimera sp TPS16 | NA | NA | NA | NA | NA | NA | NA | NA |
| Rheinheimera; Other | NA | NA | NA | NA | NA | NA | −0.353 | −0.181 |
| Rhizobiaceae; Other | NA | NA | NA | NA | NA | NA | NA | 0.081 |
| Rhizobiales; Other | NA | NA | NA | NA | NA | NA | NA | NA |
| Rhodobacteraceae; Other | NA | NA | NA | NA | NA | NA | NA | 0.092 |
| Rhodocyclaceae; Other | NA | NA | NA | NA | NA | NA | NA | NA |
| Roseburia intestinalis | 0.561 | NA | NA | NA | NA | 0.709 | 0.773 | 0.562 |
| Roseburia; Other | 0.870 | 0.917 | NA | NA | 0.857 | 0.628 | NA | 0.674 |
| Rothia dentocariosa | −0.689 | NA | −0.696 | NA | NA | −0.370 | −0.824 | −0.557 |
| Rothia mucilaginosa | −0.694 | NA | −0.895 | −0.905 | −0.947 | NA | −0.824 | −0.706 |
| Ruminococcaceae; Other | 0.545 | 0.999 | NA | NA | NA | 0.892 | 0.979 | 0.686 |
| Ruminococcus bromii | 0.562 | 0.562 | NA | NA | NA | 0.687 | 0.499 | 0.479 |
| Ruminococcus callidus | 0.500 | 1.000 | NA | NA | NA | 0.872 | 0.562 | 0.479 |
| Ruminococcus flavefaciens | NA | 0.375 | NA | NA | NA | NA | 0.375 | 0.133 |
| Ruminococcus gnavus | 0.784 | NA | 0.610 | 0.714 | NA | NA | NA | 0.430 |
| Ruminococcus obeum | 0.494 | 0.908 | NA | NA | 0.851 | NA | NA | 0.301 |
| Ruminococcus sp 5 1 39BFAA | 0.812 | NA | −0.443 | NA | 0.997 | 0.950 | 0.888 | 0.671 |
| Ruminococcus sp DJF VR70k1 | 0.874 | 0.946 | NA | NA | 0.856 | 0.917 | 0.668 | 0.762 |
| Ruminococcus sp ZS2 15 | NA | NA | NA | NA | 0.857 | NA | NA | 0.124 |
| Ruminococcus torques | 0.369 | 0.688 | NA | NA | NA | 0.687 | 0.250 | 0.337 |
| Ruminococcus; Other | NA | NA | NA | NA | 0.992 | 0.563 | 0.801 | NA |
| Salmonella enterica | NA | NA | NA | NA | NA | NA | NA | NA |
| Sarcina ventriculi | NA | NA | NA | NA | NA | NA | NA | NA |
| Sarcina; Other | NA | NA | NA | NA | NA | NA | NA | 0.092 |
| Scardovia wiggsiae | NA | NA | NA | NA | NA | NA | NA | −0.130 |
| Shinella; Other | NA | NA | NA | NA | NA | NA | NA | NA |
| Shuttleworthia satelles | NA | NA | NA | NA | NA | NA | NA | −0.085 |
| Slackia isoflavoniconvertens | 0.250 | 0.757 | 0.613 | NA | NA | 0.646 | 0.611 | 0.465 |
| Solobacterium moorei | NA | NA | NA | NA | NA | −0.538 | −0.529 | −0.320 |
| Sphingobacterium mizutaii | NA | NA | NA | NA | NA | NA | −0.706 | −0.123 |
| Sphingobacterium multivorum | NA | NA | NA | NA | NA | NA | −0.294 | −0.130 |
| Sphingobacterium sp P 7 | NA | NA | NA | NA | NA | NA | NA | NA |
| Sphingobium yanoikuyae | NA | NA | NA | NA | NA | NA | NA | −0.196 |
| Sphingomonadaceae; Other | NA | NA | NA | NA | NA | NA | NA | −0.058 |
| Sphingomonadales; Other | NA | NA | NA | NA | NA | NA | NA | 0.061 |
| Sphingomonas sp BAC84 | NA | −0.535 | NA | NA | NA | NA | NA | −0.156 |
| Sphingomonas yabuuchiae | NA | NA | NA | NA | NA | NA | NA | NA |
| Sphingomonas; Other | NA | NA | NA | NA | NA | NA | NA | −0.072 |
| Staphylococcaceae; Other | NA | NA | NA | NA | NA | NA | NA | −0.087 |
| Staphylococcus aureus | NA | −0.667 | −0.957 | NA | −1.000 | −0.535 | −0.699 | −0.621 |
| Staphylococcus; Other | NA | −0.333 | −0.913 | NA | −1.000 | NA | −0.646 | −0.478 |
| Stenotrophomonas maltophilia | NA | NA | NA | NA | −0.857 | NA | −0.471 | −0.283 |

TABLE 21-continued

| Indicator value analysis results | | | | | | | | |
|---|---|---|---|---|---|---|---|---|
| Stenotrophomonas rhizophila | NA | NA | NA | NA | NA | NA | −0.765 | −0.275 |
| Stenotrophomonas; Other | −0.733 | −0.936 | −0.669 | NA | NA | NA | NA | −0.423 |
| Streptococcaceae; Other | −0.585 | NA | 0.385 | NA | NA | NA | NA | NA |
| Streptococcus anginosus | −0.926 | NA | NA | NA | −0.779 | −0.810 | −0.584 | −0.629 |
| Streptococcus gordonii | −0.790 | NA | NA | NA | −0.867 | −0.740 | −0.880 | −0.679 |
| Streptococcus mutans | NA | NA | NA | NA | NA | NA | NA | −0.203 |
| Streptococcus parasanguinis | −0.797 | −0.624 | −0.665 | NA | NA | −0.856 | −0.718 | −0.663 |
| Streptococcus peroris | −0.944 | NA | −0.818 | NA | NA | NA | −0.997 | −0.738 |
| Streptococcus sanguinis | NA | NA | NA | NA | NA | NA | NA | NA |
| Streptococcus thermophilus | −0.913 | −0.333 | −0.901 | NA | −0.962 | NA | −0.882 | −0.721 |
| Streptococcus; Other | −0.953 | NA | NA | NA | −0.941 | NA | −0.984 | −0.562 |
| Subdoligranulum variabile | NA | 1.000 | NA | −0.622 | NA | 0.986 | 0.652 | 0.498 |
| Succinivibrio dextrinosolvens | NA | NA | NA | NA | NA | NA | −0.765 | NA |
| Sutterella sp YIT 12072 | NA | 0.791 | NA | NA | NA | 0.583 | NA | NA |
| Sutterella stercoricanis | NA | 0.563 | NA | NA | NA | NA | −0.601 | NA |
| Sutterella; Other | 0.704 | −0.883 | NA | −0.881 | NA | NA | −0.825 | −0.393 |
| Thauera terpenica | NA | NA | NA | NA | NA | NA | NA | 0.071 |
| Thauera; Other | NA | NA | NA | NA | NA | NA | NA | NA |
| Thermus igniterrae | NA | NA | NA | NA | NA | NA | NA | NA |
| Treponema porcinum | NA | NA | NA | NA | NA | NA | NA | NA |
| Treponema succinifaciens | NA | NA | NA | NA | NA | NA | NA | NA |
| Turicibacter sanguinis | 0.563 | 0.812 | 0.692 | NA | 1.000 | 0.438 | 0.375 | 0.612 |
| unclassified_Erysipelotrichaceae; Other | 0.402 | NA | NA | NA | NA | NA | NA | 0.156 |
| Ureaplasma; Other | NA | NA | NA | NA | NA | NA | NA | NA |
| Varibaculum cambriense | NA | NA | NA | NA | NA | NA | NA | NA |
| Veillonella dispar | NA | NA | NA | NA | NA | −0.811 | −0.999 | −0.537 |
| Veillonella parvula | NA | NA | NA | −0.822 | NA | −0.762 | −0.812 | NA |
| Veillonella sp S101 | NA | NA | NA | −0.865 | NA | −0.669 | −0.761 | −0.302 |
| Veillonella; Other | NA | NA | NA | NA | NA | NA | NA | −0.130 |
| Veillonellaceae; Other | 0.611 | NA | 0.766 | NA | NA | NA | −0.641 | 0.259 |
| Verrucomicrobium sp IRVE | NA | NA | NA | NA | NA | NA | NA | NA |
| Vibrio cholerae | −0.997 | −0.997 | NA | −0.998 | −0.999 | −0.966 | −0.999 | −0.990 |
| Vibrio; Other | −0.499 | NA | NA | −0.888 | −0.786 | −0.481 | −0.941 | −0.521 |
| Wautersiella falsenii | NA | NA | NA | NA | NA | NA | NA | NA |
| Weissella cibaria | NA | 0.313 | NA | NA | NA | NA | NA | NA |
| Weissella; Other | NA | NA | NA | NA | NA | 0.309 | NA | NA |
| X1760; Other | 0.500 | 0.938 | 0.385 | NA | NA | 0.492 | 0.674 | 0.486 |
| Xanthomonadaceae; Other | NA | NA | NA | NA | NA | NA | −0.353 | NA |

| | FDR-adjusted p-value for indicator value analysis (NA = not observed in individual) Subject | | | | | | | |
|---|---|---|---|---|---|---|---|---|
| Species | A | B | C | D | E | F | G | Combined (not differentiated by subject, ns = not significant) |
| Acidaminococcus intestini | 0.171 | NA | 0.479 | NA | NA | NA | NA | ns |
| Acidaminococcus; Other | 0.013 | 0.341 | 1.000 | NA | NA | NA | NA | 0.003 |
| Acidovorax avenae | NA | NA | NA | 0.211 | 1.000 | NA | NA | ns |
| Acinetobacter baumannii | 0.395 | 0.341 | 0.054 | 0.044 | 0.024 | 0.012 | 0.011 | 0.000 |
| Acinetobacter calcoaceticus | NA | 1.000 | 0.130 | NA | 0.121 | 0.572 | 0.011 | 0.000 |
| Acinetobacter johnsonii | 0.099 | 0.039 | 0.077 | 1.000 | 0.041 | 0.217 | 0.011 | 0.000 |
| Acinetobacter junii | 0.163 | 0.085 | 0.571 | 0.398 | 0.024 | 0.012 | 0.011 | 0.000 |
| Acinetobacter; Other | 0.223 | 0.091 | 0.096 | 0.267 | 0.024 | 0.023 | 0.011 | 0.000 |
| Actinobacillus porcinus | 0.422 | NA | 0.125 | 0.026 | NA | 0.041 | 0.127 | 0.000 |
| Actinomyces georgiae | NA | NA | NA | NA | 0.570 | NA | 0.133 | ns |
| Actinomyces graevenitzii | 0.107 | 0.212 | 0.194 | 0.600 | 0.024 | 0.110 | 0.011 | 0.000 |
| Actinomyces odontolyticus | 0.707 | 0.624 | 0.096 | 0.791 | 0.329 | 0.081 | 0.011 | 0.000 |
| Actinomyces oris | 0.268 | 0.978 | 0.624 | 1.000 | 0.202 | 0.410 | 0.011 | 0.001 |
| Actinomycetales; Other | NA | NA | NA | 0.078 | 1.000 | NA | NA | 0.007 |
| Aerococcus; Other | NA | 0.028 | 0.040 | NA | 0.024 | 0.126 | 0.011 | 0.000 |
| Aeromonas; Other | 0.613 | 0.166 | 0.254 | 0.968 | 0.024 | 0.012 | 0.011 | 0.000 |
| Afipia genosp 9 | NA | 1.000 | 1.000 | 0.085 | 0.196 | NA | 0.137 | ns |
| Aggregatibacter segnis | 1.000 | 0.787 | 0.314 | 0.026 | 0.446 | 0.012 | 0.159 | 0.000 |
| Agrobacterium tumefaciens | NA | NA | 0.637 | 0.168 | 0.041 | NA | 0.019 | ns |
| Alcaligenaceae; Other | NA | 0.166 | 0.644 | 0.422 | 0.121 | 1.000 | 1.000 | 0.009 |
| Alistipes finegoldii | NA | NA | NA | NA | NA | 0.041 | NA | 0.021 |
| Alistipes shahii | NA | 0.079 | 0.479 | NA | NA | 0.041 | 0.011 | 0.000 |
| Alistipes sp NML05A004 | NA | 0.185 | NA | NA | NA | 0.012 | NA | 0.000 |
| Allisonella histaminiformans | 0.013 | 0.091 | 1.000 | 1.000 | NA | 0.176 | 1.000 | 0.001 |
| Anaerobiospirillum succiniciproducens | 0.546 | NA | NA | 1.000 | NA | NA | NA | ns |
| Anaerococcus octavius | 1.000 | 0.028 | NA | NA | NA | NA | NA | 0.008 |
| Anaerococcus vaginalis | NA | NA | 0.357 | 0.648 | 0.329 | NA | 0.011 | 0.000 |
| Anaeroglobus geminatus | NA | 1.000 | NA | NA | 0.626 | NA | 0.079 | 0.036 |
| Arcobacter butzleri | NA | NA | NA | NA | NA | 0.643 | 0.011 | 0.021 |
| Atopobium sp F0209 | 0.671 | 0.624 | 0.470 | 0.600 | 0.041 | 0.081 | 0.011 | 0.000 |
| Atopobium; Other | NA | NA | NA | NA | 0.224 | NA | 1.000 | 0.040 |

TABLE 21-continued

Indicator value analysis results

| | | | | | | | | |
|---|---|---|---|---|---|---|---|---|
| *Azospirillum*; Other | NA | 0.403 | NA | NA | 1.000 | NA | NA | ns |
| Bacillaceae; Other | 0.436 | 0.687 | NA | NA | NA | NA | NA | ns |
| Bacillales; Other | 1.000 | 0.015 | 0.026 | 0.130 | 0.041 | 0.012 | 0.011 | 0.000 |
| Bacilli; Other | 0.436 | 0.832 | 0.561 | 0.568 | 0.219 | 0.012 | 0.133 | 0.000 |
| *Bacillus* sp 01082 | 0.065 | 0.127 | 0.308 | 0.026 | 0.104 | 0.012 | 0.011 | 0.000 |
| *Bacillus*; Other | NA | 0.415 | 0.615 | NA | 0.070 | 0.553 | 0.011 | 0.000 |
| Bacteria; Other | 0.013 | 0.015 | 0.040 | 0.068 | 0.129 | 0.012 | 0.011 | 0.000 |
| *Bacteriovorax* sp EPA | NA | 0.296 | 1.000 | NA | 0.353 | NA | 1.000 | 0.027 |
| *Bacteriovorax* sp F2 | NA | 0.683 | NA | NA | 0.657 | NA | NA | ns |
| Bacteroidales; Other | 0.013 | 0.015 | 0.040 | 0.648 | 0.570 | 0.012 | 0.011 | 0.000 |
| *Bacteroides caccae* | 0.469 | 0.059 | NA | 1.000 | 0.157 | 0.232 | 0.261 | 0.000 |
| *Bacteroides fragilis* | 0.013 | 0.789 | 0.040 | 0.026 | 0.612 | 0.982 | 1.000 | 0.001 |
| *Bacteroides galacturonicus* | 0.013 | 1.000 | 0.026 | 0.026 | 0.471 | 0.012 | 0.019 | 0.000 |
| *Bacteroides ovatus* | 0.013 | 0.015 | 0.130 | 0.981 | 0.024 | 0.511 | 0.011 | 0.000 |
| *Bacteroides plebeius* | 0.035 | 0.039 | 0.117 | 0.026 | 0.024 | 0.012 | 0.011 | 0.000 |
| *Bacteroides* sp CIP103040 | NA | NA | NA | 0.541 | NA | 0.012 | NA | 0.001 |
| *Bacteroides stercoris* | 0.045 | 1.000 | NA | 0.055 | 0.024 | 0.952 | 0.147 | 0.001 |
| *Bacteroides uniformis* | NA | 0.334 | 0.479 | NA | NA | 0.041 | NA | 0.004 |
| *Bacteroides vulgatus* | 0.436 | 0.069 | NA | NA | NA | 0.012 | NA | 0.000 |
| *Bacteroides*; Other | 0.045 | 0.015 | 0.088 | 0.044 | NA | 0.095 | 0.011 | 0.000 |
| Bacteroidetes; Other | 0.436 | 0.015 | 0.644 | 0.403 | 0.657 | 0.958 | 0.019 | 0.000 |
| Betaproteobacteria; Other | NA | NA | NA | 0.055 | NA | NA | NA | 0.003 |
| Bifidobacteriaceae; Other | NA | NA | NA | NA | 0.471 | NA | NA | ns |
| *Bifidobacterium bifidum* | 0.436 | 0.085 | 0.026 | 0.044 | 0.866 | 0.041 | 1.000 | 0.000 |
| *Bifidobacterium dentium* | 0.324 | 1.000 | 0.130 | 0.127 | 0.024 | NA | 0.065 | 0.041 |
| *Bifidobacterium*; Other | 0.013 | 0.015 | 0.026 | 0.026 | 0.024 | 0.012 | 0.011 | 0.000 |
| *Bilophila wadsworthia* | NA | 0.015 | 0.479 | NA | 1.000 | 0.102 | 0.011 | 0.000 |
| *Blautia producta* | 0.123 | 0.015 | 0.188 | 0.068 | 0.024 | 0.033 | 0.099 | 0.000 |
| *Blautia* sp M25 | NA | NA | NA | NA | NA | 0.088 | 0.036 | ns |
| *Blautia*; Other | 0.013 | 0.015 | 0.026 | 0.026 | 0.024 | 0.012 | 0.835 | 0.000 |
| *Brachybacterium paraconglomeratum* | 1.000 | 0.624 | 1.000 | NA | 0.250 | 1.000 | 0.284 | 0.001 |
| *Brachybacterium*; Other | NA | 1.000 | 0.590 | 1.000 | 0.121 | 1.000 | 1.000 | 0.000 |
| *Brachyspira aalborgi* | NA | NA | NA | NA | 0.024 | NA | NA | 0.000 |
| *Brachyspira pilosicoli* | NA | NA | NA | 1.000 | 0.024 | NA | 0.011 | 0.000 |
| Bradyrhizobiaceae; Other | NA | NA | 0.644 | 0.085 | 0.580 | NA | NA | ns |
| *Brevibacterium*; Other | NA | 1.000 | 0.117 | 0.434 | 0.070 | 0.646 | 0.011 | 0.000 |
| *Brevundimonas diminuta* | 1.000 | 0.212 | 0.117 | 0.648 | 0.139 | 0.581 | 0.011 | 0.000 |
| *Brevundimonas terrae* | 1.000 | 1.000 | 0.200 | 1.000 | 0.224 | 0.620 | 0.011 | 0.000 |
| *Brevundimonas vesicularis* | NA | 0.119 | 0.637 | NA | 0.104 | 0.397 | 0.072 | 0.000 |
| Brucellaceae; Other | NA | 1.000 | NA | 1.000 | 0.121 | NA | 0.314 | 0.009 |
| *Butyrivibrio crossotus* | NA | 0.015 | NA | NA | NA | 0.067 | 0.223 | 0.000 |
| *Campylobacter hyointestinalis* | 0.013 | 0.172 | 0.832 | 0.044 | 0.189 | 0.782 | 0.011 | 0.001 |
| *Campylobacter jejuni* | 0.555 | NA | 0.479 | 0.026 | 1.000 | 0.033 | 0.057 | 0.001 |
| *Campylobacter*; Other | 0.013 | 0.624 | NA | 0.026 | 0.104 | 0.769 | 0.011 | 0.000 |
| *Catenibacterium mitsuokai* | 0.013 | 0.015 | 0.026 | 1.000 | 0.525 | 0.515 | 0.011 | 0.000 |
| *Cerasicoccus arenae* | NA | 0.613 | NA | NA | NA | NA | 0.566 | ns |
| *Cetobacterium somerae* | 0.013 | 0.212 | 0.652 | 0.434 | 1.000 | 0.012 | 1.000 | ns |
| *Chryseobacterium hominis* | NA | NA | 0.644 | 0.600 | 0.248 | 0.190 | 1.000 | 0.001 |
| *Chryseobacterium*; Other | NA | NA | NA | 0.168 | NA | NA | NA | 0.040 |
| Clostridiaceae; Other | 0.013 | 0.015 | 0.026 | 0.127 | 0.024 | 0.012 | 0.011 | 0.000 |
| Clostridiales; Other | 0.013 | 0.015 | 0.791 | 0.355 | 0.024 | 0.012 | 0.011 | 0.000 |
| *Clostridium bartlettii* | 0.013 | 0.015 | 0.605 | 0.026 | 0.024 | 0.531 | 1.000 | 0.007 |
| *Clostridium bifermentans* | 0.436 | NA | NA | NA | NA | NA | 0.142 | ns |
| *Clostridium bolteae* | 0.207 | 0.110 | 0.479 | 0.666 | 0.242 | 0.297 | 0.011 | 0.000 |
| *Clostridium clostridioforme* | 0.013 | 0.039 | 0.776 | 0.026 | 0.024 | 0.705 | 0.011 | 0.006 |
| *Clostridium disporicum* | 0.013 | 0.015 | 0.026 | 0.026 | 0.024 | 0.012 | 0.284 | 0.000 |
| *Clostridium glycolicum* | 0.013 | 0.015 | 0.026 | 0.044 | 0.024 | 0.012 | 0.011 | 0.000 |
| *Clostridium glycyrrhizinilyticum* | NA | 0.637 | 0.026 | 0.055 | 0.024 | 0.012 | 0.137 | ns |
| *Clostridium hathewayi* | 0.436 | 0.039 | NA | 1.000 | 0.446 | NA | 0.011 | 0.000 |
| *Clostridium hylemonae* | NA | NA | 0.517 | NA | NA | NA | NA | ns |
| *Clostridium innocuum* | NA | NA | NA | 0.127 | NA | NA | NA | 0.036 |
| *Clostridium neonatale* | NA | NA | NA | NA | NA | NA | 0.476 | ns |
| *Clostridium nexile* | 0.013 | 0.310 | NA | 0.648 | NA | 0.851 | 0.133 | 0.008 |
| *Clostridium paraputrificum* | 0.013 | 0.624 | 0.026 | 0.597 | 0.024 | 0.033 | 0.072 | 0.000 |
| *Clostridium perfringens* | 0.218 | 0.049 | 0.054 | 0.026 | 0.084 | 0.060 | NA | 0.000 |
| *Clostridium ramosum* | 0.035 | 0.140 | 0.117 | 0.026 | NA | 0.508 | 0.576 | 0.001 |
| *Clostridium* sp L2 50 | 0.436 | 0.420 | 1.000 | 0.026 | 0.094 | 0.236 | 0.057 | 0.006 |
| *Clostridium* sp SS2 1 | 0.436 | 0.015 | NA | NA | NA | 0.232 | NA | 0.000 |
| *Clostridium*; Other | 0.679 | 0.015 | 0.164 | 1.000 | NA | 0.012 | 0.011 | 0.000 |
| *Collinsella aerofaciens* | 0.013 | 0.015 | 0.026 | 0.095 | 0.582 | 0.012 | 0.142 | 0.000 |
| *Collinsella*; Other | 0.013 | 0.015 | 0.026 | NA | NA | 0.102 | 0.011 | 0.000 |
| Comamonadaceae; Other | 1.000 | 0.637 | 0.593 | 0.055 | 0.094 | 0.012 | 0.011 | ns |
| *Comamonas aquatica* | 0.657 | 0.231 | 0.117 | NA | 0.070 | 0.041 | 0.011 | 0.000 |
| *Comamonas*; Other | NA | NA | NA | 0.078 | NA | NA | NA | 0.008 |
| *Coprococcus catus* | 0.838 | 0.015 | 0.054 | 0.026 | 0.024 | 0.901 | 0.011 | 0.023 |
| *Coprococcus comes* | 0.082 | 0.015 | 0.155 | 0.026 | 1.000 | 0.012 | 0.011 | 0.000 |
| *Coprococcus eutactus* | 0.013 | 0.015 | NA | 0.130 | 0.471 | 0.012 | 0.011 | 0.000 |
| *Coprococcus*; Other | 0.013 | 0.015 | NA | 0.203 | NA | 0.012 | 0.011 | 0.000 |

TABLE 21-continued

| Indicator value analysis results | | | | | | | | |
|---|---|---|---|---|---|---|---|---|
| Coriobacteriaceae; Other | 0.013 | 0.015 | 0.026 | 0.125 | 0.582 | 0.012 | 0.011 | 0.000 |
| *Corynebacterium aurimucosum* | NA | 0.687 | 0.212 | 1.000 | 0.157 | 0.140 | 1.000 | 0.000 |
| *Corynebacterium durum* | 1.000 | 0.624 | 0.637 | 0.722 | 0.487 | 0.657 | 0.011 | 0.018 |
| *Corynebacterium imitans* | NA | 0.133 | 0.077 | NA | 0.129 | NA | 0.019 | 0.000 |
| *Corynebacterium matruchotii* | 0.056 | NA | 0.130 | 0.130 | 0.369 | 0.183 | 0.011 | 0.000 |
| *Corynebacterium mucifaciens* | 0.630 | 0.687 | 0.066 | 0.575 | 0.056 | 0.012 | 0.052 | 0.000 |
| *Corynebacterium tuberculostearicum* | 0.240 | 0.624 | 0.066 | 0.068 | 0.056 | 0.081 | 0.011 | 0.000 |
| *Corynebacterium*; Other | 0.045 | 0.091 | 0.026 | 0.055 | 0.471 | 0.012 | 0.011 | 0.000 |
| Deltaproteobacteria; Other | NA | NA | NA | NA | 1.000 | NA | NA | ns |
| *Desulfovibrio*; Other | 0.013 | 0.091 | 0.479 | NA | NA | 0.976 | 0.011 | 0.000 |
| *Dialister invisus* | 1.000 | 0.385 | 1.000 | NA | 1.000 | 1.000 | 0.133 | ns |
| *Dialister pneumosintes* | 0.013 | 0.085 | 0.096 | 1.000 | 0.695 | 0.041 | 1.000 | 0.001 |
| *Dialister*; Other | NA | 1.000 | 1.000 | 0.327 | 0.626 | 0.429 | 0.019 | 0.003 |
| *Dolosigranulum pigrum* | NA | NA | NA | NA | 0.692 | NA | NA | ns |
| *Dorea formicigenerans* | 0.013 | 0.015 | 0.479 | 0.026 | 0.024 | 0.012 | 0.011 | 0.000 |
| *Dorea longicatena* | 0.013 | 0.015 | 0.040 | 0.044 | 0.024 | 0.864 | 1.000 | 0.000 |
| *Edwardsiella ictaluri* | NA | NA | NA | 0.571 | NA | NA | NA | ns |
| *Eggerthella lenta* | NA | 0.314 | NA | 0.078 | 0.471 | 0.204 | 0.011 | 0.000 |
| *Elusimicrobium minutum* | 0.436 | 0.613 | NA | NA | NA | NA | 0.011 | ns |
| Enterobacteriaceae; Other | 0.013 | 0.337 | 0.112 | 0.078 | 0.721 | 0.033 | 0.019 | ns |
| Enterococcaceae; Other | NA | NA | 0.096 | 0.257 | 0.129 | 0.556 | 0.133 | 0.000 |
| *Enterococcus cecorum* | 0.218 | 0.028 | 0.370 | 0.427 | NA | 0.076 | NA | 0.041 |
| *Enterococcus faecalis* | 0.073 | 0.185 | 0.992 | 0.068 | 0.309 | 0.095 | 0.085 | ns |
| *Enterococcus*; Other | 0.149 | 0.314 | 0.026 | 1.000 | 0.041 | 0.012 | 0.011 | 0.000 |
| Erysipelotrichaceae; Other | 0.207 | 0.613 | 0.096 | 0.929 | 1.000 | 0.140 | 0.127 | ns |
| *Escherichia albertii* | NA | NA | NA | 1.000 | NA | 0.353 | NA | ns |
| *Escherichia coli* | 0.025 | 0.049 | 0.538 | 1.000 | 0.821 | 0.012 | 0.011 | 0.000 |
| *Escherichia*; Other | 0.383 | 0.085 | 0.791 | 0.713 | 0.657 | 0.012 | 0.011 | 0.006 |
| *Eubacterium biforme* | 0.013 | 1.000 | 0.040 | 0.264 | 0.024 | 0.012 | 0.011 | 0.000 |
| *Eubacterium coprostanoligenes* | 0.013 | 0.015 | 0.479 | NA | 0.471 | 0.012 | 0.011 | 0.000 |
| *Eubacterium desmolans* | 0.163 | 0.015 | 0.787 | 0.897 | 0.024 | 0.012 | 0.011 | 0.008 |
| *Eubacterium eligens* | 0.013 | 0.015 | 0.125 | 0.026 | 0.041 | 0.012 | 0.425 | 0.000 |
| *Eubacterium hallii* | 0.013 | 0.015 | 0.125 | 0.812 | 1.000 | 0.012 | 0.011 | 0.000 |
| *Eubacterium limosum* | 0.436 | NA | 0.517 | NA | NA | NA | 0.287 | 0.039 |
| *Eubacterium ramulus* | 0.025 | 0.015 | NA | NA | NA | 0.088 | 0.011 | 0.000 |
| *Eubacterium rectale* | 0.679 | 0.015 | 1.000 | 1.000 | NA | 0.012 | 0.011 | 0.000 |
| *Eubacterium saburreum* | 0.013 | 0.015 | 0.308 | 0.466 | 0.149 | 0.012 | 0.011 | 0.000 |
| *Eubacterium siraeum* | NA | 0.218 | NA | NA | 0.070 | 0.095 | 0.011 | 0.000 |
| *Eubacterium* sp cL 10 1 3 | 0.436 | 0.039 | NA | NA | NA | NA | 0.011 | 0.000 |
| *Eubacterium*; Other | 0.013 | 0.015 | 0.026 | 1.000 | NA | 0.012 | 0.011 | 0.000 |
| *Faecalibacterium prausnitzii* | 0.013 | 0.015 | 0.054 | 0.095 | 0.024 | 0.012 | 0.011 | 0.000 |
| *Faecalibacterium*; Other | 0.013 | 0.015 | 0.040 | 0.314 | 0.115 | 0.012 | 0.011 | 0.000 |
| *Finegoldia magna* | NA | 0.542 | 0.066 | NA | 0.297 | 1.000 | NA | ns |
| *Firmicutes*; Other | 0.683 | 0.015 | 0.225 | 0.373 | 0.467 | 0.012 | 0.011 | 0.000 |
| Flavobacteriaceae; Other | NA | 0.655 | 1.000 | NA | 0.336 | NA | 0.576 | ns |
| Flavobacteriales; Other | NA | NA | NA | 0.689 | 1.000 | NA | NA | ns |
| *Flavobacterium*; Other | NA | NA | NA | NA | 0.657 | NA | NA | ns |
| *Flexibacter*; Other | NA | NA | NA | 0.078 | NA | NA | 0.284 | 0.032 |
| Fusobacteriaceae; Other | 0.453 | 0.655 | NA | NA | NA | 0.023 | NA | 0.007 |
| *Fusobacterium mortiferum* | 0.345 | 0.015 | 0.138 | 0.130 | 0.340 | 0.349 | 0.137 | 0.000 |
| *Fusobacterium nucleatum* | 0.082 | 0.015 | 0.320 | 0.026 | 0.104 | 0.012 | 0.011 | 0.000 |
| *Fusobacterium*; Other | 0.065 | 0.015 | 0.026 | 0.044 | 0.231 | 1.000 | 0.323 | 0.000 |
| Gammaproteobacteria; Other | 0.254 | 0.015 | 0.077 | 0.541 | 0.024 | 0.076 | 0.028 | 0.000 |
| *Granulicatella adiacens* | 0.065 | 0.953 | 0.040 | 0.373 | 0.302 | 0.012 | 0.011 | 0.000 |
| *Granulicatella elegans* | NA | 0.069 | 0.066 | 0.026 | 0.024 | 0.012 | 0.121 | 0.000 |
| *Haemophilus haemolyticus* | 0.073 | 0.687 | 0.112 | 0.026 | 0.157 | 0.012 | 0.133 | 0.000 |
| *Haemophilus*; Other | NA | NA | NA | 0.115 | 0.369 | 0.012 | 0.318 | 0.000 |
| *Halomonas*; Other | NA | 0.049 | 0.637 | NA | 0.250 | 0.343 | 0.044 | 0.000 |
| *Helicobacter cinaedi* | 0.742 | NA | 0.066 | 1.000 | NA | 0.465 | NA | ns |
| *Helicobacter winghamensis* | 1.000 | 1.000 | 0.428 | NA | 0.250 | 0.012 | 0.273 | 0.000 |
| *Helicobacter*; Other | NA | NA | 0.479 | NA | 0.242 | NA | NA | ns |
| Intrasporangiaceae; Other | NA | NA | NA | 1.000 | 0.657 | NA | 0.011 | 0.007 |
| *Jeotgalicoccus*; Other | NA | 0.015 | 0.269 | NA | 0.115 | 0.584 | 0.052 | 0.000 |
| *Kocuria marina* | 0.657 | 1.000 | NA | NA | NA | NA | 1.000 | ns |
| *Lachnospira pectinoschiza* | 0.933 | 0.039 | 0.249 | NA | NA | 0.572 | 0.278 | 0.001 |
| Lachnospiraceae; Other | 0.013 | 0.015 | 0.244 | 0.267 | 0.471 | 0.012 | 0.028 | 0.000 |
| Lactobacillaceae; Other | NA | NA | 0.112 | 0.373 | 0.636 | NA | NA | ns |
| Lactobacillales; Other | 0.218 | 0.687 | 0.249 | 0.055 | 0.056 | 0.654 | 0.057 | ns |
| *Lactobacillus delbrueckii* | NA | NA | NA | NA | 0.094 | NA | NA | 0.022 |
| *Lactobacillus fermentum* | 0.013 | 1.000 | 0.479 | NA | 0.056 | 0.346 | NA | 0.000 |
| *Lactobacillus mucosae* | 0.502 | 0.708 | 0.040 | 0.095 | 0.139 | NA | 1.000 | ns |
| *Lactobacillus ruminis* | 0.013 | 0.085 | 0.026 | 0.085 | 0.471 | 0.508 | 0.866 | ns |
| *Lactobacillus saerimneri* | 0.621 | 0.172 | 0.026 | 0.095 | 0.219 | 0.277 | 0.462 | 0.002 |
| *Lactobacillus* sp Atm5 | NA | NA | NA | 1.000 | NA | NA | NA | ns |
| *Lactobacillus* sp KLDS 1 0716 | 0.123 | NA | NA | NA | NA | NA | NA | 0.018 |
| *Lactobacillus*; Other | 0.598 | NA | 0.171 | 0.106 | 0.104 | NA | NA | ns |
| *Lactococcus garvieae* | NA | 0.624 | NA | 0.203 | 1.000 | 0.463 | 0.566 | 0.019 |
| *Leptotrichia* 591114 | NA | NA | 1.000 | NA | 0.056 | NA | 0.133 | 0.000 |

TABLE 21-continued

| Indicator value analysis results | | | | | | | | |
|---|---|---|---|---|---|---|---|---|
| *Leptotrichia buccalis* | 0.193 | 0.344 | 0.244 | 0.358 | 0.248 | 0.012 | 0.133 | 0.000 |
| *Leptotrichia shahii* | 0.013 | 0.028 | 0.040 | 0.026 | 0.024 | 0.012 | 0.011 | 0.000 |
| *Leptotrichia* sp PG10 | NA | 0.624 | NA | NA | 0.202 | 1.000 | 0.011 | 0.001 |
| *Leptotrichia*; Other | NA | 0.344 | NA | 0.288 | 0.024 | 0.154 | 0.133 | 0.000 |
| Leptotrichiaceae; Other | 0.282 | 0.127 | 0.225 | 0.115 | 0.024 | 0.012 | 0.284 | 0.000 |
| *Leucobacter komagatae* | NA | NA | NA | 0.055 | NA | NA | NA | 0.002 |
| *Leucobacter*; Other | NA | NA | NA | 0.186 | NA | NA | NA | 0.039 |
| *Leuconostoc*; Other | 0.214 | 0.613 | NA | 0.384 | 1.000 | 0.401 | NA | ns |
| *Luteimonas*; Other | NA | NA | NA | 0.249 | 0.582 | NA | 0.011 | ns |
| *Megamonas rupellensis* | 0.073 | 1.000 | 0.026 | 0.026 | 0.196 | 0.012 | NA | 0.000 |
| *Megamonas*; Other | NA | NA | 0.026 | 0.115 | 0.471 | 1.000 | NA | 0.000 |
| *Megasphaera elsdenii* | 0.013 | 0.133 | 0.026 | 1.000 | 0.483 | 0.023 | NA | 0.000 |
| *Megasphaera hominis* | 0.131 | NA | 0.026 | NA | NA | NA | NA | 0.000 |
| *Megasphaera* sp TrE9262 | 0.013 | 0.091 | 0.026 | NA | 1.000 | 1.000 | NA | 0.000 |
| *Megasphaera*; Other | 0.013 | 0.091 | NA | NA | NA | NA | NA | 0.000 |
| *Micrococcus luteus* | NA | 0.208 | 0.479 | NA | 0.275 | 1.000 | 0.566 | 0.001 |
| *Mitsuokella multacida* | 0.013 | 0.015 | 0.858 | NA | NA | 0.067 | 0.566 | 0.000 |
| *Mitsuokella*; Other | 0.013 | 0.613 | 1.000 | NA | NA | NA | 0.566 | 0.001 |
| *Mogibacterium neglectum* | NA | 0.236 | 0.833 | 0.130 | 0.666 | 1.000 | 0.011 | ns |
| *Moraxella osloensis* | 0.240 | 0.059 | 0.637 | 0.648 | 0.237 | 0.611 | 1.000 | 0.000 |
| Moraxellaceae; Other | NA | 0.133 | 1.000 | NA | 0.372 | NA | 0.576 | 0.015 |
| *Morganella morganii* | NA | NA | NA | 1.000 | 1.000 | NA | NA | ns |
| *Neisseria elongata* | 0.653 | 1.000 | 0.275 | 0.597 | 0.626 | 0.346 | 0.057 | 0.001 |
| *Neisseria subflava* | 0.123 | 0.687 | 0.117 | 0.026 | 0.626 | 0.012 | NA | 0.000 |
| *Neisseria*; Other | 0.035 | 0.015 | 0.026 | 0.026 | 0.084 | 0.012 | 0.019 | 0.000 |
| *Nevskia*; Other | NA | NA | NA | NA | 1.000 | NA | NA | ns |
| *Novosphingobium*; Other | NA | NA | NA | NA | 0.372 | NA | NA | ns |
| *Odoribacter splanchnicus* | NA | NA | NA | 0.408 | 1.000 | 0.081 | 0.028 | 0.001 |
| *Olsenella* sp A2 | 0.013 | 0.015 | 0.066 | NA | 0.897 | NA | 0.794 | 0.000 |
| *Olsenella*; Other | 0.013 | 0.613 | NA | NA | NA | NA | NA | 0.000 |
| *Oribacterium* sp oral taxon 108 | 0.531 | 0.266 | 0.496 | 1.000 | 0.094 | 1.000 | 0.028 | 0.000 |
| *Oscillibacter* sp G2 | 0.436 | 0.015 | NA | NA | NA | 0.088 | 0.011 | 0.000 |
| *Oscillibacter*; Other | 0.370 | 0.015 | 0.840 | 0.026 | NA | 0.012 | 0.435 | 0.000 |
| *Oxalobacter formigenes* | 0.436 | 0.091 | NA | NA | NA | NA | NA | 0.021 |
| *Pantoea ananatis* | 0.653 | 1.000 | NA | 1.000 | 0.613 | NA | 1.000 | ns |
| *Parabacteroides distasonis* | 0.436 | 0.015 | NA | 0.125 | NA | 0.012 | 0.019 | 0.000 |
| *Parabacteroides merdae* | 0.436 | NA | 0.212 | NA | NA | 0.012 | NA | 0.000 |
| *Parabacteroides*; Other | 0.013 | 0.015 | 0.527 | NA | NA | 0.012 | 0.011 | 0.000 |
| *Paracoccus denitrificans* | NA | NA | NA | 0.648 | 0.024 | 0.429 | 0.011 | 0.000 |
| *Paracoccus*; Other | NA | 1.000 | NA | 0.055 | 0.369 | 1.000 | 0.292 | ns |
| Pasteurellaceae; Other | 0.157 | 0.909 | 0.026 | 1.000 | 0.329 | 0.033 | 0.011 | 0.000 |
| *Pediococcus*; Other | NA | NA | 0.479 | NA | NA | NA | NA | ns |
| *Pedobacter terrae* | NA | 0.208 | 0.644 | NA | 0.378 | 1.000 | 0.137 | 0.001 |
| *Pedobacter*; Other | NA | NA | NA | 0.127 | NA | NA | NA | 0.019 |
| *Peptoniphilus harei* | NA | 1.000 | 0.077 | NA | 0.471 | 0.140 | 0.079 | ns |
| *Peptostreptococcus stomatis* | NA | 0.687 | 1.000 | NA | 0.866 | 0.228 | 0.065 | ns |
| *Peptostreptococcus*; Other | 1.000 | 1.000 | 0.054 | 0.026 | 0.237 | 0.012 | 0.011 | 0.000 |
| *Peredibacter starrii* | NA | NA | NA | NA | 0.657 | NA | NA | ns |
| *Phascolarctobacterium faecium* | NA | NA | NA | NA | NA | 0.012 | 0.011 | 0.000 |
| *Phascolarctobacterium succinatutens* | NA | 0.015 | 0.026 | 0.026 | 0.589 | NA | 0.085 | 0.000 |
| *Porphyromonas catoniae* | 0.679 | 0.069 | 0.096 | 0.026 | 0.570 | 0.060 | 0.133 | 0.000 |
| *Prevotella buccae* | 0.436 | NA | NA | NA | NA | NA | NA | ns |
| *Prevotella copri* | 0.013 | 0.015 | 0.026 | 0.479 | 0.557 | 0.012 | 0.165 | 0.000 |
| *Prevotella denticola* | NA | NA | 1.000 | NA | 0.340 | 0.572 | 0.057 | 0.005 |
| *Prevotella histicola* | 0.091 | 0.015 | 0.040 | 0.026 | 0.024 | 0.012 | 0.011 | 0.000 |
| *Prevotella nanceiensis* | 0.531 | 0.687 | 0.200 | 0.026 | 0.570 | 0.012 | 1.000 | 0.000 |
| *Prevotella oulorum* | 0.013 | 0.015 | 0.112 | 0.130 | 0.525 | 0.012 | 0.334 | 0.000 |
| *Prevotella salivae* | NA | 0.385 | 1.000 | NA | 0.282 | 0.236 | 0.057 | 0.000 |
| *Prevotella* sp DJF B112 | 0.531 | 0.049 | 0.652 | NA | 0.129 | 0.012 | 0.011 | 0.000 |
| *Prevotella* sp DJF B116 | 0.013 | 0.015 | 0.026 | 0.044 | 0.471 | 0.012 | 0.011 | 0.000 |
| *Prevotella* sp DJF CP65 | 0.013 | 0.015 | 0.088 | 0.026 | NA | 0.012 | 0.044 | 0.000 |
| *Prevotella* sp DJF LS16 | 0.013 | 0.613 | NA | NA | 0.568 | NA | NA | 0.000 |
| *Prevotella* sp oral taxon 302 | 0.013 | 0.039 | 0.088 | 0.026 | NA | 0.012 | 0.338 | 0.000 |
| *Prevotella* sp RS2 | 0.013 | 0.015 | NA | 1.000 | 0.582 | 1.000 | NA | 0.000 |
| *Prevotella stercorea* | 0.229 | 0.015 | 0.785 | 0.026 | 0.692 | 0.012 | 0.036 | ns |
| *Prevotella veroralis* | 0.099 | 1.000 | NA | NA | NA | 0.050 | 0.085 | 0.002 |
| *Prevotella*; Other | 0.679 | 0.028 | 0.288 | 0.130 | 0.115 | 0.012 | 0.011 | 0.000 |
| Prevotellaceae; Other | 0.436 | 0.015 | 0.112 | 1.000 | NA | 0.081 | 0.147 | 0.003 |
| *Prosthecobacter*; Other | NA | 1.000 | NA | NA | 1.000 | 1.000 | NA | ns |
| Proteobacteria; Other | 0.013 | 0.028 | 0.171 | 1.000 | 0.860 | 0.012 | 0.011 | 0.000 |
| *Proteus mirabilis* | NA | NA | NA | 1.000 | NA | NA | NA | ns |
| *Pseudomonas mendocina* | 0.365 | 0.015 | 0.130 | 0.648 | 0.024 | 0.067 | 0.011 | 0.000 |
| *Pseudomonas stutzeri* | 0.035 | 0.015 | 0.040 | 0.274 | 0.024 | 0.012 | 0.011 | 0.000 |
| *Pseudomonas*; Other | NA | 0.231 | 0.593 | NA | 0.041 | 0.232 | 0.019 | 0.000 |
| *Ralstonia*; Other | NA | 0.015 | 0.146 | 0.342 | 0.041 | 0.372 | NA | 0.000 |
| *Rheinheimera* sp 09BSZB 9 | NA | 0.613 | 0.593 | NA | 0.211 | 0.308 | 0.297 | 0.001 |
| *Rheinheimera* sp TPS16 | NA | NA | NA | NA | 0.657 | NA | NA | ns |
| *Rheinheimera*; Other | NA | 0.403 | 0.415 | 0.648 | 0.224 | 0.349 | 0.028 | 0.000 |

TABLE 21-continued

| Indicator value analysis results | | | | | | | | |
|---|---|---|---|---|---|---|---|---|
| Rhizobiaceae; Other | NA | NA | NA | 0.085 | NA | NA | 0.566 | 0.032 |
| Rhizobiales; Other | NA | NA | NA | NA | 0.302 | NA | NA | ns |
| Rhodobacteraceae; Other | NA | NA | NA | 0.068 | NA | NA | NA | 0.003 |
| Rhodocyclaceae; Other | NA | NA | NA | NA | 1.000 | NA | NA | ns |
| *Roseburia intestinalis* | 0.013 | 0.079 | 0.107 | 0.650 | 0.471 | 0.012 | 0.011 | 0.000 |
| *Roseburia*; Other | 0.013 | 0.015 | 0.605 | 0.267 | 0.024 | 0.012 | 0.361 | 0.000 |
| *Rothia dentocariosa* | 0.013 | 0.385 | 0.026 | 0.358 | 0.070 | 0.023 | 0.011 | 0.000 |
| *Rothia mucilaginosa* | 0.013 | 0.185 | 0.026 | 0.026 | 0.024 | 0.877 | 0.011 | 0.000 |
| Ruminococcaceae; Other | 0.013 | 0.015 | 0.188 | 0.648 | 0.471 | 0.012 | 0.011 | 0.000 |
| *Ruminococcus bromii* | 0.013 | 0.015 | NA | 0.085 | 0.681 | 0.012 | 0.028 | 0.000 |
| *Ruminococcus callidus* | 0.013 | 0.015 | NA | NA | NA | 0.012 | 0.011 | 0.000 |
| *Ruminococcus flavefaciens* | NA | 0.015 | NA | NA | NA | 0.475 | 0.011 | 0.000 |
| *Ruminococcus gnavus* | 0.013 | 0.140 | 0.026 | 0.026 | NA | 0.308 | 0.072 | 0.000 |
| *Ruminococcus obeum* | 0.013 | 0.015 | 0.442 | 1.000 | 0.024 | 0.211 | 0.570 | 0.001 |
| *Ruminococcus sp 5 1 39BFAA* | 0.013 | 0.085 | 0.040 | 0.466 | 0.024 | 0.012 | 0.011 | 0.000 |
| *Ruminococcus sp DJF VR70k1* | 0.013 | 0.015 | 0.785 | 0.085 | 0.024 | 0.012 | 0.011 | 0.000 |
| *Ruminococcus sp ZS2 15* | NA | NA | NA | NA | 0.024 | 0.147 | NA | 0.009 |
| *Ruminococcus torques* | 0.035 | 0.015 | NA | NA | 0.471 | 0.012 | 0.036 | 0.000 |
| *Ruminococcus*; Other | 0.888 | 0.960 | 0.208 | 0.127 | 0.024 | 0.012 | 0.019 | ns |
| *Salmonella enterica* | 0.082 | 0.357 | 0.212 | 0.150 | 0.896 | 0.081 | 0.866 | ns |
| *Sarcina ventriculi* | 0.436 | 0.337 | NA | NA | NA | NA | NA | ns |
| *Sarcina*; Other | 0.177 | 0.059 | NA | NA | NA | 0.228 | NA | 0.001 |
| *Scardovia wiggsiae* | 0.994 | 1.000 | NA | 0.597 | 0.297 | 0.410 | 0.057 | 0.005 |
| *Shinella*; Other | NA | NA | NA | 0.106 | 0.582 | NA | 0.133 | ns |
| *Shuttleworthia satelles* | 1.000 | 1.000 | NA | NA | 0.268 | NA | 0.284 | 0.006 |
| *Slackia isoflavoniconvertens* | 0.025 | 0.015 | 0.026 | 1.000 | NA | 0.012 | 0.011 | 0.000 |
| *Solobacterium moorei* | 0.966 | 0.602 | 0.138 | 1.000 | 0.202 | 0.012 | 0.011 | 0.000 |
| *Sphingobacterium mizutaii* | NA | NA | NA | NA | 0.359 | NA | 0.011 | 0.001 |
| *Sphingobacterium multivorum* | NA | 1.000 | 0.446 | NA | 0.167 | 0.643 | 0.044 | 0.001 |
| *Sphingobacterium sp P 7* | NA | NA | NA | NA | 1.000 | NA | NA | ns |
| *Sphingobium yanoikuyae* | NA | 0.218 | 0.254 | NA | 0.084 | 0.333 | 0.099 | 0.000 |
| Sphingomonadaceae; Other | NA | 0.624 | 1.000 | NA | 0.392 | NA | 1.000 | 0.050 |
| Sphingomonadales; Other | NA | NA | NA | 0.186 | NA | NA | NA | 0.039 |
| *Sphingomonas sp BAC84* | 0.598 | 0.015 | 0.239 | 0.597 | 0.471 | 1.000 | NA | 0.001 |
| *Sphingomonas yabuuchiae* | NA | NA | NA | NA | 1.000 | NA | NA | ns |
| *Sphingomonas*; Other | NA | NA | NA | NA | 0.398 | 0.333 | 0.566 | 0.014 |
| Staphylococcaceae; Other | NA | 0.334 | 1.000 | NA | 0.443 | NA | 0.159 | 0.010 |
| *Staphylococcus aureus* | 0.177 | 0.015 | 0.026 | 0.327 | 0.024 | 0.033 | 0.011 | 0.000 |
| *Staphylococcus*; Other | 1.000 | 0.039 | 0.026 | 1.000 | 0.024 | 0.050 | 0.011 | 0.000 |
| *Stenotrophomonas maltophilia* | 1.000 | 0.377 | 0.112 | 0.648 | 0.024 | 0.249 | 0.011 | 0.000 |
| *Stenotrophomonas rhizophila* | 1.000 | 1.000 | 0.107 | 1.000 | 0.094 | 0.343 | 0.011 | 0.000 |
| *Stenotrophomonas*; Other | 0.013 | 0.015 | 0.026 | NA | 0.589 | NA | 1.000 | 0.000 |
| Streptococcaceae; Other | 0.013 | NA | 0.040 | 0.127 | 0.250 | NA | NA | ns |
| *Streptococcus anginosus* | 0.013 | 1.000 | 0.194 | 1.000 | 0.024 | 0.012 | 0.011 | 0.000 |
| *Streptococcus gordonii* | 0.013 | 0.079 | 0.220 | 0.355 | 0.041 | 0.012 | 0.011 | 0.000 |
| *Streptococcus mutans* | 0.107 | 1.000 | NA | 1.000 | 0.353 | 1.000 | 0.133 | 0.002 |
| *Streptococcus parasanguinis* | 0.013 | 0.015 | 0.026 | 0.373 | 0.196 | 0.012 | 0.044 | 0.000 |
| *Streptococcus peroris* | 0.013 | 0.059 | 0.026 | 0.288 | 0.231 | 0.176 | 0.011 | 0.000 |
| *Streptococcus sanguinis* | NA | NA | NA | NA | 1.000 | NA | NA | ns |
| *Streptococcus thermophilus* | 0.013 | 0.049 | 0.026 | 1.000 | 0.024 | 0.459 | 0.011 | 0.000 |
| *Streptococcus*; Other | 0.013 | 0.266 | 0.475 | 0.889 | 0.024 | 0.769 | 0.011 | 0.001 |
| *Subdoligranulum variabile* | 0.683 | 0.015 | 0.077 | 0.026 | 1.000 | 0.012 | 0.011 | 0.000 |
| *Succinivibrio dextrinosolvens* | 1.000 | 1.000 | 0.652 | 1.000 | 0.626 | 0.421 | 0.011 | ns |
| *Sutterella sp YIT 12072* | NA | 0.015 | 0.054 | 0.994 | 0.626 | 0.023 | 0.472 | ns |
| *Sutterella stercoricanis* | 0.679 | 0.015 | NA | 0.434 | 1.000 | 0.465 | 0.028 | ns |
| *Sutterella*; Other | 0.013 | 0.015 | 0.581 | 0.026 | 1.000 | 0.224 | 0.011 | 0.004 |
| *Thauera terpenica* | NA | NA | NA | 0.127 | NA | NA | NA | 0.019 |
| *Thauera*; Other | NA | NA | NA | 0.378 | NA | NA | NA | ns |
| *Thermus igniterrae* | NA | NA | NA | NA | 1.000 | NA | 0.057 | ns |
| *Treponema porcinum* | NA | NA | NA | NA | 1.000 | NA | NA | ns |
| *Treponema succinifaciens* | NA | 0.613 | NA | NA | NA | NA | 0.287 | ns |
| *Turicibacter sanguinis* | 0.013 | 0.015 | 0.026 | 0.055 | 0.024 | 0.012 | 0.011 | 0.000 |
| unclassified_Erysipelotrichaceae; Other | 0.013 | 0.453 | NA | 0.085 | NA | 0.769 | 0.576 | 0.004 |
| *Ureaplasma*; Other | 0.679 | NA | 0.239 | NA | NA | NA | NA | ns |
| *Varibaculum cambriense* | NA | NA | NA | NA | 0.626 | NA | NA | ns |
| *Veillonella dispar* | 0.295 | 0.133 | 1.000 | 0.078 | 0.121 | 0.012 | 0.011 | 0.001 |
| *Veillonella parvula* | 0.426 | 0.951 | 1.000 | 0.026 | 0.242 | 0.012 | 0.011 | ns |
| *Veillonella sp S101* | 0.223 | 0.991 | 0.442 | 0.026 | 0.149 | 0.012 | 0.011 | 0.015 |
| *Veillonella*; Other | NA | 0.180 | NA | NA | 0.056 | NA | NA | 0.000 |
| Veillonellaceae; Other | 0.013 | 0.236 | 0.026 | 0.731 | 0.121 | 0.983 | 0.011 | 0.027 |
| *Verrucomicrobium sp IRVE* | NA | NA | NA | NA | 0.626 | NA | NA | ns |
| *Vibrio cholerae* | 0.013 | 0.015 | 0.146 | 0.026 | 0.024 | 0.012 | 0.011 | 0.000 |
| *Vibrio*; Other | 0.025 | 0.208 | 0.288 | 0.026 | 0.041 | 0.041 | 0.011 | 0.000 |

TABLE 21-continued

| | Indicator value analysis results | | | | | | | |
|---|---|---|---|---|---|---|---|---|
| *Wautersiella falsenii* | NA | NA | 1.000 | NA | 0.613 | NA | 0.503 | ns |
| *Weissella cibaria* | 0.502 | 0.028 | 0.440 | 1.000 | 0.847 | 0.067 | 0.927 | ns |
| *Weissella*; Other | 0.235 | 0.624 | 0.466 | 0.713 | 0.866 | 0.041 | NA | ns |
| X1760; Other | 0.013 | 0.015 | 0.026 | 1.000 | NA | 0.012 | 0.011 | 0.000 |
| Xanthomonadaceae; Other | NA | NA | NA | 0.055 | 0.582 | NA | 0.019 | ns |

TABLE 22

Correlation between bacterial species abundance in fecal microbiota of cholera patients and the samples' UniFrac distance to healthy adult Bangladeshi fecal communities

| | Species | Spearman r | P (two-tailed) | FDR adjusted p-value (Benjamini-Hochberg correction) | Indicator Value(Recovery) – Indicator Value(Diarrhea) |
|---|---|---|---|---|---|
| Positively correlated with community distance to healthy microbiota | *Pseudomonas*; Other | 0.5902 | 0.0001 | 0.0002 | −0.225 |
| | Gammaproteobacteria; Other | 0.5856 | 0.0001 | 0.0002 | −0.439 |
| | *Prevotella histicola* | 0.5265 | 0.0001 | 0.0002 | −0.667 |
| | *Prevotella veroralis* | 0.5146 | 0.0001 | 0.0002 | 0.139 |
| | *Pseudomonas mendocina* | 0.5039 | 0.0001 | 0.0002 | −0.449 |
| | *Vibrio cholerae* | 0.4877 | 0.0001 | 0.0002 | −0.990 |
| | *Prevotella salivae* | 0.4773 | 0.0001 | 0.0002 | −0.145 |
| | *Acinetobacter*; Other | 0.4392 | 0.0001 | 0.0002 | −0.449 |
| | *Vibrio*; Other | 0.4382 | 0.0001 | 0.0002 | −0.521 |
| | *Staphylococcus aureus* | 0.4381 | 0.0001 | 0.0002 | −0.621 |
| | *Leptotrichia*; Other | 0.4345 | 0.0001 | 0.0002 | −0.188 |
| | *Staphylococcus*; Other | 0.4247 | 0.0001 | 0.0002 | −0.478 |
| | *Pseudomonas stutzeri* | 0.4215 | 0.0001 | 0.0002 | −0.653 |
| | *Comamonas aquatica* | 0.4143 | 0.0001 | 0.0002 | −0.343 |
| | *Aerococcus*; Other | 0.4129 | 0.0001 | 0.0002 | −0.348 |
| | *Ralstonia*; Other | 0.395 | 0.0001 | 0.0002 | −0.246 |
| | *Actinomyces graevenitzii* | 0.3934 | 0.0001 | 0.0002 | −0.380 |
| | *Fusobacterium nucleatum* | 0.3917 | 0.0001 | 0.0002 | −0.511 |
| | *Aeromonas*; Other | 0.3869 | 0.0001 | 0.0002 | −0.442 |
| | *Oribacterium* sp oral taxon 108 | 0.3868 | 0.0001 | 0.0002 | −0.180 |
| | Leptotrichiaceae; Other | 0.3859 | 0.0001 | 0.0002 | −0.399 |
| | *Jeotgalicoccus*; Other | 0.3842 | 0.0001 | 0.0002 | −0.217 |
| | *Acinetobacter johnsonii* | 0.3819 | 0.0001 | 0.0002 | −0.388 |
| | *Stenotrophomonas rhizophila* | 0.3798 | 0.0001 | 0.0002 | −0.275 |
| | *Haemophilus haemolyticus* | 0.3785 | 0.0001 | 0.0002 | −0.463 |
| | *Corynebacterium imitans* | 0.3656 | 0.0001 | 0.0002 | −0.217 |
| | *Bacillus* sp 01082 | 0.3626 | 0.0001 | 0.0002 | −0.667 |
| | *Brevundimonas vesicularis* | 0.3612 | 0.0001 | 0.0002 | −0.167 |
| | *Brachyspira pilosicoli* | 0.3566 | 0.0001 | 0.0002 | −0.158 |
| | *Stenotrophomonas maltophilia* | 0.3513 | 0.0001 | 0.0002 | −0.283 |
| | *Veillonella dispar* | 0.3497 | 0.0001 | 0.0002 | −0.537 |
| | *Sphingobium yanoikuyae* | 0.3494 | 0.0001 | 0.0002 | −0.196 |
| | *Halomonas*; Other | 0.3471 | 0.0001 | 0.0002 | −0.167 |
| | *Neisseria subflava* | 0.3469 | 0.0001 | 0.0002 | −0.275 |
| | *Rheinheimera* sp TPS16 | 0.3451 | 0.0001 | 0.0002 | NA |
| | Comamonadaceae; Other | 0.3418 | 0.0001 | 0.0002 | NA |
| | *Eubacterium saburreum* | 0.3404 | 0.0001 | 0.0002 | 0.769 |
| | *Stenotrophomonas*; Other | 0.3376 | 0.0001 | 0.0002 | −0.423 |
| | *Streptococcus anginosus* | 0.3372 | 0.0001 | 0.0002 | −0.629 |
| | *Rothia dentocariosa* | 0.3356 | 0.0001 | 0.0002 | −0.557 |
| | *Brevundimonas diminuta* | 0.3328 | 0.0001 | 0.0002 | −0.241 |
| | *Granulicatella elegans* | 0.3312 | 0.0001 | 0.0002 | −0.452 |
| | *Acinetobacter calcoaceticus* | 0.3308 | 0.0001 | 0.0002 | −0.210 |
| | *Streptococcus gordonii* | 0.3307 | 0.0001 | 0.0002 | −0.679 |
| | *Corynebacterium tuberculostearicum* | 0.3303 | 0.0001 | 0.0002 | −0.492 |
| | *Acinetobacter baumannii* | 0.3287 | 0.0001 | 0.0002 | −0.478 |
| | *Paracoccus denitrificans* | 0.3256 | 0.0001 | 0.0002 | −0.167 |
| | *Fusobacterium*; Other | 0.3223 | 0.0001 | 0.0002 | −0.879 |
| | Bacillales; Other | 0.3213 | 0.0001 | 0.0002 | −0.529 |
| | *Veillonella* sp S101 | 0.3209 | 0.0001 | 0.0002 | −0.302 |
| | *Acinetobacter junii* | 0.3192 | 0.0001 | 0.0002 | −0.428 |
| | *Leptotrichia* sp PG10 | 0.3153 | 0.0001 | 0.0002 | −0.130 |
| | Moraxellaceae; Other | 0.3112 | 0.0001 | 0.0002 | −0.080 |
| | *Bacillus*; Other | 0.3104 | 0.0001 | 0.0002 | −0.196 |
| | *Rheinheimera*; Other | 0.3101 | 0.0001 | 0.0002 | −0.181 |
| | *Corynebacterium*; Other | 0.3083 | 0.0001 | 0.0002 | −0.488 |
| | *Leptotrichia shahii* | 0.3053 | 0.0001 | 0.0002 | −0.716 |
| | *Corynebacterium mucifaciens* | 0.303 | 0.0001 | 0.0002 | −0.326 |
| | *Sphingobacterium multivorum* | 0.3027 | 0.0001 | 0.0002 | −0.130 |

TABLE 22-continued

Correlation between bacterial species abundance in fecal microbiota of cholera patients
and the samples' UniFrac distance to healthy adult Bangladeshi fecal communities

| Species | Spearman r | P (two-tailed) | FDR adjusted p-value (Benjamini-Hochberg correction) | Indicator Value(Recovery) − Indicator Value(Diarrhea) |
|---|---|---|---|---|
| Dialister invisus | 0.3018 | 0.0001 | 0.0002 | NA |
| Prevotella oulorum | 0.2992 | 0.0001 | 0.0002 | 0.520 |
| Pedobacter; Other | 0.2984 | 0.0001 | 0.0002 | 0.071 |
| Brachybacterium; Other | 0.2972 | 0.0001 | 0.0002 | −0.114 |
| Brevundimonas terrae | 0.2942 | 0.0001 | 0.0002 | −0.202 |
| Haemophilus; Other | 0.2914 | 0.0001 | 0.0002 | −0.217 |
| Brevibacterium; Other | 0.2885 | 0.0001 | 0.0002 | −0.221 |
| Neisseria; Other | 0.285 | 0.0001 | 0.0002 | −0.613 |
| Bacteriovorax sp EPA | 0.2827 | 0.0001 | 0.0002 | −0.065 |
| Helicobacter; Other | 0.2808 | 0.0001 | 0.0002 | NA |
| Solobacterium moorei | 0.2799 | 0.0001 | 0.0002 | −0.320 |
| Sphingobacterium mizutaii | 0.2785 | 0.0001 | 0.0002 | −0.123 |
| Brachyspira aalborgi | 0.2711 | 0.0001 | 0.0002 | −0.101 |
| Campylobacter; Other | 0.2708 | 0.0001 | 0.0002 | −0.476 |
| Peptostreptococcus stomatis | 0.2705 | 0.0001 | 0.0002 | NA |
| Shuttleworthia satelles | 0.2702 | 0.0001 | 0.0002 | −0.085 |
| Leptotrichia; 591114 | 0.2688 | 0.0001 | 0.0002 | #N/A |
| Lntrasporangiaceae; Other | 0.2666 | 0.0001 | 0.0002 | −0.101 |
| Anaerococcus octavius | 0.2663 | 0.0001 | 0.0002 | 0.088 |
| Succinivibrio dextrinosolvens | 0.2643 | 0.0001 | 0.0002 | NA |
| Streptococcus sanguinis | 0.2634 | 0.0001 | 0.0002 | NA |
| Leptotrichia buccalis | 0.2627 | 0.0001 | 0.0002 | −0.283 |
| Porphyromonas catoniae | 0.2616 | 0.0001 | 0.0002 | −0.290 |
| Luteimonas; Other | 0.2611 | 0.0001 | 0.0002 | NA |
| Micrococcus luteus | 0.261 | 0.0001 | 0.0002 | −0.123 |
| Moraxella osloensis | 0.2598 | 0.0001 | 0.0002 | −0.188 |
| Alcaligenaceae; Other | 0.2581 | 0.0001 | 0.0002 | −0.111 |
| Atopobium; Other | 0.2545 | 0.0001 | 0.0002 | −0.051 |
| Brachybacterium paraconglomeratum | 0.2535 | 0.0001 | 0.0002 | −0.109 |
| Staphylococcaceae; Other | 0.2517 | 0.0001 | 0.0002 | −0.087 |
| Streptococcus parasanguinis | 0.2515 | 0.0001 | 0.0002 | −0.663 |
| Rothia mucilaginosa | 0.2512 | 0.0001 | 0.0002 | −0.706 |
| Dialister pneumosintes | 0.2495 | 0.0001 | 0.0002 | 0.400 |
| Bifidobacterium dentium | 0.2485 | 0.0001 | 0.0002 | −0.158 |
| Actinomyces oris | 0.246 | 0.0001 | 0.0002 | −0.315 |
| Agrobacterium tumefaciens | 0.2441 | 0.0002 | 0.0004 | NA |
| Corynebacterium aurimucosum | 0.2402 | 0.0002 | 0.0004 | −0.164 |
| Neisseria elongata | 0.2371 | 0.0002 | 0.0004 | −0.158 |
| Prevotella nanceiensis | 0.2361 | 0.0003 | 0.0006 | −0.268 |
| Aggregatibacter segnis | 0.2357 | 0.0003 | 0.0006 | −0.288 |
| Brucellaceae; Other | 0.2354 | 0.0003 | 0.0006 | −0.086 |
| Prevotella denticola | 0.2351 | 0.0003 | 0.0006 | −0.094 |
| Flavobacteriaceae; Other | 0.2321 | 0.0003 | 0.0006 | NA |
| Fusobacterium mortiferum | 0.2319 | 0.0003 | 0.0006 | −0.786 |
| Sphingomonas; Other | 0.2259 | 0.0005 | 0.0009 | −0.072 |
| Bacilli; Other | 0.2258 | 0.0005 | 0.0009 | −0.274 |
| Arcobacter butzleri | 0.2245 | 0.0005 | 0.0009 | −0.072 |
| Elusimicrobium minutum | 0.2224 | 0.0006 | 0.0011 | NA |
| Enterococcus; Other | 0.2221 | 0.0006 | 0.0011 | −0.460 |
| Streptococcus thermophilus | 0.2201 | 0.0007 | 0.0013 | −0.721 |
| Chryseobacterium hominis | 0.2187 | 0.0007 | 0.0013 | −0.123 |
| Azospirillum; Other | 0.2168 | 0.0008 | 0.0014 | NA |
| Thermus igniterrae | 0.2156 | 0.0009 | 0.0016 | NA |
| Wautersiella falsenii | 0.2092 | 0.0012 | 0.0021 | NA |
| Corynebacterium matruchotii | 0.208 | 0.0013 | 0.0022 | −0.311 |
| Lactobacillales; Other | 0.2053 | 0.0015 | 0.0025 | NA |
| Bacteriovorax sp F2 | 0.2043 | 0.0016 | 0.0027 | NA |
| Novosphingobium; Other | 0.1972 | 0.0023 | 0.0038 | NA |
| Scardovia wiggsiae | 0.1923 | 0.003 | 0.0048 | −0.130 |
| Anaeroglobus geminatus | 0.1921 | 0.003 | 0.0048 | −0.064 |
| Sphingomonadaceae; Other | 0.1907 | 0.0033 | 0.0053 | −0.058 |
| Lactobacillus fermentum | 0.1902 | 0.0034 | 0.0054 | −0.311 |
| Actinobacillus porcinus | 0.189 | 0.0036 | 0.0057 | −0.230 |
| Helicobacter winghamensis | 0.1871 | 0.0039 | 0.0061 | −0.210 |
| Actinomyces georgiae | 0.1851 | 0.0043 | 0.0067 | NA |
| Veillonella parvula | 0.1845 | 0.0045 | 0.0070 | NA |
| Pantoea ananatis | 0.1842 | 0.0045 | 0.0070 | NA |
| Finegoldia magna | 0.1773 | 0.0063 | 0.0096 | NA |
| Actinomyces graevenitzii | 0.1764 | 0.0066 | 0.0100 | −0.380 |
| Veillonella; Other | 0.1764 | 0.0066 | 0.0100 | −0.130 |
| Rhizobiales; Other | 0.1762 | 0.0067 | 0.0101 | NA |
| Granulicatella adiacens | 0.1754 | 0.0069 | 0.0104 | −0.615 |

TABLE 22-continued

Correlation between bacterial species abundance in fecal microbiota of cholera patients
and the samples' UniFrac distance to healthy adult Bangladeshi fecal communities

| | Species | Spearman r | P (two-tailed) | FDR adjusted p-value (Benjamini-Hochberg correction) | Indicator Value(Recovery) − Indicator Value(Diarrhea) |
|---|---|---|---|---|---|
| | Pasteurellaceae; Other | 0.173 | 0.0077 | 0.0115 | −0.568 |
| | *Streptococcus*; Other | 0.1679 | 0.0098 | 0.0145 | −0.562 |
| | *Atopobium* sp F0209 | 0.1667 | 0.0103 | 0.0152 | −0.387 |
| | *Lactobacillus delbrueckii* | 0.1658 | 0.0107 | 0.0157 | −0.072 |
| | Bifidobacteriaceae; Other | 0.1642 | 0.0115 | 0.0166 | NA |
| | *Afipia* genosp 9 | 0.1623 | 0.0125 | 0.0179 | NA |
| | *Streptococcus mutans* | 0.1613 | 0.0131 | 0.0187 | −0.203 |
| | *Prosthecobacter*; Other | 0.1592 | 0.0143 | 0.0204 | NA |
| | *Rheinheimera* sp 09BSZB 9 | 0.1567 | 0.016 | 0.0226 | −0.130 |
| | Xanthomonadaceae; Other | 0.1567 | 0.016 | 0.0226 | NA |
| | *Sphingomonas yabuuchiae* | 0.1563 | 0.0163 | 0.0229 | NA |
| | *Paracoccus*; Other | 0.1517 | 0.0197 | 0.0275 | NA |
| | *Kocuria marina* | 0.1507 | 0.0205 | 0.0285 | NA |
| | *Flavobacterium*; Other | 0.1486 | 0.0224 | 0.0309 | NA |
| | *Peredibacter starrii* | 0.1486 | 0.0224 | 0.0309 | NA |
| | Streptococcaceae; Other | 0.1469 | 0.024 | 0.0329 | NA |
| | *Varibaculum cambriense* | 0.1452 | 0.0257 | 0.0350 | NA |
| | *Verrucomicrobium* sp IRVE | 0.1452 | 0.0257 | 0.0350 | NA |
| | *Lactobacillus* sp KLDS 1 0716 | 0.1421 | 0.029 | 0.0393 | −0.065 |
| Negatively correlated with community distance to healthy microbiota | *Faecalibacterium*; Other | −0.6171 | 0.0001 | 0.0002 | 0.819 |
| | Clostridiales; Other | −0.614 | 0.0001 | 0.0002 | 0.832 |
| | *Faecalibacterium prausnitzii* | −0.5937 | 0.0001 | 0.0002 | 0.860 |
| | *Prevotella* sp DJF B112 | −0.5859 | 0.0001 | 0.0002 | −0.341 |
| | *Bacteroides vulgatus* | −0.539 | 0.0001 | 0.0002 | 0.127 |
| | *Ruminococcus callidus* | −0.5327 | 0.0001 | 0.0002 | 0.479 |
| | *Ruminococcus*; Other | −0.5226 | 0.0001 | 0.0002 | NA |
| | *Ruminococcus* sp 5 1 39BFAA | −0.522 | 0.0001 | 0.0002 | 0.671 |
| | *Eubacterium coprostanoligenes* | −0.5186 | 0.0001 | 0.0002 | 0.530 |
| | *Parabacteroides*; Other | −0.5137 | 0.0001 | 0.0002 | 0.429 |
| | 1760; Other | −0.5099 | 0.0001 | 0.0002 | #N/A |
| | *Coprococcus*; Other | −0.5065 | 0.0001 | 0.0002 | 0.438 |
| | *Clostridium disporicum* | −0.5027 | 0.0001 | 0.0002 | 0.699 |
| | *Clostridium glycolicum* | −0.5001 | 0.0001 | 0.0002 | 0.633 |
| | *Clostridium bartlettii* | −0.4979 | 0.0001 | 0.0002 | 0.341 |
| | Firmicutes; Other | −0.4909 | 0.0001 | 0.0002 | 0.725 |
| | *Eubacterium eligens* | −0.4878 | 0.0001 | 0.0002 | 0.696 |
| | *Eubacterium* sp cL 10 1 3 | −0.486 | 0.0001 | 0.0002 | 0.223 |
| | *Turicibacter sanguinis* | −0.4765 | 0.0001 | 0.0002 | 0.612 |
| | Ruminococcaceae; Other | −0.4708 | 0.0001 | 0.0002 | 0.686 |
| | *Eubacterium ramulus* | −0.4649 | 0.0001 | 0.0002 | 0.353 |
| | *Roseburia*; Other | −0.4528 | 0.0001 | 0.0002 | 0.674 |
| | Lachnospiraceae; Other | −0.4518 | 0.0001 | 0.0002 | 0.492 |
| | *Clostridium clostridioforme* | −0.4498 | 0.0001 | 0.0002 | 0.334 |
| | *Eubacterium rectale* | −0.442 | 0.0001 | 0.0002 | 0.457 |
| | *Bacteroides galacturonicus* | −0.4347 | 0.0001 | 0.0002 | 0.547 |
| | *Eubacterium biforme* | −0.4315 | 0.0001 | 0.0002 | 0.712 |
| | *Bacteroides*; Other | −0.4309 | 0.0001 | 0.0002 | 0.549 |
| | *Slackia isoflavoniconvertens* | −0.4305 | 0.0001 | 0.0002 | 0.465 |
| | *Bifidobacterium*; Other | −0.4284 | 0.0001 | 0.0002 | 0.987 |
| | *Blautia* sp M25 | −0.4267 | 0.0001 | 0.0002 | NA |
| | *Eubacterium hallii* | −0.4251 | 0.0001 | 0.0002 | 0.673 |
| | *Ruminococcus* sp ZS2 15 | −0.4231 | 0.0001 | 0.0002 | 0.124 |
| | *Eubacterium desmolans* | −0.4227 | 0.0001 | 0.0002 | 0.258 |
| | *Dorea formicigenerans* | −0.4197 | 0.0001 | 0.0002 | 0.494 |
| | *Prevotella copri* | −0.4098 | 0.0001 | 0.0002 | 0.776 |
| | *Collinsella*; Other | −0.406 | 0.0001 | 0.0002 | 0.438 |
| | *Prevotella* sp DJF B116 | −0.4032 | 0.0001 | 0.0002 | 0.633 |
| | *Coprococcus eutactus* | −0.4031 | 0.0001 | 0.0002 | 0.526 |
| | *Bacteroides ovatus* | −0.4028 | 0.0001 | 0.0002 | 0.460 |
| | *Ruminococcus obeum* | −0.4012 | 0.0001 | 0.0002 | 0.301 |
| | *Catenibacterium mitsuokai* | −0.3988 | 0.0001 | 0.0002 | 0.791 |
| | *Subdoligranulum variabile* | −0.3979 | 0.0001 | 0.0002 | 0.498 |
| | *Oscillibacter*; Other | −0.3949 | 0.0001 | 0.0002 | 0.304 |
| | Coriobacteriaceae; Other | −0.3948 | 0.0001 | 0.0002 | 0.600 |
| | *Bilophila wadsworthia* | −0.3942 | 0.0001 | 0.0002 | 0.312 |
| | *Ruminococcus bromii* | −0.386 | 0.0001 | 0.0002 | 0.479 |
| | Clostridiaceae; Other | −0.3807 | 0.0001 | 0.0002 | 0.641 |
| | *Parabacteroides distasonis* | −0.3787 | 0.0001 | 0.0002 | 0.326 |
| | *Collinsella aerofaciens* | −0.3754 | 0.0001 | 0.0002 | 0.584 |
| | Bacteroidales; Other | −0.3752 | 0.0001 | 0.0002 | 0.700 |
| | *Prevotella*; Other | −0.3565 | 0.0001 | 0.0002 | −0.391 |
| | *Clostridium*; Other | −0.3414 | 0.0001 | 0.0002 | 0.387 |

TABLE 22-continued

Correlation between bacterial species abundance in fecal microbiota of cholera patients
and the samples' UniFrac distance to healthy adult Bangladeshi fecal communities

| Species | Spearman r | P (two-tailed) | FDR adjusted p-value (Benjamini-Hochberg correction) | Indicator Value(Recovery) − Indicator Value(Diarrhea) |
|---|---|---|---|---|
| *Dorea longicatena* | −0.334 | 0.0001 | 0.0002 | 0.358 |
| *Eubacterium*; Other | −0.3318 | 0.0001 | 0.0002 | 0.508 |
| *Clostridium hathewayi* | −0.3296 | 0.0001 | 0.0002 | 0.234 |
| *Alistipes shahii* | −0.3229 | 0.0001 | 0.0002 | 0.184 |
| *Mitsuokella multacida* | −0.3184 | 0.0001 | 0.0002 | 0.255 |
| *Clostridium* sp SS2 1 | −0.3175 | 0.0001 | 0.0002 | 0.122 |
| *Clostridium bolteae* | −0.3131 | 0.0001 | 0.0002 | 0.278 |
| *Oscillibacter* sp G2 | −0.3101 | 0.0001 | 0.0002 | 0.244 |
| *Ruminococcus flavefaciens* | −0.2997 | 0.0001 | 0.0002 | 0.133 |
| *Olsenella*; Other | −0.2933 | 0.0001 | 0.0002 | 0.092 |
| *Phascolarctobacterium faecium* | −0.2906 | 0.0001 | 0.0002 | 0.122 |
| *Alistipes* sp NML05A004 | −0.2905 | 0.0001 | 0.0002 | 0.092 |
| *Bacteroides uniformis* | −0.2895 | 0.0001 | 0.0002 | 0.087 |
| *Coprococcus comes* | −0.2874 | 0.0001 | 0.0002 | 0.378 |
| *Prevotella* sp DJF LS16 | −0.2814 | 0.0001 | 0.0002 | 0.092 |
| *Clostridium* sp L2 50 | −0.281 | 0.0001 | 0.0002 | 0.242 |
| Bacteria; Other | −0.269 | 0.0001 | 0.0002 | 0.672 |
| *Coprococcus catus* | −0.2667 | 0.0001 | 0.0002 | 0.199 |
| *Prevotella stercorea* | −0.2662 | 0.0001 | 0.0002 | NA |
| *Bacteroides caccae* | −0.2596 | 0.0001 | 0.0002 | 0.143 |
| *Roseburia intestinalis* | −0.2593 | 0.0001 | 0.0002 | 0.562 |
| *Blautia*; Other | −0.2567 | 0.0001 | 0.0002 | 0.669 |
| *Desulfovibrio*; Other | −0.2443 | 0.0002 | 0.0004 | 0.274 |
| *Butyrivibrio crossotus* | −0.2353 | 0.0003 | 0.0006 | 0.273 |
| *Clostridium paraputrificum* | −0.2223 | 0.0006 | 0.0011 | 0.521 |
| *Parabacteroides merdae* | −0.2213 | 0.0006 | 0.0011 | 0.092 |
| *Ruminococcus* sp DJF VR70k1 | −0.2213 | 0.0006 | 0.0011 | 0.762 |
| *Clostridium perfringens* | −0.2211 | 0.0006 | 0.0011 | 0.286 |
| *Prevotella* sp oral taxon 302 | −0.2157 | 0.0009 | 0.0016 | 0.280 |
| *Sarcina ventriculi* | −0.2143 | 0.0009 | 0.0016 | NA |
| *Clostridium nexile* | −0.2127 | 0.001 | 0.0018 | 0.233 |
| *Bacteroides* sp CIP103040 | −0.2075 | 0.0013 | 0.0022 | 0.112 |
| Bacteroidetes; Other | −0.2055 | 0.0015 | 0.0025 | 0.377 |
| *Prevotella* sp RS2 | −0.2055 | 0.0015 | 0.0025 | 0.214 |
| *Enterococcus cecorum* | −0.2033 | 0.0017 | 0.0029 | 0.116 |
| *Bacteroides stercoris* | −0.2003 | 0.002 | 0.0033 | 0.208 |
| *Ruminococcus gnavus* | −0.1991 | 0.0021 | 0.0035 | 0.430 |
| *Clostridium bifermentans* | −0.199 | 0.0021 | 0.0035 | NA |
| *Phascolarctobacterium succinatutens* | −0.1973 | 0.0023 | 0.0038 | 0.383 |
| *Ruminococcus torques* | −0.1971 | 0.0023 | 0.0038 | 0.337 |
| *Alistipes finegoldii* | −0.1958 | 0.0025 | 0.0041 | 0.041 |
| *Megasphaera* sp TrE9262 | −0.1953 | 0.0026 | 0.0042 | 0.234 |
| *Olsenella* sp A2 | −0.1851 | 0.0043 | 0.0067 | 0.306 |
| unclassified_Erysipelotrichaceae; Other | −0.1807 | 0.0054 | 0.0083 | 0.156 |
| *Bacteroides fragilis* | −0.1727 | 0.0078 | 0.0116 | 0.445 |
| *Odoribacter splanchnicus* | −0.1717 | 0.0082 | 0.0122 | 0.129 |
| *Allisonella histaminiformans* | −0.1645 | 0.0114 | 0.0166 | 0.177 |
| *Eubacterium siraeum* | −0.1645 | 0.0114 | 0.0166 | −0.216 |
| *Bacteroides plebeius* | −0.1638 | 0.0117 | 0.0169 | 0.600 |
| *Megamonas*; Other | −0.1532 | 0.0185 | 0.0259 | 0.192 |
| *Sutterella*; Other | −0.1414 | 0.0299 | 0.0404 | −0.393 |
| *Megasphaera*; Other | −0.1362 | 0.0365 | 0.0491 | 0.092 |

TABLE 23

Composition of the artificial human gut microbial community

| Bacterium | Phylum | Strain Name | Source | Taxonomy ID* | GenBank Accession |
|---|---|---|---|---|---|
| *Bacteroides caccae* | Bacteroidetes | ATCC 43185 | ATCC | 411901 | AAVM00000000.2 |
| *Bacteroides ovatus* | Bacteroidetes | ATCC 8483 | ATCC | 411476 | AAXF00000000.2 |
| *Bacteroides thetaiotaomicron* | Bacteroidetes | VPI-5482 | ATCC | 226186 | AE015928.1 |
| *Bacteroides uniformis* | Bacteroidetes | ATCC 8492 | ATCC | 411479 | AAYH00000000.2 |
| *Bacteroides vulgatus* | Bacteroidetes | ATCC 8482 | ATCC | 435590 | CP000139.1 |
| *Bacteroides cellulosilyticus* WH2 | Bacteroidetes | N/A | Reference 8 | N/A | ATFI00000000 |
| *Clostridium scindens* | Firmicutes | ATCC 35704 | ATCC | 411468 | ABFY00000000.2 |
| *Collinsella aerofaciens* | Actinobacteria | ATCC 25986 | ATCC | 411903 | AAVN00000000.2 |
| *Dorea longicatena* | Firmicutes | DSM 13814 | DSMZ | 411462 | AAXB00000000.2 |

TABLE 23-continued

Composition of the artificial human gut microbial community

| Bacterium | Phylum | Strain Name | Source | Taxonomy ID* | GenBank Accession |
|---|---|---|---|---|---|
| *Eubacterium rectale* | Firmicutes | ATCC 33656 | ATCC | 515619 | CP001107.1 |
| *Faecalibacterium prausnitzii* | Firmicutes | M21/2 | Reference 8 | 411485 | ABED00000000.2 |
| *Parabacteroides distasonis* | Bacteroidetes | ATCC 8503 | ATCC | 435591 | CP000140.1 |
| *Ruminococcus obeum* | Firmicutes | ATCC 29174 | ATCC | 411459 | AAVO00000000.2 |
| *Ruminococcus torques* | Firmicutes | ATCC 27756 | ATCC | 411460 | AAVP00000000.2 |

*Based on NCBI Taxonomy database (www.ncbi.nlm.nih.gov/taxonomy/)

TABLE 24

EC relative abundance

| | | Fold change (mean total RPKM) | | | | | Adjusted p-value from ShotgunFunctionalizeR | | | | | Spearman correlation of relative abundance vs time | |
|---|---|---|---|---|---|---|---|---|---|---|---|---|---|
| EC | Annotation | D-Ph1-Ph2 vs healthy | D-Ph3-Ph4 vs healthy | R-Ph1 vs healthy | R-Ph2 vs healthy | R-Ph3 vs healthy | D-Ph1-Ph2 vs healthy | D-Ph3-Ph4 vs healthy | R-Ph1 vs healthy | R-Ph2 vs healthy | R-Ph3 vs healthy | Spearman r | P-value (FDR corrected) |
| EC1.1.1.35 | 3-hydroxyacyl-CoA dehydrogenase | 0.6 | 0.3 | 0.7 | 0.8 | 1.1 | 0.0000 | 1.0000 | 0.0000 | 0.0000 | 0.0000 | 0.3626 | 0.0464 |
| EC1.2.1.3 | Aldehyde dehydrogenase (NAD(+)) | 0.7 | 0.9 | 0.8 | 0.8 | 0.9 | 0.0000 | 0.2606 | 0.0000 | 0.2333 | 0.0136 | 0.2328 | 0.2424 |
| EC1.21.4.1 | D-proline reductase (dithiol) | 1.1 | 1.2 | 0.9 | 1.1 | 0.9 | 0.0000 | 0.0000 | 0.0000 | 0.0007 | 0.0317 | −0.1883 | 0.3645 |
| EC1.3.1.— | NA | 0.8 | 1.0 | 1.0 | 0.9 | 0.8 | 0.0000 | 0.0000 | 0.0000 | 0.0000 | 0.0184 | 0.0728 | 0.7097 |
| EC1.4.1.13 | Glutamate synthase (NADPH) | 0.7 | 0.7 | 0.9 | 0.8 | 0.8 | 0.0000 | 0.0000 | 0.0000 | 0.0000 | 0.1225 | 0.3019 | 0.1083 |
| EC1.4.1.3 | Glutamate dehydrogenase (NAD(P)(+)) | 0.8 | 1.1 | 1.0 | 1.0 | 1.1 | 0.0002 | 0.0000 | 0.0000 | 0.0023 | 0.0484 | 0.2383 | 0.2341 |
| EC2.1.1.— | NA | 1881.2 | 290.3 | 35.5 | 13.3 | 1380.7 | 0.0000 | 0.0000 | 0.0000 | 0.0000 | 0.0000 | −0.4938 | 0.0075 |
| EC2.1.3.11 | N-succinylornithine carbamoyltransferase | 1.3 | 1.8 | 2.1 | 1.2 | 0.8 | 0.0000 | 0.0000 | 0.0000 | 0.0014 | 0.4056 | −0.1655 | 0.4360 |
| EC2.1.3.3 | Ornithine carbamoyltransferase | 0.6 | 0.7 | 0.9 | 1.0 | 1.0 | 0.0022 | 0.0000 | 0.0000 | 0.0005 | 0.0422 | 0.5019 | 0.0075 |
| EC2.3.1.— | NA | 5.0 | 6.6 | 2.0 | 2.7 | 1.1 | 0.1143 | 0.0000 | 0.1184 | 0.6833 | 0.0000 | −0.3261 | 0.0761 |
| EC2.3.1.117 | 2,3,4,5-tetrahydropyridine-2,6-dicarboxylate N-succinyltransferase | 1.8 | 1.8 | 1.5 | 1.2 | 0.7 | 0.0000 | 0.0000 | 0.0000 | 0.0000 | 0.6294 | −0.5308 | 0.0047 |
| EC2.3.1.35 | Glutamate N-acetyltransferase | 0.6 | 0.9 | 1.0 | 1.3 | 0.9 | 0.0149 | 0.0000 | 0.0000 | 0.0000 | 0.1313 | 0.5616 | 0.0047 |
| EC2.3.3.10 | Hydroxymethylglutaryl-CoA synthase | 1.5 | 1.4 | 1.4 | 1.1 | 0.8 | 0.0000 | 0.0000 | 0.0000 | 0.0000 | 0.4787 | −0.1355 | 0.4877 |
| EC2.4.2.14 | Amidophosphoribosyl-transferase | 0.5 | 0.8 | 0.9 | 1.2 | 1.0 | 0.0000 | 0.0000 | 0.0000 | 0.0000 | 0.4790 | 0.5388 | 0.0047 |
| EC2.5.1.49 | O-acetylhomoserine aminocarboxypropyl-transferase | 0.8 | 0.8 | 1.1 | 0.9 | 0.9 | 0.0000 | 0.0000 | 0.4459 | 0.0721 | 0.6926 | 0.4012 | 0.0278 |
| EC2.6.1.2 | Alanine transaminase | 0.8 | 1.0 | 1.0 | 1.1 | 0.9 | 0.0000 | 0.0000 | 0.0000 | 0.0000 | 0.0008 | 0.3441 | 0.0608 |
| EC2.6.1.66 | Valine--pyruvate transaminase | 2.3 | 2.2 | 1.2 | 1.8 | 0.8 | 0.0000 | 0.0000 | 0.0001 | 0.0000 | 0.0000 | −0.3271 | 0.0761 |
| EC2.6.1.83 | LL-diaminopimelate aminotransferase | 1.3 | 1.1 | 1.0 | 1.1 | 0.6 | 0.0000 | 0.0000 | 0.0002 | 0.0000 | 0.3916 | −0.1562 | 0.4516 |
| EC2.7.1.39 | Homoserine kinase | 0.6 | 0.6 | 0.9 | 0.8 | 0.9 | 0.0000 | 0.0000 | 0.0600 | 0.0006 | 0.0047 | 0.4455 | 0.0144 |
| EC2.7.2.4 | Aspartate kinase | 1.2 | 2.1 | 1.9 | 1.4 | 1.0 | 0.0014 | 0.0000 | 0.0000 | 0.0000 | 0.7149 | −0.1063 | 0.5965 |
| EC3.4.—.— | NA | 0.7 | 0.9 | 1.1 | 1.1 | 1.0 | 0.0000 | 0.0000 | 0.0000 | 0.0000 | 0.3482 | 0.3816 | 0.0349 |
| EC3.4.11.5 | Prolyl aminopeptidase | 0.6 | 0.8 | 1.3 | 1.2 | 0.8 | 0.0000 | 0.0000 | 0.0000 | 0.0421 | 1.0000 | 0.2676 | 0.1734 |
| EC3.5.1.16 | Acetylornithine deacetylase | 1.4 | 1.8 | 1.6 | 0.9 | 0.8 | 0.0000 | 0.0000 | 0.0000 | 0.0065 | 0.7787 | −0.5281 | 0.0047 |
| EC3.5.1.53 | N-carbamoylputrescine amidase | 4.2 | 25.9 | 10.1 | 0.7 | 1.0 | 0.0000 | 0.0000 | 0.0000 | 0.0003 | 1.0000 | −0.1753 | 0.4062 |
| EC3.5.4.1 | Cytosine deaminase | 0.9 | 1.1 | 1.3 | 0.9 | 0.7 | 0.0000 | 0.0000 | 0.0000 | 0.0000 | 0.5662 | −0.0406 | 0.8571 |
| EC4.2.1.19 | Imidazoleglycerol-phosphate dehydratase | 0.9 | 1.1 | 1.0 | 1.0 | 0.8 | 0.0000 | 0.0001 | 0.0000 | 0.0592 | 0.2813 | −0.1084 | 0.5934 |
| EC4.2.1.20 | Tryptophan synthase | 0.6 | 1.1 | 1.3 | 0.6 | 0.7 | 0.0000 | 0.0001 | 0.0000 | 0.4848 | 0.0252 | 0.1446 | 0.4703 |
| EC4.2.1.22 | Cystathionine beta-synthase | 0.8 | 1.1 | 1.2 | 1.3 | 1.0 | 0.0000 | 0.0000 | 0.0001 | 0.0006 | 0.0006 | 0.4040 | 0.0271 |
| EC4.3.1.1 | Aspartate ammonia-lyase | 0.6 | 6.9 | 3.2 | 0.3 | 0.4 | 0.0000 | 0.0000 | 0.0000 | 0.3475 | 1.0000 | −0.0492 | 0.8212 |
| EC5.3.1.23 | S-methyl-5-thioribose-1-phosphate isomerase | 1.3 | 1.9 | 1.7 | 1.4 | 1.1 | 0.0000 | 0.0000 | 0.0039 | 0.0000 | 0.0021 | 0.0127 | 0.9363 |
| EC5.4.99.5 | Chorismate mutase | 0.8 | 0.8 | 0.7 | 0.8 | 1.0 | 0.0000 | 0.0000 | 0.0000 | 0.0000 | 0.4790 | 0.1436 | 0.4703 |

TABLE 24-continued

EC relative abundance

| | | Fold change (mean total RPKM) | | | | | Adjusted p-value from ShotgunFunctionalizeR | | | | | Spearman correlation of relative abundance vs time | |
|---|---|---|---|---|---|---|---|---|---|---|---|---|---|
| | | D-Ph1- Ph2 vs healthy | D-Ph3- Ph4 vs healthy | R-Ph1 vs healthy | R-Ph2 vs healthy | R-Ph3 vs healthy | D-Ph1- Ph2 vs healthy | D-Ph3- Ph4 vs healthy | R-Ph1 vs healthy | R-Ph2 vs healthy | R-Ph3 vs healthy | Spearman r | P-value (FDR corrected) |
| EC | Annotation | | | | | | | | | | | | |
| EC6.3.1.2 | Glutamate--ammonia ligase | 1.2 | 1.5 | 1.0 | 1.2 | 0.8 | 0.0000 | 0.0000 | 0.0000 | 0.0000 | 1.0000 | −0.1954 | 0.3426 |
| EC6.3.5.4 | Asparagine synthase (glutamine-hydrolyzing) | 0.5 | 0.2 | 0.5 | 0.9 | 0.9 | 0.0000 | 0.0000 | 0.0116 | 0.0000 | 0.9039 | 0.5007 | 0.0075 |
| EC6.3.5.5 | Carbamoyl-phosphate synthase (glutamine-hydrolyzing) | 2.1 | 3.3 | 2.3 | 1.6 | 0.9 | 0.0000 | 0.0000 | 0.0000 | 0.0000 | 0.7708 | −0.4774 | 0.0083 |
| EC1.1.1.303 | NA | 4.4 | 1.2 | 1.6 | 2.0 | 0.5 | 0.0000 | 0.0000 | 0.0001 | 0.0000 | 1.0000 | −0.3922 | 0.0325 |
| EC1.1.1.35 | 3-hydroxyacyl-CoA dehydrogenase | 0.6 | 0.3 | 0.7 | 0.8 | 1.1 | 0.0000 | 1.0000 | 0.0000 | 0.0000 | 0.0000 | 0.3626 | 0.0464 |
| EC1.1.1.37 | Malate dehydrogenase | 0.7 | 0.8 | 0.9 | 1.0 | 0.8 | 0.0509 | 0.0000 | 0.0000 | 0.0000 | 0.6533 | 0.2915 | 0.1246 |
| EC1.2.1.10 | Acetaldehyde dehydrogenase (acetylating) | 1.7 | 1.3 | 1.3 | 1.0 | 0.4 | 0.0000 | 0.0000 | 0.0000 | 0.0000 | 0.0135 | −0.3376 | 0.0667 |
| EC1.2.1.2 | Formate dehydrogenase | 1.3 | 1.4 | 1.8 | 1.0 | 0.7 | 0.0000 | 0.2032 | 0.0000 | 0.0309 | 0.0000 | −0.1387 | 0.4859 |
| EC1.2.1.3 | Aldehyde dehydrogenase (NAD(+)) | 0.7 | 0.9 | 0.8 | 0.8 | 0.9 | 0.0000 | 0.2606 | 0.0000 | 0.2333 | 0.0136 | 0.2328 | 0.2424 |
| EC1.2.4.1 | Pyruvate dehydrogenase (acetyl-transferring) | 0.4 | 0.2 | 0.4 | 0.6 | 0.8 | 0.0000 | 0.0000 | 0.0000 | 0.0000 | 0.0178 | 0.4347 | 0.0164 |
| EC1.3.1.— | NA | 0.8 | 1.0 | 1.0 | 0.9 | 0.8 | 0.0000 | 0.0000 | 0.0000 | 0.0000 | 0.0184 | 0.0728 | 0.7097 |
| EC2.3.1.— | NA | 5.0 | 6.6 | 2.0 | 2.7 | 1.1 | 0.1143 | 0.0000 | 0.1184 | 0.6833 | 0.0000 | −0.3261 | 0.0761 |
| EC2.3.3.10 | Hydroxymethylglutaryl-CoA synthase | 1.5 | 1.4 | 1.4 | 1.1 | 0.8 | 0.0000 | 0.0000 | 0.0000 | 0.0000 | 0.4787 | −0.1355 | 0.4877 |
| EC2.4.1.10 | Levansucrase | 4.5 | 9.2 | 2.3 | 1.8 | 0.4 | 0.0000 | 0.6783 | 1.0000 | 0.0000 | 1.0000 | −0.3879 | 0.0345 |
| EC2.4.1.25 | 4-alpha-glucanotransferase | 0.8 | 1.5 | 3.8 | 1.9 | 0.9 | 0.0000 | 0.0000 | 0.4014 | 0.9467 | 0.4638 | 0.1739 | 0.4062 |
| EC2.7.1.12 | Gluconokinase | 2.1 | 4.4 | 1.5 | 1.1 | 0.3 | 0.0000 | 0.2574 | 0.0421 | 0.0000 | 0.2079 | −0.4349 | 0.0164 |
| EC2.7.1.16 | Ribulokinase | 0.8 | 1.2 | 1.1 | 1.0 | 1.0 | 0.0000 | 0.0000 | 0.0000 | 0.0004 | 0.4638 | 0.0952 | 0.6347 |
| EC2.7.1.45 | 2-dehydro-3-deoxygluconokinase | 0.8 | 0.4 | 1.5 | 0.9 | 0.8 | 0.0000 | 0.0000 | 0.0000 | 0.0441 | 0.0137 | 0.1231 | 0.5309 |
| EC2.7.7.12 | UDP-glucose--hexose-1-phosphate uridylyltransferase | 0.8 | 1.0 | 0.9 | 1.0 | 0.8 | 0.0003 | 0.0000 | 0.0000 | 0.0000 | 0.0005 | 0.0197 | 0.9363 |
| EC2.7.7.13 | Mannose-1-phosphate guanylyltransferase | 0.6 | 0.3 | 0.6 | 1.0 | 1.0 | 0.0000 | 0.0000 | 0.0000 | 0.0009 | 0.6704 | 0.4360 | 0.0164 |
| EC2.7.7.22 | Mannose-1-phosphate guanylyltransferase (GDP) | 0.6 | 0.3 | 0.5 | 0.7 | 0.9 | 0.0000 | 0.0000 | 0.0000 | 0.0041 | 0.0415 | 0.2147 | 0.2925 |
| EC2.7.8.30 | NA | 1.0 | 0.4 | 0.5 | 0.6 | 0.4 | 0.0000 | 0.0392 | 0.0000 | 0.0000 | 0.1225 | −0.1518 | 0.4648 |
| EC2.7.9.1 | Pyruvate, phosphate dikinase | 0.9 | 1.3 | 1.5 | 1.1 | 0.9 | 0.0000 | 0.0000 | 0.0000 | 0.0000 | 0.0930 | 0.0342 | 0.8815 |
| EC2.7.9.2 | Pyruvate, water dikinase | 0.8 | 1.2 | 1.1 | 1.2 | 0.9 | 0.8899 | 0.0000 | 0.0000 | 0.0004 | 0.0000 | 0.1449 | 0.4703 |
| EC3.1.2.6 | Hydroxyacylglutathione hydrolase | 1.0 | 1.0 | 0.9 | 1.1 | 1.0 | 0.0000 | 0.0000 | 0.0571 | 0.8598 | 0.3280 | 0.0875 | 0.6592 |
| EC3.1.3.— | NA | 1.3 | 1.6 | 1.7 | 1.7 | 0.9 | 0.0000 | 0.0000 | 0.0000 | 0.0000 | 0.8949 | −0.0748 | 0.7097 |
| EC3.2.1.1 | Alpha-amylase | 1.0 | 2.6 | 1.8 | 1.6 | 0.5 | 0.0562 | 0.0000 | 0.0000 | 1.0000 | 0.0032 | −0.0129 | 0.9363 |
| EC3.2.1.14 | Chitinase | 0.4 | 0.7 | 0.9 | 0.9 | 1.0 | 0.0000 | 0.0000 | 0.0000 | 0.0674 | 1.0000 | 0.4655 | 0.0102 |
| EC3.2.1.20 | Alpha-glucosidase | 2.4 | 4.6 | 2.0 | 1.7 | 0.8 | 0.0000 | 0.0000 | 0.0000 | 0.0000 | 0.0000 | −0.4073 | 0.0261 |
| EC3.2.1.23 | Beta-galactosidase | 0.6 | 1.9 | 2.4 | 0.9 | 0.8 | 0.0000 | 0.0000 | 0.0000 | 0.0000 | 0.0000 | 0.0940 | 0.6347 |
| EC3.2.1.26 | Beta-fructofuranosidase | 0.3 | 0.3 | 0.8 | 0.5 | 0.9 | 0.0000 | 0.0000 | 0.0000 | 0.0000 | 0.1481 | 0.4862 | 0.0075 |
| EC3.2.1.52 | Beta-N-acetylhexosaminidase | 0.5 | 0.2 | 0.7 | 0.8 | 1.1 | 0.0295 | 0.0000 | 0.0000 | 0.0000 | 0.3981 | 0.3615 | 0.0464 |
| EC3.2.1.85 | 6-phospho-beta-galactosidase | 0.3 | 0.2 | 0.3 | 0.8 | 1.0 | 0.0000 | 0.0000 | 0.0000 | 0.0000 | 0.0613 | 0.4896 | 0.0075 |
| EC3.2.1.86 | 6-phospho-beta-glucosidase | 0.9 | 1.1 | 0.9 | 1.0 | 0.8 | 0.0000 | 0.0000 | 0.0000 | 0.0000 | 0.0000 | −0.1238 | 0.5309 |
| EC3.6.1.7 | Acylphosphatase | 0.7 | 1.0 | 1.2 | 1.0 | 0.9 | 0.0000 | 0.0000 | 0.2792 | 0.0005 | 0.2843 | 0.2195 | 0.2808 |
| EC4.1.2.40 | Tagatose-bisphosphate aldolase | 0.5 | 0.6 | 0.9 | 0.8 | 1.2 | 0.0000 | 0.0000 | 0.0000 | 0.0000 | 0.0003 | 0.4712 | 0.0093 |
| EC4.2.1.12 | Phosphogluconate dehydratase | 0.5 | 0.7 | 0.7 | 1.0 | 1.0 | 0.0000 | 0.2685 | 0.0000 | 0.0448 | 0.0030 | 0.5441 | 0.0047 |
| EC4.2.1.7 | Altronate dehydratase | 1.0 | 1.1 | 1.2 | 1.1 | 0.9 | 0.0000 | 0.0000 | 0.1942 | 0.0393 | 0.7318 | −0.0138 | 0.9363 |
| EC5.1.2.3 | 3-hydroxybutyryl-CoA epimerase | 0.6 | 0.5 | 0.8 | 0.9 | 0.8 | 0.0000 | 1.0000 | 0.0000 | 0.0000 | 0.0000 | 0.3819 | 0.0349 |
| EC5.1.3.8 | N-acylglucosamine 2-epimerase | 1.0 | 0.7 | 0.8 | 1.0 | 1.0 | 0.0000 | 0.0000 | 0.0000 | 0.0000 | 1.0000 | 0.1501 | 0.4660 |
| EC5.3.1.14 | L-rhamnose isomerase | 0.6 | 0.9 | 1.2 | 0.9 | 0.7 | 0.0000 | 0.0000 | 0.0001 | 0.0002 | 0.1062 | 0.1039 | 0.6008 |
| EC5.3.1.25 | L-fucose isomerase | 1.0 | 1.2 | 1.0 | 1.0 | 1.2 | 0.3334 | 0.0000 | 0.0000 | 0.0026 | 0.1453 | −0.0139 | 0.9363 |

TABLE 24-continued

EC relative abundance

| | | Fold change (mean total RPKM) | | | | | Adjusted p-value from ShotgunFunctionalizeR | | | | | Spearman correlation of relative abundance vs time | |
|---|---|---|---|---|---|---|---|---|---|---|---|---|---|
| | | D-Ph1- vs Ph2 | D-Ph3- vs Ph4 | R-Ph1 vs | R-Ph2 vs | R-Ph3 vs | D-Ph1- vs Ph2 | D-Ph3- vs Ph4 | R-Ph1 vs | R-Ph2 vs | R-Ph3 vs | | |
| EC | Annotation | healthy | healthy | healthy | healthy | healthy | healthy | healthy | healthy | healthy | healthy | Spearman r | P-value (FDR corrected) |
| EC5.3.1.26 | Galactose-6-phosphate isomerase | 0.7 | 1.0 | 1.0 | 0.9 | 0.8 | 0.0000 | 0.0000 | 0.0000 | 0.0002 | 0.0453 | 0.2018 | 0.3344 |
| EC5.4.2.7 | Phosphopentomutase | 1.2 | 0.5 | 0.8 | 1.0 | 0.9 | 0.0000 | 0.0000 | 0.0000 | 0.0000 | 0.1024 | −0.0206 | 0.9363 |
| EC5.4.99.16 | Maltose alpha-D-glucosyltransferase | 0.4 | 0.6 | 1.0 | 1.1 | 0.7 | 0.0000 | 0.0000 | 0.0000 | 0.0000 | 0.7244 | 0.4121 | 0.0244 |
| EC5.5.1.4 | Inositol-3-phosphate synthase | 0.6 | 0.8 | 0.8 | 0.9 | 0.9 | 0.0000 | 0.0000 | 0.0000 | 0.0000 | 0.0659 | 0.4126 | 0.0244 |
| EC6.3.1.2 | Glutamate--ammonia ligase | 1.2 | 1.5 | 1.0 | 1.2 | 0.8 | 0.0000 | 0.0000 | 0.0000 | 0.0000 | 1.0000 | −0.1954 | 0.3426 |
| EC6.4.1.2 | Acetyl-CoA carboxylase | 0.7 | 0.8 | 0.9 | 0.9 | 0.9 | 0.0000 | 0.0000 | 0.0000 | 0.0000 | 0.1821 | 0.2656 | 0.1749 |
| EC2.1.1.— | NA | 1881.2 | 290.3 | 35.5 | 13.3 | 1380.7 | 0.0000 | 0.0000 | 0.0000 | 0.0000 | 0.0000 | −0.4938 | 0.0075 |
| EC2.4.2.11 | Nicotinate phosphoribosyltransferase | 0.7 | 0.9 | 1.3 | 1.2 | 1.0 | 0.0000 | 0.0000 | 0.0001 | 0.0000 | 0.0030 | 0.1976 | 0.3426 |
| EC2.6.1.62 | Adenosylmethionine--8-amino-7-oxononanoate transaminase | 0.3 | 0.3 | 0.9 | 0.9 | 1.0 | 0.0000 | 0.0554 | 0.0000 | 0.1438 | 0.3047 | 0.5389 | 0.0047 |
| EC2.7.4.16 | Thiamine-phosphate kinase | 81.3 | 11.4 | 2.2 | 1.6 | 61.1 | 0.0000 | 0.0000 | 0.0000 | 0.0000 | 0.6166 | −0.3854 | 0.0349 |
| EC2.7.7.63 | Lipoate--protein ligase | 0.7 | 0.8 | 0.8 | 0.9 | 0.9 | 0.0000 | 0.0000 | 0.4459 | 0.0000 | 0.0007 | 0.5012 | 0.0075 |
| EC3.4.—.— | NA | 0.7 | 0.9 | 1.1 | 1.1 | 1.0 | 0.0000 | 0.0000 | 0.0000 | 0.0000 | 0.3482 | 0.3816 | 0.0349 |
| EC3.6.1.— | NA | 0.6 | 0.2 | 0.8 | 1.1 | 1.1 | 0.0000 | 0.0000 | 0.2258 | 0.0143 | 0.1579 | 0.5522 | 0.0047 |
| EC4.1.2.25 | Dihydroneopterin aldolase | 0.7 | 1.0 | 1.0 | 1.0 | 0.9 | 0.0241 | 0.0000 | 0.0505 | 0.0000 | 1.0000 | 0.1750 | 0.4062 |
| EC4.2.1.113 | o-succinylbenzoate synthase | 0.6 | 0.5 | 0.9 | 0.8 | 0.7 | 0.0040 | 0.0000 | 0.0000 | 0.0039 | 0.4056 | 0.3061 | 0.1035 |
| EC4.99.1.1 | Ferrochelatase | 0.7 | 0.6 | 0.7 | 0.8 | 0.9 | 0.0000 | 0.0031 | 0.0087 | 0.0000 | 0.2843 | 0.3563 | 0.0499 |
| EC6.1.1.17 | Glutamate--tRNA ligase | 0.6 | 0.8 | 0.9 | 0.7 | 0.8 | 0.0000 | 0.0000 | 0.0000 | 0.0000 | 0.2131 | 0.1590 | 0.4516 |
| EC6.3.1.5 | NAD(+) synthase | 0.7 | 0.8 | 0.9 | 1.1 | 0.9 | 0.0000 | 0.0000 | 0.0000 | 0.0018 | 0.6387 | 0.4611 | 0.0103 |
| EC6.3.2.1 | Pantoate--beta-alanine ligase | 5.4 | 9.5 | 2.0 | 2.5 | 1.0 | 0.0000 | 0.0000 | 0.0000 | 0.0018 | 0.0096 | −0.4800 | 0.0083 |
| EC6.3.5.1 | NAD(+) synthase (glutamine-hydrolyzing) | 1.2 | 2.1 | 1.3 | 1.3 | 0.8 | 0.0000 | 0.0000 | 0.0000 | 0.0000 | 0.1520 | −0.2431 | 0.2283 |
| EC6.1.1.1 | Tyrosine--tRNA ligase | 0.7 | 1.0 | 0.9 | 0.9 | 0.8 | 0.0000 | 0.0001 | 0.0000 | 0.2745 | 1.0000 | 0.2399 | 0.2337 |
| EC6.1.1.16 | Cysteine--tRNA ligase | 0.6 | 0.8 | 0.7 | 0.7 | 0.8 | 0.0000 | 0.0004 | 0.0000 | 0.0243 | 0.3930 | 0.1439 | 0.4703 |
| EC6.1.1.17 | Glutamate--tRNA ligase | 0.6 | 0.8 | 0.9 | 0.7 | 0.8 | 0.0000 | 0.0000 | 0.0000 | 0.0000 | 0.2131 | 0.1590 | 0.4516 |
| EC6.1.1.18 | Glutamine--tRNA ligase | 0.7 | 1.9 | 2.9 | 1.1 | 1.2 | 0.0000 | 0.0000 | 0.0000 | 0.0111 | 0.0000 | 0.3139 | 0.1562 | 0.4516 |
| EC6.1.1.21 | Histidine--tRNA ligase | 0.6 | 0.8 | 0.9 | 0.9 | 0.9 | 0.0000 | 0.3446 | 0.0000 | 0.0000 | 0.0048 | 0.4881 | 0.0075 |
| EC6.1.1.22 | Asparagine--tRNA ligase | 0.7 | 0.8 | 1.0 | 0.9 | 0.8 | 0.0000 | 0.0029 | 0.0901 | 0.0000 | 0.0703 | 0.2500 | 0.2122 |
| EC6.1.1.24 | Glutamate--tRNA(Gln) ligase | 0.7 | 0.9 | 0.9 | 1.0 | 0.9 | 0.0000 | 0.0000 | 0.0000 | 0.0000 | 0.0295 | 0.3712 | 0.0416 |
| EC6.1.1.4 | Leucine--tRNA ligase | 0.5 | 0.3 | 0.5 | 0.9 | 1.0 | 0.0000 | 0.0000 | 0.0000 | 0.0000 | 0.3546 | 0.4628 | 0.0103 |
| EC6.3.5.6 | Asparaginyl-tRNA synthase (glutamine-hydrolyzing) | 0.5 | 0.4 | 0.8 | 0.8 | 1.1 | 0.0000 | 0.0000 | 0.0000 | 0.0000 | 0.2595 | 0.4322 | 0.0167 |

TABLE 25

COPRO-seq results

| | | Days post initial gavage | % of non-*V. cholerae* reads | | | | | | |
|---|---|---|---|---|---|---|---|---|---|
| Group | Mouse | | *Bacteroides cellulosilyticus* WH2 | *Bacteroides caccae* | *Bacteroides ovatus* | *Bacteroides thetaiotaomicron* | *Bacteroides uniformis* | *Bacteroides vulgatus* | *Colinsella aerofaciens* |
| D1invasion | 1 | 1 | 27.89% | 12.66% | 2.77% | 22.48% | 5.61% | 8.54% | 0.16% |
| D1invasion | 1 | 2 | 33.03% | 10.73% | 2.94% | 26.56% | 4.42% | 11.19% | 0.24% |
| D1invasion | 1 | 3 | 46.69% | 8.35% | 3.44% | 18.14% | 4.50% | 9.98% | 0.24% |
| D1invasion | 1 | 4 | 41.90% | 8.35% | 4.87% | 13.66% | 7.54% | 11.10% | 1.22% |
| D1invasion | 1 | 7 | 45.39% | 5.49% | 5.04% | 10.62% | 5.88% | 14.61% | 1.23% |
| D1invasion | 1 | 11 | 45.30% | 6.55% | 8.99% | 7.34% | 6.58% | 16.49% | 1.68% |
| D1invasion | 1 | 12 | 43.44% | 8.04% | 13.70% | 8.03% | 5.64% | 11.74% | 0.81% |
| D1invasion | 1 | 13 | 38.19% | 9.50% | 11.67% | 10.10% | 6.27% | 11.66% | 0.56% |
| D1invasion | 1 | 14 | 32.29% | 8.30% | 12.67% | 9.36% | 5.47% | 10.79% | 1.69% |
| D1invasion | 1 | 15 | 19.42% | 10.78% | 21.02% | 12.05% | 8.46% | 13.95% | 0.77% |
| D1invasion | 1 | 16 | 21.42% | 7.74% | 21.43% | 12.10% | 9.79% | 14.25% | 0.66% |

TABLE 25-continued

COPRO-seq results

| | | | | | | | | | |
|---|---|---|---|---|---|---|---|---|---|
| D1invasion | 1 | 17 | 28.33% | 6.83% | 17.80% | 10.61% | 7.94% | 12.45% | 1.07% |
| D1invasion | 1 | 18 | 32.26% | 6.60% | 22.48% | 9.98% | 5.76% | 13.68% | 0.30% |
| D1invasion | 1 | 19 | 34.53% | 5.81% | 16.99% | 10.02% | 5.84% | 13.62% | 0.68% |
| D1invasion | 1 | 21 | 32.09% | 6.03% | 20.23% | 9.46% | 2.94% | 16.94% | 0.13% |
| D1invasion | 1 | 25 | 35.77% | 5.84% | 18.13% | 10.70% | 1.91% | 16.44% | 0.20% |
| D1invasion | 1 | 28 | 35.34% | 5.05% | 15.99% | 12.26% | 2.38% | 15.46% | 0.51% |
| D1invasion | 2 | 1 | 40.41% | 17.66% | 2.33% | 16.80% | 4.38% | 7.82% | 0.09% |
| D1invasion | 2 | 2 | 39.03% | 9.80% | 2.86% | 21.18% | 4.28% | 6.99% | 0.47% |
| D1invasion | 2 | 3 | 49.75% | 6.38% | 3.90% | 18.76% | 5.53% | 8.43% | 0.36% |
| D1invasion | 2 | 4 | 42.97% | 5.83% | 5.01% | 12.92% | 7.33% | 12.06% | 0.41% |
| D1invasion | 2 | 7 | 43.77% | 7.91% | 4.34% | 7.78% | 4.48% | 16.42% | 0.87% |
| D1invasion | 2 | 11 | 46.53% | 9.17% | 6.53% | 8.49% | 6.55% | 15.83% | 1.20% |
| D1invasion | 2 | 12 | 43.08% | 10.27% | 10.61% | 8.24% | 6.61% | 13.78% | 0.58% |
| D1invasion | 2 | 13 | 44.62% | 9.72% | 10.39% | 8.86% | 5.92% | 10.83% | 0.82% |
| D1invasion | 2 | 14 | 40.24% | 9.53% | 13.06% | 9.61% | 5.81% | 10.89% | 0.88% |
| D1invasion | 2 | 15 | 40.90% | 8.39% | 11.99% | 8.55% | 5.50% | 10.54% | 1.49% |
| D1invasion | 2 | 16 | 40.79% | 8.72% | 12.02% | 9.37% | 5.44% | 11.79% | 0.82% |
| D1invasion | 2 | 17 | 38.14% | 8.02% | 11.73% | 10.92% | 7.70% | 10.91% | 0.75% |
| D1invasion | 2 | 18 | 43.93% | 8.91% | 11.62% | 9.09% | 6.91% | 9.92% | 0.27% |
| D1invasion | 2 | 19 | 27.46% | 9.84% | 20.49% | 11.90% | 6.21% | 14.29% | 0.37% |
| D1invasion | 2 | 21 | 25.65% | 7.83% | 27.05% | 11.25% | 5.10% | 12.21% | 0.18% |
| D1invasion | 2 | 25 | 33.26% | 5.58% | 20.62% | 12.84% | 4.34% | 11.23% | 0.15% |
| D1invasion | 2 | 28 | 33.78% | 4.91% | 17.35% | 13.27% | 4.49% | 11.28% | 0.74% |
| D1invasion | 3 | 1 | 22.06% | 11.94% | 1.25% | 38.62% | 5.67% | 5.45% | 0.12% |
| D1invasion | 3 | 2 | 36.75% | 9.52% | 2.14% | 30.45% | 2.42% | 9.23% | 0.36% |
| D1invasion | 3 | 3 | 53.98% | 8.22% | 2.46% | 13.64% | 2.57% | 10.71% | 0.18% |
| D1invasion | 3 | 4 | 54.98% | 6.94% | 4.77% | 9.13% | 4.32% | 10.09% | 0.43% |
| D1invasion | 3 | 7 | 41.57% | 5.26% | 4.36% | 7.96% | 5.26% | 22.19% | 0.76% |
| D1invasion | 3 | 11 | 51.48% | 8.23% | 6.87% | 8.19% | 8.59% | 9.08% | 0.65% |
| D1invasion | 3 | 12 | 47.08% | 7.71% | 10.78% | 7.50% | 8.42% | 9.88% | 0.67% |
| D1invasion | 3 | 13 | 39.03% | 8.24% | 10.25% | 9.05% | 6.68% | 12.50% | 0.97% |
| D1invasion | 3 | 14 | 41.34% | 7.86% | 12.76% | 8.34% | 6.55% | 11.44% | 1.03% |
| D1invasion | 3 | 15 | 27.95% | 8.13% | 13.84% | 10.11% | 8.54% | 15.22% | 1.10% |
| D1invasion | 3 | 16 | 22.58% | 6.60% | 16.14% | 11.35% | 8.45% | 20.72% | 0.33% |
| D1invasion | 3 | 17 | 31.38% | 4.87% | 13.92% | 9.80% | 8.55% | 19.26% | 0.54% |
| D1invasion | 3 | 18 | 33.69% | 5.26% | 19.09% | 9.56% | 6.31% | 15.35% | 0.26% |
| D1invasion | 3 | 19 | 34.62% | 4.41% | 20.01% | 9.08% | 4.65% | 15.55% | 0.51% |
| D1invasion | 3 | 21 | 33.31% | 4.36% | 14.62% | 9.21% | 3.19% | 24.37% | 0.20% |
| D1invasion | 3 | 25 | 35.97% | 5.42% | 21.21% | 10.43% | 3.80% | 14.37% | 0.12% |
| D1invasion | 3 | 28 | 31.27% | 4.32% | 17.72% | 11.64% | 7.07% | 16.81% | 0.65% |
| D1invasion | 4 | 1 | 40.78% | 13.29% | 2.83% | 11.03% | 7.63% | 9.86% | 0.20% |
| D1invasion | 4 | 3 | 50.43% | 8.51% | 4.47% | 11.59% | 5.58% | 8.91% | 0.33% |
| D1invasion | 4 | 4 | 41.72% | 9.22% | 5.93% | 14.56% | 4.44% | 11.49% | 0.54% |
| D1invasion | 4 | 7 | 42.60% | 4.79% | 4.85% | 9.85% | 5.14% | 19.10% | 1.19% |
| D1invasion | 4 | 11 | 46.70% | 6.36% | 5.88% | 7.62% | 5.21% | 19.27% | 0.96% |
| D1invasion | 4 | 12 | 42.68% | 9.20% | 6.62% | 7.91% | 4.71% | 17.96% | 0.82% |
| D1invasion | 4 | 13 | 40.68% | 8.38% | 7.76% | 8.71% | 4.32% | 17.70% | 1.01% |
| D1invasion | 4 | 14 | 39.69% | 8.49% | 12.31% | 8.38% | 5.43% | 12.26% | 0.96% |
| D1invasion | 4 | 15 | 33.88% | 11.47% | 13.42% | 11.89% | 6.74% | 13.27% | 0.59% |
| D1invasion | 4 | 16 | 20.32% | 9.34% | 19.63% | 12.49% | 7.78% | 16.73% | 0.33% |
| D1invasion | 4 | 17 | 25.35% | 7.58% | 13.31% | 11.25% | 6.05% | 22.12% | 0.92% |
| D1invasion | 4 | 18 | 28.54% | 6.71% | 12.92% | 10.25% | 5.09% | 22.76% | 0.56% |
| D1invasion | 4 | 19 | 32.47% | 5.99% | 13.27% | 9.70% | 4.63% | 17.77% | 1.07% |
| D1invasion | 4 | 21 | 36.80% | 6.39% | 16.06% | 9.59% | 4.07% | 16.10% | 0.26% |
| D1invasion | 4 | 25 | 32.94% | 5.32% | 14.27% | 9.38% | 1.63% | 19.03% | 0.19% |
| D1invasion | 4 | 28 | 35.31% | 4.82% | 15.15% | 11.37% | 2.64% | 16.14% | 0.62% |
| D1invasion | 5 | 1 | 40.24% | 15.55% | 2.78% | 19.56% | 4.19% | 7.33% | 0.17% |
| D1invasion | 5 | 3 | 54.84% | 6.67% | 2.94% | 17.70% | 4.48% | 7.43% | 0.35% |
| D1invasion | 5 | 4 | 47.75% | 5.82% | 5.27% | 10.37% | 7.03% | 11.37% | 0.59% |
| D1invasion | 5 | 7 | 43.60% | 6.42% | 6.07% | 10.45% | 5.85% | 13.78% | 1.04% |
| D1invasion | 5 | 11 | 45.52% | 9.75% | 7.19% | 8.69% | 5.00% | 11.72% | 2.06% |
| D1invasion | 5 | 12 | 44.42% | 9.52% | 10.92% | 10.34% | 5.17% | 10.88% | 0.60% |
| D1invasion | 5 | 13 | 38.34% | 10.18% | 10.06% | 10.11% | 5.34% | 13.84% | 0.94% |
| D1invasion | 6 | 4 | 44.49% | 5.47% | 5.10% | 9.55% | 6.74% | 14.83% | 0.31% |
| D1invasion | 6 | 7 | 43.82% | 6.48% | 5.08% | 12.20% | 5.06% | 14.68% | 0.37% |
| D1invasion | 6 | 11 | 42.54% | 6.52% | 7.44% | 9.52% | 4.90% | 16.32% | 2.06% |
| D1invasion | 6 | 12 | 45.23% | 7.75% | 6.81% | 9.35% | 4.90% | 16.21% | 0.81% |
| D1invasion | 6 | 13 | 37.94% | 6.86% | 7.41% | 9.51% | 6.55% | 15.19% | 2.46% |
| D1invasion | 6 | 14 | 37.84% | 7.77% | 9.52% | 11.64% | 10.42% | 14.86% | 0.48% |
| D1invasion | 6 | 15 | 35.54% | 7.85% | 9.83% | 9.48% | 7.06% | 14.64% | 1.97% |
| D1invasion | 6 | 16 | 15.30% | 8.32% | 19.04% | 13.69% | 11.01% | 21.80% | 0.37% |
| D1invasion | 6 | 17 | 24.00% | 6.26% | 17.26% | 11.93% | 6.62% | 19.60% | 0.82% |
| D1invasion | 6 | 18 | 30.30% | 5.56% | 14.01% | 10.11% | 4.25% | 20.63% | 0.39% |
| D1invasion | 6 | 19 | 32.54% | 6.36% | 15.80% | 10.66% | 4.86% | 19.71% | 0.13% |
| D1invasion | 6 | 21 | 34.77% | 6.88% | 16.81% | 10.25% | 6.56% | 17.09% | 0.17% |
| D1invasion | 6 | 25 | 35.40% | 5.89% | 14.34% | 9.38% | 4.29% | 19.76% | 0.38% |
| D1invasion | 6 | 28 | 36.30% | 5.47% | 16.04% | 10.41% | 1.68% | 18.48% | 0.44% |
| D14invasion | 1 | 1 | 35.91% | 26.51% | 0.75% | 10.36% | 7.94% | 7.63% | 0.56% |

TABLE 25-continued

COPRO-seq results

| | | | | | | | | | |
|---|---|---|---|---|---|---|---|---|---|
| D14invasion | 1 | 2  | 46.85% | 15.62% | 2.62%  | 17.83% | 1.97% | 6.38%  | 0.18% |
| D14invasion | 1 | 3  | 50.37% | 10.69% | 4.49%  | 10.97% | 2.15% | 11.80% | 0.15% |
| D14invasion | 1 | 4  | 43.53% | 8.05%  | 7.31%  | 12.49% | 3.28% | 11.19% | 0.26% |
| D14invasion | 1 | 7  | 43.83% | 7.28%  | 8.32%  | 9.87%  | 2.85% | 17.29% | 0.47% |
| D14invasion | 1 | 11 | 41.04% | 8.25%  | 9.10%  | 10.86% | 5.62% | 13.64% | 1.01% |
| D14invasion | 1 | 12 | 45.29% | 9.92%  | 11.61% | 9.49%  | 6.05% | 13.09% | 0.21% |
| D14invasion | 1 | 13 | 44.37% | 8.18%  | 12.41% | 8.71%  | 4.64% | 14.29% | 0.31% |
| D14invasion | 1 | 14 | 45.20% | 7.21%  | 13.31% | 9.16%  | 5.54% | 13.33% | 0.27% |
| D14invasion | 1 | 15 | 41.13% | 7.49%  | 14.29% | 8.60%  | 5.05% | 15.83% | 0.34% |
| D14invasion | 1 | 16 | 28.88% | 10.95% | 11.14% | 15.91% | 4.83% | 14.59% | 0.81% |
| D14invasion | 1 | 17 | 35.92% | 6.53%  | 9.69%  | 16.28% | 6.23% | 12.98% | 0.68% |
| D14invasion | 1 | 18 | 46.69% | 4.65%  | 6.10%  | 10.58% | 8.28% | 12.14% | 0.54% |
| D14invasion | 1 | 19 | 47.28% | 3.69%  | 7.85%  | 5.43%  | 9.85% | 14.17% | 0.64% |
| D14invasion | 1 | 21 | 46.25% | 2.52%  | 6.91%  | 7.53%  | 4.52% | 21.60% | 0.43% |
| D14invasion | 1 | 25 | 41.60% | 4.50%  | 15.85% | 10.64% | 5.60% | 13.57% | 0.15% |
| D14invasion | 1 | 28 | 37.07% | 4.70%  | 13.85% | 9.86%  | 3.34% | 21.00% | 0.34% |
| D14invasion | 2 | 1  | 45.03% | 12.28% | 1.65%  | 14.64% | 7.41% | 8.82%  | 0.64% |
| D14invasion | 2 | 2  | 45.45% | 16.10% | 3.77%  | 17.66% | 2.27% | 6.49%  | 0.24% |
| D14invasion | 2 | 3  | 47.44% | 11.72% | 5.22%  | 12.22% | 1.76% | 10.67% | 0.27% |
| D14invasion | 2 | 4  | 45.60% | 8.41%  | 7.34%  | 12.57% | 2.64% | 12.87% | 0.22% |
| D14invasion | 2 | 7  | 42.00% | 7.95%  | 7.85%  | 9.11%  | 3.98% | 17.07% | 0.67% |
| D14invasion | 2 | 11 | 47.26% | 7.79%  | 10.59% | 8.69%  | 6.07% | 11.21% | 0.45% |
| D14invasion | 2 | 12 | 47.34% | 3.90%  | 10.70% | 9.64%  | 4.39% | 13.46% | 0.57% |
| D14invasion | 2 | 13 | 43.55% | 4.43%  | 11.75% | 9.92%  | 5.95% | 12.54% | 0.86% |
| D14invasion | 3 | 1  | 44.41% | 14.52% | 1.76%  | 14.48% | 6.46% | 11.12% | 0.37% |
| D14invasion | 3 | 2  | 51.66% | 15.83% | 2.53%  | 14.07% | 2.16% | 7.50%  | 0.14% |
| D14invasion | 3 | 3  | 48.22% | 12.97% | 5.49%  | 13.48% | 2.84% | 8.91%  | 0.20% |
| D14invasion | 3 | 11 | 43.53% | 9.84%  | 9.98%  | 10.25% | 4.85% | 10.91% | 0.98% |
| D14invasion | 3 | 12 | 43.27% | 10.75% | 12.53% | 9.79%  | 4.28% | 12.73% | 0.20% |
| D14invasion | 3 | 13 | 42.55% | 8.79%  | 10.35% | 8.27%  | 3.72% | 20.50% | 0.44% |
| D14invasion | 3 | 14 | 40.81% | 8.53%  | 12.97% | 7.74%  | 5.68% | 16.94% | 0.47% |
| D14invasion | 3 | 15 | 39.01% | 7.47%  | 12.66% | 8.29%  | 4.44% | 22.35% | 0.21% |
| D14invasion | 3 | 16 | 37.77% | 6.02%  | 11.21% | 7.88%  | 2.93% | 25.83% | 0.31% |
| D14invasion | 3 | 17 | 39.81% | 6.37%  | 13.37% | 8.84%  | 4.17% | 18.52% | 0.24% |
| D14invasion | 3 | 18 | 43.57% | 4.40%  | 10.67% | 9.12%  | 6.76% | 16.60% | 0.35% |
| D14invasion | 3 | 19 | 46.20% | 3.24%  | 6.24%  | 7.63%  | 7.49% | 16.19% | 0.74% |
| D14invasion | 3 | 21 | 42.41% | 1.94%  | 7.97%  | 8.90%  | 9.00% | 17.77% | 0.45% |
| D14invasion | 3 | 25 | 35.52% | 3.96%  | 12.86% | 10.60% | 4.37% | 23.09% | 0.41% |
| D14invasion | 3 | 28 | 33.25% | 5.90%  | 16.15% | 11.26% | 2.65% | 21.89% | 0.20% |
| D14invasion | 4 | 1  | 35.85% | 12.52% | 1.96%  | 17.65% | 2.89% | 4.78%  | 1.06% |
| D14invasion | 4 | 2  | 46.23% | 14.12% | 3.80%  | 17.60% | 2.20% | 6.45%  | 0.27% |
| D14invasion | 4 | 3  | 49.19% | 11.71% | 5.16%  | 14.42% | 2.44% | 8.23%  | 0.31% |
| D14invasion | 4 | 4  | 43.59% | 8.83%  | 6.43%  | 13.67% | 3.16% | 13.70% | 0.33% |
| D14invasion | 4 | 7  | 43.31% | 8.71%  | 7.49%  | 11.04% | 2.97% | 15.53% | 0.39% |
| D14invasion | 4 | 11 | 45.61% | 10.14% | 10.05% | 10.26% | 4.89% | 11.03% | 0.58% |
| D14invasion | 4 | 12 | 45.01% | 9.37%  | 9.35%  | 9.67%  | 5.11% | 12.09% | 0.45% |
| D14invasion | 4 | 13 | 39.30% | 8.58%  | 10.40% | 9.52%  | 4.10% | 14.97% | 0.76% |
| D14invasion | 4 | 14 | 41.36% | 5.28%  | 10.50% | 8.69%  | 3.93% | 21.59% | 0.43% |
| D14invasion | 4 | 15 | 38.42% | 4.75%  | 12.50% | 9.50%  | 5.07% | 19.32% | 0.63% |
| D14invasion | 4 | 16 | 34.70% | 6.91%  | 16.65% | 9.65%  | 5.50% | 16.89% | 0.34% |
| D14invasion | 4 | 17 | 37.31% | 3.76%  | 18.12% | 9.21%  | 5.92% | 15.18% | 0.42% |
| D14invasion | 4 | 18 | 42.93% | 3.13%  | 10.52% | 9.68%  | 7.74% | 16.09% | 0.59% |
| D14invasion | 4 | 19 | 45.19% | 3.27%  | 8.62%  | 8.13%  | 7.58% | 15.10% | 0.66% |
| D14invasion | 4 | 21 | 46.07% | 3.72%  | 11.57% | 8.61%  | 4.47% | 16.55% | 0.11% |
| D14invasion | 4 | 25 | 35.75% | 3.92%  | 10.07% | 9.60%  | 4.79% | 20.84% | 0.56% |
| D14invasion | 4 | 28 | 32.70% | 5.37%  | 13.07% | 9.94%  | 6.38% | 18.43% | 0.73% |
| D14invasion | 5 | 4  | 45.02% | 10.35% | 6.05%  | 13.62% | 2.65% | 10.70% | 0.29% |
| D14invasion | 5 | 7  | 43.01% | 8.15%  | 6.79%  | 10.38% | 2.19% | 18.09% | 0.52% |
| D14invasion | 5 | 11 | 46.58% | 9.38%  | 9.52%  | 8.96%  | 3.02% | 15.06% | 0.68% |
| D14invasion | 5 | 12 | 38.51% | 9.64%  | 8.66%  | 7.65%  | 3.90% | 23.56% | 0.99% |
| D14invasion | 5 | 13 | 38.32% | 7.32%  | 9.20%  | 8.47%  | 5.44% | 20.57% | 2.36% |
| D14invasion | 5 | 14 | 35.30% | 7.52%  | 12.70% | 10.81% | 7.30% | 17.25% | 0.93% |
| D14invasion | 5 | 15 | 35.63% | 7.14%  | 12.46% | 8.74%  | 5.96% | 21.53% | 0.63% |
| D14invasion | 5 | 16 | 36.52% | 5.28%  | 14.27% | 7.87%  | 6.85% | 21.60% | 0.56% |
| D14invasion | 5 | 17 | 38.59% | 3.14%  | 14.11% | 7.45%  | 5.56% | 20.68% | 0.60% |
| D14invasion | 5 | 18 | 40.69% | 2.78%  | 14.36% | 9.01%  | 4.31% | 19.08% | 0.31% |
| D14invasion | 5 | 19 | 42.87% | 2.63%  | 12.97% | 8.54%  | 2.26% | 17.91% | 0.20% |
| D14invasion | 5 | 21 | 44.13% | 2.05%  | 8.21%  | 7.26%  | 3.73% | 21.21% | 0.50% |
| D14invasion | 5 | 25 | 35.94% | 3.37%  | 9.58%  | 6.89%  | 4.81% | 24.06% | 0.96% |
| D14invasion | 5 | 28 | 33.66% | 4.45%  | 11.66% | 7.14%  | 4.36% | 25.19% | 0.60% |

TABLE 25-continued

COPRO-seq results

| Group | Mouse | Days post initial gavage | Clostridium scindens | Dorea longicatena | Eubacterium rectale | Faecalibacterium prausnitzii | Parabacteroides distasonis | Ruminococcus obeum | Ruminococcus torques | V. cholerae C6707 |
|---|---|---|---|---|---|---|---|---|---|---|
| | | | | | % of non-V. cholerae reads | | | | | % of total reads |
| D1invasion | 1 | 1 | 0.13% | 1.68% | 0.02% | 0.00% | 2.57% | 4.08% | 11.42% | 46.27% |
| D1invasion | 1 | 2 | 0.54% | 0.02% | 0.19% | 0.00% | 5.96% | 3.04% | 1.14% | 27.70% |
| D1invasion | 1 | 3 | 0.45% | 0.00% | 0.13% | 0.00% | 5.00% | 2.85% | 0.24% | 21.88% |
| D1invasion | 1 | 4 | 0.74% | 0.01% | 0.15% | 0.00% | 5.09% | 4.34% | 1.04% | 11.35% |
| D1invasion | 1 | 7 | 0.54% | 0.00% | 0.94% | 0.00% | 6.94% | 2.41% | 0.91% | 1.77% |
| D1invasion | 1 | 11 | 0.49% | 0.15% | 1.35% | 0.00% | 1.73% | 2.69% | 0.66% | 0.82% |
| D1invasion | 1 | 12 | 0.77% | 0.52% | 1.44% | 0.00% | 1.89% | 2.77% | 1.22% | 0.36% |
| D1invasion | 1 | 13 | 0.74% | 0.93% | 1.63% | 0.00% | 3.15% | 3.57% | 2.02% | 0.34% |
| D1invasion | 1 | 14 | 2.05% | 1.67% | 2.67% | 0.00% | 3.08% | 6.52% | 3.43% | 0.50% |
| D1invasion | 1 | 15 | 0.86% | 0.89% | 2.56% | 0.00% | 4.71% | 3.23% | 1.30% | 0.36% |
| D1invasion | 1 | 16 | 0.79% | 0.48% | 3.06% | 0.00% | 4.90% | 2.17% | 1.23% | 0.21% |
| D1invasion | 1 | 17 | 0.73% | 0.83% | 2.40% | 0.00% | 6.04% | 3.91% | 1.06% | 0.34% |
| D1invasion | 1 | 18 | 0.26% | 0.28% | 1.73% | 0.00% | 4.87% | 1.22% | 0.59% | 0.15% |
| D1invasion | 1 | 19 | 0.58% | 0.56% | 2.81% | 0.00% | 5.45% | 2.40% | 0.71% | 0.14% |
| D1invasion | 1 | 21 | 0.31% | 0.36% | 2.84% | 0.00% | 4.89% | 2.11% | 1.67% | 0.03% |
| D1invasion | 1 | 25 | 0.28% | 0.39% | 1.44% | 0.00% | 5.82% | 2.09% | 1.00% | 0.06% |
| D1invasion | 1 | 28 | 0.40% | 0.40% | 1.93% | 0.00% | 6.64% | 2.14% | 1.50% | 0.07% |
| D1invasion | 2 | 1 | 0.04% | 0.74% | 0.01% | 0.00% | 2.89% | 1.06% | 5.77% | 34.75% |
| D1invasion | 2 | 2 | 0.86% | 0.05% | 0.18% | 0.00% | 4.40% | 8.48% | 1.41% | 15.44% |
| D1invasion | 2 | 3 | 0.50% | 0.01% | 0.16% | 0.00% | 4.16% | 1.98% | 0.08% | 17.17% |
| D1invasion | 2 | 4 | 0.55% | 0.00% | 0.18% | 0.00% | 9.64% | 2.41% | 0.70% | 10.07% |
| D1invasion | 2 | 7 | 0.55% | 0.00% | 0.80% | 0.00% | 8.87% | 3.58% | 0.63% | 2.32% |
| D1invasion | 2 | 11 | 0.48% | 0.09% | 0.87% | 0.00% | 1.57% | 1.88% | 0.81% | 0.67% |
| D1invasion | 2 | 12 | 0.45% | 0.31% | 1.03% | 0.00% | 1.97% | 1.80% | 1.26% | 0.39% |
| D1invasion | 2 | 13 | 0.52% | 0.37% | 2.11% | 0.00% | 2.69% | 2.07% | 1.07% | 0.27% |
| D1invasion | 2 | 14 | 0.67% | 0.58% | 1.63% | 0.00% | 3.02% | 3.00% | 1.09% | 0.23% |
| D1invasion | 2 | 15 | 0.90% | 0.92% | 2.37% | 0.00% | 3.28% | 3.44% | 1.74% | 0.16% |
| D1invasion | 2 | 16 | 0.44% | 0.72% | 1.90% | 0.00% | 3.78% | 2.33% | 1.87% | 4.71% |
| D1invasion | 2 | 17 | 0.35% | 0.54% | 1.57% | 0.00% | 4.99% | 1.46% | 2.92% | 1.16% |
| D1invasion | 2 | 18 | 0.32% | 0.32% | 1.30% | 0.00% | 4.00% | 0.97% | 2.45% | 0.87% |
| D1invasion | 2 | 19 | 0.36% | 0.51% | 1.02% | 0.00% | 4.71% | 1.57% | 1.25% | 0.38% |
| D1invasion | 2 | 21 | 0.41% | 0.53% | 1.73% | 0.00% | 4.07% | 2.83% | 1.14% | 0.12% |
| D1invasion | 2 | 25 | 0.33% | 0.40% | 2.95% | 0.00% | 4.68% | 1.93% | 1.69% | 0.04% |
| D1invasion | 2 | 28 | 0.61% | 0.68% | 1.99% | 0.00% | 5.75% | 3.13% | 2.03% | 0.06% |
| D1invasion | 3 | 1 | 0.05% | 1.13% | 0.06% | 0.00% | 9.53% | 1.53% | 2.58% | 48.83% |
| D1invasion | 3 | 2 | 0.45% | 0.17% | 0.09% | 0.00% | 3.97% | 1.84% | 2.61% | 50.51% |
| D1invasion | 3 | 3 | 0.85% | 0.00% | 0.25% | 0.00% | 5.08% | 1.72% | 0.34% | 58.83% |
| D1invasion | 3 | 4 | 0.60% | 0.00% | 0.31% | 0.00% | 5.79% | 1.82% | 0.82% | 13.11% |
| D1invasion | 3 | 7 | 0.22% | 0.00% | 0.72% | 0.00% | 7.88% | 3.53% | 0.31% | 1.52% |
| D1invasion | 3 | 11 | 0.20% | 0.08% | 0.92% | 0.00% | 2.74% | 2.60% | 0.39% | 1.05% |
| D1invasion | 3 | 12 | 0.46% | 0.33% | 1.90% | 0.00% | 2.24% | 2.30% | 0.72% | 0.82% |
| D1invasion | 3 | 13 | 1.08% | 0.71% | 2.10% | 0.00% | 3.25% | 4.76% | 1.38% | 0.43% |
| D1invasion | 3 | 14 | 0.64% | 0.39% | 1.69% | 0.00% | 4.69% | 2.27% | 1.01% | 0.70% |
| D1invasion | 3 | 15 | 1.03% | 0.89% | 2.59% | 0.00% | 5.19% | 3.96% | 1.43% | 0.57% |
| D1invasion | 3 | 16 | 0.53% | 0.46% | 2.50% | 0.00% | 6.35% | 2.84% | 1.14% | 0.13% |
| D1invasion | 3 | 17 | 0.50% | 0.27% | 0.88% | 0.00% | 7.55% | 1.93% | 0.54% | 0.33% |
| D1invasion | 3 | 18 | 0.34% | 0.17% | 2.09% | 0.00% | 6.14% | 0.87% | 0.88% | 0.13% |
| D1invasion | 3 | 19 | 0.54% | 0.43% | 1.64% | 0.00% | 5.15% | 2.41% | 0.99% | 0.12% |
| D1invasion | 3 | 21 | 0.42% | 0.25% | 1.68% | 0.00% | 5.41% | 2.08% | 0.90% | 0.10% |
| D1invasion | 3 | 25 | 0.22% | 0.29% | 1.25% | 0.00% | 5.22% | 1.03% | 0.68% | 0.09% |
| D1invasion | 3 | 28 | 0.42% | 0.23% | 1.68% | 0.00% | 5.13% | 2.48% | 0.60% | 0.04% |
| D1invasion | 4 | 1 | 0.06% | 1.65% | 0.01% | 0.00% | 5.03% | 2.41% | 5.22% | 51.81% |
| D1invasion | 4 | 3 | 0.61% | 0.00% | 0.21% | 0.00% | 6.40% | 2.77% | 0.18% | 29.25% |
| D1invasion | 4 | 4 | 0.48% | 0.65% | 0.35% | 0.00% | 6.64% | 2.66% | 1.32% | 7.25% |
| D1invasion | 4 | 7 | 0.82% | 0.00% | 1.10% | 0.00% | 4.92% | 4.86% | 0.79% | 0.88% |
| D1invasion | 4 | 11 | 0.29% | 0.20% | 1.15% | 0.00% | 2.88% | 3.03% | 0.45% | 0.44% |
| D1invasion | 4 | 12 | 0.42% | 0.26% | 2.22% | 0.00% | 2.61% | 3.79% | 0.78% | 0.47% |
| D1invasion | 4 | 13 | 0.70% | 0.44% | 2.84% | 0.00% | 3.29% | 3.29% | 0.88% | 0.45% |
| D1invasion | 4 | 14 | 0.69% | 0.75% | 2.69% | 0.00% | 4.07% | 3.09% | 1.19% | 0.61% |
| D1invasion | 4 | 15 | 0.26% | 0.23% | 1.96% | 0.00% | 4.76% | 0.97% | 0.56% | 0.20% |
| D1invasion | 4 | 16 | 0.48% | 0.51% | 4.04% | 0.00% | 4.09% | 2.13% | 2.12% | 0.16% |
| D1invasion | 4 | 17 | 0.59% | 0.31% | 3.26% | 0.00% | 6.15% | 2.46% | 0.65% | 0.15% |
| D1invasion | 4 | 18 | 0.39% | 0.32% | 4.24% | 0.00% | 5.48% | 2.12% | 0.63% | 0.08% |
| D1invasion | 4 | 19 | 0.76% | 0.88% | 2.66% | 0.00% | 4.26% | 5.42% | 1.11% | 0.13% |
| D1invasion | 4 | 21 | 0.31% | 0.31% | 2.86% | 0.00% | 4.43% | 1.88% | 0.95% | 0.06% |
| D1invasion | 4 | 25 | 0.31% | 0.23% | 7.09% | 0.00% | 6.50% | 2.11% | 1.00% | 0.03% |
| D1invasion | 4 | 28 | 0.45% | 0.35% | 3.04% | 0.00% | 7.01% | 2.36% | 0.74% | 0.05% |
| D1invasion | 5 | 1 | 0.12% | 1.03% | 0.05% | 0.00% | 3.85% | 1.27% | 3.87% | 38.48% |
| D1invasion | 5 | 3 | 0.39% | 0.00% | 0.08% | 0.00% | 2.73% | 2.30% | 0.10% | 13.45% |
| D1invasion | 5 | 4 | 0.57% | 0.00% | 0.13% | 0.00% | 8.49% | 2.30% | 0.29% | 23.28% |

TABLE 25-continued

COPRO-seq results

| | | | | | | | | | | |
|---|---|---|---|---|---|---|---|---|---|---|
| D1invasion | 5 | 7 | 0.54% | 0.00% | 2.06% | 0.00% | 5.48% | 2.97% | 1.74% | 0.84% |
| D1invasion | 5 | 11 | 0.76% | 0.39% | 2.05% | 0.00% | 2.28% | 3.64% | 0.94% | 0.47% |
| D1invasion | 5 | 12 | 0.29% | 0.34% | 2.01% | 0.00% | 3.16% | 1.42% | 0.93% | 0.31% |
| D1invasion | 5 | 13 | 0.70% | 0.67% | 2.02% | 0.00% | 3.35% | 3.07% | 1.39% | 0.22% |
| D1invasion | 6 | 4 | 0.48% | 0.00% | 0.01% | 0.00% | 7.26% | 3.29% | 2.49% | 2.49% |
| D1invasion | 6 | 7 | 0.31% | 0.00% | 0.38% | 0.00% | 6.00% | 3.96% | 1.66% | 1.24% |
| D1invasion | 6 | 11 | 0.61% | 0.00% | 0.45% | 0.00% | 4.17% | 3.89% | 1.58% | 0.52% |
| D1invasion | 6 | 12 | 0.39% | 0.00% | 0.22% | 0.00% | 3.85% | 3.24% | 1.24% | 0.68% |
| D1invasion | 6 | 13 | 1.18% | 0.00% | 0.35% | 0.00% | 4.50% | 6.26% | 1.79% | 0.48% |
| D1invasion | 6 | 14 | 0.16% | 0.00% | 0.05% | 0.00% | 6.23% | 0.81% | 0.21% | 0.18% |
| D1invasion | 6 | 15 | 1.19% | 0.00% | 0.48% | 0.00% | 5.07% | 4.86% | 2.02% | 1.00% |
| D1invasion | 6 | 16 | 0.45% | 0.33% | 0.42% | 0.00% | 5.66% | 2.57% | 1.04% | 0.22% |
| D1invasion | 6 | 17 | 0.89% | 0.74% | 0.97% | 0.00% | 5.78% | 3.52% | 1.62% | 0.08% |
| D1invasion | 6 | 18 | 0.66% | 0.71% | 0.57% | 0.00% | 6.44% | 4.87% | 1.50% | 0.07% |
| D1invasion | 6 | 19 | 0.37% | 0.38% | 0.65% | 0.00% | 4.37% | 2.43% | 1.73% | 0.05% |
| D1invasion | 6 | 21 | 0.27% | 0.31% | 0.52% | 0.00% | 3.99% | 1.97% | 0.41% | 0.11% |
| D1invasion | 6 | 25 | 0.39% | 0.18% | 1.35% | 0.00% | 5.20% | 2.30% | 1.15% | 0.05% |
| D1invasion | 6 | 28 | 0.30% | 0.29% | 1.36% | 0.00% | 6.95% | 1.56% | 0.72% | 0.04% |
| D14invasion | 1 | 1 | 0.19% | 2.29% | 0.00% | 0.07% | 2.43% | 1.32% | 4.05% | 2.11% |
| D14invasion | 1 | 2 | 0.10% | 1.09% | 0.31% | 0.00% | 3.93% | 1.00% | 2.12% | 0.01% |
| D14invasion | 1 | 3 | 0.06% | 1.01% | 0.42% | 0.00% | 5.72% | 1.06% | 1.11% | 0.01% |
| D14invasion | 1 | 4 | 0.14% | 1.44% | 3.65% | 0.00% | 4.56% | 1.10% | 3.01% | 0.00% |
| D14invasion | 1 | 7 | 0.14% | 0.17% | 1.34% | 0.00% | 6.76% | 1.13% | 0.55% | 0.00% |
| D14invasion | 1 | 11 | 0.46% | 1.03% | 1.18% | 0.00% | 1.89% | 4.03% | 1.90% | 0.00% |
| D14invasion | 1 | 12 | 0.12% | 0.32% | 0.62% | 0.00% | 1.58% | 1.09% | 0.60% | 0.00% |
| D14invasion | 1 | 13 | 0.27% | 0.48% | 1.26% | 0.00% | 2.41% | 1.58% | 1.09% | 0.00% |
| D14invasion | 1 | 14 | 0.20% | 0.34% | 0.53% | 0.00% | 3.36% | 1.11% | 0.44% | 0.00% |
| D14invasion | 1 | 15 | 0.26% | 0.57% | 0.65% | 0.00% | 2.91% | 1.20% | 1.68% | 4.57% |
| D14invasion | 1 | 16 | 0.47% | 0.53% | 0.63% | 0.00% | 2.78% | 3.13% | 5.35% | 6.29% |
| D14invasion | 1 | 17 | 0.74% | 0.32% | 0.34% | 0.00% | 4.52% | 3.50% | 2.29% | 9.63% |
| D14invasion | 1 | 18 | 0.71% | 0.22% | 0.38% | 0.00% | 6.57% | 2.00% | 1.15% | 5.27% |
| D14invasion | 1 | 19 | 0.81% | 0.22% | 0.32% | 0.00% | 6.28% | 2.47% | 0.99% | 1.51% |
| D14invasion | 1 | 21 | 0.75% | 0.23% | 0.91% | 0.00% | 4.03% | 3.61% | 0.72% | 0.21% |
| D14invasion | 1 | 25 | 0.26% | 0.40% | 0.50% | 0.00% | 5.20% | 1.29% | 0.43% | 0.21% |
| D14invasion | 1 | 28 | 0.38% | 0.39% | 1.00% | 0.00% | 5.15% | 1.57% | 1.35% | 0.05% |
| D14invasion | 2 | 1 | 0.07% | 2.01% | 0.00% | 0.00% | 1.39% | 0.63% | 5.41% | 0.00% |
| D14invasion | 2 | 2 | 0.08% | 0.94% | 0.10% | 0.00% | 3.64% | 0.66% | 2.60% | 0.02% |
| D14invasion | 2 | 3 | 0.24% | 1.75% | 0.38% | 0.00% | 4.22% | 2.07% | 2.05% | 0.00% |
| D14invasion | 2 | 4 | 0.13% | 1.34% | 1.66% | 0.00% | 4.27% | 0.82% | 2.12% | 0.00% |
| D14invasion | 2 | 7 | 0.32% | 0.37% | 1.23% | 0.00% | 6.23% | 2.01% | 1.22% | 0.00% |
| D14invasion | 2 | 11 | 0.30% | 1.01% | 1.41% | 0.00% | 1.82% | 1.85% | 1.54% | 0.00% |
| D14invasion | 2 | 12 | 0.20% | 0.68% | 2.44% | 0.00% | 2.10% | 3.57% | 1.01% | 0.00% |
| D14invasion | 2 | 13 | 0.68% | 1.24% | 1.61% | 0.00% | 2.79% | 3.21% | 1.47% | 0.00% |
| D14invasion | 3 | 1 | 0.05% | 1.33% | 0.00% | 0.00% | 0.99% | 0.50% | 4.01% | 0.01% |
| D14invasion | 3 | 2 | 0.10% | 0.68% | 0.30% | 0.00% | 2.63% | 0.69% | 1.71% | 0.00% |
| D14invasion | 3 | 3 | 0.06% | 0.85% | 0.55% | 0.00% | 4.27% | 0.80% | 1.37% | 0.00% |
| D14invasion | 3 | 11 | 0.36% | 0.66% | 1.42% | 0.00% | 3.58% | 2.09% | 1.54% | 0.00% |
| D14invasion | 3 | 12 | 0.25% | 0.31% | 1.80% | 0.00% | 1.92% | 0.96% | 1.23% | 0.00% |
| D14invasion | 3 | 13 | 0.31% | 0.43% | 0.64% | 0.00% | 1.87% | 1.56% | 0.58% | 0.00% |
| D14invasion | 3 | 14 | 0.26% | 0.67% | 0.68% | 0.00% | 2.68% | 1.65% | 0.92% | 0.00% |
| D14invasion | 3 | 15 | 0.15% | 0.24% | 0.51% | 0.00% | 3.52% | 0.75% | 0.38% | 0.20% |
| D14invasion | 3 | 16 | 0.27% | 0.38% | 0.21% | 0.00% | 4.60% | 1.61% | 0.97% | 0.29% |
| D14invasion | 3 | 17 | 0.40% | 0.57% | 0.82% | 0.00% | 3.39% | 2.01% | 1.50% | 0.22% |
| D14invasion | 3 | 18 | 0.50% | 0.25% | 0.60% | 0.00% | 4.66% | 1.58% | 0.94% | 0.52% |
| D14invasion | 3 | 19 | 0.95% | 0.11% | 0.22% | 0.00% | 5.77% | 4.55% | 0.67% | 1.64% |
| D14invasion | 3 | 21 | 0.74% | 0.31% | 1.29% | 0.00% | 4.51% | 3.95% | 0.77% | 0.19% |
| D14invasion | 3 | 25 | 0.53% | 0.28% | 1.29% | 0.00% | 3.87% | 2.19% | 1.02% | 0.03% |
| D14invasion | 3 | 28 | 0.25% | 0.24% | 0.96% | 0.00% | 5.10% | 1.04% | 1.10% | 0.06% |
| D14invasion | 4 | 1 | 0.09% | 8.35% | 0.01% | 0.00% | 0.73% | 4.11% | 10.00% | 0.01% |
| D14invasion | 4 | 2 | 0.10% | 1.16% | 0.94% | 0.00% | 2.93% | 1.08% | 3.14% | 0.01% |
| D14invasion | 4 | 3 | 0.11% | 0.93% | 0.79% | 0.00% | 3.61% | 1.20% | 1.88% | 0.00% |
| D14invasion | 4 | 4 | 0.12% | 1.08% | 0.72% | 0.00% | 5.40% | 1.34% | 1.63% | 0.00% |
| D14invasion | 4 | 7 | 0.21% | 0.20% | 1.63% | 0.00% | 6.41% | 0.79% | 1.32% | 0.00% |
| D14invasion | 4 | 11 | 0.22% | 0.80% | 1.24% | 0.00% | 2.37% | 1.36% | 1.46% | 0.00% |
| D14invasion | 4 | 12 | 0.22% | 0.59% | 3.06% | 0.00% | 2.56% | 1.18% | 1.33% | 0.00% |
| D14invasion | 4 | 13 | 0.52% | 1.90% | 1.97% | 0.00% | 2.79% | 3.21% | 1.98% | 0.00% |
| D14invasion | 4 | 14 | 0.22% | 0.48% | 0.90% | 0.00% | 4.58% | 1.12% | 0.93% | 0.00% |
| D14invasion | 4 | 15 | 0.41% | 0.99% | 0.92% | 0.00% | 4.12% | 1.92% | 1.47% | 0.12% |
| D14invasion | 4 | 16 | 0.22% | 0.67% | 0.63% | 0.00% | 3.45% | 1.38% | 2.99% | 0.36% |
| D14invasion | 4 | 17 | 0.42% | 0.62% | 1.86% | 0.00% | 3.56% | 1.43% | 2.19% | 0.43% |
| D14invasion | 4 | 18 | 0.50% | 0.11% | 0.62% | 0.00% | 5.82% | 1.29% | 0.96% | 1.10% |
| D14invasion | 4 | 19 | 0.49% | 0.11% | 0.40% | 0.00% | 7.90% | 1.95% | 0.59% | 1.87% |
| D14invasion | 4 | 21 | 0.22% | 0.16% | 0.43% | 0.00% | 6.51% | 0.99% | 0.58% | 0.27% |
| D14invasion | 4 | 25 | 0.61% | 0.31% | 1.70% | 0.00% | 5.47% | 3.11% | 3.26% | 0.06% |
| D14invasion | 4 | 28 | 0.66% | 0.97% | 1.63% | 0.00% | 4.86% | 2.64% | 2.63% | 0.05% |
| D14invasion | 5 | 4 | 0.09% | 1.06% | 2.67% | 0.00% | 3.63% | 0.76% | 3.11% | 0.00% |
| D14invasion | 5 | 7 | 0.14% | 0.20% | 3.50% | 0.00% | 5.37% | 0.69% | 0.97% | 0.00% |
| D14invasion | 5 | 11 | 0.17% | 0.56% | 2.20% | 0.00% | 1.74% | 1.30% | 0.83% | 0.00% |

TABLE 25-continued

COPRO-seq results

| | | | | | | | | | | |
|---|---|---|---|---|---|---|---|---|---|---|
| D14invasion | 5 | 12 | 0.23% | 0.45% | 2.48% | 0.00% | 2.02% | 1.37% | 0.53% | 0.00% |
| D14invasion | 5 | 13 | 0.36% | 0.67% | 2.07% | 0.00% | 3.02% | 1.37% | 0.83% | 0.00% |
| D14invasion | 5 | 14 | 0.27% | 0.45% | 0.53% | 0.00% | 4.48% | 2.01% | 0.45% | 0.00% |
| D14invasion | 5 | 15 | 0.27% | 0.72% | 1.21% | 0.00% | 3.08% | 1.79% | 0.83% | 0.08% |
| D14invasion | 5 | 16 | 0.23% | 0.31% | 1.25% | 0.00% | 3.51% | 0.86% | 0.89% | 0.34% |
| D14invasion | 5 | 17 | 0.40% | 0.59% | 2.04% | 0.00% | 4.09% | 1.93% | 0.80% | 0.39% |
| D14invasion | 5 | 18 | 0.33% | 0.19% | 1.99% | 0.00% | 4.86% | 1.32% | 0.76% | 0.10% |
| D14invasion | 5 | 19 | 0.61% | 0.51% | 3.21% | 0.00% | 3.52% | 3.03% | 1.74% | 0.10% |
| D14invasion | 5 | 21 | 0.62% | 0.16% | 1.95% | 0.00% | 5.16% | 3.49% | 1.52% | 0.09% |
| D14invasion | 5 | 25 | 0.79% | 0.54% | 2.36% | 0.00% | 6.10% | 3.12% | 1.48% | 0.02% |
| D14invasion | 5 | 28 | 0.43% | 0.30% | 2.88% | 0.00% | 6.41% | 1.56% | 1.36% | 0.05% |

TABLE 26

Comparative analysis of in vivo V. cholerae and R. obeum transcriptional responses to co-colonization a. Transcriptional responses of known V. cholerae C6706 ΔluxS strain (MM883) virulence genes
Virulence gene transcripts with mean RPKM >20 in at least one group of mice. P-values based on unpaired two-tailed Student's t-test.

| Gene | Mean transcript abundance (RPKM) ± SEM in mice mono-colonized with V. cholerae | Mean transcript abundance (RPKM) ± SEM in mice co-colonized with V. cholerae and R. obeum | Fold-difference (V. cholerae mono-colonized/co-colonized) | P-value | Annotation |
|---|---|---|---|---|---|
| VC0583 | 105 ± 5 | 18 ± 2 | 5.9 | 0.0000 | hapR |
| VC0826 | 67 ± 26 | 281 ± 63 | 0.2 | 0.0310 | toxin co-regulated pilus biosynthesis protein P (tcpP) |
| VC0828 | 41 ± 10 | 11 ± 5 | 3.7 | 0.0159 | toxin co-regulated pilin (tcpA) |
| VC0984 | 61 ± 5 | 20 ± 4 | 3.1 | 0.0001 | cholera toxin transcriptional activator (toxR) |
| VC1021 | 136 ± 24 | 19 ± 5 | 7.0 | 0.0004 | LuxO represser protein (luxO) |
| VC1049 | 198 ± 35 | 35 ± 5 | 5.7 | 0.0004 | LysR family transcriptional regulator (aphB) |
| VC1446 | 64 ± 7 | 16 ± 4 | 3.9 | 0.0002 | toxin secretion transporter, putative |
| VC1447 | 31 ± 6 | 6 ± 2 | 5.0 | 0.0010 | RTX toxin transporter |
| VC1448 | 26 ± 7 | 6 ± 1 | 4.1 | 0.0072 | RTX toxin transporter |
| VC1451 | 213 ± 14 | 63 ± 10 | 3.4 | 0.0000 | RTX toxin RtxA (rtxA) |
| VC2467 | 709 ± 88 | 294 ± 52 | 2.4 | 0.0024 | RNA_polymerase sigma factor RpoE (aphA) |
| VC2724 | 21 ± 4 | 5 ± 1 | 4.4 | 0.0010 | cholera toxin secretion protein EpsM |
| VCA0219 | 96 ± 24 | 34 ± 11 | 2.8 | 0.0289 | haemolysin (hlyA) |
| VCA1084 | 172 ± 16 | 40 ± 7 | 4.4 | 0.0000 | toxin secretion ATP-binding protein |
| VC0665 | 135 ± 10 | 30 ± 5 | 4.5 | 0.0000 | sigma-54 dependent transcriptional regulator (vpsR) | b. V. cholerae C6706 ΔluxS strain (MM883) transcriptional responses to co-colonization with R. obeum
DESeq analysis of transcript differences d2 after gavage of V. cholerae into R. obeum
mono-colonized mice vs d2 after mono-colonization of mice with V. cholerae

| Gene | Fold-difference | P-value | P-value (Benjamini-Hochberg corrected) | Annotation |
|---|---|---|---|---|
| VCA1078 | 25.2 | 0.0000 | 0.0000 | LuxR family transcriptional regulator (vqmA) |
| VC0246 | 16.7 | 0.0000 | 0.0000 | lipopolysaccharide/O-antigen transport protein |
| VC0247 | 14.9 | 0.0000 | 0.0000 | lipopolysaccharide/O-antigen transport protein |
| VC0826 | 14.7 | 0.0000 | 0.0000 | toxin co-regulated pilus biosynthesis protein P |
| VC1113 | 14.7 | 0.0000 | 0.0007 | 8-amino-7-oxononanoate synthase |
| VC1112 | 14.3 | 0.0002 | 0.0106 | biotin synthase |
| VC0245 | 12.7 | 0.0000 | 0.0000 | rfbG protein |
| VC0259 | 12.5 | 0.0000 | 0.0002 | lipopolysaccharide biosynthesis protein RfbV |
| VCA0628 | 11.0 | 0.0000 | 0.0025 | SecA-related protein |
| VCA0952 | 8.1 | 0.0001 | 0.0036 | LuxR family transcriptional regulator |
| VC0185 | 7.3 | 0.0000 | 0.0004 | transposase, putative |
| VC1111 | 6.4 | 0.0015 | 0.0459 | adenosylmethionine--8-amino-7-oxononanoate transaminase |
| VC0249 | 5.7 | 0.0000 | 0.0000 | rfbL protein |
| VC2385 | 5.5 | 0.0006 | 0.0225 | RNA-directed DNA polymerase |
| VC1143 | 5.4 | 0.0000 | 0.0033 | ATP-dependent Clp protease adaptor protein ClpS |
| VC1445 | 5.2 | 0.0001 | 0.0039 | sensor histidine kinase/response regulator |
| VC0365 | 5.0 | 0.0000 | 0.0002 | bacterioferritin |
| VCA0827 | 4.6 | 0.0000 | 0.0001 | pterin-4-alpha-carbinolamine dehydratase |
| VC1962 | 3.7 | 0.0009 | 0.0307 | lipoprotein |
| VC0242 | 3.7 | 0.0000 | 0.0004 | phosphomannomutase |
| VC1838 | 3.5 | 0.0005 | 0.0201 | tolR membrane protein |
| VC2399 | 3.3 | 0.0000 | 0.0002 | cell division protein FtsQ |

TABLE 26-continued

Comparative analysis of in vivo *V. cholerae* and *R. obeum* transcriptional responses to co-colonization

| | | | | |
|---|---|---|---|---|
| VCA0947 | 3.3 | 0.0007 | 0.0270 | spermidine n1-acetyltransferase |
| VC1914 | 3.3 | 0.0012 | 0.0404 | integration host factor subunit beta |
| VC2587 | 3.3 | 0.0000 | 0.0001 | 30S ribosomal protein S17 |
| VC0364 | 3.1 | 0.0010 | 0.0348 | bacterioferritin-associated ferredoxin |
| VC1595 | 3.1 | 0.0015 | 0.0453 | galactokinase |
| VCA0198 | 3.1 | 0.0000 | 0.0025 | site-specific DNA-methyltransferase, putative |
| VC1854 | 3.0 | 0.0014 | 0.0425 | porin, putative |
| VCA0130 | 3.0 | 0.0013 | 0.0404 | D-ribose transporter subunit RbsB |
| VC2078 | 2.8 | 0.0001 | 0.0058 | ferrous iron transport protein A |
| VC1144 | 2.8 | 0.0000 | 0.0012 | ATP-dependent Clp protease ATP-binding subunit |
| VC2679 | 2.8 | 0.0001 | 0.0073 | 50S ribosomal protein L31 |
| VCA0867 | 2.8 | 0.0016 | 0.0485 | outer membrane protein W |
| VC0243 | 2.8 | 0.0002 | 0.0097 | GDP-mannose 4,6-dehydratase |
| VC0562 | 2.7 | 0.0000 | 0.0007 | 16S rRNA-processing protein RimM |
| VC0608 | 2.7 | 0.0001 | 0.0044 | iron(III) ABC transporter, periplasmic iron-compound-binding protein |
| VC0947 | 2.6 | 0.0001 | 0.0047 | D-alanyl-D-alanine carboxypeptidase |
| VC1910 | 2.6 | 0.0004 | 0.0168 | tRNA-(ms[2]io[6]A)-hydroxylase |
| VC2249 | 2.5 | 0.0005 | 0.0206 | (3R)-hydroxymyristoyl-ACP dehydratase |
| VCA0566 | 2.5 | 0.0002 | 0.0106 | transcriptional regulator |
| VC0750 | 2.4 | 0.0001 | 0.0073 | hesB family protein |
| VC0241 | 2.4 | 0.0012 | 0.0404 | mannose-1-phosphate guanylyltransferase |
| VC2291 | 2.3 | 0.0003 | 0.0118 | Na(+)-translocating NADH-quinone reductase subunit E |
| VC2634 | 2.2 | 0.0012 | 0.0404 | fimbrial assembly protein PilM, putative |
| VC0046 | 2.2 | 0.0013 | 0.0420 | peptide deformylase |
| VC2561 | 0.4 | 0.0001 | 0.0045 | uroporphyrin-III C-methyltransferase |
| VC2607 | 0.4 | 0.0004 | 0.0165 | glutathione-regulated potassium-efflux system ancillary protein KefG |
| VC1409 | 0.4 | 0.0002 | 0.0098 | multidrug resistance protein, putative |
| VC0719 | 0.4 | 0.0012 | 0.0404 | DNA-binding response regulator PhoB |
| VC2182 | 0.4 | 0.0000 | 0.0009 | 4-diphosphocytidyl-2-C-methyl-D-erythritol kinase |
| VCA0758 | 0.4 | 0.0003 | 0.0151 | arginine transporter permease subunit ArtQ |
| VC1391 | 0.4 | 0.0002 | 0.0108 | multidrug transporter, putative |
| VC2759 | 0.3 | 0.0002 | 0.0114 | 3-ketoacyl-CoA thiolase |
| VCA0665 | 0.3 | 0.0012 | 0.0404 | C4-dicarboxylate transporter DcuC |
| VC0676 | 0.3 | 0.0012 | 0.0399 | nptA protein |
| VC0720 | 0.3 | 0.0001 | 0.0066 | phosphate regulon sensor protein |
| VC1823 | 0.2 | 0.0012 | 0.0399 | PTS system, fructose-specific IIB component |
| VC0721 | 0.2 | 0.0001 | 0.0057 | phosphate ABC transporter, periplasmic phosphate-binding protein, putative |
| VC0298 | 0.2 | 0.0001 | 0.0047 | acetyl-CoA synthetase |
| VC1337 | 0.2 | 0.0005 | 0.0209 | methylcitrate synthase |
| VC0299 | 0.2 | 0.0001 | 0.0047 | DNA polymerase III subunit epsilon |
| VC1335 | 0.1 | 0.0001 | 0.0058 | GntR family transcriptional regulator | c. *R. obeum* transcriptional responses to co-colonization with *V. cholerae* C6706 ΔluxS
DESeq analysis of transcript differences d2 after gavage of *V. cholerae* into *R. obeum* mono-colonized
mice vs d7 of mono-colonization with *R. obeum* (timepoint Immediately prior to gavage of *V. cholerae*)

| Gene | Fold-difference | P-value | P-value (adjusted) | Annotation |
|---|---|---|---|---|
| RUMOBE00113 | 6.3 | 0.0000 | 0.0038 | putative sugar transport system permease protein |
| RUMOBE00114 | 4.4 | 0.0002 | 0.0428 | putative sugar transport system permease protein |
| RUMOBE00733 | 35.9 | 0.0000 | 0.0001 | anaerobic sulfite reductase subunit C [EC: 1.8.1.—] |
| RUMOBE03717 | 0.1 | 0.0000 | 0.0041 | K07112 |
| RUMOBE03830 | 0.2 | 0.0000 | 0.0031 | glutamate synthase (ferredoxin) [EC: 1.4.7.1] |
| RUMOBE03831 | 0.2 | 0.0000 | 0.0039 | glutamate synthase (NADPH/NADH) small chain [EC: 1.4.1.13 1.4.1.14] |
| RUMOBE03837 | 0.2 | 0.0001 | 0.0306 | aspartyl-tRNA(Asn)/glutamyl-tRNA (Gln) amidotransferase subunit B [EC: 6.3.5.6 6.3.5.7] |

TABLE 27

Distribution of homologs of AI-2 system genes in members of the artificial community

| Gene | Bacteroides cellulosilyticus WH2 | Bacteroides caccae | Bacteroides ovatus | Bacteroides thetaiotaomicron | Bacteroides uniformis | Bacteroides vulgatus | Colinsella aerofaciens |
|---|---|---|---|---|---|---|---|
| luxS | 0 | 0 | 0 | 0 | 1 | 0 | 1 |
| luxP | 0 | 0 | 0 | 0 | 0 | 0 | 0 |
| luxQ | 75 | 31 | 58 | 48 | 31 | 28 | 2 |
| luxO | 2 | 1 | 3 | 1 | 1 | 1 | 1 |
| luxU | 0 | 0 | 0 | 0 | 0 | 0 | 0 |
| luxR | 12 | 8 | 15 | 8 | 9 | 10 | 5 |
| lsrR | 0 | 0 | 0 | 0 | 0 | 0 | 0 |

TABLE 27-continued

Distribution of homologs of AI-2 system genes in members of the artificial community

| | | | | | | | |
|---|---|---|---|---|---|---|---|
| lsrA | 0 | 0 | 0 | 0 | 0 | 0 | 0 |
| lsrB | 0 | 0 | 0 | 0 | 0 | 0 | 0 |
| lsrC | 0 | 0 | 0 | 0 | 0 | 0 | 0 |
| lsrD | 0 | 0 | 0 | 0 | 0 | 0 | 0 |
| lsrK | 0 | 1 | 0 | 0 | 0 | 0 | 0 |
| lsrF | 1 | 0 | 0 | 0 | 0 | 0 | 0 |

| Gene | Clostridium scindens | Dorea longicatena | Eubacterium rectale | Faecalibacterium prausnitzii | Parabacteroides distasonis | Ruminococcus obeum | Ruminococcus torques |
|---|---|---|---|---|---|---|---|
| luxS | 1 | 1 | 1 | 1 | 0 | 1 | 1 |
| luxP | 0 | 0 | 0 | 0 | 0 | 0 | 0 |
| luxQ | 0 | 0 | 1 | 5 | 26 | 13 | 1 |
| luxO | 0 | 1 | 0 | 0 | 1 | 0 | 0 |
| luxU | 0 | 0 | 0 | 0 | 0 | 0 | 0 |
| luxR | 1 | 1 | 2 | 1 | 5 | 2 | 0 |
| lsrR | 2 | 0 | 0 | 0 | 0 | 0 | 0 |
| lsrA | 1 | 0 | 0 | 0 | 0 | 3 | 0 |
| lsrB | 1 | 0 | 0 | 0 | 0 | 3 | 0 |
| lsrC | 0 | 0 | 0 | 0 | 0 | 2 | 0 |
| lsrD | 1 | 0 | 0 | 0 | 0 | 1 | 0 |
| lsrK | 6 | 0 | 0 | 0 | 0 | 2 | 0 |
| lsrF | 1 | 0 | 0 | 0 | 1 | 0 | 0 |

Based on best BLASTp hit to KEGG database (10–5 e-value cutoff)

TABLE 28

Transcriptional responses of the 14-member artificial community to *V. cholerae* Fecal meta-transcriptomes of mice in D1invasion vs D14invasion treatment groups (both groups sampled 4 days after initial gavage)

| EC assignment | EC Annotation in KEGG | Fold difference (mean RPKM D14invasion)/mean RPKM D1invasion) | Benjamini-Hochberg corrected P-value (Shotgun FunctionalizeR) |
|---|---|---|---|
| EC1.2.1.2 | Formate dehydrogenase | 0.18 | 6.11E-07 |
| EC4.2.1.51 | Prephenate dehydratase | 0.32 | 1.62E-10 |
| EC3.6.1.7 | Acylphosphatase | 0.34 | 2.04E-32 |
| EC6.3.5.4 | Asparagine synthase (glutamine-hydrolyzing) | 0.35 | 2.01E-30 |
| EC2.4.1.15 | Alpha,alpha-trehalose-phosphate synthase (UDP-forming) | 0.36 | 6.50E-36 |
| EC3.2.1.10 | Oligo-1,6-glucosidase | 0.42 | 2.40E-34 |
| EC3.4.19.11 | Gamma-D-glutamyl-meso-diaminopimelate peptidase | 0.43 | 1.71E-08 |
| EC2.7.7.39 | Glycerol-3-phosphate cytidylyltransferase | 0.51 | 3.90E-14 |
| EC1.18.1.1 | Rubredoxin--NAD(+) reductase | 0.51 | 8.06E-17 |
| EC3.1.6.1 | Arylsulfatase | 0.52 | 4.67E-06 |
| EC4.1.2.40 | Tagatose-bisphosphate aldolase | 0.53 | 2.52E-12 |
| EC1.4.1.16 | Diaminopimelate dehydrogenase | 0.54 | 5.25E-59 |
| EC2.7.1.144 | Tagatose-6-phosphate kinase | 0.54 | 6.56E-15 |
| EC3.5.1.10 | Formyltetrahydrofolate deformylase | 0.55 | 1.71E-08 |
| EC2.3.1.182 | (R)-citramalate synthase | 0.56 | 6.48E-06 |
| EC1.7.2.2 | Nitrite reductase (cytochrome; ammonia-forming) | 0.56 | 7.12E-07 |
| EC6.3.1.1 | Aspartate--ammonia ligase | 0.56 | 1.85E-14 |
| EC2.1.1.37 | DNA (cytosine-5-)-methyltransferase | 0.57 | 1.83E-11 |
| EC2.6.1.83 | LL-diaminopimelate aminotransferase | 0.58 | 1.09E-12 |
| EC2.7.4.14 | Cytidylate kinase | 0.59 | 7.15E-59 |
| EC3.5.1.24 | Choloylglycine hydrolase | 0.60 | 4.58E-12 |
| EC1.4.3.5 | Pyridoxal 5'-phosphate synthase | 0.60 | 8.39E-06 |
| EC5.1.3.— | NA | 0.60 | 2.99E-78 |
| EC2.5.1.17 | Cob(I)yrinic acid a,c-diamide adenosyltransferase | 0.61 | 6.76E-19 |
| EC5.1.1.7 | Diaminopimelate epimerase | 0.62 | 1.16E-25 |
| EC2.1.1.63 | Methylated-DNA--[protein]-cysteine S-methyltransferase | 0.62 | 9.40E-06 |
| EC1.4.1.13 | Glutamate synthase (NADPH) | 0.63 | 1.09E-27 |
| EC1.4.1.14 | Glutamate synthase (NADH) | 0.63 | 1.09E-27 |
| EC3.6.3.12 | Potassium-transporting ATPase | 0.63 | 7.27E-158 |
| EC1.1.1.85 | 3-isopropylmalate dehydrogenase | 0.64 | 7.80E-10 |
| EC1.1.1.86 | Ketol-acid reductoisomerase | 0.65 | 5.89E-24 |
| EC1.1.1.44 | Phosphogluconate dehydrogenase (decarboxylating) | 0.66 | 3.12E-34 |
| EC3.4.23.36 | Signal peptidase II | 0.67 | 5.83E-14 |
| EC1.11.1.15 | Peroxiredoxin | 0.67 | 1.47E-108 |
| EC3.2.2.— | NA | 0.68 | 1.17E-21 |
| EC1.2.1.21 | Glycolaldehyde dehydrogenase | 0.68 | 6.60E-06 |
| EC1.2.1.22 | Lactaldehyde dehydrogenase | 0.68 | 6.60E-06 |
| EC1.1.1.49 | Glucose-6-phosphate dehydrogenase | 0.68 | 2.90E-20 |
| EC2.3.1.79 | Maltose O-acetyltransferase | 0.68 | 2.17E-06 |

TABLE 28-continued

Transcriptional responses of the 14-member artificial community to *V. cholerae* Fecal meta-transcriptomes of mice in D1invasion vs D14invasion treatment groups (both groups sampled 4 days after initial gavage)

| EC assignment | EC Annotation in KEGG | Fold difference (mean RPKM D14invasion)/mean RPKM D1invasion) | Benjamini-Hochberg corrected P-value (Shotgun FunctionalizeR) |
|---|---|---|---|
| EC2.5.1.47 | Cysteine synthase | 0.68 | 7.21E−15 |
| EC1.6.99.3 | NADH dehydrogenase | 0.69 | 3.35E−09 |
| EC1.11.1.9 | Glutathione peroxidase | 0.70 | 2.11E−07 |
| EC3.4.23.— | NA | 0.71 | 9.75E−13 |
| EC1.15.1.1 | Superoxide dismutase | 0.71 | 2.23E−79 |
| EC4.2.1.11 | Phosphopyruvate hydratase | 0.72 | 5.14E−24 |
| EC1.1.1.28 | D-lactate dehydrogenase | 0.74 | 3.38E−06 |
| EC2.6.1.1 | Aspartate transaminase | 0.75 | 2.16E−08 |
| EC1.5.1.2 | Pyrroline-5-carboxylate reductase | 0.76 | 1.83E−06 |
| EC3.6.3.4 | Copper-exporting ATPase | 0.76 | 2.66E−07 |
| EC2.7.7.3 | Pantetheine-phosphate adenylyltransferase | 0.76 | 3.68E−06 |
| EC3.1.3.18 | Phosphoglycolate phosphatase | 0.77 | 1.36E−16 |
| EC3.1.1.31 | 6-phosphogluconolactonase | 0.77 | 6.57E−16 |
| EC1.1.1.42 | Isocitrate dehydrogenase (NADP(+)) | 0.78 | 4.31E−08 |
| EC1.6.5.3 | NADH dehydrogenase (ubiquinone) | 0.78 | 4.30E−18 |
| EC6.5.1.2 | DNA ligase (NAD(+)) | 0.78 | 6.60E−06 |
| EC2.7.1.4 | Fructokinase | 0.78 | 3.70E−09 |
| EC3.4.21.— | NA | 0.78 | 1.85E−15 |
| EC3.4.24.— | NA | 0.79 | 6.33E−26 |
| EC4.2.1.3 | Aconitate hydratase | 0.79 | 2.18E−09 |
| EC2.7.13.3 | Histidine kinase | 0.79 | 7.26E−18 |
| EC2.7.8.— | NA | 0.80 | 6.11E−06 |
| EC2.3.3.1 | Citrate (Si)-synthase | 0.81 | 5.24E−09 |
| EC1.2.1.12 | Glyceraldehyde-3-phosphate dehydrogenase (phosphorylating) | 0.83 | 1.89E−39 |
| EC2.4.2.10 | Orotate phosphoribosyltransferase | 0.85 | 1.92E−07 |
| EC4.1.2.13 | Fructose-bisphosphate aldolase | 0.87 | 5.37E−17 |
| EC4.2.1.52 | Dihydrodipicolinate synthase | 0.87 | 8.05E−06 |
| EC3.6.3.14 | H(+)-transporting two-sector ATPase | 0.89 | 9.63E−36 |
| EC4.1.1.49 | Phosphoenolpyruvate carboxykinase (ATP) | 0.92 | 1.33E−06 |
| EC3.6.5.3 | Protein-synthesizing GTPase | 1.14 | 2.77E−33 |
| EC3.5.1.28 | N-acetylmuramoyl-L-alanine amidase | 1.16 | 6.46E−08 |
| EC5.3.1.6 | Ribose-5-phosphate isomerase | 1.18 | 4.62E−06 |
| EC2.7.7.6 | DNA-directed RNA polymerase | 1.22 | 2.64E−26 |
| EC3.2.1.23 | Beta-galactosidase | 1.22 | 1.16E−17 |
| EC1.3.99.1 | Succinate dehydrogenase | 1.23 | 4.12E−14 |
| EC3.2.1.21 | Beta-glucosidase | 1.25 | 1.40E−12 |
| EC2.3.1.179 | Beta-ketoacyl-acyl-carrier-protein synthase II | 1.25 | 5.80E−11 |
| EC3.2.1.51 | Alpha-L-fucosidase | 1.26 | 2.81E−10 |
| EC3.6.1.1 | Inorganic diphosphatase | 1.26 | 7.71E−06 |
| EC3.4.11.18 | Methionyl aminopeptidase | 1.27 | 5.04E−16 |
| EC4.1.2.17 | L-fuculose-phosphate aldolase | 1.28 | 2.92E−07 |
| EC3.2.1.52 | Beta-N-acetylhexosaminidase | 1.29 | 2.10E−22 |
| EC1.6.5.— | NA | 1.30 | 2.81E−21 |
| EC3.5.4.5 | Cytidine deaminase | 1.31 | 9.56E−08 |
| EC3.4.11.4 | Tripeptide aminopeptidase | 1.31 | 2.78E−06 |
| EC5.4.2.8 | Phosphomannomutase | 1.32 | 4.48E−14 |
| EC6.1.1.15 | Proline--tRNA ligase | 1.32 | 3.43E−10 |
| EC2.4.1.25 | 4-alpha-glucanotransferase | 1.34 | 3.23E−09 |
| EC1.21.4.2 | Glycine reductase | 1.34 | 2.61E−17 |
| EC2.3.1.129 | Acyl-[acyl-carrier-protein]--UDP-N-acetylglucosamine O-acyltransferase | 1.36 | 4.80E−11 |
| EC3.5.99.6 | Glucosamine-6-phosphate deaminase | 1.37 | 4.71E−43 |
| EC2.7.1.69 | Protein-N(pi)-phosphohistidine--sugar phosphotransferase | 1.38 | 6.38E−90 |
| EC2.4.1.1 | Phosphorylase | 1.39 | 2.87E−15 |
| EC2.1.2.5 | Glutamate formimidoyltransferase | 1.39 | 8.70E−08 |
| EC5.3.1.25 | L-fucose isomerase | 1.40 | 9.32E−46 |
| EC3.1.1.53 | Sialate O-acetylesterase | 1.41 | 2.76E−07 |
| EC2.1.2.10 | Aminomethyltransferase | 1.42 | 2.07E−15 |
| EC2.7.2.7 | Butyrate kinase | 1.46 | 2.55E−07 |
| EC3.4.13.9 | Xaa-Pro dipeptidase | 1.49 | 1.20E−12 |
| EC1.4.4.2 | Glycine dehydrogenase (decarboxylating) | 1.50 | 1.21E−07 |
| EC2.7.1.— | NA | 1.52 | 3.48E−06 |
| EC5.3.1.4 | L-arabinose isomerase | 1.52 | 1.73E−40 |
| EC2.7.2.2 | Carbamate kinase | 1.52 | 1.15E−11 |
| EC2.7.1.15 | Ribokinase | 1.53 | 2.77E−10 |
| EC4.1.1.15 | Glutamate decarboxylase | 1.55 | 6.66E−23 |
| EC4.1.3.3 | N-acetylneuraminate lyase | 1.55 | 1.35E−78 |
| EC2.7.1.5 | Rhamnulokinase | 1.59 | 2.55E−07 |
| EC2.3.1.54 | Formate C-acetyltransferase | 1.61 | 5.51E−25 |
| EC1.2.99.2 | Carbon-monoxide dehydrogenase (acceptor) | 1.61 | 1.06E−82 |
| EC3.2.1.89 | Arabinogalactan endo-1,4-beta-galactosidase | 1.66 | 6.47E−23 |

TABLE 28-continued

Transcriptional responses of the 14-member artificial community to *V. cholerae*
Fecal meta-transcriptomes of mice in D1invasion vs D14invasion
treatment groups (both groups sampled 4 days after initial gavage)

| EC assignment | EC Annotation in KEGG | Fold difference (mean RPKM D14invasion)/mean RPKM D1invasion) | Benjamini-Hochberg corrected P-value (Shotgun FunctionalizeR) |
|---|---|---|---|
| EC5.1.3.8 | N-acylglucosamine 2-epimerase | 1.68 | 5.47E−114 |
| EC3.2.1.55 | Alpha-N-arabinofuranosidase | 1.71 | 8.19E−26 |
| EC3.4.11.9 | Xaa-Pro aminopeptidase | 1.76 | 1.11E−40 |
| EC3.5.2.7 | Imidazolonepropionase | 1.77 | 3.84E−17 |
| EC6.3.4.3 | Formate--tetrahydrofolate ligase | 1.78 | 2.53E−120 |
| EC4.3.1.12 | Ornithine cyclodeaminase | 1.81 | 1.44E−10 |
| EC2.7.1.30 | Glycerol kinase | 1.81 | 1.43E−16 |
| EC3.5.4.2 | Adenine deaminase | 1.84 | 4.36E−10 |
| EC1.1.1.14 | L-iditol 2-dehydrogenase | 1.89 | 3.73E−06 |
| EC3.4.11.— | NA | 2.04 | 2.42E−12 |
| EC1.97.1.9 | Selenate reductase | 2.18 | 3.68E−06 |
| EC2.3.1.9 | Acetyl-CoA C-acetyltransferase | 2.27 | 3.97E−15 |
| EC1.21.4.1 | D-proline reductase (dithiol) | 2.38 | 0 |
| EC5.1.1.4 | Proline racemase | 2.49 | 6.89E−116 |
| EC1.17.1.4 | Xanthine dehydrogenase | 2.55 | 1.03E−26 |
| EC2.7.1.39 | Homoserine kinase | 2.73 | 1.20E−07 |
| EC3.5.4.3 | Guanine deaminase | 2.79 | 7.29E−44 |
| EC1.1.1.6 | Glycerol dehydrogenase | 2.83 | 3.27E−08 |
| EC3.5.2.10 | Creatininase | 2.84 | 4.40E−17 |
| EC1.1.1.157 | 3-hydroxybutyryl-CoA dehydrogenase | 3.22 | 2.43E−22 |
| EC4.1.2.— | NA | 5.05 | 7.58E−13 |
| EC3.4.11.5 | Prolyl aminopeptidase | 5.18 | 2.20E−84 |
| EC2.7.1.92 | 5-dehydro-2-deoxygluconokinase | 7.26 | 1.14E−06 |
| EC5.3.1.— | NA | 7.27 | 1.27E−06 |
| EC2.8.3.1 | Propionate CoA-transferase | 7.80 | 3.77E−08 |
| EC3.2.1.26 | Beta-fructofuranosidase | 10.71 | 1.93E−240 |
| EC3.7.1.— | NA | 18.78 | 3.73E−10 |
| EC2.7.10.1 | Receptor protein-tyrosine kinase | 19.32 | 1.88E−08 |

TABLE 29

PCR primers and bacterial strains

| Target gene | Primer name | Sequence | SEQ ID NO: |
|---|---|---|---|
| R. obeum luxS (RUMOBE02774) | TA-R0lux-f | CACCATGAAAAAAATTGCAAGTTTTACC | 61 |
| | TA-R0lux-r | TTATTCCGGATAAGTCAGACGTTC | 62 |
| V. cholerae luxS (VC0557) | TA-VC0557-f | CACCATGCCATTATTAGACAGTTTTACC | 63 |
| | TA-VC0557-r | TTAGTGAACCTTCAGCTCATTG | 64 |

| Strain | Strain Background | Plasmid description | Antibiotics used for maintenance of plasmid in host bacterial strain |
|---|---|---|---|
| Ptcp-lux | C6706 | pJZ376 | Cm, 1 ug/mL |
| PBAD-VCluxS | DH5a | VC0557 in pBAD202-TOPO | Km, 50 ug/mL |
| PBAD-R0luxS | DH5a | RUMOBE02774 in pBAD202-TOPO | Km, 50 ug/mL |
| PBAD-lacZ | DH5a | lacZ in pBAD202-TOPO | Km, 50 ug/mL |

Cm, chloramphenicol, Km, kanamycin

The invention claimed is:

1. A method to determine the relative maturity of a subject's gut microbiota to identify and treat a subject in need of treatment, the method comprising:
   (a) detecting a relative abundance for each bacterial taxon in a group comprising (i) obtaining a fecal sample from a subject or providing a fecal sample obtained from a subject; (ii) isolating nucleic acids from the fecal sample; (iii) amplifying nucleic acids with primers directed at a variable region of a bacterial 16S rRNA gene; and (iv) detecting nucleic acids associated with bacterial taxa in the group by 16S rRNA sequencing or hybridization array; wherein the group comprises *Faecalibacterium prausnitzii* OTU ID 326792, *Ruminococcus* sp. 5 1 39BFAA OTU ID 189827, *Lactobacillus ruminis* OTU ID 470663, *Dorea longicatena* OTU ID 191687, *Bifidobacterium longum* OTU ID 72820, and *Ruminococcus* sp. 5 1 39BFAA OTU ID 194745;
   (b) determining a microbiota age for the subject's gut microbiota comprising applying the relative abundances of the bacterial taxa from step (a) to a regression model, wherein the model regresses, for a group of healthy subjects, relative abundances of the same bacterial taxa, as determined from a plurality of gut microbiota samples obtained over time for each healthy subject in the group, against the chronological age of each healthy subject in the group at the time the gut microbiota sample was obtained;
   (c) calculating the relative maturity of the subject's gut microbiota, wherein relative maturity=(microbiota age of the subject)–(microbiota age of a healthy subject of a similar chronological age); and
   (d) providing a treatment to the subject with a relative maturity that is a negative value to increase the relative maturity value.

2. The method of claim 1, wherein the group comprises at least *Faecalibacterium prausnitzii* OTU ID 326792, *Ruminococcus* sp. 5 1 39BFAA OTU ID 189827, *Lactobacillus ruminis* OTU ID 470663, *Dorea longicatena* OTU ID 191687, *Bifidobacterium longum* OTU ID 72820, and *Ruminococcus* sp. 5 1 39BFAA OTU ID 194745 and at least one bacterial taxon from the group comprising of *Lactobacillus mucosae* OTU ID 15141, *Bifidobacterium* OTU ID 561483, *Staphylococcus* OTU ID 217996, *Ruminococcus* sp. 5 1 39BFAA OTU ID 364234, *Catenibacterium mitsuokai* OTU ID 287510, *Dorea formicigenerans* OTU ID 261912, *Ruminococcus torques* OTU ID 361809, *Streptococcus thermophilus* OTU ID 108747, *Bifidobacterium* sp. OTU ID 533785, *Haemophilus parainfluenzae* OTU ID 9514, *Streptococcus* sp. OTU ID 561636, *Clostridium* sp. OTU ID 312461, *Clostridium ramosum* OTU ID 470139, *Clostridium* sp. OTU ID 181834, *Weissella cibaria* OTU ID 148099, *Bifidobacterium* sp. OTU ID 469873, *Clostridiales* sp. OTU ID 185951, and *Ruminococcaceae* sp. OTU ID 212619.

3. The method of claim 1, wherein the group in step (a) comprises at least *Faecalibacterium prausnitzii* OTU ID 326792, *Ruminococcus* sp. 5 1 39BFAA OTU ID 189827, *Lactobacillus ruminis* OTU ID 470663, *Dorea longicatena* OTU ID 191687, *Bifidobacterium longum* OTU ID 72820, *Ruminococcus* sp. 5 1 39BFAA OTU ID 194745, *Lactobacillus mucosae* OTU ID 15141, *Bifidobacterium* OTU ID 561483, *Staphylococcus* OTU ID 217996, *Ruminococcus* sp. 5 1 39BFAA OTU ID 364234, *Catenibacterium mitsuokai* OTU ID 287510, *Dorea formicigenerans* OTU ID 261912, *Ruminococcus torques* OTU ID 361809, *Streptococcus thermophilus* OTU ID 108747, *Bifidobacterium* sp. OTU ID 533785, *Haemophilus parainfluenzae* OTU ID 9514, *Streptococcus* sp. OTU ID 561636, *Clostridium* sp. OTU ID 312461, *Clostridium ramosum* OTU ID 470139, *Clostridium* sp. OTU ID 181834, *Weissella cibaria* OTU ID 148099, *Bifidobacterium* sp. OTU ID 469873, *Clostridiales* sp. OTU ID 185951, and *Ruminococcaceae* sp. OTU ID 212619.

4. The method of claim 1, wherein the calculation for maturity is defined as a Microbiota-for-Age Z score (MAZ), wherein MAZ=((microbiota age of the subject)–(median microbiota age of a healthy subject of a similar chronological age))/(standard deviation of microbiota age of healthy subjects of the similar chronological age).

5. The method of claim 1, wherein the age of the subject and the age of the healthy subject(s) are within about 1 month, about 2 months, or about 3 months.

6. The method of claim 1, wherein the group of bacterial taxa in step (a) comprises at least 12 bacterial taxa from the group comprising of *Bifidobacterium bifidum* OTU ID 469852, *Eubacterium desmolans* OTU ID 170124, *Faecalibacterium prausnitzii* OTU ID 187010, *Prevotella copri* OTU ID 303304, *Lactobacillus reuteri* OTU ID 470527, *Enterobacteriaceae* sp. OTU ID 210269, *Clostridium glycolicum* OTU ID 182202, *Ruminococcus obeum* OTU ID 178122, *Enterococcus faecalis* OTU ID 540230, *Prevotella copri* OTU ID 309068, *Bifidobacterium* sp. OTU ID 24773, *Enterococcus* sp. OTU ID 554755, *Escherichia coli* OTU ID 305760, *Prevotella* sp. OTU ID 268604, *Faecalibacterium prausnitzii* OTU ID 188900, *Eubacterium hallii* OTU ID 174256, *Bacteroides fragilis* OTU ID 130663, *Streptococcus* sp. OTU ID 292424, *Staphylococcus* sp. OTU ID 269541, *Ruminococcus* sp. 5 1 39BFAA OTU ID 191900, *Dialister* sp. OTU ID 48207, *Collinsella aerofaciens* OTU ID 186029, *Clostridium bartlettii* OTU ID 325608, *Lactobacillus* sp. OTU ID 252321, *Prevotella* sp. OTU ID 195574, *Ruminococcus* sp. 5 1 39BFAA OTU ID 365047, *Lactobacillus ruminis* OTU ID 471308, *Enterobacteriaceae* sp. OTU ID 307981, *Streptococcus* sp. OTU ID 15382, *Clostridium disporicum* OTU ID 302844, *Streptococcus parasanguinis* OTU ID 528842, *Bifidobacterium* sp. OTU ID 131391, *Megamonas* sp. OTU ID 259261, *Clostridium* sp. OTU ID 248563, *Megasphaera* sp. OTU ID 162427, and *Lactobacillus* sp. OTU ID 545371.

7. The method of claim 1, wherein the group of bacterial taxa in step (a) comprises at least *Bifidobacterium bifidum* OTU ID 469852, *Eubacterium desmolans* OTU ID 170124, *Faecalibacterium prausnitzii* OTU ID 187010, *Prevotella copri* OTU ID 303304, *Lactobacillus reuteri* OTU ID 470527, *Enterobacteriaceae* sp. OTU ID 210269, *Clostridium glycolicum* OTU ID 182202, *Ruminococcus obeum* OTU ID 178122, *Enterococcus faecalis* OTU ID 540230, *Prevotella copri* OTU ID 309068, *Bifidobacterium* sp. OTU ID 24773, *Enterococcus* sp. OTU ID 554755, *Escherichia coli* OTU ID 305760, *Prevotella* sp. OTU ID 268604, *Faecalibacterium prausnitzii* OTU ID 188900, *Eubacterium hallii* OTU ID 174256, *Bacteroides fragilis* OTU ID 130663, *Streptococcus* sp. OTU ID 292424, *Staphylococcus* sp. OTU ID 269541, *Ruminococcus* sp. 5 1 39BFAA OTU ID 191900, *Dialister* sp. OTU ID 48207, *Collinsella aerofaciens* OTU ID 186029, *Clostridium bartlettii* OTU ID 325608, *Lactobacillus* sp. OTU ID 252321, *Prevotella* sp. OTU ID 195574, *Ruminococcus* sp. 5 1 39BFAA OTU ID 365047, *Lactobacillus ruminis* OTU ID 471308, *Enterobacteriaceae* sp. OTU ID 307981, *Streptococcus* sp. OTU ID 15382, *Clostridium disporicum* OTU ID 302844, *Streptococcus parasanguinis* OTU ID 528842, *Bifidobacterium* sp. OTU ID 131391, *Megamonas* sp. OTU ID 259261, *Clostridium* sp. OTU ID 248563, *Megasphaera* sp. OTU ID 162427, and *Lactobacillus* sp. OTU ID 545371.

8. The method of claim 1, wherein the treatment is for a gastrointestinal disease.

9. The method of claim 8, wherein the gastrointestinal disease is malnutrition, an infection caused by an enteropathogen, ulcerative colitis, necrotizing enterocolitis, Crohn's disease, chronic diarrhea, or acute diarrhea.

10. The method of claim 1, wherein the treatment is a probiotic.

11. The method of claim 1, wherein the treatment is a therapeutic food.

12. The method of claim 1, wherein the treatment is a probiotic and a therapeutic food.

* * * * *

SEQUENCE LISTING

<160> NUMBER OF SEQ ID NOS: 64

<210> SEQ ID NO 1
<211> LENGTH: 253
<212> TYPE: DNA
<213> ORGANISM: Faecalibacterium_prausnitzii

<400> SEQUENCE: 1
aacgtaggtc acaagcgttg tccggaatta ctgggtgtaa agggagcgca ggcgggagaa    60

```
caagttggaa gtgaaatcca tgggctcaac ccatgaactg ctttcaaaac tgttttctt      120 gagtagtgca gaggtaggcg gaattcccgg tgtagcggtg aatgcgtag atatcgggag       180 gaacaccagt ggcgaaggcg gcctactggg caccaactga cgctgaggct cgaaagtgtg     240
ggtagcaaac agg                                                          253

<210> SEQ ID NO 2
<211> LENGTH: 253
<212> TYPE: DNA
<213> ORGANISM: Ruminococcus_sp_5_1_39BFAA

<400> SEQUENCE: 2
tacgtagggg gcaagcgtta tccggattta ctgggtgtaa agggagcgta gacggtgtgg      60
caagtctgat gtgaaaggca tgggctcaac ctgtggactg cattggaaac tgtcatactt     120
gagtgccgga ggggtaagcg gaattcctag tgtagcggtg aaatgcgtag atattaggag     180
gaacaccagt ggcgaaggcg gcttactgga cggtaactga cgttgaggct cgaaagcgtg     240
gggagcaaac agg                                                          253

<210> SEQ ID NO 3
<211> LENGTH: 253
<212> TYPE: DNA
<213> ORGANISM: Lactobacillus ruminis

<400> SEQUENCE: 3
tacgtaggtg gcgagcgttg tccggattta ttgggcgtaa agggaacgca ggcggtctt      60 taagtctgat gtgaaagcct tcggcttaac cgaagtagtg cattggaaac tggaagactt    120
gagtgcagaa gaggagagtg gaactccatg tgtagcggtg aaatgcgtag atatatggaa    180
gaacaccagt ggcgaaagcg gctctctggt ctgtaactga cgctgaggtt cgaaagcgtg    240
ggtagcaaac agg                                                          253

<210> SEQ ID NO 4
<211> LENGTH: 253
<212> TYPE: DNA
<213> ORGANISM: Dorea longicatena

<400> SEQUENCE: 4
tacgtagggg gcaagcgtta tccggattta ctgggtgtaa agggagcgta gacggcacgg      60
caagccagat gtgaaagccc ggggctcaac cccgggactg catttggaac tgctgagcta    120
gagtgtcgga gaggcaagtg gaattcctag tgtagcggtg aaatgcgtag atattaggag    180
gaacaccagt ggcgaaggcg gcttgctgga cgatgactga cgttgaggct cgaaagcgtg    240
gggagcaaac agg                                                          253

<210> SEQ ID NO 5
<211> LENGTH: 253
<212> TYPE: DNA
<213> ORGANISM: Bifidobacterium longum

<400> SEQUENCE: 5
tacgtagggt gcaagcgtta tccggaatta ttgggcgtaa agggctcgta ggcggttcgt      60
cgcgtccggt gtgaaagtcc atcgcttaac ggtggatccg cgccgggtac gggcgggctt    120
gagtgcggta ggggagactg gaattcccgg tgtaacggtg aatgtgtag atatcgggaa     180 gaacaccaat ggcgaaggca ggtctctggg ccgttactga cgctgaggag cgaaagcgtg    240
```

```
gggagcgaac agg                                                         253

<210> SEQ ID NO 6
<211> LENGTH: 253
<212> TYPE: DNA
<213> ORGANISM: Ruminococcus_sp_5_1_39BFAA

<400> SEQUENCE: 6
tacgtagggg gcaagcgtta tccggattta ctgggtgtaa agggagcgta gacggtgtgg      60
caagtctgat gtgaaaggca tgggctcaac ccgtggactg cattggaaac tgtcatactt    120
gagtgccgga ggggtaagcg gaattcctag tgtagcggtg aaatgcgtag atattaggag    180
gaacaccagt ggcgaaggcg gcttactgga cggtaactga cgttgaggct cgaaagcgtg    240
gggagcaaac agg                                                         253

<210> SEQ ID NO 7
<211> LENGTH: 253
<212> TYPE: DNA
<213> ORGANISM: Lactobacillus mucosae

<400> SEQUENCE: 7
tacgtaggtg gcaagcgtta tccggattta ttgggcgtaa agcgagcgca ggcggtttga      60
taagtctgat gtgaaagcct ttggcttaac caaagaagtg catcggaaac tgtcagactt    120
gagtgcagaa gaggacagtg gaactccatg tgtagcggtg aatgcgtag atatatggaa     180 gaacaccagt ggcgaaggcg gctgtctggt ctgcaactga cgctgaggct cgaaagcatg    240
ggtagcgaac agg                                                         253

<210> SEQ ID NO 8
<211> LENGTH: 253
<212> TYPE: DNA
<213> ORGANISM: Bifidobacterium

<400> SEQUENCE: 8
tacgtagggt gcaagcgtta tccggaatta ttgggcgtaa agggctcgta ggcggttcgt      60
cgcgtccggt gtgaaagtcc atcgcttaac ggtggatccg cgccgggtac gggcgggctt    120
gagtgcggta ggggagactg gaattcccgg tgtaacggtg aatgtgtag atatcgggaa     180 gaacaccaat ggcgaaggca ggtctctggg ccgttactga cgctgaggag cggaagcgtg    240
gggagcgaac agg                                                         253

<210> SEQ ID NO 9
<211> LENGTH: 253
<212> TYPE: DNA
<213> ORGANISM: Staphylococcus

<400> SEQUENCE: 9
tacgtaggtg gcaagcgtta tccggaatta ttgggcgtaa agcgcgcgta ggcggttttt      60
taagtctgat gtgaaagccc acggctcaac cgtggagggt cattggaaac tggaaaactt    120
gagtgcagaa gaggaaagtg gaattccatg tgtagcggtg agatgcgcag agatatggag    180
gaacaccagt ggcgaaggcg actttctggt ctgtaactga cgctgatgtg cgaaagcgtg    240
gggatcaaac agg                                                         253

<210> SEQ ID NO 10
<211> LENGTH: 253
<212> TYPE: DNA
<213> ORGANISM: Ruminococcus_sp_5_1_39BFAA
```

```
<400> SEQUENCE: 10
tacgtagggt gcaagcgtta tccggattta ctgggtgtaa agggagcgta gacggtgtgg      60
caagtctgat gtgaaaggca tgggctcaac ctgtggactg cattggaaac tgtcatactt     120
gagtgccgga ggggtaagcg gaattcctag tgtagcggtg aaatgcgtag atattaggag     180
gaacaccagt ggcgaaggcg gcttactgga cggtaactga cgttgaggct cgaaagcgtg     240
gggagcaaac agg                                                        253

<210> SEQ ID NO 11
<211> LENGTH: 252
<212> TYPE: DNA
<213> ORGANISM: Catenibacterium mitsuokai

<400> SEQUENCE: 11
tacgtaggtg gcgagcgtta tccggaatca ttgggcgtaa agagggagca ggcggccgca      60
agggtctgtg gtgaaagacc gaagctaaac ttcgtaagc catggaaacc gggcggctag      120
agtgcggaag aggatcgtgg aattccatgt gtagcggtga aatgcgtaga tatatggagg     180
aacaccagtg gcgaaggcga cggtctgggc cgcaactgac gctcattccc gaaagcgtgg     240
ggagcaaata gg                                                        252

<210> SEQ ID NO 12
<211> LENGTH: 253
<212> TYPE: DNA
<213> ORGANISM: Dorea formicigenerans

<400> SEQUENCE: 12
tacgtagggg gcaagcgtta tccggattta ctgggtgtaa agggagcgta gacggctgtg      60
caagtctgaa gtgaaaggca tgggctcaac ctgtggactg ctttggaaac tgtgcagcta     120
gagtgtcgga gaggtaagtg gaattcctag tgtagcggtg aaatgcgtag atattaggag     180
gaacaccagt ggcgaaggcg gcttactgga cgatgactga cgttgaggct cgaaagcgtg     240
gggagcaaac agg                                                        253

<210> SEQ ID NO 13
<211> LENGTH: 253
<212> TYPE: DNA
<213> ORGANISM: Ruminococcus torques

<400> SEQUENCE: 13
tacgtatggt gcaagcgtta tccggattta ctgggtgtaa agggagcgta gacggagtgg      60
caagtctgat gtgaaaaccc ggggctcaac cccgggactg cattggaaac tgtcaatcta     120
gagtaccgga gaggtaagcg gaattcctag tgtagcggtg aaatgcgtag atattaggag     180
gaacaccagt ggcgaaggcg gcttactgga cggtaactga cgttgaggct cgaaagcgtg     240
gggagcaaac agg                                                        253

<210> SEQ ID NO 14
<211> LENGTH: 252
<212> TYPE: DNA
<213> ORGANISM: Streptococcus thermophilus

<400> SEQUENCE: 14
tacgtaggtc ccgagcgttg tccggattta ttgggcgtaa agcgagcgca ggcggtttga      60
taagtctgaa gttaaaggct gtggctcaac catagttcgc tttggaaact gtcaaacttg     120
```

```
agtgcagaag gggagagtgg aattccatgt gtagcggtga aatgcgtaga tatatggagg    180
aacaccggtg gcgaaagcgg ctctctggtc tgtaactgac gctgaggctc gaaagcgtgg    240
ggagcgaaca gg                                                        252
```

```
<210> SEQ ID NO 15
<211> LENGTH: 253
<212> TYPE: DNA
<213> ORGANISM: Bifidobacterium

<400> SEQUENCE: 15
tacgtagggc gcaagcgtta tccggattta tgggcgtaa agggctcgta ggcggttcgt    60
cgcgtccggt gtgaaagtcc atcgcttaac ggtggatccg cgccgggtac gggcgggctt    120
gagtgcggta ggggagactg gaattcccgg tgtaacggtg aatgtgtag atatcgggaa     180 gaacaccaat ggcgaaggca ggtctctggg ccgttactga cgctgaggag cgaaagcgtg    240
gggagcgaac agg                                                       253
```

```
<210> SEQ ID NO 16
<211> LENGTH: 253
<212> TYPE: DNA
<213> ORGANISM: Haemophilus parainfluenzae

<400> SEQUENCE: 16
tacggagggt gcgagcgtta atcggaataa ctgggcgtaa agggcacgca ggcggtgact    60
taagtgaggt gtgaaagccc cgggcttaac ctgggaattg catttcatac tgggtcgcta    120
gagtacttta ggaggggta gaattccacg tgtagcggtg aaatgcgtag agatgtggag     180
gaataccgaa ggcgaaggca gccccttggg aatgtactga cgctcatgtg cgaaagcgtg    240
gggagcaaac agg                                                       253
```

```
<210> SEQ ID NO 17
<211> LENGTH: 252
<212> TYPE: DNA
<213> ORGANISM: Streptococcus

<400> SEQUENCE: 17
tacgtaggtc ccgagcgtta tccggattta ttgggcgtaa agcgagcgca ggcggttaga    60
taagtctgaa gttaaaggct gtggcttaac catagtacgc tttggaaact gtttaacttg    120
agtgcaagag gggagagtgg aattccatgt gtagcggtga aatgcgtaga tatatggagg    180
aacaccggtg gcgaaagcgg ctctctggct tgtaactgac gctgaggctc gaaagcgtgg    240
ggagcaaaca gg                                                        252
```

```
<210> SEQ ID NO 18
<211> LENGTH: 252
<212> TYPE: DNA
<213> ORGANISM: Clostridium

<400> SEQUENCE: 18
tacgtagggg gctagcgtta tccggaatta ctgggcgtaa agggtgcgta ggtggtttct    60
taagtcagag gtgaaaggct acggctcaac cgtagtaagc ctttgaaact gggaacttg     120 agtgcaggag aggagagtgg aattcctagt gtagcggtga aatgcgtaga tattaggagg    180
aacaccagtt gcgaaggcgg ctctctggac tgtaactgac actgaggcac gaaagcgtgg    240
ggagcaaaca gg                                                        252
```

```
<210> SEQ ID NO 19
<211> LENGTH: 252
<212> TYPE: DNA
<213> ORGANISM: Clostridium ramosum

<400> SEQUENCE: 19
tacgtaggtg gcaagcgtta tccggaatta ttgggcgtaa agagggagca ggcggcagca      60
agggtctgtg gtgaaagcct gaagcttaac ttcagtaagc catagaaacc aggcagctag     120
agtgcaggag aggatcgtgg aattccatgt gtagcggtga aatgcgtaga tatatggagg     180
aacaccagtg gcgaaggcga cgatctggcc tgcaactgac gctcagtccc gaaagcgtgg     240
ggagcaaata gg                                                        252

<210> SEQ ID NO 20
<211> LENGTH: 253
<212> TYPE: DNA
<213> ORGANISM: Clostridium

<400> SEQUENCE: 20
tacgtagggg gcaagcgtta tccggattta ctgggtgtaa agggagcgca gacggcgatg      60
caagtctgaa gtgaaagccc ggggctcaac cccgggactg cttttggaaac tgtatggcta    120 gagtgctgga gaggcaagcg gaattcctag tgtagcggtg aaatgcgtag atattaggaa     180
gaacaccagt ggcgaaggcg gcttgctgga cagtaactga cgttcaggct cgaaagcgtg     240
gggagcaaac agg                                                       253

<210> SEQ ID NO 21
<211> LENGTH: 253
<212> TYPE: DNA
<213> ORGANISM: Weissella cibaria

<400> SEQUENCE: 21
tacgtatgtt ccaagcgtta tccggattta ttgggcgtaa agcgagcgca gacggttatt      60
taagtctgaa gtgaaagccc tcagctcaac tgaggaattg ctttggaaac tggatgactt    120
gagtgcagta gaggaaagtg gaactccatg tgtagcggtg aaatgcgtag atatatggaa     180
gaacaccagt ggcgaaggcg gctttctgga ctgtaactga cgttgaggct cgaaagtgtg     240
ggtagcaaac agg                                                       253

<210> SEQ ID NO 22
<211> LENGTH: 253
<212> TYPE: DNA
<213> ORGANISM: Bifidobacterium

<400> SEQUENCE: 22
tacgtagggt gcaagcgtta tccggaatta ttgggcgtaa agggctcgta ggcggttcgt      60
cgcgtccggt gtgaaagtcc atcgcttaac ggtggatctg cgccgggtac gggcgggctg    120
gagtgcggta ggggagactg gaattcccgg tgtaacggtg aatgtgtag atatcggaa       180 gaaccaccaat ggcgaaggca ggtctctggg ccgttactga cgctgaggag cgaaagcgtg    240
gggagcgaac agg                                                       253

<210> SEQ ID NO 23
<211> LENGTH: 253
<212> TYPE: DNA
<213> ORGANISM: Unknown
<220> FEATURE:
<223> OTHER INFORMATION: SYNTHESIZED
```

```
<400> SEQUENCE: 23
tacgtagggg gcaagcgtta tccggattta ctgggtgtaa agggagcgta gacggatgga    60
caagtctgat gtgaaaggct ggggctcaac cccgggactg cattggaaac tgcccgtctt   120
gagtgccgga gaggtaagcg gaattcctag tgtagcggtg aaatgcgtag atattaggag   180
gaacaccagt ggcgaaggcg gcttactgga cggtaactga cgttgaggct cgaaagcgtg   240
gggagcaaac agg                                                     253

<210> SEQ ID NO 24
<211> LENGTH: 253
<212> TYPE: DNA
<213> ORGANISM: Unknown
<220> FEATURE:
<223> OTHER INFORMATION: SYNTHESIZED

<400> SEQUENCE: 24
aacgtagggt gcaagcgttg tccggaatta ctgggtgtaa agggagcgca ggcggaccgg    60
caagttggaa gtgaaaacta tgggctcaac ccataaattg ctttcaaaac tgctggcctt   120
gagtagtgca gaggtaggtg gaattcccgg tgtagcggtg gaatgcgtag atatcgggag   180
gaacaccagt ggcgaaggcg acctactggg caccaactga cgctgaggct cgaaagcatg   240
ggtagcaaac agg                                                     253

<210> SEQ ID NO 25
<211> LENGTH: 253
<212> TYPE: DNA
<213> ORGANISM: Bifidobacterium bifidum

<400> SEQUENCE: 25
tacgtagggc gcaagcgtta tccggattta ttgggcgtaa agggctcgta ggcggctcgt    60
cgcgtccggt gtgaaagtcc atcgcttaac ggtggatctg cgccgggtac gggcgggctg   120
gagtgcggta ggggagactg gaattcccgg tgtaacggtg gaatgtgtag atatcggaa   180 gaacaccgat ggcgaaggca ggtctctggg ccgtcactga cgctgaggag cgaaagcgtg   240
gggagcgaac agg                                                     253

<210> SEQ ID NO 26
<211> LENGTH: 253
<212> TYPE: DNA
<213> ORGANISM: Eubacterium desmolans

<400> SEQUENCE: 26
tacgtaggga gcaagcgtta tccggattta ctgggtgtaa agggcgcgca ggcgggccgg    60
caagttggaa gtgaaatcta tgggcttaac ccataaactg ctttcaaaac tgctggtctt   120
gagtgatgga gaggcaggcg gaattccgtg tgtagcggtg aaatgcgtag atacgggag   180 gaacaccagt ggcgaaggcg gcctgctgga cattaactga cgctgaggcg cgaaagcgtg   240
gggagcaaac agg                                                     253

<210> SEQ ID NO 27
<211> LENGTH: 253
<212> TYPE: DNA
<213> ORGANISM: Faecalibacterium_prausnitzii

<400> SEQUENCE: 27
tacgtaggtc acaagcgttg tccggaatta ctgggtgtaa agggagcgca ggcgggagag    60
caagttggaa gtgaaatcca tgggctcaac ccatgaactg ctttcaaaac tgttttctt   120
```

```
gagtagtgca gaggtaggcg gaattcccgg tgtagcggtg gaatgcgtag atatcgggag    180
gaacaccagt ggcgaaggcg gcctactggg caccaactga cgctgaggct cgaaagtgtg    240
ggtagcaaac agg                                                       253
```

<210> SEQ ID NO 28
<211> LENGTH: 253
<212> TYPE: DNA
<213> ORGANISM: Prevotella copri

<400> SEQUENCE: 28

```
tacggaaggt ccgggcgtta tccggattta ttgggtttaa agggagcgta ggccggagat    60
taagcgtgtt gtgaaatgta gacgctcaac gtctgcactg cagcgcgaac tggtttcctt    120
gagtacgcac aaagtgggcg gaattcgtgg tgtagcggtg aaatgcttag atatcacgaa    180
gaactccgat tgcgaaggca gctcactgga gcgcaactga cgctgaagct cgaaagtgcg    240
ggtatcgaac agg                                                       253
```

<210> SEQ ID NO 29
<211> LENGTH: 253
<212> TYPE: DNA
<213> ORGANISM: Lactobacillus reuteri

<400> SEQUENCE: 29

```
tacgtaggtg gcaagcgtta tccggattta ttgggcgtaa agcgagcgca ggcggttgct    60
taggtctgat gtgaaagcct tcggcttaac cgaagaagtg catcggaaac cgggcgactt    120
gagtgcagaa gaggacagtg gaactccatg tgtagcggtg gaatgcgtag atatatggaa    180
gaacaccagt ggcgaaggcg gctgtctggt ctgcaactga cgctgaggct cgaaagcatg    240
ggtagcgaac agg                                                       253
```

<210> SEQ ID NO 30
<211> LENGTH: 253
<212> TYPE: DNA
<213> ORGANISM: Enterobacteriaceae

<400> SEQUENCE: 30

```
tacggagggt gcaagcgtta atcggaatta ctgggcgtaa agcgcacgca ggcggtctgt    60
caagtcggat gtgaaatccc cgggctcaac ctgggaactg cattcgaaac tggcaggcta    120
gagtcttgta gagggggggta gaattccagg tgtagcggtg aaatgcgtag agatctggag    180
gaataccggt ggcgaaggcg gccccctgga caaagactga cgctcaggtg cgaaagcgtg    240
gggagcaaac agg                                                       253
```

<210> SEQ ID NO 31
<211> LENGTH: 252
<212> TYPE: DNA
<213> ORGANISM: Clostridium glycolicum

<400> SEQUENCE: 31

```
tacgtagggg gctagcgtta tccggattta ctgggcgtaa agggtgcgta ggtggtttct    60
taagtcagga gtgaaaggct acggctcaac cgtagtaagc tcttgaaact gggaaacttg    120
agtgcaggag aggaaagtgg aattcctagt gtagcggtga aatgcgtaga tattaggagg    180
aacaccagta gcgaaggcgg cttttctgga ctgtaactga cactgaggca cgaaagcgtgg   240 ggagcaaaca gg                                                        252
```

<210> SEQ ID NO 32
<211> LENGTH: 253
<212> TYPE: DNA
<213> ORGANISM: Ruminococcus obeum

<400> SEQUENCE: 32

```
tacgtagggg gcaagcgtta tccggattta ctgggtgtaa agggagcgta gacggactgg      60
caagtctgat gtgaaaggcg ggggctcaac ccctggactg cattggaaac tgttagtctt     120
gagtgccgga gaggtaagcg gaattcctag tgtagcggtg aaatgcgtag atattaggag     180
gaacaccagt ggcgaaggcg gcttactgga cggtaactga cgttgaggct cgaaagcgtg     240
gggagcaaac agg                                                        253
```

<210> SEQ ID NO 33
<211> LENGTH: 253
<212> TYPE: DNA
<213> ORGANISM: Enterococcus faecalis

<400> SEQUENCE: 33

```
tacgtaggtg gcaagcgttg tccggattta ttgggcgtaa agcgagcgca ggcggtttct      60
taagtctgat gtgaaagccc ccggctcaac cggggagggt cattggaaac tgggagactt     120
gagtgcagaa gaggagagtg gaattccatg tgtagcggtg aaatgcgtag atatatggag     180
gaacaccagt ggcgaaggcg gctctctggt ctgtaactga cgctgaggct cgaaagcgtg     240
gggagcaaac agg                                                        253
```

<210> SEQ ID NO 34
<211> LENGTH: 253
<212> TYPE: DNA
<213> ORGANISM: Prevotella copri

<400> SEQUENCE: 34

```
tacggaaggt ccgggcgtta tccggattta ttgggtttaa agggagcgta ggccggagat      60
taagcgtgtt gtgaaatgta gatgctcaac atctgcactg cagcgcgaac tggtttcctt     120
gagtacgcac aaagtgggcg gaattcgtgg tgtagcggtg aaatgcttag atatcacgaa     180
gaactccgat tgcgaaggca gctcactgga gcgcaactga cgctgaagct cgaaagtgcg     240
ggtatcgaac agg                                                        253
```

<210> SEQ ID NO 35
<211> LENGTH: 253
<212> TYPE: DNA
<213> ORGANISM: Bifidobacterium

<400> SEQUENCE: 35

```
tacgtagggt gcaagcgtta tccggaatta ttgggcgtaa agggctcgta ggcggttcgt      60
cgcgtccggt gtgaaagtcc atcgcttaac ggtggatctg cgccgggtac gggcgggctg     120
gagtgcggta ggggagactg gaattcccgg tgtaacggtg aatgtgtag atatcgggaa     180 gaacaccgat ggcgaaggca ggtctctggg ccgtcactga cgctgaggag cgaaagcgtg     240
gggagcgaac agg                                                        253
```

<210> SEQ ID NO 36
<211> LENGTH: 253
<212> TYPE: DNA
<213> ORGANISM: Enterococcus

<400> SEQUENCE: 36

```
tacgtaggtg caagcgtta tccggattta tgggcgtaa agcgagcgca ggcggtttct     60
taagtctgat gtgaaagccc ccggctcaac cggggagggt cattggaaac tgggaaactt    120
gagtgcagaa gaggagagtg gaattccatg tgtagcggtg aaatgcgtag atatatggag   180
gaacaccagt ggcgaaagcg gctctctggt ctgtaactga cgctgaggtt cgaaagcgtg   240
ggtagcaaac agg                                                     253

<210> SEQ ID NO 37
<211> LENGTH: 253
<212> TYPE: DNA
<213> ORGANISM: Escherichia coli

<400> SEQUENCE: 37
tacggagggt gcaagcgtta atcggaatta ctgggcgtaa agcgcacgca ggcggtttgt    60
taagtcagat gtgaaatccc cgggctcaac ctgggaactg catctgatac tggcaagctt   120
gagtctcgta gaggggggta gaattccagg tgtagcggtg aaatgcgtag agatctggag   180
gaataccggt ggcgaaggcg gccccctgga cgaagactga cgctcaggtg cgaaagcgtg   240
gggagcaaac agg                                                     253

<210> SEQ ID NO 38
<211> LENGTH: 253
<212> TYPE: DNA
<213> ORGANISM: Prevotella

<400> SEQUENCE: 38
tacggaaggt ccgggcgtta tccggattta tgggtttaa agggagcgca ggcggacctt    60
taagtcagct gtgaaatacg gcggctcaac cgtcgaactg cagttgatac tggaggtctt   120
gagtgcacac agggatgctg gaattcatgg tgtagcggtg aaatgctcag atatcatgaa   180
gaactccgat cgcgaaggca ggcatccggg gtgcaactga cgctgaggct cgaaagtgcg   240
ggtatcaaac agg                                                     253

<210> SEQ ID NO 39
<211> LENGTH: 253
<212> TYPE: DNA
<213> ORGANISM: Faecalibacterium_prausnitzii

<400> SEQUENCE: 39
aacgtaggtc acaagcgttg tccggaatta ctgggtgtaa agggagcgca ggcgggagaa    60
caagttggaa gtgaaatcca tgggctcaac ccatgaactg ctttcaaaac tgttttttctt   120 gagtagtgca gaggtaggcg gaattcccgg tgtagcggtg gaatgcgtag atatcgggag   180
gaacaccagt ggcgaaggcg gcctactggg caccaactga cgctgaggct cgaaagtgtg   240
ggtagcaaac agg                                                     253

<210> SEQ ID NO 40
<211> LENGTH: 253
<212> TYPE: DNA
<213> ORGANISM: Eubacterium hallii

<400> SEQUENCE: 40
tacgtatgga gcaagcgtta tccggattta ctgggtgtaa agggtgcgta ggtggcagtg    60
caagtcagat gtgaaaggcc ggggctcaac cccggagctg catttgaaac tgctcggcta   120
gagtacagga gaggcaggcg gaattcctag tgtagcggtg aaatgcgtag atattaggag   180
```

```
gaacaccagt ggcgaaggcg gcctgctgga ctgttactga cactgaggca cgaaagcgtg      240
gggagcaaac agg                                                          253

<210> SEQ ID NO 41
<211> LENGTH: 253
<212> TYPE: DNA
<213> ORGANISM: Bacteroides fragilis

<400> SEQUENCE: 41
tacggaggat ccgagcgtta tccggattta ttgggtttaa agggagcgta ggtggactgg       60
taagtcagtt gtgaaagttt gcggctcaac cgtaaaattg cagttgatac tgtcagtctt      120
gagtacagta gaggtgggcg gaattcgtgg tgtagcggtg aaatgcttag atatcacgaa      180
gaactccgat tgcgaaggca gctcactgga ctgcaactga cactgatgct cgaaagtgtg      240
ggtatcaaac agg                                                          253

<210> SEQ ID NO 42
<211> LENGTH: 252
<212> TYPE: DNA
<213> ORGANISM: Streptococcus

<400> SEQUENCE: 42
tacgtaggtc ccgagcgttg tccggattta ttgggcgtaa agcgagcgca ggcggtttaa       60
taagtctgaa gttaaaggca gtggcttaac cattgttcgc tttggaaact gttagacttg      120
agtgcagaag gggagagtgg aattccatgt gtagcggtga aatgcgtaga tatgtggagg      180
aacaccggtg gcgaaagcgg ctctctggtc tgtaactgac gctgaggctc gaaagcgtgg      240
ggagcaaaca gg                                                           252

<210> SEQ ID NO 43
<211> LENGTH: 253
<212> TYPE: DNA
<213> ORGANISM: Staphylococcus

<400> SEQUENCE: 43
tacgtaggtg gcaagcgtta tccggaatta ttgggcgtaa agcgcgcgta ggcggttttt       60
taagtctgat gtgaaagccc acggctcaac cgtggagggt cattggaaac tggaaaactt      120
gagtgcagaa gaggaaagtg gaattccatg tgtagcggtg aaatgcgcag agatatggag      180
gaacaccagt ggcgaaggcg actttctggt ctgtaactga cgctgatatg cgaaagcgtg      240
gggatcaaac agg                                                          253

<210> SEQ ID NO 44
<211> LENGTH: 253
<212> TYPE: DNA
<213> ORGANISM: Ruminococcus_sp_5_1_39BFAA

<400> SEQUENCE: 44
tacgtagggg gcaagcgtta tccggattta ctgggtgtaa agggagcgta gacggtgcgg       60
caagtctgat gtgaaaggca tgggctcaac ctgtggactg cattggaaac tgtcatactt      120
gagtgccgga ggggtaagcg gaattcctag tgtagcggtg aaatgcgtag atattaggag      180
gaacaccagt ggcgaaggcg gcttactgga cggcaactga cgttgaggct cgaaagcgtg      240
gggagcaaac agg                                                          253

<210> SEQ ID NO 45
<211> LENGTH: 252
```

```
<212> TYPE: DNA
<213> ORGANISM: Dialister

<400> SEQUENCE: 45
tacgtaggtg gcaagcgttg tccggaatta ttgggcgtaa agcgcgcgca ggcggcttct    60
taagtccatc ttaaaagtgc ggggcttaac cccgtgatgg gatggaaact gagaggctgg   120
agtatcggag aggaaagtgg aattcctagt gtagcggtga aatgcgtaga gattaggaag   180
aacaccggtg gcgaaggcga ctttctggac gacaactgac gctgaggcgc gaaagcgtgg   240
ggagcaaaca gg                                                      252

<210> SEQ ID NO 46
<211> LENGTH: 253
<212> TYPE: DNA
<213> ORGANISM: Collinsella aerofaciens

<400> SEQUENCE: 46
tacgtagggg gcgagcgtta tccggattca ttgggcgtaa agcgcgcgta ggcggcccgg    60
caggccgggg gtcgaagcgg ggggctcaac cccccgaagc cccggaaacc tccgcggctt   120
gggtccggta ggggagggtg gaacacccgg tgtagcggtg gaatgcgcag atatcgggtg   180
gaacaccggt ggcgaaggcg gccctctggg ccgagaccga cgctgaggcg cgaaagctgg   240
gggagcgaac agg                                                     253

<210> SEQ ID NO 47
<211> LENGTH: 252
<212> TYPE: DNA
<213> ORGANISM: Clostridium bartlettii

<400> SEQUENCE: 47
tacgtagggg gctagcgtta tccggattta ctgggcgtaa agggtgcgta ggcggtctttt   60 taagtcagga gtgaaaggct acggctcaac cgtagtaagc tcttgaaact ggaggacttg   120
agtgcaggag aggagagtgg aattcctagt gtagcggtga aatgcgtaga tattaggagg   180
aacaccagta gcgaaggcgg ctctctggac tgtaactgac gctgaggcac gaaagcgtgg   240
ggagcaaaca gg                                                      252

<210> SEQ ID NO 48
<211> LENGTH: 253
<212> TYPE: DNA
<213> ORGANISM: Lactobacillus

<400> SEQUENCE: 48
tacgtagggt gcaagcgttg tccggattta ttgggcgtaa agcgagcgca ggcggaagaa    60
taagtctgat gtgaaagccc tcggcttaac cgaggaactg catcggaaac tgttttctt   120 gagtgcagaa gaggagaatg gaactccatg tgtagcggtg gaatgcgtag atatatggaa   180
gaacaccagt ggcgaaggcg gctctctggt ctgcaactga cgctgaggct cgaaagcatg   240
ggtagcgaac agg                                                     253

<210> SEQ ID NO 49
<211> LENGTH: 253
<212> TYPE: DNA
<213> ORGANISM: Prevotella

<400> SEQUENCE: 49
tacggaaggt ccgggcgtta tccggattta ttgggtttaa agggagcgta ggccggagat    60
```

```
taagcgtgtt gtgaaatgta gaggctcaac ctctgcactg cagcgcgaac tggtcttctt   120
gagtacgcac aacgtgggcg gaattcgtgg tgtagcggtg aaatgcttag atatcacgaa   180
gaactccgat tgcgaaggca gctcacggga gcgcaactga cgctgaagct cgaaagtgcg   240
ggtatcgaac agg                                                     253

<210> SEQ ID NO 50
<211> LENGTH: 253
<212> TYPE: DNA
<213> ORGANISM: Ruminococcus_sp_5_1_39BFAA

<400> SEQUENCE: 50
tacgtagggg gcaagcgtta tccggattta ctgggtgtaa agggagcgta gacggtgtgg    60
caagtctgat gtgaaaggca tgggctcaac ctgtggactg cattggaaac tgtcatactt   120
gagtgccgga ggggtaagcg gaattcctag tgtagcggtg aaatgcgtag atattaggag   180
gaacaccagt ggcgaaggcg gcttactgga cggtaactga cgttgaggct cgaaagcgtg   240
ggtagcaaac agg                                                     253

<210> SEQ ID NO 51
<211> LENGTH: 253
<212> TYPE: DNA
<213> ORGANISM: Lactobacillus ruminis

<400> SEQUENCE: 51
tacgtaggtg gcaggcgttg tccggattta ttgggcgtaa agggaacgca ggcggtctt    60 taagtctgat gtgaaagcct tcggcttaac cgaagtagtg cattggaaac tggaagactt   120
gagtgcagaa gaggagagtg gagctccatg tgtagcggtg aaatgcgtag atatatggaa   180
gaacaccagt ggcgaaagcg gctctctggt ctgtaactga cgctgaggtt cgaaagcgtg   240
ggtagcaaac agg                                                     253

<210> SEQ ID NO 52
<211> LENGTH: 253
<212> TYPE: DNA
<213> ORGANISM: Enterobacteriaceae

<400> SEQUENCE: 52
tacggagggt gcaagcgtta atcggaatta ctgggcgtaa agcgcacgca ggcggttttgt   60 taagtcagat gtgaaatccc cgggctcaac ctgggaactg catctgatac tggcaagctt   120
gagtctcgta gagggggggta gaattccagg tgtagcggtg aaatgcgtag agatctggag   180
gaataccggt ggcgaaggcg gccccctgga caaagactga cgctcaggtg cgaaagcgtg   240
gggagcaaac agg                                                     253

<210> SEQ ID NO 53
<211> LENGTH: 252
<212> TYPE: DNA
<213> ORGANISM: Streptococcus

<400> SEQUENCE: 53
tacgtaggtc ccgagcgttg tccggattta ttgggcgtaa agcgagcgca ggcggtttga    60
taagtctgaa gttaaaggct gtggctcaac catagttcgc tttggaaact gtcaaacttg   120
agtgcagaag gggagagtgg aattccatgt gtagcggtga aatgcgtaga tatatggagg   180
aacaccggtg gcgaaagcgg ctctctggtc tgtaactgac gctgaggctc gaaagcgtgg   240
ggagcaaaca gg                                                      252
```

<210> SEQ ID NO 54
<211> LENGTH: 253
<212> TYPE: DNA
<213> ORGANISM: Clostridium disporicum

<400> SEQUENCE: 54

```
tacgtaggtg gcgagcgttg tccggattta ctgggcgtaa agggagcgta ggcggacttt      60
taagtgagat gtgaaatacc cgggctcaac ttgggtgctg catttcaaac tggaagtcta     120
gagtgcagga gaggagaatg gaattcctag tgtagcggtg aaatgcgtag agattaggaa     180
gaacaccagt ggcgaaggcg attctctgga ctgtaactga cgctgaggct cgaaagcgtg     240
gggagcaaac agg                                                        253
```

<210> SEQ ID NO 55
<211> LENGTH: 252
<212> TYPE: DNA
<213> ORGANISM: Streptococcus parasanguinis

<400> SEQUENCE: 55

```
tacgtaggtc ccgagcgtta tccggattta ttgggcgtaa agcgagcgca ggcggttaga      60
taagtctgaa gttaaaggct gtggcttaac catagtacgc tttggaaact gtttaacttg     120
agtgcagaag gggagagtgg aattccatgt gtagcggtga aatgcgtaga tatatggagg     180
aacaccggtg gcgaaagcgg ctctctggtc tgtaactgac gctgaggctc gaaagcgtgg     240
ggagcaaaca gg                                                         252
```

<210> SEQ ID NO 56
<211> LENGTH: 253
<212> TYPE: DNA
<213> ORGANISM: Bifidobacterium

<400> SEQUENCE: 56

```
tacgtaggtc ccgagcgttg tccggattta ttgggcgtaa agggctcgta ggcggttcgt      60
cgcgtccggt gtgaaagtcc atcgcttaac ggtggatccg cgccgggtac gggcgggctt     120
gagtgcggta ggggagactg gaattcccgg tgtaacggtg aatgtgtag atatcgggaa      180
gaacaccaat ggcgaaggca ggtctctggg ccgttactga cgctgaggag cgaaagcgtg     240
gggagcgaac agg                                                        253
```

<210> SEQ ID NO 57
<211> LENGTH: 252
<212> TYPE: DNA
<213> ORGANISM: Megamonas

<400> SEQUENCE: 57

```
tacgtaggcg gcaagcgttg tccggaatta ttgggcgtaa agggagcgca ggcgggaaac      60
taagcggatc ttaaaagtgc ggggctcaac cccgtgatgg ggtccgaact ggttttcttg     120
agtgcaggag aggaaagcgg aattcccagt gtagcggtga aatgcgtaga tattgggaag    180
aacaccagtg gcgaaggcgg ctttctggac tgtaactgac gctgaggctc gaaagctagg     240
gtagcgaacg gg                                                         252
```

<210> SEQ ID NO 58
<211> LENGTH: 253
<212> TYPE: DNA
<213> ORGANISM: Clostridium

<400> SEQUENCE: 58

```
tacgtaggtg gcgagcgttg tccggattta ctgggcgtaa agggagcgta ggcggatttt      60
taagtgagat gtgaaatact cgggcttaac ctgagtgctg catttcaaac tggaagtcta     120
gagtgcagga gaggagaagg gaattcctag tgtagcggtg aaatgcgtag agattaggaa     180
gaacaccagt ggcgaaggcg cttctctgga ctgtaactga cgctgaggct cgaaagcgtg     240
gggagcaaac agg                                                        253
```

<210> SEQ ID NO 59
<211> LENGTH: 252
<212> TYPE: DNA
<213> ORGANISM: Megasphaera

<400> SEQUENCE: 59

```
tacgtaggtg gcaagcgttg tccggaatta ttgggcgtaa agggcgcgca ggcggcatcg      60
caagtcggtc ttaaaagtgc ggggcttaac cccgtgaggg gaccgaaaact gtgaagctcg    120
agtgtcggag aggaaagcgg aattcctagt gtagcggtga aatgcgtaga tattaggagg    180
aacaccagtg gcgaaagcgg ctttctggac gacaactgac gctgaggcgc gaaagccagg    240
ggagcaaacg gg                                                        252
```

<210> SEQ ID NO 60
<211> LENGTH: 253
<212> TYPE: DNA
<213> ORGANISM: Lactobacillus

<400> SEQUENCE: 60

```
tacgtaggtg gcaagcgttg tccggattta ttgggcgtaa agcgagcgca ggcggaaaga      60
taagtctgaa gtgaaagccc ccggcttaac cggggaactg cttcggaaac tgtccttctt    120
gagtgcagaa gaggagagtg gaactccatg tgtagcggtg gaatgcgtag atatatggaa    180
gaacaccagt ggcgaaggcg gctctctggt ctgcaactga cgctgaggct cgaaagcatg    240
ggtagcgaac agg                                                       253
```

<210> SEQ ID NO 61
<211> LENGTH: 28
<212> TYPE: DNA
<213> ORGANISM: Artificial Sequence
<220> FEATURE:
<223> OTHER INFORMATION: SYNTHESIZED

<400> SEQUENCE: 61

```
caccatgaaa aaaattgcaa gttttacc                                         28
```

<210> SEQ ID NO 62
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 62

```
ttattccgga taagtcagac gttc                                             24
```

<210> SEQ ID NO 63
<211> LENGTH: 28
<212> TYPE: DNA
<213> ORGANISM: Artificial Sequence
<220> FEATURE:
<223> OTHER INFORMATION: SYNTHESIZED
```

```
<400> SEQUENCE: 63
caccatgcca ttattagaca gttttacc                                          28

<210> SEQ ID NO 64
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 64
ttagtgaacc ttcagctcat tg                                                22
```